US009988437B2

(12) United States Patent
Williamson et al.

(10) Patent No.: US 9,988,437 B2
(45) Date of Patent: Jun. 5, 2018

(54) ANTI-HUMAN RESPIRATORY SYNCYTIAL VIRUS (RSV) ANTIBODIES AND METHODS OF USE

(71) Applicant: Janssen Vaccines & Prevention B.V., Leiden (NL)

(72) Inventors: Robert Anthony Williamson, London (GB); Jehangir Wadia, San Diego, CA (US); Gabriel Pascual, San Diego, CA (US); Elissa Keogh, San Diego, CA (US)

(73) Assignee: Janssen Vaccines & Prevention B.V., Leiden (NL)

( * ) Notice: Subject to any disclaimer, the term of this patent is extended or adjusted under 35 U.S.C. 154(b) by 9 days.

(21) Appl. No.: 15/077,558

(22) Filed: Mar. 22, 2016

(65) Prior Publication Data

US 2016/0194383 A1 Jul. 7, 2016

Related U.S. Application Data

(63) Continuation of application No. 14/297,486, filed on Jun. 5, 2014, now Pat. No. 9,403,900, which is a continuation of application No. 13/809,397, filed as application No. PCT/US2011/043463 on Jul. 8, 2011, now Pat. No. 9,139,642.

(60) Provisional application No. 61/456,454, filed on Nov. 5, 2010, provisional application No. 61/399,310, filed on Jul. 9, 2010.

(51) Int. Cl.
| | |
|---|---|
| *C07K 16/10* | (2006.01) |
| *A61K 45/06* | (2006.01) |
| *C12N 7/00* | (2006.01) |
| *C07K 16/46* | (2006.01) |
| *A61K 39/42* | (2006.01) |
| *A61K 31/7056* | (2006.01) |
| *G01N 33/569* | (2006.01) |
| *A61K 39/00* | (2006.01) |

(52) U.S. Cl.
CPC ...... *C07K 16/1027* (2013.01); *A61K 31/7056* (2013.01); *A61K 39/42* (2013.01); *A61K 45/06* (2013.01); *C07K 16/10* (2013.01); *C07K 16/468* (2013.01); *C12N 7/00* (2013.01); *G01N 33/56983* (2013.01); *A61K 2039/505* (2013.01); *A61K 2039/507* (2013.01); *A61K 2300/00* (2013.01); *C07K 2317/14* (2013.01); *C07K 2317/21* (2013.01); *C07K 2317/24* (2013.01); *C07K 2317/31* (2013.01); *C07K 2317/33* (2013.01); *C07K 2317/35* (2013.01); *C07K 2317/55* (2013.01); *C07K 2317/565* (2013.01); *C07K 2317/76* (2013.01); *C07K 2317/92* (2013.01); *C12N 2760/18534* (2013.01); *C12N 2760/18571* (2013.01); *G01N 2333/135* (2013.01)

(58) Field of Classification Search
CPC .................. A61K 39/12; A61K 39/155; A61K 2039/505; A61K 35/76; A61K 38/162; A61K 39/42; C12N 2760/00; C12N 2760/18011; C12N 2760/18511; C12N 7/00; C12N 15/86; C12N 2760/18522; C12N 2760/18534; C07K 14/005; C07K 2317/56; C07K 2317/51; C07K 2317/515; C07K 2317/622; C07K 2317/569; C07K 14/135; C07K 2317/54; C07K 2317/55
See application file for complete search history.

(56) References Cited

U.S. PATENT DOCUMENTS

| | | | |
|---|---|---|---|
| 4,391,904 A | 7/1983 | Litman et al. | |
| 4,444,887 A | 4/1984 | Hoffmann | |
| 4,472,509 A | 9/1984 | Gansow et al. | |
| 4,474,893 A | 10/1984 | Reading | |
| 4,714,681 A | 12/1987 | Reading | |
| 4,716,111 A | 12/1987 | Osband et al. | |
| 4,751,180 A | 6/1988 | Cousens et al. | |
| 4,816,397 A | 3/1989 | Boss et al. | |
| 4,816,567 A | 3/1989 | Cabilly et al. | |
| 4,880,078 A | 11/1989 | Inoue et al. | |
| 4,925,648 A | 5/1990 | Hansen et al. | |
| 4,935,233 A | 6/1990 | Bell et al. | |
| 4,946,778 A | 8/1990 | Ladner et al. | |
| 4,980,286 A | 12/1990 | Morgan et al. | |
| 4,997,764 A | 3/1991 | Dalla Favera | |
| 5,021,236 A | 6/1991 | Gries et al. | |
| 5,112,946 A | 5/1992 | Maione | |

(Continued)

FOREIGN PATENT DOCUMENTS

| | | |
|---|---|---|
| EP | 367166 A1 | 5/1990 |
| EP | 394827 A1 | 10/1990 |

(Continued)

OTHER PUBLICATIONS

Beeler et al., Neutralization epitopes of the F glycoprotein of respiratory syncytial virus: effect of mutation upon fusion function, Journal of Virology, Jul. 1989, pp. 2941-50, vol. 63, No. 7.
Collins et al., Fusion glycoprotein [Human respiratory syncytial virus], GenBank: AAB59858.1 Updated Nov. 29, 2000.
PCT International Search Report, PCT/US2011/043463, dated Aug. 7, 2011.
Written Opinion for PCT/US2011/043463, dated Aug. 7, 2011.
Heard et al., Two Neutralizing Human Anti-RSV Antibodies: Cloning, Expression, and Characterization, XP009052451 Molecular Medicine, Jan. 1999, pp. 35-45, vol. 5, No. 1.

(Continued)

*Primary Examiner* — Rachel B Gill
(74) *Attorney, Agent, or Firm* — Kramer Amado, P.C.

(57) ABSTRACT

Provided herein are antibodies or antigen-binding fragments thereof that immunospecifically bind to the fusion (F) protein of Respiratory Syncytial Virus (RSV). Also provided are methods for of prevention, treatment and diagnosis of viral infection and/or the treatment of one more symptoms of RSV-mediated disease. Methods of generating antibodies that immunospecifically bind RSV F protein also are provided.

44 Claims, 3 Drawing Sheets

(56) References Cited

U.S. PATENT DOCUMENTS

| | | |
|---|---|---|
| 5,128,326 A | 7/1992 | Balazs et al. |
| 5,223,409 A | 6/1993 | Ladner |
| 5,225,539 A | 7/1993 | Winter |
| 5,258,498 A | 11/1993 | Huston et al. |
| 5,290,540 A | 3/1994 | Prince et al. |
| 5,314,995 A | 5/1994 | Fell, Jr. et al. |
| 5,336,603 A | 8/1994 | Capon et al. |
| 5,349,053 A | 9/1994 | Landolfi |
| 5,359,046 A | 10/1994 | Capon et al. |
| 5,359,681 A | 10/1994 | Jorgenson et al. |
| 5,403,484 A | 4/1995 | Ladner et al. |
| 5,427,908 A | 6/1995 | Dower et al. |
| 5,436,146 A | 7/1995 | Shenk et al. |
| 5,447,851 A | 9/1995 | Beutler et al. |
| 5,457,035 A | 10/1995 | Balm et al. |
| 5,516,637 A | 5/1996 | Huang et al. |
| 5,530,101 A | 6/1996 | Queen et al. |
| 5,565,332 A | 10/1996 | Hoogenboom et al. |
| 5,571,698 A | 11/1996 | Ladner et al. |
| 5,573,920 A | 11/1996 | Randle |
| 5,580,717 A | 12/1996 | Dower et al. |
| 5,585,089 A | 12/1996 | Queen |
| 5,601,819 A | 2/1997 | Wong et al. |
| 5,605,793 A | 2/1997 | Stemmer |
| 5,622,929 A | 4/1997 | Willner et al. |
| 5,630,681 A | 5/1997 | Paya et al. |
| 5,658,727 A | 8/1997 | Barbas et al. |
| 5,667,988 A | 9/1997 | Barbas et al. |
| 5,679,377 A | 10/1997 | Bernstein et al. |
| 5,698,426 A | 12/1997 | Huse |
| 5,723,125 A | 3/1998 | Chang et al. |
| 5,731,168 A | 3/1998 | Carter et al. |
| 5,733,743 A | 3/1998 | Johnson et al. |
| 5,750,753 A | 5/1998 | Kimae et al. |
| 5,762,905 A | 6/1998 | Burton et al. |
| 5,780,225 A | 7/1998 | Wigler et al. |
| 5,783,181 A | 7/1998 | Browne et al. |
| 5,807,715 A | 9/1998 | Morrison et al. |
| 5,811,238 A | 9/1998 | Stemmer et al. |
| 5,811,524 A | 9/1998 | Brams et al. |
| 5,821,047 A | 10/1998 | Garrard et al. |
| 5,824,307 A | 10/1998 | Johnson |
| 5,830,721 A | 11/1998 | Stemmer et al. |
| 5,834,252 A | 11/1998 | Stemmer et al. |
| 5,837,458 A | 11/1998 | Minshull et al. |
| 5,840,298 A | 11/1998 | Brams et al. |
| 5,840,300 A | 11/1998 | Williams et al. |
| 5,844,095 A | 12/1998 | Linsley et al. |
| 5,855,913 A | 1/1999 | Hanes et al. |
| 5,874,064 A | 2/1999 | Edwards et al. |
| 5,908,626 A | 6/1999 | Chang et al. |
| 5,912,015 A | 6/1999 | Bernstein et al. |
| 5,916,597 A | 6/1999 | Lee et al. |
| 5,934,272 A | 8/1999 | Lloyd et al. |
| 5,955,364 A | 9/1999 | Brams et al. |
| 5,969,108 A | 10/1999 | McCafferty et al. |
| 5,985,309 A | 11/1999 | Edwards et al. |
| 5,989,463 A | 11/1999 | Tracy et al. |
| 6,019,968 A | 2/2000 | Platz et al. |
| 6,136,310 A | 10/2000 | Hanna et al. |
| 6,413,771 B1 | 7/2002 | Brams et al. |
| 6,537,809 B2 | 3/2003 | Brams et al. |
| 6,656,467 B2 | 12/2003 | Young et al. |
| 6,685,942 B1 | 2/2004 | Burton et al. |
| 6,759,518 B1 | 7/2004 | Kontermann et al. |
| 6,818,216 B2 | 11/2004 | Young et al. |
| 7,070,786 B2 | 7/2006 | Scallon |
| 7,083,784 B2 | 8/2006 | Dall'Acqua et al. |
| 7,217,797 B2 | 5/2007 | Hinton et al. |
| 7,229,619 B1 | 6/2007 | Young et al. |
| 7,364,737 B2 | 4/2008 | Burton et al. |
| 7,364,742 B2 | 4/2008 | Scallon |
| 7,488,477 B2 | 2/2009 | Pilkington et al. |
| 8,568,719 B2 | 10/2013 | Williamson et al. |
| 2004/0096451 A1 | 5/2004 | Young et al. |
| 2006/0024298 A1 | 2/2006 | Lazar et al. |
| 2006/0198840 A1 | 9/2006 | Dall'Acqua et al. |
| 2007/0140966 A1 | 6/2007 | Chang et al. |
| 2008/0248028 A1 | 10/2008 | Lazar et al. |
| 2008/0287657 A1 | 11/2008 | Hinton et al. |
| 2009/0104205 A1 | 4/2009 | Johnson |
| 2011/0033389 A1 | 2/2011 | Chen et al. |
| 2011/0076268 A1 | 3/2011 | Williamson et al. |
| 2014/0044719 A1 | 2/2014 | Williamson et al. |

FOREIGN PATENT DOCUMENTS

| | | |
|---|---|---|
| EP | 307434 | 9/1993 |
| EP | 307434 A1 | 9/1993 |
| EP | 396387 A2 | 12/1993 |
| EP | 519596 A1 | 2/2005 |
| WO | 1988001642 | 3/1988 |
| WO | 1989012624 | 12/1989 |
| WO | 1990002795 | 3/1990 |
| WO | 1990002809 | 3/1990 |
| WO | 1991000360 | 1/1991 |
| WO | 1991006570 | 5/1991 |
| WO | 1991009115 | 6/1991 |
| WO | 1991009967 | 7/1991 |
| WO | 1991010737 | 7/1991 |
| WO | 1991010741 | 7/1991 |
| WO | 1991014438 | 10/1991 |
| WO | 1992001047 | 1/1992 |
| WO | 1992005793 | 4/1992 |
| WO | 1992006180 | 4/1992 |
| WO | 1992008495 | 5/1992 |
| WO | 1992008802 | 5/1992 |
| WO | 1992019244 | 5/1992 |
| WO | 1992018619 | 10/1992 |
| WO | 1992020316 | 11/1992 |
| WO | 1992022324 | 12/1992 |
| WO | 1992022635 | 12/1992 |
| WO | 1993010151 | 5/1993 |
| WO | 1993011236 | 6/1993 |
| WO | 1993014188 | 7/1993 |
| WO | 1993017715 | 9/1993 |
| WO | 1993020221 | 10/1993 |
| WO | 1994008598 | 4/1994 |
| WO | 1994024164 | 10/1994 |
| WO | 1995015982 | 6/1995 |
| WO | 1995020401 | 8/1995 |
| WO | 1996004388 | 2/1996 |
| WO | 1996006641 | 3/1996 |
| WO | 9622024 A1 | 7/1996 |
| WO | 1996022024 | 7/1996 |
| WO | 9634096 A1 | 10/1996 |
| WO | 1996034096 | 10/1996 |
| WO | 1996040252 | 12/1996 |
| WO | 1997013844 | 4/1997 |
| WO | 1997032572 | 9/1997 |
| WO | 1997034631 | 9/1997 |
| WO | 1997044013 | 11/1997 |
| WO | 1998016654 | 4/1998 |
| WO | 1998024893 | 6/1998 |
| WO | 1998031346 | 7/1998 |
| WO | 1998046645 | 10/1998 |
| WO | 1998050433 | 11/1998 |
| WO | 1999004813 | 2/1999 |
| WO | 1999020253 | 4/1999 |
| WO | 1999915154 | 4/1999 |
| WO | 1999066903 | 12/1999 |
| WO | 2000071694 | 11/2000 |
| WO | 2002026233 | 6/2002 |
| WO | 2004076677 A2 | 9/2004 |
| WO | 2005063816 A2 | 7/2005 |
| WO | 1996033735 | 10/2006 |
| WO | 2007068758 A1 | 6/2007 |

(56) References Cited

FOREIGN PATENT DOCUMENTS

| WO | 2008106980 A2 | 9/2008 |
|---|---|---|
| WO | 2011020079 A1 | 2/2011 |
| WO | 2012006596 A2 | 1/2012 |

OTHER PUBLICATIONS

Huang et al., Respiratory Syncytial Virus-Neutralizing Monoclonal Antibodies Motavizumab and Palivizumab Inhibit Fusion, XP009139705 Journal of Virology, Aug. 2010, pp. 8132-8140, vol. 84, No. 16.

Wu et al., Ultra-potent Antibodies Against Respiratory Syncytial Virus: Effects of Binding Kinetics and Binding Valence on Viral Neutralization, Journal of Molecular Biology, Jul. 1, 2005, pp. 126-144, vol. 350, No. 1.

Wu et al., Development of Motavizumab, an Ultra-potent Antibody for the Prevention of Respiratory Syncytial Virus Infection in the Upper and Lower Respiratory Tract, Journal of Molecular Biology, Apr. 6, 2007, pp. 652-665, vol. 368, No. 3.

Zhao Chen FP, Sullender WM. Respiratory syncytial virus escape mutant derived in vitro resists palivizumab prophylaxis in cotton rats. Virology. Jan. 20, 2004;318(2):608-12.

Cuesta AM, Sainz-Pastor N, Bonet J, Oliva B, Alvarez-Vallina L. Multivalent antibodies: when design surpasses evolution. Trends Biotechnol. Jul. 2010;28(7):355-62. doi: 10.1016/j.tibtech.2010.03.007. Epub May 4, 2010.

Wu H, Pfarr OS, Johnson S, Brewah YA, Woods RM, Patel NK, White WI, Young JF, Kiener PA. Development of motavizumab, an ultra-potent antibody for the prevention of respiratory syncytial virus infection in the upper and lower respiratory tract. J Mol Bioi. May 4, 2007;368(3):652-65. Epub Feb. 20, 2007.

Huang K, Incognito L, Cheng X, Ulbrandt NO, Wu H. Respiratory syncytial virus-neutralizing monoclonal antibodies motavizumab and palivizumab inhibit fusion. J Virol. Aug. 2010;84(16):8132-40. doi: 10.1128/JVI.02699-09. Epub Jun. 2, 2010.

Canziani GA, Melero JA, Lacy ER. Characterization of neutralizing affinity-matured human respiratory syncytial virus F binding antibodies in the sub-picomolar affinity range. J Mol Recognit. Mar. 2012;25(3):136-46.

Ulbrandt NO, Ji H, Patel NK, Barnes AS, Wilson S, Kiener PA, Suzich J, McCarthy MP. Identification of antibody neutralization epitopes on the fusion protein of human metapneumovirus. J Gen Virol. Dec. 2008;89(Pt 12):3113-8.

Schuster JE, Cox RG, Hastings AK, Boyd KL, Wadia J, Chen Z, Burton DR, Williamson RA, Williams JV. A Broadly Neutralizing Human Monoclonal Antibody Exhibits In Vivo Efficacy Against Both Human Metapneumovirus and Respiratory Syncytial Virus. J Infect Dis. May 26, 2014. pii: jiu307. [Epub ahead of print].

Wakamatsu,A., et. al. NEDO human eDNA sequencing project focused on splicing variant. GenBank Ace. No. BAG62928. Dep. Jun. 24, 2008.

Yang DP, Zielinska E, Quiroz J, Madore D, Rappaport R. Preparation of a respiratory syncytial virus human reference serum for use in the quantitation of neutralization antibody. Biologicals. Jun. 2007;35(3):183-7. Epub Jan. 22, 2007.

Strausberg,R.L., et. al. Generation and initial analysis of more than 15,000 full-length human and mouse eDNA sequences. Proc Natl Acad Sci US A. Dec. 24, 2002;99(26):16899-903. Epub Dec. 11, 2002. GenBank Ace. No. AAH28090, Updated Nov. 7, 2006.

Mateu MG, et. al. Eur J Immunol. Jun. 1992;22(6):1385-9.

Greenspan NS, Di Cera E. Defining epitopes: It's not as easy as it seems. Nat Biotechnol. Oct. 1999;17(10):936-7.

Burgess WH, Shaheen AM, Ravera M, Jaye M, Donohue PJ, Winkles JA. Possible dissociation of the heparin-binding and mitogenic activities of heparin-binding (acidic fibroblast) growth factor-1 from its receptor-binding activities by site-directed mutagenesis of a single lysine residue. J Cell Bioi. Nov. 1990;111 (5 Pt 1):2129-38.

Lazar E, Watanabe S, Dalton S, Sporn MB. Transforming growth factor alpha: mutation of aspartic acid 47 and leucine 48 results in different biological activities. Mol Cell Bioi. Mar. 1988;8(3):1247-52.

Schwartz GP, Burke GT, Katsoyannis PG. A superactive insulin: [B1 a-aspartic acid]insulin(human). Proc Natl Acad Sci USA, Sep. 1987;84(18):6408-11.

Lin MC, Wright DE, Hruby VJ, Rodbell M. Structure-function relationships in glucagon: properties of highly purified des-His-1-, monoiodo-, and (des-Asn-28, Thr-29)(homoserine lactone-27)-glucagon. Biochemistry. Apr. 22, 1975;14 (8):1559-63.

Acland P, Dixon M, Peters G, Dickson C. Subcellular fate of the int-2 oncoprotein is determined by choice of initiation codon. Nature. Feb. 15, 1990;343(6259):662-5.

Rudikoff S, Giusti AM, Cook WD, Scharff MD. Single amino acid substitution altering antigen-binding specificity. Proc Natl Acad Sci U SA. Mar. 1982;79(6):1979-83.

Ibragimova GT, Wade RC. Stability of the beta-sheet of the WW domain: A molecular dynamics simulation study. Biophys J. Oct. 1999;77(4):2191-8.

Pre-fusion D3     Post-fusion D3

ANTI-HUMAN RESPIRATORY SYNCYTIAL VIRUS (RSV) ANTIBODIES AND METHODS OF USE

CROSS-REFERENCE TO RELATED APPLICATIONS

This application is a continuation of pending U.S. patent application Ser. No. 14/297,486, filed Jun. 5, 2014, U.S. Pat. No. 9,403,900, which is a continuation of U.S. patent application Ser. No. 13/809,397, filed Mar. 25, 2013, U.S. Pat. No. 9,139,642, issued Sep. 22, 2015, which application is a national phase entry under 35 U.S.C. § 371 of International Patent Application PCT/US2011/043463 filed on Jul. 8, 2011, designating the United States of America and published in English as International Patent Publication WO 2012/006596 A2 on Jan. 12, 2012, which claims the benefit under Article 8 of the Patent Cooperation Treaty and under 35 U.S.C. § 119(e) to U.S. Provisional Patent Application Ser. No. 61/399,310, filed Jul. 9, 2010, and to U.S. Provisional Patent Application Ser. No. 61/456,454 filed Nov. 5, 2010, the disclosure of all of which is hereby incorporated herein in its entirety by this reference.

This application is related to U.S. application Ser. No. 12/806,498, filed Aug. 13, 2010, published as US-2011-0076268 A1, and entitled "ANTIBODIES AGAINST HUMAN RESPIRATORY SYNCTIAL VIRUS (RSV) AND METHODS OF USE," now U.S. Pat. No. 8,568,719, issued Oct. 29, 2013, and International Application No. PCT/US10/045549, filed Aug. 13, 2010, published as International PCT Application No. WO 2011/020079 and entitled "ANTIBODIES AGAINST HUMAN RESPIRATORY SYNCTIAL VIRUS (RSV) AND METHODS OF USE," both of which claim priority to U.S. Provisional Application Ser. No. 61/274,395, filed Aug. 13, 2009, entitled "ANTIBODIES AGAINST HUMAN RESPIRATORY SYNCTIAL VIRUS (RSV) AND METHODS OF USE." The subject matter of each of the above-referenced applications is incorporated by reference in its entirety.

STATEMENT ACCORDING TO 37 C.F.R. § 1.821(C) OR (E)—SEQUENCE LISTING SUBMITTED AS PDF FILE WITH A REQUEST TO TRANSFER CRF FROM PARENT APPLICATION

Pursuant to 37 C.F.R. § 1.821(c) or (e), a file containing a PDF version of the Sequence Listing has been submitted concomitant with this application, the contents of which are hereby incorporated by reference. The transmittal documents of this application include a Request to Transfer CRF from the parent application.

TECHNICAL FIELD

Provided are antibodies and antigen-binding fragments thereof that immunospecifically bind to the F protein of Respiratory Syncytial Virus (RSV) and/or to RSV and/or neutralize RSV. Also provided are diagnostic and therapeutic methods that employ anti-RSV antibodies and antigen-binding fragments thereof. The therapeutic methods include administering the provided anti-RSV antibodies or antigen-binding fragments thereof for the prevention or treatment of a RSV infection and/or amelioration of one or more symptoms of a RSV infection, such as infections in infants and infections associated with organ transplantation. Combinations of a plurality of different anti-RSV antibodies and antigen-binding fragments thereof provided herein and/or with other anti-RSV antibodies and antigen-binding fragments thereof can be used for combination therapy. Compositions containing the mixtures of anti-RSV antibodies and antigen-binding fragments thereof also are provided.

BACKGROUND

RSV is the leading cause of severe respiratory illness in infants and young children and is the major cause of infantile bronchiolitis (Welliver (2003) *J Pediatr* 143:S112). An estimated 64 million cases of respiratory illness and 160,000 deaths worldwide are attributable to RSV induced disease. In the United States alone, tens of thousands of infant hospitalizations are due to infections by paramyxoviruses, such as RSV and parainfluenza virus (PIV) (Shay et al. (1999) *JAMA* 282:1440-1446). Severe RSV infection occurs most often in children and infants, especially in premature infants. Underlying health problems such as chronic lung disease or congenital heart disease can significantly increase the risk of serious illness. RSV infections also can cause serious illness in the elderly, individuals with chronic pulmonary disease and immunocompromised adults, such as bone marrow transplant recipients.

Several approaches to the prevention and treatment of RSV infection have been investigated, including vaccine development, antiviral compounds (ribavirin), antisense drugs, RNA interference technology, and antibody products, such as immunoglobulin or intravenous monoclonal antibodies. Intravenous immunoglobulin (RSV-IGIV; RESPIGAM®) isolated from donors and a monoclonal antibody, palivizumab (SYNAGIS™), have been approved for RSV prophylaxis in high risk children. A vaccine or commercially available treatment for RSV, however, is not yet available. Only ribavirin is approved for treatment of RSV infection. In order to be effective for treatment of RSV infection, high doses, frequent administrations and/or volumes of antibody products, such as RSV-IG and palivizumab, are required due to low specificity. Further, the use of products, such as intravenous immunoglobulin, is dependent on donor availability. Accordingly, there exists a need for additional agents for the prevention or treatment of RSV infections.

SUMMARY

Provided herein are isolated polypeptides, antibodies or antigen-binding fragments thereof for the prophylaxis and treatment of RSV infection and RSV-mediated diseases or conditions. Also provided herein are isolated polypeptides, antibodies or antigen-binding fragments thereof for the diagnosis and/or monitoring of RSV infection. Provided herein are isolated polypeptides, antibodies or antigen-binding fragments thereof that immunospecifically bind to and neutralize RSV. In some examples, the polypeptides provided herein immunospecifically bind to and neutralize RSV when the polypeptide provided herein is contained in an antibody or antigen-binding fragment. Also provided herein are antibodies and antigen-binding fragments that contain a polypeptide provided herein where the antibody or antigen-binding fragment immunospecifically binds to and neutralizes RSV. The polypeptides, antibodies and antigen-binding fragments provided herein can specifically bind to the F protein as well as neutralize RSV. Provided herein are isolated polypeptides, antibodies or antigen-binding fragments thereof that can neutralize RSV subtypes A and B.

Provided herein are isolated polypeptides, antibodies or antigen-binding fragments thereof that immunospecifically bind the F protein of RSV.

Provided herein are antibodies or antigen-binding fragments thereof that contain a $V_H$ CDR1 comprising the peptide of SEQ ID NOS:405, 411, 417, 423, 429, 437-441, 458, 464, 470 or 482-484 or a sequence of amino acids having at least or at least about 80%, 90%, 91%, 92%, 93%, 94%, 95%, 96%, 97%, 98%, 99% or more sequence identity to SEQ ID NOS:405, 411, 417, 423, 429, 437-441, 458, 464, 470 or 482-484; a $V_H$ CDR2 comprising the peptide of SEQ ID NOS:406, 412, 418, 424, 430, 459, 465 or 471 or a sequence of amino acids having at least or at least about 80%, 90%, 91%, 92%, 93%, 94%, 95%, 96%, 97%, 98%, 99% or more sequence identity to SEQ ID NOS:406, 412, 418, 424, 430, 459, 465 or 471; a $V_H$ CDR3 comprising the peptide of SEQ ID NOS:407, 413, 419, 425, 431, 460, 466 or 472 or a sequence of amino acids having at least or at least about 80%, 90%, 91%, 92%, 93%, 94%, 95%, 96%, 97%, 98%, 99% or more sequence identity to SEQ ID NOS:407, 413, 419, 425, 431, 460, 466 or 472; a $V_L$ CDR1 comprising the peptide of SEQ ID NOS:408, 414, 420, 426, 432, 461, 467 or 473 or a sequence of amino acids having at least or at least about 80%, 90%, 91%, 92%, 93%, 94%, 95%, 96%, 97%, 98%, 99% or more sequence identity to SEQ ID NOS:408, 414, 420, 426, 432, 461, 467 or 473; a $V_L$ CDR2 comprising the peptide of SEQ ID NOS:409, 415, 421, 427, 433, 462, 468 or 474 or a sequence of amino acids having at least or at least about 80%, 90%, 91%, 92%, 93%, 94%, 95%, 96%, 97%, 98%, 99% or more sequence identity to SEQ ID NOS:409, 415, 421, 427, 433, 462, 468 or 474; and a $V_L$ CDR3 comprising the peptide of SEQ ID NOS:410, 416, 422, 428, 434, 463, 469 or 475 or a sequence of amino acids having at least or at least about 80%, 90%, 91%, 92%, 93%, 94%, 95%, 96%, 97%, 98%, 99% or more sequence identity to SEQ ID NOS:410, 416, 422, 428, 434, 463, 469 or 475, wherein the antibody or antigen-binding fragment immunospecifically binds to RSV fusion (F) protein and/or neutralizes RSV.

In particular, provided herein is an antibody containing a VHCDR1 set forth in SEQ ID NO:405 or 437, a VHCDR2 set forth in SEQ ID NO:406, a VHCDR3 set forth in SEQ ID NO:407, a VLCDR1 set forth in SEQ ID NO:408, a VLCDR2 set forth in SEQ ID NO:409, and a VLCDR3 set forth in SEQ ID NO:410, or an antibody containing CDRs that have at least or about 80%, 90%, 91%, 92%, 93%, 94%, 95%, 96%, 97%, 98%, 99% or more sequence identity with any of SEQ ID NOS:405-410 or 437.

Also provided herein is an antibody containing a VHCDR1 set forth in SEQ ID NO:464 or 483, a VHCDR2 set forth in SEQ ID NO:465, a VHCDR3 set forth in SEQ ID NO:466, a VLCDR1 set forth in SEQ ID NO:467, a VLCDR2 set forth in SEQ ID NO:468, and a VLCDR3 set forth in SEQ ID NO:469, or an antibody containing CDRs that have at least or about 80%, 90%, 91%, 92%, 93%, 94%, 95%, 96%, 97%, 98%, 99% or more sequence identity with any of SEQ ID NOS:464-469 or 483.

Also provided herein is an antibody containing a VHCDR1 set forth in SEQ ID NO:411 or 438, a VHCDR2 set forth in SEQ ID NO:412, a VHCDR3 set forth in SEQ ID NO:413, a VLCDR1 set forth in SEQ ID NO:414, a VLCDR2 set forth in SEQ ID NO:415, and a VLCDR3 set forth in SEQ ID NO:416, or an antibody containing CDRs that have at least or about 80%, 90%, 91%, 92%, 93%, 94%, 95%, 96%, 97%, 98%, 99% or more sequence identity with any of SEQ ID NOS:411-416 or 438.

Also provided herein is an antibody containing a VHCDR1 set forth in SEQ ID NO:417 or 439, a VHCDR2 set forth in SEQ ID NO:418, a VHCDR3 set forth in SEQ ID NO:419, a VLCDR1 set forth in SEQ ID NO:420, a VLCDR2 set forth in SEQ ID NO:421, and a VLCDR3 set forth in SEQ ID NO:422, or an antibody containing CDRs that have at least or about 80%, 90%, 91%, 92%, 93%, 94%, 95%, 96%, 97%, 98%, 99% or more sequence identity with any of SEQ ID NOS:417-422 or 439.

Also provided herein is an antibody containing a VHCDR1 set forth in SEQ ID NO:423 or 440, a VHCDR2 set forth in SEQ ID NO:424, a VHCDR3 set forth in SEQ ID NO:425, a VLCDR1 set forth in SEQ ID NO:426, a VLCDR2 set forth in SEQ ID NO:427, and a VLCDR3 set forth in SEQ ID NO:428, or an antibody containing CDRs that have at least or about 80%, 90%, 91%, 92%, 93%, 94%, 95%, 96%, 97%, 98%, 99% or more sequence identity with any of SEQ ID NOS:423-428 or 440.

Also provided herein is an antibody containing a VHCDR1 set forth in SEQ ID NO:429 or 441, a VHCDR2 set forth in SEQ ID NO:430, a VHCDR3 set forth in SEQ ID NO:431, a VLCDR1 set forth in SEQ ID NO:432, a VLCDR2 set forth in SEQ ID NO:433, and a VLCDR3 set forth in SEQ ID NO:434, or an antibody containing CDRs that have at least or about 80%, 90%, 91%, 92%, 93%, 94%, 95%, 96%, 97%, 98%, 99% or more sequence identity with any of SEQ ID NOS:429-434 or 441.

Also provided herein is an antibody containing a VHCDR1 set forth in SEQ ID NO:458 or 482, a VHCDR2 set forth in SEQ ID NO:459, a VHCDR3 set forth in SEQ ID NO:460, a VLCDR1 set forth in SEQ ID NO:461, a VLCDR2 set forth in SEQ ID NO:462, and a VLCDR3 set forth in SEQ ID NO:463, or an antibody containing CDRs that have at least or about 80%, 90%, 91%, 92%, 93%, 94%, 95%, 96%, 97%, 98%, 99% or more sequence identity with any of SEQ ID NOS:458-463 or 482.

Also provided herein is an antibody containing a VHCDR1 set forth in SEQ ID NO:470 or 484, a VHCDR2 set forth in SEQ ID NO:471, a VHCDR3 set forth in SEQ ID NO:472, a VLCDR1 set forth in SEQ ID NO:473, a VLCDR2 set forth in SEQ ID NO:474, and a VLCDR3 set forth in SEQ ID NO:475, or an antibody containing CDRs that have at least or about 80%, 90%, 91%, 92%, 93%, 94%, 95%, 96%, 97%, 98%, 99% or more sequence identity with any of SEQ ID NOS:470-475 or 484.

In some examples, an isolated antibody or antigen-binding fragment thereof provided herein contains a heavy chain, which comprises the peptide of SEQ ID NO:396. In some examples, an isolated antibody or antigen-binding fragment provided herein contains a $V_H$ domain, which comprises the peptide of amino acids 1-121 of SEQ ID NO:396. In some examples, an isolated antibody or antigen-binding fragment thereof provided herein contains a light chain, which comprises the peptide of SEQ ID NO:395. In some examples, an isolated antibody or antigen-binding fragment provided herein contains a $V_L$ domain, which comprises the peptide of amino acids 1-110 of SEQ ID NO:395. In a particular example, the isolated antibody or antigen-binding fragment thereof is 30D8.

Provided herein are isolated anti-RSV antibodies or antigen-binding fragments thereof that contain a variable heavy ($V_H$) chain and a variable light ($V_L$) chain, where the antibody or antigen-binding fragment immunospecifically binds to the same epitope on a RSV fusion (F) protein as an antibody or antigen-binding fragment that contains a heavy chain set forth in SEQ ID NO:396 and a light chain set forth in SEQ ID NO:395.

In some examples, an isolated antibody or antigen-binding fragment thereof provided herein contains a $V_H$ CDR1, which comprises the peptide of SEQ ID NO:405 or 437; a $V_H$ CDR2, which comprises the peptide of SEQ ID NO:406; and a $V_H$ CDR3, which comprises the peptide of SEQ ID NO:407.

In some examples, an isolated antibody or antigen-binding fragment thereof provided herein contains a $V_L$ CDR1, which comprises the peptide of SEQ ID NO:408; a $V_L$ CDR2, which comprises the peptide of SEQ ID NO:409; and a $V_L$ CDR3, which comprises the peptide of SEQ ID NO:410.

In some examples, an isolated antibody or antigen-binding fragment thereof provided herein contains a heavy chain, which comprises the peptide of SEQ ID NO:398. In some examples, an isolated antibody or antigen-binding fragment provided herein contains a $V_H$ domain, which comprises the peptide of amino acids 1-125 of SEQ ID NO:398. In some examples, an isolated antibody or antigen-binding fragment thereof provided herein contains a light chain, which comprises the peptide of SEQ ID NO:397. In some examples, an isolated antibody or antigen-binding fragment provided herein contains a $V_L$ domain, which comprises the peptide of amino acids 1-107 of SEQ ID NO:397. In a particular example, the isolated antibody or antigen-binding fragment thereof is 104E5.

Provided herein are isolated anti-RSV antibodies or antigen-binding fragments thereof that contain a variable heavy ($V_H$) chain and a variable light ($V_L$) chain, where the antibody or antigen-binding fragment immunospecifically binds to the same epitope on a RSV fusion (F) protein as an antibody or antigen-binding fragment that contains a heavy chain set forth in SEQ ID NO:398 and a light chain set forth in SEQ ID NO:397. In some examples, an isolated antibody or antigen-binding fragment thereof provided herein contains a $V_H$ CDR1, which comprises the peptide of SEQ ID NO:411 or 438; a $V_H$ CDR2, which comprises the peptide of SEQ ID NO:412; and a $V_H$ CDR3, which comprises the peptide of SEQ ID NO:413.

In some examples, an isolated antibody or antigen-binding fragment thereof provided herein contains a $V_L$ CDR1, which comprises the peptide of SEQ ID NO:414; a $V_L$ CDR2, which comprises the peptide of SEQ ID NO:415; and a $V_L$ CDR3, which comprises the peptide of SEQ ID NO:416.

In some examples, an isolated antibody or antigen-binding fragment thereof provided herein contains a heavy chain, which comprises the peptide of SEQ ID NO:400. In some examples, an isolated antibody or antigen-binding fragment provided herein contains a $V_H$ domain, which comprises the peptide of amino acids 1-124 of SEQ ID NO:400. In some examples, an isolated antibody or antigen-binding fragment thereof provided herein contains a light chain, which comprises the peptide of SEQ ID NO:399. In some examples, an isolated antibody or antigen-binding fragment provided herein contains a $V_L$ domain, which comprises the peptide of amino acids 1-108 of SEQ ID NO:399. In a particular example, the isolated antibody or antigen-binding fragment thereof is 38F10.

Provided herein are isolated anti-RSV antibodies or antigen-binding fragments thereof that contain a variable heavy ($V_H$) chain and a variable light ($V_L$) chain, where the antibody or antigen-binding fragment immunospecifically binds to the same epitope on a RSV fusion (F) protein as an antibody or antigen-binding fragment that contains a heavy chain set forth in SEQ ID NO:400 and a light chain set forth in SEQ ID NO:399.

In some examples, an isolated antibody or antigen-binding fragment thereof provided herein contains a $V_H$ CDR1, which comprises the peptide of SEQ ID NO:417 or 439; a $V_H$ CDR2, which comprises the peptide of SEQ ID NO:418; and a $V_H$ CDR3, which comprises the peptide of SEQ ID NO:419.

In some examples, an isolated antibody or antigen-binding fragment thereof provided herein contains a $V_L$ CDR1, which comprises the peptide of SEQ ID NO:420; a $V_L$ CDR2, which comprises the peptide of SEQ ID NO:421; and a $V_L$ CDR3, which comprises the peptide of SEQ ID NO:422.

In some examples, an isolated antibody or antigen-binding fragment thereof provided herein contains a heavy chain, which comprises the peptide of SEQ ID NO:402. In some examples, an isolated antibody or antigen-binding fragment provided herein contains a $V_H$ domain, which comprises the peptide of amino acids 1-125 of SEQ ID NO:402. In some examples, an isolated antibody or antigen-binding fragment thereof provided herein contains a light chain, which comprises the peptide of SEQ ID NO:401. In some examples, an isolated antibody or antigen-binding fragment provided herein contains a $V_L$ domain, which comprises the peptide of amino acids 1-113 of SEQ ID NO:401. In a particular example, the isolated antibody or antigen-binding fragment thereof is 14G3.

Provided herein are isolated anti-RSV antibodies or antigen-binding fragments thereof that contain a variable heavy ($V_H$) chain and a variable light ($V_L$) chain, where the antibody or antigen-binding fragment immunospecifically binds to the same epitope on a RSV fusion (F) protein as an antibody or antigen-binding fragment that contains a heavy chain set forth in SEQ ID NO:402 and a light chain set forth in SEQ ID NO:401.

In some examples, an isolated antibody or antigen-binding fragment thereof provided herein contains a $V_H$ CDR1, which comprises the peptide of SEQ ID NO:423 or 440; a $V_H$ CDR2, which comprises the peptide of SEQ ID NO:424; and a $V_H$ CDR3, which comprises the peptide of SEQ ID NO:425.

In some examples, an isolated antibody or antigen-binding fragment thereof provided herein contains a $V_L$ CDR1, which comprises the peptide of SEQ ID NO:426; a $V_L$ CDR2, which comprises the peptide of SEQ ID NO:427; and a $V_L$ CDR3, which comprises the peptide of SEQ ID NO:428.

In some examples, an isolated antibody or antigen-binding fragment thereof provided herein contains a heavy chain, which comprises the peptide of SEQ ID NO:404. In some examples, an isolated antibody or antigen-binding fragment provided herein contains a $V_H$ domain, which comprises the peptide of amino acids 1-123 of SEQ ID NO:404. In some examples, an isolated antibody or antigen-binding fragment thereof provided herein contains a light chain, which comprises the peptide of SEQ ID NO:403. In some examples, an isolated antibody or antigen-binding fragment provided herein contains a $V_L$ domain, which comprises the peptide of amino acids 1-107 of SEQ ID NO:403. In a particular example, the isolated antibody or antigen-binding fragment thereof is 90D3.

Provided herein are isolated anti-RSV antibodies or antigen-binding fragments thereof that contain a variable heavy ($V_H$) chain and a variable light ($V_L$) chain, where the antibody or antigen-binding fragment immunospecifically binds to the same epitope on a RSV fusion (F) protein as an antibody or antigen-binding fragment that contains a heavy chain set forth in SEQ ID NO:404 and a light chain set forth in SEQ ID NO:403.

In some examples, an isolated antibody or antigen-binding fragment thereof provided herein contains a $V_H$ CDR1, which comprises the peptide of SEQ ID NO:429 or 441; a $V_H$ CDR2, which comprises the peptide of SEQ ID NO:430; and a $V_H$ CDR3, which comprises the peptide of SEQ ID NO:431.

In some examples, an isolated antibody or antigen-binding fragment thereof provided herein contains a $V_L$ CDR1, which comprises the peptide of SEQ ID NO:432; a $V_L$ CDR2, which comprises the peptide of SEQ ID NO:433; and a $V_L$ CDR3, which comprises the peptide of SEQ ID NO:434.

In some examples, an isolated antibody or antigen-binding fragment thereof provided herein contains a heavy chain, which comprises the peptide of SEQ ID NO:452. In some examples, an isolated antibody or antigen-binding fragment provided herein contains a $V_H$ domain, which comprises the peptide of amino acids 1-124 of SEQ ID NO:452. In some examples, an isolated antibody or antigen-binding fragment thereof provided herein contains a light chain, which comprises the peptide of SEQ ID NO:453. In some examples, an isolated antibody or antigen-binding fragment provided herein contains a $V_L$ domain, which comprises the peptide of amino acids 1-111 of SEQ ID NO:453. In a particular example, the isolated antibody or antigen-binding fragment thereof is 56E11.

Provided herein are isolated anti-RSV antibodies or antigen-binding fragments thereof that contain a variable heavy ($V_H$) chain and a variable light ($V_L$) chain, where the antibody or antigen-binding fragment immunospecifically binds to the same epitope on a RSV fusion (F) protein as an antibody or antigen-binding fragment that contains a heavy chain set forth in SEQ ID NO:452 and a light chain set forth in SEQ ID NO:453.

In some examples, an isolated antibody or antigen-binding fragment thereof provided herein contains a $V_H$ CDR1, which comprises the peptide of SEQ ID NO:458 or 482; a $V_H$ CDR2, which comprises the peptide of SEQ ID NO:459; and a $V_H$ CDR3, which comprises the peptide of SEQ ID NO:460.

In some examples, an isolated antibody or antigen-binding fragment thereof provided herein contains a $V_L$ CDR1, which comprises the peptide of SEQ ID NO:461; a $V_L$ CDR2, which comprises the peptide of SEQ ID NO:462; and a $V_L$ CDR3, which comprises the peptide of SEQ ID NO:463.

In some examples, an isolated antibody or antigen-binding fragment thereof provided herein contains a heavy chain, which comprises the peptide of SEQ ID NO:454. In some examples, an isolated antibody or antigen-binding fragment provided herein contains a $V_H$ domain, which comprises the peptide of amino acids 1-133 of SEQ ID NO:454. In some examples, an isolated antibody or antigen-binding fragment thereof provided herein contains a light chain, which comprises the peptide of SEQ ID NO:455. In some examples, an isolated antibody or antigen-binding fragment provided herein contains a $V_L$ domain, which comprises the peptide of amino acids 1-107 of SEQ ID NO:455. In a particular example, the isolated antibody or antigen-binding fragment thereof is 17C9.

Provided herein are isolated anti-RSV antibodies or antigen-binding fragments thereof that contain a variable heavy ($V_H$) chain and a variable light ($V_L$) chain, where the antibody or antigen-binding fragment immunospecifically binds to the same epitope on a RSV fusion (F) protein as an antibody or antigen-binding fragment that contains a heavy chain set forth in SEQ ID NO:454 and a light chain set forth in SEQ ID NO:455.

In some examples, an isolated antibody or antigen-binding fragment thereof provided herein contains a $V_H$ CDR1, which comprises the peptide of SEQ ID NO:464 or 483; a $V_H$ CDR2, which comprises the peptide of SEQ ID NO:465; and a $V_H$ CDR3, which comprises the peptide of SEQ ID NO:466.

In some examples, an isolated antibody or antigen-binding fragment thereof provided herein contains a $V_L$ CDR1, which comprises the peptide of SEQ ID NO:467; a $V_L$ CDR2, which comprises the peptide of SEQ ID NO:468; and a $V_L$ CDR3, which comprises the peptide of SEQ ID NO:469.

In some examples, an isolated antibody or antigen-binding fragment thereof provided herein contains a heavy chain, which comprises the peptide of SEQ ID NO:456. In some examples, an isolated antibody or antigen-binding fragment provided herein contains a $V_H$ domain, which comprises the peptide of amino acids 1-118 of SEQ ID NO:456. In some examples, an isolated antibody or antigen-binding fragment thereof provided herein contains a light chain, which comprises the peptide of SEQ ID NO:457. In some examples, an isolated antibody or antigen-binding fragment provided herein contains a $V_L$ domain, which comprises the peptide of amino acids 1-109 of SEQ ID NO:457. In a particular example, the isolated antibody or antigen-binding fragment thereof is 69F6.

Provided herein are isolated anti-RSV antibodies or antigen-binding fragments thereof that contain a variable heavy ($V_H$) chain and a variable light ($V_L$) chain, where the antibody or antigen-binding fragment immunospecifically binds to the same epitope on a RSV fusion (F) protein as an antibody or antigen-binding fragment that contains a heavy chain set forth in SEQ ID NO:456 and a light chain set forth in SEQ ID NO:457.

In some examples, an isolated antibody or antigen-binding fragment thereof provided herein contains a $V_H$ CDR1, which comprises the peptide of SEQ ID NO:470 or 484; a $V_H$ CDR2, which comprises the peptide of SEQ ID NO:471; and a $V_H$ CDR3, which comprises the peptide of SEQ ID NO:472.

In some examples, an isolated antibody or antigen-binding fragment thereof provided herein contains a $V_L$ CDR1, which comprises the peptide of SEQ ID NO:473; a $V_L$ CDR2, which comprises the peptide of SEQ ID NO:474; and a $V_L$ CDR3, which comprises the peptide of SEQ ID NO:475.

Provided herein are isolated anti-RSV antibodies or antigen-binding fragments thereof that contain a variable heavy ($V_H$) chain and a variable light ($V_L$) chain, where the antibody or antigen-binding fragment immunospecifically binds to the same epitope on a RSV fusion (F) protein as an antibody or antigen-binding fragment thereof that contains a heavy chain set forth in SEQ ID NOS:396, 398, 400, 402, 404, 452, 454 or 456 and a light chain set forth in SEQ ID NOS:395, 397, 399, 401, 403, 453, 455 or 457.

In some examples, an isolated antibody or antigen-binding fragment provided herein contains a $V_H$ complementary determining region 1 (CDR1), which comprises the peptide of SEQ ID NOS:405, 411, 417, 423, 429, 437-441, 458, 464, 470 or 482-484. In some examples, an isolated antibody or antigen-binding fragment provided herein contains a $V_H$ CDR2, which comprises the peptide of SEQ ID NOS:406, 412, 418, 424, 430, 459, 465 or 471. In some examples, an isolated antibody or antigen-binding fragment provided herein contains a $V_H$ CDR3, which comprises the peptide of SEQ ID NOS:407, 413, 419, 425, 431, 460, 466 or 472. In some examples, an isolated antibody or antigen-binding fragment provided herein contains a $V_L$ CDR1, which comprises the peptide of SEQ ID NOS:408, 414, 420, 426, 432, 461, 467 or 473. In some examples, an isolated antibody or antigen-binding fragment provided herein contains a $V_L$ CDR2, which comprises the peptide of SEQ ID NOS:409, 415, 421, 427, 433, 462, 468 or 474. In some examples, an isolated antibody or antigen-binding fragment provided herein contains a $V_L$ CDR3, which comprises the peptide of SEQ ID NO:410, 416, 422, 428, 434, 463, 469 or 475.

In some examples, an isolated antibody or antigen-binding fragment thereof provided herein contains a $V_H$ CDR1, wherein the amino acid sequence of the $V_H$ CDR1 is set forth in SEQ ID NOS:405, 411, 417, 423, 429, 437-441, 458, 464, 470 or 482-484; a $V_H$ CDR2, wherein the amino acid sequence of the $V_H$ CDR2 is set forth in SEQ ID NOS:406, 412, 418, 424, 430, 459, 465 or 471; and a $V_H$ CDR3, wherein the amino acid sequence of the $V_H$ CDR3 is set forth in SEQ ID NOS:407, 413, 419, 425, 431, 460, 466 or 472. In some examples, an isolated antibody or antigen-binding fragment thereof provided herein contains a $V_L$ CDR1, wherein the amino acid sequence of the $V_L$ CDR1 is set forth in SEQ ID NOS:408, 414, 420, 426, 432, 461, 467 or 473; a $V_L$ CDR2, wherein the amino acid sequence of the $V_L$ CDR2 is set forth in SEQ ID NOS:409, 415, 421, 427, 433, 462, 468 or 474; and a $V_L$ CDR3, wherein the amino acid sequence of the $V_L$ CDR3 is set forth in SEQ ID NOS:410, 416, 422, 428, 434, 463, 469 or 475.

Provided herein are isolated polypeptides, antibodies or antigen-binding fragments thereof that immunospecifically bind to a portion of a RSV F protein, which has the amino sequence set forth in SEQ ID NO:25.

Provided herein are isolated polypeptides, antibodies or antigen-binding fragments thereof that contain an antigen-binding domain that is a human or a humanized antibody or antigen-binding fragment thereof. In some examples, the isolated polypeptide, antibody or antigen-binding fragment provided herein is a chimeric antibody. In some examples, the isolated polypeptide, antibody or antigen-binding fragment is a single-chain Fv (scFv), Fab, Fab', F(ab')$_2$, Fv, dsFv, diabody, Fd, or Fd' fragment. In some examples, the isolated polypeptide, antibody or antigen-binding fragment provided herein contains a peptide linker. In some examples, the peptide linker contains about 1 to about 50 amino acids.

In some examples, the isolated polypeptide, antibody or antigen-binding fragment thereof provided herein is conjugated to polyethylene glycol (PEG). In some examples, the isolated polypeptide, antibody or antigen-binding fragment provided herein contains a therapeutic or diagnostic agent. Exemplary diagnostic agents include, but are not limited to, an enzyme, a fluorescent compound, an electron transfer agent, and a radiolabel.

Provided herein are isolated polypeptides, antibodies or antigen-binding fragments thereof that contain a protein transduction domain. In some examples, the protein transduction domain is selected from among a peptide having an amino acid sequence set forth in SEQ ID NOS:284-355. In some examples, the protein transduction domain is a HIV-TAT protein transduction domain.

Provided herein are multivalent antibodies, containing a first antigen-binding portion containing a polypeptide, antibody or antigen-binding fragment thereof provided herein conjugated to a multimerization domain; and a second antigen-binding portion containing an antigen-binding fragment of an antiviral antibody conjugated to a second multimerization domain. In such examples, the first multimerization domain and the second multimerization domain are complementary or the same, whereby the first antigen-binding portion and second antigen-binding portion form a multivalent antibody. In some examples, the multivalent antibodies provided herein contain 1, 2, 3, 4, or 5 additional antigen-binding portions. Exemplary multivalent antibodies include a bivalent, trivalent, tetravalent, pentavalent, hexavalent, or heptavalent antibodies. The multivalent antibodies provided herein include heterobivalent or homobivalent antibodies. The multivalent antibodies provided herein include multispecific antibodies. In some examples, the multispecific antibody is a bispecific, trispecific or tetraspecific antibody. In some examples, the multivalent antibodies provided herein contain an antigen-binding fragment that is a single-chain Fv (scFv), Fab, Fab', F(ab')$_2$, Fv, dsFv, diabody, Fd, or Fd' fragment. The first antigen-binding portion and/or second antigen-binding portion of the multivalent antibodies provided herein can be conjugated to a multimerization domain by covalent or non-covalent linkage. In some examples, the antigen-binding portion is conjugated to the multimerization domain via a linker, such as a chemical linker or a polypeptide linker. In some examples, the multimerization domain of the multivalent antibody provided herein is selected from among an immunoglobulin constant region (Fc), a leucine zipper, complementary hydrophobic regions, complementary hydrophilic regions, or compatible protein-protein interaction domains. In some examples, the Fc domain is an IgG, IgM or an IgE Fc domain.

In some examples, the multivalent antibodies provided herein contain two or more anti-RSV antibodies or antigen-binding fragments thereof. In a particular example, the multivalent antibodies provided herein contain two or more anti-RSV antibodies or antigen-binding fragments thereof.

Provided herein are multivalent antibodies, containing a first antigen-binding portion containing an anti-RSV antibody or antigen-binding fragment thereof provided herein conjugated to a multimerization domain; and a second antigen-binding portion containing an anti-RSV antibody or antigen-binding fragment thereof, selected from among palivizumab, motavizumab, AFFF, P12f2, P12f4, P11d4, A1e9, A12a6, A13c4, A17d4, A4B4, A8c7, 1X-493L1, FR H3-3F4, M3H9, Y10H6, DG, AFFF(1), 6H8, L1-7E5, L2-15B10, A13a11, A1h5, A4B4(1), A4B4L1FR-S28R, A4B4-F52S, rsv6, rsv11, rsv13, rsv19, rsv21, rsv22, rsv23, RF-1, RF-2 or an antigen-binding fragment thereof, conjugated to a second multimerization domain.

Provided herein are multivalent antibodies, containing a first antigen-binding portion containing an anti-RSV antibody or antigen-binding fragment thereof provided herein conjugated to a multimerization domain; and a second antigen-binding portion containing an antiviral antibody that immunospecifically binds an antigen of parainfluenza virus (PIV) or human metapneumovirus (hMPV), conjugated to a second multimerization domain.

Provided herein are combinations, which contain an isolated polypeptide, antibody or antigen-binding fragment thereof provided herein or a multivalent antibody provided herein, and an antiviral agent. In some examples, the antiviral agent is ribavirin. Provided herein are combinations, which contain an isolated polypeptide, antibody or antigen-binding fragment thereof provided herein and an antiviral agent formulated as a single composition or as separate compositions.

Provided herein are combinations, which contain an isolated polypeptide, antibody or antigen-binding fragment thereof provided herein or a multivalent antibody provided herein, and one or more additional antiviral antibodies. In some examples, the combination contains two or more different anti-RSV antibodies or antigen-binding fragments thereof. In some examples, the combination contains two or more different anti-RSV antibodies or antigen-binding fragments selected from among an antibody or antigen-binding fragment provided herein. In some examples, the combination contains an antibody or antigen-binding fragment thereof provided herein and an antibody selected from among palivizumab, motavizumab, AFFF, P12f2, P12f4, P11d4, A1e9, A12a6, A13c4, A17d4, A4B4, A8c7, 1X-493L1, FR H3-3F4, M3H9, Y10H6, DG, AFFF(1), 6H8, L1-7E5, L2-15B10, A13a11, A1h5, A4B4(1), A4B4L1FR-S28R, A4B4-F52S, rsv6, rsv11, rsv13, rsv19, rsv21, rsv22, rsv23, RF-1, RF-2 or antigen-binding fragments thereof. In some examples, the combination contains an antibody or antigen-binding fragment thereof provided herein and an antibody selected from among an antibody or antigen-binding fragment thereof that immunospecifically binds an antigen of parainfluenza virus (PIV) or human metapneumovirus (hMPV). In some examples, the PIV antigen is an antigen of human PIV type 1, human PIV type 2, human PIV type 3, and/or human PIV type 4. In some examples, the PIV antigen is selected from among a PIV nucleocapsid phosphoprotein, a PIV fusion (F) protein, a PIV phosphoprotein, a PIV large (L) protein, a PIV matrix (M) protein, a PIV hemagglutinin-neuraminidase (HN) glycoprotein, a PIV RNA-dependent RNA polymerase, a PIV Y1 protein, a PIV D protein, a PIV C protein, and allelic variants thereof. In some examples, the hMPV antigen is an antigen of hMPV type A or hMPV type B. In some examples, the hMPV antigen is an antigen of hMPV subtype A1, hMPV subtype A2, hMPV subtype B1, or hMPV subtype B2. In some examples, the hMPV antigen is selected from among a hMPV nucleoprotein, a hMPV phosphoprotein, a hMPV matrix protein, a hMPV small hydrophobic protein, a hMPV RNA-dependent RNA polymerase, a hMPV F protein, a hMPV G protein, and allelic variants thereof.

Provided herein are combinations, which contain an isolated polypeptide, antibody or antigen-binding fragment thereof provided herein or a multivalent antibody provided herein, and one or more additional antiviral antibodies, where the one or more additional antiviral antibodies is a single-chain Fv (scFv), Fab, Fab', F(ab')$_2$, Fv, dsFv, diabody, Fd, or Fd' fragment.

Provided herein are pharmaceutical compositions containing any isolated polypeptide, antibody or antigen-binding fragment thereof provided herein, any multivalent antibody provided herein, or any combination provided herein and a pharmaceutically acceptable carrier or excipient. In some examples, the pharmaceutical compositions provided herein are formulated as a gel, ointment, liquid, suspension, aerosol, tablet, pill, powder, or nasal spray. In some examples, the pharmaceutical compositions provided herein are formulated for pulmonary, intranasal, or parenteral administration. In some examples, the pharmaceutical compositions provided herein are formulated for single dosage administration. In some examples, the pharmaceutical compositions provided herein are formulated for sustained release.

Provided herein are pharmaceutical compositions, which contain an isolated polypeptide, antibody or antigen-binding fragment thereof provided herein or a multivalent antibody provided herein, and one or more additional antiviral antibodies. In some examples, the pharmaceutical compositions contain two or more different anti-RSV antibodies or antigen-binding fragments thereof. In some examples, the pharmaceutical compositions contain two or more different anti-RSV antibodies or antigen-binding fragments selected from among an antibody or antigen-binding fragment provided herein. In some examples, the pharmaceutical compositions contain an antibody or antigen-binding fragment provided herein and an antibody selected from among palivizumab, motavizumab, AFFF, P12f2, P12f4, P11d4, A1e9, A12a6, A13c4, A17d4, A4B4, A8c7, 1X-493L1, FR H3-3F4, M3H9, Y10H6, DG, AFFF(1), 6H8, L1-7E5, L2-15B10, A13a11, A1h5, A4B4(1), A4B4L1FR-S28R, A4B4-F52S, rsv6, rsv11, rsv13, rsv19, rsv21, rsv22, rsv23, RF-1, RF-2 or antigen-binding fragments thereof. In some examples, the pharmaceutical compositions contain an antibody or antigen-binding fragment thereof provided herein and an antibody selected from among an antibody or antigen-binding fragment thereof that immunospecifically binds an antigen of parainfluenza virus (PIV) or human metapneumovirus (hMPV). In some examples, the PIV antigen is an antigen of human PIV type 1, human PIV type 2, human PIV type 3, and/or human PIV type 4. In some examples, the Ply antigen is selected from among a P1V nucleocapsid phosphoprotein, a PIV fusion (F) protein, a PIV phosphoprotein, a PIV large (L) protein, a PIV matrix (M) protein, a PIV hemagglutinin-neuraminidase (HN) glycoprotein, a PIV RNA-dependent RNA polymerase, a PIV Y1 protein, a PIV D protein, a PIV C protein, and allelic variants thereof. In some examples, the hMPV antigen is an antigen of hMPV type A or hMPV type B. In some examples, the hMPV antigen is an antigen of hMPV subtype A1, hMPV subtype A2, hMPV subtype B1, or hMPV subtype B2. In some examples, the hMPV antigen is selected from among a hMPV nucleoprotein, a hMPV phosphoprotein, a hMPV matrix protein, a hMPV small hydrophobic protein, a hMPV RNA-dependent RNA polymerase, a hMPV F protein, a hMPV G protein, and allelic variants thereof.

Provided herein are pharmaceutical compositions, which contain an isolated polypeptide, antibody or antigen-binding fragment provided herein or a multivalent antibody provided herein, and one or more additional antiviral antibodies, where the one or more additional antiviral antibodies is a single-chain Fv (scFv), Fab, Fab'. F(ab')$_2$, Fv, dsFv, diabody, Fd, or Fd' fragment.

Provided herein are pharmaceutical compositions, which contain an isolated polypeptide, antibody or antigen-binding fragment thereof provided herein or a multivalent antibody provided herein, and an antiviral agent. In some examples, the antiviral agent is ribavirin.

Provided herein are methods of treating a viral infection in a subject, which involve administering to the subject a therapeutically effective amount of a pharmaceutical composition provided herein. Provided herein are methods of treating or inhibiting one or more symptoms of a viral infection in a subject, which involve administering to the subject a therapeutically effective amount of a pharmaceutical composition provided herein. Also provided herein are methods of preventing a viral infection in a subject, which involve administering to the subject a therapeutically effective amount of a pharmaceutical composition provided herein. In a particular example, the viral infection is a RSV infection. In a particular example, the RSV infection is an upper respiratory tract infection.

Administration can be effected by any suitable route, including but not limited to, topically, parenterally, locally, or systemically, such as for example intranasally, intramuscularly, intradermally, intraperitoneally, intravenously, subcutaneously, orally, or by pulmonary administration. In some examples, a pharmaceutical composition provided herein is administered by a nebulizer or an inhaler. The pharmaceutical compositions provided herein can be administered to any suitable subject, such as a mammal, for example, a human.

In some examples, a pharmaceutical composition provided herein is administered a human infant, a human infant born prematurely or at risk of hospitalization for a RSV infection, an elderly human, a human subject which has cystic fibrosis, bronchopulmonary dysplasia, congenital heart disease, congenital immunodeficiency, acquired immunodeficiency, leukemia, or non-Hodgkin lymphoma or a human subject who has had a transplant, such as, for example, a bone marrow transplant or a liver transplant.

In some examples, a pharmaceutical composition provided herein is administered one time, two times, three times, four times or five times during RSV season (e.g., October through May). In some examples, a pharmaceutical composition provided herein is administered one time, two times, three times, four times or five times within one month, two months or three months, prior to a RSV season.

In some examples, a pharmaceutical composition provided herein can be administered with one or more antiviral agents. In some examples, the antiviral agent is ribavirin. In some examples, the pharmaceutical composition and the antiviral agent are formulated as a single composition or as separate compositions. In the methods provided herein, the pharmaceutical composition and the antiviral agent can be administered sequentially, simultaneously or intermittently.

In some examples, a pharmaceutical composition provided herein can be administered with a hormonal therapy, immunotherapy or an anti-inflammatory agent. In some examples, a pharmaceutical composition provided herein can be administered with one or more additional antiviral antibodies or antigen-binding fragments thereof. The pharmaceutical composition and the one or more additional antiviral antibodies are formulated as a single composition or as separate compositions. The pharmaceutical composition and the one or more additional anti-RSV antibodies can be administered sequentially, simultaneously or intermittently. In some examples, the antigen-binding fragment is a single-chain Fv (scFv), Fab, Fab', F(ab')$_2$, Fv, dsFv, diabody, Fd, or Fd' fragment.

In some examples, a pharmaceutical composition provided herein can be administered with one or more additional antiviral antibodies selected from among anti-RSV antibodies or antigen-binding fragments thereof such as, for example, palivizumab, motavizumab, AFFF, P12 f2, P12f4, P11d4, A1e9, A12a6, A13c4, A17d4, A4B4, A8c7, 1X-493L1, FR H3-3F4, M3H9, Y10H6, DG, AFFF(1), 6H8, L1-7E5, L2-15B10, A13a11. A1h5, A4B4(l). A4B4L1FR-S28R, A4B4-F52S, rsv6, rsv11, rsv13, rsv19, rsv21, rsv22, rsv23, RF-1, RF-2 or antigen-binding fragments thereof.

In some examples, a pharmaceutical composition provided herein can be administered with one or more additional antiviral antibodies selected from among an antibody or antigen-binding fragment thereof that immunospecifically binds an antigen of parainfluenza virus (PIV) or human metapneumovirus (hMPV). In some examples, the PIV antigen is an antigen of human PIV type 1, human PIV type 2, human PIV type 3, and/or human PIV type 4. In some examples, the PIV antigen is selected from among a PIV nucleocapsid phosphoprotein, a PIV fusion (F) protein, a PIV phosphoprotein, a PIV large (L) protein, a PIV matrix (M) protein, a PIV hemagglutinin-neuraminidase (HN) glycoprotein, a PIV RNA-dependent RNA polymerase, a PIV Y1 protein, a PIV D protein, a PIV C protein, and allelic variants thereof. In some examples, the hMPV antigen is an antigen of hMPV type A or hMPV type B. In some examples, the hMPV antigen is an antigen of hMPV subtype A1, hMPV subtype A2, hMPV subtype B1, or hMPV subtype B2. In some examples, the hMPV antigen is selected from among a hMPV nucleoprotein, a hMPV phosphoprotein, a hMPV matrix protein, a hMPV small hydrophobic protein, a hMPV RNA-dependent RNA polymerase, a hMPV F protein, a hMPV G protein, and allelic variants thereof.

Provided herein are methods of detecting RSV infection, which involve (a) assaying the level of RSV antigen in a fluid, cell, or tissue sample using an antibody or antigen-binding fragments thereof provided herein; (b) comparing the assayed level of RSV antigen with a control level whereby an increase in the assayed level of RSV antigen compared to the control level of the RSV antigen is indicative of a RSV infection. In some examples, the cell or tissue sample is obtained from a human subject. In some examples, the cell or tissue sample is a blood, urine, saliva, lung sputum, lavage, or lymph sample.

Provided herein are isolated nucleic acids that encode the polypeptide, antibody or antigen-binding fragments thereof provided herein. Provided herein are vectors that contain a nucleic acid encoding the polypeptide, antibody or antigen-binding fragments thereof provided herein.

Provided herein are isolated cells that contain an antibody or antigen-binding fragment thereof provided herein, a nucleic acid provided herein, or a vector provided herein. The cells provided herein can be, for example, prokaryotic or eukaryotic cells. Also provided herein are transgenic animals that contain a nucleic acid provided herein or a vector provided herein. Also provided herein are methods of expressing an isolated antibody or antigen-binding fragment thereof, which involve culturing isolated cells provided herein under conditions which express the encoded antibody or by isolation of the antibody or antigen-binding fragment from the transgenic animal provided herein. In some examples, the antibody or antigen-binding fragment is isolated from the serum or milk of the transgenic animal.

Provided herein are kits containing a polypeptide, antibody or antigen-binding fragment of provided herein, a multivalent antibody provided herein, or a combination provided herein, in one or more containers, and instructions for use.

Also provided herein are uses of an antibody or antigen-binding fragment thereof provided herein for the prevention of viral infection in a subject. Also provided herein are uses of an antibody or antigen-binding fragment thereof provided herein for treatment of viral infection in a subject. Also provided herein are uses of an antibody or antigen-binding fragment thereof provided herein for treating or inhibiting one or more symptoms of a viral infection in a subject.

Also provided herein are uses of an antibody or antigen-binding fragment provided herein for the formulation of a medicament for the prevention of viral infection in a subject. Also provided herein are uses of an antibody or antigen-binding fragment provided herein for the formulation of a medicament for treatment of viral infection in a subject. Also provided herein are uses of an antibody or antigen-binding fragment provided herein for the formulation of a medicament for treating or inhibiting one or more symptoms of a viral infection in a subject.

Provided herein are anti-RSV neutralizing antibodies or antigen-binding fragments thereof, wherein RSV does not produce a virus that escapes neutralization by the antibodies or antigen-binding fragments thereof after more than 10, 11, 12, 13, 14, 15, 16, 17, 18, 19, 20 or more rounds of viral replication in the presence of the antibody or antigen-binding fragment thereof. Also provided herein are anti-RSV neutralizing antibodies or antigen-binding fragments thereof, wherein RSV does not produce a virus that escapes neutralization by the antibodies or antigen-binding fragments thereof after up to 20 rounds of viral replication in the presence of the antibodies or antigen-binding fragments thereof. In some examples, the anti-RSV antibody or antigen-binding fragment thereof specifically binds to the same epitope as the antibody designated 30D8. In other examples, the anti-RSV antibody or antigen-binding fragment thereof is designated 30D8. In some examples, the anti-RSV antibody or antigen-binding fragment specifically binds to RSV F protein. In other examples, the anti-RSV antibody or antigen-binding fragment is a Fab or scFv.

BRIEF DESCRIPTION OF THE DRAWINGS

As shown in FIG. 2, residues important for binding of antibody 58C5 are clustered only in the prefusion model. In the postfusion model, the residues are distributed over a large area of the protein surface.

DETAILED DESCRIPTION

Figure 1:
FIG. 1 is a 3D model of the RSV F protein in its prefusion conformation. Amino acid residues identified in Example 12 as being important for binding of antibody 58C5 are indicated in black, space filling models. When the residues are displayed on the 3D model of prefusion RSV F protein, they cluster on a restricted area of the spike and illustrate the antibody footprint of antibody 58C5.

Outline
A. DEFINITIONS
B. OVERVIEW
  1. Respiratory Syncytial Virus
C. ANTI-RSV ANTIBODIES
  1. General Antibody Structure and Functional Domains
  a. Structural and Functional Domains of Antibodies
  b. Antibody Fragments
  2. Exemplary Anti-RSV Antibodies
  a. Derivative Antibodies
    i. Single Chain Antibodies
    ii. Anti-idiotypic Antibodies
    iii. Multi-specific Antibodies and Antibody Multimerization
D. ADDITIONAL MODIFICATIONS OF ANTI-RSV ANTIBODIES
  1. Modifications to reduce immunogenicity
  2. Fc Modifications
  3. Pegylation
  4. Conjugation of a Detectable Moiety
  5. Conjugation of a Therapeutic Moiety
  6. Modifications to improve binding specificity
E. METHODS OF ISOLATING ANTI-RSV ANTIBODIES
F. METHODS OF PRODUCING ANTI-RSV ANTIBODIES, AND MODIFIED OR VARIANT FORMS THEREOF AND NUCLEIC ACIDS ENCODING ANTIBODIES
  1. Nucleic Acids
  2. Vectors
  3. Cell Expression Systems
  a. Prokaryotic Expression
  b. Yeast Cells
  c. Insect Cells
  d. Mammalian Cells
  e. Plants
  4. Purification of Antibodies
G. ASSESSING ANTI-RSV ANTIBODY PROPERTIES AND ACTIVITIES
  1. Binding Assays
  2. Binding specificity
  3. In vitro assays for analyzing virus neutralization effects of antibodies
  4. In vivo animal models for assessing efficacy of the anti-RSV antibodies
  5. In vitro and in vivo Assays for Measuring Antibody Efficacy
H. DIAGNOSTIC USES
  1. In vitro detection of pathogenic infection
  2. In vivo detection of pathogenic infection
  3. Monitoring Infection
I. PROPHYLACTIC AND THERAPEUTIC USES
  1. Subjects for therapy
  2. Dosages
  3. Routes of Administration
  4. Combination therapies
  a. Antiviral Antibodies for Combination Therapy
    i. Anti-RSV antibodies
    ii. Antibodies against other respiratory viruses
  5. Gene Therapy
J. Pharmaceutical Compositions, Combinations and Articles of manufacture/Kits
  1. Pharmaceutical Compositions
  2. Articles of Manufacture/Kits
  3. Combinations
K. Examples
  Example 1: Expression of RSV F protein
  Example 2: Isolation of Anti-RSV Fab Antibodies from EBV-transformed B Cells
  Example 3: Isolation of Anti-RSV Fab Antibodies by Single Cell Sorting
  Example 4: Antibody Binding to RSV F protein
  Example 5: Expression and Purification of Isolated Fabs
  Example 6: RSV Neutralization Assay
  Example 7: Cloning and Expression of IgG
  Example 8: IgG Binding Assays
  Example 9: IgG RSV Neutralization Assays
  Example 10: Competition Assays
  Example 11: RSV MARM Generation and Neutralization Assays
  Example 12: Mapping of the 58C5 and 30D8 Binding Epitopes

A. DEFINITIONS

Unless defined otherwise, all technical and scientific terms used herein have the same meaning as is commonly understood by one of skill in the art to which the invention(s) belong. All patents, patent applications, published applications and publications, GenBank sequences, databases, websites and other published materials referred to throughout the entire disclosure herein, unless noted otherwise, are incorporated by reference in their entirety. In the event that there are a plurality of definitions for terms herein, those in this section prevail. Where reference is made to a URL or other such identifier or address, it understood that such identifiers can change and particular information on the internet can come and go, but equivalent information can be found by searching the internet. Reference thereto evidences the availability and public dissemination of such information.

As used herein, "antibody" refers to immunoglobulins and immunoglobulin fragments, whether natural or partially or wholly synthetically, such as recombinantly, produced, including any fragment thereof containing at least a portion of the variable region of the immunoglobulin molecule that retains the binding specificity ability of the full-length immunoglobulin. Hence, an antibody includes any protein having a binding domain that is homologous or substantially homologous to an immunoglobulin antigen-binding domain (antibody combining site). Antibodies include antibody fragments, such as anti-RSV antibody fragments. As used herein, the term antibody, thus, includes synthetic antibodies, recombinantly produced antibodies, multispecific antibodies (e.g., bispecific antibodies), human antibodies, non-human antibodies, humanized antibodies, chimeric antibodies, intrabodies, and antibody fragments, such as, but not limited to, Fab fragments, Fab' fragments, F(ab')$_2$ fragments, Fv fragments, disulfide-linked Fvs (dsFv), Fd fragments, Fd' fragments, single-chain Fvs (scFv), single-chain Fabs (scFab), diabodies, anti-idiotypic (anti-Id) antibodies, or antigen-binding fragments of any of the above. Antibodies provided herein include members of any immunoglobulin type (e.g., IgG, IgM, IgD, IgE, IgA and IgY), any class (e.g. IgG1, IgG2, IgG3, IgG4, IgA1 and IgA2) or subclass (e.g., IgG2a and IgG2b).

As used herein, an "antibody fragment" or "antigen-binding fragment" of an antibody refers to any portion of a full-length antibody that is less than full length but contains at least a portion of the variable region of the antibody that binds antigen (e.g. one or more CDRs and/or one or more antibody combining sites) and thus retains the binding specificity, and at least a portion of the specific binding ability of the full-length antibody. Hence, an antigen-binding fragment refers to an antibody fragment that contains an antigen-binding portion that binds to the same antigen as the antibody from which the antibody fragment is derived. Antibody fragments include antibody derivatives produced by enzymatic treatment of full-length antibodies, as well as synthetically, e.g. recombinantly produced derivatives. An antibody fragment is included among antibodies. Examples of antibody fragments include, but are not limited to, Fab, Fab', F(ab')$_2$, single-chain Fv (scFv), Fv, dsFv, diabody, Fd and Fd' fragments and other fragments, including modified fragments (see, for example, Methods in Molecular Biology, Vol 207: Recombinant Antibodies for Cancer Therapy Methods and Protocols (2003); Chapter 1; p 3-25, Kipriyanov). The fragment can include multiple chains linked together, such as by disulfide bridges and/or by peptide linkers. An antibody fragment generally contains at least or about 50 amino acids and typically at least or about 200 amino acids. An antigen-binding fragment includes any antibody fragment that when inserted into an antibody framework (such as by replacing a corresponding region) results in an antibody that immunospecifically binds (i.e. exhibits Ka of at least or at least about $10^7$-$10^8$ M$^{-1}$) to the antigen.

As used herein, a "therapeutic antibody" refers to any antibody or antigen-binding fragment thereof that is administered for treatment of an animal, including a human. Such antibodies can be prepared by any known methods for the production of polypeptides, and hence, include, but are not limited to, recombinantly produced antibodies, synthetically produced antibodies, and therapeutic antibodies extracted from cells or tissues and other sources. As isolated from any sources or as produced, therapeutic antibodies can be heterogeneous in length or differ in post-translational modification, such as glycosylation (i.e. carbohydrate content). Heterogeneity of therapeutic antibodies also can differ depending on the source of the therapeutic antibodies. Hence, reference to therapeutic antibodies refers to the heterogeneous population as produced or isolated. When a homogeneous preparation is intended, it will be so-stated. References to therapeutic antibodies herein are to their monomeric, dimeric or other multimeric forms, as appropriate.

As used herein, a "neutralizing antibody" is any antibody or antigen-binding fragment thereof that binds to a pathogen and interferes with the ability of the pathogen to infect a cell and/or cause disease in a subject. Exemplary of neutralizing antibodies are neutralizing antibodies that bind to viruses, bacteria, and fungal pathogens. Typically, the neutralizing antibodies provide herein bind to the surface of the pathogen. In examples where the pathogen is a virus, a neutralizing antibody that binds to the virus typically hinds to a protein on the surface of the virus. Depending on the class of the virus, the surface protein can be a capsid protein (e.g. a capsid protein of a non-enveloped virus) or a viral envelope protein (e.g., a viral envelope protein of an enveloped virus). In some examples, the protein is a glycoprotein. The ability of the virus to inhibit virus infectivity can be measure for example, by an in vitro neutralization assay, such as, for example, a plaque reduction assay using Vero host cells.

As used herein, an "enveloped virus" is an animal virus which possesses an outer membrane or envelope, which is a lipid bilayer containing viral proteins, surrounding the virus capsid. The envelope proteins of the virus participate in the assembly of the infectious particle and also are involved in virus entry by binding to receptors present on the host cell and inducing fusion between the viral envelope and a membrane of the host cell. Enveloped viruses can be either spherical or filamentous (rod-shaped). Exemplary enveloped viruses include, but are not limited to, members of the Herpesviridae, Poxviridae, Hepadnaviridae, Togaviridae, Arenaviridae, Flaviviridae, Orthomyxoviridae, Paramyxoviridae, Bunyaviridae, Rhabdoviridae, Filoviridae, Coronaviridae, and Bornaviridae virus families. RSV is a negative sense single stranded RNA enveloped virus of the Paramyxoviridae family, Pneumovirinae subfamily.

As used herein, a "non-enveloped virus" or "naked virus" is a virus that lacks a viral envelope. For infection of a host cell, a non-enveloped virus uses proteins of the viral capsid for attachment to the target cell. Exemplary non-enveloped viruses include, but are not limited to, Adenoviridae, Papillomavirinae, Parvoviridae, Polyomavirinae, Circoviridae, Reoviridae, Picornaviridae, Caliciviridae, and Astroviridae virus families.

As used herein, a "surface protein" of a pathogen is any protein that is located on external surface of the pathogen. The surface protein can be partially or entirely exposed to the external environment (i.e. outer surface). Exemplary of surface proteins are membrane proteins, such as, for example, a protein located on the surface of a viral envelope or bacterial outer membrane (e.g., a membrane glycoprotein). Membrane proteins can be transmembrane proteins (i.e. proteins that traverse the lipid bilayer) or proteins that are non-transmembrane cell surface associated proteins (e.g., anchored or covalently attached to the surface of the membrane, such as attachment to another protein on the surface of the pathogen). Other exemplary surface proteins include viral capsid proteins of non-enveloped enveloped viruses that are at least partially exposed to the external environment.

As used herein, "monoclonal antibody" refers to a population of identical antibodies, meaning that each individual antibody molecule in a population of monoclonal antibodies is identical to the others. This property is in contrast to that of a polyclonal population of antibodies, which contains antibodies having a plurality of different sequences. Monoclonal antibodies can be produced by a number of well-known methods (Smith et al. (2004) *J. Clin. Pathol.* 57, 912-917; and Nelson et al., *J Clin Pathol* (2000), 53, 111-117). For example, monoclonal antibodies can be produced by immortalization of a B cell, for example through fusion with a myeloma cell to generate a hybridoma cell line or by infection of B cells with virus such as EBV. Recombinant technology also can be used to produce antibodies in vitro from clonal populations of host cells by transforming the host cells with plasmids carrying artificial sequences of nucleotides encoding the antibodies.

As used herein, a "conventional antibody" refers to an antibody that contains two heavy chains (which can be denoted H and H') and two light chains (which can be denoted L and L') and two antibody combining sites, where each heavy chain can be a full-length immunoglobulin heavy chain or any functional region thereof that retains antigen-binding capability (e.g. heavy chains include, but are not limited to, $V_H$, chains $V_H$-$C_H1$ chains and $V_H$-$C_H1$-$C_H2$-$C_H3$ chains), and each light chain can be a full-length light chain or any functional region of (e.g. light chains include, but are not limited to, $V_L$ chains and $V_L$-$C_L$ chains). Each heavy chain (H and H') pairs with one light chain (L and L', respectively)

As used herein, a full-length antibody is an antibody having two full-length heavy chains (e.g. $V_H$-$C_H1$-$C_H2$-$C_H3$ or $V_H$-$C_H1$-$C_H2$-$C_H3$-$C_H4$) and two full-length light chains ($V_L$-$C_L$) and hinge regions, such as human antibodies produced naturally by antibody secreting B cells and antibodies with the same domains that are synthetically produced.

As used herein, an Fv antibody fragment is composed of one variable heavy domain ($V_H$) and one variable light ($V_L$) domain linked by noncovalent interactions.

As used herein, a dsFv refers to an Fv with an engineered intermolecular disulfide bond, which stabilizes the $V_H$-$V_L$ pair.

As used herein, an Fd fragment is a fragment of an antibody containing a variable domain ($V_H$) and one constant region domain ($C_H1$) of an antibody heavy chain.

As used herein, a Fab fragment is an antibody fragment that results from digestion of a full-length immunoglobulin with papain, or a fragment having the same structure that is produced synthetically, e.g. by recombinant methods. A Fab fragment contains a light chain (containing a $V_L$ and $C_L$) and another chain containing a variable domain of a heavy chain ($V_H$) and one constant region domain of the heavy chain ($C_H1$).

As used herein, a F(ab')$_2$ fragment is an antibody fragment that results from digestion of an immunoglobulin with pepsin at pH 4.0-4.5, or a fragment having the same structure that is produced synthetically, e.g. by recombinant methods. The F(ab')$_2$ fragment essentially contains two Fab fragments where each heavy chain portion contains an additional few amino acids, including cysteine residues that form disulfide linkages joining the two fragments.

As used herein, a Fab' fragment is a fragment containing one half (one heavy chain and one light chain) of the F(ab')$_2$ fragment.

As used herein, an Fd' fragment is a fragment of an antibody containing one heavy chain portion of a F(ab')$_2$ fragment.

As used herein, an Fv' fragment is a fragment containing only the $V_H$ and $V_L$ domains of an antibody molecule.

As used herein, hsFv refers to antibody fragments in which the constant domains normally present in a Fab fragment have been substituted with a heterodimeric coiled-coil domain (see, e.g., Arndt et al. (2001) *J Mol Biol.* 7:312:221-228).

As used herein, an scFv fragment refers to an antibody fragment that contains a variable light chain ($V_L$) and variable heavy chain ($V_H$), covalently connected by a polypeptide linker in any order. The linker is of a length such that the two variable domains are bridged without substantial interference. Exemplary linkers are (Gly-Ser)$_n$ residues with some Glu or Lys residues dispersed throughout to increase solubility.

As used herein, the term "derivative" refers to a polypeptide that contains an amino acid sequence of an anti-RSV antibody or a fragment thereof which has been modified, for example, by the introduction of amino acid residue substitutions, deletions or additions, by the covalent attachment of any type of molecule to the polypeptide (e.g., by glycosylation, acetylation, pegylation, phosphorylation, amidation, derivatization by known protecting/blocking groups, proteolytic cleavage, linkage to a cellular ligand or other protein). A derivative of an anti-RSV antibody or antigen-binding fragment thereof can be modified by chemical modifications using techniques known to those of skill in the art, including, but not limited to, specific chemical cleavage, acetylation, formylation. Further, a derivative of an anti-RSV antibody or antigen-binding fragment thereof can contain one or more non-classical amino acids. Typically, a polypeptide derivative possesses a similar or identical function as an anti-RSV antibody or antigen-binding fragment thereof provided herein (e.g., neutralization of RSV).

As used herein, the phrase "derived from" when referring to antibody fragments derived from another antibody, such as a monoclonal antibody, refers to the engineering of antibody fragments (e.g., Fab, F(ab'), F(ab')$_2$, single-chain Fv (scFv), Fv, dsFv, diabody, Fd and Fd' fragments) that retain the binding specificity of the original antibody. Such fragments can be derived by a variety of methods known in the art, including, but not limited to, enzymatic cleavage, chemical crosslinking, recombinant means or combinations thereof. Generally, the derived antibody fragment shares the identical or substantially identical heavy chain variable region ($V_H$) and light chain variable region ($V_L$) of the parent antibody, such that the antibody fragment and the parent antibody bind the same epitope.

As used herein, a "parent antibody" or "source antibody" refers the to an antibody from which an antibody fragment (e.g., Fab, F(ab'), F(ab')$_2$, single-chain Fv (scFv), Fv, dsFv, diabody, Fd and Fd' fragments) is derived.

As used herein, the term "epitope" refers to any antigenic determinant on an antigen to which the paratope of an antibody binds. Epitopic determinants typically contain chemically active surface groupings of molecules such as amino acids or sugar side chains and typically have specific three dimensional structural characteristics, as well as specific charge characteristics.

As used herein, a chimeric polypeptide refers to a polypeptide that contains portions from at least two different polypeptides or from two non-contiguous portions of a single polypeptide. Thus, a chimeric polypeptide generally includes a sequence of amino acid residues from all or part of one polypeptide and a sequence of amino acids from all or part of another different polypeptide. The two portions can be linked directly or indirectly and can be linked via peptide bonds, other covalent bonds or other non-covalent interactions of sufficient strength to maintain the integrity of a substantial portion of the chimeric polypeptide under equilibrium conditions and physiologic conditions, such as in isotonic pH 7 buffered saline. For purposes herein, chimeric polypeptides include those containing all or part of an anti-RSV antibody linked to another polypeptide, such as, for example, a multimerization domain, a heterologous immunoglobulin constant domain or framework region, or a diagnostic or therapeutic polypeptide.

As used herein, a fusion protein is a polypeptide engineered to contain sequences of amino acids corresponding to two distinct polypeptides, which are joined together, such as by expressing the fusion protein from a vector containing two nucleic acids, encoding the two polypeptides, in close proximity, e.g., adjacent, to one another along the length of the vector. Generally, a fusion protein provided herein refers to a polypeptide that contains a polypeptide having the amino acid sequence of an antibody or antigen-binding fragment thereof and a polypeptide or peptide having the amino acid sequence of a heterologous polypeptide or peptide, such as, for example, a diagnostic or therapeutic polypeptide. Accordingly, a fusion protein refers to a chimeric protein containing two, or portions from two, or more proteins or peptides that are linked directly or indirectly via peptide bonds. The two molecules can be adjacent in the construct or separated by a linker, or spacer polypeptide. The spacer can encode a polypeptide that alters the properties of the polypeptide, such as solubility or intracellular trafficking.

As used herein, "linker" or "spacer" peptide refers to short sequences of amino acids that join two polypeptide sequences (or nucleic acid encoding such an amino acid sequence). "Peptide linker" refers to the short sequence of amino acids joining the two polypeptide sequences. Exemplary of polypeptide linkers are linkers joining a peptide transduction domain to an antibody or linkers joining two antibody chains in a synthetic antibody fragment such as an scFv fragment. Linkers are well-known and any known linkers can be used in the provided methods. Exemplary of polypeptide linkers are $(Gly-Ser)_n$ amino acid sequences, with some Glu or Lys residues dispersed throughout to increase solubility. Other exemplary linkers are described herein; any of these and other known linkers can be used with the provided compositions and methods.

As used herein, "antibody hinge region" or "hinge region" refers to a polypeptide region that exists naturally in the heavy chain of the gamma, delta and alpha antibody isotypes, between the $C_H1$ and $C_H2$ domains that has no homology with the other antibody domains. This region is rich in proline residues and gives the IgG, IgD and IgA antibodies flexibility, allowing the two "arms" (each containing one antibody combining site) of the Fab portion to be mobile, assuming various angles with respect to one another as they bind antigen. This flexibility allows the Fab arms to move in order to align the antibody combining sites to interact with epitopes on cell surfaces or other antigens. Two interchain disulfide bonds within the hinge region stabilize the interaction between the two heavy chains. In some embodiments provided herein, the synthetically produced antibody fragments contain one or more hinge regions, for example, to promote stability via interactions between two antibody chains. Hinge regions are exemplary of dimerization domains.

As used herein, diabodies are dimeric scFv; diabodies typically have shorter peptide linkers than scFvs, and preferentially dimerize.

As used herein, humanized antibodies refer to antibodies that are modified to include "human" sequences of amino acids so that administration to a human does not provoke an immune response. A humanized antibody typically contains complementarily determining regions (CDRs) derived from a non-human species immunoglobulin and the remainder of the antibody molecule derived mainly from a human immunoglobulin. Methods for preparation of such antibodies are known. For example, DNA encoding a monoclonal antibody can be altered by recombinant DNA techniques to encode an antibody in which the amino acid composition of the non-variable regions is based on human antibodies. Methods for identifying such regions are known, including computer programs, which are designed for identifying the variable and non-variable regions of immunoglobulins.

As used herein, idiotype refers to a set of one or more antigenic determinants specific to the variable region of an immunoglobulin molecule.

As used herein, anti-idiotype antibody refers to an antibody directed against the antigen-specific part of the sequence of an antibody or T cell receptor. In principle an anti-idiotype antibody inhibits a specific immune response.

As used herein, an Ig domain is a domain, recognized as such by those in the art, that is distinguished by a structure, called the Immunoglobulin (Ig) fold, which contains two beta-pleated sheets, each containing anti-parallel beta strands of amino acids connected by loops. The two beta sheets in the Ig fold are sandwiched together by hydrophobic interactions and a conserved intra-chain disulfide bond. Individual immunoglobulin domains within an antibody chain further can be distinguished based on function. For example, a light chain contains one variable region domain ($V_L$) and one constant region domain ($C_L$), while a heavy chain contains one variable region domain ($V_H$) and three or four constant region domains ($C_H$). Each $V_L$, $C_L$, $V_H$, and $C_H$ domain is an example of an immunoglobulin domain.

As used herein, a variable domain or variable region is a specific Ig domain of an antibody heavy or light chain that contains a sequence of amino acids that varies among different antibodies. Each light chain and each heavy chain has one variable region domain. $V_L$ and $V_H$, respectively. The variable domains provide antigen specificity, and thus are responsible for antigen recognition. Each variable region contains CDRs that are part of the antigen-binding site domain and framework regions (FRs).

As used herein, "antigen-binding domain," "antigen-binding site," "antigen combining site" and "antibody combining site" are used synonymously to refer to a domain within an antibody that recognizes and physically interacts with cognate antigen. A native conventional full-length antibody molecule has two conventional antigen-binding sites, each containing portions of a heavy chain variable region and portions of a light chain variable region. A conventional antigen-binding site contains the loops that connect the anti-parallel beta strands within the variable region domains. The antigen combining sites can contain other portions of the variable region domains. Each conventional antigen-binding site contains three hypervariable regions from the heavy chain and three hypervariable regions from the light chain. The hypervariable regions also are called complementarity-determining regions (CDRs).

As used herein, "hypervariable region," "HV," "complementarity-determining region" and "CDR" and "antibody CDR" are used interchangeably to refer to one of a plurality of portions within each variable region that together form an antigen-binding site of an antibody. Each variable region domain contains three CDRs, named CDR1, CDR2 and CDR3. The three CDRs are non-contiguous along the linear amino acid sequence, but are proximate in the folded polypeptide. The CDRs are located within the loops that join the parallel strands of the beta sheets of the variable domain. As described herein, one of skill in the art knows and can identify the CDRs based on Kabat or Chothia numbering (see e.g., Kabat, E. A. et al. (1991) *Sequences of Proteins of Immunological Interest*, Fifth Edition, U.S. Department of Health and Human Services, NIH Publication No. 91-3242, and Chothia, C. et al. (1987) *J. Mol. Biol.* 196:901-917).

As used herein, framework regions (FRs) are the domains within the antibody variable region domains that are located within the beta sheets; the FR regions are comparatively more conserved, in terms of their amino acid sequences, than the hypervariable regions.

As used herein, a "constant region" domain is a domain in an antibody heavy or light chain that contains a sequence of amino acids that is comparatively more conserved than that of the variable region domain. In conventional full-length antibody molecules, each light chain has a single light chain constant region ($C_L$) domain and each heavy chain contains one or more heavy chain constant region ($C_H$) domains, which include, $C_H1$, $C_H2$, $C_H3$ and $C_H4$. Full-length IgA, IgD and IgG isotypes contain $C_H1$, $C_H2$, $C_H3$ and a hinge region, while IgE and IgM contain $C_H1$, $C_H2$, $C_H3$ and $C_H4$. $C_H1$ and $C_L$ domains extend the Fab arm of the antibody molecule, thus contributing to the interaction with antigen and rotation of the antibody arms. Antibody constant regions can serve effector functions, such as, but not limited to, clearance of antigens, pathogens and toxins to which the antibody specifically binds, e.g., through interactions with various cells, biomolecules and tissues.

As used herein, a functional region of an antibody is a portion of the antibody that contains at least a $V_H$, $V_L$, $C_H$ (e.g. $C_H1$, $C_H2$ or $C_H3$). $C_L$ or hinge region domain of the antibody, or at least a functional region thereof.

As used herein, a functional region of a $V_H$ domain is at least a portion of the full $V_H$ domain that retains at least a portion of the binding specificity of the full $V_H$ domain (e.g. by retaining one or more CDR of the full $V_H$ domain), such that the functional region of the $V_H$ domain, either alone or in combination with another antibody domain (e.g. $V_L$ domain) or region thereof binds to antigen. Exemplary functional regions of $V_H$ domains are regions containing the CDR1, CDR2 and/or CDR3 of the $V_H$ domain.

As used herein, a functional region of a $V_L$ domain is at least a portion of the full $V_L$ domain that retains at least a portion of the binding specificity of the full $V_L$ domain (e.g. by retaining one or more CDRs of the full $V_L$ domain), such that the function region of the $V_L$ domain, either alone or in combination with another antibody domain (e.g. $V_H$ domain) or region thereof, binds to antigen. Exemplary functional regions of $V_L$ domains are regions containing the CDR1, CDR2 and/or CDR3 of the $V_L$ domain.

As used herein, "specifically bind" or "immunospecifically bind" with respect to an antibody or antigen-binding fragment thereof are used interchangeably herein and refer to the ability of the antibody or antigen-binding fragment to form one or more noncovalent bonds with a cognate antigen, by noncovalent interactions between the antibody combining site(s) of the antibody and the antigen. The antigen can be an isolated antigen or presented in a virus. Typically, an antibody that immunospecifically binds (or that specifically binds) to a virus antigen or virus is one that binds to the virus antigen (or to the antigen in the virus or to the virus) with an affinity constant Ka of about or $1\times10^7$ $M^{-1}$ or $1\times10^8$ $M^{-1}$ or greater (or a dissociation constant ($K_d$) of $1\times10^{-7}$ M or $1\times10^{-8}$ M or less). Affinity constants can be determined by standard kinetic methodology for antibody reactions, for example, immunoassays, surface plasmon resonance (SPR) (Rich and Myszka (2000) *Curr. Opin. Biotechnol* 11:54; Englebienne (1998) *Analyst.* 123:1599), isothermal titration calorimetry (ITC) or other kinetic interaction assays known in the art (see, e.g., Paul, ed., Fundamental Immunology, 2nd ed., Raven Press, New York, pages 332-336 (1989); see also U.S. Pat. No. 7,229,619 for a description of exemplary SPR and ITC methods for calculating the binding affinity of anti-RSV antibodies). Instrumentation and methods for real time detection and monitoring of binding rates are known and are commercially available (e.g., BiaCore 2000, Biacore AB, Upsala, Sweden and GE Healthcare Life Sciences; Malmqvist (2000) *Biochem. Soc. Trans.* 27:335). An antibody that immunospecifically binds to a virus antigen (or virus) can bind to other peptides, polypeptides, or proteins or viruses with equal or lower binding affinity. Typically, an antibody or antigen-binding fragment thereof provided herein that binds immunospecifically to a RSV F protein (or RSV virus) does not cross-react with other antigens or cross reacts with substantially (at least 10-100 fold) lower affinity for such antigens. Antibodies or antigen-binding fragments that immunospecifically bind to a particular virus antigen (e.g. a RSV F protein) can be identified, for example, by immunoassays, such as radioimmunoassays (RIA), enzyme-linked immunosorbent assays (ELISAs), surface plasmon resonance, or other techniques known to those of skill in the art. An antibody or antigen-binding fragment thereof that immunospecifically binds to an epitope on a RSV F protein typically is one that binds to the epitope (presented in the protein or virus) with a higher binding affinity than to any cross-reactive epitope as determined using experimental techniques, such as, but not limited to, immunoassays, surface plasmon resonance, or other techniques known to those of skill in the art. Immunospecific binding to an isolated RSV protein (i.e., a recombinantly produced protein), such as RSV F protein, does not necessarily mean that the antibody will exhibit the same immunospecific binding and/or neutralization of the virus. Such measurements and properties are distinct. The affinity for the antibody or antigen-binding fragments for virus or the antigen as presented in the virus can be determined. For purposes herein, when describing an affinity or related term, the target, such as the isolated protein or the virus, will be identified.

As used herein, the term "surface plasmon resonance" refers to an optical phenomenon that allows for the analysis of real-time interactions by detection of alterations in protein concentrations within a biosensor matrix, for example, using the BiaCore system (GE Healthcare Life Sciences).

As used herein, a "multivalent" antibody is an antibody containing two or more antigen-binding sites. Multivalent antibodies encompass bivalent, trivalent, tetravalent, pentavalent, hexavalent, heptavalent or higher valency antibodies.

As used herein, a "monospecific" is an antibody that contains two or more antigen-binding sites, where each antigen-binding site immunospecifically binds to the same epitope.

As used herein, a "multispecific" antibody is an antibody that contains two or more antigen-binding sites, where at least two of the antigen-binding sites immunospecifically bind to different epitopes.

As used herein, a "bispecific" antibody is a multispecific antibody that contains two or more antigen-binding sites and can immunospecifically bind to two different epitopes. A "trispecific" antibody is a multispecific antibody that contains three or more antigen-binding sites and can immunospecifically bind to three different epitopes, a "tetraspecific" antibody is a multispecific antibody that contains four or more antigen-binding sites and can immunospecifically bind to four different epitopes, and so on.

As used herein, a "heterobivalent" antibody is a bispecific antibody that contains two antigen-binding sites, where each antigen-binding site immunospecifically binds to a different epitope.

As used herein, a "homobivalent" antibody is a monospecific antibody that contains two antigen-binding sites, where each antigen-binding site immunospecifically binds to the same epitope. Homobivalent antibodies include, but are not limited to, conventional full length antibodies, engineered or synthetic full-length antibodies, any multimer of two identical antigen-binding fragments, or any multimer two antigen-binding fragments containing the same antigen-binding domain.

As used herein, a multimerization domain refers to a sequence of amino acids that promotes stable interaction of a polypeptide molecule with one or more additional polypeptide molecules, each containing a complementary multimerization domain, which can be the same or a different multimerization domain to form a stable multimer with the first domain. Generally, a polypeptide is joined directly or indirectly to the multimerization domain. Exemplary multimerization domains include the immunoglobulin sequences or portions thereof leucine zippers, hydrophobic regions, hydrophilic regions, and compatible protein-protein interaction domains. The multimerization domain, for example, can be an immunoglobulin constant region or domain, such as, for example, the Fc domain or portions thereof from IgG, including IgG1, IgG2, IgG3 or IgG4 subtypes, IgA, IgE, IgD and IgM and modified forms thereof.

As used herein, dimerization domains are multimerization domains that facilitate interaction between two polypeptide sequences (such as, but not limited to, antibody chains). Dimerization domains include, but are not limited to, an amino acid sequence containing a cysteine residue that facilitates formation of a disulfide bond between two polypeptide sequences, such as all or part of a full-length antibody hinge region, or one or more dimerization sequences, which are sequences of amino acids known to promote interaction between polypeptides (e.g., leucine zippers. GCN4 zippers).

As used herein, "Fe" or "Fc region" or "Fc domain" refers to a polypeptide containing the constant region of an antibody heavy chain, excluding the first constant region immunoglobulin domain. Thus, Fc refers to the last two constant region immunoglobulin domains of IgA, IgD, and IgE, or the last three constant region immunoglobulin domains of IgE and IgM. Optionally, an Fe domain can include all or part of the flexible hinge N-terminal to these domains. For IgA and IgM. Fc can include the 0.1 chain. For an exemplary Fc domain of IgG, Fc contains immunoglobulin domains $C\gamma 2$ and $C\gamma 3$, and optionally, all or part of the hinge between $C\gamma 1$ and $C\gamma 2$. The boundaries of the Fc region can vary, but typically, include at least part of the hinge region. In addition, Fc also includes any allelic or species variant or any variant or modified form, such as any variant or modified form that alters the binding to an FcR or alters an Fe-mediated effector function.

As used herein, "Fc chimera" refers to a chimeric polypeptide in which one or more polypeptides is linked, directly or indirectly, to an Fc region or a derivative thereof. Typically, an Fc chimera combines the Fc region of an immunoglobulin with another polypeptide, such as for example an anti-RSV antibody fragment. Derivatives of or modified Fc polypeptides are known to those of skill in the art.

As used herein, a "protein transduction domain" or "PTD" is a peptide domain that can be conjugated to a protein, such as an antibody provided herein, to promote the attachment to and/or uptake of the protein into a target cell.

As used herein, a "tag" or an "epitope tag" refers to a sequence of amino acids, typically added to the N- or C-terminus of a polypeptide, such as an antibody provided herein. The inclusion of tags fused to a polypeptide can facilitate polypeptide purification and/or detection. Typically, a tag or tag polypeptide refers to polypeptide that has enough residues to provide an epitope recognized by an antibody or can serve for detection or purification, yet is short enough such that it does not interfere with activity of chimeric polypeptide to which it is linked. The tag polypeptide typically is sufficiently unique so an antibody that specifically binds thereto does not substantially cross-react with epitopes in the polypeptide to which it is linked. Suitable tag polypeptides generally have at least 5 or 6 amino acid residues and usually between about 8-50 amino acid residues, typically between 9-30 residues. The tags can be linked to one or more chimeric polypeptides in a multimer and permit detection of the multimer or its recovery from a sample or mixture. Such tags are well known and can be readily synthesized and designed. Exemplary tag polypeptides include those used for affinity purification and include, His tags, the influenza hemagglutinin (HA) tag polypeptide and its antibody 12CA5, (Field et al. (1988) *Mol. Cell. Biol.* 8:2159-2165); the c-myc tag and the 8F9, 3C7, 6E10, G4, B7 and 9E10 antibodies thereto (see, e.g., Evan et al. (1985) *Molecular and Cellular Biology* 5:3610-3616); and the Herpes Simplex virus glycoprotein D (gD) tag and its antibody (Paborsky et al. (1990) *Protein Engineering* 3:547-553 (1990). An antibody used to detect an epitope-tagged antibody is typically referred to herein as a secondary antibody.

As used herein, "polypeptide" refers to two or more amino acids covalently joined. The terms "polypeptide" and "protein" are used interchangeably herein.

As used herein, a "peptide" refers to a polypeptide that is from 2 to about or 40 amino acids in length.

As used herein, an "amino acid" is an organic compound containing an amino group and a carboxylic acid group. A polypeptide contains two or more amino acids. For purposes herein, amino acids contained in the antibodies provided include the twenty naturally-occurring amino acids (Table 1), non-natural amino acids, and amino acid analogs (e.g., amino acids wherein the α-carbon has a side chain). As used herein, the amino acids, which occur in the various amino acid sequences of polypeptides appearing herein, are identified according to their well-known, three-letter or one-letter abbreviations (see Table 1). The nucleotides, which occur in the various nucleic acid molecules and fragments, are designated with the standard single-letter designations used routinely in the art.

As used herein, "amino acid residue" refers to an amino acid formed upon chemical digestion (hydrolysis) of a polypeptide at its peptide linkages. The amino acid residues described herein are generally in the "L" isomeric form. Residues in the isomeric form can be substituted for any L-amino acid residue, as long as the desired functional property is retained by the polypeptide. NH$_2$ refers to the free amino group present at the amino terminus of a polypeptide. COOH refers to the free carboxy group present at the carboxyl terminus of a polypeptide. In keeping with standard polypeptide nomenclature described in *J. Biol. Chem.*, 243:3557-59 (1968) and adopted at 37 C.F.R. §§ 1.821-1.822, abbreviations for amino acid residues are shown in Table 1:

TABLE 1

Table of Correspondence

SYMBOL

| 1-Letter | 3-Letter | AMINO ACID |
|---|---|---|
| Y | Tyr | Tyrosine |
| G | Gly | Glycine |
| F | Phe | Phenylalanine |
| M | Met | Methionine |
| A | Ala | Alanine |
| S | Ser | Serine |
| I | Ile | Isoleucine |
| L | Leu | Leucine |
| T | Thr | Threonine |
| V | Val | Valine |
| P | Pro | Proline |
| K | Lys | Lysine |
| H | His | Histidine |
| Q | Gln | Glutamine |
| E | Glu | Glutamic acid |
| Z | Glx | Glutamic Acid and/or Glutamine |
| W | Trp | Tryptophan |
| R | Arg | Arginine |
| D | Asp | Aspartic acid |
| N | Asn | Asparagine |
| B | Asx | Aspartic Acid and/or Asparagine |
| C | Cys | Cysteine |
| X | Xaa | Unknown or other |

All sequences of amino acid residues represented herein by a formula have a left to right orientation in the conventional direction of amino-terminus to carboxyl-terminus. In addition, the phrase "amino acid residue" is defined to include the amino acids listed in the Table of Correspondence (Table 1), modified, non-natural and unusual amino acids. Furthermore, a dash at the beginning or end of an amino acid residue sequence indicates a peptide bond to a further sequence of one or more amino acid residues or to an amino-terminal group such as NH$_2$ or to a carboxyl-terminal group such as COOH.

In a peptide or protein, suitable conservative substitutions of amino acids are known to those of skill in this art and generally can be made without altering a biological activity of a resulting molecule. Those of skill in this art recognize that in general, single amino acid substitutions in non-essential regions of a polypeptide do not substantially alter biological activity (see, e.g., Watson et al., *Molecular Biology of the Gene*, 4th Edition, 1987. The Benjamin/Cummings Pub. co., p. 224).

Such substitutions can be made in accordance with the exemplary substitutions set forth in Table 2 as follows:

TABLE 2

| Original residue | Conservative substitution |
|---|---|
| Ala (A) | Gly; Ser |
| Arg (R) | Lys |

TABLE 2-continued

| Original residue | Conservative substitution |
|---|---|
| Asn (N) | Gln; His |
| Cys (C) | Ser |
| Gln (Q) | Asn |
| Glu (E) | Asp |
| Gly (G) | Ala; Pro |
| His (H) | Asn; Gln |
| Ile (I) | Leu; Val |
| Leu (L) | Ile; Val |
| Lys (K) | Arg; Gln; Glu |
| Met (M) | Leu; Tyr; Ile |
| Phe (F) | Met; Leu; Tyr |
| Ser (S) | Thr |
| Thr (T) | Ser |
| Trp (W) | Tyr |
| Tyr (Y) | Trp; Phe |
| Val (V) | Ile; Leu |

Other substitutions also are permissible and can be determined empirically or in accord with other known conservative or non-conservative substitutions.

As used herein, "naturally occurring amino acids" refer to the 20 L-amino acids that occur in polypeptides.

As used herein, the term "non-natural amino acid" refers to an organic compound that has a structure similar to a natural amino acid but has been modified structurally to mimic the structure and reactivity of a natural amino acid. Non-naturally occurring amino acids thus include, for example, amino acids or analogs of amino acids other than the 20 naturally occurring amino acids and include, but are not limited to, the D-isostereomers of amino acids. Exemplary non-natural amino acids are known to those of skill in the art, and include, but are not limited to, 2-Aminoadipic acid (Aad), 3-Aminoadipic acid (Baad), β-alanine/β-Aminopropionic acid (Bala), 2-Aminobutyric acid (Abu), 4-Aminobutyric acid/piperidinic acid (4Abu), 6-Aminocaproic acid (Acp), 2-Aminoheptanoic acid (Ahe), 2-Aminoisobutyric acid (Aib), 3-Aminoisobutyric acid (Baib), 2-Aminopimelic acid (Apm), 2,4-Diaminobutyric acid (Dbu), Desmosine (Des), 2,2'-Diaminopimelic acid (Dpm), 2,3-Diaminopropionic acid (Dpr), N-Ethylglycine (EtGly), N-Ethylasparagine (EtAsn), Hydroxylysine (Hyl), allo-Hydroxylysine (Ahyl), 3-Hydroxyproline (3Hyp), 4-Hydroxyproline (4Hyp), Isodesmosine (Ide), allo-Isoleucine (Aile), N-Methylglycine, sarcosine (MeGly), N-Methylisoleucine (MeIle), 6-N-Methyllysine (MeLys), N-Methylvaline (MeVal), Norvaline (Nva), Norleucine (Nle), and Ornithine (Orn).

As used herein, a "native polypeptide" or a "native nucleic acid" molecule is a polypeptide or nucleic acid molecule, respectively, that can be found in nature. A native polypeptide or nucleic acid molecule can be the wild-type form of a polypeptide or nucleic acid molecule. A native polypeptide or nucleic acid molecule can be the predominant form of the polypeptide, or any allelic or other natural variant thereof. The variant polypeptides and nucleic acid molecules provided herein can have modifications compared to native polypeptides and nucleic acid molecules.

As used herein, the wild-type form of a polypeptide or nucleic acid molecule is a form encoded by a gene or by a coding sequence encoded by the gene. Typically, a wild-type form of a gene, or molecule encoded thereby, does not contain mutations or other modifications that alter function or structure. The term wild-type also encompasses forms with allelic variation as occurs among and between species. As used herein, a predominant form of a polypeptide or nucleic acid molecule refers to a form of the molecule that is the major form produced from a gene. A "predominant form" varies from source to source. For example, different cells or tissue types can produce different forms of polypeptides, for example, by alternative splicing and/or by alternative protein processing. In each cell or tissue type, a different polypeptide can be a "predominant form."

As used herein, an "allelic variant" or "allelic variation" references any of two or more alternative forms of a gene occupying the same chromosomal locus. Allelic variation arises naturally through mutation, and can result in phenotypic polymorphism within populations. Gene mutations can be silent (no change in the encoded polypeptide) or can encode polypeptides having altered amino acid sequence. The term "allelic variant" also is used herein to denote a protein encoded by an allelic variant of a gene. Typically the reference form of the gene encodes a wild type form and/or predominant form of a polypeptide from a population or single reference member of a species. Typically, allelic variants, which include variants between and among species typically have at least or about 80%, 85%, 90%, 95% or greater amino acid identity with a wild type and/or predominant form from the same species; the degree of identity depends upon the gene and whether comparison is interspecies or intraspecies. Generally, intraspecies allelic variants have at least or about 80%, 85%, 90% or 95% identity or greater with a wild type and/or predominant form, including 96%, 97%, 98%, 99% or greater identity with a wild type and/or predominant form of a polypeptide. Reference to an allelic variant herein generally refers to variations n proteins among members of the same species.

As used herein, "allele," which is used interchangeably herein with "allelic variant" refers to alternative forms of a gene or portions thereof. Alleles occupy the same locus or position on homologous chromosomes. When a subject has two identical alleles of a gene, the subject is said to be homozygous for that gene or allele. When a subject has two different alleles of a gene, the subject is said to be heterozygous for the gene. Alleles of a specific gene can differ from each other in a single nucleotide or several nucleotides, and can include substitutions, deletions and insertions of nucleotides. An allele of a gene also can be a form of a gene containing a mutation.

As used herein, "species variants" refer to variants in polypeptides among different species, including different mammalian species, such as mouse and human, and species of microorganisms, such as viruses and bacteria.

As used herein, a polypeptide "domain" is a part of a polypeptide (a sequence of three or more, generally 5, 10 or more amino acids) that is a structurally and/or functionally distinguishable or definable. Exemplary of a polypeptide domain is a part of the polypeptide that can form an independently folded structure within a polypeptide made up of one or more structural motifs (e.g. combinations of alpha helices and/or beta strands connected by loop regions) and/or that is recognized by a particular functional activity, such as enzymatic activity, dimerization or antigen-binding. A polypeptide can have one or more, typically more than one, distinct domains. For example, the polypeptide can have one or more structural domains and one or more functional domains. A single polypeptide domain can be distinguished based on structure and function. A domain can encompass a contiguous linear sequence of amino acids. Alternatively, a domain can encompass a plurality of non-contiguous amino acid portions, which are non-contiguous along the linear sequence of amino acids of the polypeptide. Typically, a polypeptide contains a plurality of domains. For example, each heavy chain and each light chain of an antibody molecule contains a plurality of immunoglobulin (Ig) domains, each about 110 amino acids in length.

Those of skill in the art are familiar with polypeptide domains and can identify them by virtue of structural and/or functional homology with other such domains. For exemplification herein, definitions are provided, but it is understood that it is well within the skill in the art to recognize particular domains by name. If needed, appropriate software can be employed to identify domains.

As used herein, a functional region of a polypeptide is a region of the polypeptide that contains at least one functional domain (which imparts a particular function, such as an ability to interact with a biomolecule, for example, through antigen-binding, DNA binding, ligand binding, or dimerization, or by enzymatic activity, for example, kinase activity or proteolytic activity); exemplary of functional regions of polypeptides are antibody domains, such as $V_H$, $V_L$, $C_H$, $C_L$, and portions thereof, such as CDRs, including CDR1, CDR2 and CDR3, or antigen-binding portions, such as antibody combining sites.

As used herein, a structural region of a polypeptide is a region of the polypeptide that contains at least one structural domain.

As used herein, a "property" of a polypeptide, such as an antibody, refers to any property exhibited by a polypeptide, including, but not limited to, binding specificity, structural configuration or conformation, protein stability, resistance to proteolysis, conformational stability, thermal tolerance, and tolerance to pH conditions. Changes in properties can alter an "activity" of the polypeptide. For example, a change in the binding specificity of the antibody polypeptide can alter the ability to bind an antigen, and/or various binding activities, such as affinity or avidity, or in vivo activities of the polypeptide.

As used herein, an "activity" or a "functional activity" of a polypeptide, such as an antibody, refers to any activity exhibited by the polypeptide. Such activities can be empirically determined. Exemplary activities include, but are not limited to, ability to interact with a biomolecule, for example, through antigen-binding, DNA binding, ligand binding, or dimerization, enzymatic activity, for example, kinase activity or proteolytic activity. For an antibody (including antibody fragments), activities include, but are not limited to, the ability to specifically bind a particular antigen, affinity of antigen-binding (e.g. high or low affinity), avidity of antigen-binding (e.g. high or low avidity), on-rate, off-rate, effector functions, such as the ability to promote antigen neutralization or clearance, virus neutralization, and in vivo activities, such as the ability to prevent infection or invasion of a pathogen, or to promote clearance, or to penetrate a particular tissue or fluid or cell in the body. Activity can be assessed in vitro or in vivo using recognized assays, such as ELISA, flow cytometry, surface plasmon resonance or equivalent assays to measure on- or off-rate, immunohistochemistry and immunofluorescence histology and microscopy, cell-based assays, flow cytometry and binding assays (e.g., panning assays). For example, for an antibody polypeptide, activities can be assessed by measuring binding affinities, avidities, and/or binding coefficients (e.g., for on-/off-rates), and other activities in vitro or by measuring various effects in vivo, such as immune effects, e.g. antigen clearance, penetration or localization of the antibody into tissues, protection from disease, e.g. infection, serum or other fluid antibody titers, or other assays that are well known in the art. The results of such assays that indicate that a polypeptide exhibits an activity can be correlated to activity of the polo peptide in vivo, in which in vivo activity can be referred to as therapeutic activity, or biological activity. Activity of a modified polypeptide can be any level of percentage of activity of the unmodified polypeptide, including but not limited to, 1% of the activity, 2%, 3%, 4%, 5%, 10%, 20%, 30%, 40%, 50%, 60%, 70%, 80%, 90%, 91%, 92%, 93%, 94%, 95%, 96%, 97%, 98%, 99%, 100%, 200%, 300%, 400%, 500%, or more of activity compared to the unmodified polypeptide. Assays to determine functionality or activity of modified (e.g. variant) antibodies are well known in the art.

As used herein, "therapeutic activity" refers to the in vivo activity of a therapeutic polypeptide. Generally, the therapeutic activity is the activity that is used to treat a disease or condition. Therapeutic activity of a modified polypeptide can be any level of percentage of therapeutic activity of the unmodified polypeptide, including but not limited to, 1% of the activity, 2%, 3%, 4%, 5%, 10%, 20%, 30%, 40%, 50%, 60%, 70%, 80%, 90%, 91%, 92%, 93%, 94%, 95%, 96%, 97%, 98%, 99%, 100%, 200%, 300%, 400%, 500%, or more of therapeutic activity compared to the unmodified polypeptide.

As used herein, "exhibits at least one activity" or "retains at least one activity" refers to the activity exhibited by a modified polypeptide, such as a variant polypeptide produced according to the provided methods, such as a modified, e.g. variant antibody or other therapeutic polypeptide (e.g. a modified anti-RSV antibody or antigen-binding fragment thereof), compared to the target or unmodified polypeptide, that does not contain the modification. A modified, or variant, polypeptide that retains an activity of a target polypeptide can exhibit improved activity or maintain the activity of the unmodified polypeptide. In some instances, a modified, or variant, polypeptide can retain an activity that is increased compared to an target or unmodified polypeptide. In some cases, a modified, or variant, polypeptide can retain an activity that is decreased compared to an unmodified or target polypeptide. Activity of a modified, or variant, polypeptide can be any level of percentage of activity of the unmodified or target polypeptide, including but not limited to, 1% of the activity, 2%, 3%, 4%, 5%, 10%, 20%, 30%, 40%, 50%, 60%, 70%, 80%, 90%, 91%, 92%, 93%, 94%, 95%, 96%, 97%, 98%, 99%, 100%, 200%, 300%, 400%, 500%, or more activity compared to the unmodified or target polypeptide. In other embodiments, the change in activity is at least about 2 times, 3 times, 4 times, 5 times, 6 times, 7 times, 8 times, 9 times, 10 times, 20 times, 30 times, 40 times, 50 times, 60 times, 70 times, 80 times, 90 times, 100 times, 200 times, 300 times, 400 times, 500 times, 600 times, 700 times, 800 times, 900 times, 1000 times, or more times greater than unmodified or target polypeptide. Assays for retention of an activity depend on the activity to be retained. Such assays can be performed in vitro or in vivo. Activity can be measured, for example, using assays known in the art and described in the Examples below for activities such as but not limited to ELISA and panning assays. Activities of a modified, or variant, polypeptide compared to an unmodified or target polypeptide also can be assessed in terms of an in vivo therapeutic or biological activity or result following administration of the polypeptide.

As used herein, the term "assessing" is intended to include quantitative and qualitative determination in the sense of obtaining an absolute value for the activity of a protease, or a domain thereof, present in the sample, and also of obtaining an index, ratio, percentage, visual, or other value indicative of the level of the activity. Assessment can be direct or indirect and the chemical species actually detected need not of course be the proteolysis product itself but can for example be a derivative thereof or some further substance. For example, detection of a cleavage product of a complement protein, such as by SDS-PAGE and protein staining with Coomassie blue.

As used herein, "nucleic acid" refers to at least two linked nucleotides or nucleotide derivatives, including a deoxyribonucleic acid (DNA) and a ribonucleic acid (RNA), joined together, typically by phosphodiester linkages. Also included in the term "nucleic acid" are analogs of nucleic acids such as peptide nucleic acid (PNA). phosphorothioate DNA, and other such analogs and derivatives or combinations thereof. Nucleic acids also include DNA and RNA derivatives containing, for example, a nucleotide analog or a "backbone" bond other than a phosphodiester bond, for example, a phosphotriester bond, a phosphoramidate bond, a phosphorothioate bond, a thioester bond, or a peptide bond (peptide nucleic acid). The term also includes, as equivalents, derivatives, variants and analogs of either RNA or DNA made from nucleotide analogs, single (sense or antisense) and double-stranded nucleic acids. Deoxyribonucleotides include deoxyadenosine, deoxycytidine, deoxyguanosine and deoxythymidine. For RNA, the uracil base is uridine.

Nucleic acids can contain nucleotide analogs, including, for example, mass modified nucleotides, which allow for mass differentiation of nucleic acid molecules; nucleotides containing a detectable label such as a fluorescent, radioactive, luminescent or chemiluminescent label, which allow for detection of a nucleic acid molecule; or nucleotides containing a reactive group such as biotin or a thiol group, which facilitates immobilization of a nucleic acid molecule to a solid support. A nucleic acid also can contain one or more backbone bonds that are selectively cleavable, for example, chemically, enzymatically or photolytically cleavable. For example, a nucleic acid can include one or more deoxyribonucleotides, followed by one or more ribonucleotides, which can be followed by one or more deoxyribonucleotides, such a sequence being cleavable at the ribonucleotide sequence by base hydrolysis. A nucleic acid also can contain one or more bonds that are relatively resistant to cleavage, for example, a chimeric oligonucleotide primer, which can include nucleotides linked by peptide nucleic acid bonds and at least one nucleotide at the 3' end, which is linked by a phosphodiester bond or other suitable bond, and is capable of being extended by a polymerase. Peptide nucleic acid sequences can be prepared using well-known methods (see, for example, Weiler et al. (1997) *Nucleic Acids Res.* 25:2792-2799).

As used herein, the terms "polynucleotide" and "nucleic acid molecule" refer to an oligomer or polymer containing at least two linked nucleotides or nucleotide derivatives, including a deoxyribonucleic acid (DNA) and a ribonucleic acid (RNA), joined together, typically by phosphodiester linkages. Polynucleotides also include DNA and RNA derivatives containing, for example, a nucleotide analog or a "backbone" bond other than a phosphodiester bond, for example, a phosphotriester bond, a phosphoramidate bond, a phosphorothioate bond, a thioester bond, or a peptide bond (peptide nucleic acid). Polynucleotides (nucleic acid molecules), include single-stranded and/or double-stranded polynucleotides, such as deoxyribonucleic acid (DNA), and ribonucleic acid (RNA) as well as analogs or derivatives of either RNA or DNA. The term also includes, as equivalents, derivatives, variants and analogs of either RNA or DNA made from nucleotide analogs, single (sense or antisense) and double-stranded polynucleotides. Deoxyribonucleotides include deoxyadenosine, deoxycytidine, deoxyguanosine and deoxythymidine. For RNA, the uracil base is uridine. Polynucleotides can contain nucleotide analogs, including, for example, mass modified nucleotides, which allow for mass differentiation of polynucleotides; nucleotides containing a detectable label such as a fluorescent, radioactive, luminescent or chemiluminescent label, which allow for detection of a polynucleotide; or nucleotides containing a reactive group such as biotin or a thiol group, which facilitates immobilization of a polynucleotide to a solid support. A polynucleotide also can contain one or more backbone bonds that are selectively cleavable, for example, chemically, enzymatically or photolytically cleavable. For example, a polynucleotide can include one or more deoxyribonucleotides, followed by one or more ribonucleotides, which can be followed by one or more deoxyribonucleotides, such a sequence being cleavable at the ribonucleotide sequence by base hydrolysis. A polynucleotide also can contain one or more bonds that are relatively resistant to cleavage, for example, a chimeric oligonucleotide primer, which can include nucleotides linked by peptide nucleic acid bonds and at least one nucleotide at the 3' end, which is linked by a phosphodiester bond or other suitable bond, and is capable of being extended by a polymerase. Peptide nucleic acid sequences can be prepared using well-known methods (see, for example, Weiler et al. (1997) *Nucleic Acids Res.* 25:2792-2799). Exemplary of the nucleic acid molecules (polynucleotides) provided herein are oligonucleotides, including synthetic oligonucleotides, oligonucleotide duplexes, primers, including fill-in primers, and oligonucleotide duplex cassettes.

As used herein, a "DNA construct" is a single or double stranded, linear or circular DNA molecule that contains segments of DNA combined and juxtaposed in a manner not found in nature. DNA constructs exist as a result of human manipulation, and include clones and other copies of manipulated molecules.

As used herein, a "DNA segment" is a portion of a larger DNA molecule having specified attributes. For example, a DNA segment encoding a specified polypeptide is a portion of a longer DNA molecule, such as a plasmid or plasmid fragment, which, when read from the 5' to 3' direction, encodes the sequence of amino acids of the specified polypeptide.

As used herein, a positive strand polynucleotide refers to the "sense strand" or a polynucleotide duplex, which is complementary to the negative strand or the "antisense" strand. In the case of polynucleotides which encode genes, the sense strand is the strand that is identical to the mRNA strand that is translated into a polypeptide, while the antisense strand is complementary to that strand. Positive and negative strands of a duplex are complementary to one another.

As used herein, a genetic element refers to a gene, or any region thereof, that encodes a polypeptide or protein or region thereof. In some examples, a genetic element encodes a fusion protein.

As used herein, regulatory region of a nucleic acid molecule means a cis-acting nucleotide sequence that influences expression, positively or negatively, of an operatively linked gene. Regulatory regions include sequences of nucleotides that confer inducible (i.e., require a substance or stimulus for increased transcription) expression of a gene. When an inducer is present or at increased concentration, gene expression can be increased. Regulatory regions also include sequences that confer repression of gene expression (i.e., a substance or stimulus decreases transcription). When a repressor is present or at increased concentration gene expression can be decreased. Regulatory regions are known to influence, modulate or control many in vivo biological activities including cell proliferation, cell growth and death, cell differentiation and immune modulation. Regulatory regions typically bind to one or more trans-acting proteins, which results in either increased or decreased transcription of the gene.

Particular examples of gene regulatory regions are promoters and enhancers. Promoters are sequences located around the transcription or translation start site, typically positioned 5' of the translation start site. Promoters usually are located within 1 Kb of the translation start site, but can be located further away, for example, 2 Kb, 3 Kb, 4 Kb, 5 Kb or more, up to and including 10 Kb. Enhancers are known to influence gene expression when positioned 5' or 3' of the gene, or when positioned in or a part of an exon or an intron. Enhancers also can function at a significant distance from the gene, for example, at a distance from about 3 Kb, 5 Kb, 7 Kb, 10 Kb, 15 Kb or more.

Regulatory regions also include, but are not limited to, in addition to promoter regions, sequences that facilitate translation, splicing signals for introns, maintenance of the correct reading frame of the gene to permit in-frame translation of mRNA and, stop codons, leader sequences and fusion partner sequences, internal ribosome binding site (IRES) elements for the creation of multigene, or polycistronic, messages, polyadenylation signals to provide proper polyadenylation of the transcript of a gene of interest and stop codons, and can be optionally included in an expression vector.

As used herein, "operably linked" with reference to nucleic acid sequences, regions, elements or domains means that the nucleic acid regions are functionally related to each other. For example, nucleic acid encoding a leader peptide can be operably linked to nucleic acid encoding a polypeptide, whereby the nucleic acids can be transcribed and translated to express a functional fusion protein, wherein the leader peptide effects secretion of the fusion polypeptide. In some instances, the nucleic acid encoding a first polypeptide (e.g., a leader peptide) is operably linked to nucleic acid encoding a second polypeptide and the nucleic acids are transcribed as a single mRNA transcript, but translation of the mRNA transcript can result in one of two polypeptides being expressed. For example, an amber stop codon can be located between the nucleic acid encoding the first polypeptide and the nucleic acid encoding the second polypeptide, such that, when introduced into a partial amber suppressor cell, the resulting single mRNA transcript can be translated to produce either a fusion protein containing the first and second polypeptides, or can be translated to produce only the first polypeptide. In another example, a promoter can be operably linked to nucleic acid encoding a polypeptide, whereby the promoter regulates or mediates the transcription of the nucleic acid.

As used herein, "synthetic," with reference to, for example, a synthetic nucleic acid molecule or a synthetic gene or a synthetic peptide refers to a nucleic acid molecule or polypeptide molecule that is produced by recombinant methods and/or by chemical synthesis methods.

As used herein, production by recombinant means by using recombinant DNA methods means the use of the well known methods of molecular biology for expressing proteins encoded by cloned DNA.

As used herein, "expression" refers to the process by which polypeptides are produced by transcription and translation of polynucleotides. The level of expression of a polypeptide can be assessed using any method known in art, including, for example, methods of determining the amount of the polypeptide produced from the host cell. Such methods can include, but are not limited to, quantitation of the polypeptide in the cell lysate by ELISA, Coomassie blue staining following gel electrophoresis, Lowry protein assay and Bradford protein assay.

As used herein, a "host cell" is a cell that is used in to receive, maintain, reproduce and amplify a vector. A host cell also can be used to express the polypeptide encoded by the vector. The nucleic acid contained in the vector is replicated when the host cell divides, thereby amplifying the nucleic acids. In one example, the host cell is a genetic package, which can be induced to express the variant polypeptide on its surface. In another example, the host cell is infected with the genetic package. For example, the host cells can be phage-display compatible host cells, which can be transformed with phage or phagemid vectors and accommodate the packaging of phage expressing fusion proteins containing the variant polypeptides.

As used herein, a "vector" is a replicable nucleic acid from which one or more heterologous proteins can be expressed when the vector is transformed into an appropriate host cell. Reference to a vector includes those vectors into which a nucleic acid encoding a polypeptide or fragment thereof can be introduced, typically by restriction digest and ligation. Reference to a vector also includes those vectors that contain nucleic acid encoding a polypeptide. The vector is used to introduce the nucleic acid encoding the polypeptide into the host cell for amplification of the nucleic acid or for expression/display of the polypeptide encoded by the nucleic acid. The vectors typically remain episomal, but can be designed to effect integration of a gene or portion thereof into a chromosome of the genome. Also contemplated are vectors that are artificial chromosomes, such as yeast artificial chromosomes and mammalian artificial chromosomes. Selection and use of such vehicles are well known to those of skill in the art.

As used herein, a vector also includes "virus vectors" or "viral vectors." Viral vectors are engineered viruses that are operatively linked to exogenous genes to transfer (as vehicles or shuttles) the exogenous genes into cells.

As used herein, an "expression vector" includes vectors capable of expressing DNA that is operatively linked with regulatory sequences, such as promoter regions, that are capable of effecting expression of such DNA fragments. Such additional segments can include promoter and terminator sequences, and optionally can include one or more origins of replication, one or more selectable markers, an enhancer, a polyadenylation signal, and the like. Expression vectors are generally derived from plasmid or viral DNA, or can contain elements of both. Thus, an expression vector refers to a recombinant DNA or RNA construct, such as a plasmid, a phage, recombinant virus or other vector that, upon introduction into an appropriate host cell, results in expression of the cloned DNA. Appropriate expression vectors are well known to those of skill in the art and include those that are replicable in eukaryotic cells and/or prokaryotic cells and those that remain episomal or those which integrate into the host cell genome.

As used herein, the terms "oligonucleotide" and "oligo" are used synonymously. Oligonucleotides are polynucleotides that contain a limited number of nucleotides in length. Those in the art recognize that oligonucleotides generally are less than at or about two hundred fifty, typically less than at or about two hundred, typically less than at or about one hundred, nucleotides in length. Typically, the oligonucleotides provided herein are synthetic oligonucleotides. The synthetic oligonucleotides contain fewer than at or about 250 or 200 nucleotides in length, for example, fewer than about 20, 30, 40, 50, 60, 70, 80, 90, 100, 110, 120, 130, 140, 150, 160, 170, 180, 190 or 200 nucleotides in length. Typically, the oligonucleotides are single-stranded oligonucleotides. The ending "mer" can be used to denote the length of an oligonucleotide. For example, "100-mer" can be used to refer to an oligonucleotide containing 100 nucleotides in length. Exemplary of the synthetic oligonucleotides provided herein are positive and negative strand oligonucleotides, randomized oligonucleotides, reference sequence oligonucleotides, template oligonucleotides and fill-in primers are.

As used herein, synthetic oligonucleotides are oligonucleotides produced by chemical synthesis. Chemical oligonucleotide synthesis methods are well known. Any of the known synthesis methods can be used to produce the oligonucleotides designed and used in the provided methods. For example, synthetic oligonucleotides typically are made by chemically joining single nucleotide monomers or nucleotide trimers containing protective groups. Typically, phosphoramidites, single nucleotides containing protective groups are added one at a time. Synthesis typically begins with the 3' end of the oligonucleotide. The 3' most phosphoramidite is attached to a solid support and synthesis proceeds by adding each phosphoramidite to the 5' end of the last. After each addition, the protective group is removed from the 5' phosphate group on the most recently added base, allowing addition of another phosphoramidite. Automated synthesizers generally can synthesize oligonucleotides up to about 150 to about 200 nucleotides in length. Typically, the oligonucleotides designed and used in the provided methods are synthesized using standard cyanoethyl chemistry from phosphoramidite monomers. Synthetic oligonucleotides produced by this standard method can be purchased from Integrated DNA Technologies (IDT) (Coralville, Iowa) or TriLink Biotechnologies (San Diego, Calif.).

As used herein, "primer" refers to a nucleic acid molecule (more typically, to a pool of such molecules sharing sequence identity) that can act as a point of initiation of template-directed nucleic acid synthesis under appropriate conditions (for example, in the presence of four different nucleoside triphosphates and a polymerization agent, such as DNA polymerase, RNA polymerase or reverse transcriptase) in an appropriate buffer and at a suitable temperature. It will be appreciated that certain nucleic acid molecules can serve as a "probe" and as a "primer." A primer, however, has a 3' hydroxyl group for extension. A primer can be used in a variety of methods, including, for example, polymerase chain reaction (PCR), reverse-transcriptase (RT)-PCR, RNA PCR, LCR, multiplex PCR, panhandle PCR, capture PCR, expression PCR, 3' and 5' RACE, in situ PCR, ligation-mediated PCR and other amplification protocols.

As used herein, "primer pair" refers to a set of primers (e.g. two pools of primers) that includes a 5' (upstream) primer that specifically hybridizes with the 5' end of a sequence to be amplified (e.g. by PCR) and a 3' (downstream) primer that specifically hybridizes with the complement of the 3' end of the sequence to be amplified. Because "primer" can refer to a pool of identical nucleic acid molecules, a primer pair typically is a pair of two pools of primers.

As used herein, "single primer" and "single primer pool" refer synonymously to a pool of primers, where each primer in the pool contains sequence identity with the other primer members, for example, a pool of primers where the members share at least at or about 50, 55, 60, 65, 70, 75, 80, 85, 90, 95, 96, 97, 98, 99 or 100% identity. The primers in the single primer pool (all sharing sequence identity) act as 5' (upstream) primers (that specifically hybridize with the 5' end of a sequence to be amplified (e.g. by PCR)) and as 3' (downstream) primers (that specifically hybridize with the complement of the 3' end of the sequence to be amplified). Thus, the single primer can be used, without other primers, to prime synthesis of complementary strands and amplify a nucleic acid in a polymerase amplification reaction.

As used herein, complementarity, with respect to two nucleotides, refers to the ability of the two nucleotides to base pair with one another upon hybridization of two nucleic acid molecules. Two nucleic acid molecules sharing complementarity are referred to as complementary nucleic acid molecules; exemplary of complementary nucleic acid molecules are the positive and negative strands in a polynucleotide duplex. As used herein, when a nucleic acid molecule or region thereof is complementary to another nucleic acid molecule or region thereof, the two molecules or regions specifically hybridize to each other. Two complementary nucleic acid molecules can be described in terms of percent complementarity. For example, two nucleic acid molecules, each 100 nucleotides in length, that specifically hybridize with one another but contain 5 mismatches with respect to one another, are said to be 95% complementary. For two nucleic acid molecules to hybridize with 100% complementarity, it is not necessary that complementarity exist along the entire length of both of the molecules. For example, a nucleic acid molecule containing 20 contiguous nucleotides in length can specifically hybridize to a contiguous 20 nucleotide portion of a nucleic acid molecule containing 500 contiguous nucleotide in length. If no mismatches occur along this 20 nucleotide portion, the 20 nucleotide molecule hybridizes with 100% complementarity. Typically, complementary nucleic acid molecules align with less than 25%, 20%, 15%, 10%, 5% 4%, 3%, 2% or 1% mismatches between the complementary nucleotides (in other words, at least at or about 75%, 80%, 85%, 90%, 95%, 96%, 97%, 98% or 99% complementarity). In another example, the complementary nucleic acid molecules contain at or about or at least at or about 50%, 55%, 60%, 65%, 70%, 75%, 80%, 85%, 90%, 95%, 96%, 97%, 98% or 99% complementarity. In one example, complementary nucleic acid molecules contain fewer than 5, 4, 3, 2 or 1 mismatched nucleotides. In one example, the complementary nucleotides are 100% complementary. If necessary, the percentage of complementarity will be specified. Typically the two molecules are selected such that they will specifically hybridize under conditions of high stringency.

As used herein, a complementary strand of a nucleic acid molecule refers to a sequence of nucleotides, e.g., a nucleic acid molecule, that specifically hybridizes to the molecule, such as the opposite strand to the nucleic acid molecule in a polynucleotide duplex. For example, in a polynucleotide duplex, the complementary strand of a positive strand oligonucleotide is a negative strand oligonucleotide that specifically hybridizes to the positive strand oligonucleotide in a duplex. In one example of the provided methods, polymerase reactions are used to synthesize complementary strands of polynucleotides to form duplexes, typically beginning by hybridizing an oligonucleotide primer to the polynucleotide.

As used herein, "specifically hybridizes" refers to annealing, by complementary base-pairing, of a nucleic acid molecule (e.g. an oligonucleotide or polynucleotide) to another nucleic acid molecule. Those of skill in the art are familiar with in vitro and in vivo parameters that affect specific hybridization, such as length and composition of the particular molecule. Parameters particularly relevant to in vitro hybridization further include annealing and washing temperature, buffer composition and salt concentration. It is not necessary that two nucleic acid molecules exhibit 100% complementarity in order to specifically hybridize to one another. For example, two complementary nucleic acid molecules sharing sequence complementarity, such as at or about or at least or about 99%, 98%, 97%, 96%, 95%, 90%, 85%, 80%, 75%, 70%, 65%, 60%, 55% or 50% complementarity, can specifically hybridize to one another. Parameters, for example, buffer components, time and temperature, used in in vitro hybridization methods provided herein, can be adjusted in stringency to vary the percent complementarity required for specific hybridization of two nucleic acid molecules. The skilled person can readily adjust these parameters to achieve specific hybridization of a nucleic acid molecule to a target nucleic acid molecule appropriate for a particular application.

As used herein, "primary sequence" refers to the sequence of amino acid residues in a polypeptide or the sequence of nucleotides in a nucleic acid molecule.

As used herein, "similarity" between two proteins or nucleic acids refers to the relatedness between the sequence of amino acids of the proteins or the nucleotide sequences of the nucleic acids. Similarity can be based on the degree of identity of sequences of residues and the residues contained therein. Methods for assessing the degree of similarity between proteins or nucleic acids are known to those of skill in the art. For example, in one method of assessing sequence similarity, two amino acid or nucleotide sequences are aligned in a manner that yields a maximal level of identity between the sequences. "Identity" refers to the extent to which the amino acid or nucleotide sequences are invariant. Alignment of amino acid sequences, and to some extent nucleotide sequences, also can take into account conservative differences and/or frequent substitutions in amino acids (or nucleotides). Conservative differences are those that preserve the physico-chemical properties of the residues involved. Alignments can be global (alignment of the compared sequences over the entire length of the sequences and including all residues) or local (the alignment of a portion of the sequences that includes only the most similar region or regions).

As used herein, when a polypeptide or nucleic acid molecule or region thereof contains or has "identity" or "homology" to another polypeptide or nucleic acid molecule or region, the two molecules and/or regions share greater than or equal to at or about 40% sequence identity, and typically greater than or equal to at or about 50% sequence identity, such as at least or about 60%, 65%, 70%, 75%, 80%, 85%, 90%, 95%, 96%, 97%, 98%, 99% or 100% sequence identity; the precise percentage of identity can be specified if necessary. A nucleic acid molecule, or region thereof that is identical or homologous to a second nucleic acid molecule or region can specifically hybridize to a nucleic acid molecule or region that is 100% complementary to the second nucleic acid molecule or region. Identity alternatively can be compared between two theoretical nucleotide or amino acid sequences or between a nucleic acid or polypeptide molecule and a theoretical sequence.

Sequence "identity," per se, has an art-recognized meaning and the percentage of sequence identity between two nucleic acid or polypeptide molecules or regions can be calculated using published techniques. Sequence identity can be measured along the full length of a polynucleotide or polypeptide or along a region of the molecule. (See, e.g.: *Computational Molecular Biology*, Lesk, A. M., ed., Oxford University Press, New York, 1988; *Biocomputing: Informatics and Genome Projects*, Smith, D. W., ed., Academic Press, New York, 1993; *Computer Analysis of Sequence Data*, Part I, Griffin, A. M., and Griffin, H. G., eds., Humana Press, New Jersey, 1994; *Sequence Analysis in Molecular Biology*, von Heinje, G., Academic Press, 1987; and *Sequence Analysis Primer*, Gribskov, M, and Devereux, J., eds., M Stockton Press, New York, 1991). While there exist a number of methods to measure identity between two polynucleotide or polypeptides, the term "identity" is well known to skilled artisans (Carrillo, H. & Lipman, D., *SIAM J Applied Math* 48:1073 (1988)).

Sequence identity compared along the full length of two polynucleotides or polypeptides refers to the percentage of identical nucleotide or amino acid residues along the full-length of the molecule. For example, if a polypeptide A has 100 amino acids and polypeptide B has 95 amino acids, which are identical to amino acids 1-95 of polypeptide A, then polypeptide B has 95% identity when sequence identity is compared along the full length of a polypeptide A compared to full length of polypeptide B. Alternatively, sequence identity between polypeptide A and polypeptide B can be compared along a region, such as a 20 amino acid analogous region, of each polypeptide. In this case, if polypeptide A and B have 20 identical amino acids along that region, the sequence identity for the regions is 100%. Alternatively, sequence identity can be compared along the length of a molecule, compared to a region of another molecule. Alternatively, sequence identity between polypeptide A and polypeptide B can be compared along the same length polypeptide but with amino acid replacements, such as conservative amino acid replacements or non-conservative amino acid replacements. As discussed below, and known to those of skill in the art, various programs and methods for assessing identity are known to those of skill in the art. High levels of identity, such as 90% or 95% identity, readily can be determined without software.

Whether any two nucleic acid molecules have nucleotide sequences that are at least or about 60%, 70%, 80%, 85%, 90%, 95%, 96%, 97%, 98% or 99% "identical" can be determined using known computer algorithms such as the "FASTA" program, using for example, the default parameters as in Pearson et al. (1988) *Proc. Natl. Acad. Sci. USA* 85:2444 (other programs include the GCG program package (Devereux, J. et al. (1984) *Nucleic Acids Research* 12(1): 387), BLASTP, BLASTN, FASTA (Altschul, S. F. et al. (1990) *J. Molec. Biol.* 215:403; Guide to Huge Computers, Martin J. Bishop, ed., Academic Press, San Diego, 1994, and Carrillo et al. (1988) *SIAM J Applied Math* 48:1073). For example, the BLAST function of the National Center for Biotechnology Information database can be used to determine identity. Other commercially or publicly available programs include. DNAStar "MegAlign" program (Madison, Wis.) and the University of Wisconsin Genetics Computer Group (UWG) "Gap" program (Madison Wis.)). Percent homology or identity of proteins and/or nucleic acid molecules can be determined, for example, by comparing sequence information using a GAP computer program (e.g., Needleman et al. (1970) *J. Mol. Biol.* 48:443, as revised by Smith and Waterman ((1981) *Adv. Appl. Math.* 2:482). Briefly, the GAP program defines similarity as the number of aligned symbols (i.e., nucleotides or amino acids), which are similar, divided by the total number of symbols in the shorter of the two sequences. Default parameters for the GAP program can include: (1) a unary comparison matrix (containing a value of 1 for identities and 0 for non-identities) and the weighted comparison matrix of Gribskov et al. (1986) *Nucl. Acids Res.* 14:6745, as described by Schwartz and Dayhoff, eds., *ATLAS OF PROTEIN SEQUENCE AND STRUCTURE*, National Biomedical Research Foundation, pp. 353-358 (1979); (2) a penalty of 3.0 for each gap and an additional 0.10 penalty for each symbol in each gap; and (3) no penalty for end gaps.

In general, for determination of the percentage sequence identity, sequences are aligned so that the highest order match is obtained (see, e.g.: *Computational Molecular Biology*, Lesk, A. M., ed., Oxford University Press, New York, 1988; *Biocomputing: Informatics and Genome Projects*, Smith, D. W., ed., Academic Press, New York, 1993; *Computer Analysis of Sequence Data, Part I*, Griffin, A. M., and Griffin, H. G., eds., Humana Press, New Jersey, 1994; *Sequence Analysis in Molecular Biology*, von Heinje, G., Academic Press, 1987; and *Sequence Analysis Primer*, Gribskov, M, and Devereux, J., eds., M Stockton Press, New York, 1991; Carrillo et al. (1988) *SIAM J Applied Math* 48:1073). For sequence identity, the number of conserved amino acids is determined by standard alignment algorithms programs, and can be used with default gap penalties established by each supplier. Substantially homologous nucleic acid molecules specifically hybridize typically at moderate stringency or at high stringency all along the length of the nucleic acid of interest. Also contemplated are nucleic acid molecules that contain degenerate codons in place of codons in the hybridizing nucleic acid molecule.

Therefore, the term "identity," when associated with a particular number, represents a comparison between the sequences of a first and a second polypeptide or polynucleotide or regions thereof and/or between theoretical nucleotide or amino acid sequences. As used herein, the term at least "90% identical to" refers to percent identities from 90 to 99.99 relative to the first nucleic acid or amino acid sequence of the polypeptide. Identity at a level of 90% or more is indicative of the fact that, assuming for exemplification purposes, a first and second polypeptide length of 100 amino acids are compared, no more than 10% (i.e., 10 out of 100) of the amino acids in the first polypeptide differs from that of the second polypeptide. Similar comparisons can be made between first and second polynucleotides. Such differences among the first and second sequences can be represented as point mutations randomly distributed over the entire length of a polypeptide or they can be clustered in one or more locations of varying length up to the maximum allowable, e.g. 10/100 amino acid difference (approximately 90% identity). Differences are defined as nucleotide or amino acid residue substitutions, insertions, additions or deletions. At the level of homologies or identities above about 85-90%, the result is independent of the program and gap parameters set; such high levels of identity can be assessed readily, often by manual alignment without relying on software.

As used herein, alignment of a sequence refers to the use of homology to align two or more sequences of nucleotides or amino acids. Typically, two or more sequences that are related by 50% or more identity are aligned. An aligned set of sequences refers to 2 or more sequences that are aligned at corresponding positions and can include aligning sequences derived from RNAs, such as ESTs and other cDNAs, aligned with genomic DNA sequence.

Related or variant polypeptides or nucleic acid molecules can be aligned by any method known to those of skill in the art. Such methods typically maximize matches, and include methods, such as using manual alignments and by using the numerous alignment programs available (e.g., BLASTP) and others known to those of skill in the art. By aligning the sequences of polypeptides or nucleic acids, one skilled in the art can identify analogous portions or positions, using conserved and identical amino acid residues as guides. Further, one skilled in the art also can employ conserved amino acid or nucleotide residues as guides to find corresponding amino acid or nucleotide residues between and among human and non-human sequences. Corresponding positions also can be based on structural alignments, for example by using computer simulated alignments of protein structure. In other instances, corresponding regions can be identified. One skilled in the art also can employ conserved amino acid residues as guides to find corresponding amino acid residues between and among human and non-human sequences.

As used herein, "analogous" and "corresponding" portions, positions or regions are portions, positions or regions that are aligned with one another upon aligning two or more related polypeptide or nucleic acid sequences (including sequences of molecules, regions of molecules and/or theoretical sequences) so that the highest order match is obtained, using an alignment method known to those of skill in the art to maximize matches. In other words, two analogous positions (or portions or regions) align upon best-fit alignment of two or more polypeptide or nucleic acid sequences. The analogous portions/positions/regions are identified based on position along the linear nucleic acid or amino acid sequence when the two or more sequences are aligned. The analogous portions need not share any sequence similarity with one another. For example, alignment (such that maximizing matches) of the sequences of two homologous nucleic acid molecules, each 100 nucleotides in length, can reveal that 70 of the 100 nucleotides are identical. Portions of these nucleic acid molecules containing some or all of the other non-identical 30 amino acids are analogous portions that do not share sequence identity. Alternatively, the analogous portions can contain some percentage of sequence identity to one another, such as at or about 50%, 55%, 60%, 65%, 70%, 75%, 80%, 85%, 90%, 95%, 96%, 97%, 98%, 99%, or fractions thereof. In one example, the analogous portions are 100% identical.

As used herein, a "modification" is in reference to modification of a sequence of amino acids of a polypeptide or a sequence of nucleotides in a nucleic acid molecule and includes deletions, insertions, and replacements of amino acids and nucleotides, respectively. Methods of modifying a polypeptide are routine to those of skill in the art, such as by using recombinant DNA methodologies.

As used herein, "deletion," when referring to a nucleic acid or polypeptide sequence, refers to the deletion of one or more nucleotides or amino acids compared to a sequence, such as a target polynucleotide or polypeptide or a native or wild-type sequence.

As used herein, "insertion" when referring to a nucleic acid or amino acid sequence, describes the inclusion of one or more additional nucleotides or amino acids, within a target, native, wild-type or other related sequence. Thus, a nucleic acid molecule that contains one or more insertions compared to a wild-type sequence, contains one or more additional nucleotides within the linear length of the sequence. As used herein, "additions," to nucleic acid and amino acid sequences describe addition of nucleotides or amino acids onto either termini compared to another sequence.

As used herein, "substitution" refers to the replacing of one or more nucleotides or amino acids in a native, target, wild-type or other nucleic acid or polypeptide sequence with an alternative nucleotide or amino acid, without changing the length (as described in numbers of residues) of the molecule. Thus, one or more substitutions in a molecule does not change the number of amino acid residues or nucleotides of the molecule. Substitution mutations compared to a particular polypeptide can be expressed in terms of the number of the amino acid residue along the length of the polypeptide sequence. For example, a modified polypeptide having a modification in the amino acid at the $19^{th}$ position of the amino acid sequence that is a substitution of Isoleucine (Ile; I) for cysteine (Cys: C) can be expressed as I19C, Ile19C, or simply C19, to indicate that the amino acid at the modified $19^{th}$ position is a cysteine. In this example, the molecule having the substitution has a modification at Ile 19 of the unmodified polypeptide.

As used herein, a binding property is a characteristic of a molecule, e.g. a polypeptide, relating to whether or not, and how, it binds one or more binding partners. Binding properties include ability to bind the binding partner(s), the affinity with which it binds to the binding partner (e.g. high affinity), the avidity with which it binds to the binding partner, the strength of the bond with the binding partner and specificity for binding with the binding partner.

As used herein, affinity describes the strength of the interaction between two or more molecules, such as binding partners, typically the strength of the noncovalent interactions between two binding partners. The affinity of an antibody or antigen-binding fragment thereof for an antigen epitope is the measure of the strength of the total noncovalent interactions between a single antibody combining site and the epitope. Low-affinity antibody-antigen interaction is weak, and the molecules tend to dissociate rapidly, while high affinity antibody-antigen-binding is strong and the molecules remain bound for a longer amount of time. Methods for calculating affinity are well known, such as methods for determining association/dissociation constants. Affinity can be estimated empirically or affinities can be determined comparatively, e.g. by comparing the affinity of one antibody and another antibody for a particular antigen.

As used herein, antibody avidity refers to the strength of multiple interactions between a multivalent antibody and its cognate antigen, such as with antibodies containing multiple binding sites associated with an antigen with repeating epitopes or an epitope array. A high avidity antibody has a higher strength of such interactions compared with a low avidity antibody.

As used herein, "bind" refers to the participation of a molecule in any attractive interaction with another molecule, resulting in a stable association in which the two molecules are in close proximity to one another. Binding includes, but is not limited to, non-covalent bonds, covalent bonds (such as reversible and irreversible covalent bonds), and includes interactions between molecules such as, but not limited to, proteins, nucleic acids, carbohydrates, lipids, and small molecules, such as chemical compounds including drugs. Exemplary of bonds are antibody-antigen interactions and receptor-ligand interactions. When an antibody "binds" a particular antigen, bind refers to the specific recognition of the antigen by the antibody, through cognate antibody-antigen interaction, at antibody combining sites. Binding also can include association of multiple chains of a polypeptide, such as antibody chains which interact through disulfide bonds.

As used herein, "affinity constant" refers to an association constant (Ka) used to measure the affinity of an antibody for an antigen. The higher the affinity constant the greater the affinity of the antibody for the antigen. Affinity constants are expressed in units of reciprocal molarity (i.e. $M^{-1}$) and can be calculated from the rate constant for the association-dissociation reaction as measured by standard kinetic methodology for antibody reactions (e.g., immunoassays, surface plasmon resonance, or other kinetic interaction assays known in the art).

As used herein, the term "the same," when used in reference to antibody binding affinity, means that the association constant (Ka) is within about 1 to 100 fold or 1 to 10 fold of the reference antibody (1-100 fold greater affinity or 1-100 fold less affinity, or any numerical value or range or value within such ranges, than the reference antibody).

As used herein, "substantially the same" when used in reference to association constant (Ka), means that the association constant is within about 5 to 5000 fold greater or less than the association constant, Ka, of the reference antibody (5-5000 fold greater or 5-5000 fold less than the reference antibody). The binding affinity of an antibody also can be expressed as a dissociation constant, or Kd. The dissociation constant is the reciprocal of the association constant. Kd=1/Ka.

As used herein, the phase "having the same binding specificity" when used to describe an antibody in reference to another antibody, means that the antibody specifically binds (immunospecifically binds or specifically binds to the virus) to all or a part of the same antigenic epitope as the reference antibody. Thus, an anti-RSV antibody or antigen-binding fragment thereof having the same binding specificity as the antibody denoted as 58c5 or as 30D8 specifically binds to all or a part of the same epitope as the anti-RSV antibody or antigen-binding fragment thereof denoted as 58c5 or 30D8, respectively. The epitope can be in the isolated protein, or in the protein in the virus. The ability of two antibodies to bind to the same epitope can be determined by known assays in the art such as, for example, surface plasmon resonance assays and antibody competition assays. Typically, antibodies that immunospecifically bind to the same epitope can compete for binding to the epitope, which can be measured, for example, by an in vitro binding competition assay (e.g. competition ELISA), using techniques known the art. Typically, a first antibody that immunospecifically binds to the same epitope as a second antibody can compete for binding to the epitope by about or 30%, 35%, 40%, 45%, 50%, 55%, 60%, 65%, 70%, 75%, 80%, 85%, 90%, 95%, 100%, where the percentage competition is measured ability of the second antibody to displace binding of the first antibody to the epitope. In exemplary competition assays, the antigen is incubated in the presence a predetermined limiting dilution of a labeled antibody (e.g., 50-70% saturation concentration), and serial dilutions of an unlabeled competing antibody. Competition is determined by measuring the binding of the labeled antibody to the antigen for any decreases in binding in the presence of the competing antibody. Variations of such assays, including various labeling techniques and detection methods including, for example, radiometric, fluorescent, enzymatic and colorimetric detection, are known in the art. The ability of a first antibody to bind to the same epitope as a second antibody also can be determined, for example, by virus neutralization assays using Monoclonal Antibody-Resistant Mutants (MARMs). For example, where a first anti-RSV antibody neutralizes wild-type RSV but not a particular mutant RSV, a second antibody that neutralizes the wild-type RSV but not the particular mutant RSV generally binds the same epitope on RSV as the first antibody. Where a first anti-RSV antibody neutralizes wild-type RSV but not a particular mutant RSV, a second antibody that neutralizes the wild-type RSV and the particular mutant RSV generally does not bind the same epitope on RSV as the first antibody.

As used herein, a "monoclonal antibody resistant mutant" (MARM) also referred to as a "monoclonal antibody escape mutant" is a mutant RSV that exhibits resistance to neutralization by a monoclonal antibody that neutralizes the wild-type RSV virus. In practice, the concentration of antibody needed to neutralize 50% of an RSV MARM must be at least about or at least 10-fold greater than that required to neutralize an equivalent amount of reference wild-type infectious virus particles for the MARM to be considered to have escaped the antibody.

MARMs are generated by culturing wildtype RSV in the presence of such monoclonal antibody over successive rounds of viral replication in the presence of the antibody such that after each successive round of virus replication, increasing concentrations of antibody are required to produce virus neutralization effects. Cytopathic effects (CPE) only are observed in the presence of increasing concentrations of antibodies until a mutant virus results that is no longer efficiently neutralized by the antibody. If more rounds of replication are required for the emergence of a MARM in the presence of a first antibody compared to a second antibody, one can conclude the first antibody binds to an epitope that is different from the epitope to which the second antibody binds. If a first antibody can neutralize a MARM generated against a second antibody, one can conclude that the antibodies specifically bind to or interact with different epitopes. MARMs can more finely map the antigen binding epitope of an antibody compared to a competition binding assay, such that one antibody can compete against another for binding to an antigen, but can s neutralize the MARM of its competitor. For some antibodies, it only requires a few rounds of selection to generate a MARM; for other antibodies more rounds are required. For certain antibodies provided herein, no MARMS are generated after 10, 11, 12, 13, 14, 15, 20, 25, 30 or more rounds. In some instances, it is not possible to generate a MARM.

As used herein, $EC_{50}$ refers to the effective concentration at which an antibody can inhibit virus infection 50% in an in vitro neutralization assay, such as, for example, a virus plaque reduction assay as described herein (e.g., a plaque reduction assay using Vero host cells or other host cell for infection) or other virus neutralization assays known in the art. Typically, a neutralizing virus is one that has an $EC_{50}$ of 2 nM or less for inhibition of the virus in an in vitro neutralization assay, such as a virus plaque reduction assay.

As used herein, "binding partner" refers to a molecule (such as a polypeptide, lipid, glycolipid, nucleic acid molecule, carbohydrate or other molecule), with which another molecule specifically interacts, for example, through covalent or noncovalent interactions, such as the interaction of an antibody with cognate antigen. The binding partner can be naturally or synthetically produced. In one example, desired variant polypeptides are selected using one or more binding partners, for example, using in vitro or in vivo methods. Exemplary of the in vitro methods include selection using a binding partner coupled to a solid support, such as a bead, plate, column, matrix or other solid support; or a binding partner coupled to another selectable molecule, such as a biotin molecule, followed by subsequent selection by coupling the other selectable molecule to a solid support. Typically, the in vitro methods include wash steps to remove unbound polypeptides, followed by elution of the selected variant polypeptide(s). The process can be repeated one or more times in an iterative process to select variant polypeptides from among the selected polypeptides.

As used herein, a disulfide bond (also called an S—S bond or a disulfide bridge) is a single covalent bond derived from the coupling of thiol groups. Disulfide bonds in proteins are formed between the thiol groups of cysteine residues, and stabilize interactions between polypeptide domains, such as antibody domains.

As used herein, "coupled" or "conjugated" means attached via a covalent or noncovalent interaction.

As used herein, the phrase "conjugated to an antibody" or "linked to an antibody" or grammatical variations thereof, when referring to the attachment of a moiety to an antibody or antigen-binding fragment thereof, such as a diagnostic or therapeutic moiety, means that the moiety is attached to the antibody or antigen-binding fragment thereof by any known means for linking peptides, such as, for example, by production of fusion protein by recombinant means or post-translationally by chemical means. Conjugation can employ any of a variety of linking agents to effect conjugation, including, but not limited to, peptide or compound linkers or chemical cross-linking agents.

As used herein, "phage display" refers to the expression of polypeptides on the surface of filamentous bacteriophage.

As used herein, a "phage-display compatible cell" or "phage-display compatible host cell" is a host cell, typically a bacterial host cell, that can be infected by phage and thus can support the production of phage displaying fusion proteins containing polypeptides, e.g., variant polypeptides and can thus be used for phage display. Exemplary of phage display compatible cells include, but are not limited to, XL1-blue cells.

As used herein, "panning" refers to an affinity-based selection procedure for the isolation of phage displaying a molecule with a specificity for a binding partner, for example, a capture molecule (e.g., an antigen) or sequence of amino acids or nucleotides or epitope, region, portion or locus therein.

As used herein, "display protein" or "genetic package display protein" means any genetic package polypeptide for display of a polypeptide on the genetic package, such that when the display protein is fused to (e.g., included as part of a fusion protein with) a polypeptide of interest (e.g., a polypeptide for which reduced expression is desired), the polypeptide is displayed on the outer surface of the genetic package. The display protein typically is present on or within the outer surface or outer compartment of a genetic package (e.g., membrane, cell wall, coat or other outer surface or compartment) of a genetic package, e.g., a viral genetic package, such as a phage, such that upon fusion to a polypeptide of interest, the polypeptide is displayed on the genetic package.

As used herein, a coat protein is a display protein, at least a portion of which is present on the outer surface of the genetic package, such that when it is fused to the polypeptide of interest, the polypeptide is displayed on the outer surface of the genetic package. Typically, the coat proteins are viral coat proteins, such as phage coat proteins. A viral coat protein, such as a phage coat protein associates with the virus particle during assembly in a host cell. In one example, coat proteins are used herein for display of polypeptides on genetic packages; the coat proteins are expressed as portions of fusion proteins, which contain the coat protein sequence of amino acids and a sequence of amino acids of the displayed polypeptide. The coat protein can be a full-length coat protein or any portion thereof capable of effecting display of the polypeptide on the surface of the genetic package.

Exemplary of coat proteins are phage coat proteins, such as, but not limited to, (i) minor coat proteins of filamentous phage, such as gene III protein (gIIIp, cp3), and (ii) major coat proteins (which are present in the viral coat at 10 copies or more, for example, tens, hundreds or thousands of copies) of filamentous phage such as gene VIII protein (gVIIIp, cp8); fusions to other phage coat proteins such as gene VI protein, gene VII protein, or gene IX protein (see, e.g., WO 00/71694); and portions (e.g., domains or fragments) of these proteins, such as, but not limited to domains that are stably incorporated into the phage particle, e.g. such as the anchor domain of gIIIp, or gVIIIp. Additionally, mutants of gVIIIp can be used which are optimized for expression of larger peptides, such as mutants having improved surface display properties, such as mutant gVIIp (see, for example, Sidhu et al. (2000) *J. Mol. Biol.* 296:487-495).

As used herein, "disease or disorder" refers to a pathological condition in an organism resulting from cause or condition including, but not limited to, infections, acquired conditions, genetic conditions, and characterized by identifiable symptoms. Diseases and disorders of interest herein are those involving RSV infection or those that increase the risk of a RSV infection.

As used herein, "infection" and "RSV infection" refer to all stages of a RSV life cycle in a host (including, but not limited to the invasion by and replication of RSV in a cell or body tissue), as well as the pathological state resulting from the invasion by and replication of a RSV. The invasion by and multiplication of a RSV includes, but is not limited to, the following steps: the docking of the RSV particle to a cell, fusion of a virus with a cell membrane, the introduction of viral genetic information into a cell, the expression of RSV proteins, the production of new RSV particles and the release of RSV particles from a cell. A RSV infection can be an upper respiratory tract RSV infection (URI), a lower respiratory tract RSV infection (LRI), or a combination thereof. In some examples, the pathological state resulting from the invasion by and replication of a RSV is an acute RSV disease.

As used herein, "acute RSV disease" refers to clinically significant disease in the lungs or lower respiratory tract as a result of a RSV infection, which can manifest as pneumonia and/or bronchiolitis, where such symptoms can include, for example, hypoxia, apnea, respiratory distress, rapid breathing, wheezing, and cyanosis. Acute RSV disease requires an affected individual to obtain medical intervention, such as hospitalization, administration of oxygen, intubation and/or ventilation.

As used herein, "treating" a subject with a disease or condition means that the subject's symptoms are partially or totally alleviated, or remain static following treatment. Hence treatment encompasses prophylaxis, therapy and/or cure. Prophylaxis refers to prevention of a potential disease and/or a prevention of worsening of symptoms or progression of a disease. Treatment also encompasses any pharmaceutical use of any antibody or antigen-binding fragment thereof provided or compositions provided herein.

As used herein, "prevention" or prophylaxis, and grammatically equivalent forms thereof, refers to methods in which the risk of developing disease or condition is reduced.

As used herein, a "pharmaceutically effective agent" includes any therapeutic agent or bioactive agents, including, but not limited to, for example, anesthetics, vasoconstrictors, dispersing agents, conventional therapeutic drugs, including small molecule drugs and therapeutic proteins.

As used herein, a "therapeutic effect" means an effect resulting from treatment of a subject that alters, typically improves or ameliorates the symptoms of a disease or condition or that cures a disease or condition.

As used herein, a "therapeutically effective amount" or a "therapeutically effective dose" refers to the quantity of an agent, compound, material, or composition containing a compound that is at least sufficient to produce a therapeutic effect following administration to a subject. Hence, it is the quantity necessary for preventing, curing, ameliorating, arresting or partially arresting a symptom of a disease or disorder.

As used herein, "therapeutic efficacy" refers to the ability of an agent, compound, material, or composition containing a compound to produce a therapeutic effect in a subject to whom the an agent, compound, material, or composition containing a compound has been administered.

As used herein, a "prophylactically effective amount" or a "prophylactically effective dose" refers to the quantity of an agent, compound, material, or composition containing a compound that when administered to a subject, will have the intended prophylactic effect, e.g., preventing or delaying the onset, or reoccurrence, of disease or symptoms, reducing the likelihood of the onset, or reoccurrence, of disease or symptoms, or reducing the incidence of viral infection. The full prophylactic effect does not necessarily occur by administration of one dose, and can occur only after administration of a series of doses. Thus, a prophylactically effective amount can be administered in one or more administrations.

As used herein, the terms "immunotherapeutically" or "immunotherapy" in conjunction with antibodies provided denotes prophylactic as well as therapeutic administration. Thus, the therapeutic antibodies provided can be administered to a subject at risk of contracting a virus infection (e.g. a RSV infection) in order to lessen the likelihood and/or severity of the disease, or administered to subjects already evidencing active virus infection (e.g. a RSV infection).

As used herein, amelioration of the symptoms of a particular disease or disorder by a treatment, such as by administration of a pharmaceutical composition or other therapeutic, refers to any lessening, whether permanent or temporary, lasting or transient, of the symptoms that can be attributed to or associated with administration of the composition or therapeutic.

As used herein, the term "diagnostically effective" amount refers to the quantity of an agent, compound, material, or composition containing a detectable compound that is at least sufficient for detection of the compound following administration to a subject. Generally, a diagnostically effective amount of an anti-RSV antibody or antigen-binding fragment thereof, such as a detectably-labeled antibody or antigen-binding fragment thereof or an antibody or antigen-binding fragment thereof that can be detected by a secondary agent, administered to a subject for detection is quantity of the antibody or antigen-binding fragment thereof which is sufficient to enable detection of the site having the RSV antigen for which the antibody or antigen-binding fragment thereof is specific. In using the antibodies provided herein for the in vivo detection of antigen, a detectably labeled antibody or antigen-binding fragment thereof is given in a dose which is diagnostically effective.

As used herein, a label or detectable moiety is a detectable marker (e.g., a fluorescent molecule, chemiluminescent molecule, a bioluminescent molecule, a contrast agent (e.g., a metal), a radionuclide, a chromophore, a detectable peptide, or an enzyme that catalyzes the formation of a detectable product) that can be attached or linked directly or indirectly to a molecule (e.g., an anti-RSV antibody or antigen-binding fragment thereof provided herein) or associated therewith and can be detected in vivo and/or in vitro. The detection method can be any method known in the art, including known in vivo and/or in vitro methods of detection (e.g., imaging by visual inspection, magnetic resonance (MR) spectroscopy, ultrasound signal, X-ray, gamma ray spectroscopy (e.g., positron emission tomography (PET) scanning, single-photon emission computed tomography (SPECT)), fluorescence spectroscopy or absorption). Indirect detection refers to measurement of a physical phenomenon, such as energy or particle emission or absorption, of an atom, molecule or composition that binds directly or indirectly to the detectable moiety (e.g., detection of a labeled secondary antibody or antigen-binding fragment thereof that binds to a primary antibody (e.g., an anti-RSV antibody or antigen-binding fragment thereof provided herein).

As used herein, the term "subject" refers to an animal, including a mammal, such as a human being.

As used herein, a patient refers to a human subject.

As used herein, animal includes any animal, such as, but are not limited to primates including humans, gorillas and monkeys; rodents, such as mice and rats; fowl, such as chickens; ruminants, such as goats, cows, deer, sheep; pigs and other animals. Non-human animals exclude humans as the contemplated animal. The polypeptides provided herein are from any source, animal, plant, prokaryotic and fungal. Most polypeptides are of animal origin, including mammalian origin.

As used herein, a "elderly," refers to refers to a subject, who due to age has a decreased immune response and has a decreased response to vaccination. Typically, an elderly subject is one that is human that is sixty-five and greater years of age, more typically, 70 and greater years of age.

As used herein, a "human infant" refers to a human less than or about 24 months (e.g., less than or about 16 months, less than or about 12 months, less than or about 6 months, less than or about 3 months, less than or about 2 months, or less than or about 1 month of age). Typically, the human infant is born at more than 38 weeks of gestational age.

As used herein, a "human infant born prematurely" refers to a human born at less than or about 40 weeks gestational age, typically, less than or about 38 weeks gestational age.

As used herein, a "unit dose form" refers to physically discrete units suitable for human and animal subjects and packaged individually as is known in the art.

As used herein, a "single dosage formulation" refers to a formulation for direct administration.

As used herein, an "article of manufacture" is a product that is made and sold. As used throughout this application, the term is intended to encompass any of the compositions provided herein contained in articles of packaging.

As used herein, a "fluid" refers to any composition that can flow. Fluids thus encompass compositions that are in the form of semi-solids, pastes, solutions, aqueous mixtures, gels, lotions, creams and other such compositions.

As used herein, an isolated or purified polypeptide or protein (e.g. an isolated antibody or antigen-binding fragment thereof) or biologically-active portion thereof (e.g. an isolated antigen-binding fragment) is substantially free of cellular material or other contaminating proteins from the cell or tissue from which the protein is derived, or substantially free from chemical precursors or other chemicals when chemically synthesized. Preparations can be determined to be substantially free if they appear free of readily detectable impurities as determined by standard methods of analysis, such as thin layer chromatography (TLC), gel electrophoresis and high performance liquid chromatography (HPLC), used by those of skill in the art to assess such purity, or sufficiently pure such that further purification does not detectably alter the physical and chemical properties, such as enzymatic and biological activities, of the substance. Methods for purification of the compounds to produce substantially chemically pure compounds are known to those of skill in the art. A substantially chemically pure compound, however, can be a mixture of stereoisomers. In such instances, further purification might increase the specific activity of the compound. As used herein, a "cellular extract" or "lysate" refers to a preparation or fraction which is made from a lysed or disrupted cell.

As used herein, isolated nucleic acid molecule is one which is separated from other nucleic acid molecules which are present in the natural source of the nucleic acid molecule. An "isolated" nucleic acid molecule, such as a cDNA molecule, can be substantially free of other cellular material, or culture medium when produced by recombinant techniques, or substantially free of chemical precursors or other chemicals when chemically synthesized. Exemplary isolated nucleic acid molecules provided herein include isolated nucleic acid molecules encoding an antibody or antigen-binding fragments provided.

As used herein, a "control" refers to a sample that is substantially identical to the test sample, except that it is not treated with a test parameter, or, if it is a plasma sample, it can be from a normal volunteer not affected with the condition of interest. A control also can be an internal control.

As used herein, a "composition" refers to any mixture. It can be a solution, suspension, liquid, powder, paste, aqueous, non-aqueous or any combination thereof.

As used herein, a "combination" refers to any association between or among two or more items. The combination can be two or more separate items, such as two compositions or two collections, can be a mixture thereof, such as a single mixture of the two or more items, or any variation thereof. The elements of a combination are generally functionally associated or related.

As used herein, combination therapy refers to administration of two or more different therapeutics, such as two or more different anti-RSV antibodies and/or anti-RSV antibodies and antigen-binding fragments thereof. The different therapeutic agents can be provided and administered separately, sequentially, intermittently, or can be provided in a single composition.

As used herein, a kit is a packaged combination that optionally includes other elements, such as additional reagents and instructions for use of the combination or elements thereof, for a purpose including, but not limited to, activation, administration, diagnosis, and assessment of a biological activity or property.

As used herein, the singular forms "a," "an" and "the" include plural referents unless the context clearly dictates otherwise. Thus, for example, reference to a polypeptide, comprising "an immunoglobulin domain" includes polypeptides with one or a plurality of immunoglobulin domains.

As used herein, the term "or" is used to mean "and/or" unless explicitly indicated to refer to alternatives only or the alternatives are mutually exclusive.

As used herein, ranges and amounts can be expressed as "about" a particular value or range. About also includes the exact amount. Hence "about 5 amino acids" means "about 5 amino acids" and also "5 amino acids."

As used herein, "optional" or "optionally" means that the subsequently described event or circumstance does or does not occur and that the description includes instances where said event or circumstance occurs and instances where it does not. For example, an optionally variant portion means that the portion is variant or non-variant.

As used herein, the abbreviations for any protective groups, amino acids and other compounds, are, unless indicated otherwise, in accord with their common usage, recognized abbreviations, or the IUPAC-IUB Commission on Biochemical Nomenclature (see, *Biochem.* (1972) 11(9): 1726-1732).

B. OVERVIEW

Provided are anti-RSV antibodies or antigen-binding fragments thereof that bind to and neutralize respiratory syncytial virus. The anti-RSV antibodies provided herein are neutralizing antibodies that recognize one or more epitopes on the surface of RSV. In particular, the antibodies provided herein bind to a RSV fusion (F) protein. The antibodies provided herein can be used in prophylaxis therapies. The antibodies provided herein also can be used as therapeutics. For example, the antibodies provided can be employed for the prevention and/or spread of pathogenic disease, including, but not limited to the inhibition of viral transmission between subjects, inhibition of establishment of viral infection in a host, and reduction of viral load in a subject. The antibodies also can be employed for preventing, treating, and/or alleviating one or more symptoms of a RSV infection or for reducing the duration of a RSV infection. Accordingly, treatment of patients with antibodies provided herein can decrease the mortality and/or morbidity rate associated with RSV infection.

RSV persistence is associated with the generation of escape mutants that cannot be neutralized by an antibody. Thus, the main challenges to development of therapeutic anti-viral antibodies are the generation or identification of antibodies that have a neutralization epitope that is 1) conserved across various strains or serotypes and 2) is difficult for the evolving virus to generate escape mutants against. Antibodies provided herein bind to various RSV subgroups and strains. Antibodies provided herein also exhibit improved virus neutralization activity compared to existing antibodies in the prior art. The provided antibodies effectively neutralize virus over successive rounds of replication, where RSV typically would generate escape mutants to resist neutralization. The ability to limit the generation of MARMs means that the antibodies provided herein bind to an epitope that is less susceptible to variation in the form of generated escape mutants. This epitope, therefore, is different from epitopes of other known anti-RSV antibodies. Thus, the provided anti-RSV antibodies, in addition to prophylaxis therapy, also are useful for the treatment of RSV infection. Currently, there are no known approved antibody therapeutics against RSV infection. As such, the antibodies provided herein are especially important for treatment of RSV infection among elderly patients, for example those in group or retirement homes, where proximity increases the risk for viral spread among patients. Treatment with the antibodies provided herein is also important in situations where non-compliance with dosage regimes increases risk for viral escape, as non-compliance in the prophylaxis treatment of RSV with palivizumab is increasingly leading causing viral resistance (see, e.g., Adams et al., (2010) *Clin Infect Dis.* 51(2):185-188).

Generally, the anti-RSV antibodies provided herein bind to RSV F protein with high affinity. Compared to existing approved anti-RSV antibodies (e.g. palivizumab; SYNAGIS®), the high affinity anti-RSV antibodies provided herein allow for less frequent administration for preventing and/or treating a RSV infection, for preventing, treating, and/or alleviating one or more symptoms of a RSV infection, or for reducing the duration of a RSV infection. Thus, the anti-RSV antibodies provided herein are useful as therapeutic antibodies, i.e., for treatment of RSV infection. Less frequent administration allows easier compliance with dosing regimes and therefore lessens the possibility of missed dosages which lead to increased viral resistance to the anti-RSV antibody. Lower doses of antibodies that immunospecifically bind to RSV also can reduce the likelihood of adverse effects of immunoglobulin therapy.

Generally, the anti-RSV antibodies provided herein have the ability to inhibit or reduce one or more activities of the virus, such as, for example, association of the virus with a target cell membrane, fusion of the virus with the target cell membrane and/or cell entry, production of new viral particles, including inhibition of viral replication, or cell to cell fusion of an infected cell with another cell (i.e. syncytia formation). The provided anti-RSV antibodies also can be employed to increase the immune the response against a RSV infection.

1. Respiratory Syncytial Virus

Human RSV is a member of the Pneumovirus subfamily of the family Paramyxoviridae. There are two distinct subgroups of human RSV, group A and group B. Additionally, each subtype is further divided into two strains, A1 and A2, and B1 and B2. RSV is an enveloped, non-segmented, negative-sense RNA virus with a genome of composed of approximately 15,000 nucleotides that encode eleven viral proteins.

RSV encodes two major surface glycoproteins, glycoprotein G and glycoprotein F. Glycoprotein G, or the attachment protein, mediates virus binding to the cell receptor while glycoprotein F, or the fusion protein, promotes fusion of the viral and cell membranes, allowing penetration of the viral ribonucleoprotein into the cell cytoplasm (Lopez et al. (1998) *J. Virology* 72:6922-6928). Glycoprotein F also promotes fusion of the membranes of infected cells with those of adjacent cells leading to the formation of syncytia. The F protein contains two disulfide-linked subunits, $F_1$ and $F_2$, which are produced by proteolytic cleavage of an inactive, N-glycosylated precursor. The G protein is a 80-90 kDa type II transmembrane glycoprotein, containing N- and O-linked oligosaccharides attached to a 32 kDa precursor protein.

Antibodies prepared against RSV F or G glycoproteins have been shown to neutralize RSV with high efficiency in vitro and have prophylactic effects in vivo (see e.g., Walsh et al. (1986) *J. Gen. Microbiol.* 67:505; Beeler et al. (1989) *J. Virol.* 63:2941-2950, Garcia-Borreno et al. (1989) *J. Virol.* 63:925-932, Taylor et al. (1984) *Immunology* 52:137-142, and U.S. Pat. Nos. 5,824,307 and 6,818,216). Antibodies directed against RSV F protein also are effective in inhibiting fusion of RSV-infected cells with neighboring uninfected cells.

Analysis of various monoclonal antibodies that immunospecifically bind to the RSV F protein have led to the identification of three non-overlapping antigenic sites, A, B, and C and one bridge site. AB (Beeler et al. (1989) *J. Virol.* 63:2941-2950). Each of the antigenic sites contain distinct epitopes. In one study of a panel of 18 monoclonal antibodies, five epitopes of antigenic site A, four epitopes of antigenic site B, and four epitopes of antigenic site C were identified based on monoclonal antibody escape mutants (MARMs) (see, e.g., Beeler et al. (1989) *J. Virol.* 63:2941-2950). Monoclonal antibody 1129, which binds to antigenic site A epitope 4 (Beeler et al. (1989) *J. Virology* 63(7):2841-2950), is the parental antibody from which the humanized palivizumab (SYNAGIS®) was generated (see Johnson et al. (1997) *J. Infect. Diseases* 176:1215-1224 and U.S. Pat. No. 5,824,307). Additional RSV F protein epitopes also have been identified. For example, the human anti-RSV Fab fragment Fab 19 (see Barbas et al. (1992) *Proc. Natl. Acad Sci. USA* 89:10164-10168 and Crowe et al., (1994) *Proc. Natl. Acad Sci USA* 91:1386-1390) binds to an epitope in antigenic site A that differs from the epitopes identified by Beeler et al. (see Crowe et al. (1998) *Virology* 252:373-375) and Barbas et al. (1992) *Proc. Natl. Acad. Sci. USA* 89:10164-10168).

The RSV F protein exhibits over 91% similarity across the RSV A and B subgroups, while the RSV G protein exhibits only 53% amino acid similarity between the RSV A and RSV B subgroups (Sullender (2000) *Clin. Microbial Rev.* 13:1-15). Because A and B virus subtypes co-circulate in most RSV epidemics, an antibody that neutralizes A and B subtypes of RSV, such as the anti-RSV antibodies or antigen-binding fragments provided herein, is desirable.

Human RSV, like most RNA viruses, has the capacity of undergoing rapid mutations under selective pressure. The selection of RSV escape mutants (MARMs) in vitro using monoclonal antibodies is well documented (e.g. Garcia-Barreno et al. (1989) *J. Virol.* 63:925-932). For example, it has been shown that single amino acid mutations at amino acid residues N262, I266, N268, K272, S275, N276, P389 or R429, or double amino acid mutations at F32 and K272 or A241 and K421 in the RSV A2 F protein effect escape of known anti-RSV monoclonal antibodies (see, e.g., Crowe et al. (1998) *Virology* 252:373-375; Zhao et al., (2004) *J. Infectious Disease* 190:1941-1946 and Liu et al., (2007) *Virology Journal* 4:71). Additionally, palivizumab (SYNAGIS®) has been shown to select for escape mutants, in vitro as well as in vivo, and that some of the isolated mutants are completely resistant to palivizumab prophylaxis in cotton rats (see e.g., Zhao et al. (2005) *J. Virol.* 79:3962-3968 and Zhao et al. (2004) *J. Infect. Dis.* 190:1941-1946). For example, it has been demonstrated that a single amino acid mutation in the RSV F protein results in escape from palivizumab (see, Zhao et al., (2004) *J. Infectious Disease* 190:1941-1946). Thus, an antibody that effectively neutralizes the RSV virus over successive rounds of replication without generation of an escape mutant, such as the anti-RSV antibodies or antigen-binding fragments provided herein, is preferred.

RSV infection is a major cause of lower respiratory tract disease in infants and small children. RSV infection also is the most common cause of bronchiolitis, or inflammation of the small airways in the lung, and pneumonia in children under 1 year of age in the United States. In addition, RSV infection also is recognized as an important cause of respiratory illness in older adults. Symptoms and conditions associated with RSV infection include, for example, asthma, wheezing, reactive airway disease (RAD), and chronic obstructive pulmonary disease (COPD). Accordingly, as described herein, the anti-RSV antibodies provided herein can be employed for the prophylaxis and treatment of RSV infection and/or alleviation of one or more symptoms of such RSV-mediated diseases.

C. ANTI-RSV ANTIBODIES

Provided herein are anti-RSV antibodies or antigen-binding fragments thereof that can be employed for therapeutic, prophylactic and diagnostic use. The anti-RSV antibodies or antigen-binding fragments thereof provided herein can be used, for example, for passive immunization of a subject against RSV or for treatment of a subject with a viral infection. In one example, the anti-RSV antibodies or antigen-binding fragments thereof provided herein are used for prophylaxis, i.e., the prevention of RSV infection. In another example, the anti-RSV antibodies or antigen-binding fragments thereof provided herein are used as therapeutic antibodies, i.e., for treatment of a RSV viral infection. In yet another example, the anti-RSV antibodies or antigen-binding fragments thereof provided herein are used for passive immunization of a subject against RSV. The provided anti-RSV antibodies or antigen-binding fragments thereof also can be used for detection of a RSV infection or for monitoring RSV infection in vitro and in vivo.

1. General Antibody Structure and Functional Domains

Antibodies are produced naturally by B cells in membrane-bound and secreted forms. Antibodies specifically recognize and bind antigen epitopes through cognate interactions. Antibody binding to cognate antigens can initiate multiple effector functions, which cause neutralization and clearance of toxins, pathogens and other infectious agents.

Diversity in antibody specificity arises naturally due to recombination events during B cell development. Through these events, various combinations of multiple antibody V, D and J gene segments, which encode variable regions of antibody molecules, are joined with constant region genes to generate a natural antibody repertoire with large numbers of diverse antibodies. A human antibody repertoire contains more than $10^{10}$ different antigen specificities and thus theoretically can specifically recognize any foreign antigen. Antibodies include such naturally produced antibodies, as well as synthetically, i.e. recombinantly, produced antibodies, such as antibody fragments, including the anti-RSV antibodies or antigen-binding fragments thereof provided herein.

In folded antibody polypeptides, binding specificity is conferred by antigen-binding site domains, which contain portions of heavy and/or light chain variable region domains. Other domains on the antibody molecule serve effector functions by participating in events such as signal transduction and interaction with other cells, polypeptides and biomolecules. These effector functions cause neutralization and/or clearance of the infecting agent recognized by the antibody. Domains of antibody polypeptides can be varied according to the methods herein to alter specific properties.

a. Structural and Functional Domains of Antibodies

Full-length antibodies contain multiple chains, domains and regions. A full length conventional antibody contains two heavy chains and two light chains, each of which contains a plurality of immunoglobulin (Ig) domains. An Ig domain is characterized by a structure called the Ig fold, which contains two beta-pleated sheets, each containing anti-parallel beta strands connected by loops. The two beta sheets in the Ig fold are sandwiched together by hydrophobic interactions and a conserved intra-chain disulfide bond. The Ig domains in the antibody chains are variable (V) and constant (C) region domains. Each heavy chain is linked to a light chain by a disulfide bond, and the two heavy chains are linked to each other by disulfide bonds. Linkage of the heavy chains is mediated by a flexible region of the heavy chain, known as the hinge region.

Each full-length conventional antibody light chain contains one variable region domain ($V_L$) and one constant region domain ($C_L$). Each full-length conventional heavy chain contains one variable region domain ($V_H$) and three or four constant region domains ($C_H$) and, in some cases, hinge region. Owing to recombination events discussed above, nucleic acid sequences encoding the variable region domains differ among antibodies and confer antigen-specificity to a particular antibody. The constant regions, on the other hand, are encoded by sequences that are more conserved among antibodies. These domains confer functional properties to antibodies, for example, the ability to interact with cells of the immune system and serum proteins in order to cause clearance of infectious agents. Different classes of antibodies, for example IgM, IgD, IgG, IgE and IgA, have different constant regions, allowing them to serve distinct effector functions.

Each variable region domain contains three portions called complementarity determining regions (CDRs) or hypervariable (HV) regions, which are encoded by highly variable nucleic acid sequences. The CDRs are located within the loops connecting the beta sheets of the variable region Ig domain. Together, the three heavy chain CDRs (CDR1, CDR2 and CDR3) and three light chain CDRs (CDR1, CDR2 and CDR3) make up a conventional antigen-binding site (antibody combining site) of the antibody, which physically interacts with cognate antigen and provides the specificity of the antibody. A whole antibody contains two identical antibody combining sites, each made up of CDRs from one heavy and one light chain. Because they are contained within the loops connecting the beta strands, the three CDRs are non-contiguous along the linear amino acid sequence of the variable region. Upon folding of the antibody polypeptide, the CDR loops are in close proximity, making up the antigen combining site. The beta sheets of the variable region domains form the framework regions (FRs), which contain more conserved sequences that are important for other properties of the antibody, for example, stability.

b. Antibody Fragments

Antibodies provided herein include antibody fragments, which are derivatives of full-length antibody that contain less than the full sequence of the full-length antibodies but retain at least a portion specific binding abilities of the full-length antibody. The antibody fragments also can include antigen-binding portions of an antibody that can be inserted into an antibody framework (e.g., chimeric antibodies) in order to retain the binding affinity of the parent antibody. Examples of antibody fragments include, but are not limited to, Fab, Fab', F(ab')$_2$, single-chain Fv (scFv), Fv, dsFv, diabody, Fd and Fd' fragments, and other fragments, including modified fragments (see, for example, Methods in Molecular Biology, Vol 207: Recombinant Antibodies for Cancer Therapy Methods and Protocols (2003); Chapter 1; p 3-25, Kipriyanov). Antibody fragments can include multiple chains linked together, such as by disulfide bridges and can be produced recombinantly. Antibody fragments also can contain synthetic linkers, such as peptide linkers, to link two or more domains. Methods for generating antigen-binding fragments are well-known known in the art and can be used to modify any antibody provided herein. Fragments of antibody molecules can be generated, such as for example, by enzymatic cleavage. For example, upon protease cleavage by papain, a dimer of the heavy chain constant regions, the Fc domain, is cleaved from the two Fab regions (i.e. the portions containing the variable regions).

Single chain antibodies can be recombinantly engineered by joining a heavy chain variable region ($V_H$) and light chain variable region ($V_L$) of a specific antibody. The particular nucleic acid sequences for the variable regions can be cloned by standard molecular biology methods, such as, for example, by polymerase chain reaction (PCR) and other recombination nucleic acid technologies. Methods for producing sFvs are described, for example, by Whitlow and Filpula (1991) *Methods,* 2: 97-105; Bird et al. (1988) *Science* 242:423-426: Pack et al. (1993) Bio/Technology 11:1271-77; and U.S. Pat. Nos. 4,946,778, 5,840,300, 5,667, 988, 5,658,727, 5,258,498). Single chain antibodies also can be identified by screening single chain antibody libraries for binding to a target antigen. Methods for the construction and screening of such libraries are well-known in the art.

2. Exemplary Anti-RSV Antibodies

Provided herein are antibodies or antigen-binding fragments thereof that bind to and neutralize RSV. In particular the antibodies or antigen-binding fragments immunospecifically bind to a RSV F protein. For example, the anti-RSV antibodies provided herein immunospecifically bind to an isolated or purified or recombinant RSV F protein. In other examples, the anti-RSV antibodies provided herein immunospecifically bind to the RSV virion or RSV virus encoding surface glycoprotein F (RSV F protein).

The anti-RSV antibodies provided herein exhibit properties that are advantageous or different from anti-RSV antibodies in the art. For example, antibodies provided herein include anti-RSV antibodies that exhibit lower or improved binding affinity for RSV F protein, such an lower or improved binding affinity for an isolated or purified or recombinant RSV F protein or for the RSV virus or viron expressing native F protein. In other examples, antibodies provided herein include anti-RSV antibodies that exhibit an improved or better neutralization activity of RSV. In particular examples, anti-RSV antibodies provided herein include antibodies that bind to an epitope on RSV that is less susceptible to variation in the form of generated escape mutants (MARMs) compared to other prior art or existing anti-RSV antibodies. For example, in the presence of an anti-RSV antibody provided herein, for example the antibody 30D8 or a full-length or other antibody fragment form thereof, RSV is incapable of generating an escape mutant after more than 10 rounds of viral replication, and generally after more than 11, 12, 13, 14, 15, 16, 17, 18, 19 or 20 rounds.

Anti-RSV antibodies include the antibodies sc5 or 58c5, or full-length or other antibody fragment forms thereof (see e.g. U.S. Patent publication No. US2011/0076268 and International Published PCT Application No. WO2011/020079). 58c5 is a Fab fragment that contains a heavy chain having the amino sequence set forth in SEQ ID NO:1 and a light chain having the amino acid sequence set forth in SEQ ID NO:5. Antibody or antigen-fragment forms of 58c5 and that bind to the same epitope as 58c5 contain a heavy chain having complementarity determining regions (CDRs) $V_H$ CDR1 set forth as GASINSDNYYWT (SEQ ID NO:2) or SEQ ID NO:435, a $V_H$ CDR2 set forth as HISYTGN-TYYTPSLKS (SEQ ID NO:3), and a $V_H$ CDR3 set forth as CGAYVLISNCGWFDS (SEQ ID NO:4; and a light chain having CDRs $V_L$ CDR1 set forth as QASQDISTYLN (SEQ ID NO:6), a $V_L$ CDR2 set forth as GASNLET (SEQ ID NO:7), and a $V_L$ CDR3 set forth as QQYQYLPYT (SEQ ID NO:8). Generally, antibody fragment form of 58c5 include the VH domain having the amino acid sequence set forth in amino acids 1-125 of SEQ ID NO:1 and a VL domain having the amino acid sequence set forth in amino acids 1-107 of SEQ ID NO:5. sc5 is a Fab fragment that contains a heavy chain having the amino acid sequence set forth in SEQ ID NO:9 and a light chain having the amino acid sequence set forth in SEQ ID NO:13. Antibody or antigen-fragment forms of sc5 and that bind to the same epitope as sc5 contain a heavy chain having complementarity determining regions (CDRs) $V_H$ CDR1 set forth as GDSISGSNWWN (SEQ ID NO:10) or SEQ ID NO:436, a $V_H$ CDR2 set forth as EIYYRGTTNYKSSLKG (SEQ ID NO:11), and a $V_H$ CDR3 set forth as GGRSTFGPDYYYYMDV (SEQ ID NO:12); and a light chain having CDRs $V_L$ CDR1 set forth as RASQNIKNYLN (SEQ ID NO:14), a $V_L$ CDR2 set forth as AASTLQS (SEQ ID NO:15), and a $V_L$ CDR3 set forth as QQSYNNQLT (SEQ ID NO:16). Generally, antibody fragment form of sc5 includes the VH domain having the amino acid sequence set forth in amino acids 1-125 of SEQ ID NO:9 and a VL domain having the amino acid sequence set forth in amino acids 1-107 of SEQ ID NO:13.

The anti-RSV antibodies or antigen-binding fragments thereof provided herein include monoclonal antibodies, multispecific antibodies, bispecific antibodies, human antibodies, humanized antibodies, camelised antibodies, chimeric antibodies, single-chain Fvs (scFv), single chain antibodies, single domain antibodies, Fab fragments, F(ab') fragments, disulfide-linked Fvs (sdFv), and anti-idiotypic (anti-Id) antibodies, intrabodies, or antigen-binding fragments of any of the above. In particular, antibodies include immunoglobulin molecules and immunologically active fragments of immunoglobulin molecules, i.e., molecules that contain an antigen-binding site. Immunoglobulin molecules can be of any type (e.g., IgG, IgE, IgM, IgD, IgA and IgY), class (e.g., IgG1, IgG2, IgG3, IgG4, IgA1 and IgA2) or subclass.

The anti-RSV antibodies or antigen-binding fragments thereof provided herein can be used in the methods of treatment and diagnosis in forms that include monoclonal antibodies, multispecific antibodies, human antibodies, humanized antibodies, camelised antibodies, chimeric antibodies, single-chain Fvs (scFv), single chain antibodies, single domain antibodies, Fab fragments, F(ab') fragments, disulfide-linked Fvs (sdFv), and anti-idiotypic (anti-Id) antibodies, intrabodies, or antigen-binding fragments of any of the above. In particular, the antibodies include immunoglobulin molecules and immunologically active fragments of immunoglobulin molecules, i.e., molecules that contain an antigen-binding site. Immunoglobulin molecules can be of any type (e.g., IgG, IgE, IgM, IgD, IgA and IgY), class (e.g., IgG1, IgG2, IgG3, IgG4, IgA1 and IgA2) or subclass.

Exemplary anti-RSV antibodies or antigen-binding fragments thereof provided herein that immunospecifically bind to a RSV F protein include 30D8, 104E5, 38F10, 14G3, 90D3, 56E11, 17C9 and 69F6, which are Fab fragments described in detail elsewhere herein. Exemplary anti-RSV antibodies or antigen-binding fragments thereof provided herein also include anti-RSV antibodies or antigen-binding fragments thereof that contain a heavy chain, which contains a variable heavy ($V_H$) domain and a constant heavy domain 1 ($C_H1$) and/or a light chain, which contains a variable light ($V_L$) domain and a constant light domain ($C_L$) of 30D8, 104E5, 38F10, 14G3, 90D3, 56E11, 17C9 or 69F6. For example, exemplary anti-RSV antibodies or antigen-binding fragments thereof provided herein include anti-RSV antibodies or antigen-binding fragments thereof that contain a heavy chain having the amino acid sequence set forth in SEQ ID NO:396, 398, 400, 402, 404, 452, 454 or 456 and/or a light chain having the amino acid sequence set forth in SEQ ID NO:395, 397, 399, 401, 403, 453, 455 or 457. In a particular example, the anti-RSV antibody is a Fab fragment that contains a heavy chain having the amino acid sequence set forth in SEQ ID NO:396 and a light chain having the amino acid sequence set forth in SEQ ID NO:395. In a particular example, the anti-RSV antibody is a Fab fragment that contains a heavy chain having the amino acid sequence set forth in SEQ ID NO:398 and a light chain having the amino acid sequence set forth in SEQ ID NO:397. In a particular example, the anti-RSV antibody is a Fab fragment that contains a heavy chain having the amino acid sequence set forth in SEQ ID NO:400 and a light chain having the amino acid sequence set forth in SEQ ID NO:399. In a particular example, the anti-RSV antibody is a Fab fragment that contains a heavy chain having the amino acid sequence set forth in SEQ ID NO:402 and a light chain having the amino acid sequence set forth in SEQ ID NO:401. In a particular example, the anti-RSV antibody is a Fab fragment that contains a heavy chain having the amino acid sequence set forth in SEQ ID NO:404 and a light chain having the amino acid sequence set forth in SEQ ID NO:403. In a particular example, the anti-RSV antibody is a Fab fragment that contains a heavy chain having the amino acid sequence set forth in SEQ ID NO:452 and a light chain having the amino acid sequence set forth in SEQ ID NO:453. In a particular example, the anti-RSV antibody is a Fab fragment that contains a heavy chain having the amino acid sequence set forth in SEQ ID NO:454 and a light chain having the amino acid sequence set forth in SEQ ID NO:455. In a particular example, the anti-RSV antibody is a Fab fragment that contains a heavy chain having the amino acid sequence set forth in SEQ ID NO:456 and a light chain having the amino acid sequence set forth in SEQ ID NO:457.

The antibodies provided herein include full-length antibody forms of 30D8, 104E5, 38F10, 14G3, 90D3, 56E11, 17C9 or 69F6. The antibodies provided herein also include full-length antibody forms containing the antigen-binding site (e.g. CDRs) of 30D8, 104E5, 38F10, 14G3, 90D3, 56E11, 17C9 or 69F6. Full-length anti-RSV antibodies or antigen-binding fragments thereof provided herein can contain any light chain and heavy chain constant region known in the art, such as any human constant region known in the art. For example, full-length antibodies provided herein can contain a light chain constant region (CL) that is a human light chain kappa (κ), human light chain lambda (λ). Full-length antibodies provided herein can contain a heavy chain constant region ($C_H1$-linker-$C_H2$-$C_H3$) that is of any isotype, and in particular that is an IgG. The constant region can be the constant region of subclass IgG1 (SEQ ID NO:356), the constant region of IgG2 (SEQ ID NO:357), the constant region of IgG3 (SEQ ID NO:358) or the constant region of IgG4 (SEQ ID NO:359). In particular, full-length antibody forms of any of the antibodies provided herein contain the constant region of IgG, subclass IgG1.

The antibodies provided herein include other antibody fragment forms of 30D8, 104E5, 38F10, 14G3, 90D3, 56E11, 17C9 and 69F6 that immunospecifically bind an RSV F protein. Such fragments include any antigen-binding fragment thereof or an engineered antibody containing an antigen-binding fragment(s) of 30D8, 104E5, 38F10, 14G3, 90D3, 56E11, 17C9 or 69F6 that retains the ability to bind an RSV F protein. Such antibodies include, for example, chimeric antibodies, single-chain Fvs (scFv), single chain antibodies, single domain antibodies, Fab fragments, F(ab') fragments, disulfide-linked Fvs (sdFv), anti-idiotypic (anti-Id) antibodies, intrabodies, or antigen-binding fragments of any of the above. In particular examples, the antibody is the Fab 30D8, 104E5, 38F10, 14G3, 90D3, 56E11, 17C9 or 69F6.

Exemplary anti-RSV antibodies or antigen-binding fragments thereof provided herein include anti-RSV antibodies or antigen-binding fragments thereof that contain a $V_H$ domain and/or a variable light $V_L$ domain having an amino acid sequence of the $V_H$ domain and/or $V_L$ domain, respectively, of 30D8, 104E5, 38F10, 14G3, 90D3, 56E11, 17C9 or 69F6. For example, an antibody or antigen-binding fragment thereof can contain a $V_H$ domain having the amino acid sequence set forth in amino acids 1-125 of SEQ ID NO:398 or 402, amino acids 1-121 of SEQ ID NO:396, amino acids 1-123 of SEQ ID NO:404, amino acids 1-124 of SEQ ID NO:400 or 452, amino acids 1-133 of SEQ ID NO:454 or amino acids 1-118 of SEQ ID NO:456 and/or a $V_L$ domain having the amino acid sequence set forth in amino acids 1-107 of SEQ ID NO: 397, 403 or 455, amino acids 1-108 of SEQ ID NO:399, amino acids 1-110 of SEQ ID NO:395, amino acids 1-113 of SEQ ID NO:401, amino acids 1-111 of SEQ ID NO:453 or amino acids 1-109 of SEQ ID NO:457.

Exemplary anti-RSV antibodies or antigen-binding fragments thereof provided herein include anti-RSV antibodies or antigen-binding fragments thereof that contain a $V_H$ domain and/or a $V_L$ domain having an amino acid sequence that is at least or about 80% identical to the $V_H$ domain and/or $V_L$ domain, respectively, of 30D8, 104E5, 38F10, 14G3, 90D3, 56E11, 17C9 or 69F6. For example, the antibody or antigen-binding fragment thereof provided herein can contain a $V_H$ domain having the amino acid sequence that is 80% identical to the amino acid sequence set forth in amino acids 1-125 of SEQ ID NO:398 or 402, amino acids 1-121 of SEQ ID NO:396, amino acids 1-123 of SEQ ID NO:404, amino acids 1-124 of SEQ ID NO:400 or 452, amino acids 1-133 of SEQ ID NO:454 or amino acids 1-118 of SEQ ID NO:456 and/or a $V_L$ domain having the amino acid sequence set forth in amino acids 1-107 of SEQ ID NO:397, 403 or 455, amino acids 1-108 of SEQ ID NO:399, amino acids 1-110 of SEQ ID NO:395, amino acids 1-113 of SEQ ID NO:401, amino acids 1-111 of SEQ ID NO:453 or amino acids 1-109 of SEQ ID NO:457.

In some examples, the anti-RSV antibody or antigen-binding fragment thereof provided herein can contain a $V_H$ domain having the amino acid sequence that is at least or about 81%, at least or about 82%, at least or about 83%, at least or about 84%, at least or about 85%, at least or about 86%, at least or about 87%, at least or about 88%, at least or about 89%, at least or about 90%, at least or about 91%, at least or about 92%, at least or about 93%, at least or about 94%, at least or about 95%, at least or about 96%, at least or about 97%, at least or about 98%, or at least or about 99% identical to the amino acid sequence set forth in amino acids 1-125 of SEQ ID NO:398 or 402, amino acids 1-121 of SEQ ID NO:396, amino acids 1-123 of SEQ ID NO:404, amino acids 1-124 of SEQ ID NO:400 or 452, amino acids 1-133 of SEQ ID NO:454 or amino acids 1-118 of SEQ ID NO:456 and/or a $V_L$ domain having the amino acid sequence that is at least or about 81%, at least or about 82%, at least or about 83%, at least or about 84%, at least or about 85%, at least or about 86%, at least or about 87%, at least or about 88%, at least or about 89%, at least or about 90%, at least or about 91%, at least or about 92%, at least or about 93%, at least or about 94%, at least or about 95%, at least or about 96%, at least or about 97%, at least or about 98%, or at least or about 99% identical to the amino acid sequence set forth in amino acids 1-107 of SEQ ID NO:397, 403 or 455, amino acids 1-108 of SEQ ID NO:399, amino acids 1-110 of SEQ ID NO:395, amino acids 1-113 of SEQ ID NO:401, amino acids 1-111 of SEQ ID NO:453 or amino acids 1-109 of SEQ ID NO:457.

Thus, provided herein is an antibody or antigen-binding fragment thereof that contains a $V_H$ domain having an amino acid sequence that is at least or that is about 80% to 99% identical, for example, 90% to 99% or at least 95% identical, such as 81%, 82%, 83%, 84%, 85%, 86%, 87%, 88%, 89%, 90%, 91%, 92%, 93%, 94%, 95%, 96%, 97%, 98% or 99% identical to the amino acid sequence set forth in amino acids 1-121 of SEQ ID NO:396 and that contains a $V_L$ domain having the amino acid sequence that is at least or that is about 80% to 99% identical, for example, 90% to 99% or at least 95% identical, such as 81%, 82%, 83%, 84%, 85%, 86%, 87%, 88%, 89%, 90%, 91%, 92%, 93%, 94%, 95%, 96%, 97%, 98% or 99% identical to the amino acid sequence set forth in amino acids 1-110 of SEQ ID NO:395.

Thus, provided herein is an antibody or antigen-binding fragment thereof that contains a $V_H$ domain having an amino acid sequence that is at least or that is about 80% to 99% identical, for example, 90% to 99% or at least 95% identical, such as 81%, 82%, 83%, 84%, 85%, 86%, 87%, 88%, 89%, 90%, 91%, 92%, 93%, 94%, 95%, 96%, 97%, 98% or 99% identical to the amino acid sequence set forth in amino acids 1-125 of SEQ ID NO:398 and that contains a $V_L$ domain having the amino acid sequence that is at least or that is about 80% to 99% identical, for example, 90% to 99% or at least 95% identical, such as 81%, 82%, 83%, 84%, 85%, 86%, 87%, 88%, 89%, 90%, 91%, 92%, 93%, 94%, 95%, 96%, 97%, 98% or 99% identical to the amino acid sequence set forth in amino acids 1-107 of SEQ ID NO:397.

Thus, provided herein is an antibody or antigen-binding fragment thereof that contains a $V_H$ domain having an amino acid sequence that is at least or that is about 80% to 99% identical, for example, 90% to 99% or at least 95% identical, such as 81%, 82%, 83%, 84%, 85%, 86%, 87%, 88%, 89%, 90%, 91%, 92%, 93%, 94%, 95%, 96%, 97%, 98% or 99% identical to the amino acid sequence set forth in amino acids 1-124 of SEQ ID NO:400 and that contains a $V_L$ domain having the amino acid sequence that is at least or that is about 80% to 99% identical, for example, 90% to 99% or at least 95% identical, such as 81%, 82%, 83%, 84%, 85%, 86%, 87%, 88%, 89%, 90%, 91%, 92%, 93%, 94%, 95%, 96%, 97%, 98% or 99% identical to the amino acid sequence set forth in amino acids 1-108 of SEQ ID NO:399.

Thus, provided herein is an antibody or antigen-binding fragment thereof that contains a $V_H$ domain having an amino acid sequence that is at least or that is about 80% to 99% identical, for example, 90% to 99% or at least 95% identical, such as 81%, 82%, 83%, 84%, 85%, 86%, 87%, 88%, 89%, 90%, 91%, 92%, 93%, 94%, 95%, 96%, 97%, 98% or 99% identical to the amino acid sequence set forth in amino acids 1-125 of SEQ ID NO:402 and that contains a $V_L$ domain having the amino acid sequence that is at least or that is about 80% to 99% identical, for example, 90% to 99% or at least 95% identical, such as 81%, 82%, 83%, 84%, 85%, 86%, 87%, 88%, 89%, 90%, 91%, 92%, 93%, 94%, 95%, 96%, 97%, 98% or 99% identical to the amino acid sequence set forth in amino acids 1-113 of SEQ ID NO:401.

Thus, provided herein is an antibody or antigen-binding fragment thereof that contains a $V_H$ domain having an amino acid sequence that is at least or that is about 80% to 99% identical, for example, 90% to 99% or at least 95% identical, such as 81%, 82%, 83%, 84%, 85%, 86%, 87%, 88%, 89%, 90%, 91%, 92%, 93%, 94%, 95%, 96%, 97%, 98% or 99% identical to the amino acid sequence set forth in amino acids 1-123 of SEQ ID NO:404 and that contains a $V_L$ domain having the amino acid sequence that is at least or that is about 80% to 99% identical, for example, 90% to 99% or at least 95% identical, such as 81%, 82%, 83%, 84%, 85%, 86%, 87%, 88%, 89%, 90%, 91%, 92%, 93%, 94%, 95%, 96%, 97%, 98% or 99% identical to the amino acid sequence set forth in amino acids 1-107 of SEQ ID NO:403.

Thus, provided herein is an antibody or antigen-binding fragment thereof that contains a $V_H$ domain having an amino acid sequence that is at least or that is about 80% to 99% identical, for example, 90% to 99% or at least 95% identical, such as 81%, 82%, 83%, 84%, 85%, 86%, 87%, 88%, 89%, 90%, 91%, 92%, 93%, 94%, 95%, 96%, 97%, 98% or 99% identical to the amino acid sequence set forth in amino acids 1-124 of SEQ ID NO:452 and that contains a $V_L$ domain having the amino acid sequence that is at least or that is about 80% to 99% identical, for example, 90% to 99% or at least 95% identical, such as 81%, 82%, 83%, 84%, 85%, 86%, 87%, 88%, 89%, 90%, 91%, 92%, 93%, 94%, 95%, 96%, 97%, 98% or 99% identical to the amino acid sequence set forth in amino acids 1-111 of SEQ ID NO:453.

Thus, provided herein is an antibody or antigen-binding fragment thereof that contains a $V_H$ domain having an amino acid sequence that is at least or that is about 80% to 99% identical, for example, 90% to 99% or at least 95% identical, such as 81%, 82%, 83%, 84%, 85%, 86%, 87%, 88%, 89%, 90%, 91%, 92%, 93%, 94%, 95%, 96%, 97%, 98% or 99% identical to the amino acid sequence set forth in amino acids 1-133 of SEQ ID NO:454 and that contains a $V_L$ domain having the amino acid sequence that is at least or that is about 80% to 99% identical, for example, 90% to 99% or at least 95% identical, such as 81%, 82%, 83%, 84%, 85%, 86%, 87%, 88%, 89%, 90%, 91%, 92%, 93%, 94%, 95%, 96%, 97%, 98% or 99% identical to the amino acid sequence set forth in amino acids 1-107 of SEQ ID NO:455.

Thus, provided herein is an antibody or antigen-binding fragment thereof that contains a $V_H$ domain having an amino acid sequence that is at least or that is about 80% to 99% identical, for example, 90% to 99% or at least 95% identical, such as 81%, 82%, 83%, 84%, 85%, 86%, 87%, 88%, 89%, 90%, 91%, 92%, 93%, 94%, 95%, 96%, 97%, 98% or 99% identical to the amino acid sequence set forth in amino acids 1-118 of SEQ ID NO:456 and that contains a $V_L$ domain having the amino acid sequence that is at least or that is about 80% to 99% identical, for example, 90% to 99% or at least 95% identical, such as 81%, 82%, 83%, 84%, 85%, 86%, 87%, 88%, 89%, 90%, 91%, 92%, 93%, 94%, 95%, 96%, 97%, 98% or 99% identical to the amino acid sequence set forth in amino acids 1-109 of SEQ ID NO:457.

Also provided are anti-RSV antibodies or antigen-binding fragments thereof that contain one or more $V_H$ complementarity determining regions (CDRs) selected from among the CDRs of 30D8, 104E5, 38F10, 14G3, 90D3, 56E11, 17C9 or 69F6. For example, the anti-RSV antibody or antigen-binding fragment thereof can contain a $V_H$ CDR1 having the amino acid sequence set forth in SEQ ID NOS:405, 411, 417, 423, 429, 437-441, 458, 464, 470 or 482-484. For example, the anti-RSV antibody or antigen-binding fragment thereof can contain a $V_H$ CDR1 having the amino acid sequence GFTFSGHTIA (SEQ ID NO:405), GGTFDTYTIS (SEQ ID NO:411), GFSITDFGIH (SEQ ID NO:417), GASISSDNHYWS (SEQ ID NO:423), GFTLKNYEMN (SEQ ID NO:429), GHTIA (SEQ ID NO:437), TYTIS (SEQ ID NO:438), DFGIH (SEQ ID NO:439), SDNHYWS (SEQ ID NO:440), NYEMN (SEQ ID NO:441), GVSINSNNY-FWA (SEQ ID NO:458), GDSFNDYFWT (SEQ ID NO:464), GYSFTSYWIA (SEQ ID NO:470), SNNYFWA (SEQ ID NO:482), DYFWT (SEQ ID NO:483) or SYWIA (SEQ ID NO:484).

In another example, the anti-RSV antibody or antigen-binding fragment thereof can contain a $V_H$ CDR2 having the amino acid sequence set forth in SEQ ID NOS:406, 412, 418, 424, 430, 459, 465 or 471. For example, the anti-RSV antibody or antigen-binding fragment thereof can contain a V<sub>H</sub> CDR2 having the amino acid sequence WVSTNNGN-TEYAQKIQG (SEQ ID NO:406), RIIPSLGETNYAH-KLQG (SEQ ID NO:412), LISYNEVNIHYGESVRG (SEQ ID NO:418), SIYYTGGTNYNPSLKS (SEQ ID NO:424), YISSSGNVVKYVDSVQG (SEQ ID NO:430). NIYYGGSTHYNASLQS (SEQ ID NO:459), EISHSGST-NYSPSLKS (SEQ ID NO:465) or IIFPNDSDATYSPSFQG (SEQ ID NO:471).

In another example, the anti-RSV antibody or antigen-binding fragment thereof can contain a V<sub>H</sub> CDR3 having the amino acid sequence set forth in SEQ ID NOS:407, 413, 419, 425, 431, 460, 466 or 472. For example, the anti-RSV antibody or antigen-binding fragment thereof can contain a V<sub>H</sub> CDR3 having the amino acid sequence EWLVMG-GFAFDH (SEQ ID NO:407), RITGPVDWVWDYGMDV (SEQ ID NO:413), DVWEDSWLSLACFQE (SEQ ID NO:419), GLFFITARPYWYFDL (SEQ ID NO:425) or GFSIDKYDSSVDEY (SEQ ID NO:431), SESIF-WDYYYGLDV (SEQ ID NO:460), GVRSRP-PPSYRGSGSPPYYHYGMDV (SEQ ID NO:466) or QYYLGSFES (SEQ ID NO:472).

In one particular example, the anti-RSV antibody or antigen-binding fragment thereof contains a V<sub>H</sub> CDR1 having the amino acid sequence set forth in SEQ ID NO:405, a V<sub>H</sub> CDR2 having the amino acid sequence set forth in SEQ ID NO:406, and a V<sub>H</sub> CDR3 having the amino acid sequence set forth in SEQ ID NO:407. In another particular example, the anti-RSV antibody or antigen-binding fragment thereof contains a V<sub>H</sub> CDR1 having the amino acid sequence set forth in SEQ ID NO:437, a V<sub>H</sub> CDR2 having the amino acid sequence set forth in SEQ ID NO:406, and a V<sub>H</sub> CDR3 having the amino acid sequence set forth in SEQ ID NO:407.

In one particular example, the anti-RSV antibody or antigen-binding fragment thereof contains a V<sub>H</sub> CDR1 having the amino acid sequence set forth in SEQ ID NO:411, a V<sub>H</sub> CDR2 having the amino acid sequence set forth in SEQ ID NO:412, and a V<sub>H</sub> CDR3 having the amino acid sequence set forth in SEQ ID NO:413. In another particular example, the anti-RSV antibody or antigen-binding fragment thereof contains a V<sub>H</sub> CDR1 having the amino acid sequence set forth in SEQ ID NO:438, a V<sub>H</sub> CDR2 having the amino acid sequence set forth in SEQ ID NO:412, and a V<sub>H</sub> CDR3 having the amino acid sequence set forth in SEQ ID NO:413.

In one particular example, the anti-RSV antibody or antigen-binding fragment thereof contains a V<sub>H</sub> CDR1 having the amino acid sequence set forth in SEQ ID NO:417, a V<sub>H</sub> CDR2 having the amino acid sequence set forth in SEQ ID NO:418, and a V<sub>H</sub> CDR3 having the amino acid sequence set forth in SEQ ID NO:419. In another particular example, the anti-RSV antibody or antigen-binding fragment thereof contains a V<sub>H</sub> CDR1 having the amino acid sequence set forth in SEQ ID NO:439, a V<sub>H</sub> CDR2 having the amino acid sequence set forth in SEQ ID NO:418, and a V<sub>H</sub> CDR3 having the amino acid sequence set forth in SEQ ID NO:419.

In one particular example, the anti-RSV antibody or antigen-binding fragment thereof contains a V<sub>H</sub> CDR1 having the amino acid sequence set forth in SEQ ID NO:423, a V<sub>H</sub> CDR2 having the amino acid sequence set forth in SEQ ID NO:424, and a V<sub>H</sub> CDR3 having the amino acid sequence set forth in SEQ ID NO:425. In another particular example, the anti-RSV antibody or antigen-binding fragment thereof contains a V<sub>H</sub> CDR1 having the amino acid sequence set forth in SEQ ID NO:440, a V<sub>H</sub> CDR2 having the amino acid sequence set forth in SEQ ID NO:424, and a V<sub>H</sub> CDR3 having the amino acid sequence set forth in SEQ ID NO:425.

In one particular example, the anti-RSV antibody or antigen-binding fragment thereof contains a V<sub>H</sub> CDR1 having the amino acid sequence set forth in SEQ ID NO:429, a V<sub>H</sub> CDR2 having the amino acid sequence set forth in SEQ ID N0:430, and a V<sub>H</sub> CDR3 having the amino acid sequence set forth in SEQ ID NO:431. In another particular example, the anti-RSV antibody or antigen-binding fragment thereof contains a V<sub>H</sub> CDR1 having the amino acid sequence set forth in SEQ ID NO:441, a V<sub>H</sub> CDR2 having the amino acid sequence set forth in SEQ ID NO:430, and a V<sub>H</sub> CDR3 having the amino acid sequence set forth in SEQ ID NO:431.

In one particular example, the anti-RSV antibody or antigen-binding fragment thereof contains a V<sub>H</sub> CDR1 having the amino acid sequence set forth in SEQ ID NO:458, a V<sub>H</sub> CDR2 having the amino acid sequence set forth in SEQ ID NO:459, and a V<sub>H</sub> CDR3 having the amino acid sequence set forth in SEQ ID NO:460. In another particular example, the anti-RSV antibody or antigen-binding fragment thereof contains a V<sub>H</sub> CDR1 having the amino acid sequence set forth in SEQ ID NO:482, a V<sub>H</sub> CDR2 having the amino acid sequence set forth in SEQ ID NO:459, and a V<sub>H</sub> CDR3 having the amino acid sequence set forth in SEQ ID NO:460.

In one particular example, the anti-RSV antibody or antigen-binding fragment thereof contains a V<sub>H</sub> CDR1 having the amino acid sequence set forth in SEQ ID NO:464, a V<sub>H</sub> CDR2 having the amino acid sequence set forth in SEQ ID NO:465, and a V<sub>H</sub> CDR3 having the amino acid sequence set forth in SEQ ID NO:466. In another particular example, the anti-RSV antibody or antigen-binding fragment thereof contains a V<sub>H</sub> CDR1 having the amino acid sequence set forth in SEQ ID NO:483, a V<sub>H</sub> CDR2 having the amino acid sequence set forth in SEQ ID NO:465, and a V<sub>H</sub> CDR3 having the amino acid sequence set forth in SEQ ID NO:466.

In one particular example, the anti-RSV antibody or antigen-binding fragment thereof contains a V<sub>H</sub> CDR1 having the amino acid sequence set forth in SEQ ID NO:470, a V<sub>H</sub> CDR2 having the amino acid sequence set forth in SEQ ID NO:471, and a V<sub>H</sub> CDR3 having the amino acid sequence set forth in SEQ ID NO:472. In another particular example, the anti-RSV antibody or antigen-binding fragment thereof contains a V<sub>H</sub> CDR1 having the amino acid sequence set forth in SEQ ID NO:484, a V<sub>H</sub> CDR2 having the amino acid sequence set forth in SEQ ID NO:471, and a V<sub>H</sub> CDR3 having the amino acid sequence set forth in SEQ ID NO:472.

Also provided are anti-RSV antibodies or antigen-binding fragments thereof that contain one or more V<sub>L</sub> complementarity determining regions (CDRs) selected from among the CDRs of 30D8, 104E5, 38F10, 14G3, 90D3, 56E11, 17C9 or 69F6. For example, the anti-RSV antibody or antigen-binding fragment thereof can contain a V<sub>L</sub> CDR1 having the amino acid sequence set forth in SEQ ID NOS:408, 414, 420, 426, 432, 461, 467 or 473. For example, the anti-RSV antibody or antigen-binding fragment thereof can contain a V<sub>L</sub> CDR1 having the amino acid sequence GANNIG-SQNVH (SEQ ID NO:408), RASQNIKTYLN (SEQ ID NO:414), RASQSISNWLA (SEQ ID NO:420), RSSQSLLDSDDGNTYLD (SEQ ID NO:426), RASQSIS-NFLN (SEQ ID NO:432), TGTSSDVGGYNYVS (SEQ ID NO:461), RASQNINTWLA (SEQ ID NO:467) or QASDIS-NYLN (SEQ ID NO:473).

In another example, the anti-RSV antibody or antigen-binding fragment thereof can contain a $V_L$ CDR2 having the amino acid sequence set forth in SEQ ID NOS:409, 415, 421, 427, 433, 462, 468 or 474. For example, the anti-RSV antibody or antigen-binding fragment thereof can contain a $V_L$ CDR2 having the amino acid sequence DDRDRPS(SEQ ID NO:409), AVSNLQS (SEQ ID NO:415), KASNLED (SEQ ID NO:421), TLSYRAS (SEQ ID NO:427), AASSLQG (SEQ ID NO:433), EVTKRPS (SEQ ID NO:462), AASFLQS(SEQ ID NO:468) or DASYLDT (SEQ ID NO:474).

In another example, the anti-RSV antibody or antigen-binding fragment thereof can contain a $V_L$ CDR3 having the amino acid sequence set forth in SEQ ID NOS:410, 416, 422, 428, 434, 463, 469 or 475. For example, the anti-RSV antibody or antigen-binding fragment thereof can contain a $V_L$ CDR3 having the amino acid sequence QVWDSSRDQAVI (SEQ ID NO:410), QQSFSIPLT (SEQ ID NO:416), QQYNSYSGLS (SEQ ID NO:422), MQRMEFPFT (SEQ ID NO:428), QQTYISLYT (SEQ ID NO:434), SSYAGSRHVV (SEQ ID NO:463), QQANSFPRT (SEQ ID NO:469) or QQYDDLRGGFT (SEQ ID NO:475).

In one particular example, the anti-RSV antibody or antigen-binding fragment thereof contains a $V_L$ CDR1 having the amino acid sequence set forth in SEQ ID NO:408, a $V_L$ CDR2 having the amino acid sequence set forth in SEQ ID NO:409, and a $V_L$ CDR3 having the amino acid sequence set forth in SEQ ID NO:410. In another particular example, the anti-RSV antibody or antigen-binding fragment thereof contains a $V_L$ CDR1 having the amino acid sequence set forth in SEQ ID NO:414, a $V_L$ CDR2 having the amino acid sequence set forth in SEQ ID NO:415, and a $V_L$ CDR3 having the amino acid sequence set forth in SEQ ID NO:416. In another particular example, the anti-RSV antibody or antigen-binding fragment thereof contains a $V_L$ CDR1 having the amino acid sequence set forth in SEQ ID NO:420, a $V_L$ CDR2 having the amino acid sequence set forth in SEQ ID NO:421, and a $V_L$ CDR3 having the amino acid sequence set forth in SEQ ID NO:422.

In another particular example, the anti-RSV antibody or antigen-binding fragment thereof contains a $V_L$ CDR1 having the amino acid sequence set forth in SEQ ID NO:426, a $V_L$ CDR2 having the amino acid sequence set forth in SEQ ID NO:427, and a $V_L$ CDR3 having the amino acid sequence set forth in SEQ ID NO:428. In another particular example, the anti-RSV antibody or antigen-binding fragment thereof contains a $V_L$ CDR1 having the amino acid sequence set forth in SEQ ID NO:432, a $V_L$ CDR2 having the amino acid sequence set forth in SEQ ID NO:433, and a $V_L$ CDR3 having the amino acid sequence set forth in SEQ ID NO:434. In another particular example, the anti-RSV antibody or antigen-binding fragment thereof contains a $V_L$ CDR1 having the amino acid sequence set forth in SEQ ID NO:461, a $V_L$ CDR2 having the amino acid sequence set forth in SEQ ID NO:462, and a $V_L$ CDR3 having the amino acid sequence set forth in SEQ ID NO:463. In another particular example, the anti-RSV antibody or antigen-binding fragment thereof contains a $V_L$ CDR1 having the amino acid sequence set forth in SEQ ID NO:467, a $V_L$ CDR2 having the amino acid sequence set forth in SEQ ID NO:468, and a $V_L$ CDR3 having the amino acid sequence set forth in SEQ ID NO:469. In another particular example, the anti-RSV antibody or antigen-binding fragment thereof contains a $V_L$ CDR1 having the amino acid sequence set forth in SEQ ID NO:473, a $V_L$ CDR2 having the amino acid sequence set forth in SEQ ID NO:474, and a $V_L$ CDR3 having the amino acid sequence set forth in SEQ ID NO:475.

Any combination of CDRs provided herein can be selected for the generation of an antibody or antigen-binding fragment thereof, provided that the antibody or antigen-binding fragment retains the ability to immunospecifically bind to a RSV F protein. The anti-RSV antibodies or antigen-binding fragments thereof can contain an antibody framework region known in the art. Exemplary framework regions include isolated naturally occurring or consensus framework regions, including human framework regions (see, e.g., Chothia et al. (1998) *J. Mol. Biol.* 278: 457-479). In some examples, the antibody framework region is a human antibody framework region. In some examples, the antibody or antigen-binding fragment contains a framework region of 30D8, 104E5, 38F10, 14G3, 90D3, 56E11, 17C9 or 69F6.

Exemplary isolated anti-RSV antibodies or antigen-binding fragments thereof provided herein include any anti-RSV antibody or antigen-binding fragments thereof that immunospecifically binds to the same epitope on a RSV fusion (F) protein as any of the antibodies provided herein. In one example, provided herein is an antibody that binds to the same epitope as 30D8, which is the antibody that contains a heavy chain set forth in SEQ ID NO:396 and a light chain set forth in SEQ ID NO:395. In another example, provided herein is an antibody that binds to the same epitope as 104E5, which is the antibody that contains a heavy chain set forth in SEQ ID NO:398 and a light chain set forth in SEQ ID NO:397. In another example, provided herein is an antibody that binds to the same epitope as 38F10, which is the antibody that contains a heavy chain set forth in SEQ ID NO:400 and a light chain set forth in SEQ ID NO:399. In another example, provided herein is an antibody that binds to the same epitope as 14G3, which is the antibody that contains a heavy chain set forth in SEQ ID NO:402 and a light chain set forth in SEQ ID NO:401. In another example, provided herein is an antibody that binds to the same epitope as 90D3, which is the antibody that contains a heavy chain set forth in SEQ ID NO:404 and a light chain set forth in SEQ ID NO:403. In another example, provided herein is an antibody that binds to the same epitope as 56E11, which is the antibody that contains a heavy chain set forth in SEQ ID NO:452 and a light chain set forth in SEQ ID NO:453. In another example, provided herein is an antibody that binds to the same epitope as 17C9, which is the antibody that contains a heavy chain set forth in SEQ ID NO:454 and a light chain set forth in SEQ ID NO:455. In another example, provided herein is an antibody that binds to the same epitope as 69F6, which is the antibody that contains a heavy chain set forth in SEQ ID NO:456 and a light chain set forth in SEQ ID NO:457. Typically, such antibodies contain a variable heavy ($V_H$) chain and a variable light ($V_L$) chain or antigen-binding fragments thereof.

The antibodies or antigen binding fragments provided herein exhibit a binding affinity constant ($K_a$) for the RSV F protein epitope of at least or about $1 \times 10^8$ $M^{-1}$, at least or about $2.5 \times 10^8$ $M^{-1}$, at least or about $5 \times 10^8$ $M^{-1}$, at least or about $1 \times 10^9$ $M^{-1}$, at least or about $5 \times 10^9$ $M^{-1}$, at least or about $1 \times 10^{10}$ $M^{-1}$, at least or about $5 \times 10^{10}$ $M^{-1}$, at least or about $1 \times 10^{11}$ $M^{-1}$, at least or about $5 \times 10^{11}$ $M^{-1}$, at least or about $1 \times 10^{12}$ $M^{-1}$, at least or about $5 \times 10^{12}$ $M^{-1}$, at least or about $1 \times 10^{13}$ $M^{-1}$, at least or about $5 \times 10^{13}$ $M^{-1}$, at least or about $1 \times 10^{14}$ $M^{-1}$, at least or about $5 \times 10^{14} M^{-1}$, at least or about $1 \times 10^{15} M^{-1}$, or at least or about $5 \times 10^{15} M^{-1}$. The antibodies provided herein can exhibit a binding affinity for a recombinantly purified F protein, such as the extracellular domain of RSV A2 strain F protein set forth in SEQ ID NO:25. The antibodies provided herein also can exhibit a binding affinity for native RSV F protein, such as is generated by infection and expression of RSV in cells. The antibodies provided herein can have binding affinities that are the same or different for recombinant F protein versus native RSV F protein. For example, Example 5 shows that 30D8 has a higher binding affinity for recombinant F protein than for native RSV F protein. In contrast, sc5 (see e.g. U.S. Patent publication No. US2011/0076268 and International Published PCT Application No. WO2011/020079) exhibits similar binding affinity whether the RSV F protein is native or is recombinant F protein.

In some examples, the antibodies or antigen binding fragments provided herein have a dissociation constant ($K_d$) for the RSV F protein epitope of less than or about $1\times10^{-8}$ M, less than or about $4\times10^{-9}$ M, less than or about $2\times10^{-9}$ M, less than or about $1\times10^{-9}$ M, less than or about $2\times10^{-10}$ M, less than or about $1\times10^{-10}$ M, less than or about $2\times10^{-11}$ M, less than or about $1\times10^{-11}$ M, less than or about $2\times10^{-12}$ M, less than or about $1\times10^{-12}$ M, less than or about $2\times10^{-13}$ M, less than or about $1\times10^{13}$ M, less than or about $2\times10^{-14}$ M, less than or about $1\times10^{-14}$ M, less than or about $2\times10^{-15}$ M, less than or about $1\times10^{-18}$ M, or less than or about $2\times10^{-16}$ M.

In some examples, the antibodies or antigen-binding fragments provided herein have an $EC_{50}$ of less than or about 0.005 nM, less than or about 0.01 nM, less than or about 0.025 nM, less than or about 0.05 nM, less than or about 0.075 nM, less than or about 0.1 nM, less than or about 0.5 nM, less than or about 0.75 nM, less than or about 1 nM, less than or about less than or about 1.25 nM, less than or about 1.5 nM, less than or about 1.75 nM, or less than or about 2 nM in an in vitro microneutralization assay for neutralization of RSV. In particular examples, the isolated anti-RSV antibodies or antigen-binding fragments provided herein have an $EC_{50}$ for neutralization of RSV in an in vitro plaque reduction assay of less than or about 0.005 nM to less than or about 2 nM; less than or about 0.005 nM to less than or about 1 nM; less than or about 0.005 nM to less than or about 0.5 nM; less than or about 0.01 nM to less than or about 1 nM; less than or about 0.05 nM to less than or about 1 nM; less than or about 0.05 nM to less than or about 0.5 nM; or less than or about 0.1 nM to less than or about 0.5 nM.

In some examples, an anti-RSV antibody or antigen-binding fragment thereof provided herein neutralizes monoclonal antibody escape mutants (MARMs) against various anti-RSV antibodies in an in vitro microneutralization assay for neutralization of RSV. In a particular example, an anti-RSV antibody or antigen-binding fragment thereof provided herein neutralizes a MARM with an $EC_{50}$ for neutralization of that is or is about the same as the $EC_{50}$ for neutralization of a parental RSV strain from which the MARM was generated. If a first antibody can neutralize a MARM generated against a second antibody, one can conclude that the antibodies specifically bind to or interact with different epitopes.

In some examples, an anti-RSV antibody or antigen-binding fragment thereof provided herein binds to an epitope that is less susceptible to variation in the form of generated escape mutants (MAR MS) In some examples, RSV is incapable of generating an escape mutant after 8, 9, 10, 11, 12, 13, 14, 15, 16, 17, 18, 19, 20 or more successive rounds of viral replication in the presence of an anti-RSV antibody or antigen-binding fragment thereof provided herein. In a particular example, RSV does not generate an escape mutant after 11, 12, 13, 14, 15 or more successive rounds of viral replication in the presence of an anti-RSV antibody or antigen-binding fragment thereof provided herein. In another particular example, RSV is unable to effect escape from an anti-RSV antibody or antigen-binding fragment thereof provided herein. For example, Example 11A shows that after 12 rounds of viral replication in the presence of 30D8, RSV was unable to effect escape. In contrast, RSV was able to escape MOTAVIZUMAB® after only 7 rounds of viral replication.

In some examples, an anti-RSV antibody or antigen-binding fragment thereof provided herein inhibits the binding of RSV to its host cell receptor by at least or about 99%, at least or about 95%, at least or about 90%, at least or about 85%, at least or about 80%, at least or about 75%, at least or about 70%, at least or about 65%, at least or about 60%, at least or about 55%, at least or about 50%, at least or about 45%, at least or about 40%, at least or about 35%, at least or about 30%, at least or about 25%, at least or about 20%, at least or about 15%, or at least or about 10% relative to the binding of RSV to its host cell receptor in the absence of the anti-RSV antibody or antigen-binding fragment thereof. In some examples, an anti-RSV antibody or antigen-binding fragment provided herein inhibits RSV replication by at least or about 99%, at least or about 95%, at least or about 90%, at least or about 85%, at least or about 80%, at least or about 75%, at least or about 70%, at least or about 65%, at least or about 60%, at least or about 55%, at least or about 50%, at least or about 45%, at least or about 40%, at least or about 35%, at least or about 30%, at least or about 25%, at least or about 20%, at least or about 15%, or at least or about 10% relative to RSV replication in the absence of the anti-RSV antibody or antigen-binding fragment thereof.

In some examples the antibodies or antigen-binding fragments thereof provided herein have a half-life of 15 days or longer, 20 days or longer, 25 days or longer, 30 days or longer, 40 days or longer, 45 days or longer, 50 days or longer, 55 days or longer, 60 days or longer, 3 months or longer, 4 months or longer or 5 months or longer. Methods to increase the half-life of an antibody or antigen-binding fragment thereof provided herein are known in the art. Such methods include for example, pegylation, glycosylation, and amino acid substitution as described elsewhere here herein.

a. Derivative Antibodies

The anti-RSV antibodies or antigen-binding fragments thereof provided herein can be used to generate derivative antibodies such as a chimeric antibodies or other antigen-binding fragments, such as for example, Fab, Fab', F(ab')$_2$, single-chain Fv (scFv), Fv, dsFv, diabody, Fd and Fd' fragments. Generally, the derivative antibody or antigen-binding fragment derived from a parent antibody retains the binding specificity of the parent antibody. Antibody fragments can be generated by any techniques known to those of skill in the art. For example, Fab and F(ab')$_2$ fragments can be produced by proteolytic cleavage of immunoglobulin molecules, using enzymes such as papain (to produce Fab fragments) or pepsin (to produce F(ab')$_2$ fragments), F(ab')$_2$ fragments contain the variable region, the light chain constant region and the $C_H1$ domain of the heavy chain. Further, anti-RSV antibodies or antigen-binding fragments thereof provided herein also can be generated using various phage display methods known in the art. In some examples, the antigen-binding variable regions of the anti-RSV antibodies or antigen-binding fragments thereof provided herein can be recombinantly fused to one or more constant regions known in the art to generate chimeric full length antibodies, Fab, Fab', F(ab')$_2$ or other antigen-binding fragments. Exemplary methods for generating full length antibodies from antibody fragments are known in the art and provided herein. Methods for producing chimeric antibodies are known in the art (see e.g., Morrison (1985) *Science* 229:1202; Oi et al. (1986) *BioTechniques* 4:214; Gillies et al. (1989) *J. Immunol. Methods* 125:191-202; and U.S. Pat. Nos. 5,807,715, 4,816,567, and 4,816,397).

Chimeric antibodies comprising one or more CDRs from an anti-RSV antibody provided herein and framework regions from a heterologous immunoglobulin molecule can be produced using a variety of techniques known in the art including, for example, CDR-grafting (EP 239,400; PCT publication No. WO 91/09967; and U.S. Pat. Nos. 5,225,539, 5,530,101, and 5,585,089), veneering or resurfacing (EP 592,106; EP 519,596; Padlan (1991) *Molecular Immunology* 28(4/5):489-498; Studnicka et al. (1994) *Protein Engineering* 7(6):805-814; and Roguska et al. (1994) *PNAS* 91:969-973), and chain shuffling (U.S. Pat. No. 5,565,332).

In some examples, antibodies contain one or more CDRs of 30D8 (e.g., one or more CDRs set forth in SEQ ID NOS:405-410 and 437) and a heterologous framework region. In some examples, antibodies contain one or more CDRs of 104E5 (e.g., one or more CDRs set forth in SEQ ID NOS:411-416 and 438) and a heterologous framework region. In some examples, antibodies contain one or more CDRs of 38F10 (e.g., one or more CDRs set forth in SEQ ID NOS:417-422 and 439) and a heterologous framework region. In some examples, antibodies contain one or more CDRs of 14G3 (e.g., one or more CDRs set forth in SEQ ID NOS:423-428 and 440) and a heterologous framework region. In some examples, antibodies contain one or more CDRs of 90D3 (e.g., one or more CDRs set forth in SEQ ID NOS:429-434 and 441) and a heterologous framework region. In some examples, antibodies contain one or more CDRs of 56E11 (e.g., one or more CDRs set forth in SEQ ID NOS:458-463 and 482) and a heterologous framework region. In some examples, antibodies contain one or more CDRs of 17C9 (e.g., one or more CDRs set forth in SEQ ID NOS:464-469 and 483) and a heterologous framework region. In some examples, antibodies contain one or more CDRs of 69F6 (e.g., one or more CDRs set forth in SEQ ID NOS:470-475 and 484) and a heterologous framework region. Framework residues in the framework regions can be substituted with the corresponding residue from the CDR donor antibody to alter, such as improve, antigen-binding. These framework substitutions are identified by methods well known in the art, e.g., by modeling of the interactions of the CDR and framework residues to identify framework is residues important for antigen-binding and sequence comparison to identify unusual framework residues at particular positions (see, e.g., U.S. Pat. No. 5,585,089; and Riechmann et al. (1988) *Nature* 332:323).

In some examples, the derivative anti-RSV antibodies or antigen-binding fragments thereof have a binding affinity constant ($K_a$) for the RSV F protein epitope of at least or about $1 \times 10^8$ $M^{-1}$, at least or about $2.5 \times 10^8$ $M^{-1}$, at least or about $5 \times 10^8$ $M^{-1}$, at least or about $1 \times 10^9$ $M^{-1}$, at least or about $5 \times 10^9$ $M^{-1}$, at least or about $1 \times 10^{10}$ $M^{-1}$, at least or about $5 \times 10^{10}$ $M^{-1}$, at least or about $1 \times 10^{11}$ $M^{-1}$, at least or about $5 \times 10^{11}$ $M^{-1}$, at least or about $1 \times 10^{12}$ $M^{-1}$, at least or about $5 \times 10^{12}$ $M^{-1}$, at least or about $1 \times 10^{13}$ $M^{-1}$, at least or about $5 \times 10^{13}$ $M^{-1}$, at least or about $1 \times 10^{14}$ $M^{-1}$, at least or about $5 \times 10^{14}$ $M^{-1}$, at least or about $1 \times 10^{15}$ $M^{-1}$, or at least or about $5 \times 10^{15}$ $M^{-1}$.

In some examples, the derivative anti-RSV antibodies or antigen-binding fragments thereof have a dissociation constant ($K_d$) for the RSV F protein epitope of less than or about $1 \times 10^{-8}$ M, less than or about $4 \times 10^{-9}$ M, less than or about $2 \times 10^{-9}$ M, less than or about $1 \times 10^{-9}$ M, less than or about $2 \times 10^{-10}$ M, less than or about $1 \times 10^{-10}$ M, less than or about $2 \times 10^{-11}$ M, less than or about $1 \times 10^{-11}$ M, less than or about $2 \times 10^{-12}$ M, less than or about $1 \times 10^{-12}$ M, less than or about $2 \times 10^{-13}$ M, less than or about $1 \times 10^{-13}$ M, less than or about $2 \times 10^{-14}$ M, less than or about $1 \times 10^{-14}$ M, less than or about $2 \times 10^{-15}$ M, less than or about $1 \times 10^{-15}$ M, or less than or about $2 \times 10^{-16}$ M.

In some examples, the derivative anti-RSV antibodies or antigen-binding fragments thereof neutralize monoclonal antibody escape mutants (MARMs) against various anti-RSV antibodies in an in vitro microneutralization assay for neutralization of RSV. In a particular example, an anti-RSV antibody or antigen-binding fragment thereof provided herein neutralizes a MARM with an $EC_{50}$ for neutralization of that is or is about the same as the $EC_{50}$ for neutralization of a parental RSV strain from which the MARM was generated.

In some examples, the derivative anti-RSV antibodies or antigen-binding fragments thereof bind to an epitope that is less susceptible to variation in the form of generated escape mutants. In some examples, RSV is incapable of generating an escape mutant after 8, 9, 10, 11, 12, 13, 14, 15, 16, 17, 18, 19, 20 or more successive rounds of viral replication in the presence of a derivative anti-RSV antibody or antigen-binding fragment thereof provided herein. In another particular example, RSV is unable to effect escape from a derivative anti-RSV antibody or antigen-binding fragment thereof provided herein.

In some examples, the derivative anti-RSV antibodies or antigen-binding fragments thereof have $EC_{50}$ of less than or about 0.005 nM, less than or about 0.01 nM, less than or about 0.025 nM, less than or about 0.05 nM, less than or about 0.075 nM, less than or about 0.1 nM, less than or about 0.5 nM, less than or about 0.75 nM, less than or about 1 nM, less than or about 1.25 nM, less than or about 1.5 nM, less than or about 1.75 nM, or less than or about 2 nM in an in vitro microneutralization assay for neutralization of RSV. In particular examples, the derivative anti-RSV antibodies or antigen-binding fragments thereof have an $EC_{50}$ for neutralization of RSV in an in vitro plaque reduction assay of less than or about 0.005 nM to less than or about 2 nM; less than or about 0.005 nM to less than or about 1 nM; less than or about 0.005 nM to less than or about 0.5 nM; less than or about 0.01 nM to less than or about 1 nM; less than or about 0.05 nM to less than or about 1 nM; less than or about 0.05 nM to less than or about 0.5 nM; or less than or about 0.1 nM to less than or about 0.5 nM.

Any derivative of an anti-RSV antibody or antigen-binding fragment thereof provided herein can be used in therapeutic regimens, prophylaxis therapies and/or diagnostic techniques, such as in the methods provided. For example, the derivative antibodies or antigen-binding fragments thereof can be used to bind to RSV for the treatment, prevention and/or detection of RSV infection or alleviation of one or more symptoms of a RSV infection.

i. Single Chain Antibodies

In particular examples, the anti-RSV antibody is a single chain antibody. A single-chain antibody can be generated from the antigen-binding domains of any of the anti-RSV antibodies or antigen-binding fragments thereof provided herein. Methods for generating single chain antibodies using recombinant techniques are known in the art, such as those described in, for example, Marasco et al. (1993) *Proc. Natl. Acad. Sci. USA* 90:7889-7893, Whitlow and Filpula (1991) *Methods*, 2: 97-105; Bird et al. (1988) *Science* 242:423-426;

Pack et al. (1993) *Bio/Technology* 11:1271-77; and U.S. Pat. Nos. 4,946,778, 5,840,300, 5,667,988, 5,658,727.

A single chain antibody can contain a light chain variable ($V_L$) domain or functional region thereof and a heavy chain variable ($V_H$) domain or functional region thereof of any anti-RSV antibody or antigen-binding fragment thereof provided herein. In some examples, the $V_L$ domain or functional region thereof of the single chain antibody contains a complementarity determining region 1 (CDR1), a complementarity determining region 2 (CDR2) and/or a complementarity determining region 3 (CDR3) of an anti-RSV antibody or antigen-binding fragment thereof provided herein. In some examples, the $V_H$ domain or functional region thereof of the single chain antibody contains a complementarity determining region 1 (CDR1), a complementarity determining region 2 (CDR2) and a complementarity determining region 3 (CDR3) of any anti-RSV antibody or antigen-binding fragment thereof provided herein. In some examples, the single chain antibody further contains a peptide linker. In such examples, a peptide linker can be located between the light chain variable domain ($V_L$) and the heavy chain variable domain ($V_H$).

The single chain antibody can contain a peptide spacer, or linker, between the one or more domains of the antibody. For example, the light chain variable domain ($V_L$) of an antibody can be coupled to a heavy chain variable domain ($V_H$) via a flexible linker peptide. Various peptide linkers are well-known in the art and can be employed in the provided methods. A peptide linker can include a series of glycine residues (Gly) or Serine (Ser) residues. Exemplary of polypeptide linkers are peptides having the amino acid sequences $(Gly-Ser)_n$, $(Gly_mSer)_n$ or $(Ser_mGly)_n$, in which m is 1 to 6, generally 1 to 4, and typically 2 to 4, and n is 1 to 30, or 1 to 10, and typically 1 to 4, with some glutamic acid (Glu) or lysine (Lys) residues dispersed throughout to increase solubility (see, e.g., International PCT application No. WO 96/06641, which provides exemplary linkers for use in conjugates). Exemplary peptide linkers include, but are not limited to peptides having the sequence GGSSRSSSSGGGGSGGGG (SEQ ID NO:267), GSGRSGGGGSGGGGS (SEQ ID NO:268), EGKSSGSGSESKST (SEQ ID NO:269), EGKSSGSGSESKSTQ (SEQ ID NO:270), EGKSSGSGSESKVD (SEQ ID NO:271). GSTSGSGKSSEGKG (SEQ ID NO:272). KESGSVSSEQLAQFRSLD (SEQ ID NO:273), and ESGSVSSEELAFRSLD (SEQ ID NO:274). Generally, the linker peptides are approximately 1-50 amino acids in length. The linkers used herein also can increase intracellular availability, serum stability, specificity and solubility or provide increased flexibility or relieve steric hindrance. Linking moieties are described, for example, in Huston et al. (1988) *Proc Natl Acad Sci USA* 85:5879-5883. Whitlow et al. (1993) *Protein Engineering* 6:989-995, and Newton et al., (1996) *Biochemistry* 35:545-553. Other suitable peptide linkers include any of those described in U.S. Pat. No. 4,751,180 or 4,935,233, which are hereby incorporated by reference.

ii. Anti-Idiotypic Antibodies

The anti-RSV antibodies or antigen-binding fragments thereof provided herein can be utilized to generate anti-idiotype antibodies that "mimic" the RSV F protein antigen, to which the antibody immunospecifically binds, using techniques well known to those skilled in the art (see, e.g., Greenspan & Bona (1989) *FASEB J.* 7(5):437-444; and Nissinoff (1991) *J. Immunol.* 147(8):2429-2438). For example, the anti-RSV antibodies or antigen-binding fragments thereof provided herein which bind to and competitively inhibit the binding of RSV to its host cell receptor, as determined by assays well known in the art, can be used to generate anti-idiotypes that "mimic" a RSV antigen and bind to the RSV receptors, i.e., compete with the virus for binding to the host cell, therefore decreasing the infection rate of host cells with virus. In some examples, anti-anti-idiotypes can be generated by techniques well-known to the skilled artisan. The anti-anti-idiotypes mimic the binding domain of the anti-RSV antibody or antigen-binding fragment thereof and, as a consequence, bind to and neutralize RSV.

iii. Multi-Specific Antibodies and Antibody Multimerization

Two or more antibodies or antigen-binding fragments thereof provided herein can be engineered to form multivalent derivative antibodies, or multimers, such as bivalent, trivalent, tetravalent, pentavalent, hexavalent, heptavalent, or greater valency (i.e., containing 2, 3, 4, 5, 6, 7 or more antigen-binding sites) derivative antibodies. Such multivalent derivative antibodies can be monospecific, bispecific, trispecific or of greater multispecificity. In some examples, the multivalent derivative antibodies are monospecific, containing two or more antigen-binding domains that immunospecifically bind to the same epitope. In some examples, the multivalent derivative antibodies are multispecific, containing two or more antigen-binding domains that immunospecifically bind to two or more different epitopes. In some particular examples, the multivalent derivative antibodies are bivalent, containing two antigen-binding domains. Such bivalent antibodies can be homobivalent or heterobivalent antibodies, which immunospecifically bind to the same or different epitopes, respectively.

In some examples, the multispecific antibodies can immunospecifically bind to two or more different epitopes of RSV. Techniques for engineering multispecific antibodies are known in the art, and include, for example, linkage of two or more antigen-binding fragments via covalent, non-covalent, or chemical linkage. In some instances, multivalent derivative antibodies can be formed by dimerization of two or more anti-RSV antibodies or antigen-binding fragments thereof. Multimerization between two anti-RSV antibodies or antigen-binding fragments can be spontaneous, or can occur due to forced linkage of two or more polypeptides. In one example, multimers of anti-RSV antibodies can be linked by disulfide bonds formed between cysteine residues on different anti-RSV antibodies. In another example, multivalent derivative antibodies can include anti-RSV antibodies or antigen-binding fragments thereof joined via covalent or non-covalent interactions to peptide moieties fused to the antibody or antigen-binding fragment thereof. Such peptides can be peptide linkers (spacers), or peptides that have the property of promoting multimerization. In some examples, multivalent derivative antibodies can be formed between two antibodies through chemical linkage, such as for example, by using heterobifunctional linkers.

Any multispecific and/or multivalent derivative antibody can be generated from the anti-RSV antibodies or antigen-binding fragments thereof provided herein provided that the antibody is biocompatible (e.g., for administration to animals, including humans) and maintains its activity, such as the binding to one or more epitopes of and/or neutralization of RSV. For the multispecific and multivalent derivative antibodies provided herein, the derivative antibody is at least immunospecific for an epitope recognized by 30D8, 104E5, 38F10, 14G3, 90D3, 56E11, 17C9 or 69F6. The multispecific and multivalent derivative antibody provided herein also can be immunospecific for the epitope recognized by 58c5 or sc5.

In some examples, the multispecific and/or multivalent antibody contains a $V_H$ CDR1 having the amino acid sequence set forth in SEQ ID NOS:2, 10, 405, 411, 417, 423, 429, 435-441, 458, 464, 470 or 482-484, a $V_H$ CDR2 having the amino acid sequence set forth in SEQ ID NOS:3, 11, 406, 412, 418, 424, 430, 459, 465 or 471, a $V_H$ CDR3 having the amino acid sequence set forth in SEQ ID NOS:4, 12, 407, 413, 419, 425, 431, 460, 466 or 472, a $V_L$ CDR1 having the amino acid sequence set forth in SEQ ID NOS:6, 14, 408, 414, 420, 426, 432, 461, 467 or 473, a $V_L$ CDR2 having the amino acid sequence set forth in SEQ ID NOS:7, 15, 409, 415, 421, 427, 433, 462, 468 or 474, a $V_L$ CDR3 having the amino acid sequence set forth in SEQ ID NOS:8, 16, 410, 416, 422, 428, 434, 463, 469 or 475, or any combination thereof.

In some examples, multispecific antibodies can be generated that immunospecifically bind to two or more epitopes of a RSV F protein (e.g., a RSV F protein having an amino acid sequence set forth in SEQ ID NO:282, 382 or 485). For example, the multispecific antibodies can immunospecifically bind to two or more different epitopes in the A, B or C antigenic regions of a RSV F protein. In some examples, multispecific antibodies can be generated that immunospecifically bind to an epitope of a RSV F protein and another RSV epitope. For example, the multispecific antibodies can immunospecifically bind to an epitope of a RSV F protein and an epitope of another RSV surface glycoprotein. In some examples, the multispecific antibodies can immunospecifically bind to an epitope of a RSV F protein and an epitope of a RSV protein selected from among a RSV attachment protein (e.g. having an amino acid sequence set forth in SEQ ID NO:275), a RSV RNA polymerase beta subunit large structural protein (L protein) (e.g. having an amino acid sequence set forth in SEQ ID NO:276), a RSV nucleocapsid protein (e.g. having an amino acid sequence set forth in SEQ ID NO:277), a RSV nucleoprotein (N) (e.g. having an amino acid sequence set forth in SEQ ID NO:278), a RSV phosphoprotein P (e.g. having an amino acid sequence set forth in SEQ ID NO:279), a RSV matrix protein (e.g. having an amino acid sequence set forth in SEQ ID NO:280), a RSV small hydrophobic (SH) protein (e.g. having an amino acid sequence set forth in SEQ ID NO:281), a RSV RNA-dependent polymerase, a RSV G protein (e.g. having an amino acid sequence set forth in SEQ ID NO:282), or an allelic variant of any of the above. In some examples, the multispecific antibodies can immunospecifically bind to an epitope of a RSV F protein and an epitope of a RSV G protein.

In some examples, the multispecific antibody contains an anti-RSV antigen-binding fragment derived from 30D8, 104E5, 38F10, 14G3, 90D3, 56E11, 17C9 or 69F6 and an anti-RSV antigen-binding fragment derived from another anti-RSV antibody. For example, the other anti-RSV antibody can be an antibody or antigen-binding fragment derived from 58c5 or sc5. In some examples, the multispecific antibody contains an anti-RSV antigen-binding fragment derived from 30D8, 104E5, 38F10, 14G3, 90D3, 56E11, 17C9 or 69F6 and an anti-RSV antigen-binding fragment derived from an anti-RSV antibody selected among palivizumab (SYNAGIS®), and derivatives thereof such as, but not limited to, motavizumab (NUMAX®), AFFF, P12f2, P12f4, P11d4, Ale % A12a6, A13c4, A17d4, A4B4, A8c7, 1X-493L1, FR H3-3F4, M3H9, Y10H6, DG, AFFF(1), 6H8, L1-7E5, L2-15B10, A13a11, A1h5, A4B4 (1), A4B4L1FR-S28R, A4B4-F52S (see, e.g., U.S. Pat. Nos. 5,824,307 and 6,818,216). In some examples, the multispecific antibody contains an anti-RSV antigen-binding fragment derived from 30D8, 104E5, 38F10, 14G3, 90D3, 56E11, 17C9 or 69F6 and an anti-RSV antigen-binding fragment derived from a human anti-RSV antibody, such as, but not limited to, rsv6, rsv11, rsv13, rsv19 (i.e. Fab 19), rsv21, rsv22, rsv23. RF-1, and RF-2 (see, e.g. U.S. Pat. Nos. 6,685,942 and 5,811,524). In some examples, the multispecific antibody contains an anti-RSV antigen-binding fragment derived from 30D8, 104E5, 38F10, 14G3, 90D3, 56E11, 17C9 or 69F6 and an anti-RSV antigen-binding fragment derived from an anti-RSV mouse monoclonal antibody such as, but not limited to, MAbs 1153, 1142, 1200, 1214, 1237, 1129, 1121, 1107, 1112, 1269, 1269, 1243 (Beeler et al. (1989) *J. Virology* 63(7):2841-2950). MAb151 (Mufson et al. (1987) *J. Clin. Microbiol.* 25:1635-1539). MAbs 43-1 and 13-1 (Fernie et al. (1982) *Proc. Soc. Exp. Biol. Meal.* 171:266-271). MAbs 1436C, 1302A, 1308F, and 13311-1 (Anderson el al (1984) *J. Clin. Microbiol.* 19:934-936), and humanized derivatives thereof. Additional exemplary antibodies or antigen-binding fragments thereof that can be used to generate a multispecific antibody that contains an anti-RSV antigen-binding fragment derived from 30D8, 104E5, 38F10, 14G3, 90D3, 56E11, 17C9 or 69F6 include, but are not limited to, anti-RSV antibodies or antigen-binding fragments thereof described in, for example, U.S. Pat. Nos. 6,413,771, 5,840,298, 5,811,524, 6,656,467, 6,537,809, 7,364,742, 7,070,786, 5,955,364, 7,488,477, 6,818,216, 5,824,307, 7,364,737, 6,685,942, and 5,762,905 and U.S. Patent Pub. Nos. 2007-0082002, 2005-0175986, 2004-0234528, 2006-0198840, 2009-0110684, 2006-0159695, 2006-0013824, 2005-0288491, 2005-0019758, 2008-0226630, 2009-0137003, and 2009-0092609. Tables 2A and 2B below set forth SEQ ID NOS for anti-RSV antibody heavy chains (Table 2A) and light chains (Table 2B). Included are full length sequences of heavy and light chains, sequences for heavy and light variable domains, and sequences of CDRH1, CDRH2, CDRH3, CDRL1, DRL2 and/or CDRL3, where indicated.

TABLE 2A

Anti-RSV Antibody Heavy Chain SEQ ID NOS

| | Heavy Chain | Variable Domain | CDR1 | CDR2 | CDR3 |
|---|---|---|---|---|---|
| Synagis | 103 | 104 | 105 | 106 | 107 |
| AFFF | 113 | 114 | | 115 | 116 |
| P1212 | 122 | 123 | 124 | 125 | 126 |
| P12f4 | 131 | 132 | | 133 | |
| P11d4 | 137 | 138 | | | 139 |
| Ale9 | 144 | 145 | | | |
| A12a6 | 149 | 150 | | 151 | |
| A13c4 | 155 | 156 | | 157 | |
| A17d4 | 161 | 162 | | 163 | |
| A4B4 | 167 | 168 | | | |
| A8c7 | 172 | 173 | | | |
| IX-493L1FR | 176 | 232 | | | |
| M3H9 | 179 | | | | |
| Y10H6 | 185 | | | | |
| DG | 186 | 187 | | | 188 |
| AFFF (1) | 190 | | | | |
| 6H8 | 194 | | | | |
| L1-7E5 | 198 | | | | |
| L2-15B10 | 201 | | | | |
| A13a11 | 205 | 206 | | | |
| A1h5 | 210 | | | | |
| A4B4 (1) | 215 | | | | |
| A4B4L1 | 219 | | | | |
| A4B4-F25S | 222 | | | | |
| H3-3F4 | 226 | 227 | | | |
| A3e2 | 233 | 234 | | | 235 |
| A14a4 | 239 | 240 | | | 241 |

TABLE 2A-continued

Anti-RSV Antibody Heavy Chain SEQ ID NOS

| | Heavy Chain | Variable Domain | CDR1 | CDR2 | CDR3 |
|---|---|---|---|---|---|
| A16b4 | 246 | 247 | | | |
| A17b5 | 252 | 253 | | | |
| A17f5 | 257 | 258 | | | 259 |
| Rsv6/11/21/22 | 362 | | 363 | 364 | 365 |
| Rsv13/19H | 366 | | 367 | 368 | 369 |
| Rsv23 | 362 | | 363 | 364 | 365 |

TABLE 2B

Anti-RSV Antibody Light Chain SEQ ID NOS

| | Light Chain | Variable Domain | CDR1 | CDR2 | CDR3 |
|---|---|---|---|---|---|
| Synagis | 108 | 109 | 110 | 111 | 112 |
| AFFF | 117 | 118 | 119 | 120 | 121 |
| P1212 | 127 | 128 | 129 | 130 | |
| P12f4 | 134 | 135 | | 136 | |
| P11d4 | 140 | 141 | 142 | 143 | |
| Ale9 | 146 | 147 | | 148 | |
| A12a6 | 152 | 153 | 154 | | |
| A13c4 | 158 | 159 | | 160 | |
| A17d4 | 164 | 165 | 166 | | |
| A4B4 | 169 | 170 | | 171 | |
| A8c7 | 174 | 175 | | | |
| IX-493L1FR | 177 | 178 | | | |
| M3H9 | 180 | 181 | | 231 | |
| Y10H6 | 183 | 184 | | 185 | |
| DG | 189 | | | | |
| AFFF (1) | 191 | 192 | | | 193 |
| 6H8 | 195 | 196 | | 197 | |
| L1-7E5 | 199 | 200 | | | |
| L2-15B10 | 202 | 203 | | 204 | |
| A13a11 | 207 | 208 | | 209 | |
| A1h5 | 211 | 212 | 213 | 214 | |
| A4B4 (1) | 216 | 217 | | 218 | |
| A4B4L1 | 220 | 221 | | | |
| A4B4-F25S | 223 | 224 | | 225 | |
| H3-3F4 | 228 | 229 | | | |
| A3e2 | 236 | 237 | | 238 | |
| A14a4 | 242 | 243 | 244 | 245 | |
| A16b4 | 248 | 249 | 250 | 251 | |
| A17b5 | 254 | 255 | | 256 | |
| A17f5 | 260 | 261 | | 262 | |
| A17h4 | 263 | 264 | 265 | 266 | |
| Rsv6/11/21/22 | 370 | | 371 | 372 | 373 |
| Rsv13/19H | 378 | | 379 | 380 | 381 |
| Rsv23 | 374 | | 375 | 376 | 377 |

In some examples, multispecitic antibodies or antigen-binding fragments can immunospecitically bind to an epitope of a RSV F protein and an epitope of another heterologous polypeptide or other antigenic material, such as, for example, a solid support material (see, e.g., International PCT Pub. Nos. WO 93/17715, WO 92/08802. WO 91/00360, and WO 92/05793; U.S. Pat. Nos. 4,474,893, 4,714,681, 4,925,648, 5,573,920, and 5,601,819; Tutt, et al., (1991) *J. Immunol.* 147:60-69; and Kostelny et al., (1992) *J. Immunol.* 148:1547-1553.

(1) Multimerization Via Peptide Linkers

Peptide linkers can be used to produce multivalent antibodies, such as, for example, a multimer where one multimerization partner is an anti-RSV antibody or antigen-binding fragment thereof provided herein. In one example, peptide linkers can be fused to the C-terminal end of a first polypeptide and the N-terminal end of a second polypeptide. This structure can be repeated multiples times such that at least one, such as 2, 3, 4, or more soluble polypeptides are linked to one another via peptide linkers at their respective termini. For example, a multimer polypeptide can have a sequence $Z_1$-X-$Z_2$, where $Z_1$ and $Z_2$ are each a sequence of an anti-RSV antigen-binding fragment (e.g. an anti-RSV single chain antibody; see, e.g., U.S. Pat. No. 6,759,518, describing multimerization of single chain antibodies) and where X is a sequence of a peptide linker. In some instances, $Z_1$ and/or $Z_2$ is an anti-RSV antigen-binding fragment provided herein. In another example, $Z_1$ and $Z_2$ are different anti-RSV antigen-binding fragments, where at least $Z_1$ or $Z_2$ is derived from anti-RSV antibody or antigen-binding fragment provided herein. In some examples, the multimer polypeptide has a sequence of $Z_1$-X-$Z_2$-$(X-Z)_n$, where "n" is any integer, i.e. generally 1 or 2. Typically, the peptide linker is of sufficient length to allow each anti-RSV antigen-binding fragment to bind its respective epitope without interfering with binding specificity of the antibody.

(2) Multimerization Via Heterobifunctional Linking Agents

Linkage of an anti-RSV antibody or antigen-binding fragment thereof provided herein to another anti-RSV antibody or antigen-binding fragment to create a multivalent antibody can be direct or indirect. For example, linkage of two or more anti-RSV antibodies or antigen-binding fragments can be achieved by chemical linkage or facilitated by heterobifunctional linkers, such as any known in the art or provided herein.

Numerous heterobifunctional cross-linking reagents that are used to form covalent bonds between amino groups and thiol groups and to introduce thiol groups into proteins are known to those of skill in this art (see, e.g., the PIERCE CATALOG, ImmunoTechnology Catalog & Handbook, 1992-1993, which describes the preparation of and use of such reagents and provides a commercial source for such reagents; see, also, e.g., Cumber et al., (1992) *Bioconjugate Chem.* 3:397-401; Thorpe et al., (1987) *Cancer Res.* 47:5924-5931; Gordon et al., (1987) *Proc. Natl. Acad Sci.* 84:308-312; Walden et al., (1986) *J. Mol. Cell Immunol.* 2:191-197; Carlsson et al., (1978) *Biochem. J.* 173: 723-737; Mahan et al., (1987) *Anal. Biochem.* 162:163-170; Wawryznaczak et al., (1992) *Br. J. Cancer* 66:361-366; Fattom et al, (1992) *Infection & Immun.* 60:584-589). These reagents can be used to form covalent bonds between two antibodies or between each of the antibodies and a linker. Exemplary reagents include, but are not limited to: N-succinimidyl-3-(2-pyridyldithio)propionate (SPDP; disulfide linker); sulfo-succinimidyl 6-[3-(2-pyridyldithio)-propionamido]hexanoate (sulfo-LC-SPDP); succinimidyloxycarbonyl-α-methyl benzyl thiosulfate (SMBT, hindered disulfate linker); succinimidyl 6-[3-(2-pyridyldithio) propionamido]-hexanoate (LC-SPDP); sulfosuccinimidyl 4-(N-maleimidomethyl)cyclohexane-1-carboxylate (sulfo-SMCC); succinimidyl 3-(2-pyridyldithio)butyrate (SPDB; hindered disulfide bond linker); sulfosuccinimidyl 2-(7-azido-4-methylcoumarin-3-acetamide) ethyl-1,3'-dithiopropionate (SAED); sulfo-succinimidyl 7-azido-4-methylcoumarin-3-acetate (SAMCA); sulfosuccinimidyl-6-[alpha-methyl-alpha-(2-pyridyldithio) toluamido]-hexanoate (sulfo-LC-SMPT); 1,4-di-[3'-(2'-pyridyldithio)propion-amido]butane (DPDPB); 4-succinimidyloxycarbonyl-α-methyl-α-(2-pyridylthio)toluene (SMPT, hindered disulfate linker); sulfosuccinimidyl-6-[α-methyl-α-(2-pyrimiyldi-thio)toluamido]hexanoate (sulfo-LC-SMPT); m-maleimidobenzoyl-N-hydroxy-succinimide ester (MBS); m-maleimidobenzoyl-N-hydroxysulfo-succinimide ester (sulfo-MBS); N-succinimidyl(4-iodoacetyl) aminobenzoate (SIAB; thioether linker); sulfosuccinimidyl-(4-iodoacetyl)amino benzoate (sulfo-SIAB); succinimidyl- 4-(p-maleimi-dophenyl)butyrate (SMPB); sulfosuccinimidyl4-(p-maleimido-phenyl)butyrate (sulfo-SMPB); and azidobenzoyl hydrazide (ABH). In some examples, the linkers, can be used in combination with peptide linkers, such as those that increase flexibility or solubility or that provide for or eliminate steric hindrance. Any other linkers known to those of skill in the art for linking a polypeptide molecule to another molecule can be employed.

(3) Polypeptide Multimerization Domains

Interaction of two or more antigen-binding fragments to form multivalent and/or multispecific derivative antibodies can be facilitated by their linkage, either directly or indirectly, to any moiety or other polypeptide that are themselves able to interact to form a stable structure. For example, separate encoded polypeptide chains can be joined by multimerization, whereby multimerization of the polypeptides is mediated by a multimerization domain. Typically, the multimerization domain provides for the formation of a stable protein-protein interaction between a first chimeric polypeptide and a second chimeric polypeptide. Chimeric polypeptides include, for example, linkage (directly or indirectly) of one chain (e.g., a variable heavy domain chain or variable light chain domain) of an antibody or antigen-binding fragment thereof with a multimerization domain. Typically, the multimerization domain is linked to a heavy chain domain of the antibody or antigen-binding fragment thereof. Such chimeric polypeptides can be generated as a fusion proteins using recombinant techniques for fusing nucleic acid encoding the antibody chain to nucleic acid encoding the multimerization domain.

For the multivalent and/or multispecific derivative antibodies provided herein, at least one multimerization partner is an anti-RSV antibody or antigen-binding fragment thereof linked directly or indirectly to a multimerization domain. Homo- or heteromultimeric polypeptides can be generated from co-expression of separate chimeric polypeptides. The first and second chimeric polypeptides can be the same or different.

Generally, a multimerization domain includes any polypeptide capable of forming a stable protein-protein interaction with another polypeptide. The multimerization domains can interact, for example, via an immunoglobulin sequence (e.g., an Fc domain), a leucine zipper, a hydrophobic region, a hydrophilic region, or a free thiol which forms an intermolecular disulfide bond between the chimeric molecules of a homo- or heteromultimer. In addition, a multimerization domain can include an amino acid sequence comprising a protuberance complementary to an amino acid sequence comprising a hole or pocket, such as is described, for example, in U.S. Pat. No. 5,731,168. Such a multimerization region can be engineered such that steric interactions not only promote stable interaction, but further promote the formation of heterodimers over homodimers from a mixture of chimeric monomers.

In some examples, multivalent and/or multispecific antibodies are generated by linkage of two anti-RSV antigen-binding fragments via multimerization domain. In such examples, at least one of the antigen-binding fragments is derived from an anti-RSV antibody or antigen-binding fragment thereof provided herein, such as for example, 58c5, sc5, 30D8, 104E5, 38F10, 14G3, 90D3, 56E11, 17C9 or 69F6.

An antigen-binding polypeptide, such as for example anti-RSV antigen-binding fragment, can be conjugated to a multimerization domain to form a chimeric polypeptide. For anti-RSV antigen-binding fragments containing more than one chain (e.g., a variable heavy domain chain and a variable light chain domain), the multimerization domain can be conjugated to one of the chains, typically the heavy chain. The antigen-binding fragment is typically linked via its N- or C-terminus to the N- or C-terminus of the multimerization domain. Typically, the multimerization domain is conjugated to the C-terminus of the antigen-binding fragment (e.g., the C-terminus of a single chain antibody or the C-terminus of one chain of the antigen-binding fragment). The linkage can be direct or indirect via a linker. Also, the chimeric polypeptide can be a fusion protein or can be formed by chemical linkage, such as through covalent or non-covalent interactions. For example, when preparing a chimeric polypeptide containing a multimerization domain, nucleic acid encoding all or part of an anti-RSV antigen-binding fragment can be operably linked to nucleic acid encoding the multimerization domain sequence, directly or indirectly or optionally via a linker domain. Typically, the construct encodes a chimeric protein where the C-terminus of the anti-RSV antigen-binding fragment (or single chain of the antigen-binding fragment) is joined to the N-terminus of the multimerization domain.

A multivalent antibody provided herein contains two chimeric proteins created by linking, directly or indirectly, two of the same or different anti-RSV antigen-binding fragments directly or indirectly to a multimerization domain. In some examples, where the multimerization domain is a polypeptide, a gene fusion encoding the anti-RSV antigen-binding fragment (or single chain of the antigen-binding fragment) multimerization domain chimeric polypeptide is inserted into an appropriate expression vector. The resulting anti-RSV antigen-binding fragment-multimerization domain chimeric proteins can be expressed in host cells transformed with the recombinant expression vector, and allowed to assemble into multimers, where the multimerization domains interact to form multivalent antibodies. Chemical linkage of multimerization domains to anti-RSV antigen-binding fragments also can be effected using heterobifunctional linkers as discussed above. In some examples, the multivalent antibodies are multispecific antibodies that are derived from two or more anti-RSV antigen-binding fragments which bind to different epitopes.

The resulting chimeric polypeptides, and multivalent antibodies formed therefrom, can be purified by any suitable method known in the art, such as, for example, by affinity chromatography over Protein A or Protein G columns. Where two nucleic acid molecules encoding different anti-RSV antigen-binding chimeric polypeptides are transformed into cells, formation of homo- and heterodimers will occur. Conditions for expression can be adjusted so that heterodimer formation is favored over homodimer formation.

(a) Immunoglobulin Domain

Multimerization domains include those comprising a free thiol moiety capable of reacting to form an intermolecular disulfide bond with a multimerization domain of an additional amino acid sequence. For example, a multimerization domain can include a portion of an immunoglobulin molecule, such as from $IgG_1$, $IgG_2$, $IgG_3$, $IgG_4$, IgA, IgD, IgM, and IgE. Generally, the portion of an immunoglobulin selected for use as a multimerization domain is the constant region (Fc). Preparations of fusion proteins containing polypeptides fused to various portions of antibody-derived polypeptides, including the Fc domain, have been described (see, e.g., Ashkenazi et al. (1991) *PNAS* 88: 10535; Byrn et al. (1990) *Nature*, 344:677; and Hollenbaugh and Aruffo, (1992) "Construction of Immunoglobulin Fusion Proteins." in *Current Protocols in Immunology*. Suppl. 4, pp. 10.19.1-10.19.11).

In humans, there are five antibody isotypes classified based on their heavy chains denoted as delta (δ), gamma (γ), mu (μ), alpha (α) and epsilon (ε), giving rise to the IgD, IgG, IgM, IgA, and IgE classes of antibodies, respectively. The IgA and IgG classes contain the subclasses IgA1, IgA2, IgG1, IgG2, IgG3, and IgG4. Sequence differences between immunoglobulin heavy chains cause the various isotypes to differ in, for example, the number of constant (C) domains, the presence of a hinge region, and the number and location of interchain disulfide bonds. For example, IgM and IgE heavy chains contain an extra C domain (C4), that replaces the hinge region. The Fc regions of IgG, IgD, and IgA pair with each other through their Cγ3, Cδ3, and Cα3 domains, whereas the Fc regions of IgM and IgE dimerize through their Cμ4 and Cε4 domains. IgM and IgA form multivalent structures with ten and four antigen-binding sites, respectively.

Antigen-binding chimeric polypeptides provided herein include full-length immunoglobulin polypeptides (i.e., including all domains of full-length immunoglobulins). In some examples, the antigen-binding chimeric polypeptide is less than full length (e.g. the chimeric polypeptide can contain the antigen-binding domain and one or more immunoglobulin domains for multimerization, where the chimeric polypeptide is not a full-length immunoglobulin). In some examples, the anti-RSV antigen-binding chimeric polypeptides are assembled as monovalent or hetero- or homo-multivalent antibodies, such as bivalent, trivalent, tetravalent, pentavalent, hexavalent, heptavalent or higher valency antibodies. Chains or basic units of varying structures (e.g., one more heterologous constant regions or domains) can be utilized to assemble the monovalent and hetero- and homo-multivalent antibodies. Anti-RSV antigen-binding chimeric polypeptides can be readily produced and secreted by mammalian cells transformed with the appropriate nucleic acid molecule. In some examples, one or more than one nucleic acid fusion molecule can be transformed into host cells to produce a multivalent antibody where the anti-RSV antigen-binding portions of the multivalent antibody are the same or different. Typically, at least one of the anti-RSV antigen-binding portions of the multivalent antibody is derived from an anti-RSV antibody or antigen-binding fragment thereof provided herein, such as for example, 58c5, sc5, 30D8, 104E5, 38F10, 14G3, 90D3, 56E11, 17C9 or 69F6.

(i) Fc Domain

Exemplary multimerization domains that can be used to generate multivalent and/or multispecific antibodies containing an anti-RSV antigen-binding fragment provided herein include polypeptides derived from a heavy chain constant region or domain of a selected immunoglobulin molecule. Exemplary sequences of heavy chain constant regions for human IgG sub-types are set forth in SEQ ID NOS:356 (IgG1), SEQ ID NO:357 (IgG2), SEQ ID NO:358 (IgG3), and SEQ ID NO:359 (IgG4). For example, for the exemplary heavy chain constant region set forth in SEQ ID NO:356, the $C_H1$ domain corresponds to amino acids 1-103, the hinge region corresponds to amino acids 104-119, the $C_H2$ domain corresponds to amino acids 120-223, and the $C_H3$ domain corresponds to amino acids 224-330.

In one example, an immunoglobulin polypeptide chimeric protein can include the Fc region of an immunoglobulin polypeptide. Typically, such a fusion retains at least a functionally active hinge, $C_H2$ and $C_H3$ domains of the constant region of an immunoglobulin heavy chain. For example, a full-length Fc sequence of IgG1 includes amino acids 104-330 of the sequence set forth in SEQ ID NO:356. An exemplary Fc sequence for hIgG1 is set forth in SEQ ID NO:360, and contains the hinge sequence corresponding to amino acids 104-119 of SEQ ID NO:356, and the complete sequence for the $C_H2$ and $C_H3$ domain as set forth in SEQ ID NO:356. Another exemplary Fc polypeptide is set forth in PCT application WO 93/10151, and is a single chain polypeptide extending from the N-terminal hinge region to the native C-terminus of the Fc region of a human IgG1 antibody (SEQ ID NO:361). The precise site at which the linkage is made is not critical: particular sites are well known in the art and can be selected in order to optimize the biological activity, secretion, or binding characteristics of the anti-RSV antigen-binding chimeric polypeptide. For example, other exemplary Fc polypeptide sequences begin at amino acid C109 or P113 of the sequence set forth in SEQ ID NO:356 (see e.g., US 2006/0024298).

In addition to hIgG1 Fc, other Fc regions also can be included in the anti-RSV antigen-binding chimeric polypeptides provided herein. For example, the Fc fusions can contain immunoglobulin sequences that are substantially encoded by immunoglobulin genes belonging to any of the antibody classes, including, but not limited to IgG (including human subclasses IgG1, IgG2, IgG3, or IgG4), IgA (including human subclasses IgA1 and IgA2), IgD, IgE, and IgM classes of antibodies.

In some examples, a Fc domain can be selected based on the functional properties of the domain, such as for example, the effector functions of the Fc domain in mediating an immune response. For example, where effector functions mediated by Fc/FcγR interactions are to be minimized, fusion with IgG isotypes that poorly recruit complement or effector cells, such as for example, the Fc of IgG2 or IgG4, can be used.

Modified Fc domains also are contemplated herein for use in chimeras with anti-RSV antigen-binding fragments, see e.g. U.S. Pat. No. 7,217,797; and U.S. Pat. Pub. Nos. 2006/0198840, 2006/0024298 and 2008/0287657; and International Patent Pub. No. WO 2005/063816 for exemplary modifications. Exemplary amino acid modification of Fc domains also are provided elsewhere herein.

Typically, a bivalent antibody is a dimer of two chimeric proteins created by linking, directly or indirectly, two of the same or different anti-RSV antigen-binding fragments to an Fc polypeptide. In some examples, a gene fusion encoding the chimeric protein is inserted into an appropriate expression vector. The resulting chimeric proteins can be expressed in host cells transformed with the recombinant expression vector, and allowed to assemble, where interchain disulfide bonds form between the Fc moieties to yield divalent anti-RSV antibodies. Typically, a host cell and expression system is a mammalian expression system to allow for glycosylation of the chimeric protein. The resulting chimeric polypeptides containing Fc moieties, and multivalent antibodies formed therefrom, can be easily purified by affinity chromatography over Protein A or Protein G columns. Where two nucleic acids encoding different anti-RSV chimeric polypeptides are transformed into cells, the formation of heterodimers must be biochemically achieved since anti-RSV chimeric molecules carrying the Fc-domain will be expressed as disulfide-linked homodimers as well. Thus, homodimers can be reduced under conditions that favor the disruption of inter-chain disulfides, but do not effect intra-chain disulfides. Typically, chimeric monomers with different extracellular portions are mixed in equimolar amounts and oxidized to form a mixture of homo- and heterodimers. The components of this mixture are separated by chromatographic techniques.

Alternatively, the formation of a heterodimer can be biased by genetically engineering and expressing anti-RSV antigen-binding fusion molecules that contain an anti-RSV antigen-binding fragment, followed by the Fc-domain of hIgG, followed by either c-jun or the c-fos leucine zippers. Since the leucine zippers form predominantly heterodimers, they can be used to drive the formation of the heterodimers when desired, anti-RSV chimeric polypeptides containing Fc regions also can be engineered to include a tag with metal chelates or other epitope. The tagged domain can be used for rapid purification by metal-chelate chromatography, and/or by antibodies, to allow for detection of western blots, immunoprecipitation, or activity depletion/blocking in bioassays.

D. ADDITIONAL MODIFICATIONS OF ANTI-RSV ANTIBODIES

The anti-RSV antibodies or antigen-binding fragments thereof provided herein can be further modified. Modifications of an anti-RSV antibody or antigen-binding fragment can improve one or more properties of the antibody, including, but not limited to, decreasing the immunogenicity of the antibody or antigen-binding fragment, improving the half-life of the antibody or antigen-binding fragment, such as reducing the susceptibility to proteolysis and/or reducing susceptibility to oxidation, and altering or improving of the binding properties of the antibody or antigen-binding fragment thereof. Exemplary modifications include, but are not limited to, modifications of the primary amino acid sequence of the anti-RSV antibody or antigen-binding fragment thereof and alteration of the post-translational modification of the anti-RSV antibody or antigen-binding fragment thereof. Exemplary post-translational modifications include, for example, glycosylation, acetylation, pegylation, phosphorylation, amidation, derivatization with protecting/blocking group, proteolytic cleavage, linkage to a cellular ligand or other protein. Other exemplary modifications include attachment of one or more heterologous peptides to the anti-RSV antibody or antigen-binding fragment to alter or improve one or more properties of the antibody or antigen-binding fragment thereof.

Generally, the modifications do not result in increased immunogenicity of the antibody or antigen-binding fragment thereof or significantly negatively affect the binding of the antibody or antigen-binding fragment thereof to RSV. Methods of assessing the binding of the modified antibodies or antigen-binding fragments thereof to a RSV F protein are provided herein and known in the art. For example, modified antibodies or antigen-binding fragments thereof can be assayed for binding to a RSV F protein by methods such as, but not limited to, ELISA, surface plasmon resonance (SPR), or through in vitro microneutralization assays.

Provided herein are methods of improving the half-life of any of the provided anti-RSV antibodies or antigen-binding fragments thereof. Increasing the half-life of the anti-RSV antibodies or antigen-binding fragments thereof provided herein can increase the therapeutic effectiveness of the anti-RSV antibodies or antigen-binding fragments thereof and allow for less frequent administration of the antibodies or antigen-binding fragments thereof for prophylaxis and/or treatment, such as preventing or treating a RSV infection, preventing, treating, and/or alleviating of one or more symptoms of a RSV infection, or reducing the duration of a RSV infection.

Modification of the anti-RSV antibodies or antigen-binding fragments thereof produced herein can include one or more amino acid substitutions, deletions or additions, either from natural mutation or human manipulation from the parent antibody. Methods for modification of polypeptides, such as antibodies, are known in the art and can be employed for the modification of any antibody or antigen-binding fragment thereof provided herein. In some examples, the pharmacokinetic properties of the anti-RSV antibodies or antigen-binding fragments thereof provided herein can be enhanced through Fc modifications by techniques known to those skilled in the art. Standard techniques known to those skilled in the art can be used to introduce mutations in the nucleotide molecule encoding an antibody or an antigen-binding fragment provided herein in order to produce an polypeptide with one or more amino acid substitutions. Exemplary techniques for introducing mutations include, but are not limited to, site-directed mutagenesis and PCR-mediated mutagenesis.

The anti-RSV antibodies and antigen-binding fragments thereof provided herein can be modified by the attachment of a heterologous peptide to facilitate purification. Generally such peptides are expressed as a fusion protein containing the antibody fused to the peptide at the C- or N-terminus of the antibody or antigen-binding fragment thereof. Exemplary peptides commonly used for purification include, but are not limited to, hexa-histidine peptides, hemagglutinin (HA) peptides, and flag tag peptides (see e.g., Wilson et al. (1984) *Cell* 37:767; Witzgall et al. (1994) *Anal Biochem* 223:2, 291-8). The fusion does not necessarily need to be direct, but can occur through a linker peptide. In some examples, the linker peptide contains a protease cleavage site which allows for removal of the purification peptide following purification by cleavage with a protease that specifically recognizes the protease cleavage site.

The anti-RSV antibodies and antigen-binding fragments thereof provided herein also can be modified by the attachment of a heterologous polypeptide that targets the antibody or antigen-binding fragment to a particular cell type (e.g., respiratory epithelial cells), either in vitro or in vivo. In some examples an anti-RSV antibody or antigen-binding fragment thereof provided herein can be targeted to a particular cell type by fusing or conjugating the antibody or antigen-binding fragment thereof to an antibody specific for a particular cell surface receptor or other polypeptide that interacts with a specific cell receptor.

In some examples, an anti-RSV antibody or antigen-binding fragment thereof provided herein can be targeted to a target cell surface and/or taken up by the target cell by fusing or conjugating the antibody or antigen-binding fragment thereof to a peptide that binds to cell surface glycoproteins, such as a protein transduction domain (e.g., a TAT peptide). Exemplary protein transduction domains include, but are not limited to, PTDs derived from proteins such as human immunodeficiency virus 1 (HIV-1) TAT (Ruben et al. (1989) *J. Virol.* 63:1-8; e.g., SEQ ID NOS:326-337, such as for example, GRKKRRQRRR (TAT 48-57) SEQ ID NO:330)), the herpes virus tegument protein VP22 (Elliott and O'Hare (1997) *Cell* 88:223-233; e.g., SEQ ID NO:342), the homeotic protein of *Drosophila melanogaster* Antennapedia (Antp) protein (Penetratin PTD; Derossi et al. (1996) *J. Biol. Chem.* 271:18188-18193; e.g., SEQ ID NOS:311-314), the protegrin 1 (PG-1) anti-microbial peptide SynB (e.g., SynB1, SynB3, and Syn B4; Kokryakov et al. (1993)

FEBS Lett. 327:231-236; e.g., SEQ ID NOS:323-325, respectively) and basic fibroblast growth factor (Jans (1994) FASEB J. 8:841-847; e.g., SEQ ID NO:307). PTDs also include synthetic PTDs, such as, but not limited to, polyarginine peptides (Futaki et al. (2003) J. Mol. Recognit. 16:260-264; Suzuki et al. (2001) J. Biol. Chem. 276:5836-5840; e.g. SEQ ID NOS:315-316), transportan (Pooga et al. (1988) FASEB J. 12:67-77; Pooga et al. (2001) FASEB J. 15:1451-1453; e.g., SEQ ID NOS:338-341), MAP (Oehlke et al. (1998) Biochim. Biophys. Acta. 1414:127-139; e.g., SEQ ID NO:305), KALA (Wyman et al. (1997) Biochemistry 36:3008-3017; e.g., SEQ ID NO:303) and other cationic peptides, such as, for example, various β-cationic peptides (Akkarawongsa et al. (2008) Antimicrob. Agents and Chemother. 52(6):2120-2129).

The anti-RSV antibodies and antigen-binding fragments thereof provided herein can be modified by the attachment of diagnostic and/or therapeutic moiety to the antibody or antigen-binding fragment thereof. The anti-RSV antibodies and antigen-binding fragments thereof provided herein can be modified by the covalent attachment of any type of molecule, such as a diagnostic or therapeutic molecule, to the antibody or antigen-binding fragment thereof such that covalent attachment does not prevent the antibody or antigen-binding fragment thereof from binding to its corresponding epitope. For example, an anti-RSV antibody or antigen-binding fragment thereof provided herein can be further modified by covalent attachment of a molecule such that the covalent attachment does not prevent the antibody or antigen-binding fragment thereof from binding to RSV. In some examples, the antibodies or antigen-binding fragments thereof can be recombinantly fused to a heterologous polypeptide at the N terminus or C terminus or chemically conjugated, including covalent and non-covalent conjugation, to a heterologous polypeptide or other composition. For example, the heterologous polypeptide or composition can be a diagnostic polypeptide or other diagnostic moiety or a therapeutic polypeptide or other therapeutic moiety. Exemplary diagnostic and therapeutic moieties include, but are not limited to, drugs, radionucleotides, toxins, fluorescent molecules (see, e.g. International PCT Publication Nos. WO 92/08495; WO 91/14438; WO 89/12624; U.S. Pat. No. 5,314,995; and EP 396,387). Diagnostic polypeptides or diagnostic moieties can be used, for example, as labels for in vivo or in vitro detection. Therapeutic polypeptides or therapeutic moieties can be used, for example, for therapy of a viral infection, such as RSV infection, or for treatment of one or more symptoms of a viral infection.

Additional fusion proteins of the anti-RSV antibodies or antigen-binding fragments thereof provided herein can be generated through the techniques of gene-shuffling, motif-shuffling, exon-shuffling, and/or codon-shuffling (collectively referred to as "DNA shuffling"). DNA shuffling can be employed to alter the activities of anti-RSV antibodies or antigen-binding fragments thereof provided herein, for example, to produce antibodies or antigen-binding fragments thereof with higher affinities and lower dissociation rates (see, generally, U.S. Pat. Nos. 5,605,793; 5,811,238; 5,830,721; 5,834,252; and 5,837,458, and Patten et al. (1997) Curr. Opinion Biotechnol. 8:724-33; Harayama (1998) Trends Biotechnol. 16(2):76-82; Hansson et al., (1999) J. Mol. Biol. 287:265-76; and Lorenzo and Blasco (1998) Biotechniques 24(2):308-13).

The provided anti-RSV antibodies or antigen-binding fragments thereof can also be attached to solid supports, which are useful for immunoassays or purification of the target antigen. Exemplary solid supports include, but are not limited to, glass, cellulose, polyacrylamide, nylon, polystyrene, polyvinyl chloride or polypropylene.

1. Modifications to Reduce Immunogenicity

In some examples, the antibodies or antigen-binding fragments thereof provided herein can be further modified to reduce the immunogenicity in a subject, such as a human subject. For example, one or more amino acids in the antibody or antigen-binding fragment thereof can be modified to alter potential epitopes for human T-cells in order to eliminate or reduce the immunogenicity of the antibody or antigen-binding fragment thereof when exposed to the immune system of the subject. Exemplary modifications include substitutions, deletions and insertion of one or more amino acids, which eliminate or reduce the immunogenicity of the antibody or antigen-binding fragment thereof. Generally, such modifications do not alter the binding specificity of the antibody or antigen-binding fragment thereof for its respective antigen. Reducing the immunogenicity of the antibody or antigen-binding fragment thereof can improve one or more properties of the antibody or antigen-binding fragment thereof, such as, for example, improving the therapeutic efficacy of the antibody or antigen-binding fragment thereof and/or increasing the half-life of the antibody or antigen-binding fragment thereof in vivo.

2. Fc Modifications

The anti-RSV antibodies or antigen-binding fragments thereof provided herein can contain wild-type or modified Fc region. As described elsewhere herein, a Fc region can be linked to an anti-RSV antigen-binding fragment provided herein, such as, for example, 58c5, sc5, 30D8, 104E5, 38F10, 14G3, 90D3, 56E11, 17C9 or 69F6, or an antigen-binding fragment derived from 58c5, sc5, 30D8, 104E5, 38F10, 14G3, 90D3, 56E11, 17C9 or 69F6. In some examples, the Fc region can be modified to alter one or more properties of the Fe polypeptide. For example, the Fc region can be modified to alter (i.e. more or less) effector functions compared to the effector function of an Fc region of a wild-type immunoglobulin heavy chain. The Fe regions of an antibody interact with a number of Fe receptors, and ligands, imparting an array of important functional capabilities referred to as effector functions. Fc effector functions include, for example, Fc receptor binding, complement fixation, and T cell depleting activity (see e.g., U.S. Pat. No. 6,136,310). Methods of assaying T cell depleting activity, Fc effector function, and antibody stability are known in the art. For example, the Fc region of an IgG molecule interacts with the FcγRs. These receptors are expressed in a variety of immune cells, including for example, monocytes, macrophages, neutrophils, dendritic cells, eosinophils, mast cells, platelets, B cells, large granular lymphocytes, Langerhans' cells, natural killer (NK) cells, and γδ T cells. Formation of the Fc/FcγR complex recruits these effector cells to sites of bound antigen, typically resulting in signaling events within the cells and important subsequent immune responses such as release of inflammation mediators, B cell activation, endocytosis, phagocytosis, and cytotoxic attack. The ability to mediate cytotoxic and phagocytic effector functions is a potential mechanism by which antibodies destroy targeted cells. Recognition of and lysis of bound antibody on target cells by cytotoxic cells that express FcγRs is referred to as antibody dependent cell-mediated cytotoxicity (ADCC). Other Fc receptors for various antibody isotypes include FcεRs (IgE), FcαRs (IgA), and FcγRs (IgM).

Thus, a modified Fc domain can have altered affinity, including but not limited to, increased or low or no affinity for the Fc receptor. For example, the different IgG subclasses have different affinities for the FcγRs, with IgG1 and IgG3 typically binding substantially better to the receptors than IgG2 and IgG4. In addition, different FcγRs mediate different effector functions. FcγR1, FcγRIIa/c, and FcγRIIIa are positive regulators of immune complex triggered activation, characterized by having an intracellular domain that has an immunoreceptor tyrosine-based activation motif (ITAM). FcγRIIb, however, has an immunoreceptor tyrosine-based inhibition motif (ITIM) and is therefore inhibitory. Thus, altering the affinity of an Fc region for a receptor can modulate the effector functions induced by the Fc domain.

In one example, an Fc region is used that is modified for optimized binding to certain FcγRs to better mediate effector functions, such as for example, antibody-dependent cellular cytotoxicity, ADCC. Such modified Fe regions can contain modifications at one or more of amino acid residues (according to the Kabat numbering scheme, Kabat et al. (1991) Sequences of Proteins of Immunological Interest, U.S. Department of Health and Human Services), including, but not limited to, amino acid positions 249, 252, 259, 262, 268, 271, 273, 277, 280, 281, 285, 287, 296, 300, 317, 323, 343, 345, 346, 349, 351, 352, 353, and 424. For example, modifications in an Fc region can be made corresponding to any one or more of G119S, G119A, S122D, S122E, S122N, S122Q. S122T, K129H, K129Y, D132Y, R138Y, E141Y, T143H, V147I, S150E, H151D, E155Y, E155I, E155H, K157E, G164D, E166L, E166H, S181A, S181D, S187T, S207G, S307I, K209T, K209E, K209D, A210D, A213Y, A213L, A213I, I215D, I215E, I215N, I215Q, E216Y, E216A, K217T, K217F, K217A, and P279L of the exemplary IgG1 sequence set forth in SEQ ID NO:356, or combinations thereof. A modified Fc containing these mutations can have enhanced binding to an FcR such as, for example, the activating receptor FcγIIIa and/or can have reduced binding to the inhibitory receptor FcγRIIb (see e.g., US 2006/0024298). Fc regions modified to have increased binding to FcRs can be more effective in facilitating the destruction of viral (e.g. RSV) infected cells in patients.

In some examples, the antibodies or antigen-binding fragments provided herein can be further modified to improve the interaction of the antibody or antigen-binding fragment thereof with the FcRn receptor in order to increase the in vivo half-life and pharmacokinetics of the antibody or antigen-binding fragment thereof (see, e.g. U.S. Pat. No. 7,217,797, U.S. Pat. Pub. Nos. 2006/0198840 and 2008/0287657). FcRn is the neonatal FcR, the binding of which recycles endocytosed antibody or antigen-binding fragment thereof from the endosomes back to the bloodstream. This process, coupled with preclusion of kidney filtration due to the large size of the full length molecule, results in favorable antibody serum half-lives ranging from one to three weeks. Binding of Fc to FcRn also plays a role in antibody transport.

Exemplary modifications of the Fc region include but are not limited to, mutation of the Fc described in U.S. Pat. No. 7,217,797; U.S. Pat. Pub. Nos. 2006/0198840, 2006/0024298 and 2008/0287657, and International Patent Pub. No. WO 2005/063816, such as mutations at one or more of amino acid residues (Kabat numbering. Kabat et al. (1991)) 251-256, 285-90, 308-314, in the $C_H2$ domain and/or amino acids residues 385-389, and 428-436 in the $C_H3$ domain of the Fc heavy chain constant region, where the modification alters Fe receptor binding affinity and/or serum half-life relative to unmodified antibody or antigen-binding fragment thereof. In some examples, the IgG constant domain is modified in the Fe region at one or more of amino acid positions 250, 251, 252, 254, 255, 256, 263, 308, 309, 311, 312 and 314 in the $C_H2$ domain and/or amino acid positions 385, 386, 387, 389, 428, 433, 434, 436, and 459 in the $C_H3$ domain of the IgG heavy chain constant region. Such modifications correspond to amino acids Gly120, Pro121, Ser122, Phe124, Leu125, Phe126, Thr133, Pro174, Arg175, Glu177, Gln178, and Asn180 in the $C_H2$ domain and amino acids Gln245, Val246, Ser247, Thr249, Ser283, Gly285, Ser286, Phe288, and Met311 in the $C_H3$ domain in an exemplary IgG1 sequence set forth in SEQ ID NO:356. In some examples, the modification is at one or more surface-exposed residues, and the modification is a substitution with a residue of similar charge, polarity or hydrophobicity to the residue being substituted.

In particular examples, a Fc heavy chain constant region is modified at one or more of amino acid positions 251, 252, 254, 255, and 256 (Kabat numbering), where position 251 is substituted with Leu or Arg, position 252 is substituted with Tyr, Phe, Ser, Trp or Thr, position 254 is substituted with Thr or Ser, position 255 is substituted with Leu, Gly, Ile or Arg, and/or position 256 is substituted with Ser, Arg, Gln, Glu, Asp, Ala, Asp or Thr. In some examples, a Fc heavy chain constant region is modified at one or more of amino acid positions 308, 309, 311, 312, and 314, where position 308 is substituted with Thr or Ile, position 309 is substituted with Pro, position 311 is substituted with serine or Glu, position 312 is substituted with Asp, and/or position 314 is substituted with Leu. In some examples, a Fc heavy chain constant region is modified at one or more of amino acid positions 428, 433, 434, and 436, where position 428 is substituted with Met, Thr, Leu, Phe, or Ser, position 433 is substituted with Lys, Arg, Ser, Ile, Pro, Gln, or His, position 434 is substituted with Phe, Tyr, or His, and/or position 436 is substituted with His, Asn, Asp, Thr, Lys, Met, or Thr. In some examples, a Fc heavy chain constant region is modified at one or more of amino acid positions 263 and 459, where position 263 is substituted with Gln or Glu and/or position 459 is substituted with Leu or Phe.

In some examples, a Fc heavy chain constant region can be modified to enhance binding to the complement protein C1q. In addition to interacting with FcRs, Fc also interact with the complement protein C1q to mediate complement dependent cytotoxicity (CDC). C1q forms a complex with the serine proteases C1r and C1s to form the C1 complex. C1q is capable of binding six antibodies, although binding to two IgGs is sufficient to activate the complement cascade. Similar to Fc interaction with FcRs, different IgG subclasses have different affinity for C1q, with IgG1 and IgG3 typically binding substantially better than IgG2 and IgG4. Thus, a modified Fc having increased binding to C1q can mediate enhanced CDC, and can enhance destruction of viral (e.g., RSV) infected cells. Exemplary modifications in an Fc region that increase binding to C1q include, but are not limited to, amino acid modifications at positions 345 and 353 (Kabat numbering). Exemplary modifications include those corresponding to K209W, K209Y, and E216S in an exemplary IgG1 sequence set forth in SEQ ID NO:356.

In another example, a variety of Fc mutants with substitutions to reduce or ablate binding with FcγRs also are known. Such muteins are useful in instances where there is a need for reduced or eliminated effector function mediated by Fc. This is often the case where antagonism, but not killing of the cells bearing a target antigen is desired. Exemplary of such an Fc is an Fe mutein described in U.S. Pat. No. 5,457,035, which is modified at amino acid positions 248, 249 and 251 (Kabat numbering In an exemplary IgG1 sequence set forth in SEQ ID NO:356, amino acid 117 is modified from Leu to Ala, amino acid 118 is modified from Leu to Glu, and amino acid 120 is modified from Gly to Ala. Similar mutations can be made in any Fe sequence such as, for example, the exemplary Fc sequence. This mutein exhibits reduced affinity for Fc receptors.

The antibodies or antigen-binding fragments thereof provided herein can be engineered to contain modified Fc regions. For example, methods for fusing or conjugating polypeptides to the constant regions of antibodies (i.e. making Fc fusion proteins) are known in the art and described in, for example, U.S. Pat. Nos. 5,336,603, 5,622,929, 5,359,046, 5,349,053, 5,447,851, 5,723,125, 5,783,181, 5,908,626, 5,844,095, and 5,112,946; EP 307,434; EP 367,166; EP 394,827; PCT publications WO 91/06570, WO 96/04388, WO 96/22024, WO 97/34631, and WO 99/04813; Ashkenazi et al. (1991) *Proc. Natl. Acad. Sci. USA* 88:10535-10539; Traunecker et al. (1988) *Nature* 331:84-86; Zheng et al. (1995) *J. Immunol.* 154:5590-5600; and Vil et al. (1992) *Proc. Natl. Acad Sci. USA* 89:11337-11341 (1992) and described elsewhere herein. In some examples, a modified Fc region having one or more modifications that increases the FcRn binding affinity and/or improves half-life can be fused to an anti-RSV antibody or antigen-binding fragment thereof provided herein.

3. Pegylation

The anti-RSV antibodies or antigen-binding fragments thereof provided herein can be conjugated to polymer molecules such as high molecular weight polyethylene glycol (PEG) to increase half-life and/or improve their pharmacokinetic profiles. Conjugation can be carried out by techniques known to those skilled in the art. Conjugation of therapeutic antibodies with PEG has been shown to enhance pharmacodynamics while not interfering with function (see, e.g., Deckert et al., *Int. J. Cancer* 87: 382-390, 2000; Knight et al., *Platelets* 15: 409-418, 2004; Leong et al., *Cytokine* 16: 106-119, 2001; and Yang et al., *Protein Eng.* 16: 761-770, 2003). PEG can be attached to the antibodies or antigen-binding fragments with or without a multifunctional linker either through site-specific conjugation of the PEG to the N- or C-terminus of the antibodies or antigen-binding fragments or via epsilon-amino groups present on lysine residues. Linear or branched polymer derivatization that results in minimal loss of biological activity can be used. The degree of conjugation can be monitored by SDS-PAGE and mass spectrometry to ensure proper conjugation of PEG molecules to the antibodies. Unreacted PEG can be separated from antibody-PEG conjugates by, e.g., size exclusion or ion-exchange chromatography. PEG-derivatized antibodies or antigen-binding fragments thereof can be tested for binding activity to RSV antigens as well as for in vivo efficacy using methods known to those skilled in the art, for example, by immunoassays described herein.

4. Conjugation of a Detectable Moiety

In some examples, the anti-RSV antibodies and antibody fragments provided herein can be further modified by conjugation to a detectable moiety. The detectable moieties can be detected directly or indirectly. Depending on the detectable moiety selected, the detectable moiety can be detected in vivo and/or in vitro. The detectable moieties can be employed, for example, in diagnostic methods for detecting exposure to RSV or localization of RSV or binding assays for determining the binding affinity of the anti-RSV antibody or antigen-binding fragment thereof for RSV. The detectable moieties also can be employed in methods of preparation of the anti-RSV antibodies, such as, for example, purification of the antibody or antigen-binding fragment thereof. Typically, detectable moieties are selected such that conjugation of the detectable moiety does not interfere with the binding of the antibody or antigen-binding fragment thereof to the target epitope. Generally, the choice of the detectable moiety depends on sensitivity required, ease of conjugation with the compound, stability requirements, available instrumentation, and disposal provisions. One of skill in the art is familiar with labels and can identify a detectable label suitable for and compatible with the assay employed. Methods of labeling antibodies with detectable moieties are known in the art and include, for example, recombinant and chemical methods.

The detectable moiety can be any material having a detectable physical or chemical property. Such detectable labels have been well-developed in the field of immunoassays and, in general, most any label useful in such methods can be applied in the methods provided. Thus, a label is any composition detectable by spectroscopic, photochemical, biochemical, immunochemical, electrical, optical or chemical means. Useful labels include, but are not limited to, fluorescent dyes (e.g., fluorescein isothiocyanate, Texas red, rhodamine, and the like), radiolabels (e.g., $^{3}$H, $^{125}$I, $^{35}$S, $^{14}$C, or $^{32}$P), in particular, gamma and positron emitting radio-isotopes (e.g., $^{157}$Gd, $^{55}$Mn, $^{162}$Dy, $^{52}$Cr, and $^{56}$Fe), metallic ions (e.g., $^{111}$In, $^{97}$Ru, $^{67}$Ga, $^{68}$Ga, $^{72}$As, $^{89}$Zr, and $^{201}$Tl), enzymes (e.g., horse radish peroxidase, alkaline phosphatase and others commonly used in an ELISA), electron transfer agents (e.g., including metal binding proteins and compounds), luminescent and chemiluminescent labels (e.g., luciferin and 2,3-dihydrophtahlazinediones, e.g., luminol), magnetic beads (e.g., DYNABEADS™), and colorimetric labels such as colloidal gold or colored glass or plastic beads (e.g., polystyrene, polypropylene, latex, etc.). For a review of various labeling or signal producing systems that can be used, see e.g. U.S. Pat. No. 4,391,904.

5. Conjugation of a Therapeutic Moiety

In some examples, the anti-RSV antibodies and antigen-binding fragments provided herein can be further modified by conjugation to a therapeutic moiety. Exemplary therapeutic moieties include, but are not limited to, a cytotoxin (e.g., a cytostatic or cytocidal agent), a therapeutic agent or a radioactive metal ion (e.g., alpha-emitters). Exemplary cytotoxin or cytotoxic agents include, but are not limited to, any agent that is detrimental to cells, such as, but not limited to, paclitaxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof. Exemplary therapeutic agents include, but are not limited to, antimetabolites (e.g., methotrexate, 6-mercaptopurine, 6-thioguanine, cytarabine, 5-fluorouracil decarbazine), alkylating agents (e.g., mechlorethamine, thioepa chlorambucil, melphalan, carmustine (BSNU) and lomustine (CCNU), cyclothosphamide, busulfan, dibromomannitol, streptozotocin, mitomycin C, and cis-dichlorodiamine platinum (II) (DDP) cisplatin), anthracyclines (e.g., daunorubicin (formerly daunomycin) and doxorubicin), antibiotics (e.g., dactinomycin (formerly actinomycin), bleomycin, mithramycin, and anthramycin (AMC)), anti-mitotic agents (e.g., vincristine and vinblastine), and antivirals, such as, but not limited to, nucleoside analogs, such as zidovudine, acyclovir, gangcyclovir, vidarabine, idoxuridine, trifluridine, and ribavirin; foscamet, amantadine, rimantadine, saquinavir, indinavir, ritonavir, and alpha-interferons.

In some examples, the anti-RSV antibodies and antigen-binding fragments provided herein can be further modified by conjugation to a therapeutic moiety that is a therapeutic polypeptide. Exemplary therapeutic polypeptides include, but are not limited to, a toxin, such as abrin, ricin A, *pseudomonas* exotoxin, or diphtheria toxin; or an immunostimulatory agent, such as a cytokine, such as, but not limited to, an interferon (e.g., IFN-α, β, γ, ω), a lymphokine, a hematopoietic growth factor, such as, for example, GM-CSF (granulocyte macrophage colony stimulating factor), Interleukin-2 (IL-2), Interleukin-3 (IL-3), Interleukin-4 (IL-4), Interleukin-7 (IL-7), Interleukin-10 (IL-10), Interleukin-12 (IL-12), Interleukin-14 (IL-14), and Tumor Necrosis Factor (TNF).

6. Modifications to Improve Binding Specificity

The binding specificity of the anti-RSV antibodies and antibody fragments provided can be altered or improved by techniques, such as phage display. Methods for phage display generally involve the use of a filamentous phage (phagemid) surface expression vector system for cloning and expressing antibody species of the library. Various phagemid cloning systems to produce combinatorial libraries have been described by others. See, for example the preparation of combinatorial antibody libraries on phagemids as described by Kang et al., (1991) *Proc. Natl. Acad. Sci., USA*, 88:4363-4366; Barbas et al., (1991) *Proc. Natl. Acad. Sci. USA*, 88:7978-7982; Zebedee et al., (1992) *Proc. Natl. Acad. Sci., USA*, 89:3175-3179; Kang et al., (1991) *Proc. Natl. Acad. Sci., USA*, 88:11120-11123; Barbas et al., (1992) *Proc. Natl. Acad. Sci., USA*, 89:4457-4461; and Gram et al., (1992) *Proc. Natl. Acad Sci., USA*, 89:3576-3580, which are incorporated herein by reference.

In particular examples, DNA sequences encoding $V_H$ and $V_L$ domains are amplified from animal cDNA libraries (e.g., human or murine cDNA libraries of lymphoid tissues). The DNA encoding the $V_H$ and $V_L$ domains are recombined together with an scFv linker by PCR and cloned into a phagemid vector (e.g., p CANTAB 6 or pComb 3 HSS). The vector is electroporated in *E. coli* and the *E. coli* is infected with helper phage. Phage used in these methods are typically filamentous phage including fd and M13 and the $V_H$ and $V_L$ domains are usually recombinantly fused to either the phage gene III or gene VIII. Phage expressing an antigen-binding domain that binds to a RSV antigen, for example, RSV F protein, can be selected or identified with antigen, e.g., using labeled antigen or antigen bound or captured to a solid surface or bead. Examples of phage display methods that can be used to make the antibodies by phage display include those disclosed, for example, in Brinkman et al. (1995) *J. Immunol. Methods* 182:41-50; Ames et al. (1995) *J. Immunol. Methods* 184:177-186; Kettleborough et al. (1994) *Eur. J. Immunol.* 24:952-958; Persic et al. (1997) *Gene* 187:9-18; Burton et al. (1994) *Advances in Immunology* 57:191-280; PCT publication Nos. WO 90/02809, WO 91/10737, WO 92/01047, WO 92/18619, WO 93/1 1236, WO 95/15982, WO 95/20401, and WO97/13844; and U.S. Pat. Nos. 5,698, 426, 5,223,409, 5,403,484, 5,580,717, 5,427,908, 5,750,753, 5,821,047, 5,571,698, 5,427,908, 5,516,637, 5,780,225, 5,658,727, 5,733,743 and 5,969,108; each of which is incorporated herein by reference in its entirety.

As described in the above references, after phage selection, the antibody coding regions from the phage can be isolated and used to generate whole antibodies, including human antibodies, or any other desired antigen-binding fragment, and expressed in any desired host, including mammalian cells, insect cells, plant cells, yeast, and bacteria, e.g., as described herein. Techniques to recombinantly produce Fab, Fab' and F(ab')$_2$ fragments can also be employed using methods known in the art such as those disclosed in PCT publication No. WO 92/22324; Mullinax et al. (1992) *BioTechniques* 12(6):864-869; Sawai et al. (1995) *AJRI* 34:26-34; and Better et al. (1988) *Science* 240: 1041-1043.

The resulting phagemid library can be manipulated to increase and/or alter the immunospecificities of the antibodies or antigen-binding fragments to produce and subsequently identify additional antibodies with improved properties, such as increased binding to a target antigen. For example, either or both the heavy and light chain encoding DNA can be mutagenized in a complementarity determining region (CDR) of the variable region of the immunoglobulin polypeptide, and subsequently screened for desirable immunoreaction and neutralization capabilities. The resulting antibodies can then be screened in one or more of the assays described herein for determining neutralization capacity.

For some uses, including in vivo use of antibodies in humans and in vitro detection assays, human or chimeric antibodies are used. Completely human antibodies are particularly desirable for therapeutic treatment of human subjects. Human antibodies can be made by a variety of methods known in the art including phage display methods described above using antibody libraries derived from human immunoglobulin sequences or synthetic sequences homologous to human immunoglobulin sequences. See U.S. Pat. Nos. 4,444,887 and 4,716,111; and PCT publication Nos. WO 98/46645, WO 98/50433, WO 98/24893, WO98/16654, WO 96/34096, WO 96/33735, and WO 91/10741; each of which is incorporated herein by reference in its entirety.

E. METHODS OF ISOLATING ANTI-RSV ANTIBODIES

Anti-RSV antibodies or antigen-binding fragments thereof can be identified and isolated by a variety of techniques well-known in the art including, but not limited to, murine hybridomas (see, e.g., Olsson and Kaplan (1980) *Proc Natl Acad Sci USA* 77:5429-5431; such antibodies can be humanized as described elsewhere herein for use in humans), transgenic mice expressing human immunoglobulin genes (see, e.g., Kellerman and Green (2000) *Curr. Opin Biotechnol.* 13:593-597), phage display (see, e.g., Mancini (2004) *New Microbiol.* 27:315-28), and isolation from mature human immune cells, such as B cells (see, e.g., Banchereau and Rousset (1992) *Adv Immunol.* 52: 125-262, Crotty and Ahmed (2004) *Semin Immunol.* 16: 197-203, Carsetti (2004) *Methods Mol. Biol.* 271: 25-35, McHeyzer-Williams and McHeyzer-Williams (2005) *Annu Rev Immunol.* 23:487-513). In an exemplary method provided herein, the human anti-RSV antibodies and antigen-binding fragments thereof provided herein are identified and isolated from human B cells.

Given the difficulty in obtaining stable hybridomas from human antibody secreting cells, an exemplary method that has been extensively used to produce and isolate human antibody-secreting cells is the immortalization of human B cells with Epstein Barr Virus (EBV), which is also known to induce polyclonal B cell activation and proliferation (see, e.g., Sugimoto et al. (2004) *Cancer Res.* 64:3361-3364; Bishop and Busch (2002) *Microbes Infect.* 4:853-857). Antibody-secreting cells have been produced, for example, by EBV immortalization of human B cells, such as the peripheral blood, lymph nodes, spleen, tonsils, or pleural fluids from patients or other individuals that may be exposed to the antigen or healthy subjects pre-selected using a labeled antigen (see, e.g., Casali et al. (1986) *Science* 234:476-9, Yamaguchi et al. (1987) *Proc Natl Acad Sci USA* 84:2416-

2420, Posner et al. (1991) *J Immunol.* 146:4325-4332, Raff et al. (1988) *J Exp Med.* 168:905-917, Steenbakkers et al. (1993) *Hum Antibod Hybrid* 4:166-173, Steenbakkers et al. (1994) *Mol Biol Rep.* 19:125-134, Evans et al. (1988) *J Immunol* 140:941-943, and Wallis R et al. (1989) *J Clin Invest* 84:214-219).

Due to the low transformability, low clonability, and the inherent instability and heterogeneity of EBV-infected human B cells (Chan et al. (1986) *J Immunol* 136:106-112, and James and Bell (1987) *J Immunol Methods.* 100:5-40), known techniques such as cell fusion, such as, for example with a myeloma cell line can be employed (see, e.g., Bron et al. (1984) *PNAS* 81:3214-3217; Yamaguchi et al. (1987) *Proc Natl Acad Sci USA* 84:2416-2420; Posner et al. (1991) *J Immunol.* 146:4325-4332, Niedbala and Stott (1998) *Hybridoma* 17:299-304; Li et al. (2006) *Proc Natl Acad Sci USA* 103:3557-62). Additional techniques for improving EBV immortalization include, for example, immortalization with oncogenic virus, transformation with oncogenes, mini-electrofusion, and mouse-human heterofusion in a single process (see, e.g., U.S. Pat. No. 4,997,764; Steenbakkers et al. (1993) *Hum Antibod Hybrid.* 4:166-173; Dessain et al. (2004) *J Immunol Methods.* 291:109-22). Human monoclonal antibodies can be isolated from B cells that have been activated and immortalized in the presence or in the absence of an antigen and by combining various manipulations in cell culture as described in the art (see e.g., Borrebaeck et al. (1988) *Proc Natl Acad Sci USA* 85: 3995-3999, Davenport et al. (1992) *FEMS Microbiol Immunol.* 4:335-343, Laroche-Traineau et al. (1994) *Hum Antib Hybrid* 5:165-177, Morgenthaler et al. (1996) *J. Clin Endocrinology.* 81:3155-3161, Niedbala and Kurpisz (1993) *Immunol Lett.* 35:93-100, Mulder et al. (1993) *Hum Immunol.* 36:186-192, Hur et al. (2005) *Cell Prolif.* 38:35-45, Traggiai et al. (2004) *Nat Med* 10:871-875, Tsuchiyama et al. (1997) *Hum Antibodies* 8:43-47; and PCT Pub. Nos. WO 91109115, WO 041076677, WO 88101642, WO 90102795, WO 96140252, and WO 02146233).

Methods for the isolation of human antibodies from mature B cells, generally involve the isolation of a mature B cell population and screening antibodies expressed by the B cells against a particular antigen. A variety of different populations of antibody-secreting cells can be isolated from human donors having specific profiles (e.g. naive, vaccinated, more or less recently infected and seropositive individuals) and from different tissues (e.g. blood, tonsils, spleen, lymph nodes) where B cells reside and exert their activities (Viau and Zouali (2005) *Clin Immunol.* 114:17-26). In an exemplary method provided herein, anti-RSV antibodies provided herein can be isolated from a sample of peripheral blood mononuclear cells (PBMCs), which contain B cells, isolated from human donors and/or from healthy human donors that have been or have a high probability of having been exposed to RSV, such as health care workers.

After the isolation of PBMCs from the biological samples, a specific selection of antibody-secreting cells can be performed, using one of the various methods described in the art, on the basis of the expression of cell surface markers on their surface and, if appropriate, of other proteins, as well as the proliferation activity, the metabolic and/or morphological status of the cells. In particular, various technologies for the purification of antibody-secreting cells from human samples make use of different means and conditions for positive or negative selection. These cells are more easily and efficiently selected by physically separating those expressing cell surface markers specific for cells that express and secrete antibodies (e.g. human B cells). Specific protocols are known and can be found in the literature (see, e.g. Callard and Kotowicz "Human B-cell responses to cytokines" in Cytokine Cell Biology: A practical Approach. Balkwill F. (ed.) Oxford University Press, 2000, 17-31).

The selection of specific immune cells such as B cells, is typically performed using antibodies that bind specifically to a B-cell specific cell surface protein and that can be linked to solid supports (e.g. microbeads or plastic plates) or labeled with a fluorochrome that can be detected using fluorescence-activated cell sorting (FACS). For example, human B cells have been selected on the basis of their affinity for supports (such as microbeads) binding CD19, CD27, and/or CD22 microbeads, or for the lack of binding affinity for antibodies specific for certain isotypes prior to EBV immortalization (see, e.g., Li et al. (1995) *Biochem Biophys Res Commun* 207:985-993, Bernasconi et al. (2003) *Blood* 101:4500-4504, and Traggiai et al. (2004) *Nat Med* 10:871-875). The selection of the cell marker for purification can affect the efficiency of the immortalization process, for example, due to intracellular signals that are triggered by the selection process and that may alter cell growth and viability. For example, CD22, which is a B-cell restricted transmembrane protein that controls signal transduction pathways related to antigen recognition and B cell activation is an exemplary molecule for initial B cell selection. Since the CD22 positive population contains cells that express antibodies having different isotypes and specificities, other cell surface markers also can be used for selecting the cells, either before or after the stimulation phase.

In some examples, a specific enrichment of antibody-secreting cells can be obtained by applying a CD27-based selection in addition to the CD22-based selection. CD27 is known to be a marker for human B cells that have somatically mutated variable region genes (Borst J et al. (2005) *Curr Opin Immunol.* 17:275-281). Additional markers such as CD5, CD24, CD25, CD86, CD38, CD45, CD70, or CD69 also can be used to either deplete or enrich for the desired population of cells. Thus, depending on factors, such as the donor's history of exposure to the antigen (e.g. an RSV antigen) and the antibody titer, total CD22-enriched B cells, or further enriched B cell subpopulations such as CD27 positive B cells can be selected.

Following cell selection, and before immortalization of the cells, the population of cells can be exposed to an appropriate stimulating agent. Exemplary stimulating agents include, for example, polyclonal B cell activators, such as, but not limited to, agonists of innate immune responses (e.g. Toll-like receptor agonists such as CpG oligonucleotides (Bernasconi et al. (2003) *Blood* 101:4500-4504, Bernasconi et al. (2002) *Science* 298:2199-2202, Bourke et al. (2003) *Blood* 102:956-63; e.g. CpG nucleotides, such as for example, CpG2006, CpG2395, and CpG2395, available from Cell Sciences, Canton, Mass.) and immunomodulatory molecules such as cytokines (e.g., interleukins known to have immunostimulating activities, for example, IL-2, IL-4, IL-6, IL-10, and IL-13 (see Callard and Kotowicz "Human B-cell responses to cytokines" in Cytokine Cell Biology: A practical Approach. Balkwill F (ed.) Oxford University Press, 2000, 17-31) and agonists of cell membrane receptors of the TNF receptor family, in particular those activating the NF-κB pathway and proliferation in B cells, such as, but not limited to, APRIL, BAFF, CD 40 ligand (CD40L) (see, e.g., Schneider (2005) *Curr Opin Immunol.* 17:282-289, He et al. (2004) *J Immunol.* 172:3268-3279, Craxton et al. (2003) *Blood* 101:4464-4471, and Tangye et al. (2003) *J Immunol.* 170:261-269). Exemplary methods of stimulating B cells using EBV immortalization in combination with or sequentially with one or more polyclonal activators are known in the art (see, e.g., Traggiai et al. (2004) *Nat Med* 10:871-875, Tsuchiyama et al. (1997) *Hum Antibodies* 8:43-47, Imadome et al. (2003) *Proc Natl Acad Sci USA* 100:7836-7840, and PCT Pub. Nos. WO 07/068758, WO 04/76677, WO 91/09115, and WO 94/24164). The combination of stimulating agents can be added to the cell culture medium before the immortalization phase at the same time or sequentially (e.g. adding a first stimulating agent immediately after the initial cell selection and a second stimulating agent hours or days later). The stimulating agents can be directly added in the cell culture medium from diluted stock solutions, or after being appropriately formulated, for example, using liposomes or other compounds that can improve their uptake and immunostimulatory activity (Gursel et al. (2001) *J Immunol.* 167:3324-3328). The stimulating agents also can be attached to solid matrices (microbeads or directly on the cell culture plates), which can allow for effective removal of the agent(s). The cells can be washed with fresh medium one or more times and, optionally, maintained in normal cell culture medium (for example, from 1 up to 6 days) in order to further dilute and eliminate any remaining effect of the stimulating agents. The stimulating agent(s) also can be inhibited by adding specific compounds into the cell culture.

The cells can be further selected on the basis of the isotype of the expressed antibody after stimulating the cells and before exposing said selected and stimulated cells to the immortalizing agent (i.e. between the stimulation phase and the immortalization phase). The isotype-based selection of the cells can be performed by applying means for either positive (allowing the isolation of the specific cells) or negative (allowing the elimination of unwanted cells) selection. For example, a population of stimulated IgG positive cells can be selected positively (by FACS or magnetic cell separators) or by depleting cells that express IgM from the population of cells, and consequently enriching for cells that express IgG. Separation technologies for antibody-secreting cells using fluorescence activated or magnetic cell separators are known in the literature (see, e.g., Li et al. (1995) *Biochem Biophys Res Commun* 207:985-993, Traggiai et al. (2004) *Nat Med* 10:871-875). Depending on the source of antibody-secreting cells and their final use, depletion (or enrichment) of other isotype expressing cells, such as IgD or IgA expressing cells, also can be performed. A similar approach can be used for isolating cells on the basis of the specific subclass, if such a precise selection is desired (e.g., selection of human B cells that express IgG1, IgG2, IgG3, or IgG4 antibodies).

Various viral immortalization agents are known in the art and can be used on antibody-secreting cells to obtain immortalized antibody-secreting cells. Viruses that infect and immortalize antibody-secreting cells are commonly known as lymphotropic viruses. Exemplary of such viruses are those included in the gamma class of herpesviruses. Members of this virus family infect lymphocytes in a species-specific manner, and are associated with lymphoproliferative disorders and the development of several malignancies (Nicholas (2000) *J. Mol Pathol.* 53:222-237 and Rickinson (2001) *Philos Trans R Soc Lond B Biol Sci.* 356:595-604). Exemplary viruses for use as an immortalization agent in the methods provide include EBV (Epstein-Barr virus, also known as herpesvirus 4), and HHV-8 (human herpesvirus 8, also known as KSHV, Kaposi's Sarcoma associated Herpesvirus), which can infect and immortalize human lymphocytes. Other exemplary viruses for use in the methods include, but are not limited to, MHV-68 (murine herpesvirus 68), HVS (herpesvirus Samiri), RRV (Rhesus Rhadinovirus), LCV (primate Lymphocryptovirus), EHV-2 (Equine Herpesvirus 2) HVA (Herpesvirus Ateles), and AHV-1 (Alcelaphine Herpesvirus 1), which are other oncogenic, lymphotropic herpesvirus having some common genetic features conserved amongst them and similar pathogenic effects in different mammalian host cells.

Recombinant DNA constructs that contain specific viral proteins from viruses employed for immortalize also have been used to immortalize B cells (see Damania (2004) *Nat Rev Microbiol.* 2:656-668 and Kilger et al. (1998) *EMBO J.* 17:1700-1709). Similar vectors containing viral genes can be transduced into cells in the methods provided. Methods of making such constructs are well-known in the art and include, for example, the use of retroviral systems or virus-like particles and packaging cell lines, which provide all the necessary factors in trans for the formation of such particles.

The immortalization phase can last between one and several hours, up to 2-4 days. The length of immortalization phase can be adjusted depending of various factors such as cell viability and efficiency of immortalization. In some examples, the cells are immortalized with EBV for a period of about 4 to about 24 hours. In a particular example, the cells are immortalized with EBV for a period of about 16 hours.

EBV-mediated immortalization of B cells requires the expression of the cell surface receptor CD21, which is considered as the main EBV receptor. CD21 is present on most B cell subpopulations and regulates B cell responses by forming a complex with CD19 and the B cell antigen receptor (Fearon and Carroll (2000) *Ann Rev Immun.* 18:393-422). The ability to transform cells with EBV can be enhanced by the addition of B cell stimulating agents, but the conditions must ensure that CD21 is maintained on the cell surface, allowing EBV immortalization at high efficiency.

Following the immortalization phase, the immortalized cells can cultured at a low density on feeder cell layers. The feeder layer can be constituted by irradiated non-allogenic peripheral blood cell preparations, lymphoblastoid or fibroblast cell lines, cord blood lymphocytes, or different types of embryonic cells. An example of a cell line having such properties is EL4-B5, mutant EL4 thymoma cell lines that efficiently support the growth and the proliferation of B cells. Other exemplary feeder cells include irradiated B-cell depleted PMBC feeder cells as described elsewhere herein. Growth promoting agents such as those used to stimulate the B cell population also can be used to maintain the immortalized B cell population following immortalization.

The immortalized populations of cells can be used for a series of applications, in particular related to antibody isolation, characterization and production. In some examples, DNA libraries encoding the antibodies expressed by the cells or fragments of such antibodies can be constructed from DNA isolated from the bulk population of cells using common recombinant techniques. In some examples as described herein, the immortalized cells can be further cultured and divided into pools of antibody-secreting cells. The pools of cells can be cultured, for example, on feed cell layers.

In some examples, cell culture supernatants from the pools of cells are screened in one or more rounds, for the identification of cells that express antibodies having a particular antigen specificity (e.g., antibodies that immunospecifically bind a RSV F protein). Exemplary methods for screening antibodies and measuring binding specificity are described elsewhere herein and are known in the art. Once a particular antibody is identified. DNA encoding the antibody or antigen-binding portions thereof can be isolated from the pools of cells using well-known recombinant methods. As described herein, DNA isolated from the pools of cells can then be expressed (e.g., in a prokaryotic or eukaryotic host cell) and re-screened for the identification of individual clones that express the desired antibody or antigen-binding fragment thereof. Methods of expression and purification of antibodies is well known to one of skill in the art and is described in Section F.

In some examples as described herein, the immortalized cells can be single cell sorted using a cell sorter (e.g., FACS), using a labeled antigen. In a particular example, cells expressing anti-RSV antibodies can be isolated using an RSV F antigen labeled with Alexa Fluor 647 in order to label the desired cells. Following sorting, DNA encoding the anti-RSV antibody or antigen-binding fragment thereof can then be isolated using well-known recombinant methods. DNA isolated from the pools of cells can be expressed (e.g., in a prokaryotic or eukaryotic host cell) to confirm binding to the RSV antigen.

Typically, the screening methods employed for the identification of individual antibodies that bind to a particular antigen result in the identification of the antigen-binding portion of such antibodies. To generate full length or other derivative antibodies from the antigen-binding fragment, nucleotide sequences encoding the $V_H$ and/or $V_L$ chain or antigen-binding portions thereof can be isolated and cloned into vectors expressing a $V_H$ constant region (e.g., the human gamma 1 constant region), $V_L$ constant region (e.g., human kappa or lambda constant regions), respectively. The $V_H$ and $V_L$ domains also can be cloned into a vector expressing the selected constant regions. The heavy chain conversion vectors and light chain conversion vectors are then co-transfected into cell lines to generate stable or transient cell lines that express full-length antibodies, e.g., IgG, using techniques known to those of skill in the art.

F. METHODS OF PRODUCING ANTI-RSV ANTIBODIES, AND MODIFIED OR VARIANT FORMS THEREOF AND NUCLEIC ACIDS ENCODING ANTIBODIES

The anti-RSV antibodies or antigen-binding fragments thereof provided herein can be generated by any suitable method known in the art for the preparation of antibodies, including chemical synthesis and recombinant expression techniques. Various combinations of host cells and vectors can be used to receive, maintain, reproduce and amplify nucleic acids (e.g. nucleic acids encoding antibodies such as the anti-RSV antibodies or antigen-binding fragments thereof provided), and to express polypeptides encoded by the nucleic acids. In general, the choice of host cell and vector depends on whether amplification, polypeptide expression, and/or display on a genetic package, such as a phage, is desired. Methods for transforming host cells are well known. Any known transformation method (e.g., transformation, transfection, infection, electroporation and sonoporation) can be used to transform the host cell with nucleic acids. Procedures for the production of antibodies, such as monoclonal antibodies and antibody fragments, such as, but not limited to, Fab fragments and single chain antibodies are well known in the art.

Monoclonal antibodies can be prepared using a wide variety of techniques known in the art including, but not limited to, the use of hybridoma, recombinant expression, phage display technologies or a combination thereof. For example, monoclonal antibodies can be produced using hybridoma techniques including those known in the art and taught, for example, in Harlow et al., Antibodies: A Laboratory Manual (Cold Spring Harbor Laboratory Press, 2nd ed. 1988); Hammerling, Monoclonal Antibodies and T-Cell Hybridomas 5630681 (Elsevier N.Y. 1981).

Polypeptides, such as any set forth herein, including the anti-RSV antibodies or antigen-binding fragments thereof provided herein, can be produced by any method known to those of skill in the art including in vivo and in vitro methods. Desired polypeptides can be expressed in an organism suitable to produce the required amounts and forms of the proteins, such as for example, needed for analysis, administration and treatment. Expression hosts include prokaryotic and eukaryotic organisms such as *E. coli*, yeast, plants, insect cells, mammalian cells, including human cell lines and transgenic animals (e.g., rabbits, mice, rats, and livestock, such as, but not limited to, goats, sheep, and cattle), including production in serum, milk and eggs. Expression hosts can differ in their protein production levels as well as the types of post-translational modifications that are present on the expressed proteins. The choice of expression host can be made based on these and other factors, such as regulatory and safety considerations, production costs and the need and methods for purification.

1. Nucleic Acids

Provided herein are isolated nucleic acid molecules encoding an anti-RSV antibody or antigen-binding fragment thereof provided herein. In some examples, the isolated nucleic acid molecule encodes an antibody that is 30D8, 104E5, 38F10, 14G3, 90D3, 56E11, 17C9 or 69F6. In some examples, the isolated nucleic acid molecule encodes an antibody form or other antigen-binding fragment form of 30D8, 104E5, 38F10, 14G3, 90D3, 56E11, 17C9 or 69F6.

In some examples, the isolated nucleic acid molecule provided herein encodes an antibody or antigen-binding fragment thereof containing a heavy chain having an amino acid sequence set forth in SEQ ID NOS:396, 398, 400, 402, 404, 452, 454 or 456. In some examples, the isolated nucleic acid molecule provided contains a nucleic acid having a sequence of nucleotides set forth in SEQ ID NOS:443, 445, 447, 449, 451, 477, 479 or 481.

In some examples, the isolated nucleic acid molecule provided herein encodes an antibody or antigen-binding fragment thereof containing a light chain having an amino acid sequence set forth in SEQ ID NOS:395, 397, 399, 401, 403, 453, 455 or 457. In some examples, the isolated nucleic acid molecule provided contains a nucleic acid having a sequence of nucleotides set forth in SEQ ID NOS:442, 444, 446, 448, 450, 476, 478 or 480.

In some examples, the isolated nucleic acid molecule provided encodes an antibody or antigen-binding fragment thereof containing a $V_H$ CDR1 having an amino acid sequence set forth in SEQ ID NOS:405, 411, 417, 423, 429, 437-441, 458, 464, 470 or 482-484. In some examples, the isolated nucleic acid molecule provided encodes an antibody or antigen-binding fragment thereof containing a $V_H$ CDR2 having an amino acid sequence set forth in SEQ ID NOS: 406, 412, 418, 424, 430, 459, 465 or 471. In some examples, the isolated nucleic acid molecule provided encodes an antibody or antigen-binding fragment thereof containing a $V_H$ CDR3 having an amino acid sequence set forth in SEQ ID NOS:407, 413, 419, 425, 431, 460, 466 or 472.

In some examples, the isolated nucleic acid molecule provided encodes an antibody or antigen-binding fragment thereof containing a $V_L$ CDR1 having an amino acid sequence set forth in SEQ ID NOS:408, 414, 420, 426, 432, 461, 467 or 473. In some examples, the isolated nucleic acid molecule provided encodes an antibody or antigen-binding fragment thereof containing a $V_L$ CDR2 having an amino acid sequence set forth in SEQ ID NOS: 409, 415, 421, 427, 433, 462, 468 or 474. In some examples, the isolated nucleic acid molecule provided encodes an antibody or antigen-binding fragment thereof containing a $V_L$ CDR3 having an amino acid sequence set forth in SEQ ID NOS:410, 416, 422, 428, 434, 463, 469 or 475.

Nucleic acid molecules encoding the anti-RSV antibodies or antigen-binding fragments thereof provided herein can be prepared using well-known recombinant techniques for manipulation of nucleic acid molecules (see, e.g., techniques described in Sambrook et al. (1990) Molecular Cloning, A Laboratory Manual. 2d Ed., Cold Spring Harbor Laboratory, Cold Spring Harbor, N.Y. and Ausubel et al., eds. (1998) Current Protocols in Molecular Biology, John Wiley & Sons, NY). In some examples, methods, such as, but not limited to, recombinant DNA techniques, site directed mutagenesis, and polymerase chain reaction (PCR) can be used to generate modified antibodies or antigen-binding fragments thereof having a different amino acid sequence, for example, to create amino acid substitutions, deletions, and/or insertions.

In some examples, one or more of the CDRs of an anti-RSV antibody or antigen-binding fragment thereof provided herein is inserted within framework regions using routine recombinant DNA techniques. The framework regions can be selected from naturally occurring or consensus framework regions, including human framework regions (see, e.g., Chothia et al. (1998) *J. Mol. Biol.* 278: 457-479 for exemplary framework regions). Generally, the polynucleotide generated by the combination of the framework regions and CDRs encodes an antibody or antigen-binding fragment thereof that maintains the antigen-binding specificity of the parent anti-RSV antibody or antigen-binding fragment thereof. Alterations to the polynucleotide can be made to improve one or more properties of the encoded antibody or antigen-binding fragment thereof and within the skill of the art. In some examples, one or more modifications of the polynucleotide can be made to produce amino acid substitutions within the framework regions, which, for example, improve binding of the antibody or antigen-binding fragment thereof to its antigen. Additionally, such methods can be used to make amino acid substitutions or deletions of one or more variable region cysteine residues participating in an intrachain disulfide bond to generate antibody molecules lacking one or more intrachain disulfide bonds.

2. Vectors

Provided herein are vectors that contain nucleic acid or nucleic acids (encoding the heavy and light chain) encoding the anti-RSV antibodies or antigen-binding fragments thereof. Generally, nucleic acid encoding the heavy chain of an antibody is cloned into a vector and the nucleic acid encoding the light chain of an antibody is cloned into the vector. The genes can be cloned into a single vector for dual expression thereof, or into separate vectors. If desired, the vectors also can contain further sequences encoding additional constant region(s) or hinge regions to generate other antibody forms.

Many expression vectors are available and known to those of skill in the art and can be used for expression of polypeptides. The choice of expression vector will be influenced by the choice of host expression system. Such selection is well within the level of skill of the skilled artisan. In general, expression vectors can include transcriptional promoters and optionally enhancers, translational signals, and transcriptional and translational termination signals. Expression vectors that are used for stable transformation typically have a selectable marker which allows selection and maintenance of the transformed cells. In some cases, an origin of replication can be used to amplify the copy number of the vector in the cells.

Vectors also can contain additional nucleotide sequences operably linked to the ligated nucleic acid molecule, such as, for example, an epitope tag such as for localization, e.g. a hexa-his tag or a myc tag, or a tag for purification, for example, a GST fusion, and a sequence for directing protein secretion and/or membrane association.

Expression of the antibodies or antigen-binding fragments thereof can be controlled by any promoter/enhancer known in the art. Suitable bacterial promoters are well known in the art and described herein below. Other suitable promoters for mammalian cells, yeast cells and insect cells are well known in the art and some are exemplified below. Selection of the promoter used to direct expression of a heterologous nucleic acid depends on the particular application and is within the level of skill of the skilled artisan. Promoters which can be used include but are not limited to eukaryotic expression vectors containing the SV40 early promoter (Bernoist and Chambon, (1981) *Nature* 290:304-310), the promoter contained in the 3' long terminal repeat of Rous sarcoma virus (Yamamoto et al. (1980) *Cell* 22:787-797), the herpes thymidine kinase promoter (Wagner et al., (1981) *Proc. Natl. Acad Sci. USA* 78:1441-1445), the regulatory sequences of the metallothionein gene (Brinster et al., (1982) *Nature* 296:39-42); prokaryotic expression vectors such as the β-lactamase promoter (Jay et al., (1981) *Proc. Natl. Acad Sci. USA* 78:5543) or the tac promoter (DeBoer et al., (1983) *Proc. Natl. Acad. Sci. USA* 80:21-25); see also "Useful Proteins from Recombinant Bacteria": in Scientific American 242:79-94 (1980)); plant expression vectors containing the nopaline synthetase promoter (Herrera-Estrella et al., (1984) *Nature* 303:209-213) or the cauliflower mosaic virus 35S RNA promoter (Gardner et al., (1981) *Nucleic Acids Res.* 9:2871), and the promoter of the photosynthetic enzyme ribulose bisphosphate carboxylase (Herrera-Estrella et al., (1984) *Nature* 310:115-120); promoter elements from yeast and other fungi such as the Gal4 promoter, the alcohol dehydrogenase promoter, the phosphoglycerol kinase promoter, the alkaline phosphatase promoter, and the following animal transcriptional control regions that exhibit tissue specificity and have been used in transgenic animals: elastase I gene control region which is active in pancreatic acinar cells (Swift et al., (1984) *Cell* 38:639-646; Ornitz et al., (1986) *Cold Spring Harbor Symp. Quant. Biol.* 50:399-409; MacDonald, (1987) *Hepatology* 7:425-515); insulin gene control region which is active in pancreatic beta cells (Hanahan et al., (1985) *Nature* 315:115-122), immunoglobulin gene control region which is active in lymphoid cells (Grosschedl et al., (1984) *Cell* 38:647-658; Adams et al., (1985) *Nature* 318:533-538; Alexander et al., (1987) *Mol. Cell Biol.* 7:1436-1444), mouse mammary tumor virus control region which is active in testicular, breast, lymphoid and mast cells (Leder et al., (1986) *Cell* 45:485-495), albumin gene control region which is active in liver (Pinckert et al., (1987) *Genes and Devel.* 1:268-276), alpha-fetoprotein gene control region which is active in liver (Krumlauf et al., (1985) *Mol. Cell. Biol.* 5:1639-403); Hammer et al., (1987) *Science* 235:53-58), alpha-1 antitrypsin gene control region which is active in liver (Kelsey et al, (1987) *Genes and Devel.* 1:161-171), beta globin gene control region which is active in myeloid cells (Magram et al., (1985) *Nature* 315:338-340); Kollias et al., (1986) *Cell*

46:89-94), myelin basic protein gene control region which is active in oligodendrocyte cells of the brain (Readhead et al., (1987) *Cell* 48:703-712), myosin light chain-2 gene control region which is active in skeletal muscle (Shani (1985) *Nature* 314:283-286), and gonadotrophic releasing hormone gene control region which is active in gonadotrophs of the hypothalamus (Mason et al., (1986) *Science* 234:1372-1378).

In addition to the promoter, the expression vector typically contains a transcription unit or expression cassette that contains all the additional elements required for the expression of the antibody, or portion thereof, in host cells. A typical expression cassette contains a promoter operably linked to the nucleic acid sequence encoding the antibody chain and signals required for efficient polyadenylation of the transcript, ribosome binding sites and translation termination. Additional elements of the cassette can include enhancers. In addition, the cassette typically contains a transcription termination region downstream of the structural gene to provide for efficient termination. The termination region can be obtained from the same gene as the promoter sequence or can be obtained from different genes.

Some expression systems have markers that provide gene amplification such as thymidine kinase and dihydrofolate reductase. Alternatively, high yield expression systems not involving gene amplification are also suitable, such as using a baculovirus vector in insect cells, with a nucleic acid sequence encoding a germline antibody chain under the direction of the polyhedron promoter or other strong baculovirus promoter.

For purposes herein, vectors are provided that contain a sequence of nucleotides that encodes the heavy chain and/or light chain variable region of an anti-RSV antibody. In some examples, vectors provided herein contain a sequence of nucleotides that encodes the constant region of an antibody operably linked to the nucleic acid sequence encoding the variable region of the antibody. The vector can include the sequence for one or all of a $C_H1$, $C_H2$, hinge, $C_H3$ or $C_H4$ and/or $C_L$. Generally, such as for expression of Fabs, the vector contains the sequence for a $C_H1$ or $C_L$ (kappa or lambda light chains). The sequences of constant regions or hinge regions are known to one of skill in the art (see e.g. U.S. Published Application No. 20080248028) and described herein.

Any methods known to those of skill in the art for the insertion of DNA fragments into a vector can be used to construct expression vectors containing a nucleic acid encoding an antibody or antigen-binding fragment thereof provided herein. These methods can include in vitro recombinant DNA and synthetic techniques and in vivo recombinants (genetic recombination). The insertion into a cloning vector can, for example, be accomplished by ligating the DNA fragment into a cloning vector which has complementary cohesive termini. If the complementary restriction sites used to fragment the DNA are not present in the cloning vector, the ends of the DNA molecules can be enzymatically modified. Alternatively, any site desired can be produced by ligating nucleotide sequences (linkers) onto the DNA termini; these ligated linkers can contain specific chemically synthesized nucleic acids encoding restriction endonuclease recognition sequences.

Exemplary plasmid vectors useful to produce the antibodies or antigen-binding fragments provided herein contain a strong promoter, such as the HCMV immediate early enhancer/promoter or the MHC class I promoter, an intron to enhance processing of the transcript, such as the HCMV immediate early gene intron A, and a polyadenylation (polyA) signal, such as the late SV40 polyA signal. The plasmid can be multicistronic to enable expression of the full-length heavy and light chains of the antibody, a single chain Fv fragment or other immunoglobulin fragments.

3. Cell Expression Systems

Nucleic acids encoding the anti-RSV antibodies or antigen-binding fragments thereof provided herein can be expressed in a suitable host. Cells containing the vectors and nucleic acids encoding the anti-RSV antibodies or antigen-binding fragments thereof provided herein are provided. Generally, any cell type that can be engineered to express heterologous DNA and has a secretory pathway is suitable. Expression hosts include prokaryotic and eukaryotic organisms, such as bacterial cells (e.g. *E. coli*), yeast cells, fungal cells, Archae, plant cells, insect cells and animal cells including human cells. Expression hosts can differ in their protein production levels as well as the types of post-translational modifications that are present on the expressed proteins. Further, the choice of expression host is often related to the choice of vector and transcription and translation elements used. For example, the choice of expression host is often, but not always, dependent on the choice of precursor sequence utilized. For example, many heterologous signal sequences can only be expressed in a host cell of the same species (i.e., an insect cell signal sequence is optimally expressed in an insect cell). In contrast, other signal sequences can be used in heterologous hosts such as for example, the human serum albumin (hHSA) signal sequence which works well in yeast, insect, or mammalian host cells and the tissue plasminogen activator pre/pro sequence which has been demonstrated to be functional in insect and mammalian cells (Tan et al., (2002) *Protein Eng.* 15:337). The choice of expression host can be made based on these and other factors, such as regulatory and safety considerations, production costs and the need and methods for purification. Thus, the vector system must be compatible with the host cell used.

Expression in eukaryotic hosts can include expression in yeasts such as *Saccharomyces cerevisiae* and *Pichia pastoris*, insect cells such as *Drosophila* cells and lepidopteran cells, plants and plant cells such as tobacco, corn, rice, algae, and lemna. Eukaryotic cells for expression also include mammalian cells lines such as Chinese hamster ovary (CHO) cells or baby hamster kidney (BHK) cells. Eukaryotic expression hosts also include production in transgenic animals, for example, including production in serum, milk and eggs.

Recombinant molecules can be introduced into host cells via, for example, transformation, transfection, infection, electroporation and sonoporation, so that many copies of the gene sequence are generated. Generally, standard transfection methods are used to produce bacterial, mammalian, yeast, or insect cell lines that express large quantity of antibody chains, which is then purified using standard techniques (see e.g., Colley et al. (1989) *J. Biol. Chem.*, 264: 17619-17622; Guide to Protein Purification, in Methods in Enzymology, vol. 182 (Deutscher, ed.), 1990). Transformations of eukaryotic and prokaryotic cells are performed according to standard techniques (see, e.g., Morrison (1977) *J. Bact.* 132:349-351; Clark-Curtiss and Curtiss (1983) *Methods in Enzymology*, 101, 347-362). For example, any of the well-known procedures for introducing foreign nucleotide sequences into host cells can be used. These include the use of calcium phosphate transfection, polybrene, protoplast fusion, electroporation, biolistics, liposomes, microinjection, plasma vectors, viral vectors (e.g., baculovirus, vaccinia virus, adenovirus and other viruses), and any other the other well known methods for introducing cloned genomic DNA, cDNA, plasmid DNA, cosmid DNA, synthetic DNA or other foreign genetic material into a host cell.

Generally, for purposes herein, host cells are transfected with a first vector encoding at least a VH chain or heavy chain of an anti-RSV antibody and a second vector encoding at least a VL chain or light chain of the anti-RSV antibody. Host cells also can be transfected with a single vector encoding both the heavy and light chain or portion thereof.

In one example, nucleic acid encoding the heavy chain of an antibody is ligated into a first expression vector and nucleic acid encoding the light chain of an antibody is ligated into a second expression vector. The expression vectors can be the same or different, although generally they are sufficiently compatible to allow comparable expression of proteins (heavy and light chain) therefrom. The first and second expression vectors are generally co-transfected into host cells, typically at a 1:1 ratio. Exemplary of vectors include, but are not limited to, pγ1HC and pκLC (Tiller et al. (2008) Journal of Immunological Methods, 329:112-24). Other expression vectors include the L chain expression vector pAG4622 and the heavy chain expression vector pAH4604 (Coloma et al. (1992) *J. Immunol. Methods,* 152:89-104). The pAG4622 vector contains the genomic sequence encoding the C-region domain of the human κ L chain and the gpt selectable marker. The pAH4604 vectors contain the hisD selectable marker and sequences encoding the human H chain γ1 C-region domain.

In another example, the heavy and light chain can be cloned into a single vector that has expression cassettes for both the heavy and light chain. In one example, genes encoding the heavy and light chains can be cloned into the mammalian expression vector pTT5 (NRC Biotechnology Research). In another example, genes encoding the heavy and light chains, or portions thereof, can be cloned into pCALM (SEQ ID NO:102).

For expression of a full-length Ig, sequences encoding the $V_H$-$C_H$1-hinge-$C_H$2-$C_H$3 can be cloned into a first expression vector and sequences encoding the $V_L$-$C_L$ domains can be cloned into a second expression vector. To generate a Fab, sequences encoding the $V_H$-$C_H$1 can be cloned into a first expression vector and sequences encoding the $V_L$-$C_L$ domains can be cloned into a second expression vector. For a conventional antibody, a heavy chain pairs with a light chain and a Fab monomer is generated.

Expression can be in any cell expression system known to one of skill in the art. Exemplary cells for expression include, but are not limited to, 293FS cells, HEK293-6E cells or CHO cells. Other expression vectors and host cells are described below. Upon expression, antibody heavy and light chains pair by disulfide bond to form a full-length antibody or fragments thereof.

a. Prokaryotic Expression

Prokaryotes, especially *E. coli*, provide a system for producing large amounts of proteins and can be used to express the provided anti-RSV antibodies or antigen-binding fragments thereof. Typically, *E. coli* host cells are used for amplification and expression of the provided variant polypeptides. Transformation of *E. coli* is simple and rapid technique well known to those of skill in the art. Expression vectors for *E. coli* can contain inducible promoters, such promoters are useful for inducing high levels of protein expression and for expressing proteins that exhibit some toxicity to the host cells. Examples of inducible promoters include the lac promoter, the trp promoter, the hybrid tac promoter, the T7 and SP6 RNA promoters and the temperature regulated λPL promoter.

Proteins, such as any provided herein, can be expressed in the cytoplasmic environment of *E. coli*. For some polypeptides, the cytoplasmic environment, can result in the formation of insoluble inclusion bodies containing aggregates of the proteins. Reducing agents such as dithiothreitol and β-mercaptoethanol and denaturants, such as guanidine-HCl and urea can be used to resolubilize the proteins, followed by subsequent refolding of the soluble proteins. An alternative approach is the expression of proteins in the periplasmic space of bacteria which provides an oxidizing environment and chaperonin-like and disulfide isomerases and can lead to the production of soluble protein. For example, for phage display of the proteins, the proteins are exported to the periplasm so that they can be assembled into the phage. Typically, a leader sequence is fused to the protein to be expressed which directs the protein to the periplasm. The leader is then removed by signal peptidases inside the periplasm. Examples of periplasmic-targeting leader sequences include the pelB leader from the pectate lyase gene and the leader derived from the alkaline phosphatase gene. In some cases, periplasmic expression allows leakage of the expressed protein into the culture medium. The secretion of proteins allows quick and simple purification from the culture supernatant. Proteins that are not secreted can be obtained from the periplasm by osmotic lysis. Similar to cytoplasmic expression, in some cases proteins can become insoluble and denaturants and reducing agents can be used to facilitate solubilization and refolding. Temperature of induction and growth also can influence expression levels and solubility, typically temperatures between 25° C. and 37° C. are used. Typically, bacteria produce non-glycosylated proteins. Thus, if proteins require glycosylation for function, glycosylation can be added in vitro after purification from host cells.

b. Yeast Cells

Yeasts such as *Saccharomyces cerevisae, Schizosaccharomyces pombe, Yarrowia lipolytica, Kluyveromyces lactis* and *Pichia pastoris* are well known yeast expression hosts that can be used to express the anti-RSV antibodies or antigen-binding fragments thereof provided herein. Yeast can be transformed with episomal replicating vectors or by stable chromosomal integration by homologous recombination. Typically, inducible promoters are used to regulate gene expression. Examples of such promoters include GAL1, GAL7 and GAL5 and metallothionein promoters, such as CUP1, AOX1 or other *Pichia* or other yeast promoter. Expression vectors often include a selectable marker such as LEU2, TRP1, H1S3 and URA3 for selection and maintenance of the transformed DNA. Proteins expressed in yeast are often soluble. Co-expression with chaperonins such as Bip and protein disulfide isomerase can improve expression levels and solubility. Additionally, proteins expressed in yeast can be directed for secretion using secretion signal peptide fusions such as the yeast mating type alpha-factor secretion signal from *Saccharomyces cerevisae* and fusions with yeast cell surface proteins such as the Aga2p mating adhesion receptor or the *Arxula adeninivorans* glucoamylase. A protease cleavage site such as for the Kex-2 protease, can be engineered to remove the fused sequences from the expressed polypeptides as they exit the secretion pathway. Yeast also is capable of glycosylation at Asn-X-Ser/Thr motifs.

c. Insect Cells

Insect cells, particularly using baculovirus expression, can be used to express the anti-RSV antibodies or antigen-binding fragments thereof provided herein. Insect cells express high levels of protein and are capable of most of the post-translational modifications used by higher eukaryotes. Baculovirus have a restrictive host range which improves the safety and reduces regulatory concerns of eukaryotic expression. Typical expression vectors use a promoter for high level expression such as the polyhedrin promoter of baculovirus. Commonly used baculovirus systems include the baculoviruses such as *Autographa californica* nuclear polyhedrosis virus (AcNPV), and the *Bombyx mori* nuclear polyhedrosis virus (BmNPV) and an insect cell line such as Sf9 derived from *Spodoptera frugiperda, Pseudaletia unipuncta* (A7S) and *Danaus plexippus* (DpN1). For high-level expression, the nucleotide sequence of the molecule to be expressed is fused immediately downstream of the polyhedrin initiation codon of the virus. To generate baculovirus recombinants capable of expressing human antibodies, a dual-expression transfer, such as pAcUW51 (PharMingen) is utilized. Mammalian secretion signals are accurately processed in insect cells and can be used to secrete the expressed protein into the culture medium. In addition, the cell lines *Pseudaletia unipuncta* (A7S) and *Danaus plexippus* (DpN1) produce proteins with glycosylation patterns similar to mammalian cell systems.

An alternative expression system in insect cells is the use of stably transformed cells. Cell lines such as the Schnieder 2 (S2) and Kc cells (*Drosophila melanogaster*) and C7 cells (*Aedes albopictus*) can be used for expression. The *Drosophila* metallothionein promoter can be used to induce high levels of expression in the presence of heavy metal induction with cadmium or copper. Expression vectors are typically maintained by the use of selectable markers such as neomycin and hygromycin.

Exemplary of baculovirus vectors for expression of antibodies are the bicistronic vectors pAc-κ-Fc (Progen, Biotechnik; Catalog No. PR3001); pAc-λ-Fc (Progen; PR3003); pAc-κ-CH3 (Progen; PR3000) and pAc-λ-CH3 (Progen; PR3002).

d. Mammalian Cells

Mammalian expression systems can be used to express the anti-RSV antibodies or antigen-binding fragments thereof provided herein. Expression constructs can be transferred to mammalian cells by viral infection, such as, but not limited to adenovirus or vaccinia virus, or by direct DNA transfer such as liposomes, calcium phosphate. DEAE-dextran and by physical means, such as electroporation and microinjection. Expression vectors for mammalian cells typically include an mRNA cap site, a TATA box, a translational initiation sequence (Kozak consensus sequence) and polyadenylation elements. Such vectors often include transcriptional promoter-enhancers for high-level expression, for example the SV40 promoter-enhancer, the human cytomegalovirus (CMV) promoter and the long terminal repeat of Rous sarcoma virus. These promoter-enhancers are active in many cell types. Tissue and cell-type promoters and enhancer regions also can be used for expression. Exemplary promoter/enhancer regions include, but are not limited to, those from genes such as elastase I, insulin, immunoglobulin, mouse mammary tumor virus, albumin, alpha fetoprotein, alpha 1 antitrypsin, beta globin, myelin basic protein, myosin light chain 2, and gonadotropic releasing hormone gene control. Selectable markers can be used to select for and maintain cells with the expression construct. Examples of selectable marker genes include, but are not limited to, hygromycin B phosphotransferase, adenosine deaminase, xanthine-guanine phosphoribosyl transferase, aminoglycoside phosphotransferase, dihydrofolate reductase and thymidine kinase. Antibodies can be produced using a $NEO^R$/G418 system, a dihydrofolate reductase (DHFR) system or a glutamine synthetase (GS) system. The GS system uses joint expression vectors, such as pEE12/pEE6, to express both heavy chain and light chain. Fusion with cell surface signaling molecules such as TCR-ζ and Fc$_\varepsilon$RI-γ can direct expression of the proteins in an active state on the cell surface.

Many cell lines are available for mammalian expression including mouse, rat human, monkey, chicken and hamster cells. Exemplary cell lines include, but are not limited to, CHO, Balb/3T3, BHK, HeLa, MDCK, MT2, mouse NS0 (nonsecreting) and other myeloma cell lines, hybridoma and heterohybridoma cell lines, lymphocytes, fibroblasts, Sp2/0, COS, NIH3T3, HEK293, W138, BT483, HS578T, HTB2, BT20, T47D, 293S, 2B8, and HKB cells. Cell lines also are available adapted to serum-free media which facilitates purification of secreted proteins from the cell culture media. One such example is the serum free EBNA-1 cell line (Pham et al. (2003) *Biotechnol. Bioeng.* 84:332-42.)

Exemplary mammalian vectors for expression of antibodies include pTT5 (NRC Biotechnology Research Institute) and pCALM (set forth in SEQ ID NO:102).

e. Plants

Transgenic plant cells and plants can be to express polypeptides such as any described herein. Expression constructs are typically transferred to plants using direct DNA transfer such as microprojectile bombardment and PEG-mediated transfer into protoplasts, and with *agrobacterium*-mediated transformation. Expression vectors can include promoter and enhancer sequences, transcriptional termination elements and translational control elements. Expression vectors and transformation techniques are usually divided between dicot hosts, such as *Arabidopsis* and tobacco, and monocot hosts, such as corn and rice. Examples of plant promoters used for expression include the cauliflower mosaic virus promoter, the nopaline synthase promoter, the ribose bisphosphate carboxylase promoter and the ubiquitin and UBQ3 promoters. Selectable markers such as hygromycin, phosphomannose isomerase and neomycin phosphotransferase are often used to facilitate selection and maintenance of transformed cells. Transformed plant cells can be maintained in culture as cells, aggregates (callus tissue) or regenerated into whole plants. Transgenic plant cells also can include algae engineered to produce proteases or modified proteases (see for example, Mayfield et al. (2003) *Proc Acad Sci USA* 100:438-442). Because plants have different glycosylation patterns than mammalian cells, this can influence the choice of protein produced in these hosts.

4. Purification of Antibodies

Methods for purification of polypeptides, including the anti-RSV antibodies or antigen-binding fragments thereof provided herein, from host cells will depend on the chosen host cells and expression systems. For secreted molecules, proteins generally are purified from the culture media after removing the cells. For intracellular expression, cells can be lysed and the proteins purified from the extract. In one example, polypeptides are isolated from the host cells by centrifugation and cell lysis (e.g. by repeated freeze-thaw in a dry ice/ethanol bath), followed by centrifugation and retention of the supernatant containing the polypeptides. When transgenic organisms such as transgenic plants and animals are used for expression, tissues or organs can be used as starting material to make a lysed cell extract. Additionally, transgenic animal production can include the production of polypeptides in milk or eggs, which can be collected, and if necessary further the proteins can be extracted and further purified using standard methods in the art.

Proteins, such as the anti-RSV antibodies or antigen-binding fragments thereof provided herein, can be purified, for example, from lysed cell extracts, using standard protein purification techniques known in the art including but not limited to, SDS-PAGE, size fraction and size exclusion chromatography, ammonium sulfate precipitation and ionic exchange chromatography, such as anion exchange. Affinity purification techniques also can be utilized to improve the efficiency and purity of the preparations. For example, antibodies, receptors and other molecules that bind proteases can be used in affinity purification. Expression constructs also can be engineered to add an affinity tag to a protein such as a myc epitope, GST fusion or $His_6$ and affinity purified with myc antibody, glutathione resin and Ni-resin, respectively. Purity can be assessed by any method known in the art including gel electrophoresis and staining and spectrophotometric techniques.

Typically, antibodies and portions thereof are purified by any procedure known to one of skill in the art. The antibodies can be purified to substantial purity using standard protein purification techniques known in the art including but not limited to, SDS-PAGE, size fraction and size exclusion chromatography, ammonium sulfate precipitation, chelate chromatography, ionic exchange chromatography or column chromatography. For example, antibodies can be purified by column chromatography. Exemplary of a method to purify antibodies is by using column chromatography, wherein a solid support column material is linked to Protein G, a cell surface-associated protein from *Streptococcus*, that binds immunoglobulins with high affinity. The antibodies can be purified to 60%, 70%, 80% purity and typically at least 90%, 91%, 92%, 93%, 94%, 95%, 96%, 97%, 98% or 99% purity. Purity can be assessed by standard methods such as by SDS-PAGE and coomassie staining.

The isolated polypeptides then can be analyzed, for example, by separation on a gel (e.g. SDS-Page gel), size fractionation (e.g. separation on a Sephacryl™ S-200 HiPrep™ 16×60 size exclusion column (Amersham from GE Healthcare Life Sciences, Piscataway, N.J.). Isolated polypeptides also can be analyzed in binding assays, typically binding assays using a binding partner bound to a solid support, for example, to a plate (e.g. ELISA-based binding assays) or a bead, to determine their ability to bind desired binding partners. The binding assays described in the sections below, which are used to assess binding of precipitated phage displaying the polypeptides, also can be used to assess polypeptides isolated directly from host cell lysates. For example, binding assays can be carried out to determine whether antibody polypeptides bind to one or more antigens, for example, by coating the antigen on a solid support, such as a well of an assay plate and incubating the isolated polypeptides on the solid support, followed by washing and detection with secondary reagents, e.g. enzyme-labeled antibodies and substrates.

G. ASSESSING ANTI-RSV ANTIBODY PROPERTIES AND ACTIVITIES

The anti-RSV antibodies or antigen-binding fragments thereof provided herein can be characterized in a variety of ways well-known to one of skill in the art. For example, the anti-RSV antibodies or antigen-binding fragments thereof provided herein can be assayed for the ability to immunospecifically bind to an F protein of human RSV. Such assays can be performed, for example, in solution (e.g., Houghten (1992) *Bio/Techniques* 13:412-421), on beads (Lam (1991) *Nature* 354:82-84), on chips (Fodor (1993) *Nature* 364:555-556), on bacteria (U.S. Pat. No. 5,223,409), on spores (U.S. Pat. Nos. 5,571,698; 5,403,484; and 5,223,409), on plasmids (Cull et al. (1992) *Proc. Natl. Acad Sci. USA* 89:1865-1869) or on phage (Scott and Smith (1990) *Science* 249:386-390; Devlin (1990) *Science* 249:404-406; Cwirla et al. (1990) *Proc. Natl. Acad. Sci. USA* 87:6378-6382; and Felici (1991) *J. Mol. Biol.* 222:301-310). Antibodies or antigen-binding fragments thereof that have been identified to immunospecifically bind to a RSV antigen or a fragment thereof also can be assayed for their specificity and affinity for a RSV antigen. The binding specificity, or epitope, can be determined, for example, by competition assays with other anti-RSV antibodies and/or virus neutralization assays using Monoclonal Antibody-Resistant Mutants (MARMs). In addition, in vitro assays and in vivo animal models using the anti-RSV antibodies or antigen-binding fragments thereof provided herein can be employed for measuring the level of RSV neutralization effected by contact or administration of the anti-RSV antibodies or antigen-binding fragments thereof.

1. Binding Assays

The anti-RSV antibodies or antigen-binding fragments thereof provided herein can be assessed for their ability to bind a selected target (e.g., RSV virus or isolated RSV F protein) and the specificity for such targets by any method known to one of skill in the art. Exemplary assays are provided in the Examples and described herein below. Binding assays can be performed in solution, suspension or on a solid support. For example, target antigens can be immobilized to a solid support (e.g. a carbon or plastic surface, a tissue culture dish or chip) and contacted with antibody or antigen-binding fragment thereof. Unbound antibody or target protein can be washed away and bound complexes can then be detected. Binding assays can be performed under conditions to reduce nonspecific binding, such as by using a high ionic strength buffer (e.g., 0.3-0.4 M NaCl) with nonionic detergent (e.g. 0.1% TRITON X®-100 or TWEEN® 20) and/or blocking proteins (e.g. bovine serum albumin or gelatin). Negative controls also can be included in such assays as a measure of background binding. Binding affinities can be determined using Scatchard analysis (Munson et al., (1980) *Anal. Biochem.*, 107:220), surface plasmon resonance, isothermal calorimetry, or other methods known to one of skill in the art.

Exemplary immunoassays which can be used to analyze immunospecific binding and cross-reactivity include, but are not limited to, competitive and non-competitive assay systems using techniques such as, but not limited to, western blots, radioimmunoassays, ELISA (enzyme linked immunosorbent assay), Meso Scale Discovery (MSD, Gaithersburg, Md.), "sandwich" immunoassays, immunoprecipitation assays, ELISPOT, precipitin reactions, gel diffusion precipitin reactions, immunodiffusion assays, agglutination assays, complement-fixation assays, immunoradiometric assays, fluorescent immunoassays, protein A immunoassays. Such assays are routine and well known in the art (see, e.g., Ausubel et al, eds, 1994, Current Protocols in Molecular Biology, Vol. 1, John Wiley & Sons. Inc., New York, which is incorporated by reference herein in its entirety). Other assay formats include liposome immunoassays (LIA), which use liposomes designed to bind specific molecules (e.g., antibodies) and release encapsulated reagents or markers. The released chemicals are then detected according to standard techniques (see Monroe et al., (1986) *Amer. Clin. Prod. Rev.* 5:34-41). Exemplary immunoassays not intended by way of limitation are described briefly below.

Immunoprecipitation protocols generally involve lysing a population of cells in a lysis buffer such as RIPA buffer (1% NP-40 or TRITON® X-100, 1% sodium deoxycholate, 0.1% SDS, 0.15 M NaCl, 0.01 M sodium phosphate at pH 7.2, 1% Trasylol) supplemented with protein phosphatase and/or protease inhibitors (e.g., EDTA, PMSF, aprotinin, sodium vanadate), adding the antibody or antigen-binding fragment thereof of interest to the cell lysate, incubating for a period of time (e.g., 1 to 4 hours) at 40° C., adding protein A and/or protein G sepharose beads to the cell lysate, incubating for about an hour or more at 40° C., washing the beads in lysis buffer and resuspending the beads in SDS/sample buffer. The ability of the antibody or antigen-binding fragment thereof of interest to immunoprecipitate a particular antigen can be assessed by, e.g., western blot analysis. One of skill in the art is knowledgeable as to the parameters that can be modified to increase the binding of the antibody or antigen-binding fragment thereof to an antigen and decrease the background (e.g., pre-clearing the cell lysate with sepharose beads). For further discussion regarding immunoprecipitation protocols see, e.g., Ausubel et al., eds, 1994, Current Protocols in Molecular Biology, Vol. 1, John Wiley & Sons, Inc., New York at 10.16.1.

Western blot analysis generally involves preparing protein samples, electrophoresis of the protein samples in a polyacrylamide gel (e.g., 8%-20% SDS-PAGE depending on the molecular weight of the antigen), transferring the protein sample from the polyacrylamide gel to a membrane such as nitrocellulose, PVDF or nylon, blocking the membrane in blocking solution (e.g., PBS with 3% BSA or non-fat milk), washing the membrane in washing buffer (e.g., PBS-Tween 20), blocking the membrane with primary antibody or antigen-binding fragment thereof (i.e., the antibody or antigen-binding fragment thereof of interest) diluted in blocking buffer, washing the membrane in washing buffer, blocking the membrane with a secondary antibody (which recognizes the primary antibody, e.g., an anti-human antibody) conjugated to an enzymatic substrate (e.g., horseradish peroxidase or alkaline phosphatase) or radioactive molecule (e.g., $^{32}$P or $^{125}$I) diluted in blocking buffer, washing the membrane in wash buffer, and detecting the presence of the antigen. One of skill in the art is knowledgeable as to the parameters that can be modified to increase the signal detected and to reduce the background noise. For further discussion regarding western blot protocols see, e.g., Ausubel et al, eds, 1994, Current Protocols in Molecular Biology, Vol. 1, John Wiley & Sons, Inc., New York at 10.8.1.

ELISAs involve preparing antigen, coating the well of a 96-well microtiter plate with the antigen, adding the antibody or antigen-binding fragment thereof of interest conjugated to a detectable compound such as an enzymatic substrate (e.g., horseradish peroxidase or alkaline phosphatase) to the well and incubating for a period of time, and detecting the presence of the antigen. In ELISAs, the antibody or antigen-binding fragment thereof of interest does not have to be conjugated to a detectable compound; instead, a second antibody (which recognizes the antibody of interest) conjugated to a detectable compound can be added to the well. Further, instead of coating the well with the antigen, the antibody can be coated to the well. In this case, a second antibody conjugated to a detectable compound can be added following the addition of the antigen of interest to the coated well. One of skill in the art is knowledgeable as to the parameters that can be modified to increase the signal detected as well as other variations of ELISAs known in the art. For further discussion regarding ELISAs see, e.g., Ausubel et al, eds, 1994, Current Protocols in Molecular Biology, Vol. 1, John Wiley & Sons. Inc., New York at 11.2.1. Examples 5 and 8 exemplify a binding assay for binding of anti-RSV antibodies to RSV F protein.

The binding affinity of an antibody or antigen-binding fragment thereof to an antigen and the off-rate of an antibody-antigen interaction can be determined, for example, by competitive binding assays. One example of a competitive binding assay is a radioimmunoassay comprising the incubation of labeled antigen (e.g., $^3$H or $^{125}$I) with the antibody or antigen-binding fragment thereof of interest in the presence of increasing amounts of unlabeled antigen, and the detection of the antibody or antigen-binding fragment thereof bound to the labeled antigen. The affinity of an anti-RSV antibody or antigen-binding fragment thereof provided herein for a RSV antigen and the binding off-rates can be determined from the data by Scatchard plot analysis. Competition with a second antibody can also be determined using radioimmunoassays. In this case, a RSV antigen is incubated with an anti-RSV antibody or antigen-binding fragment thereof provided herein conjugated to a labeled compound (e.g., $^3$H or $^{125}$I) in the presence of increasing amounts of an unlabeled second antibody. In some examples, surface plasmon resonance (e.g., BiaCore 2000, Biacore AB, Upsala, Sweden and GE Healthcare Life Sciences; Malmqvist (2000) *Biochem. Soc. Trans.* 27:335) kinetic analysis can be used to determine the binding on and off rates of antibodies or antigen-binding fragments thereof to a RSV antigen. Surface plasmon resonance kinetic analysis involves analyzing the binding and dissociation of a RSV antigen from chips with immobilized antibodies or fragments thereof on their surface.

The anti-RSV antibodies or antigen-binding fragments thereof provided herein also can be assayed for their ability to inhibit the binding of RSV to its host cell receptor using techniques known to those of skill in the art. For example, cells expressing the receptor for RSV can be contacted with RSV in the presence or absence of an antibody or antigen-binding fragment thereof and the ability of the antibody or fragment thereof to inhibit RSV's binding can measured by, for example, flow cytometry or a scintillation assay. RSV (e.g., a RSV antigen such as F glycoprotein or G glycoprotein) or the antibody or antibody fragment can be labeled with a detectable compound such as a radioactive label (e.g., $^{32}$P, $^{35}$S, and $^{125}$I) or a fluorescent label (e.g., fluorescein isothiocyanate, rhodamine, phycoerythrin, phycocyanin, allophycocyanin, o-phthaldehyde and fluorescamine) to enable detection of an interaction between RSV and its host cell receptor.

The ability of antibodies or antigen-binding fragments thereof to inhibit RSV from binding to its receptor also can be determined in cell-free assays. For example, RSV or a RSV antigen such as F glycoprotein can be contacted with an antibody or fragment thereof and the ability of the antibody or antibody fragment to inhibit RSV or the RSV antigen from binding to its host cell receptor can be determined. In some examples, the antibody or the antigen-binding fragment is immobilized on a solid support and RSV or a RSV antigen is labeled with a detectable compound. In some examples, RSV or a RSV antigen is immobilized on a solid support and the antibody or fragment thereof is labeled with a detectable compound. The RSV or RSV antigen can be partially or completely purified (e.g., partially or completely free of other polypeptides) or part of a cell lysate. In some examples, a RSV antigen can be a fusion protein comprising the RSV antigen and a domain such as glutathionine-S-transferase. In some examples, a RSV antigen can be biotinylated using techniques well known to those of skill in the art (e.g., biotinylation kit, Pierce Chemicals; Rockford, Ill.).

2. Binding Specificity

The binding specificity, or epitope, of the anti-RSV antibodies or antigen binding fragments thereof provided herein can be determined by any assay known to one of skill in the art, including, but not limited to surface plasmon resonance assays, competition assays and virus neutralization assays using Monoclonal Antibody-Resistant Mutants (MARMs). The epitope can be in the isolated protein, i.e., the isolated F protein, or in the protein in the virus. The ability of two antibodies to bind to the same epitope can be determined by known assays in the art such as, for example, surface plasmon resonance assays and antibody competition assays. Typically, antibodies that immunospecifically bind to the same epitope can compete for binding to the epitope, which can be measured, for example, by an in vitro binding competition assay (e.g. competition ELISA), using techniques known the art. Typically, a first antibody that immunospecifically binds to the same epitope as a second antibody can compete for binding to the epitope by about or 30%, 35%, 40%, 45%, 50%, 55%, 60%, 65%, 70%, 75%, 80%, 85%, 90%, 95%, 100%, where the percentage competition is measured ability of the second antibody to displace binding of the first antibody to the epitope. In exemplary competition assays, the antigen is incubated in the presence a predetermined limiting dilution of a labeled antibody (e.g., 50-70% saturation concentration), and serial dilutions of an unlabeled competing antibody. Competition is determined by measuring the binding of the labeled antibody to the antigen for any decreases in binding in the presence of the competing antibody. Variations of such assays, including various labeling techniques and detection methods including, for example, radiometric, fluorescent, enzymatic and colorimetric detection, are known in the art. For example, as is exemplified in Example 10 below, antibody 30D8 and motavizumab do not compete for binding to RSV F protein, thus indicating that antibody 30D8 binds a different epitope than motavizumab.

The ability of a first antibody to bind to the same epitope as a second antibody also can be determined, for example, by virus neutralization assays using Monoclonal Antibody-Resistant Mutants. A MARM is a mutant RSV that not neutralized by a monoclonal antibody that neutralizes the wildtype RSV virus, i.e., a MARM is an RSV escape mutant. MARMs are generated by culturing wildtype RSV in the presence of a monoclonal antibody for successive rounds of viral replication in the presence of the antibody such that after each successive round of virus replication, cytopathic effects (CPE) are observed in the presence of increasing concentrations of antibodies until a mutant virus results that is not neutralized by the antibody. If a first antibody can neutralize a MARM generated against a second antibody, one can conclude that the antibodies specifically bind to or interact with different epitopes. For example, where a first anti-RSV antibody neutralizes wild-type RSV but not a particular mutant RSV (i.e., MARM), a second antibody that neutralizes the wild-type RSV but not the particular mutant RSV generally binds the same epitope on RSV as the first antibody. Where a first anti-RSV antibody neutralizes wild-type RSV but not a particular mutant RSV, a second antibody that neutralizes the wild-type RSV and the particular mutant RSV generally does not bind the same epitope on RSV as the first antibody.

For example, as is exemplified in Example 9 below, 58c5 provided herein is capable of neutralizing MARMs previously generated against various anti-RSV antibodies, including MARM 1129, generated against MAb 1129, the parental antibody to palivizumab and motavizumab (see, Johnson et al. (1997) J. Infect. Diseases 176:1215-1224 and U.S. Pat. No. 5,824,307), MARM 19, generated against Fab 19 (see Barbas et al. (1992) Proc. Natl. Acad. Sci. USA 89:10164-10168) and MARM 151, generated against MAb 151 (see, Mufson et al., (1985) J. Gen. Virol, 66:2111-2124). Thus, 58c5 binds a different epitope on the F protein then antibodies Fab 19, MAb 151 and MAb 1129.

As is exemplified in Example 11 below, MARMs were generated against motavizumab and the IgG form of 58c5. The motavizumab MARM, generated after 5-7 rounds of selection, contains a single amino acid mutation (K272E, SEQ ID NO:486) compared to the wildtype RSV F protein. Mutation at amino acid K272 is consistant with known mutations that disrupt binding of the parent antibody of motavizumab (see, Zhao et al., (2004) J. Infectious Disease 190:1941-1946). The 58c5 MARM, generated after 10 rounds of selection, contains 3 amino acid mutations (N63K, M115K and E295G, SEQ ID NO:487) compared to the wildtype RSV F protein. The mutations effecting escape in the 58c5 MARM have not been previously identified as antigenic sites for various monoclonal antibodies that immunospecifically bind to the RSV F protein (see, e.g., Beeler et al. (1989) J. Virology 63(7):2841-2950, Crowe et al. (1998) Virology 252:373-375; Zhao et al., (2004) J. Infectious Disease 190:1941-1946; Liu et al., (2007) Virology Journal 4:71). After 12 rounds of viral replication in the presence of the IgG form of 30D8, the RSV virus was unable to escape neutralization (see Example 11 below). The ability of antibody 30D8 to limit the generation of MARMs means that 30D8 binds to an epitope that is less susceptible to generation of escape mutants, and as a result, antibody 30D8 is useful as a therapeutic antibody for the treatment of a RSV infection.

Additionally, as is shown in Example 11 below, 30D8 neutralizes the both the motavizumab MARM and the 58c5 MARM, 58c5 neutralizes the motavizumab MARM, and motavizumab neutralizes the 58c5 MARM. Thus, 30D8 binds a different epitope of the RSV F protein than 58c5 and motavizumab. Additionally, 58c5 binds a different epitope of the RSV F protein than 30D8 and motavizumab.

3. In Vitro Assays for Analyzing Virus Neutralization Effects of Antibodies

The anti-RSV antibodies or antigen-binding fragments thereof provided herein can be analyzed by any suitable method known in the art for the detection of viral neutralization. Methods for detection of viral neutralization include, but are not limited to, plaque assays and assays for inhibition of syncytium formation. Such assays can be employed to assess, for example, inhibition of viral attachment, viral entry and cell-to-cell spread of the virus (see, e.g. Burioni et al., (1994) Proc. Natl. Acad. Sci. U.S.A. 91:355-359; Sanna et al. (2000) Virology 270:386-3961; and De Logu et al., (1998) J Clin Microbiol 36:3198-3204). One of skill in the art can identify any assay capable of measuring viral neutralization.

Standard plaque assays include, for example, plaque reduction assays, plaque size reduction assays, neutralization assays and neutralization kinetic assays. These assays measure the formation of viral plaques (i.e. areas of lysed cells) following infection of target cell monolayers by a virus. Exemplary target cell lines that can be used in plaque reduction assays include, but are not limited to, Vero cells, MRC-5 cells, RC-37 cells, BHK-21/C13 cells and HEp-2 cells. One of skill in the art can identify appropriate target cell lines for use in a plaque assay. Selection of an appropriate cell line for a plaque assay can depend on known factors, such as, for example, cell infectivity and the ability of the virus to propagate in and lyse the target cell. Examples 6 and 9 exemplify in vitro neutralization assays.

Plaque reduction assays can be used to measure the ability of the anti-RSV antibody or antigen-binding fragment thereof to effect viral neutralization in solution. In exemplary plaque reduction assays, the antibody or antigen-binding fragment thereof and the virus are pre-incubated prior to the addition of target cells. Target cells are then infected with the antibody/virus mixture and a plaque assay is performed following a predetermined infection period. One of skill in the art can determine the incubation times required based on known examples in the art. A reduction in the number of virus plaques produced following infection of the target cells indicates the ability of the antibody or antigen-binding fragment thereof to prevent binding of the virus to the target cells independent of antibody or antigen-binding fragment thereof attachment to the target cell and/or antibody, or antigen-binding fragment thereof, internalization.

Plaque size reduction assays can be used to measure the ability of the anti-RSV antibody or antigen-binding fragment thereof to inhibit of viral cell-to-cell spread. In exemplary plaque size reduction assays, the target cells are first infected with the virus for a predetermined infection period and then the antibody or antigen-binding fragment thereof is added to the infected cell. One of skill in the art can determine the incubation times required based on known examples in the art. A reduction in the size (i.e. diameter) of the virus plaques indicates that the antibody or antigen-binding fragment thereof is capable of preventing viral cell-to-cell spread.

Virus neutralization assays can be used to measure the ability of the anti-RSV antibody or antigen-binding fragment thereof to effect viral neutralization at the target cell surface by association of the antibody or antigen-binding fragment thereof with the target cell prior to virus exposure. In exemplary virus neutralization assays, the antibody or antigen-binding fragment thereof and target cells are pre-incubated for a predetermined period of time to allow for binding of the antibody or antigen-binding fragment thereof to the targeted cell. Following the pre-incubation period, the unbound antibody is removed and the target cells are infected with the virus. A reduction in the number of plaques in this assay indicates the ability of the antibody or antigen-binding fragment thereof to prevent viral infection dependent upon attachment to the target cell and/or internalization of the antibody or antigen-binding fragment thereof. This assay also can be used to measure neutralization kinetics by varying antibody or antigen-binding fragment concentrations and pre-incubation times.

Exemplary assays for inhibition of syncytium formation can be employed to measure antibody-mediated inhibition of viral cytopathic effects by blocking the formation of syncytia when using a fusogenic viral strain. One of skill in the art can identify an appropriate fusogenic viral strain for use in the assay.

The anti-RSV antibodies or antigen-binding fragments thereof provided herein also can be assayed for their ability to inhibit or downregulate RSV replication using techniques known to those of skill in the art. For example, RSV replication can be assayed by a plaque assay such as described, e.g., by Johnson et al. (1997) *Journal of Infectious Diseases* 176:1215-1224. The anti-RSV antibodies or antigen-binding fragments thereof provided herein also can be assayed for their ability to inhibit or downregulate the expression of RSV polypeptides. Techniques known to those of skill in the art, including, but not limited to, Western blot analysis, Northern blot analysis, and RT-PCR can be used to measure the expression of RSV polypeptides.

4. In Vivo Animal Models for Assessing Efficacy of the Anti-RSV Antibodies

In vivo studies using animal models can be performed to assess the efficacy of the anti-RSV antibodies or antigen-binding fragments thereof provided herein. In vivo studies using animal models can be performed to assess any toxicity of administration of such antibodies or antigen-binding fragments thereof. A variety of assays, such as those employing in vivo animal models, are available to those of skill in the art for evaluating the ability of the anti-RSV antibodies to inhibit or treat RSV virus infection and for assaying any toxicity. The therapeutic effect of the anti-RSV antibodies can be assessed using animal models of the pathogenic infection, including animal models of viral infection. Such animal models are known in the art, and include, but are not limited to, animal models for RSV infection, such as but not limited to cotton rat, inbred mouse, calf, ferret, hamster, guinea pig, chimpanzee, owl monkey, rhesus monkey, African green monkey, cebus monkey, squirrel monkey, bonnet monkey, baboon, (see, e.g., Prince et al. (1978) *Am. J. Pathol.* 93:771-791; Prince et al. (1979) *Infect. Immunol.* 26:764-766; Byrd and Prince (1997) *Clinical Infectious Diseases* 25:1363-1368, including references cited therein, for exemplary models of RSV infection). For in vivo testing of an antibody or antigen-binding fragment or composition's toxicity, any animal model system known in the art can be used, including, but not limited to, rats, mice, cows, monkeys, and rabbits.

5. In Vitro and In Vivo Assays for Measuring Antibody Efficacy

Efficacy in treating or preventing viral infection can be demonstrated by detecting the ability of a anti-RSV antibody or antigen-binding fragment thereof provided herein to inhibit the replication of the virus, to inhibit transmission or prevent the virus from establishing itself in its host, to reduce the incidence of RSV infection, or to prevent, ameliorate or alleviate one or more symptoms associated with RSV infection. The treatment is considered therapeutic if there is, for example, a reduction is viral load, amelioration of one or more symptoms, a reduction in the duration of a RSV infection, or a decrease in mortality and/or morbidity following administration of an antibody or composition provided herein. Further, the treatment is considered therapeutic if there is an increase in the immune response following the administration of one or more antibodies or antigen-binding fragments thereof which immunospecifically bind to one or more RSV antigens.

The anti-RSV antibodies or antigen-binding fragments thereof provided herein can be tested in vitro and in vivo for the ability to induce the expression of cytokines such as IFN-α, IFN-β, IFN-γ, IL-2, IL-3, IL-4, IL-5, IL-6, IL-7, IL-8, IL-9, IL-10, IL-12 and IL-15. Techniques known to those of skill in the art can be used to measure the level of expression of cytokines. For example, the level of expression of cytokines can be measured by analyzing the level of RNA of cytokines by, for example, RT-PCR and Northern blot analysis, and by analyzing the level of cytokines by, for example, immunoprecipitation followed by Western blot analysis or ELISA.

The anti-RSV antibodies or antigen-binding fragments thereof provided herein can be tested in vitro and in vivo for their ability to modulate the biological activity of immune cells, including human immune cells (e.g., T-cells, B-cells, and Natural Killer cells). The ability of an anti-RSV antibody or antigen-binding fragment to modulate the biological activity of immune cells can be assessed by detecting the expression of antigens, detecting the proliferation of immune cells, detecting the activation of signaling molecules, detecting the effector function of immune cells, or detecting the differentiation of immune cells. Techniques known to those of skill in the art can be used for measuring these activities. For example, cellular proliferation can be assayed by $^3$H-thymidine incorporation assays and trypan blue cell counts. Antigen expression can be assayed, for example, by immunoassays including, but are not limited to, competitive and non-competitive assay systems using techniques such as western blots, immunohistochemistry radioimmunoassays, ELISA (enzyme linked immunosorbent assay), "sandwich" immunoassays, immunoprecipitation assays, precipitin reactions, gel diffusion precipitin reactions, immunodiffusion assays, agglutination assays, complement-fixation assays, immunoradiometric assays, fluorescent immunoassays, protein A immunoassays and FACS analysis. The activation of signaling molecules can be assayed, for example, by kinase assays and electrophoretic shift assays (EMSAs).

The anti-RSV antibodies or antigen-binding fragments thereof provided herein also can be tested for their ability to inhibit viral replication or reduce viral load in in vitro, ex vivo and in vivo assays. The anti-RSV antibodies or antigen-binding fragments thereof also can be assayed for their ability to decrease the time course of RSV infection. The anti-RSV antibodies or antigen-binding fragments thereof also can be assayed for their ability to increase the survival period of humans suffering from RSV infection by at least or about 25%, at least or about 50%, at least or about 60%, at least or about 75%, at least or about 85%, at least or about 95%, or at least or about 99%. Further, anti-RSV antibodies or antigen-binding fragments thereof can be assayed for their ability reduce the hospitalization period of humans suffering from RSV infection by at least or about 60%, at least or about 75%, at least or about 85%, at least or about 95%, or at least or about 99%. Techniques known to those of skill in the art can be used to analyze the function of the anti-RSV antibodies or antigen-binding fragments thereof provided herein in vivo.

In accordance with the methods and uses provided herein, clinical trials with human subjects need not be performed in order to demonstrate the prophylactic and/or therapeutic efficacy of the anti-RSV antibodies or antigen-binding fragments thereof provided herein. In vitro and animal model studies using the anti-RSV antibodies or antigen-binding fragments thereof provided herein can be extrapolated to humans and are sufficient for demonstrating the prophylactic and/or therapeutic utility of the anti-RSV antibodies or antigen-binding fragments.

H. DIAGNOSTIC USES

The anti-RSV antibodies or antigen-binding fragments thereof provided herein can be used in diagnostic assays for the detection, purification, and/or neutralization of RSV. Exemplary diagnostic assays include in vitro and in vivo detection of RSV. For example, assays using the anti-RSV antibodies or antigen-binding fragments thereof provided herein for qualitatively and quantitatively measuring levels of RSV in an isolated biological sample (e.g., sputum) or in vivo are provided.

As described herein, the anti-RSV antibodies or antigen-binding fragments thereof can be conjugated to a detectable moiety for in vitro or in vivo detection. Such antibodies can be employed, for example, to evaluate the localization and/or persistence of the anti-RSV antibody or antigen-binding fragment thereof at an in vivo site, such as, for example, a mucosal site. The anti-RSV antibodies or antigen-binding fragments thereof which are coupled to a detectable moiety can be detected in vivo by any suitable method known in the art. The anti-RSV antibodies or antigen-binding fragments thereof which are coupled to a detectable moiety also can be detected in isolated biological samples, such as tissue or fluid samples obtained from the subject following administration of the antibody or antigen-binding fragment thereof.

1. In Vitro Detection of Pathogenic Infection

In general, RSV can be detected in a subject or patient based on the presence of one or more RSV proteins and/or polynucleotides encoding such proteins in a biological sample (e.g., blood, sera, sputum urine and/or other appropriate cells or tissues) obtained from a subject or patient. Such proteins can be used as markers to indicate the presence or absence of RSV in a subject or patient. The anti-RSV antibodies or antigen-binding fragments thereof provided herein can be employed for detection of the level of antigen and/or epitope that binds to the agent in the biological sample.

A variety of assay formats are known to those of ordinary skill in the art for using a anti-RSV antibody or antigen-binding fragment thereof to detect polypeptide markers in a sample (see, e.g., Harlow and Lane, Antibodies: A Laboratory Manual, Cold Spring Harbor Laboratory, 1988). In general, the presence or absence of RSV in a subject or patient can be determined by contacting a biological sample obtained from a subject or patient with an anti-RSV antibody or antigen-binding fragment thereof provided herein and detecting in the sample a level of polypeptide that binds to the anti-RSV antibody or antigen-binding fragment thereof.

In some examples, the assay involves the use of an anti-RSV antibody or antigen-binding fragment thereof provided herein immobilized on a solid support to bind to and remove the target polypeptide from the remainder of the sample. The bound polypeptide can then be detected using a detection reagent that contains a reporter group and specifically binds to the antibody/polypeptide complex. Such detection reagents can contain, for example, a binding agent that specifically binds to the polypeptide or an antibody or other agent that specifically binds to the binding agent.

In some examples, a competitive assay can be utilized, in which a polypeptide is labeled with a reporter group and allowed to bind to the immobilized anti-RSV antibody or antigen-binding fragment thereof after incubation of the anti-RSV antibody or antigen-binding fragment thereof with the sample. The extent to which components of the sample inhibit the binding of the labeled polypeptide to the anti-RSV antibody or antigen-binding fragment thereof is indicative of the reactivity of the sample with the immobilized anti-RSV antibody or antigen-binding fragment thereof. Suitable polypeptides for use within such assays include full length RSV F proteins and portions thereof, including the extracellular domain of a RSV F protein, to which an anti-RSV antibody or antigen-binding fragment thereof binds, as described above.

The solid support can be any material known to those of ordinary skill in the art to which the protein can be attached. For example, the solid support can be a test well in a microtiter plate or a nitrocellulose or other suitable membrane. The support also can be a bead or disc, such as glass, fiberglass, latex or a plastic material such as polystyrene or polyvinylchloride. The support also can be a magnetic particle or a fiber optic sensor, such as those disclosed, for example, in U.S. Pat. No. 5,359,681. The anti-RSV antibody or antigen-binding fragment thereof can be immobilized on the solid support using a variety of techniques known to those of skill in the art. The anti-RSV antibody or antigen-binding fragment thereof can be immobilized by adsorption to a well in a microtiter plate or to a membrane. In such cases, adsorption can be achieved by contacting the anti-RSV antibody or antigen-binding fragment thereof, in a suitable buffer, with the solid support for a suitable amount of time. The contact time varies with temperature, but is typically between about 1 hour and about 1 day. In general, contacting a well of a plastic microtiter plate (such as polystyrene or polyvinylchloride) with an amount of anti-RSV antibody or antigen-binding fragment thereof ranging from about 10 ng to about 10 µg, and typically about 100 ng to about 1 µg, is sufficient to immobilize an adequate amount of anti-RSV antibody or antigen-binding fragment thereof.

Covalent attachment of anti-RSV antibody or antigen-binding fragment thereof to a solid support can generally be achieved by first reacting the support with a bifunctional reagent that will react with the support and a functional group, such as a hydroxyl or amino group, on the anti-RSV antibody or antigen-binding fragment thereof. For example, the anti-RSV antibody or antigen-binding fragment thereof can be covalently attached to supports having an appropriate polymer coating using benzoquinone or by condensation of an aldehyde group on the support with an amine and an active hydrogen on the binding partner (see, e.g., Pierce Immunotechnology Catalog and Handbook, 1991, at A12-A13).

In some examples, the assay is performed in a flow-through or strip test format, wherein the anti-RSV antibody or antigen-binding fragment thereof is immobilized on a membrane, such as nitrocellulose. In the flow-through test, polypeptides within the sample bind to the immobilized anti-RSV antibody or antigen-binding fragment thereof as the sample passes through the membrane. A second, labeled binding agent then binds to the anti-RSV antibody or antigen-binding fragment thereof-polypeptide complex as a solution containing the second binding agent flows through the membrane.

Additional assay protocols exist in the art that are suitable for use with the RSV proteins or anti-RSV antibodies or antigen-binding fragments thereof provided. The above descriptions are intended to be exemplary only. For example, it will be apparent to those of ordinary skill in the art that the above protocols can be readily modified to use RSV polypeptides to detect antibodies that bind to such polypeptides in a biological sample. The detection of such protein-specific antibodies can allow for the identification of RSV infection.

To improve sensitivity, multiple RSV protein markers can be assayed within a given sample. It will be apparent that anti-RSV antibodies or antigen-binding fragments thereof specific for different RSV polypeptides can be combined within a single assay. Further, multiple primers or probes can be used concurrently. The selection of RSV protein markers can be based on routine experiments to determine combinations that results in optimal sensitivity. In addition, or alternatively, assays for RSV proteins provided herein can be combined with assays for other known RSV antigens.

2. In Vivo Detection of Pathogenic Infection

The anti-RSV antibodies or antigen-binding fragments thereof provided herein can be employed as an in vivo diagnostic agent. For example, the anti-RSV antibodies or antigen-binding fragments thereof can provide an image of infected tissues (e.g., RSV infection in the lungs) using detection methods such as, for example, magnetic resonance imaging, X-ray imaging, computerized emission tomography and other imaging technologies. For the imaging of RSV infected tissues, for example, the antibody portion of the anti-RSV antibody generally will bind to RSV (e.g., binding a RSV F protein epitope), and the imaging agent will be an agent detectable upon imaging, such as a paramagnetic, radioactive or fluorescent agent that is coupled to the anti-RSV antibody or antigen-binding fragment thereof. Generally, for use as a diagnostic agent, the anti-RSV antibody or antigen-binding fragment thereof is coupled directly or indirectly to the imaging agent.

Many appropriate imaging agents are known in the art, as are methods for their attachment to the anti-RSV antibodies or antigen-binding fragments (see, e.g., U.S. Pat. Nos. 5,021,236 and 4,472,509). Exemplary attachment methods involve the use of a metal chelate complex employing, for example, an organic chelating agent such a DTPA attached to the antibody or antigen-binding fragment thereof (U.S. Pat. No. 4,472,509). The antibodies also can be reacted with an enzyme in the presence of a coupling agent such as glutaraldehyde or periodate. Conjugates with fluorescein markers are prepared in the presence of such coupling agents or by reaction with an isothiocyanate.

For in vivo diagnostic imaging, the type of detection instrument available is considered when selecting a given radioisotope. The radioisotope selected has a type of decay which is detectable for a given type of instrument. Another factor in selecting a radioisotope for in vivo diagnosis is that the half-life of the radioisotope be long enough so that it is still detectable at the time of maximum uptake by the target, but short enough so that deleterious radiation with respect to the host is minimized. Typically, a radioisotope used for in vivo imaging will lack a particle emission, but produce a large number of photons in the 140-250 keV range, which can be readily detected by conventional gamma cameras.

For in vivo diagnosis, radioisotopes can be bound to the antibodies or antigen-binding fragments thereof provided herein either directly or indirectly by using an intermediate functional group. Exemplary intermediate functional groups which can be used to bind radioisotopes, which exist as metallic ions, to antibodies include bifunctional chelating agents, such as diethylene-triamine pentaacetic acid (DTPA) and ethylenediaminetetraacetic acid (EDTA) and similar molecules. Examples of metallic ions which can be bound to the anti-RSV antibodies or antigen-binding fragments thereof provided include, but are not limited to, $^{72}$Arsenic, $^{211}$Astatine, $^{14}$Carbon, $^{51}$Chromium, $^{36}$Chlorine, $^{57}$Cobalt, $^{58}$Cobalt, $^{67}$Copper, $^{152}$Europium, $^{67}$Gallium, $^{68}$Gallium, $^{3}$Hydrogen, $^{123}$Iodine, $^{125}$Iodine, $^{131}$Iodine, $^{111}$Indium, $^{59}$Iron, $^{32}$Phosphorus, $^{186}$Rhenium, $^{188}$Rhenium, $^{97}$Ruthenium, $^{75}$Selenium, $^{35}$Sulphur, $^{99m}$Technicium, $^{201}$Thalium, $^{90}$Yttrium and $^{89}$Zirconium.

The anti-RSV antibodies or antigen-binding fragments thereof provided herein can be labeled with a paramagnetic isotope for purposes of in vivo diagnosis, as in magnetic resonance imaging (MRI) or electron spin resonance (ESR). In general, any conventional method for visualizing diagnostic imaging can be utilized. Generally, gamma and positron emitting radioisotopes are used for camera imaging and paramagnetic isotopes for MRI. Elements which are particularly useful in such techniques include, but are not limited to, $^{57}$Gd, $^{55}$Mn, $^{162}$Dy, $^{52}$Cr, and $^{56}$Fe.

Exemplary paramagnetic ions include, but are not limited to, chromium (III), manganese (II), iron (III), iron (II), cobalt (II), nickel (II), copper (II), neodymium (III), samarium (III), ytterbium (III), gadolinium (III), vanadium (II), terbium (III), dysprosium (III), holmium (III) and erbium (III). Ions useful, for example, in X-ray imaging, include but are not limited to lanthanum (III), gold (III), lead (II), and bismuth (III).

The concentration of detectably labeled anti-RSV antibody or antigen-binding fragment thereof which is administered is sufficient such that the binding to RSV is detectable compared to the background. Further, it is desirable that the detectably labeled anti-RSV antibody or antigen-binding fragment thereof be rapidly cleared from the circulatory system in order to give the best target-to-background signal ratio.

The dosage of detectably labeled anti-RSV antibody or antigen-binding fragment thereof for in vivo diagnosis will vary depending on such factors as age, sex, and extent of disease of the individual. The dosage of a human monoclonal antibody can vary, for example, from about 0.01 mg/m$^2$ to about 500 mg/m$^2$, 0.1 mg/m$^2$ to about 200 mg/m$^2$, or about 0.1 mg/m$^2$ to about 10 mg/m$^2$. Such dosages can vary, for example, depending on whether multiple injections are given, tissue, and other factors known to those of skill in the art.

3. Monitoring Infection

The anti-RSV antibodies or antigen-binding fragments thereof provided herein can be used in vitro and in vivo to monitor the course of pathogenic disease therapy. Thus, for example, the increase or decrease in the number of cells infected with RSV or changes in the concentration of the RSV virus particles present in the body or in various body fluids can be measured. Using such methods, the anti-RSV antibodies or antigen-binding fragments thereof can be employed to determine whether a particular therapeutic regimen aimed at ameliorating the pathogenic disease is effective.

I. PROPHYLACTIC AND THERAPEUTIC USES

The anti-RSV antibodies or antigen-binding fragments thereof provided herein and pharmaceutical compositions containing anti-RSV antibodies or antigen-binding fragments thereof provided herein can be administered to a subject for prophylaxis and therapy. For example, the antibodies or antigen-binding fragments thereof provided can be administered for treatment of a disease or condition, such as a RSV infection. In some examples, the antibodies or antigen-binding fragments thereof provided can be administered to a subject for prophylactic uses, such as the prevention and/or spread of RSV infection, including, but not limited to the inhibition of establishment of RSV infection in a host or inhibition of RSV transmission between subjects. In some examples, the antibodies or antigen-binding fragments thereof provided can be administered to a subject for the reduction of RSV viral load in the subject. The antibodies or antigen-binding fragments thereof also can be administered to a subject for preventing, treating, and/or alleviating of one or more symptoms of a RSV infection or reduce the duration of a RSV infection.

In some examples, administration of an anti-RSV antibody or antigen-binding fragment thereof provided herein inhibits the incidence of RSV infection by at least or about 99%, at least or about 95%, at least or about 90%, at least or about 85%, at least or about 80%, at least or about 75%, at least or about 70%, at least or about 65%, at least or about 60%, at least or about 55%, at least or about 50%, at least or about 45%, at least or about 40%, at least or about 35%, at least or about 30%, at least or about 25%, at least or about 20%, at least or about 15%, or at least or about 10% relative to the incidence of RSV infection in the absence of the anti-RSV antibody or antigen-binding fragment. In some examples, administration of an anti-RSV antibody or antigen-binding fragment provided herein decreases the severity of one or more symptoms of RSV infection by at least or about 99%, at least or about 95%, at least or about 90%, at least or about 85%, at least or about 80%, at least or about 75%, at least or about 70%, at least or about 65%, at least or about 60%, at least or about 55%, at least or about 50%, at least or about 45%, at least or about 40%, at least or about 35%, at least or about 30%, at least or about 25%, at least or about 20%, at least or about 15%, or at least or about 10% relative to the severity of the one or more symptoms of RSV infection in the absence of the anti-RSV antibody or antigen-binding fragment.

1. Subjects for Therapy

A subject or candidate for therapy with an anti-RSV antibody or antigen-binding fragment thereof provided herein includes, but is not limited to, a subject, such as a human patient, that has been exposed to a RSV virus, a subject, such as a human patient, who exhibits one or more symptoms of a RSV infection and a subject, such as a human patient, who is at risk of a RSV infection. Exemplary RSV virus infections include those caused by RSV viruses, such as, but not limited to, acute RSV disease, RSV upper respiratory tract infection (URI) and/or RSV lower respiratory tract infection (LRI), including, for example, bronchiolitis and pneumonia.

In some examples, the subject for therapy with an anti-RSV antibody or antigen-binding fragment thereof provided herein is a mammal. In some examples, the subject for therapy with an anti-RSV antibody or antigen-binding fragment thereof provided herein is a primate. In particular examples, the subject for therapy with an anti-RSV antibody or antigen-binding fragment thereof provided herein is a human.

The provided anti-RSV antibodies or antigen-binding fragments thereof can be administered to a subject, such as a human patient, for the treatment of any RSV-mediated disease. For example, the anti-RSV antibodies or antigen-binding fragments thereof provided herein can be administered to a subject to alleviate one or more symptoms or conditions associated with a RSV virus infection, including, but not limited to, asthma, wheezing, reactive airway disease (RAD), and chronic obstructive pulmonary disease (COPD). Such diseases and condition are well known and readily diagnosed by physicians or ordinary skill.

The anti-RSV antibodies or antigen-binding fragments thereof provided herein can be administered to a subject, such a human patient, having a RSV virus infection for the maintenance or suppression therapy of recurring RSV virus-mediated disease.

The provided anti-RSV antibodies or antigen-binding fragments thereof can be administered to a subject, such as a human patient, at risk of a RSV virus infection, including, but not limited to, a prematurely born (pre-term) infant (e.g. a human infant born less than 38 weeks of gestational age, such as, for example, 29 weeks, 30 weeks, 31 weeks, 32 weeks, 33 weeks, 34 weeks, 35 weeks, 36 weeks, or 37 weeks gestational age); an infant (e.g., a human infant born more than 37 weeks gestational age), a subject having cystic fibrosis, bronchopulmonary dysplasia, congenital heart disease, congenital immunodeficiency, or acquired immunodeficiency (e.g., an AIDS patient), leukemia, non-Hodgkin lymphoma, an immunosuppressed patient such as, for example, a recipient of a transplant (e.g. a bone marrow transplant or a kidney transplant), or elderly subjects, including individuals in nursing homes or rehabilitation centers. In some examples, the anti-RSV antibodies or antigen-binding fragments thereof provided herein can be administered to a subject, such as a pre-term infant or infant exposed to one or more environmental risk factors, such as, but not limited to attending daycare, having school aged siblings, exposure to environmental air pollutants, congenital airway abnormalities, and/or severe neuromuscular disease. In some examples, the provided anti-RSV antibodies or antigen-binding fragments thereof can be administered to a subject, such an infant or child who is younger than two years, having chronic lung disease or congenital heart disease, including congestive heart failure, pulmonary hypertension, and cyanotic heart disease.

Tests for various pathogens and pathogenic infection are known in the art and can be employed for the assessing whether a subject is a candidate for therapy with an anti-RSV antibody or antigen-binding fragment thereof provided herein. For example, tests for RSV virus infection, are known and include for example, viral culture plaque assays, antigen detection test, polymerase chain reaction (PCR) tests, and various antibody serological tests. Tests for viral infection can be performed on samples obtained from tissue or fluid samples, such as spinal fluid, blood, or urine. Additional tests include, but are not limited to chest X-rays, which can show signs of pneumonia, other blood tests, such as a chemistry screening, a complete blood count, or arterial blood gases (ABGs) analysis, and oximetry, to measure the amount of oxygen in the blood.

The anti-RSV antibodies or antigen-binding fragments thereof provided herein can be administered to a subject, who is at an increased risk of RSV infection during particular times of the year. RSV season typically extends from October through May. Subjects, who exhibit increased susceptibility to virus infection during this time, such as infants the elderly or immunocompromised patients, can be administered an anti-RSV antibody or antigen-binding fragment thereof provided herein for the prophylaxis and/or treatment of RSV infection just prior to and/or during RSV season. In some examples, the anti-RSV antibody or antigen-binding fragment thereof provided herein is administered one time, two times, three times, four times or five times during RSV season. In some examples, the anti-RSV antibody or antigen-binding fragment thereof provided herein is administered one time, two times, three times, four times or five times within one month, two months or three months, prior to a RSV season.

2. Dosages

The anti-RSV antibody or antigen-binding fragment thereof provided herein is administered in an amount sufficient to exert a therapeutically useful effect in the absence of undesirable side effects on the patient treated. The therapeutically effective concentration of an anti-RSV antibody or antigen-binding fragment thereof can be determined empirically by testing the polypeptides in known in vitro and in vivo systems such as by using the assays provided herein or known in the art.

An effective amount of antibody or antigen-binding fragment thereof to be administered therapeutically will depend, for example, upon the therapeutic objectives, the route of administration, and the condition of the patient. In addition, the attending physician takes into consideration various factors known to modify the action of drugs, including severity and type of disease, patient's health, body weight, sex, diet, time and route of administration, other medications and other relevant clinical factors. Accordingly, it will be necessary for the therapist to titer the dosage of the antibody or antigen-binding fragment thereof and modify the route of administration as required to obtain the optimal therapeutic effect. Typically, the clinician will administer the antibody or antigen-binding fragment thereof until a dosage is reached that achieves the desired effect. The progress of this therapy is easily monitored by conventional assays. Exemplary assays for monitoring treatment of a viral infection are know in the art and include for example, viral titer assays.

Generally, the dosage ranges for the administration of the anti-RSV antibodies or antigen-binding fragments thereof provided herein are those large enough to produce the desired effect in which the symptom(s) of the pathogen-mediated disease (e.g. viral disease) are ameliorated or the likelihood of virus infection is decreased. In some examples, the anti-RSV antibodies or antigen-binding fragments thereof provided herein are administered in an amount effective for inducing an immune response in the subject. The dosage is not so large as to cause adverse side effects, such as hyperviscosity syndromes, pulmonary edema or congestive heart failure. Generally, the dosage will vary with the age, condition, sex and the extent of the disease in the patient and can be determined by one of skill in the art. The dosage can be adjusted by the individual physician in the event of the appearance of any adverse side effect. Exemplary dosages for the prevention or treatment of a RSV infection and/or amelioration of one or more symptoms of a RSV infection include, but are not limited to, about or 0.01 mg/kg to about or 300 mg/kg, such as for example, about or 0.01 mg/kg, about or 0.1 mg/kg, about or 0.5 mg/kg, about or 1 mg/kg, about or 5 mg/kg, about or 10 mg/kg, about or 15 mg/kg, about or 20 mg/kg, about or 25 mg/kg, about or 30 mg/kg, about or 35 mg/kg, about or 40 mg/kg, about or 45 mg/kg, about or 50 mg/kg, about or 100 mg/kg, about or 150 mg/kg, about or 200 mg/kg, about or 250 mg/kg, or about or 300 mg/kg.

In some examples, the anti-RSV antibodies or antigen-binding fragments thereof provided herein are administered to a subject at a dosage effective to achieve a desired serum titer. In particular examples, the anti-RSV antibodies or antigen-binding fragments thereof provided herein are administered for the prevention or treatment of a RSV infection and/or amelioration of one or more symptoms of a RSV infection at an amount effective to achieve a serum titer of at least or about 1 µg/ml, at least or about 2 µg/ml, at least or about 3 µg/ml, at least or about 4 µg/ml, at least or about 5 µg/ml, at least or about 6 µg/ml, at least or about 7 µg/ml, at least or about 8 µg/ml, at least or about 9 µg/ml, at least or about 10 µg/ml, at least or about 15 µg/ml, at least or about 20 µg/ml, at least or about 25 µg/ml, at least or about 30 µg/ml, at least or about 40 µg/ml, at least or about 50 µg/ml, at least or about 60 µg/ml, at least or about 70 µg/ml, at least or about 80 µg/ml, at least or about 90 µg/ml, at least or about 100 µg/ml, at or about 1 day, 2 days, 3 days, 4 days, 5 days, 6 days, 7 days, 8 days, 9 days, 10 days, 15 days, 20 days, 25 days, 30 days, 35 days or 40 days following administration of a first dose of the antibody or antigen-binding fragment thereof and prior to a subsequent dose of the antibody or antigen-binding fragment thereof.

In some examples, the anti-RSV antibodies or antigen-binding fragments thereof provided herein are administered by pulmonary delivery to a subject at a dosage effective to achieve a desired titer in an intubation sample, sputum or lavage from the lungs. In particular examples, the anti-RSV antibodies or antigen-binding fragments thereof provided herein are administered for the prevention or treatment of a RSV infection and/or amelioration of one or more symptoms of a RSV infection at an amount effective to achieve a titer of 10 ng/mg (ng anti-RSV antibody or antigen-binding fragment thereof per mg lung protein) or about 10 ng/mg, 15 ng/mg or about 15 ng/mg, 20 ng/mg or about 20 ng/mg, 25 ng/mg or about 25 ng/mg, 30 ng/mg or about 30 ng/mg, 40 ng/mg or about 40 ng/mg, 50 ng/mg or about 50 ng/mg, 60 ng/mg or about 60 ng/mg, 70 ng/mg or about 70 ng/mg, 80 ng/mg or about 80 ng/mg, 90 ng/mg or about 90 ng/mg, 100 ng/mg or about 100 ng/mg, 110 ng/mg or about 110 ng/mg, 120 ng/mg or about 120 ng/mg, 130 ng/mg or about 130 ng/mg, 140 ng/mg or about 140 ng/mg, or 150 ng/mg or about 150 ng/mg in an intubation sample or lavage from the lungs at or about 10 days, 15 days, 20 days, 25 days, 30 days, 35 days or 40 days following administration of a first dose of the antibody or antigen-binding fragment thereof and prior to a subsequent dose of the antibody or antigen-binding fragment thereof.

For treatment of a viral infection, the dosage of the anti-RSV antibodies or antigen-binding fragments thereof can vary depending on the type and severity of the disease. The anti-RSV antibodies or antigen-binding fragments thereof can be administered single dose, in multiple separate administrations, or by continuous infusion. For repeated administrations over several days or longer, depending on the condition, the treatment can be repeated until a desired suppression of disease symptoms occurs or the desired improvement in the patient's condition is achieved. Repeated administrations can include increased or decreased amounts of the anti-RSV antibody or antigen-binding fragment thereof depending on the progress of the treatment. Other dosage regimens also are contemplated.

In some examples, the anti-RSV antibodies or antigen-binding fragments thereof provided herein are administered one time, two times, three times, four times, five times, six time, seven times, eight times, nine times, ten times or more per day or over several days. In particular examples, the anti-RSV antibodies or antigen-binding fragments thereof provided herein are administered one time, two times, three times, four times, five times, six time, seven times, eight times, nine times, ten times or more for the prevention or treatment of a RSV infection and/or amelioration of one or more symptoms of a RSV infection at an amount effective to achieve a serum titer of at least or about 1 µg/ml, at least or about 2 µg/ml, at least or about 3 µg/ml, at least or about 4 µg/ml, at least or about 5 µg/ml, at least or about 6 µg/ml, at least or about 7 µg/ml, at least or about 8 µg/ml, at least or about 9 µg/ml, at least or about 10 µg/ml, at least or about 15 µg/ml, at least or about 20 µg/ml, at least or about 25 µg/ml, at least or about 30 µg/ml, at least or about 40 µg/ml, at least or about 50 µg/ml, at least or about 60 µg/ml, at least or about 70 µg/ml, at least or about 80 µg/ml, at least or about 90 µg/ml, at least or about 100 µg/ml, at or about 1 day, 2 days, 3 days, 4 days, 5 days, 6 days, 7 days, 8 days, 9 days, 10 days, 15 days, 20 days, 25 days, 30 days, 35 days or 40 days following administration of a first dose, second dose, third dose, fourth dose, fifth dose, sixth dose, seventh dose, eighth dose, ninth dose, tenth dose of the antibody or antigen-binding fragment thereof and prior to a subsequent dose of the antibody or antigen-binding fragment thereof. In a particular example, the anti-RSV antibodies or antigen-binding fragments thereof provided herein are administered four times for the prevention or treatment of a RSV infection and/or amelioration of one or more symptoms of a RSV infection at an amount effective to achieve a serum titer of at least or about 72 µg/ml at or about 1 day, 2 days, 3 days, 4 days, 5 days, 6 days, 7 days, 8 days, 9 days, 10 days, 15 days, 20 days, 25 days, 30 days, 35 days or 40 days following administration of the fourth dose of the antibody or antigen-binding fragment thereof and prior to a subsequent dose of the antibody or antigen-binding fragment thereof.

In some examples, the anti-RSV antibodies or antigen-binding fragments thereof are administered in a sequence of two or more administrations, where the administrations are separated by a selected time period. In some examples, the selected time period is at least or about 1 day, 2 days, 3 days, 4 days, 5 days, 6 days, 1 week, 2 weeks, 3 weeks, 1 month, 2 months, or 3 months.

In some examples, a prophylactically effective amount of an anti-RSV antibody or antigen-binding fragment thereof provided herein is administered one or more times just prior to RSV season. In some examples, a prophylactically effective amount of an anti-RSV antibody or antigen-binding fragment thereof provided herein is administered one or more times just prior to RSV season and/or one or more times during RSV season.

Therapeutic efficacy of a particular dosage or dosage regimen also can be assessed, for example, by measurement of viral titer in the subject prior to and following administration of one or more doses of the anti-RSV antibody or antigen-binding fragment thereof. Dosage amounts and/or frequency of administration can be modified depending on the desired rate of clearance of the virus in the subject.

As will be understood by one of skill in the art, the optimal treatment regimen will vary and it is within the scope of the treatment methods to evaluate the status of the disease under treatment and the general health of the patient prior to, and following one or more cycles of therapy in order to determine the optimal therapeutic dosage and frequency of administration. It is to be further understood that for any particular subject, specific dosage regimens can be adjusted over time according to the individual need and the professional judgment of the person administering or supervising the administration of the pharmaceutical formulations, and that the dosages set forth herein are exemplary only and are not intended to limit the scope thereof. The amount of an anti-RSV antibody or antigen-binding fragment thereof to be administered for the treatment of a disease or condition, for example a viral infection (e.g. a RSV virus infection), can be determined by standard clinical techniques (e.g. viral titer or antigen detection assays). In addition, in vitro assays and animal models can be employed to help identify optimal dosage ranges. Such assays can provide dosages ranges that can be extrapolated to administration to subjects, such as humans. Methods of identifying optimal dosage ranges based on animal models are well known by those of skill in the art.

3. Routes of Administration

The anti-RSV antibodies or antigen-binding fragments thereof provided herein can be administered to a subject by any method known in the art for the administration of polypeptides, including for example systemic or local administration. The anti-RSV antibodies or antigen-binding fragments thereof can be administered by routes, such as parenteral (e.g., intradermal, intramuscular, intraperitoneal, intravenous, subcutaneous, or intracavity), topical, epidural, or mucosal (e.g. intranasal or oral). The anti-RSV antibodies or antigen-binding fragments thereof can be administered externally to a subject, at the site of the disease for exertion of local or transdermal action. Compositions containing anti-RSV antibodies or antigen-binding fragments thereof can be administered by any convenient route, for example by infusion or bolus injection, by absorption through epithelial or mucocutaneous linings (e.g., oral mucosa, rectal and intestinal mucosa). Compositions containing anti-RSV antibodies or antigen-binding fragments can be administered together with other biologically active agents. The mode of administration can include topical or other administration of a composition on, in or around areas of the body that may come on contact with fluid, cells, or tissues that are infected, contaminated or have associated therewith a virus, such as a RSV virus. The anti-RSV antibodies or antigen-binding fragments thereof provided herein can be administered by topical or aerosol routes for delivery directly to target organs, such as the lungs (e.g. by pulmonary aerosol). In some examples, the provided anti-RSV antibodies or antigen-binding fragments thereof can be administered as a controlled release formulation as such as by a pump (see, e.g., Langer (1990) *Science* 249:1527-1533; Sefton (1987) *CRC Crit. Ref. Biomed. Eng.* 14:20; Buchwald et al. (1980) *Surgery* 88:507; and Saudek et al. (1989) *N. Engl. J. Med.* 321:574) or via the use of various polymers known in the art and described elsewhere herein. In some examples, a controlled or sustained release system can be placed in proximity of the therapeutic target, for examples, the lungs, thus requiring only a fraction of the systemic dose (see, e.g., Goodson, in Medical Applications of Controlled Release, supra, vol. 2, pp. 115-138 (1984)).

In particular examples, the provided anti-RSV antibodies or antigen-binding fragments thereof are administered by pulmonary delivery (see, e.g., U.S. Pat. Nos. 6,019,968, 5,985,320, 5,985,309, 5,934,272, 5,874,064, 5,855,913, 5,290,540, and 4,880,078; and PCT Publication Nos. WO 92/19244, WO 97/32572, WO 97/44013, WO 98/31346, and WO 99/66903). Exemplary methods of pulmonary delivery are known in the art and include, but are not limited to, aerosol methods, such as inhalers (e.g., pressurized metered dose inhalers (MDI), dry powder inhalers (DPI), nebulizers (e.g., jet or ultrasonic nebulizers) and other single breath liquid systems), intratracheal instillation and insufflation. In some examples, pulmonary delivery can be enhanced by co-administration of or administration of a co-formulation containing the anti-RSV antibodies or antigen-binding fragments thereof provided herein and a permeation enhancer, such as, for example, surfactants, fatty acids, saccharides, chelating agents and enzyme inhibitors, such as protease inhibitors.

Appropriate methods for delivery, such as pulmonary delivery, can be selected by one of skill in the art based on the properties of the dosage amount of the anti-RSV antibody or antigen-binding fragment thereof or the pharmaceutical composition containing the antibody or antigen-binding fragment thereof. Such properties include, but are not limited to, solubility, hygroscopicity, crystallization properties, melting point, density, viscosity, flow, stability and degradation profile.

In some examples, the anti-RSV antibodies or antigen-binding fragments thereof provided herein increase the efficacy mucosal immunization against a virus. Thus, in particular examples the anti-RSV antibodies or antigen-binding fragments thereof are administered to a mucosal surface. For example, the anti-RSV antibodies or antigen-binding fragments thereof can be delivered via routes such as oral (e.g., buccal, sublingual), ocular (e.g., corneal, conjunctival, intravitreally, intra-aqueous injection), intranasal, genital (e.g., vaginal), rectal, pulmonary, stomachic, or intestinal. The anti-RSV antibodies or antigen-binding fragments thereof provided herein can be administered systemically, such as parenterally, for example, by injection or by gradual infusion over time or enterally (i.e., digestive tract). The anti-RSV antibodies or antigen-binding fragments thereof provided herein also can be administered topically, such as for example, by topical installation or application (e.g., intratracheal instillation and insufflation using a bronchoscope or other artificial airway) of liquid solutions, gels, ointments, powders or by inhalation (e.g., nasal sprays, inhalers (e.g., pressurized metered dose inhalers (MDI), dry powder inhalers (DPI), nebulizers (e.g., jet or ultrasonic nebulizers) and other single breath liquid systems)). Administration can be effected prior to exposure to the virus or subsequent to exposure to the virus.

4. Combination Therapies

The anti-RSV antibodies or antigen-binding fragments thereof provided herein can be administered alone or in combination with one or more therapeutic agents or therapies for the prophylaxis and/or treatment of a disease or condition. For example, the provided anti-RSV antibodies or antigen-binding fragments thereof can be administered in combination with one or more antiviral agents for prophylaxis. In another example, the provided anti-RSV antibodies or antigen-binding fragments thereof can be administered in combination with one or more antiviral agents treatment of a viral infection, such as a respiratory viral infection. In some examples, the respiratory viral infection is a RSV infection. The antiviral agents can include agents to decrease and/or eliminate the pathogenic infection or agents to alleviate one or more symptoms of a pathogenic infection. In some examples, a plurality of antibodies or antigen-binding fragments thereof (e.g., one or more antiviral antibodies) also can be administered in combination, where at least one of the antibodies is an anti-RSV antibody or antigen-binding fragment thereof provided herein. In some examples, a plurality of antibodies can be administered in combination for the prophylaxis, where at least one of the antibodies is an anti-RSV antibody or antigen-binding fragment thereof provided herein. In other examples, a plurality of antibodies can be administered in combination for treatment of a RSV infection or multiple viral infections, where at least one of the antibodies is an anti-RSV antibody or antigen-binding fragment thereof provided herein. In some examples, the anti-RSV antibodies provided can be administered in combination with one or more antiviral antibodies, which bind to and neutralize a virus, such as RSV. In some examples, the anti-RSV antibodies or antigen-binding fragments thereof provided can be administered in combination with one or more antibodies, which can inhibit or alleviate one or more symptoms of a viral infection, such as a RSV infection. In some examples, two or more of the anti-RSV antibodies or antigen-binding fragments thereof provided herein are administered in combination.

The one or more additional agents can be administered simultaneously, sequentially or intermittently with the anti-RSV antibody or antigen-binding fragment thereof. The agents can be co-administered with the anti-RSV antibody or antigen-binding fragment thereof for example, as part of the same pharmaceutical composition or same method of delivery. In some examples, the agents can be co-administered with the anti-RSV antibody or antigen-binding fragment thereof at the same time as the anti-RSV antibody or antigen-binding fragment thereof, but by a different means of delivery. The agents also can be administered at a different time than administration of the anti-RSV antibody or antigen-binding fragment thereof, but close enough in time to the administration of the anti-RSV antibody or antigen-binding fragment thereof to have a combined prophylactic or therapeutic effect. In some examples, the one or more additional agents are administered subsequent to or prior to the administration of the anti-RSV antibody or antigen-binding fragment thereof separated by a selected time period. In some examples, the time period is 1 day, 2 days, 3 days, 4 days, 5 days, 6 days, 1 week, 2 weeks, 3 weeks, 1 month, 2 months, or 3 months. In some examples, the one ore more additional agents are administered multiple times and/or the anti-RSV antibody or antigen-binding fragment thereof provided herein is administered multiple times.

In some examples, administration of the combination inhibits the incidence of RSV infection by at least or about 99%, at least or about 95%, at least or about 90%, at least or about 85%, at least or about 80%, at least or about 75%, at least or about 70%, at least or about 65%, at least or about 60%, at least or about 55%, at least or about 50%, at least or about 45%, at least or about 40%, at least or about 35%, at least or about 30%, at least or about 25%, at least or about 20%, at least or about 15%, or at least or about 10% relative to the incidence of RSV infection in the absence of the combination. In some examples, administration of the combination decreases the severity of one or more symptoms of RSV infection by at least or about 99%, at least or about 95%, at least or about 90%, at least or about 85%, at least or about 80%, at least or about 75%, at least or about 70%, at least or about 65%, at least or about 60%, at least or about 55%, at least or about 50%, at least or about 45%, at least or about 40%, at least or about 35%, at least or about 30%, at least or about 25%, at least or about 20%, at least or about 15%, or at least or about 10% relative to the severity of the one or more symptoms of RSV infection in the absence of the combination.

In some examples, the combination inhibits the binding of RSV to its host cell receptor by at least or about 99%, at least or about 95%, at least or about 90%, at least or about 85%, at least or about 80%, at least or about 75%, at least or about 70%, at least or about 65%, at least or about 60%, at least or about 55%, at least or about 50%, at least or about 45%, at least or about 40%, at least or about 35%, at least or about 30%, at least or about 25%, at least or about 20%, at least or about 15%, or at least or about 10% relative to the binding of RSV to its host cell receptor in the absence of the combination. In some examples, the combination inhibits RSV replication by at least or about 99%, at least or about 95%, at least or about 90%, at least or about 85%, at least or about 80%, at least or about 75%, at least or about 70%, at least or about 65%, at least or about 60%, at least or about 55%, at least or about 50%, at least or about 45%, at least or about 40%, at least or about 35%, at least or about 30%, at least or about 25%, at least or about 20%, at least or about 15%, or at least or about 10% relative to RSV replication in the absence of the combination.

Any therapy which is known to be useful, or which is or has been used for the prevention, management, treatment, or amelioration of a RSV infection or one or more symptoms thereof can be used in combination with anti-RSV antibody or antigen-binding fragment thereof provided herein (see, e.g., Gilman et al., Goodman and Gilman's: *The Pharmacological Basis of Therapeutics,* 10th ed., McGraw-Hill, New York, 2001; *The Merck Manual of Diagnosis and Therapy*, Berkow, M. D. et al. (eds.), 17th Ed., Merck Sharp & Dohme Research Laboratories, Rahway, N.J., 1999; *Cecil Textbook of Medicine,* 20th Ed., Bennett and Plum (eds.), W. B. Saunders, Philadelphia, 1996, for information regarding therapies (e.g., prophylactic or therapeutic agents) which have been or are used for preventing, treating, managing, or ameliorating a RSV infection or one or more symptoms thereof). Examples of such agents include, but are not limited to, immunomodulator) agents, anti-inflammatory agents (e.g., adrenocorticoids, corticosteroids (e.g., beclomethasone, budesonide, flunisolide, fluticasone, triamcinolone, methylprednisolone, prednisolone, prednisone, hydrocortisone), glucocorticoids, steroids, non-steroidal anti-inflammatory drugs (e.g. aspirin, ibuprofen, diclofenac, and COX-2 inhibitors)), pain relievers, leukotriene antagonists (e.g., montelukast, methyl xanthines, zafirlukast, and zileuton), bronchodilators, such as β2-agonists (e.g., bambuterol, bitolterol, clenbuterol, fenoterol, formoterol, indacaterol, isoetharine, metaproterenol, pirbuterol, procaterol, reproterol, rimiterol, salbutamol (Albuterol, Ventolin), levosalbutamol, salmeterol, tulobuterol and terbutaline) and anticholinergic agents (e.g., ipratropium bromide and oxitropium bromide), sulphasalazine, penicillamine, dapsone, antihistamines, anti-malarial agents (e.g., hydroxychloroquine), and antiviral agents. The anti-RSV antibodies or antigen-binding fragments thereof provided herein also can be administered in combination with one or more therapies for the treatment of a RSV infection, including but not limited to, administration of intravenous infusion of immunoglobulin, administration of supplemental oxygen and fluids or assisted breathing. The anti-RSV antibodies or antigen-binding fragments thereof provided herein also can be administered in combination with one or more agents that regulate lung maturation and surfactant protein expression, such as, but not limited to, glucocorticoids, PPARγ ligands, and vascular endothelial cell growth factor (VEGF).

Exemplary antiviral agents that can be selected for combination therapy with an anti-RSV antibody or antigen-binding fragment thereof provided herein include, but are not limited to, antiviral compounds, antiviral proteins, antiviral peptides, antiviral protein conjugates and antiviral peptide conjugates, including, but not limited to, nucleoside analogs, nucleotide analogs, immunomodulators (e.g. interferons) and immunostimulants. Combination therapy using antibodies and/or anti-RSV antibodies and antigen-binding fragments provided herewith are contemplated as is combination with the antibodies and/or anti-RSV antibodies and antigen-binding fragments provided herein with other anti-RSV antibodies and anti-RSV antibodies and antigen-binding fragments.

Exemplary antiviral agents for the treatment of virus infections that can be administered in combination with the anti-RSV antibodies or antigen-binding fragments thereof provided herein include, but are not limited to, acyclovir, famciclovir, ganciclovir, penciclovir, valacyclovir, valganciclovir, idoxuridine, trifluridine, brivudine, cidofovir, docosanol, fomivirsen, foscarnet, tromantadine, imiquimod, podophyllotoxin, entecavir, lamivudine, telbivudine, clevudine, adefovir, tenofovir, boceprevir, telaprevir, pleconaril, arbidol, amantadine, rimantadine, oseltamivir, zanamivir, peramivir, inosine, interferon (e.g., Interferon alfa-2b, Peginterferon alfa-2a), ribavirin/taribavirin, abacavir, emtricitabine, lamivudine, didanosine, zidovudine, apricitabine, stampidine, elvucitabine, raciviv, amdoxovir, stavudine, zalcitabine, tenofovir, efavirenz, nevirapine, etravirine, rilpivirine, loviride, delavirdine, atazanavir, fosamprenavir, lopinavir, darunavir, nelfinavir, ritonavir, saquinavir, tipranavir, amprenavir, indinavir, enfuvirtide, maraviroc, vicriviroc, PRO 140, ibalizumab, raltegravir, elvitegravir, bevirimat, vivecon, including tautomeric forms, analogs, isomers, polymorphs, solvates, derivatives, or salts thereof.

Exemplary antiviral agents for the prophylaxis and/or treatment of RSV infections that can be administered in combination with the anti-RSV antibodies or antigen-binding fragments thereof provided herein include, but are not limited to, ribavirin, NIH-351 (Gemini Technologies), recombinant RSV vaccine (Aviron), RSVf-2 (Intracel), F-50042 (Pierre Fabre), T-786 (Trimeris). VP-36676 (ViroPharma), RFI-641 (American Home Products). VP-14637 (ViroPharma). PEP-1 and PFP-2 (American Home Products). RSV vaccine (Avant Immunotherapeutics), F-50077 (Pierre Fabre), and other anti-RSV antibodies or antigen-binding fragments thereof.

The anti-RSV antibodies or antigen-binding fragments thereof provided herein also can be administered in combination with one or more agents capable of stimulating cellular immunity, such as cellular mucosal immunity. Any agent capable of stimulatory cellular immunity can be used. Exemplary immunostimulatory agents include, cytokines, such as, but not limited to, interferons (e.g., IFN-$\alpha$, $\beta$, $\gamma$, $\omega$), lymphokines and hematopoietic growth factors, such as, for example, GM-CSF (granulocyte macrophage colony stimulating factor), Interleukin-2 (IL-2), Interleukin-3 (IL-3), Interleukin-4 (IL-4), Interleukin-7 (IL-7), Interleukin-10 (IL-10), Interleukin-12 (IL-12), Interleukin-14 (IL-14), and Tumor Necrosis Factor (TNF).

For combination therapies with anti-pathogenic agents, dosages for the administration of such compounds are known in the art or can be determined by one skilled in the art according to known clinical factors (e.g., subject's species, size, body surface area, age, sex, immunocompetence, and general health, duration and route of administration, the kind and stage of the disease, and whether other treatments, such as other anti-pathogenic agents, are being administered concurrently).

a. Antiviral Antibodies for Combination Therapy

The anti-RSV antibodies or antigen-binding fragments thereof provided herein can be administered in combination with one or more additional antibodies or antigen-binding fragments thereof. In some examples, the one or more additional antibodies are antiviral antibodies. In some examples, the one or more additional antibodies bind to a viral antigen. In some examples, the one or more additional antibodies bind to a viral antigen that is a surface protein, such as a viral capsid protein or a viral envelope protein. In some examples, the one or more additional antibodies bind to a viral antigen that is expressed on the surface of an infected cell. In some examples, the one or more additional antibodies bind to a viral antigen that is expressed intracellularly (i.e., within an infected cell). In some examples, the one or more additional antibodies binds to a virus that causes respiratory disease, such as, but not limited to, RSV, parainfluenza virus (PIV) or human metapneumovirus (hMPV). Compositions containing the mixtures of antibodies also are provided herein.

Antibodies for use in combination with an anti-RSV antibody or antigen-binding fragment thereof provided herein include, but are not limited to, monoclonal antibodies, multispecific antibodies, synthetic antibodies, human antibodies, humanized antibodies, chimeric antibodies, intrabodies, single-chain Fvs (scFv), single chain antibodies, Fab fragments, F(ab') fragments, disulfide-linked Fvs (sdFv), and anti-idiotypic (anti-Id) antibodies (including, e.g., anti-Id antibodies to antibodies provided herein), and epitope-binding fragments of any of the above. The antibodies for use in combination with an anti-RSV antibody or antigen-binding fragment thereof provided herein can be of any type (e.g. IgG, IgE, IgM, IgD, IgA and IgY), class (e.g., $IgG_1$, $IgG_2$, $IgG_3$, $IgG_4$, $IgA_1$ and $IgA_2$) or subclass of immunoglobulin molecule.

Antibodies for use in combination with an anti-RSV antibody or antigen-binding fragment thereof provided herein can be from any animal origin, including birds and mammals (e.g., human, murine, donkey, sheep, rabbit, goat, guinea pig, camel, horse, or chicken). Typically, the antibodies for use in combination with an anti-RSV antibody or antigen-binding fragment thereof provided herein are human or humanized antibodies. The antibodies for use in combination with an anti-RSV antibody or antigen-binding fragment thereof provided herein can be monospecific, bispecific, trispecific or of greater multispecificity.

The antibodies for use in combination with an anti-RSV antibody or antigen-binding fragment thereof provided herein can include derivative antibodies that are modified, for example, by the attachment of any type of molecule to the antibody or antigen-binding fragment thereof such as by covalent attachment. Exemplary antibody or antigen-binding fragment thereof derivatives include antibodies that have been modified, for example, by glycosylation, acetylation, pegylation, phosphorylation, amidation, derivatization by known protecting/blocking groups, proteolytic cleavage, linkage to a cellular ligand or other protein, or contain heterologous Fc domain with higher affinities for the FcRN receptor (see, e.g. U.S. Pat. No. 7,083,784). Any of numerous chemical modifications can be carried out by known techniques, including, but not limited to, specific chemical cleavage, acetylation, formylation, or synthesis in the presence of tunicamycin. Additionally, the derivative can contain one or more non-classical amino acids.

The one or more additional antibodies for use in combination with an anti-RSV antibody or antigen-binding fragment thereof provided herein can be administered simultaneously, sequentially or intermittently with the anti-RSV antibody or antigen-binding fragment thereof. The one or more additional antibodies can be co-administered with the anti-RSV antibody or antigen-binding fragment thereof, for example, as part of the same pharmaceutical composition or same method of delivery. In some examples, the one or more additional antibodies can be co-administered with the anti-RSV antibody or antigen-binding fragment thereof at the same time as the anti-RSV antibody or antigen-binding fragment thereof, but by a different means of delivery. The one or more additional antibodies also can be administered at a different time than administration of the anti-RSV antibody or antigen-binding fragment thereof provided herein, but close enough in time to the administration of the anti-RSV antibody or antigen-binding fragment thereof to have a combined prophylactic or therapeutic effect. In some examples, the one or more additional antibodies are administered subsequent to or prior to the administration of the anti-RSV antibody or antigen-binding fragment thereof separated by a selected time period. In some examples, the time period is 1 day, 2 days, 3 days, 4 days, 5 days, 6 days, 1 week, 2 weeks, 3 weeks, 1 month, 2 months, or 3 months. In some examples, the one ore more additional antibodies are administered multiple times and/or the anti-RSV antibody or antigen-binding fragment thereof provided herein is administered multiple times.

i. Anti-RSV Antibodies

In some examples, the one or more additional antiviral antibodies are anti-RSV antibodies or antigen-binding fragments thereof. In some examples, an anti-RSV antibody or antigen-binding fragment thereof provided herein is administered in combination with the one or more additional anti-RSV antibodies or antigen-binding fragments thereof for the prophylaxis and/or treatment of a RSV infection. Exemplary anti-RSV antibodies or antigen-binding fragments thereof for combination therapy with an anti-RSV antibody or antigen-binding fragment thereof provided herein include anti-RSV antibodies or antigen-binding fragments thereof that immunospecifically bind to and neutralize RSV. In some examples, the one or more additional anti-RSV antibodies or antigen-binding fragments thereof includes an antibody or antigen-binding fragment thereof that immunospecifically binds to RSV A subtype and/or RSV B subtype.

In some examples, the one or more additional antiviral antibodies for combination therapy with an anti-RSV antibody or antigen-binding fragment provided herein includes an anti-RSV antibody that binds to a RSV attachment protein (e.g. having an amino acid sequence set forth in SEQ ID NO:276), a RSV RNA polymerase beta subunit large structural protein) (L protein) (e.g. having an amino acid sequence set forth in SEQ ID NO:276), a RSV nucleocapsid protein (e.g. having an amino acid sequence set forth in SEQ ID NO:277), a RSV nucleoprotein (N) (e.g. having an amino acid sequence set forth in SEQ ID NO:278), a RSV phosphoprotein P (e.g. having an amino acid sequence set forth in SEQ ID NO:279), a RSV matrix protein (e.g. having an amino acid sequence set forth in SEQ ID NO:280), a RSV small hydrophobic (SH) protein (e.g. having an amino acid sequence set forth in SEQ ID NO:281), a RSV RNA-dependent polymerase, a RSV F protein (e.g. having an amino acid sequence set forth in SEQ ID NO:282), a RSV G protein (e.g. having an amino acid sequence set forth in SEQ ID NO:283), or an allelic variant of any of the above. In particular examples, the one or more additional antiviral antibodies includes an anti-RSV antibody that binds to a RSV F protein. In particular examples, the one or more additional antiviral antibodies that bind to a RSV F protein bind to the A, B, C, I, II, IV, V, or VI antigenic sites of a RSV F glycoprotein (see, e.g., Lopez et al. (1998) *J. Virol.* 72:6922-6928).

In some examples, the one or more additional antiviral antibodies for combination therapy with an anti-RSV antibody or antigen-binding fragment thereof provided herein includes, but is not limited to, palivizumab (SYNAGIS®), motavizumab (NUMAX®), AFFF, P12f2, P12f4, P11d4, A1e9, A12a6, A13c4, A17d4, A4B4, A8c7, 1X-493L1, FR H3-3F4, M3H9, Y10H6, DG, AFFF(1), 6H8, L1-7E5, L2-15B10, A13a11, A1h5, A4B4(1), A4B4L1FR-S28R, A4B4-F52S, (see U.S. Pat. Nos. 5,824,307 and 6,818,216), rsv6, rsv11, rsv13, rsv19, rsv21, rsv22, rsv23 (see U.S. Pat. No. 6,685,942), RF-1, RF-2 (see U.S. Pat. No. 5,811,524), or antigen-binding fragments thereof. In some examples, the one or more additional antiviral antibodies for combination therapy includes an antibody or antigen-binding fragment thereof containing a V$_H$ chain and/or V$_L$ chain having the amino acid sequence of a V$_H$ chain and/or V$_L$ chain of palivizumab (SYNAGIS®), motavizumab (NUMAX®), AFFF, P12f2, P12f4, P11d4, A1e9, A12a6, A13c4, A17d4, A4B4, A8c7, 1X-493L1, FR H3-3F4, M3H9, Y10H6, DG, AFFF(1), 6H8, L1-7E5, L2-15B10, A13a11, A1h5, A4B4(1), A4B4L1FR-S28R, A4B4-F52S, rsv6, rsv11, rsv13, rsv19, rsv21, rsv22, rsv23, RF-1, or RF-2. In some examples, the one or more additional antiviral antibodies for combination therapy includes an antibody or antigen-binding fragment thereof containing one or more CDRs of palivizumab (SYNAGIS®), motavizumab (NUMAX®), AFFF, P12f2, P12f4, P11d4, A1e9, A12a6, A13c4, A17d4, A4B4, A8c7, 1X-493L1, FR H3-3F4, M3H9, Y10H6, DG, AFFF(1), 6H8, L1-7E5, L2-15B10, A13a11, A1h5, A4B4(1), A4B4L1FR-S28R, A4B4-F52S, rsv6, rsv11, rsv13, rsv19, rsv21, rsv22, rsv23, RF-1, or RF-2. In some examples, the one or more additional antiviral antibodies for combination therapy includes an antibody or antigen-binding fragment thereof containing one or more CDRs of from an anti-RSV mouse monoclonal antibody such as, but not limited to, MAbs 1153, 1142, 1200, 1214, 1237, 1129, 1121, 1107, 1112, 1269, 1269, 1243 (Beeler et al. (1989) *J. Virology* 63(7):2841-2950), MAb151 (Mufson et al. (1987) *J. Clin. Microbiol.* 25:1635-1539), MAbs 43-1 and 13-1 (Fernie et al. (1982) *Proc. Soc. Exp. Biol. Med* 171:266-271), MAbs 1436C, 1302A, 1308F, and 1331H (Anderson et al. (1984) *J. Clin. Microbiol.* 19:934-936). Additional exemplary antibodies or antigen-binding fragments thereof that can be used for combination therapy with an anti-RSV antibody or antigen-binding fragment provided herein include, but are not limited to, anti-RSV antibodies or antigen-binding fragments thereof described in, for example, U.S. Pat. Nos. 6,413,771, 5,840,298, 5,811,524, 6,656,467, 6,537,809, 7,364,742, 7,070,786, 5,955,364, 7,488,477, 6,818,216, 5,824,307, 7,364,737, 6,685,942, and 5,762,905 and U.S. Patent Pub. Nos. 2007-0082002, 2005-0175986, 2004-0234528, 2006-0198840, 2009-0110684, 2006-0159695, 2006-0013824, 2005-0288491, 2005-0019758, 2008-0226630, 2009-0137003, and 2009-0092609.

In some examples, the one or more additional antiviral antibodies for combination therapy with an anti-RSV antibody or antigen-binding fragment thereof provided herein includes an antibody or antigen-binding fragment thereof containing a V$_H$ chain having an amino acid sequence set forth in any of SEQ ID NOS:103, 113, 122, 131, 137, 144, 149, 155, 161, 167, 172, 176, 179, 182, 186, 190, 194, 198, 201, 205, 210, 215, 222, 226, 233, 239, 246, 252, 257, 362, and 366. In some examples, the one or more additional antiviral antibodies for combination therapy with an anti-RSV antibody or antigen-binding fragment thereof provided herein includes an antibody or antigen-binding fragment thereof containing a V$_H$ domain having an amino acid sequence set forth in any of SEQ ID NOS:104, 114, 123, 132, 138, 145, 150, 156, 162, 168, 173, 187, 206, 227, 232, 234, 240, 247, 253, and 258. In some examples, the one or more additional antiviral antibodies for combination therapy with an anti-RSV antibody or antigen-binding fragment thereof provided herein includes an antibody or antigen-binding fragment thereof containing a V$_H$ CDR1 having an amino acid sequence set forth in any of SEQ ID NOS:105, 115, 124, 363, and 367. In particular examples, the one or more additional antiviral antibodies for combination therapy with an anti-RSV antibody or antigen-binding fragment thereof provided herein includes an antibody or antigen-binding fragment thereof containing a V$_H$ CDR1 having the amino acid sequence TSGMSVG (SEQ ID NO:105), TAGMSVG (SEQ ID NO:115), AYAMS (SEQ ID NO:363), or GYTMH (SEQ ID NO:367). In some examples, the one or more additional antiviral antibodies for combination therapy with an anti-RSV antibody or antigen-binding fragment thereof provided herein includes an antibody or antigen-binding fragment thereof containing a V$_H$ CDR2 having an amino acid sequence set forth in any of SEQ ID NOS: 106, 125, 133, 157, 236, 259, 364, and 368. In a particular example, the one or more additional antiviral antibodies for combination therapy with an anti-RSV antibody or antigen-binding fragment thereof provided herein includes an antibody or antigen-binding fragment thereof containing a V$_H$ CDR2 having the amino acid sequence DIWWDDKK- DYNPSLKS (SEQ ID NO:106) or DIWWDDK-KHYNPSLKD (SEQ ID NO:125), GISGSGDSTDYADS-VKG (SEQ ID NO:364), or SITGGSNFINYSDSVKG (SEQ ID NO:368). In some examples, the one or more additional antiviral antibodies for combination therapy with an anti-RSV antibody or antigen-binding fragment thereof provided herein includes an antibody or antigen-binding fragment thereof containing a $V_H$ CDR3 having an amino acid sequence set forth in any of SEQ ID NOS:107, 116, 126, 139, 188, 241, 365, and 369. In a particular example, the one or more additional antiviral antibodies for combination therapy with an anti-RSV antibody or antigen-binding fragment thereof provided herein includes an antibody or antigen-binding fragment thereof containing a $V_H$ CDR3 having the amino acid sequence SMITNWYFDV (SEQ ID NO:107), DMIFNFYFDV (SEQ ID NO:126), HLPDYWN-LDYTRFFYYMDV (SEQ ID NO:365), or APIAPPYFDH (SEQ ID NO:369).

In some examples, the one or more additional antiviral antibodies for combination therapy with an anti-RSV antibody or antigen-binding fragment thereof provided herein includes an antibody or antigen-binding fragment thereof containing a $V_L$ chain having an amino acid sequence set forth in any of SEQ ID NOS:108, 117, 127, 134, 140, 146, 152, 158, 164, 169, 174, 177, 180, 183, 189, 191, 195, 199, 202, 207, 211, 216, 220, 223, 228, 236, 242, 248, 254, 260, 263, 370, 374, and 378. In some examples, the one or more additional antiviral antibodies for combination therapy with an anti-RSV antibody or antigen-binding fragment thereof provided herein includes an antibody or antigen-binding fragment thereof containing a $V_L$ domain having an amino acid sequence set forth in any of SEQ ID NOS:109, 118, 128, 135, 141, 147, 153, 159, 165, 170, 175, 178, 181, 184, 192, 196, 200, 203, 208, 212, 217, 221, 224, 229, 237, 243, 249, 255, 261 and 264. In some examples, the one or more additional antiviral antibodies for combination therapy with an anti-RSV antibody or antigen-binding fragment thereof provided herein includes an antibody or antigen-binding fragment thereof containing a $V_L$ CDR1 having an amino acid sequence set forth in any of SEQ ID NOS:110, 119, 129, 142, 154, 166, 244, 250, 265, 371, 375, and 379. In a particular example, the one or more additional antiviral antibodies for combination therapy with an anti-RSV antibody or antigen-binding fragment thereof provided herein includes an antibody or antigen-binding fragment thereof containing a $V_L$ CDR1 having the amino acid sequence KCQLSVGYMH (SEQ ID NO:110), SASSRVGYMH (SEQ ID NO:154). RATQSISSNYLA (SEQ ID NO:371), KASQNINDNLA (SEQ ID NO:375), or RATQSVSNFLN (SEQ ID NO:379). In some examples, the one or more additional antiviral antibodies for combination therapy with an anti-RSV antibody or antigen-binding fragment thereof provided herein includes an antibody or antigen-binding fragment thereof containing a $V_L$ CDR2 having an amino acid sequence set forth in any of SEQ ID NOS:111, 120, 136, 143, 160, 171, 185, 218, 225, 230, 238, 245, 251, 256, 262, 266, 372, 376, and 380. In a particular example, the one or more additional antiviral antibodies for combination therapy with an anti-RSV antibody or antigen-binding fragment thereof provided herein includes an antibody or antigen-binding fragment thereof containing a $V_L$ CDR2 having the amino acid sequence DTSKLAS (SEQ ID NO:111), DTLLLDS (SEQ ID NO:218), GASNRAT (SEQ ID NO:372), GASSRAT (SEQ ID NO:376), or DASTSQS (SEQ ID NO:380). In some examples, the one or more additional antiviral antibodies for combination therapy with an anti-RSV antibody or antigen-binding fragment thereof provided herein includes an antibody or antigen-binding fragment thereof containing a $V_L$ CDR3 having an amino acid sequence set forth in any of SEQ ID NOS:112, 121, 193, 373, 377, and 381. In a particular example, the one or more additional antiviral antibodies for combination therapy with an anti-RSV antibody or antigen-binding fragment thereof provided herein includes an antibody or antigen-binding fragment thereof containing a $V_L$ CDR3 having the amino acid sequence FQGSGYPFT (SEQ ID NO:112), QQYDISPYT (SEQ ID NO:373), QQYGGSPYT (SEQ ID NO:377), or QASINTPL (SEQ ID NO:381).

In some examples, the anti-RSV antibody or antigen-binding fragment thereof provided herein can be administered in combination with hyperimmune serum or immune globulin enriched for anti-RSV antibodies, such as, for example, RSV hyperimmune globulin (RSV IVIG; RESPIGAM®; MedImmune Inc, Gaithersburg, Md.; see, e.g., Groothius et al. (1993) *New Eng. J. Med* 329:1524-1530).

ii. Antibodies Against Other Respiratory Viruses

In some examples, the one or more additional antiviral antibodies for combination therapy with an anti-RSV antibody or antigen-binding fragment thereof provided herein includes an antibody or antigen-binding fragment thereof to a respiratory virus other than RSV, for example, selected from among an anti-human metapneumovirus (hMPV) antibody, an anti-parainfluenzavirus (PIV) antibody, an anti-avian pneumovirus (APV) antibody or other antiviral antibody known in the art.

In some examples, where the one or more additional antiviral antibodies for combination therapy with an anti-RSV antibody or antigen-binding fragment thereof provided herein is an anti-PIV antibody, an antibody that immunospecifically binds to a PIV antigen, such as, for example, a PIV nucleocapsid phosphoprotein, a PIV fusion (F) protein, a PIV phosphoprotein, a PIV large (L) protein, a PIV matrix (M) protein, a PIV hemagglutinin-neuraminidase (HN) glycoprotein, a PIV RNA-dependent RNA polymerase, a PIV Y1 protein, a PIV D protein, a PIV C protein, or an allelic variant of any of the above. In particular examples, the PIV antigen is PIV F protein. In some examples, the anti-PIV antibody is an antibody that immunospecifically binds to an antigen of human PIV type 1, human PIV type 2, human PIV type 3, and/or human PIV type 4.

In some examples, where the one or more additional antiviral antibodies for combination therapy with an anti-RSV antibody or antigen-binding fragment thereof provided herein is an anti-hMPV antibody, an antibody that immunospecifically binds to a hMPV antigen, such as, for example, a hMPV nucleoprotein, a hMPV phosphoprotein, a hMPV matrix protein, a hMPV small hydrophobic protein, a hMPV RNA-dependent RNA polymerase, a hMPV F protein, a hMPV G protein, or an allelic variant of any of the above. In particular examples, the hMPV antigen is PIV F protein. In some examples, the anti-hMPV antibody is an antibody that immunospecifically binds to an antigen of hMPV type A and/or hMPV type B. In some examples, the anti-hMPV antibody is an antibody that immunospecifically binds to an antigen of hMPV sub-type A1 and/or A2 and/or hMPV sub-type B1 and/or B2.

Antibodies administered in combination with an anti-RSV antibody or antigen-binding fragment thereof provided herein can be any type of antibody or antigen-binding fragment known in the art. For example, an antibody or antigen-binding fragment thereof administered in combination with an anti-RSV antibody or antigen-binding fragment thereof provided herein can include, but is not limited to, a monoclonal antibody, a human antibody, a non-human antibody, a recombinantly produced antibody, a chimeric antibody, a humanized antibody, a multispecific antibody (e.g., a bispecific antibody), an intrabody, and an antibody fragment, such as, but not limited to, a Fab fragment, a Fab' fragment, a F(ab')$_2$ fragment, a Fv fragment, a disulfide-linked Fv (dsFv), a Fd fragment, a Fd' fragment, a single-chain Fv (scFv), a single-chain Fab (scFab), a diabody, an anti-idiotypic (anti-Id) antibody, or antigen-binding fragments of any of the above. Antibodies administered in combination with an anti-RSV antibody provided herein can include members of any immunoglobulin type (e.g., IgG, IgM, IgD, IgE, IgA and IgY), any class (e.g. IgG1, IgG2, IgG3, IgG4, IgA1 and IgA2) or subclass (e.g., IgG2a and IgG2b).

In some examples, administration of the combination of antiviral antibodies or antigen-binding fragments inhibits the incidence of RSV infection by at least or about 99%, at least or about 95%, at least or about 90%, at least or about 85%, at least or about 80%, at least or about 75%, at least or about 70%, at least or about 65%, at least or about 60%, at least or about 55%, at least or about 50%, at least or about 45%, at least or about 40%, at least or about 35%, at least or about 30%, at least or about 25%, at least or about 20%, at least or about 15%, or at least or about 10% relative to the incidence of RSV infection in the absence of the anti-RSV antibody or antigen-binding fragment. In some examples, administration of the combination of antiviral antibodies or antigen-binding fragments decreases the severity of one or more symptoms of RSV infection by at least or about 99%, at least or about 95%, at least or about 90%, at least or about 85%, at least or about 80%, at least or about 75%, at least or about 70%, at least or about 65%, at least or about 60%, at least or about 55%, at least or about 50%, at least or about 45%, at least or about 40%, at least or about 35%, at least or about 30%, at least or about 25%, at least or about 20%, at least or about 15%, or at least or about 10% relative to the severity of the one or more symptoms of RSV infection in the absence of the combination of antiviral antibodies or antigen-binding fragments.

In some examples, the combination of antiviral antibodies or antigen-binding fragments inhibits the binding of RSV to its host cell receptor by at least or about 99%, at least or about 95%, at least or about 90%, at least or about 85%, at least or about 80%, at least or about 75%, at least or about 70%, at least or about 65%, at least or about 60%, at least or about 55%, at least or about 50%, at least or about 45%, at least or about 40%, at least or about 35%, at least or about 30%, at least or about 25%, at least or about 20%, at least or about 15%, or at least or about 10% relative to the binding of RSV to its host cell receptor in the absence of the combination of antiviral antibodies or antigen-binding fragments. In some examples, the combination of antiviral antibodies or antigen-binding fragments inhibits RSV replication by at least or about 99%, at least or about 95%, at least or about 90%, at least or about 85%, at least or about 80%, at least or about 75%, at least or about 70%, at least or about 65%, at least or about 60%, at least or about 55%, at least or about 50%, at least or about 45%, at least or about 40%, at least or about 35%, at least or about 30%, at least or about 25%, at least or about 20%, at least or about 15%, or at least or about 10% relative to RSV replication in the absence of the combination of antiviral antibodies or antigen-binding fragments.

5. Gene Therapy

In some examples, nucleic acids comprising sequences encoding the anti-RSV antibodies, antigen-binding fragments and/or derivatives thereof, are administered to treat, prevent or ameliorate one or more symptoms associated with RSV infection, by way of gene therapy. Gene therapy refers to therapy performed by the administration to a subject of an expressed or expressible nucleic acid. In this example, the nucleic acids produce their encoded antibody or antigen-binding fragment thereof that mediates a prophylactic or therapeutic effect.

Any of the methods for gene therapy available in the art can be employed for administration of nucleic acid encoding the anti-RSV antibodies, antigen-binding fragments and/or derivatives thereof. Exemplary methods are described below.

For general reviews of the methods of gene therapy, see, for example, Goldspiel et al. (1993) *Clinical Pharmacy* 12:488-505; Wu and Wu (1991) *Biotherapy* 3:87-95; Tolstoshev (1993) *Ann. Rev. Pharmacol. Toxicol.* 32:573-596; Mulligan (1993) *Science* 260:926-932; Morgan and Anderson (1993) *Ann. Rev. Biochem.* 62:191-217; and *TIBTECH* 11(5):155-215. Methods commonly known in the art of recombinant DNA technology which can be used are described in Ausubel et al. (eds.), Current Protocols in Molecular Biology, John Wiley & Sons, NY (1993); and Kriegler, Gene Transfer and Expression, A Laboratory Manual, Stockton Press, NY (1990).

In some examples, a composition provided herein contains nucleic acids encoding an anti-RSV antibody, an antigen-binding fragment and/or derivative thereof, where the nucleic acids are part of an expression vector that expresses the anti-RSV antibody, antigen-binding fragment and/or derivative thereof in a suitable host. In particular, such nucleic acids have promoters, such as heterologous promoters, operably linked to the antibody coding region, said promoter being inducible or constitutive, and, optionally, tissue-specific. In another particular embodiment, nucleic acid molecules are used in which the antibody coding sequences and any other desired sequences are flanked by regions that promote homologous recombination at a desired site in the genome, thus providing for intrachromosomal expression of the antibody encoding nucleic acids (Koller and Smithies (1989) *Proc. Natl. Acad. Sci. USA* 86:8932-8935; Zijlstra et al. (1989) *Nature* 342:435-438). In some examples, the expressed antibody molecule is a single chain antibody. In some examples, the nucleic acid sequences include sequences encoding the heavy and light chains, or fragments thereof, of the antibody. In a particular example, the nucleic acid sequences include sequences encoding an anti-RSV Fab fragment. In a particular example, the nucleic acid sequences include sequences encoding a full-length anti-RSV antibody. In some examples, the encoded anti-RSV antibody is a chimeric antibody.

Delivery of the nucleic acids into a subject can be either direct, in which case the subject is directly exposed to the nucleic acid or nucleic acid-carrying vectors, or indirect, in which case, cells are first transformed with the nucleic acids in vitro, then transplanted into the subject. These two approaches are known, respectively, as in vivo or ex vivo gene therapy.

In some examples, the nucleic acid sequences are directly administered in vivo, where it is expressed to produce the encoded product. This can be accomplished by any of numerous methods known in the art, for example, by constructing them as part of an appropriate nucleic acid expression vector and administering it so that they become intracellular, for example, by infection using defective or attenuated retroviral or other viral vectors (see U.S. Pat. No. 4,980,286), or by direct injection of naked DNA, or by use of microparticle bombardment (e.g., a gene gun: Biolistic. Dupont), or coating with lipids or cell-surface receptors or transfecting agents, encapsulation in liposomes, microparticles, or microcapsules, or by administering them in linkage to a peptide which is known to enter the nucleus, by administering it in linkage to a ligand subject to receptor-mediated endocytosis (see, e.g., Wu and Wu (1987) *J. Biol. Chem.* 262:4429-4432) which can be used, for example, to target cell types specifically expressing the receptors. In some examples, nucleic acid-ligand complexes can be formed in which the ligand contains a fusogenic viral peptide to disrupt endosomes, allowing the nucleic acid to avoid lysosomal degradation. In some examples, the nucleic acid can be targeted in vivo for cell specific uptake and expression, by targeting a specific receptor (see, e.g., PCT Publications WO 92/06180; WO 92/22635; WO92/203 16; WO93/14188, and WO 93/20221). Alternatively, the nucleic acid can be introduced intracellularly and incorporated within host cell DNA for expression, by homologous recombination (Koller and Smithies (1989) *Proc. Natl. Acad. Sci. USA* 86:8932-8935; and Zijlstra et al. (1989) *Nature* 342: 435-438).

In some examples, viral vectors that contain nucleic acid sequences encoding an anti-RSV antibody, antigen-binding fragments and/or derivatives thereof are used. For example, a retroviral vector can be used (see, e.g., Miller et al. (1993) *Meth. Enzymol.* 217:581-599). Retroviral vectors contain the components necessary for the correct packaging of the viral genome and integration into the host cell DNA. The nucleic acid sequences encoding the antibody or antigen-binding fragment thereof to be used in gene therapy are cloned into one or more vectors, which facilitate delivery of the gene into a subject. More detail about retroviral vectors can be found, for example, in Boesen et al. (1994) *Biotherapy* 6:291-302. Other references illustrating the use of retroviral vectors in gene therapy include, for example, Clowes et al. (1994) *J. Clin. Invest.* 93:644-651; Klein et al. (1994) *Blood* 83:1467-1473; Salmons and Gunzberg (1993) *Human Gene Therapy* 4:129-141; and Grossman and Wilson (1993) *Curr. Opin, in Genetics and Devel.* 3:110-114.

Adenoviruses also are viral vectors that can be used in gene therapy. Adenoviruses are especially attractive vehicles for delivering genes to respiratory epithelia. Adenoviruses naturally infect respiratory epithelia where they cause a mild disease. Other targets for adenovirus-based delivery systems include the liver, central nervous system, endothelial cells, and muscle. Adenoviruses have the advantage of being capable of infecting non-dividing cells. Kozarsky and Wilson (1993) *Current Opinion in Genetics and Development* 3:499-503 present a review of adenovirus-based gene therapy. Bout et al. (1994) *Human Gene Therapy* 5:3-10 demonstrated the use of adenovirus vectors to transfer genes to the respiratory epithelia of rhesus monkeys. Other instances of the use of adenoviruses in gene therapy can be found, for examples, in Rosenfeld et al. (1991) *Science* 252:431-434; Rosenfeld et al. (1992) *Cell* 68:143-155; Mastrangeli et al. (1993) *J. Clin. Invest.* 91:225-234; PCT Publication WO94/12649; and Wang et al. (1995) *Gene Therapy* 2:775-783. In a particular example, adenovirus vectors are used to deliver nucleic acid encoding the anti-RSV antibodies, antigen-binding fragments and/or derivatives thereof provided herein.

Adeno-associated virus (AAV) also can be used in gene therapy (Walsh et al. (1993) *Proc. Soc. Exp. Biol. Med.* 204:289-300; and U.S. Pat. No. 5,436,146). In a particular example, adeno-associated virus (AAV) vectors are used to deliver nucleic acid encoding the anti-RSV antibodies, antigen-binding fragments and/or derivatives thereof provided herein.

Another approach to gene therapy involves transferring a gene to cells in tissue culture by such methods as electroporation, lipofection, calcium phosphate mediated transfection, or viral infection. Generally, the method of transfer includes the transfer of a selectable marker to the cells. The cells are then placed under selection to isolate those cells that have taken up and are expressing the transferred gene. The cells expressing the gene are then delivered to a subject.

In some examples, the nucleic acid encoding an anti-RSV antibody, antigen-binding fragments and/or derivatives thereof provided herein is introduced into a cell prior to administration in vivo of the resulting recombinant cell. Such introduction can be carried out by any method known in the art, including, but not limited to, transfection, electroporation, microinjection, infection with a viral or bacteriophage vector containing the nucleic acid sequences, cell fusion, chromosome-mediated gene transfer, microcell-mediated gene transfer, and spheroplast fusion. Numerous techniques are known in the art for the introduction of foreign genes into cells (see, e.g., Loeffler and Behr (1993) *Meth. Enzymol.* 217:599-618: Cohen et al. (1993) *Meth. Enzymol.* 217:618-644; Cline (1985) *Pharmacol. Ther.* 29:69-92) and can be used for the administration of nucleic acid encoding an anti-RSV antibody, antigen-binding fragment and/or derivative thereof provided herein, provided that the necessary developmental and physiological functions of the recipient cells are not disrupted. The technique provides for the stable transfer of the nucleic acid to the cell, so that the nucleic acid is expressible by the cell and typically heritable and expressible by its cell progeny.

The resulting recombinant cells can be delivered to a subject by various methods known in the art. Recombinant blood cells (e.g., hematopoietic stem or progenitor cells) can be administered intravenously. The amount of cells for administration depends on various factors, including, for example, the desired prophylactic and/or therapeutic effect and patient state, and can be determined by one skilled in the art.

Cells into which a nucleic acid can be introduced for purposes of gene therapy encompass any desired, available cell type, and include, but are not limited to, epithelial cells, endothelial cells, keratinocytes, fibroblasts, muscle cells, hepatocytes; blood cells such as T lymphocytes, B lymphocytes, monocytes, macrophages, neutrophils, eosinophils, megakaryocytes, granulocytes; various stem or progenitor cells, in particular hematopoietic stem or progenitor cells, for example, as obtained from bone marrow, umbilical cord blood, peripheral blood, and fetal liver. In particular examples, the cell used for gene therapy is autologous to the subject.

In some examples in which recombinant cells are used in gene therapy, nucleic acid sequences encoding an anti-RSV antibody, antigen-binding fragment and/or derivative thereof provided herein are introduced into the cells such that they are expressible by the cells or their progeny, and the recombinant cells are then administered in vivo for therapeutic effect. In a particular example, stem or progenitor cells are used. Any stem and/or progenitor cells which can be isolated and maintained in vitro can be used (see e.g., PCT Publication WO 94/08598; Stemple and Anderson (1992) *Cell* 7 1:973-985; Rheinwald (1980) *Meth. Cell Bio.* 21A:229; and Pittelkow and Scott (1986) *Mayo Clinic Proc.* 61:771).

In a particular example, the nucleic acid to be introduced for purposes of gene therapy contains an inducible promoter operably linked to the coding region, such that expression of the nucleic acid is controllable by controlling the presence or absence of the appropriate inducer of transcription.

J. PHARMACEUTICAL COMPOSITIONS, COMBINATIONS AND ARTICLES OF MANUFACTURE/KITS

1. Pharmaceutical Compositions

Provided herein are pharmaceutical compositions containing an anti-RSV antibody or antigen-binding fragment thereof provided herein. The pharmaceutical composition can be used for therapeutic, prophylactic, and/or diagnostic applications. The anti-RSV antibodies or antigen-binding fragments thereof provided herein can be formulated with a pharmaceutical acceptable carrier or diluent. Generally, such pharmaceutical compositions utilize components which will not significantly impair the biological properties of the antibody or antigen-binding fragment thereof, such as the binding of to its specific epitope (e.g. binding to an epitope on a RSV F protein). Each component is pharmaceutically and physiologically acceptable in the sense of being compatible with the other ingredients and not injurious to the patient. The formulations can conveniently be presented in unit dosage form and can be prepared by methods well known in the art of pharmacy, including but not limited to, tablets, pills, powders, liquid solutions or suspensions (e.g., including injectable, ingestible and topical formulations (e.g., eye drops, gels or ointments), aerosols (e.g., nasal sprays), liposomes, suppositories, injectable and infusible solution and sustained release forms. See, e.g., Gilman, et al. (eds. 1990) Goodman and Gilman's: The Pharmacological Bases of Therapeutics, 8th Ed., Pergamon Press; and Remington's Pharmaceutical Sciences, 17th ed. (1990). Mack Publishing Co., Easton. Pa.; Avis, et al (eds. 1993) Pharmaceutical Dosage Forms: Parenteral Medications, Dekker, NY; Lieberman, et al. (eds. 1990) Pharmaceutical Dosage Forms: Tablets, Dekker, NY; and Lieberman, et al. (eds. 1990) Pharmaceutical Dosage Forms: Disperse Systems, Dekker, NY. When administered systematically, the therapeutic composition is sterile, pyrogen-free, generally free of particulate matter, and in a parenterally acceptable solution having due regard for pH, isotonicity, and stability. These conditions are known to those skilled in the art. Methods for preparing parenterally administrable compositions are well known or will be apparent to those skilled in the art and are described in more detail in, e.g., "Remington: The Science and Practice of Pharmacy (Formerly Remington's Pharmaceutical Sciences)," 19th ed., Mack Publishing Company, Easton, Pa. (1995).

Pharmaceutical compositions provided herein can be in various forms, e.g., in solid, semi-solid, liquid, powder, aqueous, or lyophilized form. Examples of suitable pharmaceutical carriers are known in the art and include but are not limited to water, buffering agents, saline solutions, phosphate buffered saline solutions, various types of wetting agents, sterile solutions, alcohols, gum arabic, vegetable oils, benzyl alcohols, gelatin, glycerin, carbohydrates such as lactose, sucrose, amylose or starch, magnesium stearate, talc, silicic acid, viscous paraffin, perfume oil, fatty acid monoglycerides and diglycerides, pentaerythritol fatty acid esters, hydroxy methylcellulose, powders, among others. Pharmaceutical compositions provided herein can contain other additives including, for example, antioxidants, preservatives, antimicrobial agents, analgesic agents, binders, disintegrants, coloring, diluents, excipients, extenders, glidants, solubilizers, stabilizers, tonicity agents, vehicles, viscosity agents, flavoring agents, emulsions, such as oil/water emulsions, emulsifying and suspending agents, such as acacia, agar, alginic acid, sodium alginate, bentonite, carbomer, carrageenan, carboxymethylcellulose, cellulose, cholesterol, gelatin, hydroxyethyl cellulose, hydroxypropyl cellulose, hydroxypropyl methylcellulose, methylcellulose, octoxynol 9, oleyl alcohol, povidone, propylene glycol monostearate, sodium lauryl sulfate, sorbitan esters, stearyl alcohol, tragacanth, xanthan gum, and derivatives thereof, solvents, and miscellaneous ingredients such as crystalline cellulose, microcrystalline cellulose, citric acid, dextrin, dextrose, liquid glucose, lactic acid, lactose, magnesium chloride, potassium metaphosphate, starch, among others (see, generally, Alfonso R. Gennaro (2000) Remington: The Science and Practice of Pharmacy, 20th Edition. Baltimore, Md.: Lippincott Williams & Wilkins). Such carriers and/or additives can be formulated by conventional methods and can be administered to the subject at a suitable dose. Stabilizing agents such as lipids, nuclease inhibitors, polymers, and chelating agents can preserve the compositions from degradation within the body.

Pharmaceutical compositions suitable for use include compositions wherein one or more anti-RSV antibodies are contained in an amount effective to achieve their intended purpose. Determination of a therapeutically effective amount is well within the capability of those skilled in the art. Therapeutically effective dosages can be determined by using in vitro and in vivo methods as described herein. Accordingly, an anti-RSV antibody or antigen-binding fragment thereof provided herein, when in a pharmaceutical preparation, can be present in unit dose forms for administration.

An anti-RSV antibody or antigen-binding fragment thereof provided herein can be lyophilized for storage and reconstituted in a suitable carrier prior to use. This technique has been shown to be effective with conventional immunoglobulins and protein preparations and art-known lyophilization and reconstitution techniques can be employed.

An anti-RSV antibody or antigen-binding fragment thereof provided herein can be provided as a controlled release or sustained release composition. Polymeric materials are known in the art for the formulation of pills and capsules which can achieve controlled or sustained release of the antibodies or antigen-binding fragments thereof provided herein (see, e.g., Medical Applications of Controlled Release, Langer and Wise (eds.), CRC Pres., Boca Raton, Fla. (1974); Controlled Drug Bioavailability, Drug Product Design and Performance, Smolen and Ball (eds.), Wiley, New York (1984); Ranger and Peppas (1983) J., Macromol. Sci. Rev. Macromol. Chem. 23:61; see also Levy et al. (1985) Science 228:190; During et al. (1989) Ann. Neurol. 25:351; Howard et al. (1989) J. Neurosurg. 7 1:105; U.S. Pat. Nos. 5,679,377, 5,916,597, 5,912,015, 5,989,463, 5,128,326; PCT Publication Nos. WO 99/15154 and WO 99/20253). Examples of polymers used in sustained release formulations include, but are not limited to, poly(2-hydroxy ethyl methacrylate), poly(methyl methacrylate), poly(acrylic acid), poly(ethylene-co-vinyl acetate), poly(methacrylic acid), polyglycolides (PLG), polyanhydrides, poly(N-vinyl pyrrolidone), poly(vinyl alcohol), polyacrylamide, poly(ethylene glycol), polylactides (PLA), poly(lactide-co-glycolides) (PLGA), and polyorthoesters. Generally, the polymer used in a sustained release formulation is inert, free of leachable impurities, stable on storage, sterile, and biodegradable. Any technique known in the art for the production of sustained release formulation can be used to produce a sustained release formulation containing one or more anti-RSV antibodies or antigen-binding fragments provided herein.

In some examples, the pharmaceutical composition contains an anti-RSV antibody or antigen-binding fragment thereof provided herein and one or more additional antibodies. In some examples, the one or more additional antibodies includes, but is not limited to, palivizumab (SYNAGIS®), and derivatives thereof, such as, but not limited to, motavizumab (NUMAX®), AFFF, P12f2, P12f4, P11d4, A1e9, A12a6, A13c4, A17d4, A4B4, A8c7, 1X-493L1, FR H3-3F4, M3H9, Y10H6, DG, AFFF(1), 6H8, L1-7E5, L2-15B10, A13a11, A1h5, A4B4(1), A4B4L1FR-S28R, and A4B4-F52S (see U.S. Pat. Nos. 5,824,307 and 6,818,216), rsv6, rsv11, rsv13, rsv19, rsv21, rsv22, rsv23 (see, e.g. U.S. Pat. Nos. 5,824,307, 6,685,942 and 6,818,216), a human anti-RSV antibody, such as, but not limited to, rsv6, rsv11, rsv13, rsv19 (i.e. Fab 19), rsv21, rsv22, rsv23, RF-1, RF-2 (see, e.g. U.S. Pat. Nos. 6,685,942 and 5,811,524), a humanized antibody derived from an anti-RSV mouse monoclonal antibody such as, but not limited to, MAbs 1153, 1142, 1200, 1214, 1237, 1129, 1121, 1107, 1112, 1269, 1269, 1243 (Beeler et al. (1989) *J. Virology* 63(7):2841-2950), MAb151 (Mufson et al. (1987) *J. Clin. Microbiol.* 25:1635-1539), MAbs 43-1 and 13-1 (Fernie et al. (1982) *Proc. Soc. Exp. Biol. Med.* 171:266-271), MAbs 1436C, 1302A, 1308F, and 1331H (Anderson et al. (1984) *J. Clin. Microbiol.* 19:934-936), or antigen-binding fragments thereof. Additional exemplary antibodies or antigen-binding fragments thereof that can be used in a pharmaceutical composition containing an anti-RSV antibody or antigen-binding fragment thereof provided herein include, but are not limited to, anti-RSV antibodies or antigen-binding fragments thereof described in, for example, U.S. Pat. Nos. 6,413,771, 5,840,298, 5,811, 524, 6,656,467, 6,537,809, 7,364,742, 7,070,786, 5,955,364, 7,488,477, 6,818,216, 5,824,307, 7,364,737, 6,685,942, and 5,762,905 and U.S. Patent Pub. Nos. 2007-0082002, 2005-0175986, 2004-0234528, 2006-0198840, 2009-0110684, 2006-0159695, 2006-0013824, 2005-0288491, 2005-0019758, 2008-0226630, 2009-0137003, and 2009-0092609.

2. Articles of Manufacture/Kits

Pharmaceutical compositions of anti-RSV antibodies or nucleic acids encoding anti-RSV antibodies, or a derivative or a biologically active portion thereof can be packaged as articles of manufacture containing packaging material, a pharmaceutical composition which is effective for prophylaxis (i.e. vaccination, passive immunization) and/or treating the RSV-mediated disease or disorder, and a label that indicates that the antibody or nucleic acid molecule is to be used for vaccination and/or treating the disease or disorder. The pharmaceutical compositions can be packaged in unit dosage forms contain an amount of the pharmaceutical composition for a single dose or multiple doses. The packaged compositions can contain a lyophilized powder of the pharmaceutical compositions containing the anti-RSV antibodies or antigen-binding fragments thereof provided, which can be reconstituted (e.g. with water or saline) prior to administration.

The articles of manufacture provided herein contain packaging materials. Packaging materials for use in packaging pharmaceutical products are well known to those of skill in the art. Examples of pharmaceutical packaging materials include, but are not limited to, blister packs, bottles, tubes, inhalers, inhalers (e.g., pressurized metered dose inhalers (MDI), dry powder inhalers (DPI), nebulizers (e.g., jet or ultrasonic nebulizers) and other single breath liquid systems), pumps, bags, vials, containers, syringes, bottles, and any packaging material suitable for a selected formulation and intended mode of administration and treatment. The pharmaceutical composition also can be incorporated in, applied to or coated on a barrier or other protective device that is used for contraception from infection.

The anti-RSV antibodies or antigen-binding fragments thereof, nucleic acid molecules encoding the antibodies thereof, pharmaceutical compositions or combinations provided herein also can be provided as kits. Kits can optionally include one or more components such as instructions for use, devices and additional reagents (e.g., sterilized water or saline solutions for dilution of the compositions and/or reconstitution of lyophilized protein), and components, such as tubes, containers and syringes for practice of the methods. Exemplary kits can include the anti-RSV antibodies or antigen-binding fragments thereof provided herein, and can optionally include instructions for use, a device for administering the anti-RSV antibodies or antigen-binding fragments thereof to a subject, a device for detecting the anti-RSV antibodies or antigen-binding fragments thereof in a subject, a device for detecting the anti-RSV antibodies or antigen-binding fragments thereof in samples obtained from a subject, and a device for administering an additional therapeutic agent to a subject.

The kit can, optionally, include instructions. Instructions typically include a tangible expression describing the anti-RSV antibodies or antigen-binding fragments thereof and, optionally, other components included in the kit, and methods for administration, including methods for determining the proper state of the subject, the proper dosage amount, dosing regimens, and the proper administration method for administering the anti-RSV antibodies or antigen-binding fragments thereof. Instructions also can include guidance for monitoring the subject over the duration of the treatment time Kits also can include a pharmaceutical composition described herein and an item for diagnosis. For example, such kits can include an item for measuring the concentration, amount or activity of the selected anti-RSV antibody or antigen-binding fragment thereof in a subject.

In some examples, the anti-RSV antibody or antigen-binding fragment thereof is provided in a diagnostic kit for the detection of RSV in an isolated biological sample (e.g., a fluid sample, such as blood, sputum, lavage, lung intubation sample, saliva, urine or lymph obtained from a subject). In some examples, the diagnostic kit contains a panel of one or more anti-RSV antibodies or antigen-binding fragments thereof and/or one or more control antibodies (i.e. non-RSV binding antibodies), where one or more antibodies in the panel is an anti-RSV antibody or antigen-binding fragment provided herein.

Kits provided herein also can include a device for administering the anti-RSV antibodies or antigen-binding fragments thereof to a subject. Any of a variety of devices known in the art for administering medications to a subject can be included in the kits provided herein. Exemplary devices include, but are not limited to, an inhaler (e.g., pressurized metered dose inhaler (MDI), dry powder inhaler (DPI), nebulizer (e.g., jet or ultrasonic nebulizers) and other single breath liquid system), a hypodermic needle, an intravenous needle, a catheter, and a liquid dispenser such as an eye-dropper. Typically the device for administering the anti-RSV antibodies or antigen-binding fragments thereof of the kit will be compatible with the desired method of administration of the anti-RSV antibodies or antigen-binding fragments thereof. For example, an anti-RSV antibody or antigen-binding fragment thereof to be delivered by pulmonary administration can be included in a kit with or contained in an inhaler or a nebulizer.

3. Combinations

Provided are combinations of the anti-RSV antibodies or antigen-binding fragments thereof provided herein and a second agent, such as a second anti-RSV antibody or antigen-binding fragment thereof or other therapeutic or diagnostic agent. A combination can include any anti-RSV antibody or antigen-binding fragment thereof or reagent for effecting therapy thereof in accord with the methods provided herein. For example, a combination can include any anti-RSV antibody or antigen-binding fragment thereof and an antiviral agent. Combinations also can include an anti-RSV antibody or antigen-binding fragment thereof provided herein with one or more additional therapeutic antibodies. Combinations of the anti-RSV antibodies or antigen-binding fragments thereof provided also can contain pharmaceutical compositions containing the anti-RSV antibodies or antigen-binding fragments thereof or host cells containing nucleic acids encoding the anti-RSV antibodies or antigen-binding fragments thereof as described herein. The combinations provided herein can be formulated as a single composition or in separate compositions.

K. EXAMPLES

The following examples are included for illustrative purposes only and are not intended to limit the scope of the invention.

Example 1: Expression of RSV F Protein

In this example, the RSV fusion protein (F protein) from Respiratory Syncytial Virus strain A2 was expressed and purified by capture on ELISA plates using anti-RSV monoclonal antibody clone 2F7, which recognizes both the F0 and F1 subunits of the fusion glycoprotein. In the first example, recombinant RSV F protein was cloned and expressed in 293F cells. In the second example, native RSV F protein was expressed by infection of HEp-2 cells with RSV A2 strain.

A. Recombinant RSV F Protein

In this example, the gene encoding the RSV F protein from the A2 RSV strain was cloned and expressed. The RSV A2 F gene (SEQ ID NO:21), containing only the extracellular domain was synthesized according to standard DNA synthesis protocols by GeneArt (Burlingame, Calif.). The RSV A2 F gene was engineered to contain a Kozak sequence (nucleotides 7-16 of SEQ ID NO:21), a c-myc sequence (nucleotides 1600-1629 of SEQ ID NO:21), and a 6x-His tag (nucleotides 1645-417 of SEQ ID NO:21). Additionally, NheI (SEQ ID NO:22) and HindIII (SEQ ID NO:23) restriction sites were engineered at the 5' and 3' ends, respectively, to allow cloning into an expression vector. The DNA was digested using standard molecular biology techniques and ligated into the similarly digested mammalian expression vector pcDNA™3.1/myc-His(-) C (SEQ ID NO:24, Invitrogen). The vector containing the RSV A2 F gene was s transformed into electrocompetent XL1-Blue cells (Stratégene). Individual colonies were selected and grown, and the plasmid DNA was purified. The presence of the RSV A2 F gene insert in the isolated vector was verified by DNA sequencing, and one clone containing the insert was used to produce large-scale preparations of DNA (Megaprep kit, Qiagen).

The RSV A2 F protein was expressed in mammalian cells using the FreeStyle™ 293 Expression System (Invitrogen) according to the manufacturer's instructions. Briefly, $3 \times 10^7$ cells were co-transfected with 30 μg of RSV A2 F/pcDNA3.1/myc-His(-) C plasmid DNA and 5 μg pAdVAntage (Promega) and incubated at 37° C. for 72 hrs. Cells were pelleted by centrifugation and 3 mL of cold lysis buffer (300 mM NaCl, 50 mM $NaH_2PO_4$, 1% TRITON® X-100, Complete™ Protease Inhibitor cocktail (Cat. No, sc-29131, Santa Cruz), pH 8) was added to for every $3 \times 10^7$ RSV F-transfected 293-F cells. The mixture was rocked at 4° C. for 30 min followed by centrifugation at 14,000 rpm for 30 min at 4° C. The cleared supernatant was transferred to a fresh tube and frozen at −80° C. until ready for use. Prior to capture on an ELISA plate, the supernatant was thawed, briefly centrifuged and diluted 1:1 v/v with PBS containing 0.8% nonfat dry milk (final concentration of 0.4% nonfat dry milk).

B. Native RSV F Protein

In this example, native RSV F protein from the RSV A2 strain (SEQ ID NO:382) was purified from RSV infected HEp-2 cells as follows. Briefly, HEp-2 cells are seeded in a ten-layer cell culture stacker (Corning 3270) using complete EMEM (ATCC 30-2003; containing 10% FBS, 1% L-glutamine, and 1% pen-Strep) and incubated at 37° C., and 5% $CO_2$. Once the cells reached 80% confluence, the HEp-2 monolayer was infected with the RSV A2 virus (ATCC VR-1540) at an multiplicity of infection (MOI) of 0.01-0.1. The infected cells were cultured for 3-5 days until apparent cell syncytia was observed. The infected cells were washed once with PBS and the cells were harvested by adding 500 mL PBS with 5 mM EDTA to the culture stacker and incubating at 37° C. for 1 hr. Cells were collected into 50 mL conical tubes ($5 \times 10^7$ cells per tube) and pelleted by centrifugation. The cell pellets were washed 2x with PBS and centrifuged at 1200 rpm for 5 minutes. The cell pellets were stored at −20° C. until further processed. Frozen cells were thawed and 3 mL of cold lysis buffer (300 mM NaCl, 50 mM $NaH_2PO_4$, 1% TRITON® X-100, Complete™ Protease Inhibitor cocktail (Cat. No. sc-29131, Santa Cruz), pH 8) was added to each cell pellet. The cells were rocked at 4° C. for 30 min followed by sonication (3 pulses for 10 seconds each at 10% power) and finally centrifuged at 14,000 rpm for 30 min at 4° C. The cleared supernatant was transferred to a fresh tube and frozen at −80° C. until ready for use. Prior to capture on an ELISA plate, the supernatant was thawed, briefly centrifuged and diluted 1:2000.

C. Capture with Anti-RSV mAb

ELISA plates were coated using 50 μL/well of a 1:400 dilution of anti-RSV mAb (Cat. No. NB110-37246, clone 2F7, Novus Biologicals) in PBS. Unbound antibody was removed and the plates were used immediately for ELISA (see Examples 2 and 4). Alternatively, the plates were frozen for up to 2 weeks at −20° C.

Immediately before use, the plates were blocked with 4% nonfat dry milk in 1xPBS for 2 hours at 37° C. The plates were washed twice with PBS containing 0.05% TWEEN®-20 (wash buffer) before addition of the lysate. Capture of the RSV F protein (either recombinant or native) was effected by adding 50 μL of either of the above prepared lysates to each well of the anti-RSV mAb ELISA plate and incubating at 37° C. for 2 hours.

Example 2: Isolation of Anti-RSV Fab Antibodies from EBV-Transformed B Cells In this example, anti-RSV antibodies were isolated from stimulated Epstein Barr virus transformed donor memory B cells, which were screened for binding to RSV F protein followed by in vitro antibody generation. Sections A and B describe two slightly different procedures for generating and cloning of EBV-transformed B cells and screening for binding to the RSV F protein. The differences are as follows: (1) the source of the PMBCs in step 1; (2) isolation of IgG+ B cells in step 2 (depleted of IgM, IgD and IgA expressing cells in section A and additionally depleted of CD3 positive cells in section B); and (3) preparation of irradiated B-cell depleted feeder cells in step 3.a.

A. Generation and Cloning of EBV-Transformed B Cells and Screening for Binding to RSV F Protein (Procedure A)

Peripheral blood mononuclear cells (PBMCs) were obtained from a child care worker who may have been exposed to RSV through contact with children. PBMCs were isolated by density centrifugation over Ficoll Hypaque, according to the manufacturer's instructions 1. CD22+ Isolation and Activation of CD22+ B Cells $3.2\times10^6$ CD22+ B cells were isolated from donor PBMCs using CD22 magnetic beads (Miltenyi, cat.#130-046-401) and LS columns (Miltenyi, cat.#130-042-401). Isolated CD22+ B cells were cultured at $1\times10^6$ cells per well in a 48 well plate in RPMI (Hyclone, cat.# SH30096.01) containing 10% heat-inactivated low IgG fetal bovine serum (FBS, Invitrogen, cat.#16250-078), 1% antibiotics (Hyclone, cat.# SV30010), 1% sodium pyruvate (Hyclone, cat.# SH30239.01) and 1% L-glutamine (Hyclone, cat.# SH30034.01). The isolated B cells were activated with a selection of polyclonal B cell stimulating agents to induce proliferation and antibody production.

2. EBV-Mediated Immortalization of IgG+ B Cells $4.5\times10^6$ activated CD22+ B cells were washed and incubated with 40 μL of FITC-conjugated anti-IgM (BD Biosciences, cat.#555782), 40 μL of FITC-conjugated anti-IgD (BD Biosciences, cat.#555778) and 4 μL of FITC-conjugated anti-IgA (Jacksons Immunoresearch, cat. 309-096-043) antibodies for 15 minutes at 4° C. Cells were washed 1× in PBS (containing 0.5% BSA and 2 mM EDTA) and resuspended in 90 uL of the same buffer. IgG+ B cells were enriched by negative selection of IgM, IgD, IgA expressing cells using 10 μL anti-FITC magnetic beads (Miltenyi, cat.#130-048-701) and LS columns (Miltenyi, cat.#130-042-401) according to the manufacturer's instructions.

Bulk immortalization of B cells was performed by incubating $1.87\times10^6$ IgG+, CD22+ enriched B cells with 0.5 ml EBV supernatant (50% v/v in RMPI-1640 with 10% FCS, ATCC Cat. No. VR-1492 from B95-8 cells) for 16 hours. After infection the cells were washed and cultured ($10^6$/mL in each of two wells in RPMI (Hyclone, cat.# SH30096.01) containing 10% heat-inactivated low IgG fetal bovine serum (Invitrogen, cat.#16250-078), 1% antibiotics (Hyclone, cat.# SV30010), 1% sodium pyruvate (Hyclone, cat.# SH30239.01) and 1% L-glutamine (Hyclone, cat.# SH30034.01), 200 IU/ml rhIL-2 (R&D Systems #202-IL-50) with $0.5\times10^6$ irradiated feeder cells per well of a 24 well plate for a further 9 days.

3. B Cell Cloning a. Preparation of Irradiated B-Cell Depleted Feeder Cells for Cloning of B Cells Irradiated B-cell depleted feeder cells were used to help maintain growth of the EBV-transformed B cells. PBMCs from a mixture of 3 healthy donors were obtained by Ficoll separation, irradiated with 3250 rads (at the UCSD Moore's Cancer Center), and depleted of B cells using anti-CD19 magnetic beads (Miltenyi Biotec. Cat. No. 130-050-301) and LD columns (Miltenyi Biotec, cat.#130-091-509). Briefly, frozen and irradiated PMBCs, obtained from Ficoll separation, were thawed, washed twice and counted. The cells were then centrifuged at 300 g for 10 minutes, and the supernatant was aspirated. The cell pellet was resuspended in 80 μl MACS buffer (PBS with 0.5% BSA and 2 mM EDTA) per every $10^7$ cells and 20 III CD19 MicroBeads (per every $10^7$ cells) was added. Following thorough mixing, the cells were incubated at 4° C. for 15 minutes. The cells were then washed by adding 1-2 mL buffer (per every $10^7$ cells) followed by centrifuging at 300 g for 10 minutes and the supernatant was aspirated. Up to $10^8$ cells were then resuspended in 500 μl buffer. Magnetic separation was effected by placing a LD column (composed of ferromagnetic spheres covered with a plastic coating to allow fast and gentle separation of cells) in the magnetic field of a MACS separator. The LD column was washed with 2 mL buffer and the cell suspension was applied to the top of the column. Non-B cells were collected as they passed through the column after the addition of 2×1 mL buffer.

b. B Cell Cloning

Approximately 20 EBV-transformed B-cells were co-cultured with polyclonal B cell stimulating agents and 50,000 irradiated B-cell depleted feeder cells per well in a 96 well plate and grown for 13 days. A total of 120 96-well plates were generated.

4. Screening of B Cell Supernatant for Binding to RSV F Protein

Supernatants from each well were transferred to a new 96-well plate and the cells were washed 1× in PBS and frozen at −80° C. in 100 μL of RLT buffer (Qiagen, cat.#79216) containing 10 μL/mL 2-mercaptoethanol. The supernatant was used in an ELISA to determine which wells are producing antibodies that are capable of binding to RSV F protein. Briefly, the ELISA was performed as follows: (I) RSV F Protein ELISA plates were prepared as described in Example 1 using 96 well half-area plates with the following modifications: anti-RSV mAb (clone 2F7, mouse ascites fluid, Cat. No. ab43812, Abcam) was used as the capture antibody and the RSV F protein was incubated with the capture antibody overnight at 4° C. (2) 10 μL B cell supernatant from each of 2 wells (a total of 20 μL pooled) was added to a 96 half-well ELISA plate and incubated for 2 h at 37° C. Plasma from a pool of Blood Bank donors (collected and frozen after Ficoll Hypaque separation, diluted 1:1000) was used as a positive control. (3) Plates were washed 4× as above and 50 μL of goat anti-human Fc IgG HRP-conjugated antibody (diluted 1:1000 in PBS with 0.05% TWEEN®20) was added to each well and the plate was incubated at 37° C. for 1 hour. (4) Plates were washed 6× as above and developed using 50 μL of 1:1 v/v TMB: peroxide solution (Pierce, Cat No. 34021) substrate and allowed to develop for 7 minutes. The reaction was immediately halted by the addition of 50 μL 2N $H_2SO_4$ and the absorbance at 450 nm was measured using an ELISA plate reader. Positive binding was indicated by an $OD_{450}$ greater than 0.5 (0.5-0.9 is moderate binding, >1 is strong binding) and a response that was 3-fold above background.

To determine which of the two pooled wells contained anti-RSV antibodies, 20 μL of B cell supernatant (diluted 1:2 v/v with PBS/0.05% TWEEN® 20) from each well was retested individually against captured RSV F protein.

A total of 18 plates (or 1080 wells) were screened for binding to RSV F lysate (as purified in Example 1). Six wells were identified as binders to RSV F lysate. Five of the six wells were reconfirmed by an additional ELISA and used to generate anti-RSV antibodies by PCR (described below).

B. Generation and Cloning of EBV-Transformed B Cells and Screening for Binding to RSV F Protein (Procedure B)

Peripheral blood mononuclear cells (PMBCs) were obtained from a San Diego Blood Bank donor. PBMCs were isolated by density centrifugation over Ficoll Hypaque, according to the manufacturer's instructions.

1. CD22+ Isolation and Activation of CD22+ B Cells $10.5 \times 10^6$ CD22+ B cells were isolated from donor PBMCs using CD22 magnetic beads and the isolated CD22+ B cells were cultured and activated in 24 well plates, as described in Section A.1. above.

2. EBV-Mediated Immortalization of IgG+ B Cells a. Isolation of IgG+ B Cells $11.3 \times 10^6$ activated CD22+ B cells were washed and incubated with 110 μL of biotin-conjugated anti-IgM (BD Biosciences, cat. #555781), 22 μL of biotin-conjugated anti-IgD (BD Biosciences, cat. #555777) and 22 μL of biotin-conjugated anti-IgA (Invitrogen, cat. #62-7440) and 220 μL of biotin-conjugated anti-CD3 (BD Bioscience, cat. #555331) antibodies for 15 minutes at 4° C. Cells were washed 1× in PBS (containing 0.5% BSA and 2 mM EDTA) and resuspended in 1.045 mL of the same buffer. IgG+ B cells were enriched by negative selection of IgM, IgD, IgA and CD3 expressing cells using 55 μL anti-biotin magnetic beads (Miltenyi, cat.#130-090-485) and LD columns (Miltenyi, cat.#130-042-901) according to the manufacturer's instructions.

b. Preparation of Irradiated Feeder Cells for Culture of EBV Transformed Cells

Irradiated feeder cells were used to help maintain growth of the EBV-transformed B cells. PBMCs from a mixture of 2-3 healthy donors were obtained and isolated by Ficoll separation, irradiated with 3300 rads (at the UCSD Moore's Cancer Center) and frozen at $5 \times 10^6$ cells per vial in FBS containing 10% dimethylsulfoxide (Sigma cat. # D2650-100), Before use, one vial of cells was thawed and washed 3× with RPMI (Hyclone, cat.# SH30096.01) containing 10% heat-inactivated low IgG fetal bovine serum (Invitrogen, cat. #16250-078), 1% antibiotics (Hyclone, cat. # SV30010), 1% sodium pyruvate (Hyclone, cat.# SH30239.01) and 1% L-glutamine (Hyclone, cat. # SH30034.01). The cells were counted, resuspended at $1 \times 10^6$ cells/ml and plated at $0.25 \times 10^6$ cells per well of a 48 well plate.

c. EBV-Mediated Immortalization

Bulk immortalization of B cells was performed by incubating $0.58 \times 10^6$ IgG+, CD22+ enriched B cells with 0.5 ml EBV supernatant (50% v/v in RMPI-1640 with 10% FCS, ATCC Cat. No. VR-1492 from B95-8 cells) for 16 hours. After infection the cells were washed and cultured ($0.58 \times 10^6$/0.5 mL in one well in RPMI (Hyclone, cat.# SH30096.01) containing 10% heat-inactivated low 12G fetal bovine serum (Invitrogen, cat.#16250-078), 1% antibiotics (Hyclone, cat.# SV30010), 1% sodium pyruvate (Hyclone, cat. # SH30239.01) and 1% L-glutamine (Hyclone, cat.# SH30034.01) with $0.5 \times 10^6$ irradiated feeder cells per well of a 48 well plate. After 48 hours, 200 IU/ml rhIL-2 (R&D Systems, cat. #202-IL-50) was added and the cells were cultured for a further 7 days.

3. B Cell Cloning a. Preparation of Irradiated B-Cell Depleted Feeder Cells for Cloning of B Cells Irradiated B-cell depleted feeder cells were prepared for cloning of B cells. Buffy coats from 5-6 healthy donors were obtained and stored overnight at ambient temperature. The PBMCs were isolated by Ficoll separation, and depleted of B cells using anti-CD19 magnetic beads (Miltenyi Biotec, Cat. No. 130-050-301) and LD columns (Miltenyi Biotec, cat. #130-042-901).

Briefly, frozen PMBCs, obtained from Ficoll separation, were thawed, washed twice and counted. The cells were then centrifuged at 300 g for 10 minutes, and the supernatant was aspirated. The cell pellet was resuspended in 80 μl MACS buffer (PBS with 0.5% BSA and 2 mM EDTA) per every $10^7$ cells and 20 μl CD19 MicroBeads (per every $10^7$ cells) was added. Following thorough mixing, the cells were incubated at 4° C. for 15 minutes. The cells were then washed by adding 1-2 mL buffer (per every $10^7$ cells) followed by centrifuging at 300 g for 10 minutes and the supernatant was aspirated. Up to $10^8$ cells were then resuspended in 500 μl buffer. Magnetic separation was effected by placing a LD column (composed of ferromagnetic spheres covered with a plastic coating to allow fast and gentle separation of cells) in the magnetic field of a MACS separator. The LD column was washed with 2 mL buffer and the cell suspension was applied to the top of the column. Non-B cells were collected as they passed through the column after the addition of 2×1 mL buffer. The cells were centrifuged at 300 g for 10 minutes and resuspended at $5 \times 10^6$ cells/mL in PBS containing 2% low IgG fetal calf serum. The cells were irradiated with 4000 rads (at the UCSD Moore's Cancer Center), centrifuged at 300 g for 6 minutes, resuspended in 90% low IgG FBS and 10% dimethylsulfoxide (DMSO, $25 \times 10^6$ cells/mL) and stored frozen in liquid nitrogen.

Before use, the cells were thawed and washed three times with Iscove's Modified Dulbeccos Medium (IMDM, Hyclone #SH30228.01) containing 10% heat-inactivated low IgG fetal bovine serum (Invitrogen, cat. #16250-078), 1% antibiotics (Hyclone, cat. # SV30010), 1% nonessential amino acids (Hyclone, cat. # SH30238.01) and 1% L-glutamine (Hyclone, cat. # SH30034.01).

b. B Cell Cloning

Approximately 100 EBV-transformed B-cells were co-cultured with polyclonal B cell stimulating agents and 50,000 irradiated B-cell depleted feeder cells per well in a 96 well plate and grown for 13 days in IMDM (Hyclone, cat. # SH30228.01) containing 10% heat-inactivated low IgG fetal bovine serum (Invitrogen, cat. #16250-078), 1% antibiotics (Hyclone, cat. # SV30010), 1% nonessential amino acids (Hyclone, cat. #SH30238.01) and 1% L-glutamine (Hyclone, cat. # SH30034.01). A total of 120 96-well plates were generated.

4. Screening of B Cell Supernatant for Binding to RSV F Protein

Supernatant from each well was screened by ELISA to determine which wells were producing antibodies that are capable of binding to RSV F protein. The ELISA was performed as described in Section A.5. above in 96-well half-area ELISA plates coated with RSV F protein (as described in Example 1). As described above, to determine which of the two pooled wells contained anti-RSV antibodies, 20 μL of B cell supernatant (diluted 1:2 v/v with PBS/0.05% TWEEN® 20) from each well was retested individually against captured RSV F protein.

A total of 120 plates (or 7200 wells) were screened for binding to RSV F lysate (as purified in Example 1). Twenty nine wells were identified as binders to RSV F lysate. Ten of the twenty five wells were reconfirmed by an additional ELISA and used to generate anti-RSV antibodies by PCR (described below).

C. Generation of Anti-RSV Antibodies by PCR

Following initial screening of EBV-transformed B cells for production of antibodies that bind to RSV F protein, genes encoding individual antibodies were amplified from B cell RNA by PCR. Five wells identified as hits from Section A above were selected for cloning. Ten wells identified as hits in Section B above were selected for cloning.

1. RNA Extraction

RNA was extracted from the B cells (for each well corresponding to a positive binder to RSV F protein) using an RNeasy Micro Kit (Qiagen, Cat. No. 1402-2408) according to the manufacturer's instructions with the following modifications: 1) B cells were frozen in 100 μL RLT buffer with β-mercaptoethanol (10 μL per mL buffer); 2) the cells were not homogenized; 3) RNA was precipitated with 70% ethanol (in RNase-free water); and 4) DNase treatment was carried out "in-column" according the manufacturer's supplemental protocol. The RNA was eluted into a final volume of 26 μL.

2. First Strand cDNA Synthesis

Following RNA extraction, cDNA was generated according to the Superscript III (Invitrogen; Cat No. 19090-051) First Strand Synthesis protocol. Briefly, 8 μl RNA (isolated as described above), 1 μl oligo dT primer and 1 μl dNTPs were combined in a sterile 0.2 mL tube and incubated at 65° C. for 5 minutes followed by incubation on ice for 1 minute. Subsequently, 2 μl 0.1 mM DTT, 4 μl 25 mM $MgCl_2$ 2 μl RT buffer, 1 μl RNaseOut, and 1 μl SuperScript III RT were added to the tube, and the reaction mixture was incubated at 50° C. for 50 minutes followed by incubation at 85° C. for 15 minutes. The cDNA was used immediately or frozen at −80° C. for long term storage.

3. Isolation of IgG Heavy Chain and Kappa and Lambda Light Chain Genes by PCR Amplification IgG heavy chains and kappa and lambda light chains were generated by PCR amplification from the B cell first strand cDNA synthesis reaction (see above). The kappa light chain genes were amplified by a single-step PCR, whereas the heavy chain genes and lambda light chain genes were amplified using a two-step, nested PCR approach. The amplified heavy and light chain genes were subsequently linked into a single cassette using "overlap PCR".

Step I. Amplification or IgG Heavy Chain Genes and Lambda Light Chain Genes

In Step I, Heavy Chain A, 2 μL cDNA generated by First Strand Synthesis (see above) was used as a template to individually amplify IgG heavy chains by PCR. In this step, pools of Step I primers were utilized (see Table 3A below). The reaction conditions were as follows:

PCR Step I: Heavy Chain A:

| Reagent | μL |
| --- | --- |
| $H_2O$ | 16 |
| 10x buffer | 2.5 |
| 10x Enhancer buffer | 2.5 |
| dNTP (10 mM each) | 0.75 |
| cDNA | 2.0 |
| VH pool leader (9 μM each) | 0.5 |
| VH Reverse pool (20 μM) | 0.25 |
| Pfx50 | 0.5 |
| | 25 |

Alternatively, in Step I, Heavy Chain B, 2.5 μL cDNA generated by First Strand Synthesis (see above) was used as a template to individually amplify IgG heavy chains by PCR. In this step, the same pool of Step I primers was utilized for the forward primers and VH gamma-1(a/b) reverse was used as the reverse primer (see Table 3A below). The reaction conditions were as follows:

PCR Step I: Heavy Chain B:

| Reagent | μL |
| --- | --- |
| $H_2O$ | 15.5 |
| 10x buffer | 2.5 |
| 10x Enhancer buffer | 2.5 |
| dNTP (10 mM each) | 0.75 |
| cDNA | 2.5 |
| VH pool leader (9 μM each) | 0.5 |
| VH-g1(a/b)-REV (20 μM) | 0.25 |
| Pfx50 | 0.5 |
| | 25 |

In Step I, Lambda Light Chain, 2.5 μL cDNA generated by First Strand Synthesis (see above) was used as a template to individually amplify IgG heavy chains by PCR. In this step, a pool of Step I primers was utilized for the forward primers and pCALCL(T)-R was used as the reverse primer (see Table 3B below). The reaction conditions were as follows:

PCR Step I: Lambda Light Chain:

| Reagent | μL |
| --- | --- |
| $H_2O$ | 16 |
| 10x buffer | 2.5 |
| 10x Enhancer buffer | 2.5 |
| dNTP (10 mM each) | 0.75 |
| cDNA | 2.0 |
| Vλ pool (14.2 μM each) | 0.5 |
| pCALCL(T)-R (20 μM) | 0.25 |
| Pfx50 | 0.5 |
| | 25 |

For the PCR reaction, a touchdown approach was implemented in order to add specificity to the reaction amplification. At each touchdown step, the annealing temperature is decreased by 1° C. every cycle. The PCR thermocycler conditions were as follows.

1) 94° C. for 2 minutes
2) 10 cycles of:
   94° C. for 15 seconds; 62° C. for 20 seconds (Touchdown); 68° C. for 1 minute
3) 25 cycles of:
   94° C. for 15 seconds; 52° C. for 20 seconds; 68° C. for 1 minute
4) 68° C. for 3 minutes
5) 4° C. hold The resultant reaction mixtures were used as template DNA for Step II (see below) without any further purification.

TABLE 3A

Step I Primers for Amplifying IgG Heavy Chain Genes

| | VH Forward Primer Pool: | SEQ ID NO: |
| --- | --- | --- |
| VH1a | GGATCCTCTTCTTGGTGGCAGCAG | 26 |
| VH1b | GCATCCTTTTCTTGGTGGCAGCAC | 27 |
| VH1c | GGGTCTTCTGCTTGCTGGCTGTAG | 28 |

TABLE 3A-continued

Step I Primers for Amplifying IgG Heavy Chain Genes

| | | |
|---|---|---|
| VH1d | GGATCCTCTTCTTGGTGGCAGCAG | 29 |
| VH2a | CTGACCATCCCTTCATGGCTCTTG | 30 |
| VH2b | CTGACCACCCCTTCCTGGGTCTTG | 31 |
| VH3a | GCTATTTTARAAGGTGTCCAGTGT | 32 |
| VH3b | GCTCTTTTAAGAGGTGTCCAGTGT | 33 |
| VH3c | GCTATTTAAAAAGGTGTCCAATGT | 34 |
| VH4a | CTGGTGGCAGCTCCCAGATGGGTC | 35 |
| VH5a | CTCCTGGCTGTTCTCCAAGGAGTC | 36 |

| VH Reverse Primer Pool: | | SEQ ID NO: |
|---|---|---|
| VH-g 1-REV | ACAAGATTTGGGCTCAACTTTCTTGTCC | 37 |
| VH-g 2-REV | TTTGCGCTCAACTGTCTTGTCCACCTTG | 38 |
| VH-g 3-REV | TTTGAGCTCAACTCTCTTGTCCACCTTG | 39 |
| VH-g 4-REV | ATATTTGGACTCAACTCTCTTGTCCACC | 40 |

| Reverse Primer: | | SEQ ID NO: |
|---|---|---|
| VH-g1(a/b)-REV | ACAAGATTTGGGCTCAACTYTCTTGTCC | 383 |

TABLE 3B

Step I Primers for Amplifying Lambda Light Chain Genes

| Forward Primer Pool: | | SEQ ID NO: |
|---|---|---|
| 5' L Vλ 1 | GGTCCTGGGCCCAGTCTGTGCTG | 384 |
| 5' L Vλ 2 | GGTCCTGGGCCCAGTCTGCCCTG | 385 |
| 5' L Vλ 3 | GCTCTGTGACCTCCTATGAGCTG | 386 |
| 5' L Vλ 4/5 | GGTCTCTCTCSCAGCYTGTGCTG | 387 |
| 5' L Vλ 6 | GTTCTTGGGCCAATTTTATGCTG | 388 |
| 5' L Vλ 7 | GGTCCAATTCYCAGGCTGTGGTG | 389 |
| 5' L Vλ 8 | GAGTGGATTCTCAGACTGTGGTG | 390 |

| Reverse Primer: | | SEQ ID NO: |
|---|---|---|
| pCALCL(T)-R | CTCCTTATTAATTAATTATGAGCATTC TGYAKGGGCMAYTGTC | 80 |

Step II. Amplification of Heavy and Light Chain Genes

In Step II, the heavy chain and lambda light chain reaction mixtures from Step I were used as templates for second round PCR reactions with pools of forward and reverse primers that amplify from the framework 1 region of each chain to the end of the constant region ($C_H1$ for heavy chain, $C_L$ for light chain).

The heavy chain forward primers (see Table 4) were designed to introduce a SfiI restriction site (SEQ ID NO:41). The reaction conditions were as follows:

PCR II: Heavy Chain

| Reagent | μL |
|---|---|
| H₂O | 12.75 |
| 10x buffer | 2.5 |
| 10X Enhancer | 2.5 |
| dNTP (10 mM each) | 0.75 |
| Step I reaction | 2.5 |
| pCAL24VH-F pool (2 μM) | 2.5 |
| CH1-R Pool-Sfi (20 μM) | 1 |
| Pfx50 | 0.5 |
| | 25 |

The lambda light chain forward primers (see Table 6) were designed to introduce a SfiI restriction site (SEQ ID NO:41). The reaction conditions were as follows:

PCR II: Lambda Light Chain

| Reagent | μL |
|---|---|
| H₂O | 15.5 |
| 10x buffer | 2.5 |
| 10X Enhancer | 2.5 |
| dNTP (10 mM each) | 0.75 |
| Step I reaction | 2.5 |
| Vλ primer pool (2 μM) | 2.5 |
| pCALCL(T)R (20 μM) | 1 |
| Pfx50 | 0.5 |
| | 25 |

The PCR thermocycler conditions for Step II reactions were as follows:
1) 94° C. for 2 minutes
2) 30 cycles of:
   94° C. for 15 seconds; 52° C. for 20 seconds; 68° C. for 1 minute
3) 68° C. for 3 minutes
4) 4° C. hold For amplification of kappa light chain genes, 2 μL cDNA generated by First Strand Synthesis (see above) was used as a template to individually amplify IgG kappa light chains by PCR. The light chain kappa forward primers (see Table 5) were used as primer pools and were designed to introduce a SfiI restriction site (SEQ ID NO:41).

The reaction conditions were as follows:

PCR II: Kappa Light Chain

| Reagent | μL |
|---|---|
| H₂O | 16 |
| 10x buffer | 2.5 |
| 10X Enhancer | 2.5 |
| dNTP (10 mM each) | 0.75 |
| First Strand cDNA | 2 |
| Vκ Primer Pool (9.1 μM) | 0.5 |
| pCALCK(G)L (20 μM) | 0.25 |
| Pfx50 | 0.50 |
| | 25 |

The PCR thermocycler conditions for Step II reactions were as follows:
1) 94° C. fort minutes
2) 35 cycles of:
   94° C. for 15 seconds; 54° C. for 20 seconds: 68° C. for 1 minute
3) 8° C. for 3 minutes
4° C. hold Following amplification, the PCR reaction products were separated on a 1% agarose gel and the band corresponding to the heavy chain (675 bp) and the light chain (650 bp) were purified by gel extraction (Qiagen Gel Extraction Kit; Cat. No. 28706). The PCR products were eluted in 30 μl.

TABLE 4

Primers for Amplifying IgG Heavy Chain Genes

| Forward Primer Pool | | SEQ ID NO: |
|---|---|---|
| pCal30 VH1a | ggctttgctaccgtagcgCAGGCGGCCGCACAGGTKCAGCTGGTGCAG | 42 |
| pCal30 VH1b | ggctttgctaccgtagcgCAGGCGGCCGCACAGGTCCAGCTTGTGCAG | 43 |
| pCal30 VH1c | ggctttgctaccgtagcgCAGGCGGCCGCASAGGTCCAGCTGGTACAG | 44 |
| pCal30 VH1d | ggctttgctaccgtagcgCAGGCGGCCGCACARATGCAGCTGGTGCAG | 45 |
| pCal30 VH2a | ggctttgctaccgtagcgCAGGCGGCCGCACAGATCACCTTGAAGGAG | 46 |
| pCal30 VH3a | ggctttgctaccgtagcgCAGGCGGCCGCAGARGTGCAGCTGGTGGAG | 47 |
| pCal30 VH4a | ggctttgctaccgtagcgCAGGCGGCCGCACAGSTGCAGCTGCAGGAG | 48 |
| pCal30 VH4b | ggctttgctaccgtagcgCAGGCGGCCGCACAGGTGCAGCTACAGCAG | 49 |
| pCal30 VH5a | ggctttgctaccgtagcgCAGGCGGCCGCAGARGTGCAGCTGGTGCAG | 50 |
| pCal30 VH6 | ggctttgctaccgtagcgCAGGCGGCCGCACAGGTACAGCTGCAGCAG | 51 |
| pCal30 VH7 | ggctttgctaccgtagcgCAGGCGGCCGCACAGGTSCAGCTGGTGCAA | 52 |

| Reverse Primer Pool | | SEQ ID NO: |
|---|---|---|
| VHII-g1-Rev | TGCGGCCGGCCTGGCCGACCACAAGATTTGGGCTCAACTTTC | 53 |
| VHII-g2-Rev | TGCGGCCGGCCTGGCCGACCTTTGCGCTCAACTGTCTTGTCC | 54 |
| VHII-g3-Rev | TGCGGCCGGCCTGGCCGACCTTTGAGCTCAACTCTCTTGTCC | 55 |
| VHII-g4-Rev | TGCGGCCGGCCTGGCCGACCATATTTGGACTCAACTCTCTTG | 56 |

TABLE 5

Primers for Amplifying Kappa Light Chain Genes

| Forward Primer Pool | | SEQ ID NO: |
|---|---|---|
| VK1a | AAggcccagccggccatggccgccggtGACATCCAGATGACCCAG | 57 |
| VK1b | AAggcccagccggccatggccgccggtGACATCCAGTTGACCCAG | 58 |
| VK1c | AAggcccagccggccatggccgccggtGCCATCCGGTTGACCCAG | 59 |
| VK2a | AAggcccagccggccatggccgccggtGATATTGTGATGACYCAG | 60 |
| VK3a | AAggcccagccggccatggccgccggtGAAATTGTGTTGACGCAG | 61 |
| VK3b | AAggcccagccggccatggccgccggtGAAATTGTGTTGACACAG | 62 |
| VK3c | AAggcccagccggccatggccgccggtGAAATAGTGATGACGCAG | 63 |
| VK4a | AAggcccagccggccatggccgccggtGACATCGTGATGACCCAG | 64 |
| VK5a | AAggcccagccggccatggccgccggtGAAACGACACTCACGCAG | 65 |
| VK6a | AAggcccagccggccatggccgccggtGAAATTGTGCTGACTCAG | 66 |
| VK6b | AAggcccagccggccatggccgccggtGATGTTGTGATGACACAG | 67 |

| Reverse Primer | | SEQ ID NO: |
|---|---|---|
| pCALCK (G) L | CTCCTTATTAATTAATTAGCACTCTCCCCTGTTGAAGCTCTTTG | 68 |

TABLE 6

Primers for Amplifying Lambda Light Chain Genes

| Forward Primer Pool | | SEQ ID NO: |
|---|---|---|
| VL1-F | AAGGCCCAGCCGGCCATGGCCGCCGGTGTTCAGTCTGTGCTGACKCAGCC | 69 |
| VL2-F | AAGGCCCAGCCGGCCATGGCCGCCGGTGTTCAGTCTGCCCTGACTCAGCC | 70 |
| VL3A-F | AAGGCCCAGCCGGCCATGGCCGCCGGTGTTTCCTATGAGCTGACWCAGCY | 71 |
| VL3B-F | AAGGCCCAGCCGGCCATGGCCGCCGGTGTTTCTTCTGAGCTGACTCAGGAC | 72 |
| VL3C-F | AAGGCCCAGCCGGCCATGGCCGCCGGTGTTTCCTATGWGCTGACTCAGCC | 73 |
| VL4A-F | AAGGCCCAGCCGGCCATGGCCGCCGGTGTTCTGCCTGTGCTGACTCAGCCC | 74 |
| VL4B-F | AAGGCCCAGCCGGCCATGGCCGCCGGTGTTCAGCYTGTGCTGACTCAATCR | 75 |
| VL5/9-F | AAGGCCCAGCCGGCCATGGCCGCCGGTGTTCAGSCTGTGCTGACTCAGCCR | 76 |
| VL6-F | AAGGCCCAGCCGGCCATGGCCGCCGGTGTTAATTTTATGCTGACTCAGCCC | 77 |
| VL7/8-F | AAGGCCCAGCCGGCCATGGCCGCCGGTGTTCAGRCTGTGGTGACTCAGGAG | 78 |
| VL10-F | AAGGCCCAGCCGGCCATGGCCGCCGGTGTTCAGGCAGGGCTGACTCAGCCA | 79 |
| Reverse Primer | | SEQ ID NO: |
| pCALCL(T)-R | CTCCTTATTAATTAATTATGAGCATTCTGYAKGGGCMAYTGTC | 80 |

Step III. Overlap PCR

In Step III, the heavy chain and light chain DNA segments generated in Step II were 1) linked in an overlap reaction with a Fab linker (see Table 7, below) that anneals to the 3' end of the light chain and the 5' end of the heavy chain and 2) amplified with a SE forward and reverse primers (see Table 7, below), thereby allowing amplification of a 1200 base pair (bp) antibody fragment containing the light chain-linker-heavy chain.

The Fab Kappa Linker was amplified from the 2gI2/pCAL vector (SEQ ID NO:81) using either the FabLinker-Rev or the FabLinker-Rev-IT* primers (see Table 7 below). The PCR reaction conditions for the formation of the Fab Kappa Linker were as follows:

Fab Kappa Linker

| Reagent | μL |
|---|---|
| H₂O | 19.75 |
| 10x buffer | 2.5 |
| dNTP (10 mM each) | 0.75 |
| 2g12/pCAL Vector (10 ng) | 1 |
| FabLinkerCK-Fwd (20 μM) | 0.25 |
| Reverse Primer (20 μM) | 0.25 |
| Pfx50 | 0.5 |
| | 25 |

The Fab Lambda Linker was amplified from the 28d11/pCAL vector (SEQ ID NO:1636). The PCR reaction conditions for the formation of the Fab Kappa Linker were as follows:

Fab Lambda Linker

| Reagent | μL |
|---|---|
| H₂O | 35.5 |
| 10x buffer | 5 |
| 10x enhancer | 5 |
| dNTP (10 mM each) | 1.5 |
| 28d11/pCAL Vector (10 ng) | 1 |
| FabLinkerCλ-Fwd (20 μM) | 0.5 |
| FabLinker-Rev IT* (20 μM) | 0.5 |
| Pfx50 | 0.5 |
| | 25 |

The PCR thermocycler conditions for the formation of the Fab Linkers were as follows:

1) 94° C. for 2 minutes 2) 30 cycles of:

94° C. for 15 seconds; 54° C. for 20 seconds; 68° C. for 1 minute 3) 68° C. for 3 minutes 4) 4° C. hold The PCR reaction was run on a 1% agarose gel and the 120 bp linker was gel extracted according to the Qiagen Gel Extraction protocol. 2 μl of the purified linker was used for each overlap reaction.

The PCR reaction conditions for Overlap were as follows (the Sfi F/R Primers are added to the PCR reaction after the first 15 cycles):

PCR III: Overlap

| Reagent | μL |
|---|---|
| H₂O | 24.5 |
| 10x buffer | 5 |
| 10X Enhancer | 5 |
| dNTP (10 mM each) | 1.5 |
| Light Chain product | 5 |
| Heavy Chain product | 5 |
| Linker | 2 |

-continued

| Reagent | μL |
|---|---|
| Sfi F/R Primers (20 μM) | 1 |
| Pfx50 | 1 |
| | 50 |

The PCR thermocycler conditions were as follows:
1) 94° C. for 2 minutes
2) 15 cycles of:
94° C. for 15 seconds: 68° C. for 1 minute;
Add Sfi F/R Primers (1 μL), then:
3) 94° C. for 2 minutes
4) 30 cycles of:
94° C. for 15 seconds; 60° C. for 20 seconds; 68° C. for 2 minutes
5) 68° C. for 3 minutes
6) 4° C. hold Following amplification, 10 μl of the total 50 μl PCR overlap reaction product light chain-linker-heavy chain was separated on a 1% agarose gel to determine the size and the remaining 40 μl of the PCR product was purified by the Qiagen PCR Purification Kit (Qiagen; Cat. No. 28106) into 30 μl total volume. Briefly, 5 times the PCR reaction volume of PBI buffer is added PCR product. The mix was bound to QIA Spin column and washed twice with PE buffer. The sample was eluted in 30 μl and spun for 1.5 minutes at top speed to elute all 30 μl. About 1 μg of overlap product was the typical yield per 50 μl overlap reaction.

TABLE 7

Step III Oligonucleotides

| Oligonucleotide | | SEQ ID NO: |
|---|---|---|
| FabLinkerCK-Fwd | GAGCTTCAACAGGGGAGAGTGCTAATT AATTAATAAGGAG | 82 |
| FabLinker-Rev | TGCGGCCGCCTGCGCTACGGTAGCAAAG GCCACCAGTGCCAC | 83 |
| FabLinkerCλ-Fwd | GACARTKGCCCMTRCAGAATGCTCATA ATTAATTAATAAGGAGGATATAATTATG AAAAAG | 392 |
| FabLinker-Rev-IT* | TGCGGCCGCCTACGCTACGGTAGCAAAG CCAGCCAGTGCCAC | 393 |
| Sfi Forward | TCGCggcccagccggccatggc | 84 |
| Sfi Reverse | TGCGGCCGGCCTGGCCGA | 85 |

Step IV. Digestion with Sfi and Cloning into Either the pCAL or pCAL IT* Expression Vector Following overlap PCR reaction and purification of the PCR product, the reaction product was digested with SfiI. To the 30 μl eluate (see above), the following was added for the digestion:

| 4 μl | Reaction buffer 2 (New England Biolabs) |
|---|---|
| 0.4 μl | BSA |
| 1.6 μl | SfiI enzyme (New England Biolabs) |
| 4 μl | H2O |
| 40 μl | Total Volume |

The reaction is incubated for 1 hour at 37° C. Following digestion, the digested overlap product was separated on a 1% agarose gel and the band corresponding to the antibody (~1.45 kB) was purified by gel extraction (Qiagen, Gel Extraction Purification Kit Cat. No. 28706). Briefly, the gel slice was digested with 500 μl of buffer QC (Qiagen). 150 μl of isopropanol was added to digest and the sample was applied to the QiaSpin column. The column was washed twice with buffer PE (Qiagen) and the sample is eluted in 30 μl of EB buffer (Qiagen). About 15 ng/μl of digested sample is recovered from approximately 1 μg of PCR overlap product.

Finally, the digested overlap product was ligated into the pCAL (SEQ ID NO:86) or the pCAL IT* (SEQ ID NO:394) bacterial expression vector. The ligation reaction conditions were as follows:

| 25 ng | SfiI digested pCAL or pCAL IT* vector |
|---|---|
| 25 ng | digested overlap product |
| 2 μl | T4 Ligase reaction buffer |
| 1 μl | T4 Ligase (NEB Cat. No. MC202L, 400,000 Units/ml) |
| adjusted to 20 μl | total volume with H2O |

The sample was ligated for 1 hour at room temperature. 1 μl of the ligation was diluted in 4 μl of H₂O before proceeding to transformation.

Step V. Transformation into E. coli

Following ligation, the ligation product was transformed into DH5α Max Efficiency cells (Invitrogen; Cat No. 18258; Genotype: F– φ80lacZΔM15 Δ(lacZY A-argF) U169 recA1 endA1 hsdR17 (rk–, mk+) phoA supE44 λ– thi-1 gyrA96 relA1). In short, 1 μl ligation product (1/5 dilution) was added to 50 μl DH5α and incubated on ice for 30 minutes. Transformation was effected by heat shock at 42° C. for 45 seconds followed by 2 minutes on ice. 0.9 mL SOC medium was added and the cells were allowed to recover at 37° C. for 1 hour with shaking. Cells were plated on LB plates supplemented with carbenicillin (100 μg/mL) and 20 mM glucose. The plates were incubated overnight at 37° C.

Step VI. Selection of Individual Colonies.

For each antibody amplification, a total of 88 individual colonies were selected and grown in 1 mL Super Broth (SB) supplemented with 1 carbenicillin (100 μg/mL) in a 96-well plate for 2 hours at 37° C. A daughter plate was generated by transferring 500 μl of each culture into another 96-well format bacterial plate with 500 μl of SB supplemented with 40 mM glucose (final 20 mM) and 100 μg/ml of carbenicillin. The original or mother plate was fed 500 μl of SB supplemented with 100 ug/ml carbenicillin. The original plate was grown at 30° C. overnight and the daughter plate (containing glucose) was grown at 37° C. overnight. The cell lysate from the 30° C. plate was used for bacterial ELISAs (see Example 4 below) and the 37° C. plate cultures were used for mini-prep DNA preparations (Qiagen).

Summary

The five wells identified as hits from Section A above were amplified using kappa light chain primers and cloned into the pCAL expression vector. The ten wells identified as hits in Section B above were amplified with kappa light chain primers and cloned into the pCAL IT* expression vector. One well was additionally amplified with lambda light chain primers and cloned into the pCAL IT* expression vector.

Example 3: Isolation of Anti-RSV Fab Antibodies by Single Cell Sorting

In this example, anti-RSV antibodies were isolated from CD19/CD27/IgG positive cells. The CD19/CD27/IgG positive cells were obtained by 1) B cell isolation; and 2) FACS single cell sorting. The sorted cells were then used to isolate RNA which served as a template for the in vitro production of Fab antibodies.

B Cell Isolation

B cells were isolated from PBMCs (harvested from an anonymous blood bank donor) using a B Cell Isolation Kit (Miltenyi Biotec, Cat. No. 130-091-151). The kit is used to isolate highly pure B cells by magnetic labeling and depletion of CD2, CD14, CD16, CD36, CD43, and CD235a-expressing cells (activated B cells, plasma cells and CD5$^+$ B-1a cells) and non-B cells (e.g., T cells, NK cells, dendritic cells, macrophages, granulocytes, and erythroid cells). According to the manufacturer's protocol, non-B cells were indirectly magnetically labeled by using a cocktail of biotin-conjugated monoclonal antibodies as a primary labeling reagent (Biotin-Antibody Cocktail) and anti-biotin monoclonal antibody conjugated to microbeads as a secondary labeling reagent (Anti-Biotin MicroBeads). The non-B cells were then removed from the pure resting B cells by magnetic separation.

Briefly, frozen PMBCs, obtained from Ficoll separation, were thawed, washed twice and counted. The cells were then centrifuged at 300 g for 10 minutes, and the supernatant was aspirated. The cell pellet was resuspended in 40 μl MACS buffer (per every $10^7$ cells) and 10 μl Biotin-Antibody Cocktail (per every $10^7$ cells) was added. Following thorough mixing, the cells were incubated at 4° C. for 10 minutes. After the incubation period, 30 μl buffer (per every $10^7$ cells) and 20 μl Anti-Biotin MicroBeads (per every $10^7$ cells) was added. Following thorough mixing, the cells were incubated at 4° C. for 15 minutes. The cells were then washed by adding 1-2 mL buffer (per every $10^7$ cells) followed by centrifuging at 300 g for 10 minutes and the supernatant was aspirated. Up to $10^8$ cells were then resuspended in 500 μl buffer.

Magnetic separation was effected by placing a LS column (composed of ferromagnetic spheres covered with a plastic coating to allow fast and gentle separation of cells) in the magnetic field of a MACS separator. The LS column was washed with 3 mL buffer and the cell suspension was applied to the top of the column. Unlabeled B cells were collected as they passed through the column after the addition of 3×3 mL buffer.

Single Cell Sorting

In this example, isolated B cells were sorted by antigen specificity using an FACSAria Flow Cytometer (BD Biosciences). Selected cells were CD19/CD27/IgG positive. RSV-F antigen was labeled with Alexa Fluor 647 following the manufacturer's instructions (Molecular Probes, A-20186).

In short, the isolated B cells were aliquotted into 16 separate tubes. Fourteen tubes received 1×10$^8$ cells and were used to determine the photomultiplier settings and sort parameters on the FACSAria. The remaining 1.8×10$^6$ cells were labeled with Alexa Fluor 647/RSV-F at a final concentration of 20 nM. Labeled protein was added to the sample 15 minutes prior to the addition of antibodies. CD19 and CD27 antibodies were used at dilution of 1:20 while IgG antibody was used at a dilution of 1:50. Following the addition of Alexa Fluor 647/RSV-F protein and antibodies, the tubes were incubated on ice for 30 minutes and subsequently washed twice. Single cell sorting was effected using the FACSAria Flow Cytometer (BD Biosciences). The labels included PE-Cy5 (anti-human CD19), PE-Cy7 (anti-human CD27), PE (goat anti-human IgG Fcg), Pacific Blue (mouse anti-human CD3), FITC (mouse anti-human IgD, mouse anti-human IgM, mouse anti-human IgA and mouse anti-human CD14), propidium iodide and Alexa Fluor 647 (labeled RSV-F protein).

Cell sorting was performed by first excluding dead cells followed by exclusion of CD3 positive cells. CD19 and CD27 positive cells were further identified and within this population, cells were gated for IgG Fcγ expression. Cells expressing IgD, IgM and IgA were excluded from the remaining cells. Finally, CD19/CD27/IgG Fcγ positive cells were sorted for RSV-F binding and each positive B cell was deposited into an individual well of a 96 well plate containing 2 μl cDNA reaction buffer (Superscript III 10× buffer. Invitrogen; Cat No. 19090-051), 0.5 μl RNaseOUT and 7.5 μl sterile water. Plates were stored at −80° C. until further processed.

First Strand cDNA Synthesis

Following sorting, cDNA was generated individually in each well according to the Invitrogen First Strand Synthesis protocol. In short, 0.5 μl 10% NP-40, 1 μl oligo dT primer and 1 μl dNTPs were added to each well and the plate was incubated at 65° C. for 5 minutes followed by incubation on ice for 1 minute. Subsequently, 2 μl DTT, 4 μl MgCl$_2$ and 1 μl SuperScript III RT were added and the reaction mixture was incubated at 50° C. for 1 hour followed by incubation at 85° C. for 5 minutes. The cDNA was used immediately or frozen at −80° C. for long term storage.

IgG Heavy Chain and Kappa Light Chain Amplification

IgG heavy chains and kappa light chains were subsequently generated by four sequential steps of PCR.

Step I. Amplification

In Step I, 2.5 μL cDNA generated by First Strand Synthesis (see above) was used as a template to individually amplify kappa light chains and IgG heavy chains by PCR. In this step, pools of Step I primers were utilized (see Tables 8 and 9 below). The reaction conditions were as follows:

PCR Step I:

| | |
|---|---|
| H$_2$O | 16 |
| 10x buffer | 2.5 |
| 10x Enhancer buffer | 2.5 |
| dNTP (10 mM each) | 0.75 |
| cDNA | 2.5 |
| Step I pool(20 μM each) | 0.25 |
| Reverse Primer (20 μM) | 0.25 |
| Pfx50 | 0.25 |
| | 25 μL |

The PCR thermocycler conditions were as follows:

1) 94° C. for 2:00

2) 10 cycles of:

94° C. for 0:15; 62° C. for 0:20 (TOUCHDOWN); 68° C. for 1:00

3) 40 cycles of

94° C. for 0:15; 52° C. for 0:20; 68° C. for 1:00

4) 68° C. for 3:00

5) 4° C. hold

The reaction mixtures were used as template DNA for Step II (see below) without any further purification.

TABLE 8

Step I Primers for Amplifying Kappa Light Chains

| Forward Primer Pool | | SEQ ID NO: |
|---|---|---|
| 5' LVκ1/2 | ATGAGGSTCCCYGCTCAGCTGCTGG | 87 |
| 5' LVκ3 | CTCTTCCTCCTGCTACTCTGGCTCCCAG | 88 |
| 5' LVκ4 | ATTTCTCTGTTGCTCTGGATCTCTG | 89 |

| Reverse Primer | | SEQ ID NO: |
|---|---|---|
| VK-Rev | GCACTCTCCCCTGTTGAAGCTCTTTG | 90 |

TABLE 9

Step I Primers for Amplifying IgG Heavy Chains

| Forward Primer Pool | | SEQ ID NO: |
|---|---|---|
| 5' L-VH1 | ACAGGTGCCCACTCCCAGGTGCAG | 91 |
| 5' L-VH3 | AAGGTGTCCAGTGTGARGTGCAG | 92 |
| 5' L-VH4/6 | CCCAGATGGGTCCTGTCCCAGGTGCAG | 93 |
| 5' L-VH5 | CAAGGAGTCTGTTCCGAGGTGCAG | 94 |

| Reverse Primer | | SEQ ID NO: |
|---|---|---|
| 3' CγCH1 | GGAAGGTGTGCACGCCGCTGGTC | 95 |

Step II. Amplification

In Step II, the reaction mixtures from Step I were used as templates for second PCR reactions with pools of forward and reverse primers for either the light chain or heavy chain, respectively. These reactions amplified the DNA from the framework 1 region of each chain. The light chain forward primers (see Table 10) were designed to introduce a SfiI restriction site (SEQ ID NO:41). The reaction conditions were as follows:

PCR II: Light Chain

| | |
|---|---|
| H₂O | 15.75 |
| 10x buffer | 2.5 |
| 10X Enhancer | 2.5 |
| dNTP (10 mM each) | 0.75 |
| Step I reaction | 2.5 |
| Vk Primer Pool (9.1 µM) | 0.5 |
| pCALCK(G)L (20 µM) | 0.25 |
| Pfx50 | 0.25 |
| | 25 µL |

The heavy chain forward primers (see Table 11) were designed to introduce a SalI restriction site (SEQ ID NO:96). The reaction conditions were as follows:

PCR II: Heavy Chain

| | |
|---|---|
| H₂O | 14.25 |
| 10x buffer | 2.5 |
| 10X Enhancer | 2.5 |
| dNTP (10 mM each) | 0.75 |
| Step I reaction | 2.5 |
| pCAL24VH-F pool (2 µM) | 2 |
| SalI JH-Rev pool (20 µM) | 0.25 |
| Pfx50 | 0.25 |
| | 25 µL |

The PCR thermocycler conditions were as follows:

1) 94° C. for 2 minutes
2) 50 cycles of:
   94° C. for 15 seconds; 54° C. for 20 seconds; 68° C. for 1 minute
3) 68° C. for 3 minutes
4) 4° C. hold Following amplification, the PCR reaction products were separated on a 1% agarose gel and the band corresponding to the heavy chain (400 bp) and the light chain (650 bp) were purified by gel extraction (Qiagen).

TABLE 10

Primers for Amplifying Kappa Light Chains

| Forward Primer Pool | | SEQ ID NO: |
|---|---|---|
| VK1a | AAggcccagccggccatggccgccggtGACATCCAGATGACCCAG | 57 |
| VK1b | AAggcccagccggccatggccgccggtGACATCCAGTTGACCCAG | 58 |
| VK1c | AAggcccagccggccatggccgccggtGCCATCCGGTTGACCCAG | 59 |
| VK2a | AAggcccagccggccatggccgccggtGATATTGTGATGACYCAG | 60 |
| VK3a | AAggcccagccggccatggccgccggtGAAATTGTGTTGACGCAG | 61 |
| VK3b | AAggcccagccggccatggccgccggtGAAATTGTGTTGACACAG | 62 |
| VK3c | AAggcccagccggccatggccgccggtGAAATAGTGATGACGCAG | 63 |
| VK4a | AAggcccagccggccatggccgccggtGACATCGTGATGACCCAG | 64 |
| VK5a | AAggcccagccggccatggccgccggtGAAACGACACTCACGCAG | 65 |

TABLE 10-continued

Primers for Amplifying Kappa Light Chains

| | | |
|---|---|---|
| VK6a | AAggcccagccggccatggccgccggtGAAATTGTGCTGACTCAG | 66 |
| VK6b | AAggcccagccggccatggccgccggtGATGTTGTGATGACACAG | 67 |

| Reverse Primer | | SEQ ID NO: |
|---|---|---|
| pCALCK (G) L | CTCCTTATTAATTAATTAGCACTCTCCCCTGTTGAAGCTCTTTG | 68 |

TABLE 11

Primers for Amplifying IgG Heavy Chains

| | Forward Primer Pool | SEQ ID NO: |
|---|---|---|
| pCal30 VH1a | ggctttgctaccgtagcgCAGGCGGCCGCACAGGTKCAGCTGGTGCAG | 42 |
| pCal30 VH1b | ggctttgctaccgtagcgCAGGCGGCCGCACAGGTCCAGCTTGTGCAG | 43 |
| pCal30 VH1c | ggctttgctaccgtagcgCAGGCGGCCGCASAGGTCCAGCTGGTACAG | 44 |
| pCal30 VH1d | ggctttgctaccgtagcgCAGGCGGCCGCACARATGCAGCTGGTGCAG | 45 |
| pCal30 VH2a | ggctttgctaccgtagcgCAGGCGGCCGCACAGATCACCTTGAAGGAG | 46 |
| pCal30 VH3a | ggctttgctaccgtagcgCAGGCGGCCGCAGARGTGCAGCTGGTGGAG | 47 |
| pCal30 VH4a | ggctttgctaccgtagcgCAGGCGGCCGCACAGSTGCAGCTGCAGGAG | 48 |
| pCal30 VH4b | ggctttgctaccgtagcgCAGGCGGCCGCACAGGTGCAGCTACAGCAG | 49 |
| pCal30 VH5a | ggctttgctaccgtagcgCAGGCGGCCGCAGARGTGCAGCTGGTGCAG | 50 |
| pCal30 VH6 | ggctttgctaccgtagcgCAGGCGGCCGCACAGGTACAGCTGCAGCAG | 51 |
| pCal30 VH7 | ggctttgctaccgtagcgCAGGCGGCCGCACAGGTSCAGCTGGTGCAA | 52 |

| | Reverse Primer Pool | SEQ ID NO: |
|---|---|---|
| 3' SalIJH 1/2/4/5 | TGCGAAGTCGACGCTGAGGAGACGGTGACCAG | 97 |
| 3' SalIJH3 | TGCGAAGTCGACGCTGAAGAGACGGTGACCATTG | 98 |
| 3' SalIJH6 | TGCGAAGTCGACGCTGAGGAGACGGTGACCGTG | 99 |

Step III. Overlap PCR

In Step III, the heavy chain and light chain DNA segments generated in step II were: 1) linked in an overlap reaction with a Fab linker (see Table 12, below) that anneals to the 3' end of the light chain and the 5' end of the heavy chain and 2) amplified with a Sfi forward primer (see Table 12, below) that anneals to the 5' end of the light chain and JH reverse primers (see Table 11, above) that anneal to the 3' end of the heavy chain, thereby allowing amplification of a 1200 base pair (bp) antibody fragment containing the light chain-linker-heavy chain. The reaction conditions were as follows (the linker was generated as described in Example 2 above):

| | |
|---|---|
| H$_2$O | 24.5 |
| 10x buffer | 5 |
| 10X Enhancer | 5 |
| dNTP (10 mM each) | 1.5 |
| Light Chain | 5 |
| Heavy Chain | 5 |
| Linker | 2 |
| Sfi F/JH-R Primers (20 μM) | 1 |
| Pfx50 | 1 |
| | 50 μL |

The PCR thermocycler conditions were as follows:
Overlap with Linker
1) 94° C. for 2 minutes
2) 15 cycles of:
   94° C. for 15 seconds: 68° C. for 1 minute
Add primers
3) 94° C. for 2 minutes
4) 30 cycles of:
   94° C. for 15 seconds; 60° C. for 20 seconds; 68° C. for 1 minute
5) 68° C. for 3 minutes
6) 4° C. hold Following amplification, the PCR reaction product light chain-linker-heavy chain was separated on a 1% agarose gel and was purified by gel extraction (Qiagen).

Step IV. Introduction of C$_H$1 region

Following overlap, the amplified light chain-linker-heavy chain was digested with Sal I and ligated to a Sal1 digested heavy chain constant region 1 (CHγ1 region) introducing a SfiI restriction site at the 3' end of the heavy chain constant region. The ligation reaction conditions were as follows:

2 μl of Ligation reaction buffer
2 μl of C$_H$1
5 μl of 1.2 kB gel purified product from step III 10 µl of water
1 µl T4 Ligase The ligation reaction mixture was incubated for 30 minutes at room temperature.

Following ligation, the full length Fab was amplified by PCR with SfiI Forward and Reverse primers (see Table 12, below) resulting in a 1.45 kb fragment. The reaction conditions were as follows:

| | |
|---|---|
| H₂O | 31.5 |
| 10x buffer | 5 |
| 10X Enhancer | 5 |
| dNTP (10 mM each) | 1.5 |
| Ligation reaction mixture | 5 |
| Sfi F/R Primers (20 µM) | 1 |
| Pfx50 | 1 |
| | 50 µL |

The PCR thermocycler conditions were as follows:
1) 94° C. for 2 minutes
2) 30 cycles of:
   94° C. for 15 seconds; 60° C. for 20 seconds; 68° C. for 1 minute
3) 68° C. for 3 minutes
4) 4° C. hold The reaction product was a 1.45 kB fragment of a light chain and heavy chain linked together in a single cassette.

TABLE 12

Step III and Step IV Oligonucleotides

| | Oligonucleotide | SEQ ID NO: |
|---|---|---|
| Fab Linker | GAGCTTCAACAGGGGAGAGTGCTAATTAATTAATAAGGAGGat<br>ataattatgaaaaagacagctatcgcgattgcaGTGGCACTGG<br>CTGGCTTTGCTACCGTAGCGCAGGCGGCCGCA | 100 |
| Sfi Forward | TCGCggcccagccggccatggc | 84 |
| Sfi Reverse | TGCGGCCGGCCTGGCCGA | 85 |
| CH1 fragment | gtcgaccaaaggtccgtctgttttcccgctggctccgtcttct<br>aaatctacctctggtggtaccgctgctctgggttgcctggtta<br>aagactacttcccggaaccggttaccgtttcttggaactctgg<br>tgctctgacctctggtgttcacaccttcccggctgttctgcag<br>tcttctggtctgtactctctgtcttctgttgttaccgttccgt<br>cttcttctctgggtacccagacctacatctgcaacgttaacca<br>caaaccgtctaacaccaaagttgacaagaaagttgaaccgaaa<br>tcttgcctgcgatcgcggccaggccggccgcaccatcaccatc<br>accatggcgcatacccgtacgacgttccggactacgcttctac<br>tagt | 101 |

Step V. Digestion with Sfi and Cloning into pCAL Expression Vector

Following overlap PCR reaction and purification of the PCR product, the reaction product was digested with SfiI. To the 30 µl eluate (see above), the following was added for the digestion:

| | |
|---|---|
| 4 µl | Reaction buffer 2 (New England Biolabs) |
| 0.4 µl | BSA |
| 1.6 µl | SfiI enzyme (New England Biolabs) |
| 4 µl | H₂O |
| 40 µl | Total Volume |

The reaction is incubated for 1 hour at 37° C. Following digestion, the digested overlap product was separated on a 1% agarose gel and the band corresponding to the antibody (~1.45 kB) was purified by gel extraction (Qiagen Gel Extraction Purification Kit Cat. No. 28706). Briefly, the gel slice was digested with 500 µl of buffer QC (Qiagen). 150 µl of isopropanol was added to digest and the sample was applied to the QiaSpin column. The column was washed twice with buffer PE (Qiagen) and the sample is eluted in 30 µl of EB buffer (Qiagen). About 15 ng/µl of digested sample is recovered from approximately 1 µg of PCR overlap product.

Finally, the digested overlap product was ligated into a pCAL bacterial expression vector (SEQ ID NO:86). The ligation reaction conditions were as follows:

| | |
|---|---|
| 25 ng | SfiI digested pCAL vector |
| 25 ng | digested overlap product |
| 1 µl | T4 Ligase (NEB Cat. No. MC202L, 400,000 Units/ml) |
| 20 µl | total volume |

The sample was ligated for 1 hour at room temperature. 1 µl of the ligation was diluted in 4 µl of H₂O before proceeding to transformation.

Step VI. Transformation into *E. coli*

Following ligation, the ligation product was transformed into DH5a Max Efficiency cells (Invitrogen; Cat No. 18258; Genotype: F− φ80lacZΔM15 Δ(lacZY A-argF) U169 recA1 endA1 hsdR17 (rk−, mk+) phoA supE44 λ− thi-1 gyrA96 relA1). In short, 1 µl ligation product (1/5 dilution) was added to 50 µl DH5α and incubated on ice for 30 minutes. Transformation was effected by heat shock at 42° C. for 45 seconds followed by 2 minutes on ice. 0.9 mL SOC medium was added and the cells were allowed to recover at 37° C. for 1 hour with shaking. Cells were plated on LB plates supplemented with carbenicillin (100 µg/mL) and 20 mM glucose. The plates were incubated overnight at 37° C.

Step VII. Selection of Individual Colonies.

A total of 88 individual colonies were selected and grown in 1 mL Super Broth (SB) supplemented with 1 carbenicillin (100 µg/mL) in a 96-well plate for 2 hours at 37° C. A daughter plate was generated by transferring 500 µl of each culture into another 96-well format bacterial plate with 500 µl of SB supplemented with 40 mM glucose (final 20 mM) and 100 µg/ml of carbenicillin. The original or mother plate was fed 500 µl of SB supplemented with 100 µg/ml carbenicillin. The original plate was grown at 30° C. overnight and the daughter plate (containing glucose) was grown at 37° C. overnight. The cell lysate from the 30° C. plate was used for bacterial ELISAs (see Example 4 below) and the 37° C. plate cultures were used for mini-prep DNA preparations (Qiagen).

Example 4: Antibody Binding to RSV F Protein

In this example, Fab antibodies generated in Examples 2 and 3 were tested for their ability to bind to purified RSV F1 lysate by ELISA. Briefly, 50 µL bacterial cell lysate diluted 1 volume into 3 volumes total with PBS/3% BSA/0.01% TWEEN®20 was added to a 96-well ELISA plate previously coated with RSV F1 lysate (see Example 1, above). The plate was incubated at 37° C. for 2 hours, or alternatively at 4° C. overnight, followed by washing 4× with wash buffer (PBS/0.05% TWEEN®20). 50 µL goat anti-human IgG F(ab)-HRP antibody (Jackson Labs Cat. No. 109-036-097) diluted 1:1000 in PBS/3% BSA/0.01% TWEEN®20 was added and the plate was incubated at 37° C. for 1 hour. Following washing 6× with wash buffer, 50 µL 1:1 v/v TMB:peroxide solution (Pierce, Cat No. 34021) was added and allowed to develop for 7 minutes. The reaction was immediately halted by the addition of 50 µL 2N H₂SO₄ and the absorbance at 450 nm was measured using an ELISA plate reader. Positive binding was indicated by an $OD_{450}$ greater than 0.5 (0.5-0.9 is moderate binding, >1 is strong binding) and a response that was 3-fold above background.

In addition to binding to RSV F1 lysate, several positive and negative control antigens were also utilized. Plasma from a pool of Blood Bank donors (collected and frozen after Ficoll Hypaque separation, diluted 1:1000) was used as a positive control for RSV F1 lysate binding. As a positive control to determine that each bacterial cell lysate contains an intact Fab, an Affinipure goat anti-human F(ab)2 antibody (1 µg/ml Jackson Immunoresearch Cat. No. 109-006-097) was used to coat a 96-well ELISA plate to capture intact Fab. This antibody binds only to the F(ab) portion of an IgG antibody. Fab expression was then detected by using anti-HA Peroxidase (Roche. Cat. #12013819001; the bacterial expressed Fabs have an HA-tag). Actin (1 µg/ml, Sigma Cat. No. A3653) was used as a negative control for Fab binding to any protein and as a positive control for the ELISA reaction using mouse anti-actin antibody (1.25 µg/ml, Sigma Cat. No. A3853) and goat anti-mouse IgG F(ab)-HRP antibody (Santa Cruz Biotech Cat. No. SC3697). The mouse anti-RSV mAb (clone 2F7, mouse ascites fluid, Cat. No. ab43812. Abcam) was also included as negative control for specificity of binding to the RSV F protein since this antibody was employed to bind RSV F protein to the ELISA plate and thus was present on the ELISA plates during screening of the human anti-RSV antibodies.

A. Binding of Cell Lysates for Fabs Generated from EBV-Transformed B Cells (See Example 2, Sections a and C, Kappa Light Chains, Cloned into pCAL Vector)

Eighty-eight (88) cell lysates generated in Example 2 above were tested by ELISA for their ability to 1) bind to an anti-Fab antibody; and 2) bind RSV F1 lysate. ELISA confirmed that 76 of 88 cell lysates were positive for Fab production while 59 of the 88 cell lysates bound RSV F lysate. Confirmation ELISA revealed that 72 of the 76 cell lysates were indeed producing Fab and 46 of the initial 59 positive hits were reconfirmed as binders to RSV F lysate.

Three of the positive binders were identified by DNA sequencing of the corresponding DNA prep. Sequencing revealed they all had the same sequence, identified as Fab 58c5, which has the following light and heavy chains:

Fab 58c5

```
Light Chain                             (SEQ ID NO: 5)
EIVMTQSPSSLSASIGDPVTITCQASQDISTYLNWYQQKPGQAPRLLIYG

ASNLETGVPSPFTGSGYGTDFSVTISSLQPEDIATYYCQQYQYLPYTFAP

GTKVEIKRTVAAPSVFIFPPSDEQLKSGTASVVCLLNNFYPREAKVQWKV

DNALQSGNSQESVTEQDSKDSTYSLSSTLTLSKADYEKHKVYACEVTHQG

LSSPVTKSFNRGEC

Heavy Chain                             (SEQ ID NO: 1)
QVQLVQSGPGLVKPSQTLALTCNVSGASINSDNYYWTWIRQRPGGGLEWI

GHISYTGNTYYTPSLKSPLSMSLETSQSQFSLRLTSVTAADSAVYFCAAC

GAYVLISNCGWFDSWGQGTQVTVSSASTKGPSVFPLAPSSKSTSGGTAAL

GCLVKDYFPEPVTVSWNSGALTSGVHTFPAVLQSSGLYSLSSVVTVPSSS

LGTQTYICNVNHKPSNTKVDKKVEPKSC
```

B. Binding of Cell Lysates for Fabs Generated from Single Cell Sorting (See Example 3)

The results indicated that 64 of 88 cell lysates generated in Example 3 bound RSV F1 protein. Twenty four positive binders were identified by DNA sequencing of the corresponding DNA prep.

One of the positive binders identified was Fab sc5 which has the following light and heavy chains:

Fab sc5

```
Light Chain                             (SEQ ID NO: 13)
DIQMTQSPSSLSASVGDRVTITCRASQNIKNYLNWYQQKPGKVPKLLIYA

ASTLQSGVPSRFSGSGSGTDFTLTISSLQPEDFATYSCQQSYNNQLTFGG

GTKVEIKRTVAAPSVFIFPPSDEQLKSGTASVVCLLNNFYPREAKVQWKV

DNALQSGNSQESVTEQDSKDSTYSLSSTLTLSKADYEKHKVYACEVTHQG

LSSPVTKSFNRGEC

Heavy Chain                             (SEQ ID NO: 9)
QVQLQESGPGLVKPSGTLSLTCTVSGDSISGSNWWNWVRQPPGKGLEWIG

EIYYRGTTNYKSSLKGRVTMSVDTSKNQFSLKLTSVTAADTAVYYCARGG

RSTFGPDYYYYMDVWGRGTTVTVSSASTKGPSVFPLAPSSKSTSGGTAAL

GCLVKDYFPEPVTVSWNSGALTSGVHTFPAVLQSSGLYSLSSVVTVPSSS

LGTQTYICNVNHKPSNTKVDKKVEPKSC
```

C. Binding of Cell Lysates for Fabs Generated from EBV-Transformed B Cells (See Example 2, Sections B and C, Kappa or Lambda Light Chains, Cloned into pCAL IT* Vector)

For the following experiments, the ELISA assays were performed as described above with the following modifications: Bacterial supernatant expressing 58c5 and sc5 Fab were used as positive controls for binding to RSV F1 lysate (recombinant source) and HEp2 lysate (native RSV F source), respectively, at a 1:3 dilution in PBS containing 3% BSA and 0.01% TWEEN®20.

Fab 30D8

For 30D8, 77 cell lysates generated in Example 2 above were tested by ELISA for their ability to 1) bind to an anti-Fab antibody; and 2) bind RSV F1 lysate. ELISA confirmed that 70 cell lysates were positive for Fab production while 63 of the 77 cell lysates bound RSV F lysate. Confirmation ELISA on 8 clones revealed that 8 of the 8 cell lysates were indeed producing Fab and 6 of the 8 hits tested were reconfirmed as binders to RSV F lysate. Three of the positive binders were sequenced and all contained the same antibody with the following light and heavy chains (30D8):

Light Chain (SEQ ID NO: 395)
QSVLTQASSVSVAPGQTARITCGANNIGSQNVHWYQQKPGQAPVLVVYDD
RDRPSGIPDRFSGSNSGNTATLTISRVEAGDEADYYCQVWDSSRDQAVIF
GGGTKLTVLGQPKAAPSVTLFPPSSEELQANKATLVCLISDFYPGAVTVA
WKADSSPVKAGVETTTPSKQSNNKYAASSYLSLTPEQWKSHRSYSCQVTH
EGSTVEKTIAPTECS Heavy Chain (SEQ ID NO: 396)
EVQLLQSGAELKKPGASVKISCKTSGFTFSGHTIAWVRQAPGQGLEWMGW
VSTNNGNTEYAQKIQGRVTMTMDTSTSTVYMELRSLTSDDTAVYFCAREW
LVMGGFAFDHWGQGTLLTVSSASTKGPSVFPLAPSSKSTSGGTAALGCLV
KDYFPEPVTVSWNSGALTSGVHTFPAVLQSSGLYSLSSVVTVPSSSLGTQ
TYICNVNHKPSNTKVDKRVEPKSC Fab 104E5

For 104E5, 88 cell lysates generated in Example 2 above were tested by ELISA for their ability to 1) bind to an anti-Fab antibody; and 2) bind RSV F1 lysate. ELISA confirmed that 15 cell lysates were positive for Fab production while 4 of the 88 cell lysates bound RSV F lysate. Confirmation ELISA on 24 clones revealed that 10 of the 24 cell lysates were indeed producing Fab and 7 of the 24 hits tested were reconfirmed as binders to RSV F lysate. Two of the positive binders were sequenced and contained the same antibody with the following light and heavy chains (104E5):

Light Chain (SEQ ID NO: 397)
DIQMTQSPSSLPASVGDPVTITCRASQNIKTYLNWYQQKPGRAPKLLISA
VSNLQSGVPSRFSGTGSGTDFTLTISSLQPEDFATYYCQQSFSIPLTEGG
GAKVEIKRTVAAPSVFIFPPSDEQLKSGTASVVCLLNNFYPREAKVQWKV
DNALQSGNSQESVTEQDSKDSTYSLSSTLTLSKADYEKHKLYACEVTHQG
LSSPVTKSFNRGEC Heavy Chain (SEQ ID NO: 398)
QVQLEQSGAEVKKPGSSVKVSCKPSGGTFDTYTISWVRQAPGQRLEWLGR
IIPSLGETNYAHKLQGRVTITADKATSVVYMDLSDLTSEDAAVYYCAERI
TGPVDWVWDYGMDVWGQGTTVSVSSASSKGPSVFPLAPSSKSTSGGTAAL
GCLVKDYFPEPVTVSWNSGALTSGVHTFPAVLQSSGLYSLSSVVTVPSSS
LGTQTYICNVNHKPSNTKVDKRVEPKSC Fab 38F10

For 38F10, 88 cell lysates generated in Example 2 above were tested by ELISA for their ability to 1) bind to an anti-Fab antibody; and 2) bind RSV F1 lysate. ELISA confirmed that 65 cell lysates were positive for Fab production while 40 of the 88 cell lysates bound RSV F lysate. Confirmation ELISA on 16 clones revealed that 13 of the 16 cell lysates were indeed producing Fab and 13 of the 16 positive hits tested were reconfirmed as binders to RSV F lysate. Five of the positive binders were sequenced and all contained the same antibody with the following light and heavy chains (38F10):

Light Chain (SEQ ID NO: 399)
DIQLTQSPPTLSASVGDRVSMTCRASQSISNWLAWYQQKPGKAPKLLIQK
ASNLEDGVPSRFTASGFGTEFTLTISSLQPDDFATYYCQQYNSYSGLSFG
GGTKVDIKRTVAAPSVFIFPPSDEQLKSGTASVVCLLNNFYPREAKVQWK
VDNALQSGNSQESVTEQDSKDSTYSLSSTLTLSKADYEKHKVYACEVTHQ
GLSSPVTKSFNRGEC Heavy Chain (SEQ ID NO: 400)
EVQLLESGGDVVQPGKSLRLSCTASGESITDFGIHWVRQAPGKGLEWVAL
ISYNEVNIHYGESVRGRFTISRDIAKNTVYLQMNGLRPEDTGVYFCARDV
WEDSWLSLACFQEWGQGSLVVVSSASTKGPSVFPLAPSSKSTSGGTAALG
CLVKDYFPEPVTVSWNSGALTSGVHTFPAVLQSSGLYSLSSVVTVPSSSL
GTQTYICNVNHKPSNTKVDKKVEPKSC Fab 14G3

For 14G3, 88 cell lysates generated in Example 2 above were tested by ELISA for their ability to 1) bind to an anti-Fab antibody; and 2) bind RSV F1 lysate. ELISA confirmed that 71 cell lysates were positive for Fab production while 13 of the 88 cell lysates bound RSV F lysate. Confirmation ELISA on 16 clones revealed that 14 of the 16 cell lysates were indeed producing Fab and 5 of the 16 positive hits tested were reconfirmed as binders to RSV F lysate. Four of the positive binders were sequenced and all contained the same antibody with the following light and heavy chains (14G3):

Light Chain (SEQ ID NO: 401)
DVVMTQTPLSLSVTPGEPASISCRSSQSLLDSDDGNTYLDWYLQKPGQSP
QLLIYTLSYRASGVPDRFSGSGSGTDFTLKISRVEADDVGIYYCMQRMEF
PFTFGQGTRLDIKRTVAAPSVFIFPPSDEQLKSGTASVVCLLNNFYPREA
KVQWKVDNALQSGNSQESVTEQDSKDSTYSLSSTLTLSKADYEKHKVYAC
EVTHQGLSSPVTKSFNRGEC Heavy Chain (SEQ ID NO: 402)
QVQLQESGPGLVKPSQTLSLTCTVSGASISSDNHYWSWIRQPPGKGLEWI
ASIYYTGGTNYNPSLKSRLALSIDTSGDQFSLKLSSVTAADTAVYYCVRG
LFFITARPYWYFDLWGRGTLVAVSSASTKGPSVFPLAPSSKSTSGGTAAL
GCLVKDYFPEPVTVSWNSGALTSGVHTFPAVLQSSGLYSLSSVVTVPSSS
LGTQTYICNVNHKPSNTKVDKRVEPKSC Fab 90D3

For 90D3, 88 cell lysates generated in Example 2 above were tested by ELISA for their ability to 1) bind to an anti-Fab antibody; and 2) bind RSV F1 lysate. ELISA confirmed that 80 cell lysates were positive for Fab production while 2 of the 88 cell lysates hound RSV F lysate. Confirmation ELISA on 8 clones revealed that 7 of the 8 cell lysates were indeed producing Fab and 3 of the 8 positive hits tested were reconfirmed as binders to RSV F lysate. Two of the positive binders were sequenced and each contained the same antibody with the following light and heavy chains (90D3):

Light Chain (SEQ ID NO: 403)
AIRLTQSPSSLSASVGDRVSITCRASQSISNFLNWYQQKPGRAPKLLISA

ASSLQGGVPSRFSGSGSGTDFTLTISSLQPEDFATYYCQQTYISLYTFGQ

GTKLEIKRTVAAPSVFIFPPSDEQLKSGTASVVCLLNNFYPREAKVQWKV

DNALQSGNSQESVTEQDSKDSTYSLSSTLTLSKADYEKHKVYACEVTHQG

LSSPVTKSFNRGEC

Heavy Chain (SEQ ID NO: 404)
QVQLVESGGGLVKPGGSLRLSCVGSGFTLKNYEMNWVRQAPGQGLQYISY

ISSSGNVVKYVDSVQGRFTISRDNAGNSLYLQMNNLRAEDTATYYCVRGF

SIDKYDSSVDEYWGQGIAVTVSSASTKGPSVFPLAPSSKSTSGGTAALGC

LVKDYFPEPVTVSWNSGALTSGVHTFPAVLQSSGLYSLSSVVTVPSSSLG

TQTYICNVNHKPSNTKVDKKVEPKSC

D. Additional Anti-RSV Antibodies

Three additional antibodies, Fabs 56E11, 17C9 and 69F6, were isolated as described in Example 2, Sections B and C above, amplified using primers for both kappa or lambda light chains. The sequences of the heavy and light chains are set forth below.

Fab 56E11

Light Chain (SEQ ID NO: 453)
QAVLTQPPSASGSPGQSVTISCTGTSSDVGGYNYVSWYQQHPGKAPRLII

SEVTKRPSGVPGRFSGSKSGNTASLTVSGLQAEDEADYYCSSYAGSRHVV

EGGGTKLTVLGQPKAAPSVTLEPPSSEELQANKATLVCLISDFYPGAVTV

AWKADSSPVKAGVETTTPSKQSNNKYAASSYLSLTPEQWKSHRSYSCQVT

HEGSTVEKTIAPAECS

Heavy Chain (SEQ ID NO: 452)
EVQLQESGPGLVKPSETLSLTCSVSGVSINSNNYFWAWIRQPPGKGLEWI

GNIYYGGSTHYNASLQSRVTISVDTSKSQFSLKLNSVTSADTAVYYCAAS

ESIFWDYYYGLDVWGQGTTVTVSSASTKGPSVFPLAPSSKSTSGGTAALG

CLVKDYFPEPVTVSWNSGALTSGVHTFPAVLQSSGLYSLSSVVTVPSSSL

GTQTYICNVNHKPSNTKVDKKVEPKSC

Fab 17C9

Light Chain (SEQ ID NO: 455)
EIVLTQSPSTLSASVGDRVTITCRASQNINTWLAWYQQKPGKAPKLLIYA

ASFLQSGVPSRFSGSGSGTDFTLTISNLQPEDFATYFCQQANSFPRTFGQ

GTKVEVKRTVAAPSVFIFPPSDEQLKSGTASVVCLLNNFYPREAKVQWKV

DNALQSGNSQESVTEQDSKDSTYSLSSTLTLSKADYEKHKVYACEVTHQG

LSSPVTKSFNRGEC

Heavy Chain (SEQ ID NO: 454)
QVQLQQWGAGLVRPSETLSLTCAVYGDSENDYFWTWIRQTPGKGLEWIGE

ISHSGSTNYSPSLKSRVTISVDTSKNQFSLKLSAVTAADTTVYFCARGVR

SRPPPSYRGSGSPPYYHYGMDVWGQGITVTVSSASTKGPSVFPLAPSSKS

TSGGTAALGCLVKDYFPEPVTVSWNSGALTSGVHTFPAVLQSSGLYSLSS

VVTVPSSSLGTQTYICNVNHKPSNTKVDKRVEPKSC

Fab 69F6

Light Chain (SEQ ID NO: 457)
EIVLTQSPSSLSASVGDRVTISCQASQDISNYLNWYQQKPGKAPRLLIYD

ASYLDTGVPSRFSGSGSGTDETETISSLQPEDFATYYCQQYDDLRGGFTE

GPGTKVDVKRTVAAPSVFIFRPSDEQLKSGTASVVCLLNNEYPREAKVQW

KVDNALQSGNSQESVTEQDSKDSTYSLSSTLTLSKADYEKHKVYACEVTH

QGLSSPVTKSFNRGEC

Heavy Chain (SEQ ID NO: 456)
QMQLVQSGAEVRKPGESLKIACKGSGYSFTSYWIAWVRQMPGKGLEWLGI

IFPNDSDATYSPSFQGQVTMSVDKSISTAYLQWNSLKASDTAVYFCARQY

YLGSFESWGQGTTVTVSSASTKGPSVFPLAPSSKSTSGGTAALGCLVKDY

FPEPVTVSWNSGALTSGVHTFPAVLQSSGLYSLSSVVTVPSSSLGTQTYI

CNVNHKPSNTKVDKKVEPKSC

The antibody domains and CDR regions of the isolated Fabs are provided in Tables 13A-13C below.

TABLE 13A

Antibody domains and VH CDR regions of isolated Fabs

| Ab | Heavy chain | VH domain | VH CDR1 | VH CDR2 | VH CDR3 |
|---|---|---|---|---|---|
| 58c5 | SEQ ID NO: 1 | Amino acids 1-125 of SEQ ID NO: 1 | GASINSDNYYWT (SEQ ID NO: 2) | HISYTGNTYYTPSLKS (SEQ ID NO: 3) | CGAYVLISNCGWFDS (SEQ ID NO: 4) |
| sc5 | SEQ ID NO: 9 | Amino acids 1-125 of SEQ ID NO: 9 | GDSISGSNWWN (SEQ ID NO: 10) | EIYYRGTTNYKSSLKG (SEQ ID NO: 11) | GGRSTFGPDYYYYMDV (SEQ ID NO: 12) |
| 30D8 | SEQ ID NO: 396 | Amino acids 1-121 of SEQ ID NO: 396 | GFTFSGHTIA (SEQ ID NO: 405) | WVSTNNGNTEYAQKIQG (SEQ ID NO: 406) | EWLVMGGFAFDH (SEQ ID NO: 407) |
| 104E5 | SEQ ID NO: 398 | Amino acids 1-125 of SEQ ID NO: 398 | GGTFDTYTIS (SEQ ID NO: 411) | RIIPSLGETNYAHKLQG (SEQ ID NO: 412) | RITGPVDWVWDYGMDV (SEQ ID NO: 413) |

TABLE 13A-continued

Antibody domains and VH CDR regions of isolated Fabs

| Ab | Heavy chain | VH domain | VH CDR1 | VH CDR2 | VH CDR3 |
|---|---|---|---|---|---|
| 38F10 | SEQ ID NO: 400 | Amino acids 1-124 of SEQ ID NO: 400 | GFSITDFGIH (SEQ ID NO: 417) | LISYNEVNIHYGESVRG (SEQ ID NO: 418) | DVWEDSWLSLACFQE (SEQ ID NO: 419) |
| 14G3 | SEQ ID NO: 402 | Amino acids 1-125 of SEQ ID NO: 402 | GASISSDNHYWS (SEQ ID NO: 423) | SIYYTGGTNYNPSLKS (SEQ ID NO: 424) | GLFFITARPYWYFDL (SEQ ID NO: 425) |
| 90D3 | SEQ ID NO: 404 | Amino acids 1-123 of SEQ ID NO: 404 | GFTLKNYEMN (SEQ ID NO: 429) | YISSSGNVVKYVDSVQG (SEQ ID NO: 430) | GFSIDKYDSSVDEY (SEQ ID NO: 431) |
| 56E11 | SEQ ID NO: 452 | Amino acids 1-124 of SEQ ID NO: 452 | GVSINSNNYFWA (SEQ ID NO: 458) | NIYYGGSTHYNASLQS (SEQ ID NO: 459) | SESIFWDYYYGLDV (SEQ ID NO: 460) |
| 17C9 | SEQ ID NO: 454 | Amino acids 1-133 of SEQ ID NO: 454 | GDSFNDYFWT (SEQ ID NO: 464) | EISHSGSTNYSPSLKS (SEQ ID NO: 465) | GVRSRPPPSYRGSGSPPY YHYGMDV (SEQ ID NO: 466) |
| 69F6 | SEQ ID NO: 456 | Amino acids 1-118 of SEQ ID NO: 456 | GYSFTSYWIA (SEQ ID NO: 470) | IIFPNDSDATYSPSFQG (SEQ ID NO: 471) | QYYLGSFES (SEQ ID NO: 472) |

TABLE 13B

Antibody domains and VL CDR regions of isolated Fabs

| Ab | Light chain | VL domain | VL CDR1 | VL CDR2 | VL CDR3 |
|---|---|---|---|---|---|
| 58c5 | SEQ ID NO: 5 | Amino acids 1-107 of SEQ ID NO: 5 | QASQDISTYLN (SEQ ID NO: 6) | GASNLET (SEQ ID NO: 7) | QQYQYLPYT (SEQ ID NO: 8) |
| sc5 | SEQ ID NO: 13 | Amino acids 1-107 of SEQ ID NO: 13 | RASQNIKNYLN (SEQ ID NO: 14) | AASTLQS (SEQ ID NO: 15) | QQSYNNQLT (SEQ ID NO: 16) |
| 30D8 | SEQ ID NO: 395 | Amino acids 1-110 of SEQ ID NO: 395 | GANNIGSQNVH (SEQ ID NO: 408) | DDRDRPS (SEQ ID NO: 409) | QVWDSSRDQAVI (SEQ ID NO: 410) |
| 104E5 | SEQ ID NO: 397 | Amino acids 1-107 of SEQ ID NO: 397 | RASQNIKTYLN (SEQ ID NO: 414) | AVSNLQS (SEQ ID NO: 415) | QQSFSIPLT (SEQ ID NO: 416) |
| 38F10 | SEQ ID NO: 399 | Amino acids 1-108 of SEQ ID NO: 399 | RASQSISNWLA (SEQ ID N0: 420) | KASNLED (SEQ ID NO: 421) | QQYNSYSGLS (SEQ ID NO: 422) |
| 14G3 | SEQ ID NO: 401 | Amino acids 1-113 of SEQ ID NO: 401 | RSSQSLLDSDDGNTYLD (SEQ ID NO: 426) | TLSYRAS (SEQ ID NO: 427) | MQRMEFPFT (SEQ ID NO: 428) |
| 90D3 | Amino acids SEQ ID NO: 403 | Amino acids 1-107 of SEQ ID NO: 403 | RASQSISNFLN (SEQ ID NO: 432) | AASSLQG (SEQ ID NO: 433) | QQTYISLYT (SEQ ID NO: 434) |
| 56E11 | SEQ ID NO: 453 | Amino acids 1-111 of SEQ ID NO: 453 | TGTSSDVGGYNYVS (SEQ ID NO: 461) | EVTKRPS (SEQ ID NO: 462) | SSYAGSRHVV (SEQ ID NO: 463) |
| 17C9 | SEQ ID NO: 455 | Amino acids 1-107 of SEQ ID NO: 455 | RASQNINTWLA (SEQ ID NO: 467) | AASFLQS (SEQ ID NO: 468) | QQANSFPRT (SEQ ID NO: 469) |
| 69F6 | SEQ ID NO: 457 | Amino acids 1-109 of SEQ ID NO: 457 | QASDISNYLN (SEQ ID NO: 473) | DASYLDT (SEQ ID NO: 474) | QQYDDLRGGFT (SEQ ID NO: 475) |

TABLE 13C

Heavy chain CDR1 (Kabat numbering)

| Ab | VH CDR1 | Ab | VH CDR1 |
|---|---|---|---|
| 58C5 | SDNYYWT (SEQ ID NO: 435) | 14G3 | SDNHYWS (SEQ ID NO: 440) |
| sc5 | GSNWWN (SEQ ID NO: 436) | 90D3 | NYEMN (SEQ ID NO: 441) |
| 30D8 | GHTIA (SEQ ID NO: 437) | 56E11 | SNNYFWA (SEQ ID NO: 482) |
| 104E5 | TYTIS (SEQ ID NO: 438) | 17C9 | DYFWT (SEQ ID NO: 483) |
| 38F10 | DFGIH (SEQ ID NO: 439) | 69F6 | SYWIA (SEQ ID NO: 484) |

Example 5: Expression and Purification of Isolated Fabs

In this example, individual Fab antibodies that were determined to bind RSV F lysate by ELISA using cell lysate were subsequently expressed and purified from the bacterial cells using column chromatography.

The DNA encoding each individual Fab antibody was transformed into Top10 cells (Invitrogen) for expression. Each Fab antibody was grown in 2 L SB at 37° C. to an $OD_{600}$ of 0.8. Protein expression was induced by the addition of 1 mM IPTG and allowed to occur overnight at 30° C. Following expression, the bacterial cultures were centrifuged and the cell pellet was resuspended in 10 mL Phosphate Buffered Saline (PBS) With protease inhibitors (Complete Protease Inhibitor Cocktail, Santa Cruz Biotech, Cat. # sc-29131). Lysozyme (0.2 mg) was added to the resuspended cells and the mixture was incubated at room temperature for 15 minutes. The cells were lysed by two freeze/thaw cycles. In short, the resuspended bacterial cells were frozen in an ethanol/dry ice bath followed by thawing in a 37° C. water bath. Once lysed, the bacterial lysate was centrifuged at 18000 rpm and the supernatant was filtered and sterilized by passing through a 0.4 micron filter.

Each individual Fab antibody was then purified by affinity column chromatography. In short, the filtered supernatant was passed slowly over an anti-Fab/Protein A column allowing the Fab protein to bind. Following washing with 50 mL PBS, the bound Fab was eluted with 9 mL of 0.2 M glycine, pH 2.2 and collected in a conical tube containing 1 mL of 2M Tris, thereby neutralizing the eluted protein. The eluted Fab was then dialyzed using a 10K MWCO dialysis cassette (Pierce) against 4 L PBS. The protein was stored at 4° C. overnight and subsequently concentrated to a volume of 1 mL using a 10 kDa Amicon Ultra Filter (Millipore). Binding of each purified Fab antibody to RSV F lysate (recombinant source, Example 1A) and HEp2 lysate (native source, Example 1B) was then reconfirmed by ELISA (see Example 4 above). Additionally, each purified Fab antibody was tested for its ability to neutralize RSV using the assay described in Example 6.

Binding of Fabs 58c5 and Sc5 to RSV F Lysate and Purified RSV F Protein

The binding of antibodies 58C5 and sc5 to either captured RSV F protein from transfected 293 cells (recombinant) or purified RSV F protein from RSV A2 infected Hep2 cells (native) was measured by ELISA. The results indicate that Fab 58C5 and Fab sc5 bind to RSV F protein (recombinant) in a dose dependent manner but only sc5 was able to recognize the purified F protein (native) (see Tables 14-15 below).

TABLE 14

Binding of Fab sc5 and 58c5 to captured RSV F lysate (recombinant)

| Fab [µg/ml] | sc5 | 58c5 |
|---|---|---|
| 2 | 2.963 | 2.9165 |
| 0.4 | 2.827 | 2.9705 |
| 0.08 | 2.151 | 2.518 |
| 0.016 | 0.651 | 1.433 |
| 0.0032 | 0.3205 | 0.5905 |
| 0.00064 | 0.284 | 0.415 |
| 0.000128 | 0.337 | 0.3785 |
| 0.0000256 | 0.22 | 0.2485 |

TABLE 15

Binding of Fab sc5 and 58c5 to purified RSV-F Protein (native)

| Fab [µg/ml] | sc5 | 58c5 |
|---|---|---|
| 2 | 2.623 | 0.417 |
| 0.4 | 2.704 | 0.2665 |
| 0.08 | 2.744 | 0.1505 |
| 0.016 | 2.66 | 0.098 |
| 0.0032 | 1.7685 | 0.0805 |
| 0.00064 | 0.6035 | 0.087 |
| 0.000128 | 0.2325 | 0.1065 |
| 0.0000256 | 0.1445 | 0.13 |

Binding of Fabs 30D8, 104E5, 38F10, 90D3 and 14G3 to RSV F Lysate and Purified RSV F Protein The estimated EC50s for binding of Fabs 30D8, 104E5, 38F10, 90D3 and 14G3 are set forth in Table 16A below, Fabs 30D8 and 14G3 both bind RSV F1 lysate (recombinant) at an EC50 of approximately 5 nM (3.8 nM and 8.2 nM, respectively). Fabs 104E5 and 90D3 bind native RSV strain A2 F protein at an EC50 of approximately 80 pM with Fab 38F10 binding native RSV strain A2 F protein at an EC50 of 177 pM.

TABLE 16A

Estimated EC50 for Fabs 30D8, 104E5, 38F10, 90D3 and 14G3

| Purified Fab | EC50 | Antigen Source |
|---|---|---|
| 30D8 | 3.8 nM | RSV F1 Lysate (recombinant) |
| 104E5 | 80 pM | HEp2 Lysate (native) |
| 38F10 | 177 pM | HEp2 Lysate (native) |
| 90D3 | 72 pM | HEp2 Lysate (native) |
| 14G3 | 8.2 nM | RSV F1 Lysate (recombinant) |

Binding of Fabs 56E11, 17C9 and 69F6 to Purified RSV F Protein

The estimated EC50s for binding of Fabs 56E11, 17C9 and 69F6 are set forth in Table 16B below. Fab 56E11 binds RSV F1 lysate (recombinant) with an EC50 of 545 pM. Fabs 17C9 and 69F6 bind RSV F1 lysate (recombinant) with an EC50 of 136 pM and 135 pM, respectively.

TABLE 16B

Estimated EC50 for Fabs 30D8, 104E5, 38F10, 90D3 and 14G3

| Purified Fab | EC50 | Antigen Source |
| --- | --- | --- |
| 56E11 | 545 pM | RSV F1 Lysate (recombinant) |
| 17C9 | 136 pM | RSV F1 Lysate (recombinant) |
| 69F6 | 135 pM | RSV F1 Lysate (recombinant) |

Example 6: RSV Neutralization Assay

In this example, the anti-RSV antibodies were analyzed for their ability to bind to and neutralize RSV virus in solution as assessed by a plaque reduction assay. In this experiment, the RSV virus and the antibodies were pre-incubated in the absence of target cells. The mixture was then added to the cells and virus infection was measured by a standard plaque reduction assay described herein. The anti-RSV antibodies were analyzed for their ability to neutralize several strains of RSV virus, including RSV A2 (ATCC Cat. No. VR-1540), RSV B-wash (ATCC Cat. No. VR-1580, strain 18537), and RSV B-1 (ATCC Cat. No. 1400).

Vero cells (ATCC, cat no: CCL-81; Manassas, Va.) were employed for host cell infection. Vero cells were grown in DMEM (HyClone, cat no: SH 30285.01) with 10% fetal bovine serum (FBS) (HyClone, cat no: SH30070.03), supplemented with 1% L-Glutamine (HyClone, cat no: SH30034.01) and 1% Penicillin-Streptomycin solution (HyClone, cat no: SV30010). The Vero cells were maintained in a 37° C. incubator with 5% CO2 and passaged twice per week.

On day 1 of the experiment. Vero cells were cultured in 24-well cell culture plates. The cells were plated at a density (approximately $1 \times 10^6$ cells per well) which allows formation of a cell monolayers (>90% confluence) by day 2. On day 2, each antibody was serially diluted in plain Eagle's minimal essential medium (EMEM, ATCC, cat no: 30-2003) (final antibody concentrations tested: 20 µg/ml, 4 µg/ml, 0.8 µg/ml, 0.16 µg/ml, 0.032 µg/ml, and 0.006 µg/ml). The RSV virus was also diluted in plain EMEM to a concentration of $2 \times 10^3$ pfu/ml (100 pfu/50 ul). And, 110 µl of the diluted RSV virus was added to 110 µl of each diluted antibody solution and mixed by pipetting. For the virus control sample, 110 µl of the diluted RSV virus was added to 110 µl plain EMEM. The antibody-virus or virus control mixtures were incubated at 37° C. for 2 hours. Following incubation, the culture media was decanted from the 24-well cell culture plates containing the Vero host cells and 100 µl of the pre-incubated virus-antibody or virus control mixture was then transferred to each well. Each test and control sample was prepared in triplicate. The cells were then incubated at 37° C. for one hour with mixing every 15 min.

Following the incubation period, the culture media containing the virus-antibody or virus control mixture was aspirated and 1 ml of overlay medium was added to each well (overlay medium contained EMEM, 2% FBS, 1% L-glutamine, 0.75% methylcellulose). The 24-well cell culture plates were then incubated at 37° C. (with 5% $CO_2$) for approximately 72 hours. Cell plates were fixed with 10% formalin for 1 hour at room temperature, washed 10 times with ddH$_2$O and blocked with 5% non-fat dry milk (NFDM) in PBS with 0.05% TWEEN® 20) at 37° C. for one hour.

Following incubation, the blocking solution was decanted and 200 µL of mouse anti-RSV antibody (ab10018, Abcam, 1:1000 dilution in 5% NFDM) was added to each well. The plates were incubated at 37° C. for 2 hrs, washed 10 times with ddH$_2$O and 200 µL of goat anti-mouse HRP-conjugated IgG (Pierce, Cat. No. 31432, 1:1000 dilution in 5% NFDM) was added to each well. The plates were incubated at 37° C. for 2 hrs. The plates were washed 10 times with ddH$_2$O and 2004 of TrueBlue™ peroxidase substrate (KPL Cat. No. 50-78-02) was added to each well. The plates were developed for 10 min at room temperature. The plates were washed twice with ddH20 and dried on a paper towel and the number of blue plaques was counted. The ED50 (effective dilution for 50% neutralization) was calculated using Prism (GraphPad). The plaque reduction rate was calculated according to the following formula:

Plaque Reduction Rate(percentile)=(1−average plaque number in each antibody dilution/average plaque number in virus control wells)*100

The data is shown in Tables 17-19 below. Table 17 lists the $ED_{50}$ for each Fab for the various RSV strains. Table 18 lists the plaque counts for the various RSV strains and at the varying concentrations for Fab 58c5. Table 19 lists the plaque reduction rate for Fab 58c5. Table 20 lists the plaque reduction rates for Fabs 56E11, 17C9, 69F6 and 30D8 for RSV A2. The results indicate Fabs 58c5 and 30D8 are capable of neutralizing all three strains of RSV while Fab sc5 neutralizes only RSV A2 and RSV B-1, albeit at much higher antibody concentrations. Based on the data obtained in the neutralization assay and the molecular weight of the Fab fragment (approximately 50 kDa), the $ED_{50}$ of Fab 58c5 for in vitro neutralization of RSV A2 is approximately 320 pM whereas the $ED_{50}$ of Fab 30D8 for in vitro neutralization of RSV A2 is approximately 3-times lower (107 pM). Fab 30D8 is more effective against RSV B-1 and RSV B/wash than Fab 58c5.

TABLE 17

Fab Neutralization $ED_{50}$ Data

| Antigen | RSV A2 | RSV B-1 | RSV B/wash |
| --- | --- | --- | --- |
| 58c5 | 320 pM (0.016 µg/mL) | 840 pM (0.042 µg/mL) | 500 pM (0.025 µg/mL) |
| sc5 | 0.016 µM (0.8 µg/mL) | 0.042 µM (2.1 µg/mL) | >0.2 µM (>10 µg/mL) |
| 30D8 | 107 pM (5.35 ng/mL) | 51 pM (2.55 ng/mL) | 112 pM (5.6 ng/mL) |
| 104E5 | 580 pM (29 ng/mL) | ND | ND |
| 38F10 | 800 pM (40 ng/mL) | ND | ND |
| 14G3 | 3400 pM (172 ng/mL) | ND | ND |
| 90D3 | 800 pM (40 ng/mL) | 560 pM (28 mg/mL) | 660 pM (33 ng/mL) |
| 56E11 | 930 pM (46.5 ng/mL) | ND | ND |
| 17C9 | 352 pM (17.6 ng/mL) | ND | ND |
| 69F6 | 260 pM (13 ng/mL) | ND | ND |

ND = Not Determined

TABLE 18

Average Plaque Count for Neutralization with Fab 58c5

| Antigen | 10 µg/ml | 2 µg/ml | 0.4 µg/ml | 0.08 µg/ml | 0.016 µg/ml | 0.003 µg/ml | 0 µg/ml |
|---|---|---|---|---|---|---|---|
| RSV A2 | 0 | 0 | 0 | 5.7 | 28.7 | 52.3 | 57.7 |
| RSV B/wash | 1.3 | 0.7 | 0 | 5 | 16.3 | 23.3 | 26.3 |
| RSV B-1 | 0.3 | 0 | 0 | 4.7 | 8.7 | 11.7 | 12.3 |

TABLE 19

Plaque reduction rate (%) for Neutralization with Fab 58c5

| Antigen | 10 µg/ml | 2 µg/ml | 0.4 µg/ml | 0.08 µg/ml | 0.016 µg/ml | 0.003 µg/ml | 0 µg/ml |
|---|---|---|---|---|---|---|---|
| RSV A2 | 100 | 100 | 100 | 90 | 50 | 9.4 | 0 |
| RSV B/wash | 95 | 97 | 100 | 81 | 38 | 11 | 0 |
| RSV B-1 | 97.6 | 100 | 100 | 62 | 29 | 5 | 0 |

TABLE 20

Plaque reduction rate (%) for Neutralization with Fabs 56E11, 17C9 and 69F6 for RSV A2

| Antibody | 10 µg/ml | 2 µg/ml | 0.4 µg/ml | 0.08 µg/ml | 0.016 µg/ml | 0.0032 µg/ml | 0.00064 µg/ml |
|---|---|---|---|---|---|---|---|
| 56E11 | 100 | 100 | 98.5 | 65.98 | 20.8 | 0 | — |
| 17C9 | 100 | 100 | 99.9 | 91.2 | 46.7 | 3.4 | — |
| 69F6 | 99.7 | 99.8 | 99.6 | 97.5 | 63.0 | 2.3 | — |
| 30D8 | 100 | 100 | 100 | 96.1 | 60.7 | 31.5 | 0.8 |

*30D8 was used as a positive control

Example 7: Cloning and Expression of IgG

In this example, Fab antibodies that showed potential to neutralize RSV were converted into IgGs by cloning into the pCALM mammalian expression vector (SEQ ID NO:102). Primers specific to each antibody were generated and the heavy and light chains of each Fab as originally cloned into the pCAL vector (see Example 2) were amplified by PCR. Light chain amplification resulted in a 650 bp fragment and heavy chain amplification resulted in a 400 bp fragment. Additionally, a linker was generated that allowed overlap of the heavy chain and the light chain. The linker also included a standard heavy chain constant region. Overlap of the heavy and light chains resulted in a 2.1 kB cassette for each antibody that had SfiI restriction sites (SEQ ID NO:41) at both ends. Each cassette was digested with SfiI and cloned into the pCALM vector. After confirmation of the correct sequence in bacteria, DNA for mammalian transfections was isolated using a Maxi Prep Kit (Qiagen).

To express each IgG, each pCALM vector was used to infect about 200 million 293F cells resulting in about 200 micrograms of IgG. The 293F cells were transfected with 293fectin (Invitrogen, Cat. No. 51-0031) and allowed to produce IgG for 72 hours. After 72 hours post transfection, the cell media was harvested, centrifuged to remove the cells, and filter sterilized through a 0.4 micron filter unit. Purification was effected by column chromatography using a Protein A column. The filtered media, containing the expressed IgG, was passed twice through a Protein A column. Following washing with 50 mL of PBS, IgG was eluted with 9 mL of 0.2 M glycine at pH 2.2 and collected in 2 M Tris to effect neutralization. The elute was dialyzed against 4 liters of PBS using a 10 kDa dialysis cassette (Pierce). The sample was concentrated down to 1 mL with a 10 kDa Amicon Ultra (Millipore).

Example 8: IgG Binding Assays

In this example, the IgG forms of 58c5, 30D8, 104E5, 38F10, 14G3, 56E11, 17C9 and 69F6, generated in Example 7 above, and anti-RSV antibody Motavizumab (Wu et al. (2007) *J. Mol. Biol.* 368(3):652-665) were tested for their ability to bind to RSV F protein (recombinant) or RSV F protein (native) lysate by ELISA (see Example 4 above). The estimated EC50s for binding (determined by titrating each IgG) are set forth in Table 21 below. The IgG form of 30D8 has the highest affinity with the IgG forms of 58c5, 104E, 38F10, 56E11, 17C9 and 69F6 having about 10-fold less affinity. Additionally, the IgG form of 30D8 has an affinity for RSV strain A2 F protein about 10-fold greater than motavizumab.

TABLE 21

IgG Binding to RSV F Protein

| Antigen | IgG $EC_{50}$ (estimated) | Antigen Source |
|---|---|---|
| IgG form of 58c5 | 24 pM | RSV F1 Lysate (recombinant) |
| IgG form of 30D8 | 2.5 pM | RSV F1 Lysate (recombinant) |
| IgG form of 104E5 | 14.5 pM | HEp2 Lysate (native) |
| IgG form of 38F10 | 35 pM | HEp2 Lysate (native) |
| IgG form of 14G3 | 251 pM | RSV F1 Lysate (recombinant) |
| IgG form of 56E11 | 73 pM | RSV F1 Lysate (recombinant) |
| IgG form of 17C9 | 59 pM | HEp2 Lysate (native) |
| IgG form of 69F6 | 63 pM | RSV F1 Lysate (recombinant) |
| Motavizumab | 27 pM | HEp2 Lysate (native) |

Example 9: IgG RSV Neutralization Assays

In this example the IgG forms of 58c5, 30D8, 104E5, 38F10, 14G3, 56E11, 17C9 and 69F6, generated in Example 7 above, and anti-RSV antibody Motavizumab (Wu et al. (2007) *J. Mol. Biol.* 368(3):652-665) were tested for their ability to neutralize various strains of RSV. Additionally, the IgG form of 58c5 was analyzed for its ability to neutralize various monoclonal antibody resistant RSV escape mutants (MARMs). A MARM is a mutant RSV strain that is no longer capable of being neutralized by the antibody that it was generated against. Therefore, the ability of 58c5 to neutralize a specific MARM indicates that the binding epitope of 58c5 is different from that of the antibody to which the MARM was generated.

A. Neutralization of RSV

The IgG forms of 58c5, 30D8, 104E5, 38F10, 14G3, 56E11, 17C9 and 69F6 were tested for their ability to neutralize RSV (as described in Example 6 above). The data is shown in Tables 22-24 below. Table 22 lists the $ED_{50}$ (effective dilution for 50% neutralization) for each RSV strain. Table 23 lists the plaque counts for the various RSV strains and at varying antibody concentrations of the IgG form of 58c5. Table 24 lists the plaque reduction rate for the various RSV strains and at varying antibody concentrations of IgG 58c5. The results indicate the IgG forms of 58c5, 30D8, 104E5, 38F10, 14G3, 90D3, 56E11 and 17C9 are capable of neutralizing all 3 strains of RSV, albeit at varying concentrations. The IgG form of 69F6 is selective for the RSV strain A2. Based on the data obtained in the neutralization assay and the molecular weight of the IgG fragment (approximately 150 kDa), the $ED_{50}$ of the IgG form of 58c5 for in vitro neutralization of RSV A2 is approximately 133 pM. The $ED_{50}$s for the IgG forms of 30D8 and 14G3 for in vitro neutralization of RSV A2 are 89 pM and 106 pM, respectively.

Comparison of the neutralization activity of the IgG form of 30D8 and anti-RSV antibody motavizumab (Wu et al (2007) *J. Mol. Biol.* 368(3):652-665) for the three strains of RSV indicates IgG 30D8 is a more potent neutralizing antibody. For RSV strain A2, the IgG form of 30D8 shows 4-fold improvement in neutralization (89 pM versus 360 pM). The IgG form of 30D8 is 15-fold better at neutralizing RSV strain B-1 than motavizumab. For RSV strain B/wash, the IgG form of 30D8 shows a 25-fold increase in neutralization (115 pM versus 2.9 nM). The IgG form of 30D8 was additionally shown to neutralize both the Long and B/9320 strains of RSV.

(1998)), contains the amino acid mutation isoleucine 266 to methionine. MARM 151, generated against murine mAb 151, contains the amino acid mutation lysine 272 to asparagine. MARM 1129, generated against the murine mAb 1129 which is the parental antibody to palivizumab (SYNAGIS), contains the amino acid mutation serine 275 to phenylalanine.

The IgG form of 58c5 was also tested for its ability to neutralize several RSV Monoclonal Antibody Resistant Mutants (MARMs). The data is shown in Tables 25-26 below. Table 25 lists the plaque counts for neutralization against the various MARMs at varying antibody concentrations. Table 26 lists the plaque reduction rate for neutralization against the various MARMs at varying antibody concentrations. The results indicate the IgG form of 58c5 is capable of neutralizing all 3 RSV MARMS. Thus, the IgG

TABLE 22

IgG Neutralization Data ($ED_{50}$)

| Antigen | RSV A2 | RSV B-1 | RSV B/wash | RSV Long | RSV B/9320 |
|---|---|---|---|---|---|
| IgG form of 58c5 | 133 pM (0.02 µg/mL) | 280 pM (0.042 µg/mL) | 193 pM (0.029 µg/mL) | ND | ND |
| IgG form of 30D8 | 89 pM (13.3 ng/mL) | 55 pM (8.3 ng/mL) | 115 pM (17.2 ng/mL) | 95 pM | 85 pM |
| IgG form of 104E5 | 800 pM (122 ng/mL) | 1.7 nM (253 ng/mL) | 8 nM (1.2 µg/mL) | ND | ND |
| IgG form of 38F10 | 553 pM (83 ng/mL) | 1.4 nM (212 ng/mL) | 5.3 nM (789 ng/mL) | ND | ND |
| IgG form of 14G3 | 106 pM (16 ng/mL) | 10.7 nM (1.6 µg/mL) | 4.5 nM (683 ng/mL) | ND | ND |
| IgG form of 90D3 | 1.8 nM (263 ng/mL) | 1.4 nM (211 ng/mL) | 1.4 nM (207 ng/mL) | ND | ND |
| IgG form of 56E11 | 853 pM | 295 pM | 282 pM | ND | ND |
| IgG form of 17C9 | 363 pM | 329 pM | 860 pM | ND | ND |
| IgG form of 69F6 | 225 pM | >67 nM | >67 nM | ND | ND |
| Motavizumab | 360 pM | 833 pM | 2.9 nM | ND | ND |

TABLE 23

Average Plaque Count for Neutralization with the IgG form of 58c5

| Antigen | 10 µg/ml | 2 µg/ml | 0.4 µg/ml | 0.08 µg/ml | 0.016 µg/ml | 0.003 µg/ml | 0 µg/ml |
|---|---|---|---|---|---|---|---|
| RSV A2 | 0.3 | 0 | 0.7 | 16.3 | 31 | 40.3 | 57.7 |
| RSV B/wash | 0 | 0 | 1.3 | 7.7 | 16.3 | 20.7 | 26.3 |
| RSV B-1 | 0 | 0 | 0.3 | 4 | 9.3 | 11.7 | 12.3 |

TABLE 24

Plaque reduction rate (%) for Neutralization with the IgG form of 58c5

| Antigen | 10 µg/ml | 2 µg/ml | 0.4 µg/ml | 0.08 µg/ml | 0.016 µg/ml | 0.003 µg/ml | 0 µg/ml |
|---|---|---|---|---|---|---|---|
| RSV A2 | 99.5 | 100 | 99 | 72 | 46 | 30 | 0 |
| RSV B/wash | 100 | 100 | 95 | 71 | 38 | 21 | 0 |
| RSV B-1 | 100 | 100 | 97.6 | 67.5 | 24 | 5 | 0 |

B. Neutralization of RSV Monoclonal Antibody Resistant RSV Escape Mutants

The IgG form of 58c5 was also tested for its ability to neutralize several monoclonal antibody resistant RSV escape mutants (provided by Dr. James Crowe, Vanderbilt University), as described in Example 6 above. The MARMS, listed in Table 23 below, were derived from RSV wild-type strain A2. MARM 19, generated against human Fab 19 (see, e.g., Crowe et al., Virology, 252:373-375 form of 58c5 binds a different epitope of RSV strain A2 than Fab 19, murine mAb 1129 and murine mAb 151.

TABLE 25

Average Plaque Count for Neutralization of IgG form of 58c5 versus RSV MARMS

| MARM | 10 µg/ml | 2 µg/ml | 0.4 µg/ml | 0.08 µg/ml | 0.016 µg/ml | 0.003 µg/ml | 0 µg/ml |
|---|---|---|---|---|---|---|---|
| MARM 19 | 0.7 | 16.7 | 72 | 89.3 | 135 | 143 | 156 |
| MARM 151 | 0 | 15.3 | 64.7 | 112 | 128 | 151 | 151 |
| MARM 1129 | 0 | 0 | 2.3 | 5.7 | 11.7 | 17.7 | 22.3 |

TABLE 26

Plaque reduction rate for Neutralization of IgG form of 58c5 versus RSV MARMS

| MARM | 10 µg/ml | 2 µg/ml | 0.4 µg/ml | 0.08 µg/ml | 0.016 µg/ml | 0.003 µg/ml | 0 µg/ml |
|---|---|---|---|---|---|---|---|
| MARM 19 | 100 | 89 | 53.8 | 42.7 | 14 | 8 | 0 |
| MARM 151 | 100 | 90 | 57 | 26 | 15 | 0 | 0 |
| MARM 1129 | 100 | 100 | 90 | 74 | 47 | 21 | 0 |

Example 10: Competition Assays

In this example, competition assays were performed in which Fabs 58c5, 30D8, 56E11, 17C9 and 69F6 were tested for their ability to compete against Motavizumab IgG (Wu et al. (2007) *J. Mol. Biol.* 368(3):652-665) for binding to the RSV F protein. Fabs 58c5 and 30D8 were additionally tested for their ability to compete against the IgG forms of 17C9 and 69F6 for binding to recombinant RSV F protein. Fabs 56E11, 17C9 and 69F6 were additionally tested for their ability to compete against the IgG forms of 58c5 and 30D8 for binding to recombinant RSV F protein. As positive controls for competition, the IgG forms of the various antibodies were tested for their ability to compete against the respective Fab forms of the same antibodies.

Briefly, ELISA plates were prepared as described in Example 1 above, with either recombinant or native RSV strain A2 F protein. The plates were blocked with 4% nonfat dry milk in 1×PBS for 2 hours at 37° C. followed by washing 4× with wash buffer (PBS/0.05% TWEEN®20). Fabs were titrated in PBS/3% BSA/0.01% TWEEN®20 from 9 µg/mL to 0.0001 µg/mL (actual concentrations tested: 9, 3, 1, 0.3, 0.1, 0.03, 0.01, 0.003, 0.001, 0.0003, 0.0001 µg/mL). The IgG forms of the tested antibodies and Motavizumab were added at fixed concentrations of either 0.5 µg/mL, 0.1 µg/mL, 0.05 µg/mL and 0.01 µg/mL (as indicated in Table 27 below). 50 µL each of diluted Fab and fixed concentration of IgG was added simultaneously to each well of a plate, in duplicate, as indicated in Table 27 below, and the plates were incubated at 37° C. for 2 hours followed by washing 4× with wash buffer. Goat anti-human IgG Fc-gamma HRP (Jackson ImmunoResearch, Cat. No. 109-035-098, diluted 1:1000, was added and the plates were incubated at 37° C. for 1 hour. Following washing 6× with wash buffer, 50 µL 1:1 v/v TMB:peroxide solution (Pierce, Cat No. 34021) was added and allowed to develop for 7 minutes. The reaction was immediately halted by the addition of 50 µL 2N $H_2SO_4$ and the absorbance at 450 nm was measured using an ELISA plate reader.

TABLE 27

| Competition Assays | | |
|---|---|---|
| | Antigen | |
| | Recombinant F protein | Native F protein |
| Fab 30D8 | 0.05 µg/mL | 0.5 µg/mL |
| (9 to 0.0001 µg/mL) | IgG form of 30D8 | IgG form of 30D8 |
| | 0.05 µg/mL | 0.05 µg/mL |
| | IgG form of 58c5 | IgG form of 58c5 |
| | 0.1 µg/mL | 0.01 µg/mL |
| | motavizumab IgG | motavizumab IgG |
| Fab 58c5 | 0.5 µg/mL | 0.5 µg/mL |
| (9 to 0.0001 µg/mL) | IgG form of 30D8 | IgG form of 30D8 |
| | 0.05 µg/mL | 0.05 µg/mL |
| | IgG form of 58c5 | IgG form of 58c5 |
| | 0.1 µg/mL | 0.01 µg/mL |
| | motavizumab IgG | motavizumab IgG |

The results are summarized in Table 28 below. Fabs 58C5, 30D3, 56E11, 17C9 and 69F6 do not compete for binding to RSV strain A2 F protein with Motavizumab. Fab 30D8 did not compete for binding with any of the tested antibodies. Fab 58C5 competed with the IgG form of 69F6 for binding to RSV F protein. Fabs 56E11 and 69F6 both competed with the IgG form of 58c5 for binding to the RSV F protein. Antibodies 58C5, 69F6 and 56E11 share common epitope binding sites on the RSV fusion protein.

TABLE 28

| Summary of Competition Assays | | | | | |
|---|---|---|---|---|---|
| | 58C5 Fab | 30D8 Fab | 56E11 Fab | 17C9 Fab | 69F6 Fab |
| Motavizumab IgG | NO | NO | NO | NO | NO |
| IgG form of 58C5 | YES | NO | YES | NO | YES |
| IgG form of 30D8 | NO | YES | NO | NO | NO |
| IgG form of 56E11 | YES | NO | ND | ND | ND |
| IgG form of 17C9 | NO | NO | ND | YES | ND |
| IgG form of 69F6 | YES | NO | ND | ND | YES |

ND: Not Determined

Example 11: RSV MARM Generation and Neutralization Assays

In this example, monoclonal antibody resistant RSV escape mutants (MARMs) were generated for Motavizumab and the IgG form of 58C5. For the IgG form of 30D8, 12 rounds of selection were performed and no escape mutants were identified. Motavizumab, the IgG forms of 58C5 and 30D8 and Fabs 56E11, 17C9 and 69F6 were further analyzed for their ability to neutralize the newly generated MARMs.

A. MARM Generation

1. Motavizumab

The concentration of motavizumab IgG that reduces RSV viral titers by 3 logs (corresponding to 99.9% inhibition of RSV A2 virus by neutralization assay) was previously determined to be 3.2 µg/mL. RSV A2 viral particles ($2\times10^6$) were preincubated with dilutions of motavizumab IgG and this mixture was used to infect Vero cell monolayers (as described in Example 6 above). Wells with the highest antibody concentrations still demonstrating cytotoxic effects were selected for additional rounds of selection. After 10 rounds of selection, plaques from virus grown in the presence of 8 µg/mL motavizumab were obtained. Virus particles from these plaques were tested in neutralization assays (as described in Example 6 above) and RNA from positive particles was prepared using a RNeasy extraction kit (Qiagen). Six escape mutants were selected and the F gene was amplified by PCR. The DNA was sequenced and all six clones encoded a single amino acid substitution of glutamic acid for lysine at position 272 (K272E, SEQ ID NO:486) compared to the parental RSV A2 strain (set forth in SEQ ID NO:485).

Table 29 below sets forth the highest antibody concentration demonstrating cytopathic effects (CPE) for each round of selection. As shown in Table 29 below, motavizumab escape mutants were identified after 7 rounds of selection, as identified by an antibody concentration demonstrating CPE greater than the concentration of motavizumab that corresponds to 99.9% inhibition of RSV A2 virus as determined by neutralization assay (i.e., >3.2 µg/mL).

TABLE 29

| Motavizumab MARM Selection | |
|---|---|
| Selection Round | Antibody Concentration (µg/mL) |
| 1 | 0.5 |
| 2 | 0.5 |
| 3 | 0.75 |
| 4 | 1 |
| 5 | 2 |

TABLE 29-continued

Motavizumab MARM Selection

| Selection Round | Antibody Concentration (µg/mL) |
|---|---|
| 6 | 3 |
| 7 | 4 |
| 8 | 8 |
| 9 | 8 |
| 10 | 8 |

2. 58C5

The concentration of the IgG form of 58C5 that reduces RSV viral titers by 3 logs (corresponding to 99.9% inhibition of RSV A2 virus by neutralization assay) was determined to be 0.8 µg/mL. RSV A2 viral particles ($2 \times 10^6$) were preincubated with dilutions of the IgG form of 58C5 and this mixture was used to infect Vero cell monolayers (as described in Example 6 above). Wells with the highest antibody concentrations still demonstrating cytotoxic effects were selected for additional rounds of selection. After 12 rounds of selection, plaques from virus grown in the presence of 2 µg/mL of the IgG form of 58C5 were obtained. Virus particles from these plaques were tested in neutralization assays (as described in Example 6 above) and RNA from positive particles was prepared using a RNeasy extraction kit (Qiagen). Five escape mutants were selected and the F gene was amplified by PCR. The DNA was sequenced and all five clones encoded three amino acid substitutions (N63K, M115K and E295G; SEQ ID NO:487) compared to the parental RSV A2 strain (set forth in SEQ ID NO:485).

Table 30 below sets forth the highest antibody concentration demonstrating cytopathic effects (CPE) for each round of selection. As shown in Table 30 below, 58C5 escape mutants were identified after 10 rounds of selection, as identified by an antibody concentration demonstrating CPE greater than the concentration of the IgG form of 58C5 that corresponds to 99.9% inhibition of RSV A2 virus as determined by neutralization assay (i.e., >0.8 µg/mL).

TABLE 30

58C5 MARM Selection

| Selection Round | Antibody Concentration (µg/mL) |
|---|---|
| 1 | 0.2 |
| 2 | 0.2 |
| 3 | 0.3 |
| 4 | 0.4 |
| 5 | 0.6 |
| 6 | 0.6 |
| 7 | 0.6 |
| 8 | 0.6 |
| 9 | 0.6 |
| 10 | 1.2 |
| 11 | 1.6 |
| 12 | 2 |

3. 30D8

The concentration of the IgG form of 30D8 that reduces RSV viral titers by 3 logs was determined to be 1 µg/mL. RSV A2 viral particles ($2 \times 10^6$) were preincubated with dilutions of the IgG form of 30D8 and this mixture was used to infect Vero cell monolayers (generated as described in Example 6 above). Wells with the highest antibody concentrations still demonstrating cytotoxic effects were selected for additional rounds of selection. After 12 rounds of selection, no 30D8 escape mutants were identified, as shown in Table 31 below.

TABLE 31

30D8 MARM Selection

| Selection Round | Antibody Concentration (µg/mL) |
|---|---|
| 1 | 0.2 |
| 2 | 0.2 |
| 3 | 0.3 |
| 4 | 0.4 |
| 5 | 0.4 |
| 6 | 0.4 |
| 7 | 0.4 |
| 8 | 0.4 |
| 9 | 0.4 |
| 10 | 0.4 |
| 11 | 0.4 |
| 12 | 0.4 |

B. Neutralization Assays

Motavizumab, the IgG forms of 58C5 and 30D8 and Fabs 56E11, 17C9 and 69F6 were tested for their ability to neutralize the RSV A2 parental virus strain, the motavizumab MARM and the 58C5 MARM. The neutralization assay procedure is described in Example 6 above. The data is shown in Tables 32-35 below. Table 32 lists the plaque reduction rate for neutralization against the RSV A2 parental virus. Table 33 lists the plaque reduction rate for neutralization against the Motavizumab MARM. Table 34 lists the plaque reduction rate for neutralization against the 58c5 MARM. Table 35 is a summary of the neutralization data ($ED_{50}$ values).

The results indicate all antibodies are capable of neutralizing the parental RSV A2 strain, with the IgG forms of 58c5 and 30D8 showing the strongest activity (see Tables 32 and 35). All of the tested antibodies strongly neutralize the Motavizumab MARM with no difference compared to the parental strain (see Tables 33 and 35). As expected, motavizumab cannot neutralize the motavizumab MARM at any of the tested concentrations. Motavizumab, the IgG form of 30D8 and Fab 17C9 strongly neutralize the 58C5 MARM with no difference in neutralization potency (see Tables 34 and 35). As expected, the IgG form of 58c5 cannot neutralize the 58c5 MARM at any of the tested concentrations. The results show that the IgG forms of 58c5 and 30D8 and Fabs 56E11, 17C9 and 69F6 all neutralized the motavizumab MARM indicating no competition. Thus, the epitopes of 58c5, 30D8, 56E11, 17C9 and 69F6 do not overlap with that of motavizumab, as no competition was observed (see Table 28 above) and all antibodies neutralized the motavizumab MARM.

Fab 69F6 competed with the IgG form of 58c5 for binding to the RSV F protein (see Table 28 above) but still neutralized the 58c5 MARM, albeit with a slightly higher $ED_{50}$ than that for neutralization of the parental A2 strain (353 pM versus 256 pM). In contrast, Fab 56E11 competed for binding to the RSV F protein with the IgG form of 58c5 (see Table 28 above) but did not neutralize the 58c5 MARM at any of the tested concentrations. Thus, the 56E11 epitope overlaps with 58c5 as a competition between the two antibodies is observed and 56E11 Fab was unable to neutralize 58C5 MARM. Antibodies 69F6 and 17C9 neutralized the 58c5 MARM indicating that their epitopes are not overlapping with that of antibody 58c5. However, competition was observed between 58c5 and 69F6 (see Table 28), but because 69F6 neutralized the 58c5 MARM, the observed competition is more than likely due to steric hindrance.

TABLE 32

Plaque reduction rate for Neutralization of RSV A2 parental virus

| Antibody | 10000 ng/ml | 2000 ng/ml | 400 ng/ml | 80 ng/ml | 16 ng/ml | 3.2 ng/ml |
|---|---|---|---|---|---|---|
| Motavizumab | 100.0 | 98.87 | 82.27 | 50.40 | 19.25 | 0.40 |
| IgG form of 58C5 | 100.0 | 100.0 | 99.6 | 87.0 | 49.2 | 6.1 |
| IgG form of 30D8 | 100.0 | 100.0 | 96.2 | 81.0 | 58.2 | 11.9 |

TABLE 33

Plaque reduction rate for Neutralization of Motavizumab MARM

| Antibody | 10000 ng/ml | 2000 ng/ml | 400 ng/ml | 80 ng/ml | 16 ng/ml | 3.2 ng/ml |
|---|---|---|---|---|---|---|
| Motavizumab | 13.3 | 1.7 | 0.0 | 0.2 | 3.3 | 0.0 |
| IgG form of 58C5 | 97.6 | 95.8 | 92.0 | 74.6 | 43.0 | 1.5 |
| IgG form of 30D8 | 98.7 | 98.6 | 98.2 | 91.8 | 55.7 | 8.7 |

TABLE 34

Plaque reduction rate for Neutralization of 58C5 MARM

| Antibody | 10000 ng/ml | 2000 ng/ml | 400 ng/ml | 80 ng/ml | 16 ng/ml | 3.2 ng/ml |
|---|---|---|---|---|---|---|
| Motavizumab | 94.8 | 92.9 | 83.9 | 47.1 | 6.5 | 0.0 |
| IgG form of 58C5 | 3.3 | 0.0 | 0.0 | 0.0 | 0.0 | 0.0 |
| IgG form of 30D8 | 93.6 | 87.7 | 83.9 | 80.0 | 58.1 | 8.4 |

TABLE 35

Summary of Neutralization ($ED_{50}$) values

|  | RSV A2 Parental ($ED_{50}$) | Motavizumab MARM ($ED_{50}$) | 58C5 MARM ($ED_{50}$) |
|---|---|---|---|
| Motavizumab IgG | 519 pM | >66.7 nM | 641 pM |
| IgG form of 58C5 | 115 pM | 173 pM | >66.7 nM |
| IgG form of 30D8 | 96 pM | 93 pM | 113 pM |
| 56E11 | 1 nM | 1.6 nM | >200 nM |
| 17C9 | 436 pM | 356 pM | 353 pM |
| 69F6 | 256 pM | 266 pM | 353 pM |

Example 12: Mapping of the 58C5 and 30D8 Binding Epitopes

In this example, residues of the RSV F protein involved in binding of antibodies 58C5 and 30D8 were determined by screening a library of single mutants of the RSV F protein for binding to antibodies 58C5 or 30D8.

The RSV F protein mutant library \was generated using Shotgun Mutagenesis Mapping Technology from Integral Molecular (Philadelphia, Pa.). In short, the technology allows for the expression and analysis of large libraries of mutated target proteins within eukaryotic cells. Every residue in a target protein is individually mutated, usually to multiple other amino acids, in order to assay for changes in monoclonal antibody (MAb) binding or function. The proteins are expressed within mammalian cell lines, so even complex proteins that require eukaryotic translational or post-translational processing can be epitope mapped.

Human RSV F A2 Strain (NCBI Ref # FJ614814) was used as the parental plasmid for the RSV F protein. A C-terminal V5 tag was included to allow for screening. The F proteins were expressed in HEK 293 cells and binding was determined using immunoluminescence. Using a random mutation strategy, a library of RSV F proteins containing 1029 mutant clones was generated. All 549 amino acids of the F protein were mutated, with an average of 1.34 mutations per clones and an average of 2.46 mutations per amino acid residue. Every amino acid was mutated at least once (100%), and at least 457 amino acids (83.2%) were mutated twice. Motivizumab and a polyclonal serum that binds the F protein were used as positive controls to determine if the expressed F protein was properly folded. Motivizumab is known to bind both the pre- and the post-fusion conformation of the RSV F protein. In addition, both 58C5 and 30D8 are sensitive to the conformational changes, therefore, 58C5 was also used as a control for 30D8 and 30D8 was used as a control for 58C5. As shown in Example 10 above, 58C5 and 30D8 bind to two independent sites of the RSV F protein and additionally, both are sensitive to conformational changes.

The screening was performed several times with two independent minipreps of the transfectants. The selection criteria for the evaluation of residues that contribute to antibody binding was as follows:
- mutant residue results in a signal for binding to 58C5 that is 2× less than the signal for binding to 30D8;
- mutant residue results in a signal for binding to 30D8 that is 2× less than the signal for binding to 58C5;
- positive control (polyclonal serum or Motivizumab)>20% luminescence; and
- preferably also another substitution at the same site.

Each identified clone was also verified for surface expression using a polyclonal antibody. Samples were tested at least 3 times.

1. Binding to Antibody 58C5

The results are shown in Tables 36-37 below, which set forth the immunoluminescence for at least three samples (S1, S2 and S3) for binding of 58C5 and 30D8 to each F protein mutant, binding of motavizumab and/or the polyclonal serum, the mean of the values for 58C5 and 30D8, the ratio of binding to 30D8/58C5 and the mutation in the F protein. As shown in Tables 36-37 below, mutation of residues N63, E82, Y86, K168, V207, N371, S405 and/or E463 in the F protein resulted in reduced binding of the antibody 58C5. Residue E82 was identified in both miniprep screens. Residue N63 was previously identified in the escape mutant, or MARK for 58C5. This mutation was also confirmed by FACS analysis. When the combined identified residues are displayed on a 3D model of prefusion RSV-F, they cluster on a restricted area of the spike, in the same area as the escape mutants in the top of the spike and illustrate the antibody footprint of Mab 58C5 (see FIG. 1). Thus, 58C5 binds a conformational epitope.

Figure 2:
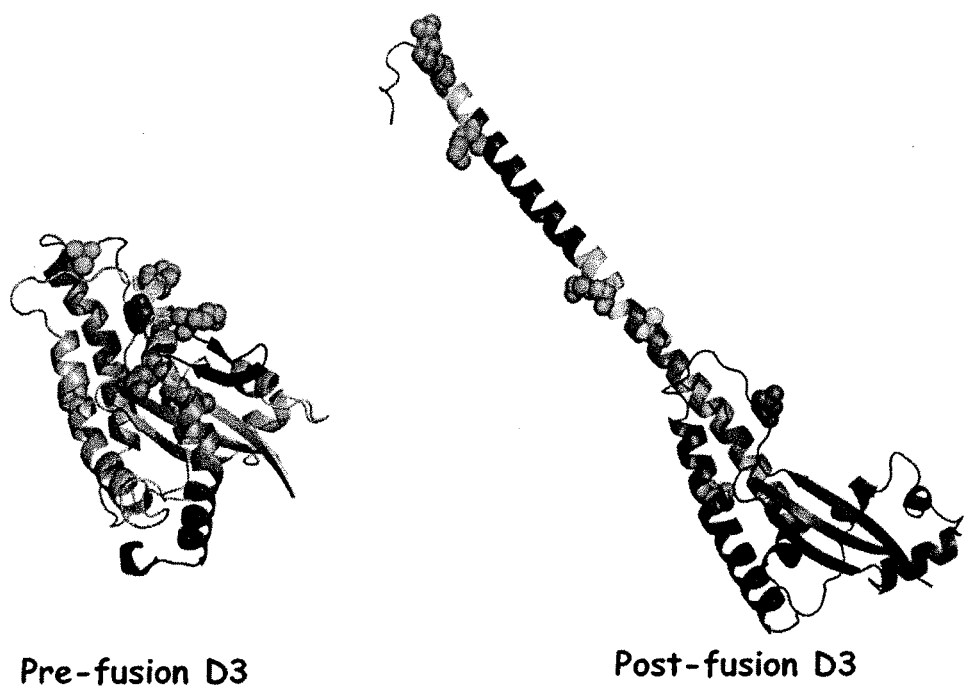
FIG. 2 shows a 3D model X-ray structure of the D3 region of RSV F protein containing RSV F protein residues important for binding of antibody 58C5 in a prefusion and postfusion conformation.

When these residues are displayed on the X-ray structure of the postfusion RSV-F protein trimeric spike, the residues are distributed over a large area of the protein surface which would be impossible to be part of an antibody footprint (see. FIG. 2, and Morton et al., (2003) *Virology* 311:275-288: McLellan et al., (2010) *J Virology* 84(23):12236-12244; and McLellan et al., (2011) *J Mol Biol* 409:853-866). The epitope of 58C5 is located on a domain that goes through the most dramatic conformational change of the F protein when it moves from prefusion to the postfusion state. Only the clustered region on the pre-fusion spike agrees with the footprint of an antibody. Therefore, the location of the epitope agrees with data that 58C5 is specific for the prefusion conformation and it also confirms lack of competition with Motivizumab, F101 and 30D8. Thus, 58C5 does not bind the same epitope as Motivizumab or 30D8.

TABLE 36

Screening of 58C5 with Library including first miniprep

| 58C5 | | | 30D8 | | | Polyclonal | 58C5 | 30D8 | | Ratio |
|---|---|---|---|---|---|---|---|---|---|---|
| S1 | S2 | S3 | S1 | S2 | S3 | S1 | Mean | Mean | Mutation | 30D8/58C5 |
| 7.6 | 4.8 | 4.8 | | 50.7 | 55.7 | 64.7 | 5.8 | 53.2 | K168E | 9.2 |
| 13.2 | 4.8 | 4.6 | 22.6 | 20.8 | 27.1 | 68.0 | 7.5 | 23.5 | N63H | 3.1 |
| 22.4 | 10.0 | 11.0 | 17.5 | 27.9 | 36.6 | 60.5 | 14.5 | 27.3 | V207D | 1.9 |
| 50.7 | 30.7 | 33.9 | 59.8 | 87.9 | 80.0 | 82.3 | 38.4 | 75.9 | S405A | 2.0 |
| 5.4 | 1.6 | 3.6 | 9.7 | 20.7 | 12.5 | 18.9 | 3.6 | 14.3 | E82G | 4.0 |

TABLE 37

Screening of 58C5 with Library including second miniprep

| Antibody | | | | | |
|---|---|---|---|---|---|
| 58C5 | S1 | 8.6 | 55.6 | 13.1 | 11.1 |
|  | S2 | 8.9 | 16.1 | 10.2 | 7.2 |
|  | S3 | 7.9 | 25.3 | 10.2 | 6.3 |
|  | S4 | 2.1 | 54.5 | 1.2 | 2.4 |
| 30D8 | S1 | 35.7 | 74.9 | 9.3 | 17.2 |
|  | S2 | 12 | 111.1 | 42.1 | 12.1 |
|  | S3 | 12 | 52.3 | 36.6 | 12.1 |
|  | S4 | 15.2 | 80 | 2.4 | 19.7 |
| Motivizumab | Mean | 42.1 | 100.9 | 26.9 | 24.8 |
| Polyclonal | S1 | 37.1 | 137.1 | 14.4 | 7.7 |
| 58C5 | Mean | 6.9 | 37.9 | 8.7 | 6.8 |
| 30D8 | Mean | 18.7 | 79.6 | 22.6 | 15.3 |
| Mutation |  | E82G | E463A | N371D | Y86C |
| Ratio 30D8/58C5 |  | 2.7 | 2.1 | 2.6 | 2.3 |

2. Binding to Antibody 30D8

Figure 3:
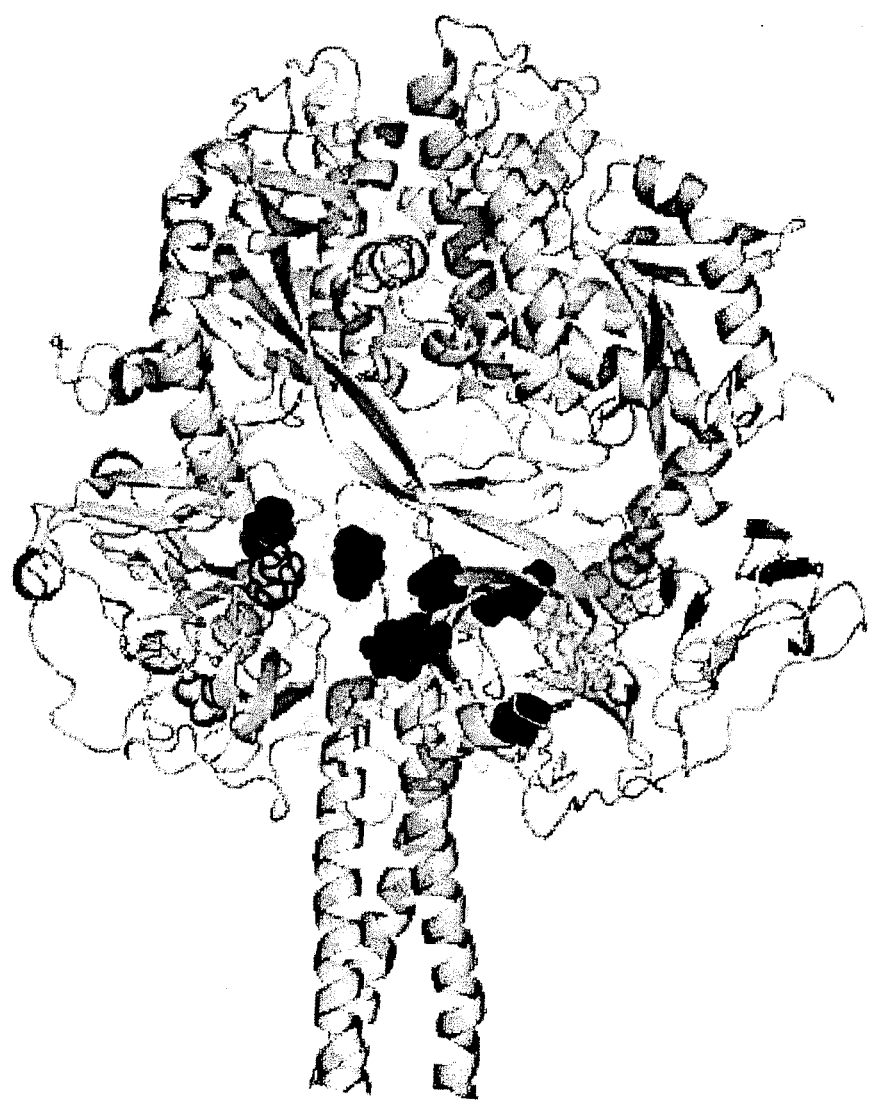
FIG. 3 is a 3D model of the RSV F protein in its prefusion conformation. Amino acid residues identified in Example 12 as being important for binding of antibody 30D8 are indicated in black, space filling models. The residues cluster in the D1 domain at the base of the lollipop just above the stem/stalk region.

The results are shown in Tables 38-39 below, which set forth the immunoluminescence for at least three samples (S1, S2 and S3) for binding of 58C5 and 30D8 to each F protein mutant, binding of motavizumab and/or the polyclonal serum, the mean of the values for 58C5 and 30D8, the ratio of binding to 58C5/30D8 and the mutation in the F protein. As shown in Tables 38-39 below, mutation of residues V278, R339, F351, P353, M370, N371, C382, D392, M396 and/or S403 in the F protein resulted in reduced binding of the antibody 30D8. Residue R339 was identified in both miniprep screens. Two different mutations of both M370 and C382 resulted in a reduced binding of antibody 30D8 to the RSV F protein. As shown above for 58C5, the identified residues are restricted to one domain of the RSV F protein. When all identified residues for binding are combined, they all cluster in the D1 domain, at the base of the lollipop just above the stem/stalk region. Some residues are internal according to the 3D model, whereas other residues that are exposed cluster in the interface in the crevice between D1 domains of different protomers in the prefusion trimer model (see FIG. 3). When the residues are displayed in the postfusion trimer, all identified residues are internal. Although the conformational change of the D1 region is expected to be very limited between pre and postfusion conformations, the protomer subunits do rearrange between pre and post fusion, resulting in a postfusion structure that is more condensed and less open. The mapping of the 30D8 Mab to the D1 region agrees with our results that it is dependent on the RSV F protein structural conformation. Moreover, just as for 58C5, the epitope does not compete with 58C5, Motivizumab or antibody 101F. This agrees with the location on the 3D model. Thus, 30D8 does not bind the same epitope as Motivizumab or 58C5.

TABLE 38

Screening of 30D8 with Library including first miniprep

| Antibody | | | | | | | |
|---|---|---|---|---|---|---|---|
| 58C5 | S1 | 28.3 | 10 | 32.4 | 18.1 | 13.8 | 2.9 |
|  | S2 |  |  |  |  |  |  |
|  | S3 | 28.7 | 23.5 | 31.5 | 43.2 | 26.4 | 6.1 |
|  | S4 | 44.1 | 13.9 | 32.7 | 26.3 | 13.2 | 14.7 |
| 30D8 | S1 | 16.8 | 7.3 | 20.1 | 14.1 | 9.3 | 1.4 |
|  | S2 | 6.6 | 4.9 | 3.3 | 10.7 | 3.1 | −1.4 |
|  | S3 | 1.9 | 1.1 | 2.3 | 7.2 | 1.5 | −1.3 |
|  | S4 | 12.2 | 11.3 | 23.7 | 17.2 | 19.4 | 5 |
| Motivizumab | Mean |  |  | 28 |  |  |  |
| Polyclonal | S1 | 24.8 | 76.3 | 3 | 75.9 | 13.1 | 3.8 |
| 58C5 | Mean | 32.4 | 17.7 | 33.8 | 32.7 | 19.9 | 7.4 |
| 30D8 | Mean | 9.4 | 6.2 | 12.4 | 12.3 | 8.3 | 0.9 |
| Mutations |  | C382R | R339W | S403A | P353S | C382S | F351S |
| Ratio 58C5/30D8 |  | 3.5 | 2.9 | 2.7 | 2.7 | 2.4 | 8.2 |

TABLE 39

Screening of 30D8 with Library including second miniprep

| 58C5 | | | 30D8 | | | Polyclonal | 58C5 | 30D8 | | Ratio |
|---|---|---|---|---|---|---|---|---|---|---|
| S1 | S2 | S3 | S1 | S2 | S3 | S1 | Mean | Mean | Mutations | 58C5/30D8 |
| 27.1 | 29.0 | 41.7 | 10.3 | 9.0 | 3.6 | 118.7 | 32.6 | 7.6 | R339Q | 4.3 |
| 26.0 | 37.6 | 43.5 | 16.8 | 3.1 | 9.0 | 61.2 | 35.7 | 9.7 | M370R | 3.7 |

TABLE 39-continued

Screening of 30D8 with Library including second miniprep

| 58C5 | | | 30D8 | | | Polyclonal | 58C5 | 30D8 | | Ratio |
|---|---|---|---|---|---|---|---|---|---|---|
| S1 | S2 | S3 | S1 | S2 | S3 | S1 | Mean | Mean | Mutations | 58C5/30D8 |
| 93.0 | 47.6 | 46.1 | 38.8 | 10.1 | 6.7 | 35.2 | 62.2 | 18.5 | M370T | 3.4 |
| 45.2 | 66.4 | 133.6 | 46.6 | 11.8 | 16.6 | 69.1 | 81.7 | 25.0 | N371Y | 3.3 |
| 13.0 | 39.4 | 43.9 | 15.3 | 8.3 | 6.4 | 73.5 | 32.1 | 10.0 | M396V | 3.2 |
| 86.1 | 51.2 | 63.6 | 44.0 | 11.2 | 10.3 | 66.8 | 67.0 | 21.9 | D392N | 3.1 |
| 122.1 | 97.6 | 79.6 | 63.6 | 21.0 | 11.6 | 57.5 | 99.8 | 32.1 | V278M | 3.1 |

Since modifications will be apparent to those of skill in this art, it is intended that this invention be limited only by the scope of the appended claims.

What is claimed is:

1. A chimeric anti-respiratory syncytial virus (RSV) antibody or antigen-binding fragment thereof, comprising:
   a heavy chain CDR1 of SEQ ID NO: 458,
   a heavy chain CDR2 of SEQ ID NO: 459,
   a heavy chain CDR3 of SEQ ID NO: 460;
   a light chain CDR1 of SEQ ID NO: 461,
   a light chain CDR2 of SEQ ID NO: 462, and
   a light chain CDR3 of SEQ ID NO: 463.

2. The chimeric anti-RSV antibody of claim 1, wherein the chimeric anti-RSV antibody is a full-length antibody.

3. The chimeric anti-RSV antibody of claim 1, wherein the chimeric anti-RSV antibody is a full-length IgG antibody.

4. The chimeric anti-RSV antibody or antigen-binding fragment of claim 1, wherein the chimeric anti-RSV antibody or antigen-binding fragment is an antigen-binding fragment selected from the group consisting of a Fab, Fab', F(ab')$_2$, single-chain Fv (scFv), Fv, dsFv, diabody, Fd and Fd' fragments.

5. The chimeric anti-RSV antibody or antigen-binding fragment of claim 1, wherein the chimeric anti-RSV antibody or antigen-binding fragment is a Fab or scFv.

6. The chimeric antibody or antigen-binding fragment of claim 1, wherein the chimeric anti-RSV antibody or antigen-binding fragment neutralizes RSV.

7. The chimeric antibody or antigen-binding fragment of claim 1, wherein the chimeric anti-RSV antibody or antigen-binding fragment neutralizes RSV subtypes A and B.

8. A multivalent antibody comprising:
- a first antigen-binding portion comprising the chimeric antibody or antigen-binding fragment of claim 1 or such an antigen-binding fragment thereof conjugated to a multimerization domain; and
- a second antigen-binding portion comprising an antigen-binding fragment of an antiviral antibody conjugated to a second multimerization domain, wherein:
- the first multimerization domain and the second multimerization domain are complementary or the same, whereby the first antigen-binding portion and second antigen-binding portion form a multivalent antibody.

9. The multivalent antibody of claim 8, wherein the second antigen-binding portion comprises an anti-RSV antibody or antigen-binding fragment thereof.

10. The multivalent antibody of claim 8, wherein the anti-RSV antibody or antigen-binding fragment is an antibody or antigen-binding fragment, wherein RSV does not produce a virus that escapes neutralization by the antibody or antigen-binding fragment thereof after more than 10 or more rounds of viral replication in the presence of the antibody or antigen-binding fragment thereof.

11. A pharmaceutical composition comprising:
- the antibody or antigen-binding fragment of claim 1; and
- a pharmaceutically acceptable carrier or excipient.

12. The pharmaceutical composition of claim 11 formulated as a gel, ointment, liquid, suspension, aerosol, tablet, pill or powder.

13. The pharmaceutical composition of claim 11 formulated as a nasal spray.

14. The pharmaceutical composition of claim 11 formulated for pulmonary, intranasal, or parenteral administration.

15. The pharmaceutical composition of claim 11 formulated for single dosage administration.

16. The pharmaceutical composition of claim 11 that is a sustained release formulation.

17. A method of treating a viral infection in a subject, the method comprising:
- administering to the subject a therapeutically effective amount of the pharmaceutical composition of claim 11.

18. A method of treating or inhibiting one or more symptoms of a viral infection in a subject, the method comprising:
- administering to the subject a therapeutically effective amount of the pharmaceutical composition of claim 11.

19. A method of inhibiting a viral infection in a subject, the method comprising:
- administering to the subject a prophylactically effective amount of the pharmaceutical composition of claim 11.

20. The method of claim 17, wherein the viral infection is an RSV infection.

21. The method of claim 20, wherein the infection is an upper respiratory tract infection.

22. The method of claim 17, wherein the subject is a mammal.

23. The method of claim 22, wherein the subject is a human.

24. The method of claim 23, wherein the human subject is a human infant, a human infant born prematurely or at risk of hospitalization for a RSV infection, an elderly human, a human subject who has cystic fibrosis, bronchopulmonary dysplasia, congenital heart disease, congenital immunodeficiency, acquired immunodeficiency, leukemia, or non-Hodgkin lymphoma or a human subject having an organ or tissue transplant or a blood transfusion.

25. The method of claim 24, wherein the transplant is a bone marrow transplant or a liver transplant.

26. The method of claim 17, wherein the pharmaceutical composition is administered topically, parenterally, locally, or systemically.

27. The method of claim 17, wherein the pharmaceutical composition is administered intranasally, intramuscularly, intradermally, intraperitoneally, intravenously, subcutaneously, orally, or by pulmonary administration.

28. The method of claim 17, wherein the composition is administered by a nebulizer or an inhaler.

29. The method of claim 17, wherein the composition is administered one time, two times, three times, four times or five times during RSV season.

30. The method of claim 17, wherein the composition is administered one time, two times, three times, four times or five times within one month, two months or three months, prior to a RSV season.

31. The method of claim 17, further comprising administration of one or more antiviral agents.

32. The method of claim 31, wherein the antiviral agent is ribavirin.

33. The method of claim 17, further comprising administration of one or more additional antiviral antibodies or antigen-binding fragments thereof.

34. The method of claim 33, wherein the one or more additional antiviral antibodies are anti-RSV antibodies or antigen-binding fragments thereof.

35. The method of claim 34, wherein the one or more additional anti-RSV antibodies are selected from the group consisting of palivizumab, motavizumab, AFFF, P12f2, P12f4, P11d4, Ale9, A12a6, A13c4, A17d4, A4B4, A8c7, 1X-493L1, FR H3-3F4, M3H9, Y10H6, DG, AFFF(1), 6H8, L1-7E5, L2-15B10, A13a11, A1h5, A4B4(1), A4B4LIFR-S28R, A4B4-F52S, rsv6, rsvl 1, rsvl 3, rsvl 9, rsv21, rsv22, rsv23, RF-1, RF-2, and antigen-binding fragments thereof.

36. The method of claim 33, wherein the one or more additional antiviral antibodies is selected from the group consisting of an antibody or antigen-binding fragment that immunospecifically binds an antigen of parainfluenza virus (PIV) or human metapneumovirus (hMPV).

37. The method of claim 31, wherein the pharmaceutical composition and the antiviral agent are formulated as separate compositions.

38. The method of claim 31, wherein the pharmaceutical composition and the antiviral agent are administered sequentially, simultaneously, or intermittently.

39. The method of claim 17, further comprising administration of hormonal therapy, immunotherapy or an anti-inflammatory agent.

40. A method of detecting respiratory syncytial virus (RSV) infection in a subject, the method comprising:
- (a) assaying the level of RSV antigen in a fluid, cell, or tissue sample from the subject utilizing the antibody or antigen-binding fragment of claim 1; and
- (b) comparing the assayed level of RSV antigen with a control level wherein an increase in the assayed level of RSV antigen compared to the control level of the RSV antigen is indicative of a RSV infection.

41. A polynucleotide encoding the chimeric antibody or antigen-binding fragment of claim 1.

42. A polynucleotide encoding the heavy chain of the chimeric antibody of claim 1.

43. A polynucleotide encoding the light chain of the chimeric antibody of claim 1.

44. A kit comprising the chimeric antibody or antigen-binding fragment of claim 1, in one or more containers, and instructions for use.

* * * * *

```
                       SEQUENCE LISTING

<160> NUMBER OF SEQ ID NOS: 487

<210> SEQ ID NO 1
<211> LENGTH: 228
<212> TYPE: PRT
<213> ORGANISM: Homo sapiens
<220> FEATURE:
<223> OTHER INFORMATION: 58c5 Fab Heavy Chain

<400> SEQUENCE: 1

Gln Val Gln Leu Val Gln Ser Gly Pro Gly Leu Val Lys Pro Ser Gln
  1               5                  10                  15

Thr Leu Ala Leu Thr Cys Asn Val Ser Gly Ala Ser Ile Asn Ser Asp
             20                  25                  30

Asn Tyr Tyr Trp Thr Trp Ile Arg Gln Arg Pro Gly Gly Gly Leu Glu
         35                  40                  45

Trp Ile Gly His Ile Ser Tyr Thr Gly Asn Thr Tyr Tyr Thr Pro Ser
     50                  55                  60

Leu Lys Ser Arg Leu Ser Met Ser Leu Glu Thr Ser Gln Ser Gln Phe
 65                  70                  75                  80

Ser Leu Arg Leu Thr Ser Val Thr Ala Ala Asp Ser Ala Val Tyr Phe
                 85                  90                  95

Cys Ala Ala Cys Gly Ala Tyr Val Leu Ile Ser Asn Cys Gly Trp Phe
            100                 105                 110

Asp Ser Trp Gly Gln Gly Thr Gln Val Thr Val Ser Ser Ala Ser Thr
        115                 120                 125

Lys Gly Pro Ser Val Phe Pro Leu Ala Pro Ser Ser Lys Ser Thr Ser
    130                 135                 140

Gly Gly Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Leu Tyr Ser Leu Ser Ser
            180                 185                 190

Val Val Thr Val Pro Ser Ser Ser Leu Gly Thr Gln Thr Tyr Ile Cys
        195                 200                 205

Asn Val Asn His Lys Pro Ser Asn Thr Lys Val Asp Lys Lys Val Glu
    210                 215                 220

Pro Lys Ser Cys
225
```

-continued

<210> SEQ ID NO 2
<211> LENGTH: 12
<212> TYPE: PRT
<213> ORGANISM: Homo sapiens
<220> FEATURE:
<223> OTHER INFORMATION: 58c5 VH CDR1

<400> SEQUENCE: 2

Gly Ala Ser Ile Asn Ser Asp Asn Tyr Tyr Trp Thr
1               5                   10

<210> SEQ ID NO 3
<211> LENGTH: 16
<212> TYPE: PRT
<213> ORGANISM: Homo sapiens
<220> FEATURE:
<223> OTHER INFORMATION: 58c5 VH CDR2

<400> SEQUENCE: 3

His Ile Ser Tyr Thr Gly Asn Thr Tyr Tyr Thr Pro Ser Leu Lys Ser
1               5                   10                  15

<210> SEQ ID NO 4
<211> LENGTH: 15
<212> TYPE: PRT
<213> ORGANISM: Homo sapiens
<220> FEATURE:
<223> OTHER INFORMATION: 58c5 VH CDR3

<400> SEQUENCE: 4

Cys Gly Ala Tyr Val Leu Ile Ser Asn Cys Gly Trp Phe Asp Ser
1               5                   10                  15

<210> SEQ ID NO 5
<211> LENGTH: 214
<212> TYPE: PRT
<213> ORGANISM: Homo sapiens
<220> FEATURE:
<223> OTHER INFORMATION: 58c5 Light Chain

<400> SEQUENCE: 5

Glu Ile Val Met Thr Gln Ser Pro Ser Ser Leu Ser Ala Ser Ile Gly
1               5                   10                  15

Asp Arg Val Thr Ile Thr Cys Gln Ala Ser Gln Asp Ile Ser Thr Tyr
                20                  25                  30

Leu Asn Trp Tyr Gln Gln Lys Pro Gly Gln Ala Pro Arg Leu Leu Ile
            35                  40                  45

Tyr Gly Ala Ser Asn Leu Glu Thr Gly Val Pro Ser Arg Phe Thr Gly
50                  55                  60

Ser Gly Tyr Gly Thr Asp Phe Ser Val Thr Ile Ser Ser Leu Gln Pro
65                  70                  75                  80

Glu Asp Ile Ala Thr Tyr Tyr Cys Gln Gln Tyr Gln Tyr Leu Pro Tyr
                85                  90                  95

Thr Phe Ala Pro Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser

```
                165                 170                 175
Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 6
<211> LENGTH: 11
<212> TYPE: PRT
<213> ORGANISM: Homo sapiens
<220> FEATURE:
<223> OTHER INFORMATION: 58c5 VL CDR1

<400> SEQUENCE: 6

Gln Ala Ser Gln Asp Ile Ser Thr Tyr Leu Asn
1               5                   10

<210> SEQ ID NO 7
<211> LENGTH: 7
<212> TYPE: PRT
<213> ORGANISM: Homo sapiens
<220> FEATURE:
<223> OTHER INFORMATION: 58c5 VL CDR2

<400> SEQUENCE: 7

Gly Ala Ser Asn Leu Glu Thr
1               5

<210> SEQ ID NO 8
<211> LENGTH: 9
<212> TYPE: PRT
<213> ORGANISM: Homo sapiens
<220> FEATURE:
<223> OTHER INFORMATION: 58c5 VL CDR3

<400> SEQUENCE: 8

Gln Gln Tyr Gln Tyr Leu Pro Tyr Thr
1               5

<210> SEQ ID NO 9
<211> LENGTH: 228
<212> TYPE: PRT
<213> ORGANISM: Homo sapiens
<220> FEATURE:
<223> OTHER INFORMATION: sc5 Fab Heavy Chain

<400> SEQUENCE: 9

Gln Val Gln Leu Gln Glu Ser Gly Pro Gly Leu Val Lys Pro Ser Gly
1               5                   10                  15

Thr Leu Ser Leu Thr Cys Thr Val Ser Gly Asp Ser Ile Ser Gly Ser
            20                  25                  30

Asn Trp Trp Asn Trp Val Arg Gln Pro Pro Gly Lys Gly Leu Glu Trp
        35                  40                  45

Ile Gly Glu Ile Tyr Tyr Arg Gly Thr Thr Asn Tyr Lys Ser Ser Leu
    50                  55                  60

Lys Gly Arg Val Thr Met Ser Val Asp Thr Ser Lys Asn Gln Phe Ser
65                  70                  75                  80

Leu Lys Leu Thr Ser Val Thr Ala Ala Asp Thr Ala Val Tyr Tyr Cys
                85                  90                  95

Ala Arg Gly Gly Arg Ser Thr Phe Gly Pro Asp Tyr Tyr Tyr Tyr Met
```

```
                  100                 105                 110
Asp Val Trp Gly Arg Gly Thr Thr Val Thr Val Ser Ser Ala Ser Thr
            115                 120                 125

Lys Gly Pro Ser Val Phe Pro Leu Ala Pro Ser Ser Lys Ser Thr Ser
        130                 135                 140

Gly Gly Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Leu Tyr Ser Leu Ser Ser
            180                 185                 190

Val Val Thr Val Pro Ser Ser Ser Leu Gly Thr Gln Thr Tyr Ile Cys
        195                 200                 205

Asn Val Asn His Lys Pro Ser Asn Thr Lys Val Asp Lys Lys Val Glu
    210                 215                 220

Pro Lys Ser Cys
225

<210> SEQ ID NO 10
<211> LENGTH: 11
<212> TYPE: PRT
<213> ORGANISM: Homo sapiens
<220> FEATURE:
<223> OTHER INFORMATION: sc5 VH CDR1

<400> SEQUENCE: 10

Gly Asp Ser Ile Ser Gly Ser Asn Trp Trp Asn
1               5                   10

<210> SEQ ID NO 11
<211> LENGTH: 16
<212> TYPE: PRT
<213> ORGANISM: Homo sapiens
<220> FEATURE:
<223> OTHER INFORMATION: sc5 VH CDR2

<400> SEQUENCE: 11

Glu Ile Tyr Tyr Arg Gly Thr Thr Asn Tyr Lys Ser Ser Leu Lys Gly
1               5                   10                  15

<210> SEQ ID NO 12
<211> LENGTH: 16
<212> TYPE: PRT
<213> ORGANISM: Homo sapiens
<220> FEATURE:
<223> OTHER INFORMATION: sc5 VH CDR3

<400> SEQUENCE: 12

Gly Gly Arg Ser Thr Phe Gly Pro Asp Tyr Tyr Tyr Met Asp Val
1               5                   10                  15

<210> SEQ ID NO 13
<211> LENGTH: 214
<212> TYPE: PRT
<213> ORGANISM: Homo sapiens
<220> FEATURE:
<223> OTHER INFORMATION: sc5 Light Chain

<400> SEQUENCE: 13

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asn Ile Lys Asn Tyr
```

```
            20                  25                  30
Leu Asn Trp Tyr Gln Gln Lys Pro Gly Lys Val Pro Lys Leu Leu Ile
            35                  40                  45

Tyr Ala Ala Ser Thr Leu Gln Ser Gly Val Pro Ser Arg Phe Ser Gly
        50                  55                  60

Ser Gly Ser Gly Thr Asp Phe Thr Leu Thr Ile Ser Ser Leu Gln Pro
 65                  70                  75                  80

Glu Asp Phe Ala Thr Tyr Ser Cys Gln Gln Ser Tyr Asn Asn Gln Leu
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 14
<211> LENGTH: 11
<212> TYPE: PRT
<213> ORGANISM: Homo sapiens
<220> FEATURE:
<223> OTHER INFORMATION: sc5 VL CDR1

<400> SEQUENCE: 14

Arg Ala Ser Gln Asn Ile Lys Asn Tyr Leu Asn
 1               5                  10

<210> SEQ ID NO 15
<211> LENGTH: 7
<212> TYPE: PRT
<213> ORGANISM: Homo sapiens
<220> FEATURE:
<223> OTHER INFORMATION: sc5 VL CDR2

<400> SEQUENCE: 15

Ala Ala Ser Thr Leu Gln Ser
 1               5

<210> SEQ ID NO 16
<211> LENGTH: 9
<212> TYPE: PRT
<213> ORGANISM: Homo sapiens
<220> FEATURE:
<223> OTHER INFORMATION: sc5 VL CDR3

<400> SEQUENCE: 16

Gln Gln Ser Tyr Asn Asn Gln Leu Thr
 1               5

<210> SEQ ID NO 17
```

```
<211> LENGTH: 702
<212> TYPE: DNA
<213> ORGANISM: Homo sapiens
<220> FEATURE:
<223> OTHER INFORMATION: 58c5 Heavy Chain

<400> SEQUENCE: 17
caggtccagc ttgtgcagtc gggcccagga ctggtgaagc cttcacagac cctggccctc      60
acctgcaatg tctctggtgc ctccatcaat agtgataatt actactggac gtggatccgt     120
cagcgcccag ggggggcct ggagtggatt ggccacatct cttacactgg aacacctac       180
tacaccccgt cactcaagag ccgactttcc atgtcactag agacatctca gagccaattc     240
tccctgaggc tgacctctgt gactgccgcg gactcggccg tctatttctg tgcggcctgc     300
gggcatatg ttttaatatc aaactgtggc tggttcgact cctggggcca gggaacccag      360
gtcaccgtct cctcagcctc caccaagggc ccatcggtct tccccctggc accctcctcc     420
aagagcacct ctgggggcac agcggccctg ggctgcctgg tcaaggacta cttccccgaa     480
ccggtgacgg tgtcgtggaa ctcaggcgcc ctgaccagcg gcgtgcacac cttcccggct     540
gtcctacagt cctcaggact ctactccctc agcagcgtgg tgaccgtgcc ctccagcagc     600
ttgggcaccc agacctacat ctgcaacgtg aatcacaagc ccagcaacac caaggtggac     660
aagaaagttg agcccaaatc ttgtggtcgg ccaggccggc cg                        702

<210> SEQ ID NO 18
<211> LENGTH: 645
<212> TYPE: DNA
<213> ORGANISM: Homo sapiens
<220> FEATURE:
<223> OTHER INFORMATION: 58c5 Light Chain

<400> SEQUENCE: 18
gaaatagtga tgacgcagtc tccatcctcc ctgtctgcat ctataggaga cagagtcacc      60
atcacttgcc aggcgagtca ggacattagc acctatttaa attggtatca gcagaaacca     120
gggcaagccc ctaggctcct gatctacgga gcgtccaatt tggagacagg ggtcccatca     180
aggttcactg gaagtggata tgggacagac ttctctgtca ccatcagcag cctgcagcct     240
gaagatattg caacatatta ctgtcaacag taccaatatc tcccgtacac ttttgccccg     300
gggaccaagg tcgagatcaa acgaactgtg gctgcaccat ctgtcttcat cttcccgcca     360
tctgatgagc agttgaaatc tggaactgcc tctgttgtgt gcctgctgaa taacttctat     420
cccagagagg ccaaagtaca gtggaaggtg gataacgccc tccaatcggg taactcccag     480
gagagtgtca cagagcagga cagcaaggac agcacctaca gcctcagcag cccctgacg     540
ctgagcaaag cagactacga gaaacacaaa gtctacgcct gcgaagtcac ccatcagggc     600
ctgagctcgc ccgtcacaaa gagcttcaac aggggagagt gctaa                    645

<210> SEQ ID NO 19
<211> LENGTH: 687
<212> TYPE: DNA
<213> ORGANISM: Homo sapiens
<220> FEATURE:
<223> OTHER INFORMATION: sc5 Heavy Chain

<400> SEQUENCE: 19
caggtgcagc tgcaggagtc gggcccagga ctggtgaagc cttcggggac cctgtccctc      60
acttgcactg tctctggtga ctccatcagc ggctctaact ggtggaattg ggtccgccag     120
cccccaggga aggggctgga gtggattggg gaaatctatt atcgtgggac taccaattat     180
```

```
aagtcgtccc tcaagggtcg agtcaccatg tcagttgaca cgtccaagaa ccagttctcc      240
ctgaagctga cctctgtgac cgccgcggac acggccgtat attattgtgc gagaggggga      300
aggtccacct ttggtccgga ctactactac tacatggacg tctggggcag agggaccacg      360
gtcaccgtct cctcagcgtc gaccaaaggt ccgtctgttt tcccgctggc tccgtcttct      420
aaatctacct ctggtggtac cgctgctctg ggttgcctgg ttaaagacta cttcccggaa      480
ccggttaccg tttcttggaa ctctggtgct ctgacctctg tgttcacac cttcccggct       540 gttctgcagt cttctggtct gtactctctg tcttctgttg ttaccgttcc gtcttcttct      600
ctgggtaccc agacctacat ctgcaacgtt aaccacaaac cgtctaacac caaagttgac      660
aagaaagttg aaccgaaatc ttgcctg                                          687

<210> SEQ ID NO 20
<211> LENGTH: 642
<212> TYPE: DNA
<213> ORGANISM: Homo sapiens
<220> FEATURE:
<223> OTHER INFORMATION: sc5 Light Chain

<400> SEQUENCE: 20
gacatccaga tgacccagtc tccatcctcc ctgtctgcct ctgtaggtga cagagtcacc      60
atcacttgcc gggcaagtca gaacattaag aactatttaa attggtatca acaaaaacca     120
gggaaagtcc cgaagctcct gatctatgct gcatccactt tgcagagtgg ggtcccatcg     180
aggttcagtg gcagtggatc tgggacagac ttcactctca ccatcagcag tctgcaacct     240
gaagattttg caacttactc ctgtcaacag agttacaata ccagctcac tttcggcggt      300 gggaccaagg tggagatcaa acgaactgtg gctgcaccat ctgtcttcat cttcccgcca     360
tctgatgagc agttgaaatc tggaactgcc tctgttgtgt gcctgctgaa taacttctat     420
cccagagagg ccaaagtaca gtggaaggtg gataacgccc tccaatcggg taactcccag     480
gagagtgtca cagagcagga cagcaaggac agcacctaca gcctcagcag caccctgacg     540
ctgagcaaag cagactacga gaaacacaaa gtctacgcct gcgaagtcac ccatcagggc     600
ctgagctcgc ccgtcacaaa gagcttcaac aggggagagt gc                        642

<210> SEQ ID NO 21
<211> LENGTH: 1665
<212> TYPE: DNA
<213> ORGANISM: Artificial Sequence
<220> FEATURE:
<223> OTHER INFORMATION: RSV A2 F protein

<400> SEQUENCE: 21
gctagcggta ccatgggcga gctcctcatc ctgaaggcca cgccatcac caccatcctg       60 accgctgtga ccttctgctt cgccagcggc cagaacatca ccgaggaatt ctaccagagc     120
acctgcagcg ccgtgagcaa gggctacctg agcgccctgc ggaccggctg gtacaccagc     180
gtgatcacca tcgagctgtc caacatcaaa gaaaacaagt gcaacggcac cgacgccaaa     240
gtgaagctga tcaagcagga actggacaag tacaagaacg ccgtgaccga gctgcagctg     300
ctgatgcaga gcacccccc caccaacaac cgggccagaa gagaactgcc ccggttcatg     360
aactacaccc tgaacaacgc caagaaaacc aacgtgaccc tgagcaagaa gcggaagcgg     420
cggttcctgg gcttcctgct gggcgtgggc agcgccattg ccagcggcgt ggccgtgtcc     480
aaagtgctgc acctggaagg cgaagtgaac aagatcaagt ccgccctgct gtccaccaac     540
```

-continued

```
aaggccgtgg tgtccctgag caacggcgtg agcgtgctga ccagcaaggt gctggatctg      600
aagaactaca tcgacaagca gctgctgccc atcgtgaaca agcagagctg cagcatcagc      660
aacatcgaga cagtgatcga gttccagcag aagaacaacc ggctgctgga aatcacccgg      720
gagttcagcg tgaacgctgg cgtgaccacc cccgtgtcca cctacatgct gaccaactcc      780
gagctgctct ccctgatcaa tgacatgccc atcaccaacg accagaaaaa gctgatgagc      840
aacaacgtgc agatcgtgcg gcagcagagc tactccatca tgagcatcat caaagaagag      900
gtgctggcct acgtggtgca gctgcccctg tacggcgtga tcgacacccc ctgctggaag      960
ctgcacacca gccccctgtg caccaccaac accaaagagg gcagcaacat ctgcctgacc     1020
cggaccgacc ggggctggta ctgcgacaac gccggcagcg tgtcattctt cccacaagcc     1080
gagacatgca aggtgcagag caaccgggtg ttctgcgaca ccatgaacag cctgaccctg     1140
cccagcgaga tcaacctgtg caacgtggac atcttcaacc ccaagtacga ctgcaagatc     1200
atgacctcca agaccgacgt gtccagctcc gtgatcacct ccctgggcgc catcgtgtcc     1260
tgctacggca agaccaagtg caccgccagc aacaagaacc ggggcatcat caagaccttc     1320
agcaacggct gcgactacgt gtccaacaag ggcatggaca ccgtgtccgt gggcaacaca     1380
ctgtactacg tgaataagca ggaaggcaag agcctgtacg tgaagggcga gcccatcatc     1440
aacttctacg acccctggt gttccccagc gacgagttcg acgccagcat cagccaggtg     1500
aacgagaaga tcaaccagag cctggccttc atcagaaaga gcgacgagct gctgcacaat     1560
gtgaatgccg gcaagtccac caccaaccaa gcttacgtag aacaaaaact catctcagaa     1620
gaggatctga atagcgccgt cgaccatcat catcatcatc attga                     1665
```

<210> SEQ ID NO 22
<211> LENGTH: 6
<212> TYPE: DNA
<213> ORGANISM: Artificial Sequence
<220> FEATURE:
<223> OTHER INFORMATION: NheI Restriction Site

<400> SEQUENCE: 22

```
gctagc                                                                    6
```

<210> SEQ ID NO 23
<211> LENGTH: 6
<212> TYPE: DNA
<213> ORGANISM: Artificial Sequence
<220> FEATURE:
<223> OTHER INFORMATION: HindIII Restriction Site

<400> SEQUENCE: 23

```
aagctt                                                                    6
```

<210> SEQ ID NO 24
<211> LENGTH: 5521
<212> TYPE: DNA
<213> ORGANISM: Artificial Sequence
<220> FEATURE:
<223> OTHER INFORMATION: pcDNA 3.1/myc-His(-) C vector

<400> SEQUENCE: 24

```
gacggatcgg gagatctccc gatcccctat ggtgcactct cagtacaatc tgctctgatg       60
ccgcatagtt aagccagtat ctgctccctg cttgtgtgtt ggaggtcgct gagtagtgcg      120
cgagcaaaat ttaagctaca acaaggcaag gcttgaccga caattgcatg aagaatctgc      180
ttagggttag gcgttttgcg ctgcttcgcg atgtacgggc cagatatacg cgttgacatt      240
```

```
gattattgac tagttattaa tagtaatcaa ttacggggtc attagttcat agcccatata      300
tggagttccg cgttacataa cttacggtaa atggcccgcc tggctgaccg cccaacgacc      360
cccgcccatt gacgtcaata atgacgtatg ttcccatagt aacgccaata gggactttcc      420
attgacgtca atgggtggag tatttacggt aaactgccca cttggcagta catcaagtgt      480
atcatatgcc aagtacgccc cctattgacg tcaatgacgg taaatggccc gcctggcatt      540
atgcccagta catgacctta tgggactttc ctacttggca gtacatctac gtattagtca      600
tcgctattac catggtgatg cggttttggc agtacatcaa tgggcgtgga tagcggtttg      660
actcacgggg atttccaagt ctccacccca ttgacgtcaa tgggagtttg ttttggcacc      720
aaaatcaacg ggactttcca aaatgtcgta acaactccgc cccattgacg caaatgggcg      780
gtaggcgtgt acggtgggag gtctatataa gcagagctct ctggctaact agagaaccca      840
ctgcttactg gcttatcgaa attaatacga ctcactatag ggagacccaa gctggctagc      900
gtttaaacgg gccctctaga ctcgagcggc cgccactgtg ctggatatct gcagaattcc      960
accacactgg actagtggat ccgagctcgg taccaagctt acgtagaaca aaaactcatc     1020
tcagaagagg atctgaatag cgccgtcgac catcatcatc atcatcattg agtttaaacg     1080
gtctccagct taagtttaaa ccgctgatca gcctcgactg tgccttctag ttgccagcca     1140
tctgttgttt gcccctcccc cgtgccttcc ttgaccctgg aaggtgccac tcccactgtc     1200
ctttcctaat aaaatgagga aattgcatcg cattgtctga gtaggtgtca ttctattctg     1260
gggggtgggg tggggcagga cagcaagggg gaggattggg aagacaatag caggcatgct     1320
ggggatgcgg tgggctctat ggcttctgag gcggaaagaa ccagctgggg ctctaggggg     1380
tatccccacg cgccctgtag cggcgcatta agcgcggcgg gtgtggtggt tacgcgcagc     1440
gtgaccgcta cacttgccag cgccctagcg cccgctcctt tcgctttctt cccttccttt     1500
ctcgccacgt tcgccggctt tccccgtcaa gctctaaatc gggggctccc tttagggttc     1560
cgatttagtg ctttacggca cctcgacccc aaaaaacttg attagggtga tggttcacgt     1620
agtgggccat cgccctgata gacggttttt cgccctttga cgttggagtc acgttctttt     1680
aatagtggac tcttgttcca aactggaaca acactcaacc ctatctcggt ctattctttt     1740
gatttataag ggattttgcc gatttcggcc tattggttaa aaaatgagct gatttaacaa     1800
aaatttaacg cgaattaatt ctgtggaatg tgtgtcagtt agggtgtgga agtccccag      1860 gctcccagc aggcagaagt atgcaaagca tgcatctcaa ttagtcagca accaggtgtg     1920
gaaagtcccc aggctcccca gcaggcagaa gtatgcaaag catgcatctc aattagtcag     1980
caaccatagt cccgccccta actccgccca tcccgcccct aactccgccc agttccgccc     2040
attctccgcc ccatggctga ctaatttttt tatttatgc agaggccgag gccgcctctg     2100
cctctgagct attccagaag tagtgaggag gcttttttgg aggcctaggc ttttgcaaaa     2160
agctcccggg agcttgtata tccatttcg gatctgatca agagacagga tgaggatcgt     2220
ttcgcatgat tgaacaagat ggattgcacg caggttctcc ggccgcttgg gtggagaggc     2280
tattcggcta tgactgggca caacagacaa tcggctgctc tgatgccgcc gtgttccggc     2340
tgtcagcgca ggggcgcccg gttcttttg tcaagaccga cctgtccggt gccctgaatg     2400
aactgcagga cgaggcagcg cggctatcgt ggctggccac gacgggcgtt ccttgcgcag     2460
ctgtgctcga cgttgtcact gaagcggaa gggactggct gctattgggc gaagtgccgg     2520
ggcaggatct cctgtcatct caccttgctc ctgccgagaa agtatccatc atggctgatg     2580
```

```
caatgcggcg gctgcatacg cttgatccgg ctacctgccc attcgaccac caagcgaaac    2640
atcgcatcga gcgagcacgt actcggatgg aagccggtct tgtcgatcag gatgatctgg    2700
acgaagagca tcagggcctc gcgccagccg aactgttcgc caggctcaag gcgcgcatgc    2760
ccgacgcgca ggatctcgtc gtgacccatg gcgatgcctg cttgccgaat atcatggtgg    2820
aaaatggccg cttttctgga ttcatcgact gtggccggct gggtgtggcg gaccgctatc    2880
aggacatagc gttggctacc cgtgatattg ctgaagagct tggcggcgaa tgggctgacc    2940
gcttcctcgt gctttacggt atcgccgctc ccgattcgca gcgcatcgcc ttctatcgcc    3000
ttcttgacga gttcttctga gcgggactct ggggttcgaa atgaccgacc aagcgacgcc    3060
caacctgcca tcacgagatt tcgattccac cgccgccttc tatgaaaggt tgggcttcgg    3120
aatcgttttc cgggacgccg gctggatgat cctccagcgc ggggatctca tgctggagtt    3180
cttcgcccac cccaacttgt ttattgcagc ttataatggt tacaaataaa gcaatagcat    3240
cacaaatttc acaataaag cattttttc actgcattct agttgtggtt tgtccaaact    3300
catcaatgta tcttatcatg tctgtatacc gtcgacctct agctagagct tggcgtaatc    3360
atggtcatag ctgtttcctg tgtgaaattg ttatccgctc acaattccac acaacatacg    3420
agccggaagc ataaagtgta aagcctgggg tgcctaatga gtgagctaac tcacattaat    3480
tgcgttgcgc tcactgcccg ctttccagtc gggaaacctg tcgtgccagc tgcattaatg    3540
aatcggccaa cgcgcgggga gaggcggttt gcgtattggg cgctcttccg cttcctcgct    3600
cactgactcg ctgcgctcgg tcgttcggct gcggcgagcg gtatcagctc actcaaaggc    3660
ggtaatacgg ttatccacag aatcagggga taacgcagga agaacatgt gagcaaaagg    3720
ccagcaaaag gccaggaacc gtaaaaaggc cgcgttgctg gcgttttcc ataggctccg    3780
cccccctgac gagcatcaca aaaatcgacg ctcaagtcag aggtggcgaa acccgacagg    3840
actataaaga taccaggcgt ttccccctgg aagctccctc gtgcgctctc ctgttccgac    3900
cctgccgctt accggatacc tgtccgcctt tctcccttcg ggaagcgtgg cgctttctca    3960
tagctcacgc tgtaggtatc tcagttcggt gtaggtcgtt cgctccaagc tgggctgtgt    4020
gcacgaaccc cccgttcagc ccgaccgctg cgccttatcc ggtaactatc gtcttgagtc    4080
caacccggta agacacgact tatcgccact ggcagcagcc actggtaaca ggattagcag    4140
agcgaggtat gtaggcggtg ctacagagtt cttgaagtgg tggcctaact acggctacac    4200
tagaagaaca gtatttggta tctgcgctct gctgaagcca gttaccttcg gaaaaagagt    4260
tggtagctct tgatccggca aacaaaccac cgctggtagc ggtggttttt tgtttgcaa    4320
gcagcagatt acgcgcagaa aaaaggatc tcaagaagat cctttgatct tttctacggg    4380
gtctgacgct cagtggaacg aaaactcacg ttaagggatt ttggtcatga gattatcaaa    4440
aaggatcttc acctagatcc ttttaaatta aaaatgaagt tttaaatcaa tctaaagtat    4500
atatgagtaa acttggtctg acagttacca atgcttaatc agtgaggcac ctatctcagc    4560
gatctgtcta tttcgttcat ccatagttgc ctgactcccc gtcgtgtaga taactacgat    4620
acgggagggc ttaccatctg gccccagtgc tgcaatgata ccgcgagacc cacgctcacc    4680
ggctccagat ttatcagcaa taaaccagcc agccggaagg gccgagcgca gaagtggtcc    4740
tgcaacttta tccgcctcca tccagtctat taattgttgc cgggaagcta gagtaagtag    4800
ttcgccagtt aatagtttgc gcaacgttgt tgccattgct acaggcatcg tggtgtcacg    4860
ctcgtcgttt ggtatggctt cattcagctc cggttcccaa cgatcaaggc gagttacatg    4920
atccccccatg ttgtgcaaaa aagcggttag ctccttcggt cctccgatcg ttgtcagaag    4980
```

```
taagttggcc gcagtgttat cactcatggt tatggcagca ctgcataatt ctcttactgt    5040
catgccatcc gtaagatgct tttctgtgac tggtgagtac tcaaccaagt cattctgaga    5100
atagtgtatg cggcgaccga gttgctcttg cccggcgtca atacgggata ataccgcgcc    5160
acatagcaga actttaaaag tgctcatcat tggaaaacgt tcttcggggc gaaaactctc    5220
aaggatctta ccgctgttga gatccagttc gatgtaaccc actcgtgcac ccaactgatc    5280
ttcagcatct tttactttca ccagcgtttc tgggtgagca aaaacaggaa ggcaaaatgc    5340
cgcaaaaaag ggaataaggg cgacacggaa atgttgaata ctcatactct ccttttttca    5400
atattattga agcatttatc agggttattg tctcatgagc ggatacatat ttgaatgtat    5460
ttagaaaaat aaacaaatag gggttccgcg cacatttccc cgaaaagtgc cacctgacgt    5520
c                                                                    5521
```

<210> SEQ ID NO 25
<211> LENGTH: 550
<212> TYPE: PRT
<213> ORGANISM: Artificial Sequence
<220> FEATURE:
<223> OTHER INFORMATION: RSV A2 F protein

<400> SEQUENCE: 25

```
Met Gly Glu Leu Leu Ile Leu Lys Ala Asn Ala Ile Thr Thr Ile Leu
 1               5                  10                  15

Thr Ala Val Thr Phe Cys Phe Ala Ser Gly Gln Asn Ile Thr Glu Glu
            20                  25                  30

Phe Tyr Gln Ser Thr Cys Ser Ala Val Ser Lys Gly Tyr Leu Ser Ala
        35                  40                  45

Leu Arg Thr Gly Trp Tyr Thr Ser Val Ile Thr Ile Glu Leu Ser Asn
    50                  55                  60

Ile Lys Glu Asn Lys Cys Asn Gly Thr Asp Ala Lys Val Lys Leu Ile
65                  70                  75                  80

Lys Gln Glu Leu Asp Lys Tyr Lys Asn Ala Val Thr Glu Leu Gln Leu
                85                  90                  95

Leu Met Gln Ser Thr Pro Pro Thr Asn Asn Arg Ala Arg Arg Glu Leu
            100                 105                 110

Pro Arg Phe Met Asn Tyr Thr Leu Asn Asn Ala Lys Lys Thr Asn Val
        115                 120                 125

Thr Leu Ser Lys Lys Arg Lys Arg Arg Phe Leu Gly Phe Leu Leu Gly
    130                 135                 140

Val Gly Ser Ala Ile Ala Ser Gly Val Ala Val Ser Lys Val Leu His
145                 150                 155                 160

Leu Glu Gly Glu Val Asn Lys Ile Lys Ser Ala Leu Leu Ser Thr Asn
                165                 170                 175

Lys Ala Val Val Ser Leu Ser Asn Gly Val Ser Val Leu Thr Ser Lys
            180                 185                 190

Val Leu Asp Leu Lys Asn Tyr Ile Asp Lys Gln Leu Leu Pro Ile Val
        195                 200                 205

Asn Lys Gln Ser Cys Ser Ile Ser Asn Ile Glu Thr Val Ile Glu Phe
    210                 215                 220

Gln Gln Lys Asn Asn Arg Leu Leu Glu Ile Thr Arg Glu Phe Ser Val
225                 230                 235                 240

Asn Ala Gly Val Thr Thr Pro Val Ser Thr Tyr Met Leu Thr Asn Ser
                245                 250                 255
```

```
Glu Leu Leu Ser Leu Ile Asn Asp Met Pro Ile Thr Asn Asp Gln Lys
            260                 265                 270

Lys Leu Met Ser Asn Asn Val Gln Ile Val Arg Gln Gln Ser Tyr Ser
        275                 280                 285

Ile Met Ser Ile Ile Lys Glu Glu Val Leu Ala Tyr Val Val Gln Leu
    290                 295                 300

Pro Leu Tyr Gly Val Ile Asp Thr Pro Cys Trp Lys Leu His Thr Ser
305                 310                 315                 320

Pro Leu Cys Thr Thr Asn Thr Lys Glu Gly Ser Asn Ile Cys Leu Thr
                325                 330                 335

Arg Thr Asp Arg Gly Trp Tyr Cys Asp Asn Ala Gly Ser Val Ser Phe
                340                 345                 350

Phe Pro Gln Ala Glu Thr Cys Lys Val Gln Ser Asn Arg Val Phe Cys
            355                 360                 365

Asp Thr Met Asn Ser Leu Thr Leu Pro Ser Glu Ile Asn Leu Cys Asn
        370                 375                 380

Val Asp Ile Phe Asn Pro Lys Tyr Asp Cys Lys Ile Met Thr Ser Lys
385                 390                 395                 400

Thr Asp Val Ser Ser Val Ile Thr Ser Leu Gly Ala Ile Val Ser
                405                 410                 415

Cys Tyr Gly Lys Thr Lys Cys Thr Ala Ser Asn Lys Asn Arg Gly Ile
                420                 425                 430

Ile Lys Thr Phe Ser Asn Gly Cys Asp Tyr Val Ser Asn Lys Gly Met
            435                 440                 445

Asp Thr Val Ser Val Gly Asn Thr Leu Tyr Tyr Val Asn Lys Gln Glu
        450                 455                 460

Gly Lys Ser Leu Tyr Val Lys Gly Glu Pro Ile Ile Asn Phe Tyr Asp
465                 470                 475                 480

Pro Leu Val Phe Pro Ser Asp Glu Phe Asp Ala Ser Ile Ser Gln Val
                485                 490                 495

Asn Glu Lys Ile Asn Gln Ser Leu Ala Phe Ile Arg Lys Ser Asp Glu
            500                 505                 510

Leu Leu His Asn Val Asn Ala Gly Lys Ser Thr Thr Asn Gln Ala Tyr
        515                 520                 525

Val Glu Gln Lys Leu Ile Ser Glu Glu Asp Leu Asn Ser Ala Val Asp
    530                 535                 540

His His His His His His
545                 550

<210> SEQ ID NO 26
<211> LENGTH: 24
<212> TYPE: DNA
<213> ORGANISM: Artificial Sequence
<220> FEATURE:
<223> OTHER INFORMATION: VH1a Forward Primer

<400> SEQUENCE: 26
ggatcctctt cttggtggca gcag                                          24

<210> SEQ ID NO 27
<211> LENGTH: 24
<212> TYPE: DNA
<213> ORGANISM: Artificial Sequence
<220> FEATURE:
<223> OTHER INFORMATION: VH1b Forward Primer

<400> SEQUENCE: 27
```
gcatcctttt cttggtggca gcac                                              24

<210> SEQ ID NO 28
<211> LENGTH: 24
<212> TYPE: DNA
<213> ORGANISM: Artificial Sequence
<220> FEATURE:
<223> OTHER INFORMATION: VH1c Forward Primer

<400> SEQUENCE: 28
gggtcttctg cttgctggct gtag                                              24

<210> SEQ ID NO 29
<211> LENGTH: 24
<212> TYPE: DNA
<213> ORGANISM: Artificial Sequence
<220> FEATURE:
<223> OTHER INFORMATION: VH1d Forward Primer

<400> SEQUENCE: 29
ggatcctctt cttggtggga gcag                                              24

<210> SEQ ID NO 30
<211> LENGTH: 24
<212> TYPE: DNA
<213> ORGANISM: Artificial Sequence
<220> FEATURE:
<223> OTHER INFORMATION: VH2a Forward Primer

<400> SEQUENCE: 30
ctgaccatcc cttcatggct cttg                                              24

<210> SEQ ID NO 31
<211> LENGTH: 24
<212> TYPE: DNA
<213> ORGANISM: Artificial Sequence
<220> FEATURE:
<223> OTHER INFORMATION: VH2b Forward Primer

<400> SEQUENCE: 31
ctgaccaccc cttcctgggt cttg                                              24

<210> SEQ ID NO 32
<211> LENGTH: 24
<212> TYPE: DNA
<213> ORGANISM: Artificial Sequence
<220> FEATURE:
<223> OTHER INFORMATION: VH3a Forward Primer

<400> SEQUENCE: 32
gctattttar aaggtgtcca gtgt                                              24

<210> SEQ ID NO 33
<211> LENGTH: 24
<212> TYPE: DNA
<213> ORGANISM: Artificial Sequence
<220> FEATURE:
<223> OTHER INFORMATION: VH3b Forward Primer

<400> SEQUENCE: 33
gctcttttaa gaggtgtcca gtgt                                              24

<210> SEQ ID NO 34
<211> LENGTH: 24
<212> TYPE: DNA
<213> ORGANISM: Artificial Sequence

```
<220> FEATURE:
<223> OTHER INFORMATION: VH3c Forward Primer

<400> SEQUENCE: 34
gctatttaaa aaggtgtcca atgt                                          24

<210> SEQ ID NO 35
<211> LENGTH: 24
<212> TYPE: DNA
<213> ORGANISM: Artificial Sequence
<220> FEATURE:
<223> OTHER INFORMATION: VH4a Forward Primer

<400> SEQUENCE: 35
ctggtggcag ctcccagatg ggtc                                          24

<210> SEQ ID NO 36
<211> LENGTH: 24
<212> TYPE: DNA
<213> ORGANISM: Artificial Sequence
<220> FEATURE:
<223> OTHER INFORMATION: VH5a Forward Primer

<400> SEQUENCE: 36
ctcctggctg ttctccaagg agtc                                          24

<210> SEQ ID NO 37
<211> LENGTH: 28
<212> TYPE: DNA
<213> ORGANISM: Artificial Sequence
<220> FEATURE:
<223> OTHER INFORMATION: VH-g 1-REV Reverse Primer

<400> SEQUENCE: 37
acaagatttg ggctcaactt tcttgtcc                                      28

<210> SEQ ID NO 38
<211> LENGTH: 28
<212> TYPE: DNA
<213> ORGANISM: Artificial Sequence
<220> FEATURE:
<223> OTHER INFORMATION: VH-g 2-REV Reverse Primer

<400> SEQUENCE: 38
tttgcgctca actgtcttgt ccaccttg                                      28

<210> SEQ ID NO 39
<211> LENGTH: 28
<212> TYPE: DNA
<213> ORGANISM: Artificial Sequence
<220> FEATURE:
<223> OTHER INFORMATION: VH-g 3-REV Reverse Primer

<400> SEQUENCE: 39
tttgagctca actctcttgt ccaccttg                                      28

<210> SEQ ID NO 40
<211> LENGTH: 28
<212> TYPE: DNA
<213> ORGANISM: Artificial Sequence
<220> FEATURE:
<223> OTHER INFORMATION: VH-g 4-REV Reverse Primer

<400> SEQUENCE: 40
atatttggac tcaactctct tgtccacc                                      28
```

```
<210> SEQ ID NO 41
<211> LENGTH: 13
<212> TYPE: DNA
<213> ORGANISM: Artificial Sequence
<220> FEATURE:
<223> OTHER INFORMATION: SfiI Restriction Site
<220> FEATURE:
<221> NAME/KEY: misc_feature
<222> LOCATION: (5)...(9)
<223> OTHER INFORMATION: N = a or g or c or t

<400> SEQUENCE: 41
ggccnnnnng gcc                                                              13

<210> SEQ ID NO 42
<211> LENGTH: 48
<212> TYPE: DNA
<213> ORGANISM: Artificial Sequence
<220> FEATURE:
<223> OTHER INFORMATION: pCal30 VH1a Forward Primer

<400> SEQUENCE: 42
ggctttgcta ccgtagcgca ggcggccgca caggtkcagc tggtgcag                        48

<210> SEQ ID NO 43
<211> LENGTH: 48
<212> TYPE: DNA
<213> ORGANISM: Artificial Sequence
<220> FEATURE:
<223> OTHER INFORMATION: pCal30 VH1b Forward Primer

<400> SEQUENCE: 43
ggctttgcta ccgtagcgca ggcggccgca caggtccagc ttgtgcag                        48

<210> SEQ ID NO 44
<211> LENGTH: 48
<212> TYPE: DNA
<213> ORGANISM: Artificial Sequence
<220> FEATURE:
<223> OTHER INFORMATION: pCal30 VH1c Forward Primer

<400> SEQUENCE: 44
ggctttgcta ccgtagcgca ggcggccgca saggtccagc tggtacag                        48

<210> SEQ ID NO 45
<211> LENGTH: 48
<212> TYPE: DNA
<213> ORGANISM: Artificial Sequence
<220> FEATURE:
<223> OTHER INFORMATION: pCal30 VH1d Forward Primer

<400> SEQUENCE: 45
ggctttgcta ccgtagcgca ggcggccgca caratgcagc tggtgcag                        48

<210> SEQ ID NO 46
<211> LENGTH: 48
<212> TYPE: DNA
<213> ORGANISM: Artificial Sequence
<220> FEATURE:
<223> OTHER INFORMATION: pCal30 VH2a Forward Primer

<400> SEQUENCE: 46
ggctttgcta ccgtagcgca ggcggccgca cagatcacct tgaaggag                        48

<210> SEQ ID NO 47
<211> LENGTH: 48
```

```
<212> TYPE: DNA
<213> ORGANISM: Artificial Sequence
<220> FEATURE:
<223> OTHER INFORMATION: pCal30 VH3a Forward Primer

<400> SEQUENCE: 47
ggctttgcta ccgtagcgca ggcggccgca gargtgcagc tggtggag            48

<210> SEQ ID NO 48
<211> LENGTH: 48
<212> TYPE: DNA
<213> ORGANISM: Artificial Sequence
<220> FEATURE:
<223> OTHER INFORMATION: pCal30 VH4a Forward Primer

<400> SEQUENCE: 48
ggctttgcta ccgtagcgca ggcggccgca cagstgcagc tgcaggag            48

<210> SEQ ID NO 49
<211> LENGTH: 48
<212> TYPE: DNA
<213> ORGANISM: Artificial Sequence
<220> FEATURE:
<223> OTHER INFORMATION: pCal30 VH4b Forward Primer

<400> SEQUENCE: 49
ggctttgcta ccgtagcgca ggcggccgca caggtgcagc tacagcag            48

<210> SEQ ID NO 50
<211> LENGTH: 48
<212> TYPE: DNA
<213> ORGANISM: Artificial Sequence
<220> FEATURE:
<223> OTHER INFORMATION: pCal30 VH5a Forward Primer

<400> SEQUENCE: 50
ggctttgcta ccgtagcgca ggcggccgca gargtgcagc tggtgcag            48

<210> SEQ ID NO 51
<211> LENGTH: 48
<212> TYPE: DNA
<213> ORGANISM: Artificial Sequence
<220> FEATURE:
<223> OTHER INFORMATION: pCal30 VH6 Forward Primer

<400> SEQUENCE: 51
ggctttgcta ccgtagcgca ggcggccgca caggtacagc tgcagcag            48

<210> SEQ ID NO 52
<211> LENGTH: 48
<212> TYPE: DNA
<213> ORGANISM: Artificial Sequence
<220> FEATURE:
<223> OTHER INFORMATION: pCal30 VH7 Forward Primer

<400> SEQUENCE: 52
ggctttgcta ccgtagcgca ggcggccgca caggtscagc tggtgcaa            48

<210> SEQ ID NO 53
<211> LENGTH: 42
<212> TYPE: DNA
<213> ORGANISM: Artificial Sequence
<220> FEATURE:
<223> OTHER INFORMATION: VHII-g1-Rev Reverse Primer

<400> SEQUENCE: 53
```
tgcggccggc ctggccgacc acaagatttg ggctcaactt tc        42

<210> SEQ ID NO 54
<211> LENGTH: 42
<212> TYPE: DNA
<213> ORGANISM: Artificial Sequence
<220> FEATURE:
<223> OTHER INFORMATION: VHII-g2-Rev Reverse Primer

<400> SEQUENCE: 54
tgcggccggc ctggccgacc tttgcgctca actgtcttgt cc        42

<210> SEQ ID NO 55
<211> LENGTH: 42
<212> TYPE: DNA
<213> ORGANISM: Artificial Sequence
<220> FEATURE:
<223> OTHER INFORMATION: VHII-g3-Rev Reverse Primer

<400> SEQUENCE: 55
tgcggccggc ctggccgacc tttgagctca actctcttgt cc        42

<210> SEQ ID NO 56
<211> LENGTH: 42
<212> TYPE: DNA
<213> ORGANISM: Artificial Sequence
<220> FEATURE:
<223> OTHER INFORMATION: VHII-g4-Rev Reverse Primer

<400> SEQUENCE: 56
tgcggccggc ctggccgacc atatttggac tcaactctct tg        42

<210> SEQ ID NO 57
<211> LENGTH: 45
<212> TYPE: DNA
<213> ORGANISM: Artificial Sequence
<220> FEATURE:
<223> OTHER INFORMATION: VK 1a Forward Primer

<400> SEQUENCE: 57
aaggcccagc cggccatggc cgccggtgac atccagatga cccag        45

<210> SEQ ID NO 58
<211> LENGTH: 45
<212> TYPE: DNA
<213> ORGANISM: Artificial Sequence
<220> FEATURE:
<223> OTHER INFORMATION: VK 1b Forward Primer

<400> SEQUENCE: 58
aaggcccagc cggccatggc cgccggtgac atccagttga cccag        45

<210> SEQ ID NO 59
<211> LENGTH: 45
<212> TYPE: DNA
<213> ORGANISM: Artificial Sequence
<220> FEATURE:
<223> OTHER INFORMATION: VK 1c Forward Primer

<400> SEQUENCE: 59
aaggcccagc cggccatggc cgccggtgcc atccggttga cccag        45

<210> SEQ ID NO 60
<211> LENGTH: 45
<212> TYPE: DNA
<213> ORGANISM: Artificial Sequence
<220> FEATURE:
<223> OTHER INFORMATION: VK 2a Forward Primer

<400> SEQUENCE: 60
aaggcccagc cggccatggc cgccggtgat attgtgatga cycag    45

<210> SEQ ID NO 61
<211> LENGTH: 45
<212> TYPE: DNA
<213> ORGANISM: Artificial Sequence
<220> FEATURE:
<223> OTHER INFORMATION: VK 3a Forward Primer

<400> SEQUENCE: 61
aaggcccagc cggccatggc cgccggtgaa attgtgttga cgcag    45

<210> SEQ ID NO 62
<211> LENGTH: 45
<212> TYPE: DNA
<213> ORGANISM: Artificial Sequence
<220> FEATURE:
<223> OTHER INFORMATION: VK 3b Forward Primer

<400> SEQUENCE: 62
aaggcccagc cggccatggc cgccggtgaa attgtgttga cacag    45

<210> SEQ ID NO 63
<211> LENGTH: 45
<212> TYPE: DNA
<213> ORGANISM: Artificial Sequence
<220> FEATURE:
<223> OTHER INFORMATION: VK 4a Forward Primer

<400> SEQUENCE: 63
aaggcccagc cggccatggc cgccggtgaa atagtgatga cgcag    45

<210> SEQ ID NO 64
<211> LENGTH: 45
<212> TYPE: DNA
<213> ORGANISM: Artificial Sequence
<220> FEATURE:
<223> OTHER INFORMATION: VK 4a  Forward Primer

<400> SEQUENCE: 64
aaggcccagc cggccatggc cgccggtgac atcgtgatga cccag    45

<210> SEQ ID NO 65
<211> LENGTH: 45
<212> TYPE: DNA
<213> ORGANISM: Artificial Sequence
<220> FEATURE:
<223> OTHER INFORMATION: VK 5a  Forward Primer

<400> SEQUENCE: 65
aaggcccagc cggccatggc cgccggtgaa acgacactca cgcag    45

<210> SEQ ID NO 66
<211> LENGTH: 45
<212> TYPE: DNA
<213> ORGANISM: Artificial Sequence
<220> FEATURE:
<223> OTHER INFORMATION: VK 6a  Forward Primer

<400> SEQUENCE: 66
aaggcccagc cggccatggc cgccggtgaa attgtgctga ctcag    45

<210> SEQ ID NO 67
<211> LENGTH: 45
<212> TYPE: DNA
<213> ORGANISM: Artificial Sequence
<220> FEATURE:
<223> OTHER INFORMATION: VK 6b Forward Primer

<400> SEQUENCE: 67
aaggcccagc cggccatggc cgccggtgat gttgtgatga cacag          45

<210> SEQ ID NO 68
<211> LENGTH: 44
<212> TYPE: DNA
<213> ORGANISM: Artificial Sequence
<220> FEATURE:
<223> OTHER INFORMATION: pCALCK(G)L Reverse Primer

<400> SEQUENCE: 68
ctccttatta attaattagc actctcccct gttgaagctc tttg          44

<210> SEQ ID NO 69
<211> LENGTH: 50
<212> TYPE: DNA
<213> ORGANISM: Artificial Sequence
<220> FEATURE:
<223> OTHER INFORMATION: VL1-F Forward Primer

<400> SEQUENCE: 69
aaggcccagc cggccatggc cgccggtgtt cagtctgtgc tgackcagcc          50

<210> SEQ ID NO 70
<211> LENGTH: 50
<212> TYPE: DNA
<213> ORGANISM: Artificial Sequence
<220> FEATURE:
<223> OTHER INFORMATION: VL2-F Forward Primer

<400> SEQUENCE: 70
aaggcccagc cggccatggc cgccggtgtt cagtctgccc tgactcagcc          50

<210> SEQ ID NO 71
<211> LENGTH: 50
<212> TYPE: DNA
<213> ORGANISM: Artificial Sequence
<220> FEATURE:
<223> OTHER INFORMATION: VL3A-F Forward Primer

<400> SEQUENCE: 71
aaggcccagc cggccatggc cgccggtgtt tcctatgagc tgacwcagcy          50

<210> SEQ ID NO 72
<211> LENGTH: 51
<212> TYPE: DNA
<213> ORGANISM: Artificial Sequence
<220> FEATURE:
<223> OTHER INFORMATION: VL3B-F Forward Primer

<400> SEQUENCE: 72
aaggcccagc cggccatggc cgccggtgtt tcttctgagc tgactcagga c          51

<210> SEQ ID NO 73
<211> LENGTH: 50
<212> TYPE: DNA
<213> ORGANISM: Artificial Sequence
<220> FEATURE:
<223> OTHER INFORMATION: VL3C-F Forward Primer

<400> SEQUENCE: 73
aaggcccagc cggccatggc cgccggtgtt tcctatgwgc tgactcagcc        50

<210> SEQ ID NO 74
<211> LENGTH: 51
<212> TYPE: DNA
<213> ORGANISM: Artificial Sequence
<220> FEATURE:
<223> OTHER INFORMATION: VL4A-F Forward Primer

<400> SEQUENCE: 74
aaggcccagc cggccatggc cgccggtgtt ctgcctgtgc tgactcagcc c      51

<210> SEQ ID NO 75
<211> LENGTH: 51
<212> TYPE: DNA
<213> ORGANISM: Artificial Sequence
<220> FEATURE:
<223> OTHER INFORMATION: VL4B-F Forward Primer

<400> SEQUENCE: 75
aaggcccagc cggccatggc cgccggtgtt cagcytgtgc tgactcaatc r      51

<210> SEQ ID NO 76
<211> LENGTH: 51
<212> TYPE: DNA
<213> ORGANISM: Artificial Sequence
<220> FEATURE:
<223> OTHER INFORMATION: VL5/9-F Forward Primer

<400> SEQUENCE: 76
aaggcccagc cggccatggc cgccggtgtt cagsctgtgc tgactcagcc r      51

<210> SEQ ID NO 77
<211> LENGTH: 51
<212> TYPE: DNA
<213> ORGANISM: Artificial Sequence
<220> FEATURE:
<223> OTHER INFORMATION: VL6-F Forward Primer

<400> SEQUENCE: 77
aaggcccagc cggccatggc cgccggtgtt aattttatgc tgactcagcc c      51

<210> SEQ ID NO 78
<211> LENGTH: 51
<212> TYPE: DNA
<213> ORGANISM: Artificial Sequence
<220> FEATURE:
<223> OTHER INFORMATION: VL7/8-F Forward Primer

<400> SEQUENCE: 78
aaggcccagc cggccatggc cgccggtgtt cagrctgtgg tgactcagga g      51

<210> SEQ ID NO 79
<211> LENGTH: 51
<212> TYPE: DNA
<213> ORGANISM: Artificial Sequence
<220> FEATURE:
<223> OTHER INFORMATION: VL10-F Forward Primer

<400> SEQUENCE: 79
aaggcccagc cggccatggc cgccggtgtt caggcagggc tgactcagcc a      51

<210> SEQ ID NO 80

```
<211> LENGTH: 43
<212> TYPE: DNA
<213> ORGANISM: Artificial Sequence
<220> FEATURE:
<223> OTHER INFORMATION: pCALCL(T)-R Reverse Primer

<400> SEQUENCE: 80
ctccttatta attaattatg agcattctgy akgggcmayt gtc                          43

<210> SEQ ID NO 81
<211> LENGTH: 4765
<212> TYPE: DNA
<213> ORGANISM: Artificial Sequence
<220> FEATURE:
<223> OTHER INFORMATION: 2g12/pCal Vector

<400> SEQUENCE: 81
gtggcacttt tcggggaaat gtgcgcggaa cccctatttg tttatttttc taaatacatt         60
caaatatgta tccgctcatg agacaataac cctgataaat gcttcaataa tattgaaaaa        120
ggaagagtat gagtattcaa catttccgtg tcgcccttat tcccttttt  gcggcatttt        180 gccttcctgt ttttgctcac ccagaaacgc tggtgaaagt aaaagatgct gaagatcagt        240
tgggtgcacg agtgggttac atcgaactgg atctcaacag cggtaagatc cttgagagtt        300
ttcgccccga agaacgtttt ccaatgatga gcacttttaa agttctgcta tgtggcgcgg        360
tattatcccg tattgacgcc gggcaagagc aactcggtcg ccgcatacac tattctcaga        420
atgacttggt tgagtactca ccagtcacag aaaagcatct tacggatggc atgacagtaa        480
gagaattatg cagtgctgcc ataaccatga gtgataacac tgcggccaac ttacttctga        540
caacgatcgg aggaccgaag gagctaaccg cttttttgca acatggggg  gatcatgtaa        600 ctcgccttga tcgttgggaa ccggagctga atgaagccat accaaacgac gagcgtgaca        660
ccacgatgcc tgtagcaatg gcaacaacgt tgcgcaaact attaactggc gaactactta        720
ctctagcttc ccggcaacaa ttaatagact ggatggaggc ggataaagtt gcaggaccac        780
ttctgcgctc ggcccttccg gctggctggt ttattgctga taaatctgga gccggtgagc        840
gtgggtctcg cggtatcatt gcagcactgg ggccagatgg taagccctcc cgtatcgtag        900
ttatctacac gacggggagt caggcaacta tggatgaacg aaatagacag atcgctgaga        960
taggtgcctc actgattaag cattggtaac tgtcagacca agtttactca tatatacttt       1020
agattgattt aaaacttcat ttttaattta aaaggatcta ggtgaagatc ctttttgata       1080
atctcatgac caaaatccct aacgtgagt  tttcgttcca ctgagcgtca ccccgtag         1140 aaaagatcaa aggatcttct tgagatcctt ttttctgcg  cgtaatctgc tgcttgcaaa       1200
caaaaaaacc accgctacca gcggtggttt gtttgccgga tcaagagcta ccaactcttt       1260
ttccgaaggt aactggcttc agcagagcgc agataccaaa tactgtcctt ctagtgtagc       1320
cgtagttagg ccaccacttc aagaactctg tagcaccgcc tacatacctc gctctgctaa       1380
tcctgttacc agtggctgct gccagtggcg ataagtcgtg tcttaccggg ttggactcaa       1440
gacgatagtt accggataag gcgcagcggt cgggctgaac ggggggttcg tgcacacagc       1500
ccagcttgga gcgaacgacc tacaccgaac tgagatacct acagcgtgag ctatgagaaa       1560
gcgccacgct tcccgaaggg agaaaggcgg acaggtatcc ggtaagcggc agggtcggaa       1620
caggagagcg cacgagggag cttccagggg gaaacgcctg gtatctttat agtcctgtcg       1680
ggtttcgcca cctctgactt gagcgtcgat ttttgtgatg ctcgtcaggg gggcggagcc       1740
tatggaaaaa cgccagcaac gcggcctttt tacggttcct ggccttttgc tggccttttg       1800
```

-continued

```
ctcacatgtt cttctcctgcg ttatcccctg attctgtgga taaccgtatt accgcctttg    1860
agtgagctga taccgctcgc cgcagccgaa cgaccgagcg cagcgagtca gtgagcgagg    1920
aagcggaaga gcgcccaata cgcaaaccgc ctctccccgc gcgttggccg attcattaat    1980
gcagctggca cgacaggttt cccgactgga aagcgggcag tgagcgcaac gcaattaatg    2040
tgagttagct cactcattag gcaccccagg ctttacactt tatgcttccg gctcgtatgt    2100
tgtgtggaat tgtgagcgga taacaattga attaaggagg atataattat gaaatacctg    2160
ctgccgaccg cagccgctgg tctgctgctg ctcgcggccc agccggccat ggccgccggt    2220
gttgttatga cccagtctcc gtctaccctg tctgcttctg ttggtgacac catcaccatc    2280
acctgccgtg cttctcagtc tatcgaaacc tggctggctt ggtaccagca gaaaccgggt    2340
aaagctccga actgctgat ctacaaggct ctacccctga aaaccggtgt tccgtctcgt    2400
ttctctggtt ctggttctgg taccgagttc accctgacca tctctggtct gcagttcgac    2460
gacttcgcta cctaccactg ccagcactac gctggttact ctgctacctt cggtcagggt    2520
acccgtgttg aaatcaaacg taccgttgct gctccgtctg ttttcatctt cccgccgtct    2580
gacgaacagc tgaaatctgg taccgcttct gttgtttgcc tgctgaacaa cttctacccg    2640
cgtgaagcta aagttcagtg gaaagttgac aacgctctgc agtctggtaa ctctcaggaa    2700
tctgttaccg aacaggactc taaagactct acctactctc tgtcttctac cctgaccctg    2760
tctaaagctg actacgaaaa gcacaaagtt tacgcttgcg aagttaccca ccagggtctg    2820
tcttctccgg ttaccaaatc tttcaaccgt ggtgaatgct aattaattaa taaggaggat    2880
ataattatga aaagacagc tatcgcgatt gcagtggcac tggctggttt cgctaccgta    2940
gcccaggcgg ccgcagaagt tcagctggtt gaatctggtg gtggtctggt aaaagctggt    3000
ggttctctga tcctgtcttg cggtgtttct aacttccgta tctctgctca caccatgaac    3060
tgggttcgtc gtgttccggg tggtggtctg aatgggttg cttctatctc tacctcttct    3120
acctaccgtg actacgctga cgctgttaaa ggtcgtttca ccgtttctcg tgacgacctg    3180
gaagacttcg tttacctgca gatgcataaa atgcgtgttg aagacaccgc tatctactac    3240
tgcgctcgta aaggttctga ccgtctgtct gacaacgacc cgttcgacgc ttggggtccg    3300
ggtaccgttg ttaccgtttc tccggcgtcg accaaaggtc cgtctgtttt cccgctggct    3360
ccgtcttcta atctacctc tggtggtacc gctgctctgg gttgcctggt taaagactac    3420
ttcccggaac cggttaccgt ttcttggaac tctggtgctc tgacctctgg tgttcacacc    3480
ttcccggctg tttctgcagtc ttctggtctg tactctctgt cttctgttgt taccgttccg    3540
tcttcttctc tgggtaccca gacctacatc tgcaacgtta ccacaaaacc gtctaacacc    3600
aaagttgaca agaaagttga accgaaatct tgcctgcgat cgcggccagg ccggccgcac    3660
catcaccatc accatggcgc atacccgtac gacgttccgg actacgcttc tactagttag    3720
aagggtggtg gctctgaggg tggcggttct gagggtggcg gctctgaggg aggcggttcc    3780
ggtggtggct ctggttccgg tgatttgat tatgaaaaga tggcaaacgc taataagggg    3840
gctatgaccg aaaatgccga tgaaaacgcg ctacagtctg acgctaaagg caaacttgat    3900
tctgtcgcta ctgattacgg tgctgctatc gatggtttca ttggtgacgt ttccggcctt    3960
gctaatggta atggtgctac tggtgatttt gctggctcta attcccaaat ggctcaagtc    4020
ggtgacggtg ataattcacc tttaatgaat aatttccgtc aatatttacc ttccctccct    4080
caatcggttg aatgtcgccc ttttgtcttt ggcgctggta accatatga attttctatt    4140
```

-continued

```
gattgtgaca aaataaactt attccgtggt gtctttgcgt ttctttata tgttgccacc    4200 tttatgtatg tattttctac gtttgctaac atactgcgta ataaggagtc ttaagctagc    4260
taacgatcgc ccttcccaac agttgcgcag cctgaatggc gaatgggacg cgccctgtag    4320
cggcgcatta agcgcggcgg gtgtggtggt tacgcgcagc gtgaccgcta cacttgccag    4380
cgccctagcg cccgctcctt tcgctttctt cccttccttt ctcgccacgt tcgccggctt    4440
tccccgtcaa gctctaaatc ggggctccc tttaggggttc cgatttagtg ctttacggca    4500
cctcgacccc aaaaaacttg attagggtga tggttcacgt agtgggccat cgccctgata    4560
gacggttttt cgccctttga cgttggagtc cacgttcttt aatagtggac tcttgttcca    4620
aactggaaca acactcaacc ctatctcggt ctattctttt gatttataag ggattttgcc    4680
gatttcggcc tattggttaa aaatgagct gatttaacaa aaatttaacg cgaattttaa    4740
caaaatatta acgcttacaa tttag                                          4765
```

<210> SEQ ID NO 82
<211> LENGTH: 40
<212> TYPE: DNA
<213> ORGANISM: Artificial Sequence
<220> FEATURE:
<223> OTHER INFORMATION: FabLinkerCK-Fwd

<400> SEQUENCE: 82

```
gagcttcaac aggggagagt gctaattaat taataaggag                            40
```

<210> SEQ ID NO 83
<211> LENGTH: 42
<212> TYPE: DNA
<213> ORGANISM: Artificial Sequence
<220> FEATURE:
<223> OTHER INFORMATION: FabLinker-Rev

<400> SEQUENCE: 83

```
tgcggccgcc tgcgctacgg tagcaaagcc agccagtgcc ac                         42
```

<210> SEQ ID NO 84
<211> LENGTH: 22
<212> TYPE: DNA
<213> ORGANISM: Artificial Sequence
<220> FEATURE:
<223> OTHER INFORMATION: Sfi Forward Primer

<400> SEQUENCE: 84

```
tcgcggccca gccggccatg gc                                               22
```

<210> SEQ ID NO 85
<211> LENGTH: 18
<212> TYPE: DNA
<213> ORGANISM: Artificial Sequence
<220> FEATURE:
<223> OTHER INFORMATION: Sfi Reverse Primer

<400> SEQUENCE: 85

```
tgcggccggc ctggccga                                                    18
```

<210> SEQ ID NO 86
<211> LENGTH: 4779
<212> TYPE: DNA
<213> ORGANISM: Artificial Sequence
<220> FEATURE:
<223> OTHER INFORMATION: 4E10 pCAL vector

<400> SEQUENCE: 86

```
gtggcacttt tcggggaaat gtgcgcggaa cccctatttg tttatttttc taaatacatt    60
caaatatgta tccgctcatg agacaataac cctgataaat gcttcaataa tattgaaaaa   120
ggaagagtat gagtattcaa catttccgtg tcgcccttat tccctttttt gcggcatttt   180
gccttcctgt ttttgctcac ccagaaacgc tggtgaaagt aaaagatgct gaagatcagt   240
tgggtgcacg agtgggttac atcgaactgg atctcaacag cggtaagatc cttgagagtt   300
ttcgccccga agaacgtttt ccaatgatga gcacttttaa agttctgcta tgtggcgcgg   360
tattatcccg tattgacgcc gggcaagagc aactcggtcg ccgcatacac tattctcaga   420
atgacttggt tgagtactca ccagtcacag aaaagcatct tacgatggca tgacagtaa    480
gagaattatg cagtgctgcc ataaccatga gtgataacac tgcggccaac ttacttctga   540
caacgatcgg aggaccgaag gagctaaccg cttttttgca caacatgggg gatcatgtaa   600
ctcgccttga tcgttgggaa ccggagctga atgaagccat accaaacgac gagcgtgaca   660
ccacgatgcc tgtagcaatg gcaacaacgt tgcgcaaact attaactggc gaactactta   720
ctctagcttc ccggcaacaa ttaatagact ggatggaggc ggataaagtt gcaggaccac   780
ttctgcgctc ggcccttccg gctggctggt ttattgctga taaatctgga gccggtgagc   840
gtgggtctcg cggtatcatt gcagcactgg ggccagatgg taagccctcc cgtatcgtag   900
ttatctacac gacggggagt caggcaacta tggatgaacg aaatagacag atcgctgaga   960
taggtgcctc actgattaag cattggtaac tgtcagacca agtttactca tatatacttt  1020
agattgattt aaaacttcat ttttaattta aaaggatcta ggtgaagatc ctttttgata  1080
atctcatgac caaaatccct taacgtgagt tttcgttcca ctgagcgtca gaccccgtag  1140
aaaagatcaa aggatcttct tgagatcctt ttttctgcg cgtaatctgc tgcttgcaaa   1200
caaaaaaacc accgctacca gcggtggttt gtttgccgga tcaagagcta ccaactcttt  1260
ttccgaaggt aactggcttc agcagagcgc agataccaaa tactgtcctt ctagtgtagc  1320
cgtagttagg ccaccacttc aagaactctg tagcaccgcc tacatacctc gctctgctaa  1380
tcctgttacc agtggctgct gccagtggcg ataagtcgtg tcttaccggg ttggactcaa  1440
gacgatagtt accggataag cgcagcggt cgggctgaac ggggggttcg tgcacacagc   1500
ccagcttgga gcgaacgacc tacaccgaac tgagatacct acagcgtgag ctatgagaaa  1560
gcgccacgct tcccgaaggg agaaaggcgg acaggtatcc ggtaagcggc agggtcggaa  1620
caggagagcg cacgagggag cttccagggg gaaacgcctg gtatctttat agtcctgtcg  1680
ggtttcgcca cctctgactt gagcgtcgat ttttgtgatg ctcgtcaggg gggcggagcc  1740
tatgaaaaaa cgccagcaac gcggcctttt tacggttcct ggccttttgc tggccttttg  1800
ctcacatgtt ctttcctgcg ttatcccctg attctgtgga taaccgtatt accgcctttg  1860
agtgagctga taccgctcgc cgcagccgaa cgaccgagcg cagcgagtca gtgagcgagg  1920
aagcggaaga gcgcccaata cgcaaaccgc ctctccccgc gcgttggccg attcattaat  1980
gcagctggca cgacaggttt cccgactgga aagcgggcag tgagcgcaac gcaattaatg  2040
tgagttagct cactcattag gcaccccagg ctttacactt tatgcttccg gctcgtatgt  2100
tgtgtggaat tgtgagcgga taacaattga attaaggagg atataattat gaaataccctg  2160
ctgccgaccg cagccgctgg tctgctgctg ctcgcggccc agccggccat ggccgccggt  2220
gaaattgtct tgacgcaaag cccgggggacc cagtcgctgt ccccgggaga gcgcgcgacc  2280
ctgtcatgtc gtgcgagtca aagtgtcggt aacaataaac tggcttggta ccagcaacgt  2340
```

```
cctgggcagg caccgcgctt actcatttac ggagcctctt cacgtcccag cggggtagcg    2400
gatcgtttct ccggttctgg cagcggcact gatttcacct taacaatctc gcgtctggaa    2460
ccggaagatt ttgccgtcta ttactgtcag caatacggcc agtccttgtc tacatttggc    2520
cagggaacga aagtggaggt aaaacgtacc gttgctgccc ccagtgtttt catctttcca    2580
ccgtcagacg agcagctgaa gtctggtacc gcaagtgtgg tttgcctcct gaataacttt    2640
tatcctcgcg aagcgaaagt tcagtggaag gtggataatg ccctgcagtc gggtaatagc    2700
caggaaagcg tgaccgaaca agattcaaaa gactccacat attctctgag ttcgactctt    2760
acgttaagca aagctgacta tgaaaagcac aaagtttatg catgcgaggt gacgcatcag    2820 ggtcttttcca gcccagtaac taaatcattc aaccgcggcg aatgttaatt aataaggagg    2880
atataattat gaaaaagaca gctatcgcga ttgcagtggc actggctggt ttcgctaccg    2940
tagcccaggc ggccgcacag gtgcaactgg tgcagagtgg ggccgaagtt aaacgcccag    3000
gttcgtccgt aaccgtctca tgcaaggcca gcggtggctc tttctctacg tacgcgctgt    3060
cctgggttcg tcaggccccg ggtcgtggac ttgaatggat gggcggcgta ataccgctgc    3120
tcaccatcac taattacgca ccgcgttttc agggccgcat tacaatcacc gcggaccgtt    3180
cgacctcaac ggcatatctc gagttaaact cactgcgtcc tgaagatacc gcagtgtatt    3240
actgcgctcg tgaaggtacc actggctggg gctggttggg taaaccgatt ggtgcgttcg    3300
cacattgggg gcaaggcaca cttgttactg tcagctctgc ctctacgaaa ggaccgagcg    3360 tctttcccctt ggctccaagt agcaaatcaa cgagcggagg gacagccgcg ttaggatgtc    3420
tggtgaagga ctattttccg gaaccagtta ccgtcagttg gaactcgggc gcgttaactt    3480
ccggtgttca cacatttccc gctgttctgc aaagtagcgg tctgtattcc ctgtcctcag    3540
tagtgacagt tccttcgagt tctctgggca ctcagaccta tatttgcaat gtgaaccata    3600
aacctagcaa tacgaaagtg gataagaaag tagagccgaa atcttgtctg cgatcgcggc    3660
caggccggcc gcaccatcac catcaccatg gcgcataccc gtacgacgtt ccggactacg    3720
cttctactag ttagaagggt ggtggctctg agggtggcgg ttctgagggt ggcggctctg    3780
agggaggcgg ttccggtggt ggctctggtt ccggtgattt tgattatgaa agatggcaa    3840 acgctaataa gggggctatg accgaaaatg ccgatgaaaa cgcgctacag tctgacgcta    3900
aaggcaaact tgattctgtc gctactgatt acggtgctgc tatcgatggt ttcattggtg    3960
acgtttccgg ccttgctaat ggtaatggtg ctactggtga ttttgctggc tctaattccc    4020
aaatggctca gtcggtgac ggtgataatt cacctttaat gaataatttc cgtcaatatt    4080
taccttccct ccctcaatcg gttgaatgtc gcccttttgt ctttggcgct ggtaaaccat    4140
atgaattttc tattgattgt gacaaaataa acttattccg tggtgtcttt gcgtttcttt    4200
tatatgttgc cacctttatg tatgtatttt ctacgtttgc taacatactg cgtaataagg    4260
agtcttaagc tagctaacga tcgcccttcc caacagttgc gcagcctgaa tggcgaatgg    4320
gacgcgccct gtagcggcgc attaagcgcg gcgggtgtgg tggttacgcg cagcgtgacc    4380
gctacacttg ccagcgccct agcgcccgct cctttcgctt tcttcccttc ctttctcgcc    4440
acgttcgccg gctttccccg tcaagctcta aatcggggggc tccctttagg gttccgattt    4500
agtgctttac ggcacctcga ccccaaaaaa cttgattagg gtgatggttc acgtagtggg    4560
ccatcgccct gatagacggt ttttcgccct ttgacgttgg agtccacgtt ctttaatagt    4620
ggactcttgt tccaaactgg aacaacactc aaccctatct cggtctattc ttttgattta    4680
taagggattt tgccgatttc ggcctattgg ttaaaaaatg agctgattta acaaaaattt    4740
```

-continued aacgcgaatt ttaacaaaat attaacgctt acaatttag     4779

<210> SEQ ID NO 87
<211> LENGTH: 25
<212> TYPE: DNA
<213> ORGANISM: Artificial Sequence
<220> FEATURE:
<223> OTHER INFORMATION: 5' LVKappa1/2 Forward Primer

<400> SEQUENCE: 87
atgaggstcc cygctcagct gctgg     25

<210> SEQ ID NO 88
<211> LENGTH: 28
<212> TYPE: DNA
<213> ORGANISM: Artificial Sequence
<220> FEATURE:
<223> OTHER INFORMATION: 5' LVKappa3 Forward Primer

<400> SEQUENCE: 88
ctcttcctcc tgctactctg gctcccag     28

<210> SEQ ID NO 89
<211> LENGTH: 25
<212> TYPE: DNA
<213> ORGANISM: Artificial Sequence
<220> FEATURE:
<223> OTHER INFORMATION: 5' LVKappa4 Forward Primer

<400> SEQUENCE: 89
atttctctgt tgctctggat ctctg     25

<210> SEQ ID NO 90
<211> LENGTH: 26
<212> TYPE: DNA
<213> ORGANISM: Artificial Sequence
<220> FEATURE:
<223> OTHER INFORMATION: VK-rev Reverse Primer

<400> SEQUENCE: 90
gcactctccc ctgttgaagc tctttg     26

<210> SEQ ID NO 91
<211> LENGTH: 24
<212> TYPE: DNA
<213> ORGANISM: Artificial Sequence
<220> FEATURE:
<223> OTHER INFORMATION: 5' L-VH1 Forward Primer

<400> SEQUENCE: 91
acaggtgccc actcccaggt gcag     24

<210> SEQ ID NO 92
<211> LENGTH: 23
<212> TYPE: DNA
<213> ORGANISM: Artificial Sequence
<220> FEATURE:
<223> OTHER INFORMATION: 5' L-VH3 Forward Primer

<400> SEQUENCE: 92
aaggtgtcca gtgtgargtg cag     23

<210> SEQ ID NO 93
<211> LENGTH: 27
<212> TYPE: DNA

```
<213> ORGANISM: Artificial Sequence
<220> FEATURE:
<223> OTHER INFORMATION: 5' L-VH4/6 Forward Primer

<400> SEQUENCE: 93
cccagatggg tcctgtccca ggtgcag                                        27

<210> SEQ ID NO 94
<211> LENGTH: 24
<212> TYPE: DNA
<213> ORGANISM: Artificial Sequence
<220> FEATURE:
<223> OTHER INFORMATION: 5' L-VH5 Forward Primer

<400> SEQUENCE: 94
caaggagtct gttccgaggt gcag                                           24

<210> SEQ ID NO 95
<211> LENGTH: 23
<212> TYPE: DNA
<213> ORGANISM: Artificial Sequence
<220> FEATURE:
<223> OTHER INFORMATION: 3' CgammaCH1 Reverse Primer

<400> SEQUENCE: 95
ggaaggtgtg cacgccgctg gtc                                            23

<210> SEQ ID NO 96
<211> LENGTH: 6
<212> TYPE: DNA
<213> ORGANISM: Artificial Sequence
<220> FEATURE:
<223> OTHER INFORMATION: SalI restriction site

<400> SEQUENCE: 96 gtcgac                                                                6

<210> SEQ ID NO 97
<211> LENGTH: 32
<212> TYPE: DNA
<213> ORGANISM: Artificial Sequence
<220> FEATURE:
<223> OTHER INFORMATION: 3' SalIJH 1/2/4/5 Forward Primer

<400> SEQUENCE: 97
tgcgaagtcg acgctgagga gacggtgacc ag                                  32

<210> SEQ ID NO 98
<211> LENGTH: 34
<212> TYPE: DNA
<213> ORGANISM: Artificial Sequence
<220> FEATURE:
<223> OTHER INFORMATION: 3' SalIJH3 Forward Primer

<400> SEQUENCE: 98
tgcgaagtcg acgctgaaga gacggtgacc attg                                34

<210> SEQ ID NO 99
<211> LENGTH: 33
<212> TYPE: DNA
<213> ORGANISM: Artificial Sequence
<220> FEATURE:
<223> OTHER INFORMATION: 3' SalIJH6 Forward Primer

<400> SEQUENCE: 99
tgcgaagtcg acgctgagga gacggtgacc gtg                                 33
```

<210> SEQ ID NO 100
<211> LENGTH: 118
<212> TYPE: DNA
<213> ORGANISM: Artificial Sequence
<220> FEATURE:
<223> OTHER INFORMATION: Fab Linker

<400> SEQUENCE: 100
gagcttcaac aggggagagt gctaattaat taataaggag gatataatta tgaaaaagac      60
agctatcgcg attgcagtgg cactggctgg ctttgctacc gtagcgcagg cggccgca      118

<210> SEQ ID NO 101
<211> LENGTH: 391
<212> TYPE: DNA
<213> ORGANISM: Artificial Sequence
<220> FEATURE:
<223> OTHER INFORMATION: CH1 fragment

<400> SEQUENCE: 101
gtcgaccaaa ggtccgtctg ttttcccgct ggctccgtct tctaaatcta cctctggtgg      60
taccgctgct ctgggttgcc tggttaaaga ctacttcccg gaaccggtta ccgtttcttg     120
gaactctggt gctctgacct ctggtgttca caccttcccg gctgttctgc agtcttctgg     180
tctgtactct ctgtcttctg ttgttaccgt tccgtcttct tctctgggta cccagaccta     240
catctgcaac gttaaccaca accgtctaa caccaaagtt gacaagaaag ttgaaccgaa      300
atcttgcctg cgatcgcggc caggccggcc gcaccatcac catcaccatg gcgcataccc     360
gtacgacgtt ccggactacg cttctactag t                                    391

<210> SEQ ID NO 102
<211> LENGTH: 5432
<212> TYPE: DNA
<213> ORGANISM: Artificial Sequence
<220> FEATURE:
<223> OTHER INFORMATION: pCALM

<400> SEQUENCE: 102
atgcattagt tattaatagt aatcaattac ggggtcatta gttcatagcc catatatgga      60
gttccgcgtt acataactta cggtaaatgg cccgcctggc tgaccgccca acgacccccg     120
cccattgacg tcaataatga cgtatgttcc catagtaacg ccaataggga ctttccattg     180
acgtcaatgg gtggagtatt tacggtaaac tgcccacttg gcagtacatc aagtgtatca     240
tatgccaagt acgccccta tgacgtcaa tgacggtaaa tggcccgcct ggcattatgc     300
ccagtacatg accttatggg actttcctac ttggcagtac atctacgtat tagtcatcgc     360
tattaccatg gtgatgcggt tttggcagta catcaatggg cgtggatagc ggtttgactc     420
acggggattt ccaagtctcc accccattga cgtcaatggg agtttgtttt ggcaccaaaa     480
tcaacgggac tttccaaaat gtcgtaacaa ctccgcccca ttgacgcaaa tgggcggtag     540
gcgtgtacgg tgggaggtct atataagcag agctggttta gtgaaccgtc agatccgcta     600
gcgattacgc caagctcgaa attaaccctc actaaaggga acaaaagctg gagctccacc     660
gcggtggcgg ccgcccacca tggactgac ctggcggatc ctgttcctgg tggccgcggc      720
caccggggcc cacagcaaag ggaaagggaa aggggctagc accaagggcc cagcgtgtt     780 ccccctggcc cccagcagca agagcaccag cggcggcacc gccgccctgg gctgcctggt     840
gaaggactac ttccccgagc ccgtgaccgt gagctggaac agcggcgccc tgaccagcgg     900

```
cgtgcacacc ttccccgccg tgctgcagag cagcggcctg tacagcctga gcagcgtggt    960
gaccgtgccc agcagcagcc tgggcaccca gacctacatc tgcaacgtga accacaagcc   1020
cagcaacacc aaggtggaca agaaggtgga gcccaagagc tgcgacaaaa ctcacacatg   1080
cccaccgtgc ccagcacctg aactcctggg gggaccgtca gtcttcctct tccccccaaa   1140
acccaaggac accctcatga tctcccggac ccctgaggtc acatgcgtgg tggtggacgt   1200
gagccacgaa gaccctgagg tcaagttcaa ctggtacgtg gacggcgtgg aggtgcataa   1260
tgccaagaca aagccgcggg aggagcagta caacagcacg taccgggtgg tcagcgtcct   1320
caccgtcctg caccaggact ggctgaatgg caaggagtac aagtgcaagg tctccaacaa   1380
agccctccca gcccccatcg agaaaaccat ctccaaagcc aaagggcagc ccgagaacc    1440 acaggtgtac accctgcccc catcccggga tgagctgacc aagaaccagg tcagcctgac   1500
ctgcctggtc aaaggcttct atcccagcga catcgccgtg gagtgggaga gcaatgggca   1560
gccggagaac aactacaaga ccacgcctcc cgtgctggac tccgacggct ccttcttcct   1620
ctacagcaag ctcaccgtgg acaagagcag gtggcagcag gggaacgtct tctcatgctc   1680
cgtgatgcat gaggctctgc acaaccacta cacgcagaag agcctctccc tgtctccggg   1740
taaacgggcc aagcgggcac ccgtgaagca gacccctgaa ttcgacctgc tgaagctggc   1800
cggcgacgtg gagagcaacc ccggccccat gaggctccct gctcagctcc tggggctgct   1860
aatgctctgg gtccctggct cgagtgagaa agggaaaggg aaataaggta ccaggtaagt   1920
gtacccaatt cgccctatag tgagtcgtat tacaattcac tcgatcgccc ttcccaacag   1980
ttgcgcagcc tgaatggcga atggagatcc aattttttaag tgtataatgt gttaaactac   2040
tgattctaat tgtttgtgta ttttagattc acagtcccaa ggctcatttc aggcccctca   2100
gtcctcacag tctgttcatg atcataatca gccataccac atttgtagag gttttacttg   2160
ctttaaaaaa cctcccacac ctccccctga acctgaaaca taaaatgaat gcaattgttg   2220
ttgttaactt gttattgca gcttataatg gttacaaata aagcaatagc atcacaaatt   2280
tcacaaataa agcatttttt tcactgcatt ctagttgtgg tttgtccaaa ctcatcaatg   2340
tatcttaacg cgtaaattgt aagcgttaat attttgttaa aattcgcgtt aaattttgt    2400 taaatcagct cattttttaa ccaataggcc gaaatcggca aaatccctta taaatcaaaa   2460
gaatagaccg agatagggtt gagtgttgtt ccagtttgga acaagagtcc actattaaag   2520
aacgtggact ccaacgtcaa agggcgaaaa accgtctatc agggcgatgg cccactacgt   2580
gaaccatcac cctaatcaag ttttttgggg tcgaggtgcc gtaaagcact aaatcggaac   2640
cctaaaggga gcccccgatt tagagcttga cggggaaagc cggcgaacgt ggcgagaaag   2700
gaagggaaga agcgaaagg agcgggcgct agggcgctgg caagtgtagc ggtcacgctg   2760
cgcgtaacca ccacacccgc cgcgcttaat gcgccgctac agggcgcgtc aggtggcact   2820
tttcggggaa atgtgcgcgg aacccctatt tgtttatttt tctaaataca ttcaaatatg   2880
tatccgctca tgagacaata accctgataa atgcttcaat aatattgaaa aaggaagaat   2940
cctgaggcgg aaagaaccag ctgtggaatg tgtgtcagtt agggtgtgga agtccccag    3000 gctcccagc aggcagaagt atgcaaagca tgcatctcaa ttagtcagca accaggtgtg   3060
gaaagtcccc aggctcccca gcaggcagaa gtatgcaaag catgcatctc aattagtcag   3120
caaccatagt cccgccccta actccgccca tcccgcccct aactccgccc agttccgccc   3180
attctccgcc ccatggctga ctaatttttt ttatttatgc agaggccgag gccgcctcgg   3240
cctctgagct attccagaag tagtgaggag gcttttttgg aggcctaggc ttttgcaaag   3300
```

```
atcgatcaag agacaggatg aggatcgttt cgcatgattg aacaagatgg attgcacgca    3360
ggttctccgg ccgcttgggt ggagaggcta ttcggctatg actgggcaca acagacaatc    3420
ggctgctctg atgccgccgt gttccggctg tcagcgcagg gcgcccggt tctttttgtc     3480 aagaccgacc tgtccggtgc cctgaatgaa ctgcaagacg aggcagcgcg gctatcgtgg    3540
ctggccacga cgggcgttcc ttgcgcagct gtgctcgacg ttgtcactga agcgggaagg    3600
gactggctgc tattgggcga agtgccgggg caggatctcc tgtcatctca ccttgctcct    3660
gccgagaaag tatccatcat ggctgatgca atgcggcggc tgcatacgct tgatccggct    3720
acctgcccat tcgaccacca agcgaaacat cgcatcgagc gagcacgtac tcggatggaa    3780
gccggtcttg tcgatcagga tgatctggac gaagaacatc aggggctcgc gccagccgaa    3840
ctgttcgcca ggctcaaggc gagcatgccc gacggcgagg atctcgtcgt gacccatggc    3900
gatgcctgct tgccgaatat catggtggaa aatggccgct tttctggatt catcgactgt    3960
ggccggctgg gtgtggcgga ccgctatcag gacatagcgt tggctacccg tgatattgct    4020
gaagaacttg gcggcgaatg ggctgaccgc ttcctcgtgc tttacggtat cgccgctccc    4080
gattcgcagc gcatcgcctt ctatcgcctt cttgacgagt tcttctgagc gggactctgg    4140
ggttcgaaat gaccgaccaa gcgacgccca acctgccatc acgagatttc gattccaccg    4200
ccgccttcta tgaaaggttg gcttcggaa tcgttttccg gacgccggc tggatgatcc       4260 tccagcgcgg ggatctcatg ctggagttct cgcccaccc taggggagg ctaactgaaa      4320 cacggaagga caataccg gaaggaaccc gcgctatgac ggcaataaaa agacagaata      4380
aaacgcacgg tgttgggtcg tttgttcata acgcggggt tcggtcccag ggctggcact     4440
ctgtcgatac cccaccgaga ccccattggg gccaatacgc ccgcgtttct tccttttccc    4500
caccccaccc cccaagttcg ggtgaaggcc cagggctcgc agccaacgtc ggggcggcag    4560
gccctgccat agcctcaggt tactcatata tactttagat tgatttaaaa cttcattttt    4620
aatttaaaag gatctaggtg aagatccttt ttgataatct catgaccaaa atcccttaac    4680
gtgagttttc gttccactga gcgtcagacc ccgtagaaaa gatcaaagga tcttcttgag    4740
atcctttttt tctgcgcgta atctgctgct tgcaaacaaa aaaaccaccg ctaccagcgg    4800
tggtttgttt gccggatcaa gagctaccaa ctcttttcc gaaggtaact ggcttcagca     4860
gagcgcagat accaaatact gtccttctag tgtagccgta gttaggccac cacttcaaga    4920
actctgtagc accgcctaca tacctcgctc tgctaatcct gttaccagtg gctgctgcca    4980
gtggcgataa gtcgtgtctt accgggttgg actcaagacg atagttaccg gataaggcgc    5040
agcggtcggg ctgaacgggg ggttcgtgca cacagcccag cttggagcga acgacctaca    5100
ccgaactgag atacctacag cgtgagctat gagaaagcgc cacgcttccc gaagggagaa    5160
aggcggacag gtatccggta agcggcaggg tcggaacagg agagcgcacg agggagcttc    5220 caggggggaaa cgcctggtat ctttatagtc ctgtcgggtt tcgccacctc tgacttgagc   5280
gtcgattttt gtgatgctcg tcaggggggc ggagcctatg gaaaaacgcc agcaacgcgg    5340
cctttttacg gttcctggcc ttttgctggc cttttgctca catgttcttt cctgcgttat    5400
cccctgattc tgtggataac cgtattaccg cc                                  5432
```

<210> SEQ ID NO 103
<211> LENGTH: 450
<212> TYPE: PRT
<213> ORGANISM: Artificial Sequence
<220> FEATURE:

<223> OTHER INFORMATION: Synagis VH chain

<400> SEQUENCE: 103

```
Gln Val Thr Leu Arg Glu Ser Gly Pro Ala Leu Val Lys Pro Thr Gln
 1               5                  10                  15
Thr Leu Thr Leu Thr Cys Thr Phe Ser Gly Phe Ser Leu Ser Thr Ser
            20                  25                  30
Gly Met Ser Val Gly Trp Ile Arg Gln Pro Pro Gly Lys Ala Leu Glu
        35                  40                  45
Trp Leu Ala Asp Ile Trp Trp Asp Asp Lys Lys Asp Tyr Asn Pro Ser
    50                  55                  60
Leu Lys Ser Arg Leu Thr Ile Ser Lys Asp Thr Ser Lys Asn Gln Val
65                  70                  75                  80
Val Leu Lys Val Thr Asn Met Asp Pro Ala Asp Thr Ala Thr Tyr Tyr
                85                  90                  95
Cys Ala Arg Ser Met Ile Thr Asn Trp Tyr Phe Asp Val Trp Gly Gln
            100                 105                 110
Gly Thr Thr Val Thr Val Ser Ser Ala Ser Thr Lys Gly Pro Ser Val
        115                 120                 125
Phe Pro Leu Ala Pro Ser Ser Lys Ser Thr Ser Gly Gly Thr Ala Ala
    130                 135                 140
Leu Gly Cys Leu Val Lys Asp Tyr Phe Pro Glu Pro Val Thr Val Ser
145                 150                 155                 160
Trp Asn Ser Gly Ala Leu Thr Ser Gly Val His Thr Phe Pro Ala Val
                165                 170                 175
Leu Gln Ser Ser Gly Leu Tyr Ser Leu Ser Ser Val Val Thr Val Pro
            180                 185                 190
Ser Ser Ser Leu Gly Thr Gln Thr Tyr Ile Cys Asn Val Asn His Lys
        195                 200                 205
Pro Ser Asn Thr Lys Val Asp Lys Arg Val Glu Pro Lys Ser Cys Asp
    210                 215                 220
Lys Thr His Thr Cys Pro Pro Cys Pro Ala Pro Glu Leu Leu Gly Gly
225                 230                 235                 240
Pro Ser Val Phe Leu Phe Pro Pro Lys Pro Lys Asp Thr Leu Met Ile
                245                 250                 255
Ser Arg Thr Pro Glu Val Thr Cys Val Val Val Asp Val Ser His Glu
            260                 265                 270
Asp Pro Glu Val Lys Phe Asn Trp Tyr Val Asp Gly Val Glu Val His
        275                 280                 285
Asn Ala Lys Thr Lys Pro Arg Glu Glu Gln Tyr Asn Ser Thr Tyr Arg
    290                 295                 300
Val Val Ser Val Leu Thr Val Leu His Gln Asp Trp Leu Asn Gly Lys
305                 310                 315                 320
Glu Tyr Lys Cys Lys Val Ser Asn Lys Ala Leu Pro Ala Pro Ile Glu
                325                 330                 335
Lys Thr Ile Ser Lys Ala Lys Gly Gln Pro Arg Glu Pro Gln Val Tyr
            340                 345                 350
Thr Leu Pro Pro Ser Arg Glu Glu Met Thr Lys Asn Gln Val Ser Leu
        355                 360                 365
Thr Cys Leu Val Lys Gly Phe Tyr Pro Ser Asp Ile Ala Val Glu Trp
    370                 375                 380
Glu Ser Asn Gly Gln Pro Glu Asn Asn Tyr Lys Thr Thr Pro Pro Val
385                 390                 395                 400
```

```
Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450

<210> SEQ ID NO 104
<211> LENGTH: 120
<212> TYPE: PRT
<213> ORGANISM: Artificial Sequence
<220> FEATURE:
<223> OTHER INFORMATION: Synagis VH domain

<400> SEQUENCE: 104

Gln Val Thr Leu Arg Glu Ser Gly Pro Ala Leu Val Lys Pro Thr Gln
1               5                   10                  15

Thr Leu Thr Leu Thr Cys Thr Phe Ser Gly Phe Ser Leu Ser Thr Ser
                20                  25                  30

Gly Met Ser Val Gly Trp Ile Arg Gln Pro Pro Gly Lys Ala Leu Glu
            35                  40                  45

Trp Leu Ala Asp Ile Trp Trp Asp Asp Lys Lys Asp Tyr Asn Pro Ser
    50                  55                  60

Leu Lys Ser Arg Leu Thr Ile Ser Lys Asp Thr Ser Lys Asn Gln Val
65                  70                  75                  80

Val Leu Lys Val Thr Asn Met Asp Pro Ala Asp Thr Ala Thr Tyr Tyr
                85                  90                  95

Cys Ala Arg Ser Met Ile Thr Asn Trp Tyr Phe Asp Val Trp Gly Ala
            100                 105                 110

Gly Thr Thr Val Thr Val Ser Ser
        115                 120

<210> SEQ ID NO 105
<211> LENGTH: 7
<212> TYPE: PRT
<213> ORGANISM: Artificial Sequence
<220> FEATURE:
<223> OTHER INFORMATION: Synagis VH CDR1

<400> SEQUENCE: 105

Thr Ser Gly Met Ser Val Gly
1               5

<210> SEQ ID NO 106
<211> LENGTH: 16
<212> TYPE: PRT
<213> ORGANISM: Artificial Sequence
<220> FEATURE:
<223> OTHER INFORMATION: Synagis VH CDR2

<400> SEQUENCE: 106

Asp Ile Trp Trp Asp Asp Lys Lys Asp Tyr Asn Pro Ser Leu Lys Ser
1               5                   10                  15

<210> SEQ ID NO 107
<211> LENGTH: 10
<212> TYPE: PRT
<213> ORGANISM: Artificial Sequence
<220> FEATURE:
<223> OTHER INFORMATION: Synagis VH CDR3
```

<400> SEQUENCE: 107

Ser Met Ile Thr Asn Trp Tyr Phe Asp Val
1               5                   10

<210> SEQ ID NO 108
<211> LENGTH: 213
<212> TYPE: PRT
<213> ORGANISM: Artificial Sequence
<220> FEATURE:
<223> OTHER INFORMATION: Synagis VL chain

<400> SEQUENCE: 108

Asp Ile Gln Met Thr Gln Ser Pro Ser Thr Leu Ser Ala Ser Val Gly
1               5                   10                  15

Asp Arg Val Thr Ile Thr Cys Lys Cys Gln Leu Ser Val Gly Tyr Met
            20                  25                  30

His Trp Tyr Gln Gln Lys Pro Gly Lys Ala Pro Lys Leu Leu Ile Tyr
        35                  40                  45

Asp Thr Ser Lys Leu Ala Ser Gly Val Pro Ser Arg Phe Ser Gly Ser
    50                  55                  60

Gly Ser Gly Thr Glu Phe Thr Leu Thr Ile Ser Ser Leu Gln Pro Asp
65                  70                  75                  80

Asp Phe Ala Thr Tyr Tyr Cys Phe Gln Gly Ser Gly Tyr Pro Phe Thr
                85                  90                  95

Phe Gly Gly Gly Thr Lys Val Glu Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210

<210> SEQ ID NO 109
<211> LENGTH: 106
<212> TYPE: PRT
<213> ORGANISM: Artificial Sequence
<220> FEATURE:
<223> OTHER INFORMATION: Synagis VL domain

<400> SEQUENCE: 109

Asp Ile Gln Met Thr Gln Ser Pro Ser Thr Leu Ser Ala Ser Val Gly
1               5                   10                  15

Asp Arg Val Thr Ile Thr Cys Lys Cys Gln Leu Ser Val Gly Tyr Met
            20                  25                  30

His Trp Tyr Gln Gln Lys Pro Gly Lys Ala Pro Lys Leu Leu Ile Tyr
        35                  40                  45

Asp Thr Ser Lys Leu Ala Ser Gly Val Pro Ser Arg Phe Ser Gly Ser
    50                  55                  60

```
Gly Ser Gly Thr Glu Phe Thr Leu Thr Ile Ser Ser Leu Gln Pro Asp
65                  70                  75                  80

Asp Phe Ala Thr Tyr Tyr Cys Phe Gln Gly Ser Gly Tyr Pro Phe Thr
                85                  90                  95

Phe Gly Gly Gly Thr Lys Leu Glu Ile Lys
            100                 105
```

<210> SEQ ID NO 110
<211> LENGTH: 10
<212> TYPE: PRT
<213> ORGANISM: Artificial Sequence
<220> FEATURE:
<223> OTHER INFORMATION: Synagis VL CDR1

<400> SEQUENCE: 110

```
Lys Cys Gln Leu Ser Val Gly Tyr Met His
1               5                   10
```

<210> SEQ ID NO 111
<211> LENGTH: 7
<212> TYPE: PRT
<213> ORGANISM: Artificial Sequence
<220> FEATURE:
<223> OTHER INFORMATION: Synagis VL CDR2

<400> SEQUENCE: 111

```
Asp Thr Ser Lys Leu Ala Ser
1               5
```

<210> SEQ ID NO 112
<211> LENGTH: 9
<212> TYPE: PRT
<213> ORGANISM: Artificial Sequence
<220> FEATURE:
<223> OTHER INFORMATION: Synagis VL CDR3

<400> SEQUENCE: 112

```
Phe Gln Gly Ser Gly Tyr Pro Phe Thr
1               5
```

<210> SEQ ID NO 113
<211> LENGTH: 450
<212> TYPE: PRT
<213> ORGANISM: Artificial Sequence
<220> FEATURE:
<223> OTHER INFORMATION: AFFF VH CHAIN

<400> SEQUENCE: 113

```
Gln Val Thr Leu Arg Glu Ser Gly Pro Ala Leu Val Lys Pro Thr Gln
1               5                   10                  15

Thr Leu Thr Leu Thr Cys Thr Phe Ser Gly Phe Ser Leu Ser Thr Ala
                20                  25                  30

Gly Met Ser Val Gly Trp Ile Arg Gln Pro Pro Gly Lys Ala Leu Glu
            35                  40                  45

Trp Leu Ala Asp Ile Trp Trp Asp Asp Lys Lys Asp Tyr Asn Pro Ser
    50                  55                  60

Leu Lys Ser Arg Leu Thr Ile Ser Lys Asp Thr Ser Lys Asn Gln Val
65                  70                  75                  80

Val Leu Lys Val Thr Asn Met Asp Pro Ala Asp Thr Ala Thr Tyr Tyr
                85                  90                  95

Cys Ala Arg Ser Met Ile Thr Asn Phe Tyr Phe Asp Val Trp Gly Gln
            100                 105                 110
```

```
Gly Thr Thr Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Arg Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450

<210> SEQ ID NO 114
<211> LENGTH: 120
<212> TYPE: PRT
<213> ORGANISM: Artificial Sequence
<220> FEATURE:
<223> OTHER INFORMATION: AFFF VH DOMAIN

<400> SEQUENCE: 114

Gln Val Thr Leu Arg Glu Ser Gly Pro Ala Leu Val Lys Pro Thr Gln
1               5                   10                  15
```

```
Thr Leu Thr Leu Thr Cys Thr Phe Ser Gly Phe Ser Leu Ser Thr Ala
            20                  25                  30

Gly Met Ser Val Gly Trp Ile Arg Gln Pro Pro Gly Lys Ala Leu Glu
        35                  40                  45

Trp Leu Ala Asp Ile Trp Trp Asp Asp Lys Asp Tyr Asn Pro Ser
50                  55                  60

Leu Lys Ser Arg Leu Thr Ile Ser Lys Asp Thr Ser Lys Asn Gln Val
65                  70                  75                  80

Val Leu Lys Val Thr Asn Met Asp Pro Ala Asp Thr Ala Thr Tyr Tyr
                85                  90                  95

Cys Ala Arg Ser Met Ile Thr Asn Phe Tyr Phe Asp Val Trp Gly Ala
            100                 105                 110

Gly Thr Thr Val Thr Val Ser Ser
        115                 120
```

<210> SEQ ID NO 115
<211> LENGTH: 7
<212> TYPE: PRT
<213> ORGANISM: Artificial Sequence
<220> FEATURE:
<223> OTHER INFORMATION: AFFF VH CDR1

<400> SEQUENCE: 115

```
Thr Ala Gly Met Ser Val Gly
1               5
```

<210> SEQ ID NO 116
<211> LENGTH: 10
<212> TYPE: PRT
<213> ORGANISM: Artificial Sequence
<220> FEATURE:
<223> OTHER INFORMATION: AFFF VH CDR3

<400> SEQUENCE: 116

```
Ser Met Ile Thr Asn Phe Tyr Phe Asp Val
1               5                   10
```

<210> SEQ ID NO 117
<211> LENGTH: 213
<212> TYPE: PRT
<213> ORGANISM: Artificial Sequence
<220> FEATURE:
<223> OTHER INFORMATION: AFFF VL CHAIN

<400> SEQUENCE: 117

```
Asp Ile Gln Met Thr Gln Ser Pro Ser Thr Leu Ser Ala Ser Val Gly
1               5                   10                  15

Asp Arg Val Thr Ile Thr Cys Ser Ala Ser Ser Ser Val Gly Tyr Met
            20                  25                  30

His Trp Tyr Gln Gln Lys Pro Gly Lys Ala Pro Lys Leu Leu Ile Tyr
        35                  40                  45

Asp Thr Phe Lys Leu Ala Ser Gly Val Pro Ser Arg Phe Ser Gly Ser
50                  55                  60

Gly Ser Gly Thr Glu Phe Thr Leu Thr Ile Ser Ser Leu Gln Pro Asp
65                  70                  75                  80

Asp Phe Ala Thr Tyr Tyr Cys Phe Gln Phe Ser Gly Tyr Pro Phe Thr
                85                  90                  95

Phe Gly Gly Gly Thr Lys Val Glu Ile Lys Arg Thr Val Ala Ala Pro
            100                 105                 110
```

```
Ser Val Phe Ile Phe Pro Pro Ser Asp Glu Gln Leu Lys Ser Gly Thr
            115                 120                 125

Ala Ser Val Val Cys Leu Leu Asn Asn Phe Tyr Pro Arg Glu Ala Lys
        130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
        210

<210> SEQ ID NO 118
<211> LENGTH: 106
<212> TYPE: PRT
<213> ORGANISM: Artificial Sequence
<220> FEATURE:
<223> OTHER INFORMATION: AFFF VL DOMAIN

<400> SEQUENCE: 118

Asp Ile Gln Met Thr Gln Ser Pro Ser Thr Leu Ser Ala Ser Val Gly
1               5                   10                  15

Asp Arg Val Thr Ile Thr Cys Ser Ala Ser Ser Ser Val Gly Tyr Met
            20                  25                  30

His Trp Tyr Gln Gln Lys Pro Gly Lys Ala Pro Lys Leu Leu Ile Tyr
        35                  40                  45

Asp Thr Phe Lys Leu Ala Ser Gly Val Pro Ser Arg Phe Ser Gly Ser
    50                  55                  60

Gly Ser Gly Thr Glu Phe Thr Leu Thr Ile Ser Ser Leu Gln Pro Asp
65                  70                  75                  80

Asp Phe Ala Thr Tyr Tyr Cys Phe Gln Phe Ser Gly Tyr Pro Phe Thr
                85                  90                  95

Phe Gly Gly Gly Thr Lys Leu Glu Ile Lys
            100                 105

<210> SEQ ID NO 119
<211> LENGTH: 10
<212> TYPE: PRT
<213> ORGANISM: Artificial Sequence
<220> FEATURE:
<223> OTHER INFORMATION: AFFF VL CDR1

<400> SEQUENCE: 119

Ser Ala Ser Ser Ser Val Gly Tyr Met His
1               5                   10

<210> SEQ ID NO 120
<211> LENGTH: 7
<212> TYPE: PRT
<213> ORGANISM: Artificial Sequence
<220> FEATURE:
<223> OTHER INFORMATION: AFFF VL CDR2

<400> SEQUENCE: 120

Asp Thr Phe Lys Leu Ala Ser
1               5
```

```
<210> SEQ ID NO 121
<211> LENGTH: 9
<212> TYPE: PRT
<213> ORGANISM: Artificial Sequence
<220> FEATURE:
<223> OTHER INFORMATION: AFFF VL CDR3

<400> SEQUENCE: 121

Phe Gln Phe Ser Gly Tyr Pro Phe Thr
1               5

<210> SEQ ID NO 122
<211> LENGTH: 450
<212> TYPE: PRT
<213> ORGANISM: Artificial Sequence
<220> FEATURE:
<223> OTHER INFORMATION: P1212 VH CHAIN

<400> SEQUENCE: 122

Gln Val Thr Leu Arg Glu Ser Gly Pro Ala Leu Val Lys Pro Thr Gln
1               5                   10                  15

Thr Leu Thr Leu Thr Cys Thr Phe Ser Gly Phe Ser Leu Ser Thr Pro
            20                  25                  30

Gly Met Ser Val Gly Trp Ile Arg Gln Pro Pro Gly Lys Ala Leu Glu
        35                  40                  45

Trp Leu Ala Asp Ile Trp Trp Asp Asp Lys Lys His Tyr Asn Pro Ser
    50                  55                  60

Leu Lys Asp Arg Leu Thr Ile Ser Lys Asp Thr Ser Lys Asn Gln Val
65                  70                  75                  80

Val Leu Lys Val Thr Asn Met Asp Pro Ala Asp Thr Ala Thr Tyr Tyr
                85                  90                  95

Cys Ala Arg Asp Met Ile Phe Asn Phe Tyr Phe Asp Val Trp Gly Gln
            100                 105                 110

Gly Thr Thr Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Arg Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300
```

```
Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
            325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
        355                 360                 365

Thr Cys Leu Val Lys Gly Phe Tyr Pro Ser Asp Ile Ala Val Glu Trp
        370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
            435                 440                 445

Gly Lys
    450

<210> SEQ ID NO 123
<211> LENGTH: 120
<212> TYPE: PRT
<213> ORGANISM: Artificial Sequence
<220> FEATURE:
<223> OTHER INFORMATION: P1212 VH DOMAIN

<400> SEQUENCE: 123

Gln Val Thr Leu Arg Glu Ser Gly Pro Ala Leu Val Lys Pro Thr Gln
1               5                   10                  15

Thr Leu Thr Leu Thr Cys Thr Phe Ser Gly Phe Ser Leu Ser Thr Pro
            20                  25                  30

Gly Met Ser Val Gly Trp Ile Arg Gln Pro Pro Gly Lys Ala Leu Glu
        35                  40                  45

Trp Leu Ala Asp Ile Trp Trp Asp Asp Lys Lys His Tyr Asn Pro Ser
    50                  55                  60

Leu Lys Asp Arg Leu Thr Ile Ser Lys Asp Thr Ser Lys Asn Gln Val
65                  70                  75                  80

Val Leu Lys Val Thr Asn Met Asp Pro Ala Asp Thr Ala Thr Tyr Tyr
                85                  90                  95

Cys Ala Arg Asp Met Ile Phe Asn Phe Tyr Phe Asp Val Trp Gly Ala
            100                 105                 110

Gly Thr Thr Val Thr Val Ser Ser
        115                 120

<210> SEQ ID NO 124
<211> LENGTH: 7
<212> TYPE: PRT
<213> ORGANISM: Artificial Sequence
<220> FEATURE:
<223> OTHER INFORMATION: P1212 VH CDR1

<400> SEQUENCE: 124

Thr Pro Gly Met Ser Val Gly
1               5

<210> SEQ ID NO 125
```

```
<211> LENGTH: 16
<212> TYPE: PRT
<213> ORGANISM: Artificial Sequence
<220> FEATURE:
<223> OTHER INFORMATION: P1212 VH CDR2

<400> SEQUENCE: 125

Asp Ile Trp Trp Asp Asp Lys Lys His Tyr Asn Pro Ser Leu Lys Asp
 1               5                  10                  15

<210> SEQ ID NO 126
<211> LENGTH: 10
<212> TYPE: PRT
<213> ORGANISM: Artificial Sequence
<220> FEATURE:
<223> OTHER INFORMATION: P1212 VH CDR3

<400> SEQUENCE: 126

Asp Met Ile Phe Asn Phe Tyr Phe Asp Val
 1               5                  10

<210> SEQ ID NO 127
<211> LENGTH: 213
<212> TYPE: PRT
<213> ORGANISM: Artificial Sequence
<220> FEATURE:
<223> OTHER INFORMATION: P1212 VL CHAIN

<400> SEQUENCE: 127

Asp Ile Gln Met Thr Gln Ser Pro Ser Thr Leu Ser Ala Ser Val Gly
 1               5                  10                  15

Asp Arg Val Thr Ile Thr Cys Ser Leu Ser Ser Arg Val Gly Tyr Met
                20                  25                  30

His Trp Tyr Gln Gln Lys Pro Gly Lys Ala Pro Lys Leu Leu Ile Tyr
            35                  40                  45

Asp Thr Phe Tyr Leu Ser Ser Gly Val Pro Ser Arg Phe Ser Gly Ser
        50                  55                  60

Gly Ser Gly Thr Glu Phe Thr Leu Thr Ile Ser Ser Leu Gln Pro Asp
 65                 70                  75                  80

Asp Phe Ala Thr Tyr Tyr Cys Phe Gln Gly Ser Gly Tyr Pro Phe Thr
                85                  90                  95

Phe Gly Gly Gly Thr Lys Val Glu Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210

<210> SEQ ID NO 128
<211> LENGTH: 106
```

<212> TYPE: PRT
<213> ORGANISM: Artificial Sequence
<220> FEATURE:
<223> OTHER INFORMATION: P1212 VL DOMAIN

<400> SEQUENCE: 128

Asp Ile Gln Met Thr Gln Ser Pro Ser Thr Leu Ser Ala Ser Val Gly
1               5                   10                  15

Asp Arg Val Thr Ile Thr Cys Ser Leu Ser Ser Arg Val Gly Tyr Met
            20                  25                  30

His Trp Tyr Gln Gln Lys Pro Gly Lys Ala Pro Lys Leu Leu Ile Tyr
        35                  40                  45

Asp Thr Phe Tyr Leu Ser Ser Gly Val Pro Ser Arg Phe Ser Gly Ser
    50                  55                  60

Gly Ser Gly Thr Glu Phe Thr Leu Thr Ile Ser Ser Leu Gln Pro Asp
65                  70                  75                  80

Asp Phe Ala Thr Tyr Tyr Cys Phe Gln Gly Ser Gly Tyr Pro Phe Thr
                85                  90                  95

Phe Gly Gly Gly Thr Lys Val Glu Ile Lys
            100                 105

<210> SEQ ID NO 129
<211> LENGTH: 10
<212> TYPE: PRT
<213> ORGANISM: Artificial Sequence
<220> FEATURE:
<223> OTHER INFORMATION: P1212 VL CDR1

<400> SEQUENCE: 129

Ser Leu Ser Ser Arg Val Gly Tyr Met His
1               5                   10

<210> SEQ ID NO 130
<211> LENGTH: 7
<212> TYPE: PRT
<213> ORGANISM: Artificial Sequence
<220> FEATURE:
<223> OTHER INFORMATION: P1212 VL CDR2

<400> SEQUENCE: 130

Asp Thr Phe Tyr Leu Ser Ser
1               5

<210> SEQ ID NO 131
<211> LENGTH: 450
<212> TYPE: PRT
<213> ORGANISM: Artificial Sequence
<220> FEATURE:
<223> OTHER INFORMATION: P12f4 VH CHAIN

<400> SEQUENCE: 131

Gln Val Thr Leu Arg Glu Ser Gly Pro Ala Leu Val Lys Pro Thr Gln
1               5                   10                  15

Thr Leu Thr Leu Thr Cys Thr Phe Ser Gly Phe Ser Leu Ser Thr Pro
            20                  25                  30

Gly Met Ser Val Gly Trp Ile Arg Gln Pro Pro Gly Lys Ala Leu Glu
        35                  40                  45

Trp Leu Ala Asp Ile Trp Trp Asp Asp Lys Lys His Tyr Asn Pro Ser
    50                  55                  60

Leu Lys Asp Arg Leu Thr Ile Ser Lys Asp Thr Ser Lys Asn Gln Val
65                  70                  75                  80

Val Leu Lys Val Thr Asn Met Asp Pro Ala Asp Thr Ala Thr Tyr Tyr
            85                  90                  95

Cys Ala Arg Asp Met Ile Phe Asn Phe Tyr Phe Asp Val Trp Gly Gln
            100                 105                 110

Gly Thr Thr Val Thr Val Ser Ser Ala Ser Thr Lys Gly Pro Ser Val
            115                 120                 125

Phe Pro Leu Ala Pro Ser Ser Lys Ser Thr Ser Gly Gly Thr Ala Ala
130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
                180                 185                 190

Ser Ser Ser Leu Gly Thr Gln Thr Tyr Ile Cys Asn Val Asn His Lys
            195                 200                 205

Pro Ser Asn Thr Lys Val Asp Lys Arg Val Glu Pro Lys Ser Cys Asp
210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
                260                 265                 270

Asp Pro Glu Val Lys Phe Asn Trp Tyr Val Asp Gly Val Glu Val His
            275                 280                 285

Asn Ala Lys Thr Lys Pro Arg Glu Glu Gln Tyr Asn Ser Thr Tyr Arg
290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
                340                 345                 350

Thr Leu Pro Pro Ser Arg Glu Glu Met Thr Lys Asn Gln Val Ser Leu
            355                 360                 365

Thr Cys Leu Val Lys Gly Phe Tyr Pro Ser Asp Ile Ala Val Glu Trp
370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
                420                 425                 430

Glu Ala Leu His Asn His Tyr Thr Gln Lys Ser Leu Ser Leu Ser Pro
            435                 440                 445

Gly Lys
450

<210> SEQ ID NO 132
<211> LENGTH: 120
<212> TYPE: PRT
<213> ORGANISM: Artificial Sequence
<220> FEATURE:
<223> OTHER INFORMATION: P12f4 VH DOMAIN

```
<400> SEQUENCE: 132

Gln Val Thr Leu Arg Glu Ser Gly Pro Ala Leu Val Lys Pro Thr Gln
  1               5                  10                  15

Thr Leu Thr Leu Thr Cys Thr Phe Ser Gly Phe Ser Leu Ser Thr Pro
             20                  25                  30

Gly Met Ser Val Gly Trp Ile Arg Gln Pro Pro Gly Lys Ala Leu Glu
         35                  40                  45

Trp Leu Ala Asp Ile Trp Trp Asp Gly Lys Lys His Tyr Asn Pro Ser
 50                  55                  60

Leu Lys Asp Arg Leu Thr Ile Ser Lys Asp Thr Ser Lys Asn Gln Val
 65                  70                  75                  80

Val Leu Lys Val Thr Asn Met Asp Pro Ala Asp Thr Ala Thr Tyr Tyr
             85                  90                  95

Cys Ala Arg Asp Met Ile Phe Asn Phe Tyr Phe Asp Val Trp Gly Gln
            100                 105                 110

Gly Thr Thr Val Thr Val Ser Ser
            115                 120

<210> SEQ ID NO 133
<211> LENGTH: 16
<212> TYPE: PRT
<213> ORGANISM: Artificial Sequence
<220> FEATURE:
<223> OTHER INFORMATION: P12f4 VH CDR2

<400> SEQUENCE: 133

Asp Ile Trp Trp Asp Gly Lys Lys His Tyr Asn Pro Ser Leu Lys Asp
  1               5                  10                  15

<210> SEQ ID NO 134
<211> LENGTH: 208
<212> TYPE: PRT
<213> ORGANISM: Artificial Sequence
<220> FEATURE:
<223> OTHER INFORMATION: P12f4 VL CHAIN

<400> SEQUENCE: 134

Asp Ile Gln Met Thr Gln Ser Pro Ser Thr Leu Ser Ala Ser Val Gly
  1               5                  10                  15

Asp Arg Val Thr Ile Thr Cys Ser Leu Ser Ser Arg Val Gly Tyr Met
             20                  25                  30

His Trp Tyr Gln Gln Lys Pro Gly Lys Ala Pro Lys Leu Leu Ile Tyr
         35                  40                  45

Asp Thr Arg Gly Leu Pro Ser Gly Val Pro Ser Arg Phe Ser Gly Ser
 50                  55                  60

Gly Ser Gly Thr Glu Phe Thr Leu Thr Ile Ser Ser Leu Gln Pro Asp
 65                  70                  75                  80

Asp Phe Ala Thr Tyr Tyr Cys Phe Gln Gly Ser Gly Tyr Pro Phe Thr
             85                  90                  95

Phe Gly Gly Gly Thr Lys Val Glu Ile Lys Arg Thr Val Ala Ala Pro
            100                 105                 110

Ser Val Phe Ile Phe Pro Pro Ser Asp Glu Gln Leu Lys Ser Gly Thr
            115                 120                 125

Ala Ser Val Val Cys Leu Leu Asn Asn Phe Tyr Pro Arg Glu Ala Lys
        130                 135                 140

Val Gln Trp Lys Val Asp Asn Ala Leu Gln Ser Gly Asn Ser Gln Glu
145                 150                 155                 160
```

-continued

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

<210> SEQ ID NO 135
<211> LENGTH: 106
<212> TYPE: PRT
<213> ORGANISM: Artificial Sequence
<220> FEATURE:
<223> OTHER INFORMATION: P12f4 VL DOMAIN

<400> SEQUENCE: 135

Asp Ile Gln Met Thr Gln Ser Pro Ser Thr Leu Ser Ala Ser Val Gly
1               5                   10                  15

Asp Arg Val Thr Ile Thr Cys Ser Leu Ser Ser Arg Val Gly Tyr Met
            20                  25                  30

His Trp Tyr Gln Gln Lys Pro Gly Lys Ala Pro Lys Leu Leu Ile Tyr
        35                  40                  45

Asp Thr Arg Gly Leu Pro Ser Gly Val Pro Ser Arg Phe Ser Gly Ser
    50                  55                  60

Gly Ser Gly Thr Glu Phe Thr Leu Thr Ile Ser Ser Leu Gln Pro Asp
65                  70                  75                  80

Asp Phe Ala Thr Tyr Tyr Cys Phe Gln Gly Ser Gly Tyr Pro Phe Thr
                85                  90                  95

Phe Gly Gly Gly Thr Lys Val Glu Ile Lys
            100                 105

<210> SEQ ID NO 136
<211> LENGTH: 7
<212> TYPE: PRT
<213> ORGANISM: Artificial Sequence
<220> FEATURE:
<223> OTHER INFORMATION: P12f4 VL CDR2

<400> SEQUENCE: 136

Asp Thr Arg Gly Leu Pro Ser
1               5

<210> SEQ ID NO 137
<211> LENGTH: 450
<212> TYPE: PRT
<213> ORGANISM: Artificial Sequence
<220> FEATURE:
<223> OTHER INFORMATION: P11d4 VH CHAIN

<400> SEQUENCE: 137

Gln Val Thr Leu Arg Glu Ser Gly Pro Ala Leu Val Lys Pro Thr Gln
1               5                   10                  15

Thr Leu Thr Leu Thr Cys Thr Phe Ser Gly Phe Ser Leu Ser Thr Pro
            20                  25                  30

Gly Met Ser Val Gly Trp Ile Arg Gln Pro Pro Gly Lys Ala Leu Glu
        35                  40                  45

Trp Leu Ala Asp Ile Trp Trp Asp Gly Lys Lys His Tyr Asn Pro Ser
    50                  55                  60

Leu Lys Asp Arg Leu Thr Ile Ser Lys Asp Thr Ser Lys Asn Gln Val
65                  70                  75                  80

-continued

```
Val Leu Lys Val Thr Asn Met Asp Pro Ala Asp Thr Ala Thr Tyr Tyr
            85                  90                  95

Cys Ala Arg Asp Met Ile Phe Asn Trp Tyr Phe Asp Val Trp Gly Gln
           100                 105                 110

Gly Thr Thr Val Thr Val Ser Ser Ala Ser Thr Lys Gly Pro Ser Val
           115                 120                 125

Phe Pro Leu Ala Pro Ser Ser Lys Ser Thr Ser Gly Gly Thr Ala Ala
130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Arg Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450

<210> SEQ ID NO 138
<211> LENGTH: 120
<212> TYPE: PRT
<213> ORGANISM: Artificial Sequence
<220> FEATURE:
<223> OTHER INFORMATION: P11d4 VH DOMAIN
```

<400> SEQUENCE: 138

```
Gln Val Thr Leu Arg Glu Ser Gly Pro Ala Leu Val Lys Pro Thr Gln
1               5                   10                  15

Thr Leu Thr Leu Thr Cys Thr Phe Ser Gly Phe Ser Leu Ser Thr Pro
            20                  25                  30

Gly Met Ser Val Gly Trp Ile Arg Gln Pro Pro Gly Lys Ala Leu Glu
        35                  40                  45

Trp Leu Ala Asp Ile Trp Trp Asp Gly Lys Lys His Tyr Asn Pro Ser
    50                  55                  60

Leu Lys Asp Arg Leu Thr Ile Ser Lys Asp Thr Ser Lys Asn Gln Val
65                  70                  75                  80

Val Leu Lys Val Thr Asn Met Asp Pro Ala Asp Thr Ala Thr Tyr Tyr
                85                  90                  95

Cys Ala Arg Asp Met Ile Phe Asn Trp Tyr Phe Asp Val Trp Gly Gln
            100                 105                 110

Gly Thr Thr Val Thr Val Ser Ser
        115                 120
```

<210> SEQ ID NO 139
<211> LENGTH: 10
<212> TYPE: PRT
<213> ORGANISM: Artificial Sequence
<220> FEATURE:
<223> OTHER INFORMATION: P11d4 VH CDR3

<400> SEQUENCE: 139

```
Asp Met Ile Phe Asn Trp Tyr Phe Asp Val
1               5                   10
```

<210> SEQ ID NO 140
<211> LENGTH: 213
<212> TYPE: PRT
<213> ORGANISM: Artificial Sequence
<220> FEATURE:
<223> OTHER INFORMATION: P11d4 VL CHAIN

<400> SEQUENCE: 140

```
Asp Ile Gln Met Thr Gln Ser Pro Ser Thr Leu Ser Ala Ser Val Gly
1               5                   10                  15

Asp Arg Val Thr Ile Thr Cys Ser Pro Ser Ser Arg Val Gly Tyr Met
            20                  25                  30

His Trp Tyr Gln Gln Lys Pro Gly Lys Ala Pro Lys Leu Leu Ile Tyr
        35                  40                  45

Asp Thr Met Arg Leu Ala Ser Gly Val Pro Ser Arg Phe Ser Gly Ser
    50                  55                  60

Gly Ser Gly Thr Glu Phe Thr Leu Thr Ile Ser Ser Leu Gln Pro Asp
65                  70                  75                  80

Asp Phe Ala Thr Tyr Tyr Cys Phe Gln Gly Ser Gly Tyr Pro Phe Thr
                85                  90                  95

Phe Gly Gly Gly Thr Lys Val Glu Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160
```

-continued

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
                180                 185                 190

Cys Glu Val Thr His Gln Gly Leu Ser Ser Pro Val Thr Lys Ser Phe
                195                 200                 205

Asn Arg Gly Glu Cys
        210

<210> SEQ ID NO 141
<211> LENGTH: 106
<212> TYPE: PRT
<213> ORGANISM: Artificial Sequence
<220> FEATURE:
<223> OTHER INFORMATION: P11d4 VL DOMAIN

<400> SEQUENCE: 141

Asp Ile Gln Met Thr Gln Ser Pro Ser Thr Leu Ser Ala Ser Val Gly
1               5                   10                  15

Asp Arg Val Thr Ile Thr Cys Ser Pro Ser Ser Arg Val Gly Tyr Met
                20                  25                  30

His Trp Tyr Gln Gln Lys Pro Gly Lys Ala Pro Lys Leu Leu Ile Tyr
            35                  40                  45

Asp Thr Met Arg Leu Ala Ser Gly Val Pro Ser Arg Phe Ser Gly Ser
        50                  55                  60

Gly Ser Gly Thr Glu Phe Thr Leu Thr Ile Ser Ser Leu Gln Pro Asp
65                  70                  75                  80

Asp Phe Ala Thr Tyr Tyr Cys Phe Gln Gly Ser Gly Tyr Pro Phe Thr
                85                  90                  95

Phe Gly Gly Gly Thr Lys Val Glu Ile Lys
            100                 105

<210> SEQ ID NO 142
<211> LENGTH: 10
<212> TYPE: PRT
<213> ORGANISM: Artificial Sequence
<220> FEATURE:
<223> OTHER INFORMATION: P11d4 VL CDR1

<400> SEQUENCE: 142

Ser Pro Ser Ser Arg Val Gly Tyr Met His
1               5                   10

<210> SEQ ID NO 143
<211> LENGTH: 7
<212> TYPE: PRT
<213> ORGANISM: Artificial Sequence
<220> FEATURE:
<223> OTHER INFORMATION: P11d4 VL CDR2

<400> SEQUENCE: 143

Asp Thr Met Arg Leu Ala Ser
1               5

<210> SEQ ID NO 144
<211> LENGTH: 450
<212> TYPE: PRT
<213> ORGANISM: Artificial Sequence
<220> FEATURE:
<223> OTHER INFORMATION: A1e9 VH CHAIN

<400> SEQUENCE: 144

-continued

```
Gln Val Thr Leu Arg Glu Ser Gly Pro Ala Leu Val Lys Pro Thr Gln
  1               5                  10                  15

Thr Leu Thr Leu Thr Cys Thr Phe Ser Gly Phe Ser Leu Ser Thr Ala
             20                  25                  30

Gly Met Ser Val Gly Trp Ile Arg Gln Pro Pro Gly Lys Ala Leu Glu
         35                  40                  45

Trp Leu Ala Asp Ile Trp Trp Asp Gly Lys Lys His Tyr Asn Pro Ser
     50                  55                  60

Leu Lys Asp Arg Leu Thr Ile Ser Lys Asp Thr Ser Lys Asn Gln Val
 65                  70                  75                  80

Val Leu Lys Val Thr Asn Met Asp Pro Ala Asp Thr Ala Thr Tyr Tyr
             85                  90                  95

Cys Ala Arg Asp Met Ile Phe Asn Trp Tyr Phe Asp Val Trp Gly Gln
             100                 105                 110

Gly Thr Thr Val Thr Val Ser Ser Ala Ser Thr Lys Gly Pro Ser Val
         115                 120                 125

Phe Pro Leu Ala Pro Ser Ser Lys Ser Thr Ser Gly Gly Thr Ala Ala
     130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
             165                 170                 175

Leu Gln Ser Ser Gly Leu Tyr Ser Leu Ser Ser Val Val Thr Val Pro
         180                 185                 190

Ser Ser Ser Leu Gly Thr Gln Thr Tyr Ile Cys Asn Val Asn His Lys
     195                 200                 205

Pro Ser Asn Thr Lys Val Asp Lys Arg Val Glu Pro Lys Ser Cys Asp
210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
             245                 250                 255

Ser Arg Thr Pro Glu Val Thr Cys Val Val Val Asp Val Ser His Glu
             260                 265                 270

Asp Pro Glu Val Lys Phe Asn Trp Tyr Val Asp Gly Val Glu Val His
         275                 280                 285

Asn Ala Lys Thr Lys Pro Arg Glu Glu Gln Tyr Asn Ser Thr Tyr Arg
     290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
             325                 330                 335

Lys Thr Ile Ser Lys Ala Lys Gly Gln Pro Arg Glu Pro Gln Val Tyr
             340                 345                 350

Thr Leu Pro Pro Ser Arg Glu Glu Met Thr Lys Asn Gln Val Ser Leu
         355                 360                 365

Thr Cys Leu Val Lys Gly Phe Tyr Pro Ser Asp Ile Ala Val Glu Trp
     370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
             405                 410                 415
```

-continued

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
            435                 440                 445

Gly Lys
    450

<210> SEQ ID NO 145
<211> LENGTH: 120
<212> TYPE: PRT
<213> ORGANISM: Artificial Sequence
<220> FEATURE:
<223> OTHER INFORMATION: A1e9 VH DOMAIN

<400> SEQUENCE: 145

Gln Val Thr Leu Arg Glu Ser Gly Pro Ala Leu Val Lys Pro Thr Gln
1               5                   10                  15

Thr Leu Thr Leu Thr Cys Thr Phe Ser Gly Phe Ser Leu Ser Thr Pro
            20                  25                  30

Gly Met Ser Val Gly Trp Ile Arg Gln Pro Pro Gly Lys Ala Leu Glu
        35                  40                  45

Trp Leu Ala Asp Ile Trp Trp Asp Gly Lys Lys His Tyr Asn Pro Ser
50                  55                  60

Leu Lys Asp Arg Leu Thr Ile Ser Lys Asp Thr Ser Lys Asn Gln Val
65                  70                  75                  80

Val Leu Lys Val Thr Asn Met Asp Pro Ala Asp Thr Ala Thr Tyr Tyr
                85                  90                  95

Cys Ala Arg Asp Met Ile Phe Asn Trp Tyr Phe Asp Val Trp Gly Gln
            100                 105                 110

Gly Thr Thr Val Thr Val Ser Ser
        115                 120

<210> SEQ ID NO 146
<211> LENGTH: 213
<212> TYPE: PRT
<213> ORGANISM: Artificial Sequence
<220> FEATURE:
<223> OTHER INFORMATION: A1e9 VL CHAIN

<400> SEQUENCE: 146

Asp Ile Gln Met Thr Gln Ser Pro Ser Thr Leu Ser Ala Ser Val Gly
1               5                   10                  15

Asp Arg Val Thr Ile Thr Cys Ser Leu Ser Ser Arg Val Gly Tyr Met
            20                  25                  30

His Trp Tyr Gln Gln Lys Pro Gly Lys Ala Pro Lys Leu Leu Ile Tyr
        35                  40                  45

Asp Thr Phe Lys Leu Ser Ser Gly Val Pro Ser Arg Phe Ser Gly Ser
50                  55                  60

Gly Ser Gly Thr Glu Phe Thr Leu Thr Ile Ser Ser Leu Gln Pro Asp
65                  70                  75                  80

Asp Phe Ala Thr Tyr Tyr Cys Phe Gln Gly Ser Gly Tyr Pro Phe Thr
                85                  90                  95

Phe Gly Gly Gly Thr Lys Val Glu Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

```
Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210

<210> SEQ ID NO 147
<211> LENGTH: 106
<212> TYPE: PRT
<213> ORGANISM: Artificial Sequence
<220> FEATURE:
<223> OTHER INFORMATION: A1e9 VL DOMAIN

<400> SEQUENCE: 147

Asp Ile Gln Met Thr Gln Ser Pro Ser Thr Leu Ser Ala Ser Val Gly
1               5                   10                  15

Asp Arg Val Thr Ile Thr Cys Ser Leu Ser Ser Arg Val Gly Tyr Met
            20                  25                  30

His Trp Tyr Gln Gln Lys Pro Gly Lys Ala Pro Lys Leu Leu Ile Tyr
        35                  40                  45

Asp Thr Phe Lys Leu Ser Ser Gly Val Pro Ser Arg Phe Ser Gly Ser
    50                  55                  60

Gly Ser Gly Thr Glu Phe Thr Leu Thr Ile Ser Ser Leu Gln Pro Asp
65                  70                  75                  80

Asp Phe Ala Thr Tyr Tyr Cys Phe Gln Gly Ser Gly Tyr Pro Phe Thr
                85                  90                  95

Phe Gly Gly Gly Thr Lys Val Glu Ile Lys
            100                 105

<210> SEQ ID NO 148
<211> LENGTH: 7
<212> TYPE: PRT
<213> ORGANISM: Artificial Sequence
<220> FEATURE:
<223> OTHER INFORMATION: A1e9 VL CDR2

<400> SEQUENCE: 148

Asp Thr Phe Lys Leu Ser Ser
1               5

<210> SEQ ID NO 149
<211> LENGTH: 450
<212> TYPE: PRT
<213> ORGANISM: Artificial Sequence
<220> FEATURE:
<223> OTHER INFORMATION: A12a6 VH CHAIN

<400> SEQUENCE: 149

Gln Val Thr Leu Arg Glu Ser Gly Pro Ala Leu Val Lys Pro Thr Gln
1               5                   10                  15

Thr Leu Thr Leu Thr Cys Thr Phe Ser Gly Phe Ser Leu Ser Thr Ala
            20                  25                  30

Gly Met Ser Val Gly Trp Ile Arg Gln Pro Pro Gly Lys Ala Leu Glu
        35                  40                  45
```

-continued

```
Trp Leu Ala Asp Ile Trp Trp Asp Gly Lys Lys Asp Tyr Asn Pro Ser
     50                  55                  60
Leu Lys Asp Arg Leu Thr Ile Ser Lys Asp Thr Ser Lys Asn Gln Val
 65                  70                  75                  80
Val Leu Lys Val Thr Asn Met Asp Pro Ala Asp Thr Ala Thr Tyr Tyr
                     85                  90                  95
Cys Ala Arg Asp Met Ile Phe Asn Phe Tyr Phe Asp Val Trp Gly Gln
                100                 105                 110
Gly Thr Thr Val Thr Val Ser Ser Ala Ser Thr Lys Gly Pro Ser Val
                115                 120                 125
Phe Pro Leu Ala Pro Ser Ser Lys Ser Thr Ser Gly Gly Thr Ala Ala
130                 135                 140
Leu Gly Cys Leu Val Lys Asp Tyr Phe Pro Glu Pro Val Thr Val Ser
145                 150                 155                 160
Trp Asn Ser Gly Ala Leu Thr Ser Gly Val His Thr Phe Pro Ala Val
                165                 170                 175
Leu Gln Ser Ser Gly Leu Tyr Ser Leu Ser Ser Val Val Thr Val Pro
                180                 185                 190
Ser Ser Ser Leu Gly Thr Gln Thr Tyr Ile Cys Asn Val Asn His Lys
                195                 200                 205
Pro Ser Asn Thr Lys Val Asp Lys Arg Val Glu Pro Lys Ser Cys Asp
210                 215                 220
Lys Thr His Thr Cys Pro Pro Cys Pro Ala Pro Glu Leu Leu Gly Gly
225                 230                 235                 240
Pro Ser Val Phe Leu Phe Pro Pro Lys Pro Lys Asp Thr Leu Met Ile
                245                 250                 255
Ser Arg Thr Pro Glu Val Thr Cys Val Val Val Asp Val Ser His Glu
                260                 265                 270
Asp Pro Glu Val Lys Phe Asn Trp Tyr Val Asp Gly Val Glu Val His
                275                 280                 285
Asn Ala Lys Thr Lys Pro Arg Glu Glu Gln Tyr Asn Ser Thr Tyr Arg
                290                 295                 300
Val Val Ser Val Leu Thr Val Leu His Gln Asp Trp Leu Asn Gly Lys
305                 310                 315                 320
Glu Tyr Lys Cys Lys Val Ser Asn Lys Ala Leu Pro Ala Pro Ile Glu
                325                 330                 335
Lys Thr Ile Ser Lys Ala Lys Gly Gln Pro Arg Glu Pro Gln Val Tyr
                340                 345                 350
Thr Leu Pro Pro Ser Arg Glu Glu Met Thr Lys Asn Gln Val Ser Leu
                355                 360                 365
Thr Cys Leu Val Lys Gly Phe Tyr Pro Ser Asp Ile Ala Val Glu Trp
370                 375                 380
Glu Ser Asn Gly Gln Pro Glu Asn Asn Tyr Lys Thr Pro Pro Val
385                 390                 395                 400
Leu Asp Ser Asp Gly Ser Phe Phe Leu Tyr Ser Lys Leu Thr Val Asp
                405                 410                 415
Lys Ser Arg Trp Gln Gln Gly Asn Val Phe Ser Cys Ser Val Met His
                420                 425                 430
Glu Ala Leu His Asn His Tyr Thr Gln Lys Ser Leu Ser Leu Ser Pro
                435                 440                 445
Gly Lys
450
```

```
<210> SEQ ID NO 150
<211> LENGTH: 120
<212> TYPE: PRT
<213> ORGANISM: Artificial Sequence
<220> FEATURE:
<223> OTHER INFORMATION: A12a6 VH DOMAIN

<400> SEQUENCE: 150

Gln Val Thr Leu Arg Glu Ser Gly Pro Ala Leu Val Lys Pro Thr Gln
 1               5                  10                  15

Thr Leu Thr Leu Thr Cys Thr Phe Ser Gly Phe Ser Leu Ser Thr Ala
             20                  25                  30

Gly Met Ser Val Gly Trp Ile Arg Gln Pro Pro Gly Lys Ala Leu Glu
         35                  40                  45

Trp Leu Ala Asp Ile Trp Trp Asp Gly Lys Lys Asp Tyr Asn Pro Ser
     50                  55                  60

Leu Lys Asp Arg Leu Thr Ile Ser Lys Asp Thr Ser Lys Asn Gln Val
 65                  70                  75                  80

Val Leu Lys Val Thr Asn Met Asp Pro Ala Asp Thr Ala Thr Tyr Tyr
                 85                  90                  95

Cys Ala Arg Asp Met Ile Phe Asn Phe Tyr Phe Asp Val Trp Gly Gln
             100                 105                 110

Gly Thr Thr Val Thr Val Ser Ser
         115                 120

<210> SEQ ID NO 151
<211> LENGTH: 16
<212> TYPE: PRT
<213> ORGANISM: Artificial Sequence
<220> FEATURE:
<223> OTHER INFORMATION: A12a6 VH CDR2

<400> SEQUENCE: 151

Asp Ile Trp Trp Asp Gly Lys Lys Asp Tyr Asn Pro Ser Leu Lys Asp
 1               5                  10                  15

<210> SEQ ID NO 152
<211> LENGTH: 213
<212> TYPE: PRT
<213> ORGANISM: Artificial Sequence
<220> FEATURE:
<223> OTHER INFORMATION: A12a6 VL CHAIN

<400> SEQUENCE: 152

Asp Ile Gln Met Thr Gln Ser Pro Ser Thr Leu Ser Ala Ser Val Gly
 1               5                  10                  15

Asp Arg Val Thr Ile Thr Cys Ser Ala Ser Ser Arg Val Gly Tyr Met
             20                  25                  30

His Trp Tyr Gln Gln Lys Pro Gly Lys Ala Pro Lys Leu Leu Ile Tyr
         35                  40                  45

Asp Thr Phe Lys Leu Ser Ser Gly Val Pro Ser Arg Phe Ser Gly Ser
     50                  55                  60

Gly Ser Gly Thr Glu Phe Thr Leu Thr Ile Ser Ser Leu Gln Pro Asp
 65                  70                  75                  80

Asp Phe Ala Thr Tyr Tyr Cys Phe Gln Gly Ser Gly Tyr Pro Phe Thr
                 85                  90                  95

Phe Gly Gly Gly Thr Lys Val Glu Ile Lys Arg Thr Val Ala Ala Pro
             100                 105                 110

Ser Val Phe Ile Phe Pro Pro Ser Asp Glu Gln Leu Lys Ser Gly Thr
         115                 120                 125
```

Ala Ser Val Val Cys Leu Leu Asn Asn Phe Tyr Pro Arg Glu Ala Lys
            130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210

<210> SEQ ID NO 153
<211> LENGTH: 106
<212> TYPE: PRT
<213> ORGANISM: Artificial Sequence
<220> FEATURE:
<223> OTHER INFORMATION: A12a6 VL DOMAIN

<400> SEQUENCE: 153

Asp Ile Gln Met Thr Gln Ser Pro Ser Thr Leu Ser Ala Ser Val Gly
1               5                   10                  15

Asp Arg Val Thr Ile Thr Cys Ser Ala Ser Ser Arg Val Gly Tyr Met
            20                  25                  30

His Trp Tyr Gln Gln Lys Pro Gly Lys Ala Pro Lys Leu Leu Ile Tyr
        35                  40                  45

Asp Thr Phe Lys Leu Ser Ser Gly Val Pro Ser Arg Phe Ser Gly Ser
    50                  55                  60

Gly Ser Gly Thr Glu Phe Thr Leu Thr Ile Ser Ser Leu Gln Pro Asp
65                  70                  75                  80

Asp Phe Ala Thr Tyr Tyr Cys Phe Gln Gly Ser Gly Tyr Pro Phe Thr
                85                  90                  95

Phe Gly Gly Gly Thr Lys Val Glu Ile Lys
            100                 105

<210> SEQ ID NO 154
<211> LENGTH: 10
<212> TYPE: PRT
<213> ORGANISM: Artificial Sequence
<220> FEATURE:
<223> OTHER INFORMATION: A12a6 VL CDR1

<400> SEQUENCE: 154

Ser Ala Ser Ser Arg Val Gly Tyr Met His
1               5                   10

<210> SEQ ID NO 155
<211> LENGTH: 450
<212> TYPE: PRT
<213> ORGANISM: Artificial Sequence
<220> FEATURE:
<223> OTHER INFORMATION: A13c4 VH CHAIN

<400> SEQUENCE: 155

Gln Val Thr Leu Arg Glu Ser Gly Pro Ala Leu Val Lys Pro Thr Gln
1               5                   10                  15

Thr Leu Thr Leu Thr Cys Thr Phe Ser Gly Phe Ser Leu Ser Thr Ala
            20                  25                  30

-continued

```
Gly Met Ser Val Gly Trp Ile Arg Gln Pro Pro Gly Lys Ala Leu Glu
         35                  40                  45

Trp Leu Ala Asp Ile Trp Trp Asp Gly Lys Ser Tyr Asn Pro Ser
 50                  55                  60

Leu Lys Asp Arg Leu Thr Ile Ser Lys Asp Thr Ser Lys Asn Gln Val
 65                  70                  75                  80

Val Leu Lys Val Thr Asn Met Asp Pro Ala Asp Thr Ala Thr Tyr Tyr
                 85                  90                  95

Cys Ala Arg Asp Met Ile Phe Asn Phe Tyr Phe Asp Val Trp Gly Gln
             100                 105                 110

Gly Thr Thr Val Thr Val Ser Ser Ala Ser Thr Lys Gly Pro Ser Val
             115                 120                 125

Phe Pro Leu Ala Pro Ser Ser Lys Ser Thr Ser Gly Gly Thr Ala Ala
             130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                 165                 170                 175

Leu Gln Ser Ser Gly Leu Tyr Ser Leu Ser Ser Val Val Thr Val Pro
             180                 185                 190

Ser Ser Ser Leu Gly Thr Gln Thr Tyr Ile Cys Asn Val Asn His Lys
             195                 200                 205

Pro Ser Asn Thr Lys Val Asp Lys Arg Val Glu Pro Lys Ser Cys Asp
             210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                 245                 250                 255

Ser Arg Thr Pro Glu Val Thr Cys Val Val Val Asp Val Ser His Glu
             260                 265                 270

Asp Pro Glu Val Lys Phe Asn Trp Tyr Val Asp Gly Val Glu Val His
             275                 280                 285

Asn Ala Lys Thr Lys Pro Arg Glu Glu Gln Tyr Asn Ser Thr Tyr Arg
290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                 325                 330                 335

Lys Thr Ile Ser Lys Ala Lys Gly Gln Pro Arg Glu Pro Gln Val Tyr
             340                 345                 350

Thr Leu Pro Pro Ser Arg Glu Glu Met Thr Lys Asn Gln Val Ser Leu
             355                 360                 365

Thr Cys Leu Val Lys Gly Phe Tyr Pro Ser Asp Ile Ala Val Glu Trp
             370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                 405                 410                 415

Lys Ser Arg Trp Gln Gln Gly Asn Val Phe Ser Cys Ser Val Met His
             420                 425                 430

Glu Ala Leu His Asn His Tyr Thr Gln Lys Ser Leu Ser Leu Ser Pro
             435                 440                 445

Gly Lys
```

<210> SEQ ID NO 156
<211> LENGTH: 120
<212> TYPE: PRT
<213> ORGANISM: Artificial Sequence
<220> FEATURE:
<223> OTHER INFORMATION: A13c4 VH DOMAIN

<400> SEQUENCE: 156

```
Gln Val Thr Leu Arg Glu Ser Gly Pro Ala Leu Val Lys Pro Thr Gln
  1               5                  10                  15

Thr Leu Thr Leu Thr Cys Thr Phe Ser Gly Phe Ser Leu Ser Thr Ala
             20                  25                  30

Gly Met Ser Val Gly Trp Ile Arg Gln Pro Pro Gly Lys Ala Leu Glu
         35                  40                  45

Trp Leu Ala Asp Ile Trp Trp Asp Gly Lys Lys Ser Tyr Asn Pro Ser
 50                  55                  60

Leu Lys Asp Arg Leu Thr Ile Ser Lys Asp Thr Ser Lys Asn Gln Val
 65                  70                  75                  80

Val Leu Lys Val Thr Asn Met Asp Pro Ala Asp Thr Ala Thr Tyr Tyr
                 85                  90                  95

Cys Ala Arg Asp Met Ile Phe Asn Phe Tyr Phe Asp Val Trp Gly Gln
            100                 105                 110

Gly Thr Thr Val Thr Val Ser Ser
            115                 120
```

<210> SEQ ID NO 157
<211> LENGTH: 16
<212> TYPE: PRT
<213> ORGANISM: Artificial Sequence
<220> FEATURE:
<223> OTHER INFORMATION: A13c4 VH CDR2

<400> SEQUENCE: 157

```
Asp Ile Trp Trp Asp Gly Lys Lys Ser Tyr Asn Pro Ser Leu Lys Asp
  1               5                  10                  15
```

<210> SEQ ID NO 158
<211> LENGTH: 213
<212> TYPE: PRT
<213> ORGANISM: Artificial Sequence
<220> FEATURE:
<223> OTHER INFORMATION: A13c4 VL CHAIN

<400> SEQUENCE: 158

```
Asp Ile Gln Met Thr Gln Ser Pro Ser Thr Leu Ser Ala Ser Val Gly
  1               5                  10                  15

Asp Arg Val Thr Ile Thr Cys Ser Leu Ser Ser Arg Val Gly Tyr Met
             20                  25                  30

His Trp Tyr Gln Gln Lys Pro Gly Lys Ala Pro Lys Leu Leu Ile Tyr
         35                  40                  45

Asp Thr Met Tyr Gln Ser Ser Gly Val Pro Ser Arg Phe Ser Gly Ser
 50                  55                  60

Gly Ser Gly Thr Glu Phe Thr Leu Thr Ile Ser Ser Leu Gln Pro Asp
 65                  70                  75                  80

Asp Phe Ala Thr Tyr Tyr Cys Phe Gln Gly Ser Gly Tyr Pro Phe Thr
                 85                  90                  95

Phe Gly Gly Gly Thr Lys Val Glu Ile Lys Arg Thr Val Ala Ala Pro
            100                 105                 110
```

```
Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
        210

<210> SEQ ID NO 159
<211> LENGTH: 106
<212> TYPE: PRT
<213> ORGANISM: Artificial Sequence
<220> FEATURE:
<223> OTHER INFORMATION: A13c4 VL DOMAIN

<400> SEQUENCE: 159

Asp Ile Gln Met Thr Gln Ser Pro Ser Thr Leu Ser Ala Ser Val Gly
1               5                   10                  15

Asp Arg Val Thr Ile Thr Cys Ser Leu Ser Ser Arg Val Gly Tyr Met
            20                  25                  30

His Trp Tyr Gln Gln Lys Pro Gly Lys Ala Pro Lys Leu Leu Ile Tyr
        35                  40                  45

Asp Thr Met Tyr Gln Ser Ser Gly Val Pro Ser Arg Phe Ser Gly Ser
    50                  55                  60

Gly Ser Gly Thr Glu Phe Thr Leu Thr Ile Ser Ser Leu Gln Pro Asp
65                  70                  75                  80

Asp Phe Ala Thr Tyr Tyr Cys Phe Gln Gly Ser Gly Tyr Pro Phe Thr
                85                  90                  95

Phe Gly Gly Gly Thr Lys Val Glu Ile Lys
            100                 105

<210> SEQ ID NO 160
<211> LENGTH: 7
<212> TYPE: PRT
<213> ORGANISM: Artificial Sequence
<220> FEATURE:
<223> OTHER INFORMATION: A13c4 VL CDR2

<400> SEQUENCE: 160

Asp Thr Met Tyr Gln Ser Ser
1               5

<210> SEQ ID NO 161
<211> LENGTH: 450
<212> TYPE: PRT
<213> ORGANISM: Artificial Sequence
<220> FEATURE:
<223> OTHER INFORMATION: A17d4 VH CHAIN

<400> SEQUENCE: 161

Gln Val Thr Leu Arg Glu Ser Gly Pro Ala Leu Val Lys Pro Thr Gln
1               5                   10                  15
```

-continued

Thr Leu Thr Leu Thr Cys Thr Phe Ser Gly Phe Ser Leu Ser Thr Ala
            20                  25                  30

Gly Met Ser Val Gly Trp Ile Arg Gln Pro Pro Gly Lys Ala Leu Glu
        35                  40                  45

Trp Leu Ala Asp Ile Trp Trp Asp Gly Lys Lys Ser Tyr Asn Pro Ser
50                  55                  60

Leu Lys Asp Arg Leu Thr Ile Ser Lys Asp Thr Ser Lys Asn Gln Val
65                  70                  75                  80

Val Leu Lys Val Thr Asn Met Asp Pro Ala Asp Thr Ala Thr Tyr Tyr
                85                  90                  95

Cys Ala Arg Asp Met Ile Phe Asn Phe Tyr Phe Asp Val Trp Gly Gln
            100                 105                 110

Gly Thr Thr Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Arg Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro

<210> SEQ ID NO 162
<211> LENGTH: 120
<212> TYPE: PRT
<213> ORGANISM: Artificial Sequence
<220> FEATURE:
<223> OTHER INFORMATION: A17d4 VH DOMAIN

<400> SEQUENCE: 162

```
Gln Val Thr Leu Arg Glu Ser Gly Pro Ala Leu Val Lys Pro Thr Gln
  1               5                  10                  15

Thr Leu Thr Leu Thr Cys Thr Phe Ser Gly Phe Ser Leu Ser Thr Ala
             20                  25                  30

Gly Met Ser Val Gly Trp Ile Arg Gln Pro Pro Gly Lys Ala Leu Glu
         35                  40                  45

Trp Leu Ala Asp Ile Trp Trp Asp Gly Lys Lys Ser Tyr Asn Pro Ser
 50                  55                  60

Leu Lys Asp Arg Leu Thr Ile Ser Lys Asp Thr Ser Lys Asn Gln Val
 65                  70                  75                  80

Val Leu Lys Val Thr Asn Met Asp Pro Ala Asp Thr Ala Thr Tyr Tyr
                 85                  90                  95

Cys Ala Arg Asp Met Ile Phe Asn Phe Tyr Phe Asp Val Trp Gly Gln
            100                 105                 110

Gly Thr Thr Val Thr Val Ser Ser
        115                 120
```

<210> SEQ ID NO 163
<211> LENGTH: 16
<212> TYPE: PRT
<213> ORGANISM: Artificial Sequence
<220> FEATURE:
<223> OTHER INFORMATION: A17d4 VH CDR2

<400> SEQUENCE: 163

```
Asp Ile Trp Trp Asp Gly Lys Lys Ser Tyr Asn Pro Ser Leu Lys Asp
  1               5                  10                  15
```

<210> SEQ ID NO 164
<211> LENGTH: 213
<212> TYPE: PRT
<213> ORGANISM: Artificial Sequence
<220> FEATURE:
<223> OTHER INFORMATION: A17d4 VL CHAIN

<400> SEQUENCE: 164

```
Asp Ile Gln Met Thr Gln Ser Pro Ser Thr Leu Ser Ala Ser Val Gly
  1               5                  10                  15

Asp Arg Val Thr Ile Thr Cys Leu Pro Ser Ser Arg Val Gly Tyr Met
             20                  25                  30

His Trp Tyr Gln Gln Lys Pro Gly Lys Ala Pro Lys Leu Leu Ile Tyr
         35                  40                  45

Asp Thr Met Tyr Gln Ser Ser Gly Val Pro Ser Arg Phe Ser Gly Ser
 50                  55                  60

Gly Ser Gly Thr Glu Phe Thr Leu Thr Ile Ser Ser Leu Gln Pro Asp
 65                  70                  75                  80

Asp Phe Ala Thr Tyr Tyr Cys Phe Gln Gly Ser Gly Tyr Pro Phe Thr
                 85                  90                  95
```

```
Phe Gly Gly Gly Thr Lys Val Glu Ile Lys Arg Thr Val Ala Ala Pro
                100                 105                 110

Ser Val Phe Ile Phe Pro Pro Ser Asp Glu Gln Leu Lys Ser Gly Thr
            115                 120                 125

Ala Ser Val Val Cys Leu Leu Asn Asn Phe Tyr Pro Arg Glu Ala Lys
        130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210
```

<210> SEQ ID NO 165
<211> LENGTH: 106
<212> TYPE: PRT
<213> ORGANISM: Artificial Sequence
<220> FEATURE:
<223> OTHER INFORMATION: A17d4 VL DOMAIN

<400> SEQUENCE: 165

```
Asp Ile Gln Met Thr Gln Ser Pro Ser Thr Leu Ser Ala Ser Val Gly
1               5                   10                  15

Asp Arg Val Thr Ile Thr Cys Leu Pro Ser Ser Arg Val Gly Tyr Met
            20                  25                  30

His Trp Tyr Gln Gln Lys Pro Gly Lys Ala Pro Lys Leu Leu Ile Tyr
        35                  40                  45

Asp Thr Met Tyr Gln Ala Ser Gly Val Pro Ser Arg Phe Ser Gly Ser
    50                  55                  60

Gly Ser Gly Thr Glu Phe Thr Leu Thr Ile Ser Ser Leu Gln Pro Asp
65                  70                  75                  80

Asp Phe Ala Thr Tyr Tyr Cys Phe Gln Phe Ser Gly Tyr Pro Phe Thr
                85                  90                  95

Phe Gly Gly Gly Thr Lys Leu Glu Ile Lys
                100                 105
```

<210> SEQ ID NO 166
<211> LENGTH: 10
<212> TYPE: PRT
<213> ORGANISM: Artificial Sequence
<220> FEATURE:
<223> OTHER INFORMATION: A17d4 VL CDR1

<400> SEQUENCE: 166

```
Leu Pro Ser Ser Arg Val Gly Tyr Met His
1               5                   10
```

<210> SEQ ID NO 167
<211> LENGTH: 450
<212> TYPE: PRT
<213> ORGANISM: Artificial Sequence
<220> FEATURE:
<223> OTHER INFORMATION: A4B4 VH CHAIN

<400> SEQUENCE: 167

```
Gln Val Thr Leu Arg Glu Ser Gly Pro Ala Leu Val Lys Pro Thr Gln
 1               5                  10                  15

Thr Leu Thr Leu Thr Cys Thr Phe Ser Gly Phe Ser Leu Ser Thr Ala
            20                  25                  30

Gly Met Ser Val Gly Trp Ile Arg Gln Pro Pro Gly Lys Ala Leu Glu
            35                  40                  45

Trp Leu Ala Asp Ile Trp Trp Asp Asp Lys Lys His Tyr Asn Pro Ser
 50                  55                  60

Leu Lys Asp Arg Leu Thr Ile Ser Lys Asp Thr Ser Lys Asn Gln Val
 65                  70                  75                  80

Val Leu Lys Val Thr Asn Met Asp Pro Ala Asp Thr Ala Thr Tyr Tyr
                85                  90                  95

Cys Ala Arg Asp Met Ile Phe Asn Phe Tyr Phe Asp Val Trp Gly Gln
            100                 105                 110

Gly Thr Thr Val Thr Val Ser Ser Ala Ser Thr Lys Gly Pro Ser Val
            115                 120                 125

Phe Pro Leu Ala Pro Ser Ser Lys Ser Thr Ser Gly Gly Thr Ala Ala
            130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
            195                 200                 205

Pro Ser Asn Thr Lys Val Asp Lys Arg Val Glu Pro Lys Ser Cys Asp
            210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
            275                 280                 285

Asn Ala Lys Thr Lys Pro Arg Glu Glu Gln Tyr Asn Ser Thr Tyr Arg
            290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
            355                 360                 365

Thr Cys Leu Val Lys Gly Phe Tyr Pro Ser Asp Ile Ala Val Glu Trp
            370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
```

-continued

```
                     420                 425                 430
Glu Ala Leu His Asn His Tyr Thr Gln Lys Ser Leu Ser Leu Ser Pro
            435                 440                 445
Gly Lys
    450

<210> SEQ ID NO 168
<211> LENGTH: 120
<212> TYPE: PRT
<213> ORGANISM: Artificial Sequence
<220> FEATURE:
<223> OTHER INFORMATION: A4B4 VH DOMAIN

<400> SEQUENCE: 168

Gln Val Thr Leu Arg Glu Ser Gly Pro Ala Leu Val Lys Pro Thr Gln
  1               5                  10                  15

Thr Leu Thr Leu Thr Cys Thr Phe Ser Gly Phe Ser Leu Ser Thr Ala
             20                  25                  30

Gly Met Ser Val Gly Trp Ile Arg Gln Pro Pro Gly Lys Ala Leu Glu
         35                  40                  45

Trp Leu Ala Asp Ile Trp Trp Asp Asp Lys Lys His Tyr Asn Pro Ser
 50                  55                  60

Leu Lys Asp Arg Leu Thr Ile Ser Lys Asp Thr Ser Lys Asn Gln Val
 65                  70                  75                  80

Val Leu Lys Val Thr Asn Met Asp Pro Ala Asp Thr Ala Thr Tyr Tyr
                 85                  90                  95

Cys Ala Arg Asp Met Ile Phe Asn Phe Tyr Phe Asp Val Trp Gly Gln
            100                 105                 110

Gly Thr Thr Val Thr Val Ser Ser
        115                 120

<210> SEQ ID NO 169
<211> LENGTH: 213
<212> TYPE: PRT
<213> ORGANISM: Artificial Sequence
<220> FEATURE:
<223> OTHER INFORMATION: A4B4 VL CHAIN

<400> SEQUENCE: 169

Asp Ile Gln Met Thr Gln Ser Pro Ser Thr Leu Ser Ala Ser Val Gly
  1               5                  10                  15

Asp Arg Val Thr Ile Thr Cys Ser Ala Ser Ser Arg Val Gly Tyr Met
             20                  25                  30

His Trp Tyr Gln Gln Lys Pro Gly Lys Ala Pro Lys Leu Leu Ile Tyr
         35                  40                  45

Asp Thr Phe Phe Leu Asp Ser Gly Val Pro Ser Arg Phe Ser Gly Ser
 50                  55                  60

Gly Ser Gly Thr Glu Phe Thr Leu Thr Ile Ser Ser Leu Gln Pro Asp
 65                  70                  75                  80

Asp Phe Ala Thr Tyr Tyr Cys Phe Gln Gly Ser Gly Tyr Pro Phe Thr
                 85                  90                  95

Phe Gly Gly Gly Thr Lys Val Glu Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140
```

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
            165                 170                 175

Thr Leu Thr Leu Ser Lys Ala Asp Tyr Glu Lys His Lys Val Tyr Ala
        180                 185                 190

Cys Glu Val Thr His Gln Gly Leu Ser Ser Pro Val Thr Lys Ser Phe
    195                 200                 205

Asn Arg Gly Glu Cys
    210

<210> SEQ ID NO 170
<211> LENGTH: 106
<212> TYPE: PRT
<213> ORGANISM: Artificial Sequence
<220> FEATURE:
<223> OTHER INFORMATION: A4B4 VL DOMAIN

<400> SEQUENCE: 170

Asp Ile Gln Met Thr Gln Ser Pro Ser Thr Leu Ser Ala Ser Val Gly
1               5                   10                  15

Asp Arg Val Thr Ile Thr Cys Ser Ala Ser Ser Arg Val Gly Tyr Met
            20                  25                  30

His Trp Tyr Gln Gln Lys Pro Gly Lys Ala Pro Lys Leu Leu Ile Tyr
        35                  40                  45

Asp Thr Phe Phe Leu Asp Ser Gly Val Pro Ser Arg Phe Ser Gly Ser
    50                  55                  60

Gly Ser Gly Thr Glu Phe Thr Leu Thr Ile Ser Ser Leu Gln Pro Asp
65                  70                  75                  80

Asp Phe Ala Thr Tyr Tyr Cys Phe Gln Gly Ser Gly Tyr Pro Phe Thr
                85                  90                  95

Phe Gly Gly Gly Thr Lys Leu Glu Ile Lys
            100                 105

<210> SEQ ID NO 171
<211> LENGTH: 7
<212> TYPE: PRT
<213> ORGANISM: Artificial Sequence
<220> FEATURE:
<223> OTHER INFORMATION: A4B4 VL CDR2

<400> SEQUENCE: 171

Asp Thr Phe Phe Leu Asp Ser
1               5

<210> SEQ ID NO 172
<211> LENGTH: 450
<212> TYPE: PRT
<213> ORGANISM: Artificial Sequence
<220> FEATURE:
<223> OTHER INFORMATION: A8c7 VH CHAIN

<400> SEQUENCE: 172

Gln Val Thr Leu Arg Glu Ser Gly Pro Ala Leu Val Lys Pro Thr Gln
1               5                   10                  15

Thr Leu Thr Leu Thr Cys Thr Phe Ser Gly Phe Ser Leu Ser Thr Ala
            20                  25                  30

Gly Met Ser Val Gly Trp Ile Arg Gln Pro Pro Gly Lys Ala Leu Glu
        35                  40                  45

Trp Leu Ala Asp Ile Trp Trp Asp Asp Lys Lys Ser Tyr Asn Pro Ser

```
                50                  55                  60
Leu Lys Asp Arg Leu Thr Ile Ser Lys Asp Thr Ser Lys Asn Gln Val
 65                  70                  75                  80

Val Leu Lys Val Thr Asn Met Asp Pro Ala Asp Thr Ala Thr Tyr Tyr
                     85                  90                  95

Cys Ala Arg Asp Met Ile Phe Asn Trp Tyr Phe Asp Val Trp Gly Gln
                    100                 105                 110

Gly Thr Thr Val Thr Val Ser Ser Ala Ser Thr Lys Gly Pro Ser Val
                115                 120                 125

Phe Pro Leu Ala Pro Ser Ser Lys Ser Thr Ser Gly Gly Thr Ala Ala
            130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                    165                 170                 175

Leu Gln Ser Ser Gly Leu Tyr Ser Leu Ser Ser Val Val Thr Val Pro
                180                 185                 190

Ser Ser Ser Leu Gly Thr Gln Thr Tyr Ile Cys Asn Val Asn His Lys
                195                 200                 205

Pro Ser Asn Thr Lys Val Asp Lys Arg Val Glu Pro Lys Ser Cys Asp
210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
                260                 265                 270

Asp Pro Glu Val Lys Phe Asn Trp Tyr Val Asp Gly Val Glu Val His
                275                 280                 285

Asn Ala Lys Thr Lys Pro Arg Glu Glu Gln Tyr Asn Ser Thr Tyr Arg
            290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                    325                 330                 335

Lys Thr Ile Ser Lys Ala Lys Gly Gln Pro Arg Glu Pro Gln Val Tyr
                340                 345                 350

Thr Leu Pro Pro Ser Arg Glu Glu Met Thr Lys Asn Gln Val Ser Leu
            355                 360                 365

Thr Cys Leu Val Lys Gly Phe Tyr Pro Ser Asp Ile Ala Val Glu Trp
370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
                420                 425                 430

Glu Ala Leu His Asn His Tyr Thr Gln Lys Ser Leu Ser Leu Ser Pro
            435                 440                 445

Gly Lys
450

<210> SEQ ID NO 173
```

```
<211> LENGTH: 120
<212> TYPE: PRT
<213> ORGANISM: Artificial Sequence
<220> FEATURE:
<223> OTHER INFORMATION: A8c7 VH DOMAIN

<400> SEQUENCE: 173
```

Gln Val Thr Leu Arg Glu Ser Gly Pro Ala Leu Val Lys Pro Thr Gln
1               5                   10                  15

Thr Leu Thr Leu Thr Cys Thr Phe Ser Gly Phe Ser Leu Ser Thr Ala
            20                  25                  30

Gly Met Ser Val Gly Trp Ile Arg Gln Pro Pro Gly Lys Ala Leu Glu
        35                  40                  45

Trp Leu Ala Asp Ile Trp Trp Asp Asp Lys Ser Tyr Asn Pro Ser
    50                  55                  60

Leu Lys Asp Arg Leu Thr Ile Ser Lys Asp Thr Ser Lys Asn Gln Val
65                  70                  75                  80

Val Leu Lys Val Thr Asn Met Asp Pro Ala Asp Thr Ala Thr Tyr Tyr
                85                  90                  95

Cys Ala Arg Asp Met Ile Phe Asn Trp Tyr Phe Asp Val Trp Gly Gln
            100                 105                 110

Gly Thr Thr Val Thr Val Ser Ser
            115                 120

```
<210> SEQ ID NO 174
<211> LENGTH: 213
<212> TYPE: PRT
<213> ORGANISM: Artificial Sequence
<220> FEATURE:
<223> OTHER INFORMATION: A8c7 VL CHAIN

<400> SEQUENCE: 174
```

Asp Ile Gln Met Thr Gln Ser Pro Ser Thr Leu Ser Ala Ser Val Gly
1               5                   10                  15

Asp Arg Val Thr Ile Thr Cys Ser Pro Ser Ser Arg Val Gly Tyr Met
            20                  25                  30

His Trp Tyr Gln Gln Lys Pro Gly Lys Ala Pro Lys Leu Leu Ile Tyr
        35                  40                  45

Asp Thr Arg Tyr Gln Ser Ser Gly Val Pro Ser Arg Phe Ser Gly Ser
    50                  55                  60

Gly Ser Gly Thr Glu Phe Thr Leu Thr Ile Ser Ser Leu Gln Pro Asp
65                  70                  75                  80

Asp Phe Ala Thr Tyr Tyr Cys Phe Gln Gly Ser Gly Tyr Pro Phe Thr
                85                  90                  95

Phe Gly Gly Gly Thr Lys Val Glu Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe

Asn Arg Gly Glu Cys
            210

<210> SEQ ID NO 175
<211> LENGTH: 106
<212> TYPE: PRT
<213> ORGANISM: Artificial Sequence
<220> FEATURE:
<223> OTHER INFORMATION: A8c7 VL DOMAIN

<400> SEQUENCE: 175

Asp Ile Gln Met Thr Gln Ser Pro Ser Thr Leu Ser Ala Ser Val Gly
1               5                   10                  15

Asp Arg Val Thr Ile Thr Cys Ser Ala Ser Ser Arg Val Gly Tyr Met
            20                  25                  30

His Trp Tyr Gln Gln Lys Pro Gly Lys Ala Pro Lys Leu Leu Ile Tyr
        35                  40                  45

Asp Thr Arg Tyr Gln Ser Ser Gly Val Pro Ser Arg Phe Ser Gly Ser
    50                  55                  60

Gly Ser Gly Thr Glu Phe Thr Leu Thr Ile Ser Ser Leu Gln Pro Asp
65                  70                  75                  80

Asp Phe Ala Thr Tyr Tyr Cys Phe Gln Gly Ser Gly Tyr Pro Phe Thr
                85                  90                  95

Phe Gly Gly Gly Thr Lys Leu Glu Ile Lys
            100                 105

<210> SEQ ID NO 176
<211> LENGTH: 451
<212> TYPE: PRT
<213> ORGANISM: Artificial Sequence
<220> FEATURE:
<223> OTHER INFORMATION: IX-493L1FR VH CHAIN

<400> SEQUENCE: 176

Gln Val Thr Leu Arg Glu Ser Gly Pro Ala Leu Val Lys Pro Thr Gln
1               5                   10                  15

Thr Leu Thr Leu Thr Cys Thr Phe Ser Gly Phe Ser Leu Ser Thr Ser
            20                  25                  30

Gly Met Ser Val Gly Tyr Trp Ile Arg Gln Pro Pro Gly Lys Ala Leu
        35                  40                  45

Glu Trp Leu Ala Asp Ile Trp Trp Asp Asp Lys Lys Asp Tyr Asn Pro
    50                  55                  60

Ser Leu Lys Ser Arg Leu Thr Ile Ser Lys Asp Thr Ser Lys Asn Gln
65                  70                  75                  80

Val Val Leu Lys Val Thr Asn Met Asp Pro Ala Asp Thr Ala Thr Tyr
                85                  90                  95

Tyr Cys Ala Arg Ser Met Ile Thr Asn Trp Tyr Phe Asp Val Trp Gly
            100                 105                 110

Gln Gly Thr Thr Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
                180                 185                 190

Pro Ser Ser Ser Leu Gly Thr Gln Thr Tyr Ile Cys Asn Val Asn His
            195                 200                 205

Lys Pro Ser Asn Thr Lys Val Asp Lys Arg Val Glu Pro Lys Ser Cys
210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
            245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
            275                 280                 285

His Asn Ala Lys Thr Lys Pro Arg Glu Glu Gln Tyr Asn Ser Thr Tyr
            290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
            325                 330                 335

Glu Lys Thr Ile Ser Lys Ala Lys Gly Gln Pro Arg Glu Pro Gln Val
            340                 345                 350

Tyr Thr Leu Pro Pro Ser Arg Glu Glu Met Thr Lys Asn Gln Val Ser
            355                 360                 365

Leu Thr Cys Leu Val Lys Gly Phe Tyr Pro Ser Asp Ile Ala Val Glu
            370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
            435                 440                 445

Pro Gly Lys
    450

<210> SEQ ID NO 177
<211> LENGTH: 213
<212> TYPE: PRT
<213> ORGANISM: Artificial Sequence
<220> FEATURE:
<223> OTHER INFORMATION: IX-493L1FR VL CHAIN

<400> SEQUENCE: 177

Asp Ile Gln Met Thr Gln Ser Pro Ser Thr Leu Ser Ala Ser Val Gly
1               5                   10                  15

Asp Arg Val Thr Ile Thr Cys Ser Ala Ser Ser Ser Val Gly Tyr Met
            20                  25                  30

His Trp Tyr Gln Gln Lys Pro Gly Lys Ala Pro Lys Leu Leu Ile Tyr
            35                  40                  45

Asp Thr Ser Lys Leu Ala Ser Gly Val Pro Ser Arg Phe Ser Gly Ser
        50                  55                  60

Gly Ser Gly Thr Glu Phe Thr Leu Thr Ile Ser Ser Leu Gln Pro Asp
65                  70                  75                  80

```
Asp Phe Ala Thr Tyr Tyr Cys Phe Gln Gly Ser Gly Tyr Pro Phe Thr
                85                  90                  95

Phe Gly Gly Gly Thr Lys Val Glu Ile Lys Arg Thr Val Ala Ala Pro
            100                 105                 110

Ser Val Phe Ile Phe Pro Pro Ser Asp Glu Gln Leu Lys Ser Gly Thr
            115                 120                 125

Ala Ser Val Val Cys Leu Leu Asn Asn Phe Tyr Pro Arg Glu Ala Lys
130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
            195                 200                 205

Asn Arg Gly Glu Cys
    210
```

<210> SEQ ID NO 178
<211> LENGTH: 106
<212> TYPE: PRT
<213> ORGANISM: Artificial Sequence
<220> FEATURE:
<223> OTHER INFORMATION: IX-493L1FR VL DOMAIN

<400> SEQUENCE: 178

```
Asp Ile Gln Met Thr Gln Ser Pro Ser Thr Leu Ser Ala Ser Val Gly
1               5                   10                  15

Asp Arg Val Thr Ile Thr Cys Ser Ala Ser Ser Ser Val Gly Tyr Met
            20                  25                  30

His Trp Tyr Gln Gln Lys Pro Gly Lys Ala Pro Lys Leu Leu Ile Tyr
        35                  40                  45

Asp Thr Ser Lys Leu Ala Ser Gly Val Pro Ser Arg Phe Ser Gly Ser
50                  55                  60

Gly Ser Gly Thr Glu Phe Thr Leu Thr Ile Ser Ser Leu Gln Pro Asp
65                  70                  75                  80

Asp Phe Ala Thr Tyr Tyr Cys Phe Gln Gly Ser Gly Tyr Pro Phe Thr
                85                  90                  95

Phe Gly Gly Gly Thr Lys Leu Glu Ile Lys
            100                 105
```

<210> SEQ ID NO 179
<211> LENGTH: 450
<212> TYPE: PRT
<213> ORGANISM: Artificial Sequence
<220> FEATURE:
<223> OTHER INFORMATION: M3H9 VH CHAIN

<400> SEQUENCE: 179

```
Gln Val Thr Leu Arg Glu Ser Gly Pro Ala Leu Val Lys Pro Thr Gln
1               5                   10                  15

Thr Leu Thr Leu Thr Cys Thr Phe Ser Gly Phe Ser Leu Ser Thr Ala
            20                  25                  30

Gly Met Ser Val Gly Trp Ile Arg Gln Pro Pro Gly Lys Ala Leu Glu
        35                  40                  45

Trp Leu Ala Asp Ile Trp Trp Asp Asp Lys Lys Asp Tyr Asn Pro Ser
50                  55                  60
```

-continued

Leu Lys Ser Arg Leu Thr Ile Ser Lys Asp Thr Ser Lys Asn Gln Val
 65                  70                  75                  80

Val Leu Lys Val Thr Asn Met Asp Pro Ala Asp Thr Ala Thr Tyr Tyr
                 85                  90                  95

Cys Ala Arg Asp Met Ile Phe Asn Trp Tyr Phe Asp Val Trp Gly Gln
            100                 105                 110

Gly Thr Thr Val Thr Val Ser Ser Ala Ser Thr Lys Gly Pro Ser Val
            115                 120                 125

Phe Pro Leu Ala Pro Ser Ser Lys Ser Thr Ser Gly Gly Thr Ala Ala
130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
            195                 200                 205

Pro Ser Asn Thr Lys Val Asp Lys Arg Val Glu Pro Lys Ser Cys Asp
210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
            275                 280                 285

Asn Ala Lys Thr Lys Pro Arg Glu Glu Gln Tyr Asn Ser Thr Tyr Arg
290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
            355                 360                 365

Thr Cys Leu Val Lys Gly Phe Tyr Pro Ser Asp Ile Ala Val Glu Trp
370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
            435                 440                 445

Gly Lys
450

<210> SEQ ID NO 180
<211> LENGTH: 213

<212> TYPE: PRT
<213> ORGANISM: Artificial Sequence
<220> FEATURE:
<223> OTHER INFORMATION: M3H9 VL CHAIN

<400> SEQUENCE: 180

Asp Ile Gln Met Thr Gln Ser Pro Ser Thr Leu Ser Ala Ser Val Gly
1               5                   10                  15

Asp Arg Val Thr Ile Thr Cys Ser Ala Ser Ser Val Gly Tyr Met
            20                  25                  30

His Trp Tyr Gln Gln Lys Pro Gly Lys Ala Pro Lys Leu Leu Ile Tyr
        35                  40                  45

Asp Thr Tyr Lys Gln Thr Ser Gly Val Pro Ser Arg Phe Ser Gly Ser
    50                  55                  60

Gly Ser Gly Thr Glu Phe Thr Leu Thr Ile Ser Ser Leu Gln Pro Asp
65                  70                  75                  80

Asp Phe Ala Thr Tyr Tyr Cys Phe Gln Gly Ser Gly Tyr Pro Phe Thr
            85                  90                  95

Phe Gly Gly Gly Thr Lys Val Glu Ile Lys Arg Thr Val Ala Ala Pro
        100                 105                 110

Ser Val Phe Ile Phe Pro Pro Ser Asp Glu Gln Leu Lys Ser Gly Thr
    115                 120                 125

Ala Ser Val Val Cys Leu Leu Asn Asn Phe Tyr Pro Arg Glu Ala Lys
130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
            165                 170                 175

Thr Leu Thr Leu Ser Lys Ala Asp Tyr Glu Lys His Lys Val Tyr Ala
        180                 185                 190

Cys Glu Val Thr His Gln Gly Leu Ser Ser Pro Val Thr Lys Ser Phe
    195                 200                 205

Asn Arg Gly Glu Cys
    210

<210> SEQ ID NO 181
<211> LENGTH: 106
<212> TYPE: PRT
<213> ORGANISM: Artificial Sequence
<220> FEATURE:
<223> OTHER INFORMATION: M3H9 VL DOMAIN

<400> SEQUENCE: 181

Asp Ile Gln Met Thr Gln Ser Pro Ser Thr Leu Ser Ala Ser Val Gly
1               5                   10                  15

Asp Arg Val Thr Ile Thr Cys Ser Ala Ser Ser Val Gly Tyr Met
            20                  25                  30

His Trp Tyr Gln Gln Lys Pro Gly Lys Ala Pro Lys Leu Leu Ile Tyr
        35                  40                  45

Asp Thr Tyr Lys Gln Thr Ser Gly Val Pro Ser Arg Phe Ser Gly Ser
    50                  55                  60

Gly Ser Gly Thr Glu Phe Thr Leu Thr Ile Ser Ser Leu Gln Pro Asp
65                  70                  75                  80

Asp Phe Ala Thr Tyr Tyr Cys Phe Gln Gly Ser Gly Tyr Pro Phe Thr
            85                  90                  95

Phe Gly Gly Gly Thr Lys Leu Glu Ile Lys
        100                 105

<210> SEQ ID NO 182
<211> LENGTH: 450
<212> TYPE: PRT
<213> ORGANISM: Artificial Sequence
<220> FEATURE:
<223> OTHER INFORMATION: Y10H6 VH CHAIN

<400> SEQUENCE: 182

```
Gln Val Thr Leu Arg Glu Ser Gly Pro Ala Leu Val Lys Pro Thr Gln
  1               5                  10                  15

Thr Leu Thr Leu Thr Cys Thr Phe Ser Gly Phe Ser Leu Ser Thr Ala
             20                  25                  30

Gly Met Ser Val Gly Trp Ile Arg Gln Pro Pro Gly Lys Ala Leu Glu
         35                  40                  45

Trp Leu Ala Asp Ile Trp Trp Asp Asp Lys Lys Asp Tyr Asn Pro Ser
 50                  55                  60

Leu Lys Ser Arg Leu Thr Ile Ser Lys Asp Thr Ser Lys Asn Gln Val
 65                  70                  75                  80

Val Leu Lys Val Thr Asn Met Asp Pro Ala Asp Thr Ala Thr Tyr Tyr
                 85                  90                  95

Cys Ala Arg Asp Met Ile Phe Asn Trp Tyr Phe Asp Val Trp Gly Gln
            100                 105                 110

Gly Thr Thr Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Arg Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
        355                 360                 365
```

```
Thr Cys Leu Val Lys Gly Phe Tyr Pro Ser Asp Ile Ala Val Glu Trp
        370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450
```

<210> SEQ ID NO 183
<211> LENGTH: 213
<212> TYPE: PRT
<213> ORGANISM: Artificial Sequence
<220> FEATURE:
<223> OTHER INFORMATION: Y10H6 VL CHAIN

<400> SEQUENCE: 183

```
Asp Ile Gln Met Thr Gln Ser Pro Ser Thr Leu Ser Ala Ser Val Gly
1               5                   10                  15

Asp Arg Val Thr Ile Thr Cys Ser Ala Ser Ser Ser Val Gly Tyr Met
            20                  25                  30

His Trp Tyr Gln Gln Lys Pro Gly Lys Ala Pro Lys Leu Leu Ile Tyr
        35                  40                  45

Asp Thr Arg Tyr Leu Ser Ser Gly Val Pro Ser Arg Phe Ser Gly Ser
    50                  55                  60

Gly Ser Gly Thr Glu Phe Thr Leu Thr Ile Ser Leu Gln Pro Asp Asp
65                  70                  75                  80

Asp Phe Ala Thr Tyr Tyr Cys Phe Gln Gly Ser Gly Tyr Pro Phe Thr
                85                  90                  95

Phe Gly Gly Gly Thr Lys Val Glu Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210
```

<210> SEQ ID NO 184
<211> LENGTH: 106
<212> TYPE: PRT
<213> ORGANISM: Artificial Sequence
<220> FEATURE:
<223> OTHER INFORMATION: Y10H6 VL DOMAIN

<400> SEQUENCE: 184

Asp Ile Gln Met Thr Gln Ser Pro Ser Thr Leu Ser Ala Ser Val Gly
1               5                   10                  15

Asp Arg Val Thr Ile Thr Cys Ser Ala Ser Ser Val Gly Tyr Met
            20                  25                  30

His Trp Tyr Gln Gln Lys Pro Gly Lys Ala Pro Lys Leu Leu Ile Tyr
        35                  40                  45

Asp Thr Arg Tyr Leu Ser Ser Gly Val Pro Ser Arg Phe Ser Gly Ser
    50                  55                  60

Gly Ser Gly Thr Glu Phe Thr Leu Thr Ile Ser Ser Leu Gln Pro Asp
65                  70                  75                  80

Asp Phe Ala Thr Tyr Tyr Cys Phe Gln Gly Ser Gly Tyr Pro Phe Thr
                85                  90                  95

Phe Gly Gly Gly Thr Lys Leu Glu Ile Lys
            100                 105

<210> SEQ ID NO 185
<211> LENGTH: 7
<212> TYPE: PRT
<213> ORGANISM: Artificial Sequence
<220> FEATURE:
<223> OTHER INFORMATION: Y10H6 VL CDR2

<400> SEQUENCE: 185

Asp Thr Arg Tyr Leu Ser Ser
1               5

<210> SEQ ID NO 186
<211> LENGTH: 450
<212> TYPE: PRT
<213> ORGANISM: Artificial Sequence
<220> FEATURE:
<223> OTHER INFORMATION: DG VH CHAIN

<400> SEQUENCE: 186

Gln Val Thr Leu Arg Glu Ser Gly Pro Ala Leu Val Lys Pro Thr Gln
1               5                   10                  15

Thr Leu Thr Leu Thr Cys Thr Phe Ser Gly Phe Ser Leu Ser Thr Ala
            20                  25                  30

Gly Met Ser Val Gly Trp Ile Arg Gln Pro Pro Gly Lys Ala Leu Glu
        35                  40                  45

Trp Leu Ala Asp Ile Trp Trp Asp Asp Lys Lys Asp Tyr Asn Pro Ser
    50                  55                  60

Leu Lys Ser Arg Leu Thr Ile Ser Lys Asp Thr Ser Lys Asn Gln Val
65                  70                  75                  80

Val Leu Lys Val Thr Asn Met Asp Pro Ala Asp Thr Ala Thr Tyr Tyr
                85                  90                  95

Cys Ala Arg Asp Met Ile Thr Asn Phe Tyr Phe Asp Val Trp Gly Gln
            100                 105                 110

Gly Thr Thr Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

```
Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
            195                 200                 205

Pro Ser Asn Thr Lys Val Asp Lys Arg Val Glu Pro Lys Ser Cys Asp
            210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
            245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
            275                 280                 285

Asn Ala Lys Thr Lys Pro Arg Glu Glu Gln Tyr Asn Ser Thr Tyr Arg
            290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
            325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
            355                 360                 365

Thr Cys Leu Val Lys Gly Phe Tyr Pro Ser Asp Ile Ala Val Glu Trp
370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
            405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
            435                 440                 445

Gly Lys
    450

<210> SEQ ID NO 187
<211> LENGTH: 120
<212> TYPE: PRT
<213> ORGANISM: Artificial Sequence
<220> FEATURE:
<223> OTHER INFORMATION: DG VH DOMAIN

<400> SEQUENCE: 187

Gln Val Thr Leu Arg Glu Ser Gly Pro Ala Leu Val Lys Pro Thr Gln
  1               5                  10                  15

Thr Leu Thr Leu Thr Cys Thr Phe Ser Gly Phe Ser Leu Ser Thr Ala
            20                  25                  30

Gly Met Ser Val Gly Trp Ile Arg Gln Pro Pro Gly Lys Ala Leu Glu
            35                  40                  45

Trp Leu Ala Asp Ile Trp Trp Asp Asp Lys Lys Asp Tyr Asn Pro Ser
    50                  55                  60

Leu Lys Ser Arg Leu Thr Ile Ser Lys Asp Thr Ser Lys Asn Gln Val
65                  70                  75                  80
```

```
Val Leu Lys Val Thr Asn Met Asp Pro Ala Asp Ala Thr Tyr Tyr
                 85                  90                  95

Cys Ala Arg Asp Met Ile Thr Asn Phe Tyr Phe Asp Val Trp Gly Ala
            100                 105                 110

Gly Thr Thr Val Thr Val Ser Ser
            115             120

<210> SEQ ID NO 188
<211> LENGTH: 10
<212> TYPE: PRT
<213> ORGANISM: Artificial Sequence
<220> FEATURE:
<223> OTHER INFORMATION: DG VH CDR3

<400> SEQUENCE: 188

Asp Met Ile Thr Asn Phe Tyr Phe Asp Val
1               5                   10

<210> SEQ ID NO 189
<211> LENGTH: 213
<212> TYPE: PRT
<213> ORGANISM: Artificial Sequence
<220> FEATURE:
<223> OTHER INFORMATION: DG VL CHAIN

<400> SEQUENCE: 189

Asp Ile Gln Met Thr Gln Ser Pro Ser Thr Leu Ser Ala Ser Val Gly
1               5                   10                  15

Asp Arg Val Thr Ile Thr Cys Ser Ala Ser Ser Ser Val Gly Tyr Met
                20                  25                  30

His Trp Tyr Gln Gln Lys Pro Gly Lys Ala Pro Lys Leu Leu Ile Tyr
            35                  40                  45

Asp Thr Phe Lys Leu Ala Ser Gly Val Pro Ser Arg Phe Ser Gly Ser
        50                  55                  60

Gly Ser Gly Thr Glu Phe Thr Leu Thr Ile Ser Ser Leu Gln Pro Asp
65                  70                  75                  80

Asp Phe Ala Thr Tyr Tyr Cys Phe Gln Gly Ser Gly Tyr Pro Phe Thr
                85                  90                  95

Phe Gly Gly Gly Thr Lys Val Glu Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210

<210> SEQ ID NO 190
<211> LENGTH: 450
<212> TYPE: PRT
<213> ORGANISM: Artificial Sequence
```

```
<220> FEATURE:
<223> OTHER INFORMATION: AFFF(1) VH CHAIN

<400> SEQUENCE: 190

Gln Val Thr Leu Arg Glu Ser Gly Pro Ala Leu Val Lys Pro Thr Gln
  1               5                  10                  15

Thr Leu Thr Leu Thr Cys Thr Phe Ser Gly Phe Ser Leu Ser Thr Ala
             20                  25                  30

Gly Met Ser Val Gly Trp Ile Arg Gln Pro Pro Gly Lys Ala Leu Glu
         35                  40                  45

Trp Leu Ala Asp Ile Trp Trp Asp Asp Lys Lys Asp Tyr Asn Pro Ser
     50                  55                  60

Leu Lys Ser Arg Leu Thr Ile Ser Lys Asp Thr Ser Lys Asn Gln Val
 65                  70                  75                  80

Val Leu Lys Val Thr Asn Met Asp Pro Ala Asp Thr Ala Thr Tyr Tyr
                 85                  90                  95

Cys Ala Arg Ser Met Ile Thr Asn Phe Tyr Phe Asp Val Trp Gly Gln
             100                 105                 110

Gly Thr Thr Val Thr Val Ser Ser Ala Ser Thr Lys Gly Pro Ser Val
         115                 120                 125

Phe Pro Leu Ala Pro Ser Ser Lys Ser Thr Ser Gly Gly Thr Ala Ala
     130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                 165                 170                 175

Leu Gln Ser Ser Gly Leu Tyr Ser Leu Ser Ser Val Val Thr Val Pro
             180                 185                 190

Ser Ser Ser Leu Gly Thr Gln Thr Tyr Ile Cys Asn Val Asn His Lys
         195                 200                 205

Pro Ser Asn Thr Lys Val Asp Lys Arg Val Glu Pro Lys Ser Cys Asp
     210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                 245                 250                 255

Ser Arg Thr Pro Glu Val Thr Cys Val Val Val Asp Val Ser His Glu
             260                 265                 270

Asp Pro Glu Val Lys Phe Asn Trp Tyr Val Asp Gly Val Glu Val His
         275                 280                 285

Asn Ala Lys Thr Lys Pro Arg Glu Glu Gln Tyr Asn Ser Thr Tyr Arg
     290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                 325                 330                 335

Lys Thr Ile Ser Lys Ala Lys Gly Gln Pro Arg Glu Pro Gln Val Tyr
             340                 345                 350

Thr Leu Pro Pro Ser Arg Glu Glu Met Thr Lys Asn Gln Val Ser Leu
         355                 360                 365

Thr Cys Leu Val Lys Gly Phe Tyr Pro Ser Asp Ile Ala Val Glu Trp
     370                 375                 380

Glu Ser Asn Gly Gln Pro Glu Asn Asn Tyr Lys Thr Thr Pro Pro Val
385                 390                 395                 400
```

```
Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450

<210> SEQ ID NO 191
<211> LENGTH: 213
<212> TYPE: PRT
<213> ORGANISM: Artificial Sequence
<220> FEATURE:
<223> OTHER INFORMATION: AFFF(1) VL CHAIN

<400> SEQUENCE: 191

Asp Ile Gln Met Thr Gln Ser Pro Ser Thr Leu Ser Ala Ser Val Gly
1               5                   10                  15

Asp Arg Val Thr Ile Thr Cys Ser Ala Ser Ser Ser Val Gly Tyr Met
            20                  25                  30

His Trp Tyr Gln Gln Lys Pro Gly Lys Ala Pro Lys Leu Leu Ile Tyr
        35                  40                  45

Asp Thr Phe Lys Leu Ala Ser Gly Val Pro Ser Arg Phe Ser Gly Ser
    50                  55                  60

Gly Ser Gly Thr Glu Phe Thr Leu Thr Ile Ser Ser Leu Gln Pro Asp
65                  70                  75                  80

Asp Phe Ala Thr Tyr Tyr Cys Phe Gln Gly Ser Phe Tyr Pro Phe Thr
                85                  90                  95

Phe Gly Gly Gly Thr Lys Val Glu Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210

<210> SEQ ID NO 192
<211> LENGTH: 106
<212> TYPE: PRT
<213> ORGANISM: Artificial Sequence
<220> FEATURE:
<223> OTHER INFORMATION: AFFF(1) VL DOMAIN

<400> SEQUENCE: 192

Asp Ile Gln Met Thr Gln Ser Pro Ser Thr Leu Ser Ala Ser Val Gly
1               5                   10                  15

Asp Arg Val Thr Ile Thr Cys Ser Ala Ser Ser Ser Val Gly Tyr Met
```

```
                    20                  25                  30
His Trp Tyr Gln Gln Lys Pro Gly Lys Ala Pro Lys Leu Leu Ile Tyr
                35                  40                  45

Asp Thr Phe Lys Leu Ala Ser Gly Val Pro Ser Arg Phe Ser Gly Ser
     50                  55                  60

Gly Ser Gly Thr Glu Phe Thr Leu Thr Ile Ser Ser Leu Gln Pro Asp
 65                  70                  75                  80

Asp Phe Ala Thr Tyr Tyr Cys Phe Gln Gly Ser Phe Tyr Pro Phe Thr
                 85                  90                  95

Phe Gly Gly Gly Thr Lys Leu Glu Ile Lys
            100                 105

<210> SEQ ID NO 193
<211> LENGTH: 9
<212> TYPE: PRT
<213> ORGANISM: Artificial Sequence
<220> FEATURE:
<223> OTHER INFORMATION: AFFF(1) VL CDR3

<400> SEQUENCE: 193

Phe Gln Gly Ser Phe Tyr Pro Phe Thr
 1               5

<210> SEQ ID NO 194
<211> LENGTH: 450
<212> TYPE: PRT
<213> ORGANISM: Artificial Sequence
<220> FEATURE:
<223> OTHER INFORMATION: 6H8 VH CHAIN

<400> SEQUENCE: 194

Gln Val Thr Leu Arg Glu Ser Gly Pro Ala Leu Val Lys Pro Thr Gln
 1               5                  10                  15

Thr Leu Thr Leu Thr Cys Thr Phe Ser Gly Phe Ser Leu Ser Thr Ala
                 20                  25                  30

Gly Met Ser Val Gly Trp Ile Arg Gln Pro Pro Gly Lys Ala Leu Glu
             35                  40                  45

Trp Leu Ala Asp Ile Trp Trp Asp Asp Lys Lys Asp Tyr Asn Pro Ser
     50                  55                  60

Leu Lys Ser Arg Leu Thr Ile Ser Lys Asp Thr Ser Lys Asn Gln Val
 65                  70                  75                  80

Val Leu Lys Val Thr Asn Met Asp Pro Ala Asp Thr Ala Thr Tyr Tyr
                 85                  90                  95

Cys Ala Arg Asp Met Ile Thr Asn Phe Tyr Phe Asp Val Trp Gly Gln
            100                 105                 110

Gly Thr Thr Val Thr Val Ser Ser Ala Ser Thr Lys Gly Pro Ser Val
            115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
            195                 200                 205
```

```
Pro Ser Asn Thr Lys Val Asp Lys Arg Val Glu Pro Lys Ser Cys Asp
    210                 215                 220
Lys Thr His Thr Cys Pro Pro Cys Pro Ala Pro Glu Leu Leu Gly Gly
225                 230                 235                 240
Pro Ser Val Phe Leu Phe Pro Pro Lys Pro Lys Asp Thr Leu Met Ile
                245                 250                 255
Ser Arg Thr Pro Glu Val Thr Cys Val Val Val Asp Val Ser His Glu
            260                 265                 270
Asp Pro Glu Val Lys Phe Asn Trp Tyr Val Asp Gly Val Glu Val His
        275                 280                 285
Asn Ala Lys Thr Lys Pro Arg Glu Glu Gln Tyr Asn Ser Thr Tyr Arg
290                 295                 300
Val Val Ser Val Leu Thr Val Leu His Gln Asp Trp Leu Asn Gly Lys
305                 310                 315                 320
Glu Tyr Lys Cys Lys Val Ser Asn Lys Ala Leu Pro Ala Pro Ile Glu
                325                 330                 335
Lys Thr Ile Ser Lys Ala Lys Gly Gln Pro Arg Glu Pro Gln Val Tyr
            340                 345                 350
Thr Leu Pro Pro Ser Arg Glu Glu Met Thr Lys Asn Gln Val Ser Leu
        355                 360                 365
Thr Cys Leu Val Lys Gly Phe Tyr Pro Ser Asp Ile Ala Val Glu Trp
370                 375                 380
Glu Ser Asn Gly Gln Pro Glu Asn Asn Tyr Lys Thr Thr Pro Pro Val
385                 390                 395                 400
Leu Asp Ser Asp Gly Ser Phe Phe Leu Tyr Ser Lys Leu Thr Val Asp
                405                 410                 415
Lys Ser Arg Trp Gln Gln Gly Asn Val Phe Ser Cys Ser Val Met His
            420                 425                 430
Glu Ala Leu His Asn His Tyr Thr Gln Lys Ser Leu Ser Leu Ser Pro
        435                 440                 445
Gly Lys
    450

<210> SEQ ID NO 195
<211> LENGTH: 213
<212> TYPE: PRT
<213> ORGANISM: Artificial Sequence
<220> FEATURE:
<223> OTHER INFORMATION: 6H8 VL CHAIN

<400> SEQUENCE: 195

Asp Ile Gln Met Thr Gln Ser Pro Ser Thr Leu Ser Ala Ser Val Gly
1               5                   10                  15
Asp Arg Val Thr Ile Thr Cys Ser Ala Ser Ser Val Gly Tyr Met
            20                  25                  30
His Trp Tyr Gln Gln Lys Pro Gly Lys Ala Pro Lys Leu Leu Ile Tyr
        35                  40                  45
Asp Thr Phe Lys Leu Thr Ser Gly Val Pro Ser Arg Phe Ser Gly Ser
    50                  55                  60
Gly Ser Gly Thr Glu Phe Thr Leu Thr Ile Ser Ser Leu Gln Pro Asp
65                  70                  75                  80
Asp Phe Ala Thr Tyr Tyr Cys Phe Gln Gly Ser Gly Tyr Pro Phe Thr
                85                  90                  95
Phe Gly Gly Gly Thr Lys Val Glu Ile Lys Arg Thr Val Ala Ala Pro
            100                 105                 110
```

Ser Val Phe Ile Phe Pro Pro Ser Asp Glu Gln Leu Lys Ser Gly Thr
                115                 120                 125

Ala Ser Val Val Cys Leu Leu Asn Asn Phe Tyr Pro Arg Glu Ala Lys
        130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210

<210> SEQ ID NO 196
<211> LENGTH: 106
<212> TYPE: PRT
<213> ORGANISM: Artificial Sequence
<220> FEATURE:
<223> OTHER INFORMATION: 6H8 VL DOMAIN

<400> SEQUENCE: 196

Asp Ile Gln Met Thr Gln Ser Pro Ser Thr Leu Ser Ala Ser Val Gly
1               5                   10                  15

Asp Arg Val Thr Ile Thr Cys Ser Ala Ser Ser Ser Val Gly Tyr Met
                20                  25                  30

His Trp Tyr Gln Gln Lys Pro Gly Lys Ala Pro Lys Leu Leu Ile Tyr
            35                  40                  45

Asp Thr Phe Lys Leu Thr Ser Gly Val Pro Ser Arg Phe Ser Gly Ser
    50                  55                  60

Gly Ser Gly Thr Glu Phe Thr Leu Thr Ile Ser Ser Leu Gln Pro Asp
65                  70                  75                  80

Asp Phe Ala Thr Tyr Tyr Cys Phe Gln Gly Ser Gly Tyr Pro Phe Thr
                85                  90                  95

Phe Gly Gly Gly Thr Lys Leu Glu Ile Lys
            100                 105

<210> SEQ ID NO 197
<211> LENGTH: 7
<212> TYPE: PRT
<213> ORGANISM: Artificial Sequence
<220> FEATURE:
<223> OTHER INFORMATION: 6H8 VL CDR2

<400> SEQUENCE: 197

Asp Thr Phe Lys Leu Thr Ser
1               5

<210> SEQ ID NO 198
<211> LENGTH: 450
<212> TYPE: PRT
<213> ORGANISM: Artificial Sequence
<220> FEATURE:
<223> OTHER INFORMATION: L1-7E5 VH CHAIN

<400> SEQUENCE: 198

Gln Val Thr Leu Arg Glu Ser Gly Pro Ala Leu Val Lys Pro Thr Gln
1               5                   10                  15

Thr Leu Thr Leu Thr Cys Thr Phe Ser Gly Phe Ser Leu Ser Thr Ala

-continued

```
                20                  25                  30
Gly Met Ser Val Gly Trp Ile Arg Gln Pro Gly Lys Ala Leu Glu
            35                  40                  45
Trp Leu Ala Asp Ile Trp Trp Asp Asp Lys Lys Asp Tyr Asn Pro Ser
 50                  55                  60
Leu Lys Ser Arg Leu Thr Ile Ser Lys Asp Thr Ser Lys Asn Gln Val
 65                  70                  75                  80
Val Leu Lys Val Thr Asn Met Asp Pro Ala Asp Thr Ala Thr Tyr Tyr
                85                  90                  95
Cys Ala Arg Asp Met Ile Thr Asn Phe Tyr Phe Asp Val Trp Gly Gln
               100                 105                 110
Gly Thr Thr Val Thr Val Ser Ser Ala Ser Thr Lys Gly Pro Ser Val
           115                 120                 125
Phe Pro Leu Ala Pro Ser Ser Lys Ser Thr Ser Gly Gly Thr Ala Ala
           130                 135                 140
Leu Gly Cys Leu Val Lys Asp Tyr Phe Pro Glu Pro Val Thr Val Ser
145                 150                 155                 160
Trp Asn Ser Gly Ala Leu Thr Ser Gly Val His Thr Phe Pro Ala Val
               165                 170                 175
Leu Gln Ser Ser Gly Leu Tyr Ser Leu Ser Ser Val Val Thr Val Pro
           180                 185                 190
Ser Ser Ser Leu Gly Thr Gln Thr Tyr Ile Cys Asn Val Asn His Lys
           195                 200                 205
Pro Ser Asn Thr Lys Val Asp Lys Arg Val Glu Pro Lys Ser Cys Asp
 210                 215                 220
Lys Thr His Thr Cys Pro Pro Cys Pro Ala Pro Glu Leu Leu Gly Gly
225                 230                 235                 240
Pro Ser Val Phe Leu Phe Pro Pro Lys Pro Lys Asp Thr Leu Met Ile
               245                 250                 255
Ser Arg Thr Pro Glu Val Thr Cys Val Val Val Asp Val Ser His Glu
           260                 265                 270
Asp Pro Glu Val Lys Phe Asn Trp Tyr Val Asp Gly Val Glu Val His
           275                 280                 285
Asn Ala Lys Thr Lys Pro Arg Glu Glu Gln Tyr Asn Ser Thr Tyr Arg
 290                 295                 300
Val Val Ser Val Leu Thr Val Leu His Gln Asp Trp Leu Asn Gly Lys
305                 310                 315                 320
Glu Tyr Lys Cys Lys Val Ser Asn Lys Ala Leu Pro Ala Pro Ile Glu
               325                 330                 335
Lys Thr Ile Ser Lys Ala Lys Gly Gln Pro Arg Glu Pro Gln Val Tyr
           340                 345                 350
Thr Leu Pro Pro Ser Arg Glu Glu Met Thr Lys Asn Gln Val Ser Leu
           355                 360                 365
Thr Cys Leu Val Lys Gly Phe Tyr Pro Ser Asp Ile Ala Val Glu Trp
           370                 375                 380
Glu Ser Asn Gly Gln Pro Glu Asn Asn Tyr Lys Thr Thr Pro Pro Val
385                 390                 395                 400
Leu Asp Ser Asp Gly Ser Phe Phe Leu Tyr Ser Lys Leu Thr Val Asp
               405                 410                 415
Lys Ser Arg Trp Gln Gln Gly Asn Val Phe Ser Cys Ser Val Met His
           420                 425                 430
Glu Ala Leu His Asn His Tyr Thr Gln Lys Ser Leu Ser Leu Ser Pro
           435                 440                 445
```

Gly Lys
    450

<210> SEQ ID NO 199
<211> LENGTH: 213
<212> TYPE: PRT
<213> ORGANISM: Artificial Sequence
<220> FEATURE:
<223> OTHER INFORMATION: L1-7E5 VL CHAIN

<400> SEQUENCE: 199

Asp Ile Gln Met Thr Gln Ser Pro Ser Thr Leu Ser Ala Ser Val Gly
1               5                   10                  15

Asp Arg Val Thr Ile Thr Cys Ser Ala Ser Ser Arg Val Gly Tyr Met
            20                  25                  30

His Trp Tyr Gln Gln Lys Pro Gly Lys Ala Pro Lys Leu Leu Ile Tyr
        35                  40                  45

Asp Thr Phe Lys Leu Ala Ser Gly Val Pro Ser Arg Phe Ser Gly Ser
    50                  55                  60

Gly Ser Gly Thr Glu Phe Thr Leu Thr Ile Ser Ser Leu Gln Pro Asp
65                  70                  75                  80

Asp Phe Ala Thr Tyr Tyr Cys Phe Gln Gly Ser Gly Tyr Pro Phe Thr
                85                  90                  95

Phe Gly Gly Gly Thr Lys Val Glu Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210

<210> SEQ ID NO 200
<211> LENGTH: 106
<212> TYPE: PRT
<213> ORGANISM: Artificial Sequence
<220> FEATURE:
<223> OTHER INFORMATION: L1-7E5 VL DOMAIN

<400> SEQUENCE: 200

Asp Ile Gln Met Thr Gln Ser Pro Ser Thr Leu Ser Ala Ser Val Gly
1               5                   10                  15

Asp Arg Val Thr Ile Thr Cys Ser Ala Ser Ser Val Gly Tyr Met
            20                  25                  30

His Trp Tyr Gln Gln Lys Pro Gly Lys Ala Pro Lys Leu Leu Ile Tyr
        35                  40                  45

Asp Thr Phe Arg Leu Ala Ser Gly Val Pro Ser Arg Phe Ser Gly Ser
    50                  55                  60

Gly Ser Gly Thr Glu Phe Thr Leu Thr Ile Ser Ser Leu Gln Pro Asp

```
                65                  70                  75                  80
Asp Phe Ala Thr Tyr Tyr Cys Phe Gln Gly Ser Gly Tyr Pro Phe Thr
                    85                  90                  95

Phe Gly Gly Gly Thr Lys Leu Glu Ile Lys
                    100                 105

<210> SEQ ID NO 201
<211> LENGTH: 450
<212> TYPE: PRT
<213> ORGANISM: Artificial Sequence
<220> FEATURE:
<223> OTHER INFORMATION: L2-15B10 VH CHAIN

<400> SEQUENCE: 201

Gln Val Thr Leu Arg Glu Ser Gly Pro Ala Leu Val Lys Pro Thr Gln
 1               5                  10                  15

Thr Leu Thr Leu Thr Cys Thr Phe Ser Gly Phe Ser Leu Ser Thr Ala
                20                  25                  30

Gly Met Ser Val Gly Trp Ile Arg Gln Pro Pro Gly Lys Ala Leu Glu
            35                  40                  45

Trp Leu Ala Asp Ile Trp Trp Asp Lys Lys Asp Tyr Asn Pro Ser
 50                  55                  60

Leu Lys Ser Arg Leu Thr Ile Ser Lys Asp Thr Ser Lys Asn Gln Val
65                  70                  75                  80

Val Leu Lys Val Thr Asn Met Asp Pro Ala Asp Thr Ala Thr Tyr Tyr
                85                  90                  95

Cys Ala Arg Asp Met Ile Thr Asn Phe Tyr Phe Asp Val Trp Gly Gln
            100                 105                 110

Gly Thr Thr Val Thr Val Ser Ser Ala Ser Thr Lys Gly Pro Ser Val
            115                 120                 125

Phe Pro Leu Ala Pro Ser Ser Lys Ser Thr Ser Gly Gly Thr Ala Ala
            130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
            195                 200                 205

Pro Ser Asn Thr Lys Val Asp Lys Arg Val Glu Pro Lys Ser Cys Asp
            210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
            275                 280                 285

Asn Ala Lys Thr Lys Pro Arg Glu Glu Gln Tyr Asn Ser Thr Tyr Arg
            290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
```

```
              325                 330                 335
Lys Thr Ile Ser Lys Ala Lys Gly Gln Pro Arg Glu Pro Gln Val Tyr
                340                 345                 350

Thr Leu Pro Pro Ser Arg Glu Glu Met Thr Lys Asn Gln Val Ser Leu
                355                 360                 365

Thr Cys Leu Val Lys Gly Phe Tyr Pro Ser Asp Ile Ala Val Glu Trp
                370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
                420                 425                 430

Glu Ala Leu His Asn His Tyr Thr Gln Lys Ser Leu Ser Leu Ser Pro
                435                 440                 445

Gly Lys
    450

<210> SEQ ID NO 202
<211> LENGTH: 213
<212> TYPE: PRT
<213> ORGANISM: Artificial Sequence
<220> FEATURE:
<223> OTHER INFORMATION: L2-15B10 VL CHAIN

<400> SEQUENCE: 202

Asp Ile Gln Met Thr Gln Ser Pro Ser Thr Leu Ser Ala Ser Val Gly
1               5                   10                  15

Asp Arg Val Thr Ile Thr Cys Ser Ala Ser Ser Ser Val Gly Tyr Met
                20                  25                  30

His Trp Tyr Gln Gln Lys Pro Gly Lys Ala Pro Lys Leu Leu Ile Tyr
            35                  40                  45

Asp Thr Phe Arg Leu Ala Ser Gly Val Pro Ser Arg Phe Ser Gly Ser
        50                  55                  60

Gly Ser Gly Thr Glu Phe Thr Leu Thr Ile Ser Ser Leu Gln Pro Asp
65                  70                  75                  80

Asp Phe Ala Thr Tyr Tyr Cys Phe Gln Gly Ser Gly Tyr Pro Phe Thr
                85                  90                  95

Phe Gly Gly Gly Thr Lys Val Glu Ile Lys Arg Thr Val Ala Ala Pro
                100                 105                 110

Ser Val Phe Ile Phe Pro Pro Ser Asp Glu Gln Leu Lys Ser Gly Thr
            115                 120                 125

Ala Ser Val Val Cys Leu Leu Asn Asn Phe Tyr Pro Arg Glu Ala Lys
        130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
                180                 185                 190

Cys Glu Val Thr His Gln Gly Leu Ser Ser Pro Val Thr Lys Ser Phe
            195                 200                 205

Asn Arg Gly Glu Cys
    210
```

```
<210> SEQ ID NO 203
<211> LENGTH: 106
<212> TYPE: PRT
<213> ORGANISM: Artificial Sequence
<220> FEATURE:
<223> OTHER INFORMATION: L2-15B10 VL DOMAIN

<400> SEQUENCE: 203

Asp Ile Gln Met Thr Gln Ser Pro Ser Thr Leu Ser Ala Ser Val Gly
 1               5                  10                  15

Asp Arg Val Thr Ile Thr Cys Ser Ala Ser Ser Val Gly Tyr Met
             20                  25                  30

His Trp Tyr Gln Gln Lys Pro Gly Lys Ala Pro Lys Leu Leu Ile Tyr
         35                  40                  45

Asp Thr Phe Arg Leu Ala Ser Gly Val Pro Ser Arg Phe Ser Gly Ser
     50                  55                  60

Gly Ser Gly Thr Glu Phe Thr Leu Thr Ile Ser Ser Leu Gln Pro Asp
 65                  70                  75                  80

Asp Phe Ala Thr Tyr Tyr Cys Phe Gln Gly Ser Gly Tyr Pro Phe Thr
                 85                  90                  95

Phe Gly Gly Gly Thr Lys Leu Glu Ile Lys
            100                 105

<210> SEQ ID NO 204
<211> LENGTH: 7
<212> TYPE: PRT
<213> ORGANISM: Artificial Sequence
<220> FEATURE:
<223> OTHER INFORMATION: L2-15B10 VL CDR2

<400> SEQUENCE: 204

Asp Thr Phe Arg Leu Ala Ser
 1               5

<210> SEQ ID NO 205
<211> LENGTH: 450
<212> TYPE: PRT
<213> ORGANISM: Artificial Sequence
<220> FEATURE:
<223> OTHER INFORMATION: A13a11 VH CHAIN

<400> SEQUENCE: 205

Gln Val Thr Leu Arg Glu Ser Gly Pro Ala Leu Val Lys Pro Thr Gln
 1               5                  10                  15

Thr Leu Thr Leu Thr Cys Thr Phe Ser Gly Phe Ser Leu Ser Thr Ala
             20                  25                  30

Gly Met Ser Val Gly Trp Ile Arg Gln Pro Pro Gly Lys Ala Leu Glu
         35                  40                  45

Trp Leu Ala Asp Ile Trp Trp Asp Asp Lys Lys His Tyr Asn Pro Ser
     50                  55                  60

Leu Lys Asp Arg Leu Thr Ile Ser Lys Asp Thr Ser Lys Asn Gln Val
 65                  70                  75                  80

Val Leu Lys Val Thr Asn Met Asp Pro Ala Asp Thr Ala Thr Tyr Tyr
                 85                  90                  95

Cys Ala Arg Ser Met Ile Thr Asn Trp Tyr Phe Asp Val Trp Gly Gln
            100                 105                 110

Gly Thr Thr Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140
```

```
Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Arg Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
                260                 265                 270

Asp Pro Glu Val Lys Phe Asn Trp Tyr Val Asp Gly Val Glu Val His
            275                 280                 285

Asn Ala Lys Thr Lys Pro Arg Glu Glu Gln Tyr Asn Ser Thr Tyr Arg
        290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
                340                 345                 350

Thr Leu Pro Pro Ser Arg Glu Glu Met Thr Lys Asn Gln Val Ser Leu
            355                 360                 365

Thr Cys Leu Val Lys Gly Phe Tyr Pro Ser Asp Ile Ala Val Glu Trp
        370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
                420                 425                 430

Glu Ala Leu His Asn His Tyr Thr Gln Lys Ser Leu Ser Leu Ser Pro
            435                 440                 445

Gly Lys
    450

<210> SEQ ID NO 206
<211> LENGTH: 120
<212> TYPE: PRT
<213> ORGANISM: Artificial Sequence
<220> FEATURE:
<223> OTHER INFORMATION: A13a11 VH DOMAIN

<400> SEQUENCE: 206

Gln Val Thr Leu Arg Glu Ser Gly Pro Ala Leu Val Lys Pro Thr Gln
1               5                   10                  15

Thr Leu Thr Leu Thr Cys Thr Phe Ser Gly Phe Ser Leu Ser Thr Ala
            20                  25                  30

Gly Met Ser Val Gly Trp Ile Arg Gln Pro Pro Gly Lys Ala Leu Glu
        35                  40                  45
```

Trp Leu Ala Asp Ile Trp Trp Asp Asp Lys His Tyr Asn Pro Ser
 50                  55                  60

Leu Lys Asp Arg Leu Thr Ile Ser Lys Asp Thr Ser Lys Asn Gln Val
 65                  70                  75                  80

Val Leu Lys Val Thr Asn Met Asp Pro Ala Asp Thr Ala Thr Tyr Tyr
                 85                  90                  95

Cys Ala Arg Asp Met Ile Phe Asn Trp Tyr Phe Asp Val Trp Gly Ala
            100                 105                 110

Gly Thr Thr Val Thr Val Ser Ser
            115                 120

<210> SEQ ID NO 207
<211> LENGTH: 214
<212> TYPE: PRT
<213> ORGANISM: Artificial Sequence
<220> FEATURE:
<223> OTHER INFORMATION: A13a11 VL CHAIN

<400> SEQUENCE: 207

Asp Ile Gln Met Thr Gln Ser Pro Ser Thr Leu Ser Ala Ser Val Gly
  1               5                  10                  15

Asp Arg Val Thr Ile Thr Cys Ser Pro Ser Ser Arg Val Gly Tyr Met
                 20                  25                  30

His Trp Tyr Gln Gln Lys Pro Gly Lys Ala Pro Lys Leu Leu Ile Tyr
             35                  40                  45

Asp Thr Tyr Arg His Leu Ala Ser Gly Val Pro Ser Arg Phe Ser Gly
         50                  55                  60

Ser Gly Ser Gly Thr Glu Phe Thr Leu Thr Ile Ser Ser Leu Gln Pro
 65                  70                  75                  80

Asp Asp Phe Ala Thr Tyr Tyr Cys Phe Gln Gly Ser Gly Tyr Pro Phe
                 85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 208
<211> LENGTH: 106
<212> TYPE: PRT
<213> ORGANISM: Artificial Sequence
<220> FEATURE:
<223> OTHER INFORMATION: A13a11 VL DOMAIN

<400> SEQUENCE: 208

Asp Ile Gln Met Thr Gln Ser Pro Ser Thr Leu Ser Ala Ser Val Gly

```
                1               5                  10                 15
Asp Arg Val Thr Ile Thr Cys Ser Ala Ser Ser Ser Val Gly Tyr Met
                20                  25                  30

His Trp Tyr Gln Gln Lys Pro Gly Lys Ala Pro Lys Leu Leu Ile Tyr
                35                  40                  45

Asp Thr Tyr Arg His Ala Ser Gly Val Pro Ser Arg Phe Ser Gly Ser
                50                  55                  60

Gly Ser Gly Thr Glu Phe Thr Leu Thr Ile Ser Ser Leu Gln Pro Asp
 65                 70                  75                  80

Asp Phe Ala Thr Tyr Tyr Cys Phe Gln Gly Ser Gly Tyr Pro Phe Thr
                85                  90                  95

Phe Gly Gly Gly Thr Lys Leu Glu Ile Lys
                100                 105

<210> SEQ ID NO 209
<211> LENGTH: 7
<212> TYPE: PRT
<213> ORGANISM: Artificial Sequence
<220> FEATURE:
<223> OTHER INFORMATION: A13a11 VL CDR2

<400> SEQUENCE: 209

Asp Thr Tyr Arg His Ser Ser
 1               5

<210> SEQ ID NO 210
<211> LENGTH: 450
<212> TYPE: PRT
<213> ORGANISM: Artificial Sequence
<220> FEATURE:
<223> OTHER INFORMATION: A1h5 VH CHAIN

<400> SEQUENCE: 210

Gln Val Thr Leu Arg Glu Ser Gly Pro Ala Leu Val Lys Pro Thr Gln
 1               5                  10                  15

Thr Leu Thr Leu Thr Cys Thr Phe Ser Gly Phe Ser Leu Ser Thr Ala
                20                  25                  30

Gly Met Ser Val Gly Trp Ile Arg Gln Pro Pro Gly Lys Ala Leu Glu
                35                  40                  45

Trp Leu Ala Asp Ile Trp Trp Asp Gly Lys Lys His Tyr Asn Pro Ser
 50                 55                  60

Leu Lys Asp Arg Leu Thr Ile Ser Lys Asp Thr Ser Lys Asn Gln Val
 65                 70                  75                  80

Val Leu Lys Val Thr Asn Met Asp Pro Ala Asp Thr Ala Thr Tyr Tyr
                85                  90                  95

Cys Ala Arg Asp Met Ile Phe Asn Trp Tyr Phe Asp Val Trp Gly Gln
                100                 105                 110

Gly Thr Thr Val Thr Val Ser Ser Ala Ser Thr Lys Gly Pro Ser Val
                115                 120                 125

Phe Pro Leu Ala Pro Ser Ser Lys Ser Thr Ser Gly Gly Thr Ala Ala
                130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
                180                 185                 190
```

```
Ser Ser Ser Leu Gly Thr Gln Thr Tyr Ile Cys Asn Val Asn His Lys
            195                 200                 205

Pro Ser Asn Thr Lys Val Asp Lys Arg Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
                260                 265                 270

Asp Pro Glu Val Lys Phe Asn Trp Tyr Val Asp Gly Val Glu Val His
            275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
    355                 360                 365

Thr Cys Leu Val Lys Gly Phe Tyr Pro Ser Asp Ile Ala Val Glu Trp
370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
    435                 440                 445

Gly Lys
    450

<210> SEQ ID NO 211
<211> LENGTH: 213
<212> TYPE: PRT
<213> ORGANISM: Artificial Sequence
<220> FEATURE:
<223> OTHER INFORMATION: A1h5 VL CHAIN

<400> SEQUENCE: 211

Asp Ile Gln Met Thr Gln Ser Pro Ser Thr Leu Ser Ala Ser Val Gly
1               5                   10                  15

Asp Arg Val Thr Ile Thr Cys Ser Leu Ser Ser Ser Val Gly Tyr Met
            20                  25                  30

His Trp Tyr Gln Gln Lys Pro Gly Lys Ala Pro Lys Leu Leu Ile Tyr
        35                  40                  45

Asp Thr Phe Phe His Arg Ser Gly Val Pro Ser Arg Phe Ser Gly Ser
    50                  55                  60

Gly Ser Gly Thr Glu Phe Thr Leu Thr Ile Ser Ser Leu Gln Pro Asp
65                  70                  75                  80

Asp Phe Ala Thr Tyr Tyr Cys Phe Gln Gly Ser Gly Tyr Pro Phe Thr
                85                  90                  95
```

Phe Gly Gly Gly Thr Lys Val Glu Ile Lys Arg Thr Val Ala Ala Pro
                100                 105                 110

Ser Val Phe Ile Phe Pro Pro Ser Asp Glu Gln Leu Lys Ser Gly Thr
            115                 120                 125

Ala Ser Val Val Cys Leu Leu Asn Asn Phe Tyr Pro Arg Glu Ala Lys
        130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210

<210> SEQ ID NO 212
<211> LENGTH: 106
<212> TYPE: PRT
<213> ORGANISM: Artificial Sequence
<220> FEATURE:
<223> OTHER INFORMATION: A1h5 VL DOMAIN

<400> SEQUENCE: 212

Asp Ile Gln Met Thr Gln Ser Pro Ser Thr Leu Ser Ala Ser Val Gly
1               5                   10                  15

Asp Arg Val Thr Ile Thr Cys Ser Leu Ser Ser Val Gly Tyr Met
            20                  25                  30

His Trp Tyr Gln Gln Lys Pro Gly Lys Ala Pro Lys Leu Leu Ile Tyr
        35                  40                  45

Asp Thr Phe Phe His Arg Ser Gly Val Pro Ser Arg Phe Ser Gly Ser
    50                  55                  60

Gly Ser Gly Thr Glu Phe Thr Leu Thr Ile Ser Ser Leu Gln Pro Asp
65                  70                  75                  80

Asp Phe Ala Thr Tyr Tyr Cys Phe Gln Gly Ser Gly Tyr Pro Phe Thr
                85                  90                  95

Phe Gly Gly Gly Thr Lys Leu Glu Ile Lys
            100                 105

<210> SEQ ID NO 213
<211> LENGTH: 10
<212> TYPE: PRT
<213> ORGANISM: Artificial Sequence
<220> FEATURE:
<223> OTHER INFORMATION: A1h5 VL CDR1

<400> SEQUENCE: 213

Ser Leu Ser Ser Ser Val Gly Tyr Met His
1               5                   10

<210> SEQ ID NO 214
<211> LENGTH: 7
<212> TYPE: PRT
<213> ORGANISM: Artificial Sequence
<220> FEATURE:
<223> OTHER INFORMATION: A1h5 VL CDR2

<400> SEQUENCE: 214

Asp Thr Phe Phe His Arg Ser

<210> SEQ ID NO 215
<211> LENGTH: 450
<212> TYPE: PRT
<213> ORGANISM: Artificial Sequence
<220> FEATURE:
<223> OTHER INFORMATION: A4B4(1) VH CHAIN

<400> SEQUENCE: 215

```
Gln Val Thr Leu Arg Glu Ser Gly Pro Ala Leu Val Lys Pro Thr Gln
 1               5                  10                  15

Thr Leu Thr Leu Thr Cys Thr Phe Ser Gly Phe Ser Leu Ser Thr Ala
             20                  25                  30

Gly Met Ser Val Gly Trp Ile Arg Gln Pro Pro Gly Lys Ala Leu Glu
         35                  40                  45

Trp Leu Ala Asp Ile Trp Trp Asp Asp Lys Lys His Tyr Asn Pro Ser
 50                  55                  60

Leu Lys Asp Arg Leu Thr Ile Ser Lys Asp Thr Ser Lys Asn Gln Val
 65                  70                  75                  80

Val Leu Lys Val Thr Asn Met Asp Pro Ala Asp Thr Ala Thr Tyr Tyr
                 85                  90                  95

Cys Ala Arg Asp Met Ile Phe Asn Phe Tyr Phe Asp Val Trp Gly Gln
            100                 105                 110

Gly Thr Thr Val Thr Val Ser Ser Ala Ser Thr Lys Gly Pro Ser Val
            115                 120                 125

Phe Pro Leu Ala Pro Ser Ser Lys Ser Thr Ser Gly Gly Thr Ala Ala
130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
            195                 200                 205

Pro Ser Asn Thr Lys Val Asp Lys Arg Val Glu Pro Lys Ser Cys Asp
210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
            275                 280                 285

Asn Ala Lys Thr Lys Pro Arg Glu Glu Gln Tyr Asn Ser Thr Tyr Arg
        290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
```

```
                    355                 360                 365
Thr Cys Leu Val Lys Gly Phe Tyr Pro Ser Asp Ile Ala Val Glu Trp
        370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
                420                 425                 430

Glu Ala Leu His Asn His Tyr Thr Gln Lys Ser Leu Ser Leu Ser Pro
                435                 440                 445

Gly Lys
    450

<210> SEQ ID NO 216
<211> LENGTH: 213
<212> TYPE: PRT
<213> ORGANISM: Artificial Sequence
<220> FEATURE:
<223> OTHER INFORMATION: A4B4(1) VL CHAIN

<400> SEQUENCE: 216

Asp Ile Gln Met Thr Gln Ser Pro Ser Thr Leu Ser Ala Ser Val Gly
1               5                   10                  15

Asp Arg Val Thr Ile Thr Cys Ser Ala Ser Ser Arg Val Gly Tyr Met
                20                  25                  30

His Trp Tyr Gln Gln Lys Pro Gly Lys Ala Pro Lys Leu Leu Ile Tyr
            35                  40                  45

Asp Thr Leu Leu Asp Ser Gly Val Pro Ser Arg Phe Ser Gly Ser
    50                  55                  60

Gly Ser Gly Thr Glu Phe Thr Leu Thr Ile Ser Ser Leu Gln Pro Asp
65                  70                  75                  80

Asp Phe Ala Thr Tyr Tyr Cys Phe Gln Gly Ser Gly Tyr Pro Phe Thr
                85                  90                  95

Phe Gly Gly Gly Thr Lys Val Glu Ile Lys Arg Thr Val Ala Ala Pro
                100                 105                 110

Ser Val Phe Ile Phe Pro Pro Ser Asp Glu Gln Leu Lys Ser Gly Thr
            115                 120                 125

Ala Ser Val Val Cys Leu Leu Asn Asn Phe Tyr Pro Arg Glu Ala Lys
        130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
                180                 185                 190

Cys Glu Val Thr His Gln Gly Leu Ser Ser Pro Val Thr Lys Ser Phe
            195                 200                 205

Asn Arg Gly Glu Cys
    210

<210> SEQ ID NO 217
<211> LENGTH: 106
<212> TYPE: PRT
<213> ORGANISM: Artificial Sequence
<220> FEATURE:
<223> OTHER INFORMATION: A4B4(1) VL DOMAIN
```

<400> SEQUENCE: 217

Asp Ile Gln Met Thr Gln Ser Pro Ser Thr Leu Ser Ala Ser Val Gly
1               5                   10                  15

Asp Arg Val Thr Ile Thr Cys Ser Ala Ser Ser Arg Val Gly Tyr Met
            20                  25                  30

His Trp Tyr Gln Gln Lys Pro Gly Lys Ala Pro Lys Leu Leu Ile Tyr
        35                  40                  45

Asp Thr Leu Leu Asp Ser Gly Val Pro Ser Arg Phe Ser Gly Ser
    50                  55                  60

Gly Ser Gly Thr Glu Phe Thr Leu Thr Ile Ser Ser Leu Gln Pro Asp
65              70                  75                  80

Asp Phe Ala Thr Tyr Tyr Cys Phe Gln Gly Ser Gly Tyr Pro Phe Thr
            85                  90                  95

Phe Gly Gly Gly Thr Lys Leu Glu Ile Lys
            100                 105

<210> SEQ ID NO 218
<211> LENGTH: 7
<212> TYPE: PRT
<213> ORGANISM: Artificial Sequence
<220> FEATURE:
<223> OTHER INFORMATION: A4B4(1) VL CDR2

<400> SEQUENCE: 218

Asp Thr Leu Leu Asp Ser
1               5

<210> SEQ ID NO 219
<211> LENGTH: 450
<212> TYPE: PRT
<213> ORGANISM: Artificial Sequence
<220> FEATURE:
<223> OTHER INFORMATION: A4B4L1 VH CHAIN

<400> SEQUENCE: 219

Gln Val Thr Leu Arg Glu Ser Gly Pro Ala Leu Val Lys Pro Thr Gln
1               5                   10                  15

Thr Leu Thr Leu Thr Cys Thr Phe Ser Gly Phe Ser Leu Ser Thr Ala
            20                  25                  30

Gly Met Ser Val Gly Trp Ile Arg Gln Pro Pro Gly Lys Ala Leu Glu
        35                  40                  45

Trp Leu Ala Asp Ile Trp Trp Asp Asp Lys Lys His Tyr Asn Pro Ser
    50                  55                  60

Leu Lys Asp Arg Leu Thr Ile Ser Lys Asp Thr Ser Lys Asn Gln Val
65              70                  75                  80

Val Leu Lys Val Thr Asn Met Asp Pro Ala Asp Thr Ala Thr Tyr Tyr
            85                  90                  95

Cys Ala Arg Asp Met Ile Phe Asn Phe Tyr Phe Asp Val Trp Gly Gln
            100                 105                 110

Gly Thr Thr Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
            165                 170                 175

-continued

Leu Gln Ser Ser Gly Leu Tyr Ser Leu Ser Val Val Thr Val Pro
            180                 185                 190

Ser Ser Ser Leu Gly Thr Gln Thr Tyr Ile Cys Asn Val Asn His Lys
            195                 200                 205

Pro Ser Asn Thr Lys Val Asp Lys Arg Val Glu Pro Lys Ser Cys Asp
210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
            275                 280                 285

Asn Ala Lys Thr Lys Pro Arg Glu Glu Gln Tyr Asn Ser Thr Tyr Arg
290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
            355                 360                 365

Thr Cys Leu Val Lys Gly Phe Tyr Pro Ser Asp Ile Ala Val Glu Trp
370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
            435                 440                 445

Gly Lys
    450

<210> SEQ ID NO 220
<211> LENGTH: 213
<212> TYPE: PRT
<213> ORGANISM: Artificial Sequence
<220> FEATURE:
<223> OTHER INFORMATION: A4B4L1 VL CHAIN

<400> SEQUENCE: 220

Asp Ile Gln Met Thr Gln Ser Pro Ser Thr Leu Ser Ala Ser Val Gly
1               5                   10                  15

Asp Arg Val Thr Ile Thr Cys Ser Ala Ser Ser Arg Val Gly Tyr Met
            20                  25                  30

His Trp Tyr Gln Gln Lys Pro Gly Lys Ala Pro Lys Leu Leu Ile Tyr
            35                  40                  45

Asp Thr Ser Lys Leu Ala Ser Gly Val Pro Ser Arg Phe Ser Gly Ser
        50                  55                  60

Gly Ser Gly Thr Glu Phe Thr Leu Thr Ile Ser Ser Leu Gln Pro Asp
65                  70                  75                  80

```
Asp Phe Ala Thr Tyr Tyr Cys Phe Gln Gly Ser Gly Tyr Pro Phe Thr
                85                  90                  95

Phe Gly Gly Gly Thr Lys Val Glu Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210
```

```
<210> SEQ ID NO 221
<211> LENGTH: 106
<212> TYPE: PRT
<213> ORGANISM: Artificial Sequence
<220> FEATURE:
<223> OTHER INFORMATION: A4B4L1 VL DOMAIN

<400> SEQUENCE: 221

Asp Ile Gln Met Thr Gln Ser Pro Ser Thr Leu Ser Ala Ser Val Gly
1               5                   10                  15

Asp Arg Val Thr Ile Thr Cys Ser Ala Ser Ser Arg Val Gly Tyr Met
            20                  25                  30

His Trp Tyr Gln Gln Lys Pro Gly Lys Ala Pro Lys Leu Leu Ile Tyr
        35                  40                  45

Asp Thr Ser Lys Leu Ala Ser Gly Val Pro Ser Arg Phe Ser Gly Ser
    50                  55                  60

Gly Ser Gly Thr Glu Phe Thr Leu Thr Ile Ser Ser Leu Gln Pro Asp
65                  70                  75                  80

Asp Phe Ala Thr Tyr Tyr Cys Phe Gln Gly Ser Gly Tyr Pro Phe Thr
                85                  90                  95

Phe Gly Gly Gly Thr Lys Leu Glu Ile Lys
            100                 105
```

```
<210> SEQ ID NO 222
<211> LENGTH: 450
<212> TYPE: PRT
<213> ORGANISM: Artificial Sequence
<220> FEATURE:
<223> OTHER INFORMATION: A4B4-F25S VH CHAIN

<400> SEQUENCE: 222

Gln Val Thr Leu Arg Glu Ser Gly Pro Ala Leu Val Lys Pro Thr Gln
1               5                   10                  15

Thr Leu Thr Leu Thr Cys Thr Phe Ser Gly Phe Ser Leu Ser Thr Ala
            20                  25                  30

Gly Met Ser Val Gly Trp Ile Arg Gln Pro Pro Gly Lys Ala Leu Glu
        35                  40                  45

Trp Leu Ala Asp Ile Trp Trp Asp Asp Lys Lys His Tyr Asn Pro Ser
```

```
            50                  55                  60
Leu Lys Asp Arg Leu Thr Ile Ser Lys Asp Thr Ser Lys Asn Gln Val
 65                  70                  75                  80

Val Leu Lys Val Thr Asn Met Asp Pro Ala Asp Thr Ala Thr Tyr Tyr
                 85                  90                  95

Cys Ala Arg Asp Met Ile Phe Asn Phe Tyr Phe Asp Val Trp Gly Gln
                100                 105                 110

Gly Thr Thr Val Thr Val Ser Ser Ala Ser Thr Lys Gly Pro Ser Val
                115                 120                 125

Phe Pro Leu Ala Pro Ser Ser Lys Ser Thr Ser Gly Gly Thr Ala Ala
130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
                180                 185                 190

Ser Ser Ser Leu Gly Thr Gln Thr Tyr Ile Cys Asn Val Asn His Lys
                195                 200                 205

Pro Ser Asn Thr Lys Val Asp Lys Arg Val Glu Pro Lys Ser Cys Asp
210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
                260                 265                 270

Asp Pro Glu Val Lys Phe Asn Trp Tyr Val Asp Gly Val Glu Val His
                275                 280                 285

Asn Ala Lys Thr Lys Pro Arg Glu Glu Gln Tyr Asn Ser Thr Tyr Arg
                290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
                340                 345                 350

Thr Leu Pro Pro Ser Arg Glu Glu Met Thr Lys Asn Gln Val Ser Leu
                355                 360                 365

Thr Cys Leu Val Lys Gly Phe Tyr Pro Ser Asp Ile Ala Val Glu Trp
370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
                420                 425                 430

Glu Ala Leu His Asn His Tyr Thr Gln Lys Ser Leu Ser Leu Ser Pro
                435                 440                 445

Gly Lys
450

<210> SEQ ID NO 223
```

<211> LENGTH: 213
<212> TYPE: PRT
<213> ORGANISM: Artificial Sequence
<220> FEATURE:
<223> OTHER INFORMATION: A4B4-F25S VL CHAIN

<400> SEQUENCE: 223

```
Asp Ile Gln Met Thr Gln Ser Pro Ser Thr Leu Ser Ala Ser Val Gly
  1               5                  10                  15

Asp Arg Val Thr Ile Thr Cys Ser Ala Ser Ser Arg Val Gly Tyr Met
             20                  25                  30

His Trp Tyr Gln Gln Lys Pro Gly Lys Ala Pro Lys Leu Leu Ile Tyr
         35                  40                  45

Asp Thr Ser Phe Leu Asp Ser Gly Val Pro Ser Arg Phe Ser Gly Ser
     50                  55                  60

Gly Ser Gly Thr Glu Phe Thr Leu Thr Ile Ser Ser Leu Gln Pro Asp
 65                  70                  75                  80

Asp Phe Ala Thr Tyr Tyr Cys Phe Gln Gly Ser Gly Tyr Pro Phe Thr
                 85                  90                  95

Phe Gly Gly Gly Thr Lys Val Glu Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210
```

<210> SEQ ID NO 224
<211> LENGTH: 106
<212> TYPE: PRT
<213> ORGANISM: Artificial Sequence
<220> FEATURE:
<223> OTHER INFORMATION: A4B4-F25S VL DOMAIN

<400> SEQUENCE: 224

```
Asp Ile Gln Met Thr Gln Ser Pro Ser Thr Leu Ser Ala Ser Val Gly
  1               5                  10                  15

Asp Arg Val Thr Ile Thr Cys Ser Ala Ser Ser Arg Val Gly Tyr Met
             20                  25                  30

His Trp Tyr Gln Gln Lys Pro Gly Lys Ala Pro Lys Leu Leu Ile Tyr
         35                  40                  45

Asp Thr Ser Phe Leu Asp Ser Gly Val Pro Ser Arg Phe Ser Gly Ser
     50                  55                  60

Gly Ser Gly Thr Glu Phe Thr Leu Thr Ile Ser Ser Leu Gln Pro Asp
 65                  70                  75                  80

Asp Phe Ala Thr Tyr Tyr Cys Phe Gln Gly Ser Gly Tyr Pro Phe Thr
                 85                  90                  95

Phe Gly Gly Gly Thr Lys Leu Glu Ile Lys
            100                 105
```

-continued

<210> SEQ ID NO 225
<211> LENGTH: 7
<212> TYPE: PRT
<213> ORGANISM: Artificial Sequence
<220> FEATURE:
<223> OTHER INFORMATION: A4B4-F25S VL CDR2

<400> SEQUENCE: 225

Asp Thr Ser Phe Leu Asp Ser
 1               5

<210> SEQ ID NO 226
<211> LENGTH: 450
<212> TYPE: PRT
<213> ORGANISM: Artificial Sequence
<220> FEATURE:
<223> OTHER INFORMATION: H3-3F4 VH CHAIN

<400> SEQUENCE: 226

Gln Val Thr Leu Arg Glu Ser Gly Pro Ala Leu Val Lys Pro Thr Gln
 1               5                  10                  15

Thr Leu Thr Leu Thr Cys Thr Phe Ser Gly Phe Ser Leu Ser Thr Ala
                20                  25                  30

Gly Met Ser Val Gly Trp Ile Arg Gln Pro Pro Gly Lys Ala Leu Glu
            35                  40                  45

Trp Leu Ala Asp Ile Trp Trp Asp Asp Lys Lys Asp Tyr Asn Pro Ser
    50                  55                  60

Leu Lys Ser Arg Leu Thr Ile Ser Lys Asp Thr Ser Lys Asn Gln Val
65                  70                  75                  80

Val Leu Lys Val Thr Asn Met Asp Pro Ala Asp Thr Ala Thr Tyr Tyr
                85                  90                  95

Cys Ala Arg Asp Met Ile Phe Asn Trp Tyr Phe Asp Val Trp Gly Gln
            100                 105                 110

Gly Thr Thr Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Arg Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

```
Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
        355                 360                 365

Thr Cys Leu Val Lys Gly Phe Tyr Pro Ser Asp Ile Ala Val Glu Trp
370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450

<210> SEQ ID NO 227
<211> LENGTH: 120
<212> TYPE: PRT
<213> ORGANISM: Artificial Sequence
<220> FEATURE:
<223> OTHER INFORMATION: H3-3F4 VH DOMAIN

<400> SEQUENCE: 227

Gln Val Thr Leu Arg Glu Ser Gly Pro Ala Leu Val Lys Pro Thr Gln
1               5                   10                  15

Thr Leu Thr Leu Thr Cys Thr Phe Ser Gly Phe Ser Leu Ser Thr Ala
            20                  25                  30

Gly Met Ser Val Gly Trp Ile Arg Gln Pro Pro Gly Lys Ala Leu Glu
        35                  40                  45

Trp Leu Ala Asp Ile Trp Trp Asp Asp Lys Lys Asp Tyr Asn Pro Ser
    50                  55                  60

Leu Lys Ser Arg Leu Thr Ile Ser Lys Asp Thr Ser Lys Asn Gln Val
65                  70                  75                  80

Val Leu Lys Val Thr Asn Met Asp Pro Ala Asp Thr Ala Thr Tyr Tyr
                85                  90                  95

Cys Ala Arg Asp Met Ile Phe Asn Trp Tyr Phe Asp Val Trp Gly Ala
            100                 105                 110

Gly Thr Thr Val Thr Val Ser Ser
        115                 120

<210> SEQ ID NO 228
<211> LENGTH: 213
<212> TYPE: PRT
<213> ORGANISM: Artificial Sequence
<220> FEATURE:
<223> OTHER INFORMATION: H3-3F4 VL CHAIN

<400> SEQUENCE: 228

Asp Ile Gln Met Thr Gln Ser Pro Ser Thr Leu Ser Ala Ser Val Gly
1               5                   10                  15
```

```
Asp Arg Val Thr Ile Thr Cys Ser Ala Ser Ser Val Gly Tyr Met
            20                  25                  30

His Trp Tyr Gln Gln Lys Pro Gly Lys Ala Pro Lys Leu Leu Ile Tyr
        35                  40                  45

Asp Thr Phe Lys Leu Ala Ser Gly Val Pro Ser Arg Phe Ser Gly Ser
    50                  55                  60

Gly Ser Gly Thr Glu Phe Thr Leu Thr Ile Ser Ser Leu Gln Pro Asp
65                  70                  75                  80

Asp Phe Ala Thr Tyr Tyr Cys Phe Gln Gly Ser Gly Tyr Pro Phe Thr
                85                  90                  95

Phe Gly Gly Gly Thr Lys Val Glu Ile Lys Arg Thr Val Ala Ala Pro
            100                 105                 110

Ser Val Phe Ile Phe Pro Pro Ser Asp Glu Gln Leu Lys Ser Gly Thr
            115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
            195                 200                 205

Asn Arg Gly Glu Cys
    210

<210> SEQ ID NO 229
<211> LENGTH: 106
<212> TYPE: PRT
<213> ORGANISM: Artificial Sequence
<220> FEATURE:
<223> OTHER INFORMATION: H3-3F4 VL DOMAIN

<400> SEQUENCE: 229

Asp Ile Gln Met Thr Gln Ser Pro Ser Thr Leu Ser Ala Ser Val Gly
1               5                   10                  15

Asp Arg Val Thr Ile Thr Cys Ser Ala Ser Ser Val Gly Tyr Met
            20                  25                  30

His Trp Tyr Gln Gln Lys Pro Gly Lys Ala Pro Lys Leu Leu Ile Tyr
        35                  40                  45

Asp Thr Phe Lys Leu Ala Ser Gly Val Pro Ser Arg Phe Ser Gly Ser
    50                  55                  60

Gly Ser Gly Thr Glu Phe Thr Leu Thr Ile Ser Ser Leu Gln Pro Asp
65                  70                  75                  80

Asp Phe Ala Thr Tyr Tyr Cys Phe Gln Gly Ser Gly Tyr Pro Phe Thr
                85                  90                  95

Phe Gly Gly Gly Thr Lys Leu Glu Ile Lys
            100                 105

<210> SEQ ID NO 230
<211> LENGTH: 7
<212> TYPE: PRT
<213> ORGANISM: Artificial Sequence
<220> FEATURE:
<223> OTHER INFORMATION: VL CDR2
```

```
<400> SEQUENCE: 230

Asp Thr Arg Tyr Gln Ser Ser
1               5

<210> SEQ ID NO 231
<211> LENGTH: 7
<212> TYPE: PRT
<213> ORGANISM: Artificial Sequence
<220> FEATURE:
<223> OTHER INFORMATION: M3H9 VL CDR2

<400> SEQUENCE: 231

Asp Thr Tyr Lys Gln Thr Ser
1               5

<210> SEQ ID NO 232
<211> LENGTH: 120
<212> TYPE: PRT
<213> ORGANISM: Artificial Sequence
<220> FEATURE:
<223> OTHER INFORMATION: IX-493L1FR VH domain

<400> SEQUENCE: 232

Gln Val Thr Leu Arg Glu Ser Gly Pro Ala Leu Val Lys Pro Thr Gln
1               5                   10                  15

Thr Leu Thr Leu Thr Cys Thr Phe Ser Gly Phe Ser Leu Ser Thr Ser
            20                  25                  30

Gly Met Ser Val Gly Trp Ile Arg Gln Pro Pro Gly Lys Ala Leu Glu
        35                  40                  45

Trp Leu Ala Asp Ile Trp Trp Asp Asp Lys Lys Asp Tyr Asn Pro Ser
    50                  55                  60

Leu Lys Ser Arg Leu Thr Ile Ser Lys Asp Thr Ser Lys Asn Gln Val
65                  70                  75                  80

Val Leu Lys Val Thr Asn Met Asp Pro Ala Asp Thr Ala Thr Tyr Tyr
                85                  90                  95

Cys Ala Arg Ser Met Ile Thr Asn Trp Tyr Phe Asp Val Trp Gly Gln
            100                 105                 110

Gly Thr Thr Val Thr Val Ser Ser
        115                 120

<210> SEQ ID NO 233
<211> LENGTH: 450
<212> TYPE: PRT
<213> ORGANISM: Artificial Sequence
<220> FEATURE:
<223> OTHER INFORMATION: A3e2 VH chain

<400> SEQUENCE: 233

Gln Val Thr Leu Arg Glu Ser Gly Pro Ala Leu Val Lys Pro Thr Gln
1               5                   10                  15

Thr Leu Thr Leu Thr Cys Thr Phe Ser Gly Phe Ser Leu Ser Thr Ala
            20                  25                  30

Gly Met Ser Val Gly Trp Ile Arg Gln Pro Pro Gly Lys Ala Leu Glu
        35                  40                  45

Trp Leu Ala Asp Ile Trp Trp Gly Asp Lys Gly His Tyr Asn Pro Ser
    50                  55                  60

Leu Lys Asp Arg Leu Thr Ile Ser Lys Asp Thr Ser Lys Asn Gln Val
65                  70                  75                  80

Val Leu Lys Val Thr Asn Met Asp Pro Ala Asp Thr Ala Thr Tyr Tyr
                85                  90                  95
```

Cys Ala Arg Asp Met Ile Phe Asn Trp Tyr Phe Asp Val Trp Gly Gln
            100                 105                 110

Gly Thr Thr Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Arg Val Glu Pro Lys Ser Cys Asp
210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
        355                 360                 365

Thr Cys Leu Val Lys Gly Phe Tyr Pro Ser Asp Ile Ala Val Glu Trp
370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450

<210> SEQ ID NO 234
<211> LENGTH: 120
<212> TYPE: PRT
<213> ORGANISM: Artificial Sequence
<220> FEATURE:
<223> OTHER INFORMATION: A3e2 VH domain

<400> SEQUENCE: 234

```
Gln Val Thr Leu Arg Glu Ser Gly Pro Ala Leu Val Lys Pro Thr Gln
1               5                   10                  15

Thr Leu Thr Leu Thr Cys Thr Phe Ser Gly Phe Ser Leu Ser Thr Ala
            20                  25                  30

Gly Met Ser Val Gly Trp Ile Arg Gln Pro Pro Gly Lys Ala Leu Glu
        35                  40                  45

Trp Leu Ala Asp Ile Trp Trp Gly Asp Lys Gly His Tyr Asn Pro Ser
50                  55                  60

Leu Lys Asp Arg Leu Thr Ile Ser Lys Asp Thr Ser Lys Asn Gln Val
65                  70                  75                  80

Val Leu Lys Val Thr Asn Met Asp Pro Ala Asp Thr Ala Thr Tyr Tyr
                85                  90                  95

Cys Ala Arg Asp Met Ile Phe Asn Trp Tyr Phe Asp Val Trp Gly Gln
            100                 105                 110

Gly Thr Thr Val Thr Val Ser Ser
        115                 120

<210> SEQ ID NO 235
<211> LENGTH: 16
<212> TYPE: PRT
<213> ORGANISM: Artificial Sequence
<220> FEATURE:
<223> OTHER INFORMATION: A3e2 VH CDR2

<400> SEQUENCE: 235

Asp Ile Trp Trp Gly Asp Lys Gly His Tyr Asn Pro Ser Leu Lys Asp
1               5                   10                  15

<210> SEQ ID NO 236
<211> LENGTH: 213
<212> TYPE: PRT
<213> ORGANISM: Artificial Sequence
<220> FEATURE:
<223> OTHER INFORMATION: A3e2 VL chain

<400> SEQUENCE: 236

Asp Ile Gln Met Thr Gln Ser Pro Ser Thr Leu Ser Ala Ser Val Gly
1               5                   10                  15

Asp Arg Val Thr Ile Thr Cys Ser Ala Ser Ser Ser Val Gly Tyr Met
            20                  25                  30

His Trp Tyr Gln Gln Lys Pro Gly Lys Ala Pro Lys Leu Leu Ile Tyr
        35                  40                  45

Asp Thr Phe Tyr Leu His Ser Gly Val Pro Ser Arg Phe Ser Gly Ser
50                  55                  60

Gly Ser Gly Thr Glu Phe Thr Leu Thr Ile Ser Ser Leu Gln Pro Asp
65                  70                  75                  80

Asp Phe Ala Thr Tyr Tyr Cys Phe Gln Gly Ser Gly Tyr Pro Phe Thr
                85                  90                  95

Phe Gly Gly Gly Thr Lys Val Glu Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
```

```
                165                 170                 175
Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210

<210> SEQ ID NO 237
<211> LENGTH: 106
<212> TYPE: PRT
<213> ORGANISM: Artificial Sequence
<220> FEATURE:
<223> OTHER INFORMATION: A3e2 VL domain

<400> SEQUENCE: 237

Asp Ile Gln Met Thr Gln Ser Pro Ser Thr Leu Ser Ala Ser Val Gly
1               5                   10                  15

Asp Arg Val Thr Ile Thr Cys Ser Ala Ser Ser Val Gly Tyr Met
            20                  25                  30

His Trp Tyr Gln Gln Lys Pro Gly Lys Ala Pro Lys Leu Leu Ile Tyr
            35                  40                  45

Asp Thr Phe Tyr Leu His Ser Gly Val Pro Ser Arg Phe Ser Gly Ser
    50                  55                  60

Gly Ser Gly Thr Glu Phe Thr Leu Thr Ile Ser Ser Leu Gln Pro Asp
65                  70                  75                  80

Asp Phe Ala Thr Tyr Tyr Cys Phe Gln Gly Ser Gly Tyr Pro Phe Thr
                85                  90                  95

Phe Gly Gly Gly Thr Lys Val Glu Ile Lys
            100                 105

<210> SEQ ID NO 238
<211> LENGTH: 7
<212> TYPE: PRT
<213> ORGANISM: Artificial Sequence
<220> FEATURE:
<223> OTHER INFORMATION: A3e2 VL CDR2

<400> SEQUENCE: 238

Asp Thr Phe Tyr Leu His Ser
1               5

<210> SEQ ID NO 239
<211> LENGTH: 450
<212> TYPE: PRT
<213> ORGANISM: Artificial Sequence
<220> FEATURE:
<223> OTHER INFORMATION: A14a4 VH chain

<400> SEQUENCE: 239

Gln Val Thr Leu Arg Glu Ser Gly Pro Ala Leu Val Lys Pro Thr Gln
1               5                   10                  15

Thr Leu Thr Leu Thr Cys Thr Phe Ser Gly Phe Ser Leu Ser Thr Ala
            20                  25                  30

Gly Met Ser Val Gly Trp Ile Arg Gln Pro Pro Gly Lys Ala Leu Glu
            35                  40                  45

Trp Leu Ala Asp Ile Trp Trp Asp Asp Lys Lys Ser Tyr Asn Pro Ser
    50                  55                  60

Leu Lys Asp Arg Leu Thr Ile Ser Lys Asp Thr Ser Lys Asn Gln Val
65                  70                  75                  80
```

Val Leu Lys Val Thr Asn Met Asp Pro Ala Asp Thr Ala Thr Tyr Tyr
            85                  90                  95

Cys Ala Arg Asp Met Ile Thr Asn Trp Tyr Phe Asp Val Trp Gly Gln
                100                 105                 110

Gly Thr Thr Val Thr Val Ser Ser Ala Ser Thr Lys Gly Pro Ser Val
            115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Arg Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
    275                 280                 285

Asn Ala Lys Thr Lys Pro Arg Glu Glu Gln Tyr Asn Ser Thr Tyr Arg
290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
    355                 360                 365

Thr Cys Leu Val Lys Gly Phe Tyr Pro Ser Asp Ile Ala Val Glu Trp
370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
    435                 440                 445

Gly Lys
    450

<210> SEQ ID NO 240
<211> LENGTH: 120
<212> TYPE: PRT
<213> ORGANISM: Artificial Sequence
<220> FEATURE:

<223> OTHER INFORMATION: A14a4 VH domain

<400> SEQUENCE: 240

Gln Val Thr Leu Arg Glu Ser Gly Pro Ala Leu Val Lys Pro Thr Gln
1               5                   10                  15

Thr Leu Thr Leu Thr Cys Thr Phe Ser Gly Phe Ser Leu Ser Thr Ala
            20                  25                  30

Gly Met Ser Val Gly Trp Ile Arg Gln Pro Pro Gly Lys Ala Leu Glu
        35                  40                  45

Trp Leu Ala Asp Ile Trp Trp Asp Asp Lys Lys Ser Tyr Asn Pro Ser
    50                  55                  60

Leu Lys Asp Arg Leu Thr Ile Ser Lys Asp Thr Ser Lys Asn Gln Val
65                  70                  75                  80

Val Leu Lys Val Thr Asn Met Asp Pro Ala Asp Thr Ala Thr Tyr Tyr
                85                  90                  95

Cys Ala Arg Asp Met Ile Thr Asn Trp Tyr Phe Asp Val Trp Gly Gln
            100                 105                 110

Gly Thr Thr Val Thr Val Ser Ser
        115                 120

<210> SEQ ID NO 241
<211> LENGTH: 10
<212> TYPE: PRT
<213> ORGANISM: Artificial Sequence
<220> FEATURE:
<223> OTHER INFORMATION: A14a4 VH CDR3

<400> SEQUENCE: 241

Asp Met Ile Thr Asn Trp Tyr Phe Asp Val
1               5                   10

<210> SEQ ID NO 242
<211> LENGTH: 197
<212> TYPE: PRT
<213> ORGANISM: Artificial Sequence
<220> FEATURE:
<223> OTHER INFORMATION: A14a4 VL chain

<400> SEQUENCE: 242

Asp Arg Val Thr Ile Thr Cys Leu Leu Ser Ser Arg Val Gly Tyr Met
1               5                   10                  15

His Trp Tyr Gln Gln Lys Pro Gly Lys Ala Pro Lys Leu Leu Ile Tyr
            20                  25                  30

Asp Thr Tyr Tyr Gln Thr Ser Gly Val Pro Ser Arg Phe Ser Gly Ser
        35                  40                  45

Gly Ser Gly Thr Glu Phe Thr Leu Thr Ile Ser Ser Leu Gln Pro Asp
    50                  55                  60

Asp Phe Ala Thr Tyr Tyr Cys Phe Gln Gly Ser Gly Tyr Pro Phe Thr
65                  70                  75                  80

Phe Gly Gly Gly Thr Lys Val Glu Ile Lys Arg Thr Val Ala Ala Pro
                85                  90                  95

Ser Val Phe Ile Phe Pro Pro Ser Asp Glu Gln Leu Lys Ser Gly Thr
            100                 105                 110

Ala Ser Val Val Cys Leu Leu Asn Asn Phe Tyr Pro Arg Glu Ala Lys
        115                 120                 125

Val Gln Trp Lys Val Asp Asn Ala Leu Gln Ser Gly Asn Ser Gln Glu
    130                 135                 140

Ser Val Thr Glu Gln Asp Ser Lys Asp Ser Thr Tyr Ser Leu Ser Ser

-continued

```
                145                 150                 155                 160
Thr Leu Thr Leu Ser Lys Ala Asp Tyr Glu Lys His Lys Val Tyr Ala
            165                 170                 175
Cys Glu Val Thr His Gln Gly Leu Ser Ser Pro Val Thr Lys Ser Phe
            180                 185                 190
Asn Arg Gly Glu Cys
        195

<210> SEQ ID NO 243
<211> LENGTH: 106
<212> TYPE: PRT
<213> ORGANISM: Artificial Sequence
<220> FEATURE:
<223> OTHER INFORMATION: A14a4 VL domain

<400> SEQUENCE: 243

Asp Ile Gln Met Thr Gln Ser Pro Ser Thr Leu Ser Ala Ser Val Gly
1               5                   10                  15
Asp Arg Val Thr Ile Thr Cys Leu Leu Ser Ser Arg Val Gly Tyr Met
            20                  25                  30
His Trp Tyr Gln Gln Lys Pro Gly Lys Ala Pro Lys Leu Leu Ile Tyr
        35                  40                  45
Asp Thr Tyr Tyr Gln Thr Ser Gly Val Pro Ser Arg Phe Ser Gly Ser
    50                  55                  60
Gly Ser Gly Thr Glu Phe Thr Leu Thr Ile Ser Ser Leu Gln Pro Asp
65                  70                  75                  80
Asp Phe Ala Thr Tyr Tyr Cys Phe Gln Gly Ser Gly Tyr Pro Phe Thr
                85                  90                  95
Phe Gly Gly Gly Thr Lys Val Glu Ile Lys
            100                 105

<210> SEQ ID NO 244
<211> LENGTH: 10
<212> TYPE: PRT
<213> ORGANISM: Artificial Sequence
<220> FEATURE:
<223> OTHER INFORMATION: A14a4 VL CDR1

<400> SEQUENCE: 244

Leu Leu Ser Ser Arg Val Gly Tyr Met His
1               5                   10

<210> SEQ ID NO 245
<211> LENGTH: 7
<212> TYPE: PRT
<213> ORGANISM: Artificial Sequence
<220> FEATURE:
<223> OTHER INFORMATION: A14a4 VL CDR2

<400> SEQUENCE: 245

Asp Thr Tyr Tyr Gln Thr Ser
1               5

<210> SEQ ID NO 246
<211> LENGTH: 450
<212> TYPE: PRT
<213> ORGANISM: Artificial Sequence
<220> FEATURE:
<223> OTHER INFORMATION: A16b4 VH chain

<400> SEQUENCE: 246

Gln Val Thr Leu Arg Glu Ser Gly Pro Ala Leu Val Lys Pro Thr Gln
```

-continued

```
           1               5              10              15
         Thr Leu Thr Leu Thr Cys Thr Phe Ser Gly Phe Ser Leu Ser Thr Ala
                         20                  25                  30
         Gly Met Ser Val Gly Trp Ile Arg Gln Pro Pro Gly Lys Ala Leu Glu
                         35                  40                  45
         Trp Leu Ala Asp Ile Trp Trp Asp Asp Lys His Tyr Asn Pro Ser
          50                  55                  60
         Leu Lys Asp Arg Leu Thr Ile Ser Lys Asp Thr Ser Lys Asn Gln Val
          65                  70                  75                  80
         Val Leu Lys Val Thr Asn Met Asp Pro Ala Asp Thr Ala Thr Tyr Tyr
                         85                  90                  95
         Cys Ala Arg Asp Met Ile Phe Asn Trp Tyr Phe Asp Val Trp Gly Gln
                         100                 105                 110
         Gly Thr Thr Val Thr Val Ser Ser Ala Ser Thr Lys Gly Pro Ser Val
                         115                 120                 125
         Phe Pro Leu Ala Pro Ser Ser Lys Ser Thr Ser Gly Gly Thr Ala Ala
                         130                 135                 140
         Leu Gly Cys Leu Val Lys Asp Tyr Phe Pro Glu Pro Val Thr Val Ser
         145                 150                 155                 160
         Trp Asn Ser Gly Ala Leu Thr Ser Gly Val His Thr Phe Pro Ala Val
                         165                 170                 175
         Leu Gln Ser Ser Gly Leu Tyr Ser Leu Ser Ser Val Val Thr Val Pro
                         180                 185                 190
         Ser Ser Ser Leu Gly Thr Gln Thr Tyr Ile Cys Asn Val Asn His Lys
                         195                 200                 205
         Pro Ser Asn Thr Lys Val Asp Lys Arg Val Glu Pro Lys Ser Cys Asp
                         210                 215                 220
         Lys Thr His Thr Cys Pro Pro Cys Pro Ala Pro Glu Leu Leu Gly Gly
         225                 230                 235                 240
         Pro Ser Val Phe Leu Phe Pro Pro Lys Pro Lys Asp Thr Leu Met Ile
                         245                 250                 255
         Ser Arg Thr Pro Glu Val Thr Cys Val Val Val Asp Val Ser His Glu
                         260                 265                 270
         Asp Pro Glu Val Lys Phe Asn Trp Tyr Val Asp Gly Val Glu Val His
                         275                 280                 285
         Asn Ala Lys Thr Lys Pro Arg Glu Glu Gln Tyr Asn Ser Thr Tyr Arg
                         290                 295                 300
         Val Val Ser Val Leu Thr Val Leu His Gln Asp Trp Leu Asn Gly Lys
         305                 310                 315                 320
         Glu Tyr Lys Cys Lys Val Ser Asn Lys Ala Leu Pro Ala Pro Ile Glu
                         325                 330                 335
         Lys Thr Ile Ser Lys Ala Lys Gly Gln Pro Arg Glu Pro Gln Val Tyr
                         340                 345                 350
         Thr Leu Pro Pro Ser Arg Glu Glu Met Thr Lys Asn Gln Val Ser Leu
                         355                 360                 365
         Thr Cys Leu Val Lys Gly Phe Tyr Pro Ser Asp Ile Ala Val Glu Trp
                         370                 375                 380
         Glu Ser Asn Gly Gln Pro Glu Asn Asn Tyr Lys Thr Thr Pro Pro Val
         385                 390                 395                 400
         Leu Asp Ser Asp Gly Ser Phe Phe Leu Tyr Ser Lys Leu Thr Val Asp
                         405                 410                 415
         Lys Ser Arg Trp Gln Gln Gly Asn Val Phe Ser Cys Ser Val Met His
                         420                 425                 430
```

Glu Ala Leu His Asn His Tyr Thr Gln Lys Ser Leu Ser Leu Ser Pro
            435                 440                 445

Gly Lys
    450

<210> SEQ ID NO 247
<211> LENGTH: 120
<212> TYPE: PRT
<213> ORGANISM: Artificial Sequence
<220> FEATURE:
<223> OTHER INFORMATION: A16b4 VH domain

<400> SEQUENCE: 247

Gln Val Thr Leu Arg Glu Ser Gly Pro Ala Leu Val Lys Pro Thr Gln
 1               5                  10                  15

Thr Leu Thr Leu Thr Cys Thr Phe Ser Gly Phe Ser Leu Ser Thr Ala
            20                  25                  30

Gly Met Ser Val Gly Trp Ile Arg Gln Pro Pro Gly Lys Ala Leu Glu
        35                  40                  45

Trp Leu Ala Asp Ile Trp Trp Asp Asp Lys Lys His Tyr Asn Pro Ser
 50                  55                  60

Leu Lys Asp Arg Leu Thr Ile Ser Lys Asp Thr Ser Lys Asn Gln Val
65                  70                  75                  80

Val Leu Lys Val Thr Asn Met Asp Pro Ala Asp Thr Ala Thr Tyr Tyr
                85                  90                  95

Cys Ala Arg Asp Met Ile Phe Asn Trp Tyr Phe Asp Val Trp Gly Gln
            100                 105                 110

Gly Thr Thr Val Thr Val Ser Ser
        115                 120

<210> SEQ ID NO 248
<211> LENGTH: 197
<212> TYPE: PRT
<213> ORGANISM: Artificial Sequence
<220> FEATURE:
<223> OTHER INFORMATION: A16b4 VL chain

<400> SEQUENCE: 248

Asp Arg Val Thr Ile Thr Cys Leu Leu Ser Ser Arg Val Gly Tyr Met
 1               5                  10                  15

His Trp Tyr Gln Gln Lys Pro Gly Lys Ala Pro Lys Leu Leu Ile Tyr
            20                  25                  30

Asp Thr Met Tyr Gln Ala Ser Gly Val Pro Ser Arg Phe Ser Gly Ser
        35                  40                  45

Gly Ser Gly Thr Glu Phe Thr Leu Thr Ile Ser Ser Leu Gln Pro Asp
 50                  55                  60

Asp Phe Ala Thr Tyr Tyr Cys Phe Gln Gly Ser Gly Tyr Pro Phe Thr
65                  70                  75                  80

Phe Gly Gly Gly Thr Lys Val Glu Ile Lys Arg Thr Val Ala Ala Pro
                85                  90                  95

Ser Val Phe Ile Phe Pro Pro Ser Asp Glu Gln Leu Lys Ser Gly Thr
            100                 105                 110

Ala Ser Val Val Cys Leu Leu Asn Asn Phe Tyr Pro Arg Glu Ala Lys
        115                 120                 125

Val Gln Trp Lys Val Asp Asn Ala Leu Gln Ser Gly Asn Ser Gln Glu
 130                 135                 140

Ser Val Thr Glu Gln Asp Ser Lys Asp Ser Thr Tyr Ser Leu Ser Ser

```
                145                 150                 155                 160
Thr Leu Thr Leu Ser Lys Ala Asp Tyr Glu Lys His Lys Val Tyr Ala
            165                 170                 175

Cys Glu Val Thr His Gln Gly Leu Ser Ser Pro Val Thr Lys Ser Phe
        180                 185                 190

Asn Arg Gly Glu Cys
        195

<210> SEQ ID NO 249
<211> LENGTH: 106
<212> TYPE: PRT
<213> ORGANISM: Artificial Sequence
<220> FEATURE:
<223> OTHER INFORMATION: A16b4 VL domain

<400> SEQUENCE: 249

Asp Ile Gln Met Thr Gln Ser Pro Ser Thr Leu Ser Ala Ser Val Gly
1               5                   10                  15

Asp Arg Val Thr Ile Thr Cys Leu Leu Ser Ser Arg Val Gly Tyr Met
            20                  25                  30

His Trp Tyr Gln Gln Lys Pro Gly Lys Ala Pro Lys Leu Leu Ile Tyr
        35                  40                  45

Asp Thr Met Tyr Gln Ala Ser Gly Val Pro Ser Arg Phe Ser Gly Ser
    50                  55                  60

Gly Ser Gly Thr Glu Phe Thr Leu Thr Ile Ser Ser Leu Gln Pro Asp
65                  70                  75                  80

Asp Phe Ala Thr Tyr Tyr Cys Phe Gln Gly Ser Gly Tyr Pro Phe Thr
                85                  90                  95

Phe Gly Gly Gly Thr Lys Val Glu Ile Lys
            100                 105

<210> SEQ ID NO 250
<211> LENGTH: 10
<212> TYPE: PRT
<213> ORGANISM: Artificial Sequence
<220> FEATURE:
<223> OTHER INFORMATION: A16b4 VL CDR1

<400> SEQUENCE: 250

Leu Leu Ser Ser Arg Val Gly Tyr Met His
1               5                   10

<210> SEQ ID NO 251
<211> LENGTH: 7
<212> TYPE: PRT
<213> ORGANISM: Artificial Sequence
<220> FEATURE:
<223> OTHER INFORMATION: A16b4 VL CDR2

<400> SEQUENCE: 251

Asp Thr Met Tyr Gln Ala Ser
1               5

<210> SEQ ID NO 252
<211> LENGTH: 450
<212> TYPE: PRT
<213> ORGANISM: Artificial Sequence
<220> FEATURE:
<223> OTHER INFORMATION: A17b5 VH chain

<400> SEQUENCE: 252

Gln Val Thr Leu Arg Glu Ser Gly Pro Ala Leu Val Lys Pro Thr Gln
```

-continued

```
  1               5               10              15
Thr Leu Thr Leu Thr Cys Thr Phe Ser Gly Phe Ser Leu Ser Thr Ala
                    20              25              30
Gly Met Ser Val Gly Trp Ile Arg Gln Pro Pro Gly Lys Ala Leu Glu
            35              40              45
Trp Leu Ala Asp Ile Trp Trp Asp Asp Lys His Tyr Asn Pro Ser
50                  55                  60
Leu Lys Asp Arg Leu Thr Ile Ser Lys Asp Thr Ser Lys Asn Gln Val
65                  70                  75              80
Val Leu Lys Val Thr Asn Met Asp Pro Ala Asp Thr Ala Thr Tyr Tyr
                    85              90              95
Cys Ala Arg Asp Met Ile Phe Asn Trp Tyr Phe Asp Val Trp Gly Gln
                100             105             110
Gly Thr Thr Val Thr Val Ser Ser Ala Ser Thr Lys Gly Pro Ser Val
            115             120             125
Phe Pro Leu Ala Pro Ser Ser Lys Ser Thr Ser Gly Gly Thr Ala Ala
        130             135             140
Leu Gly Cys Leu Val Lys Asp Tyr Phe Pro Glu Pro Val Thr Val Ser
145             150             155             160
Trp Asn Ser Gly Ala Leu Thr Ser Gly Val His Thr Phe Pro Ala Val
                165             170             175
Leu Gln Ser Ser Gly Leu Tyr Ser Leu Ser Ser Val Val Thr Val Pro
            180             185             190
Ser Ser Ser Leu Gly Thr Gln Thr Tyr Ile Cys Asn Val Asn His Lys
        195             200             205
Pro Ser Asn Thr Lys Val Asp Lys Arg Val Glu Pro Lys Ser Cys Asp
210             215             220
Lys Thr His Thr Cys Pro Pro Cys Pro Ala Pro Glu Leu Leu Gly Gly
225             230             235             240
Pro Ser Val Phe Leu Phe Pro Pro Lys Pro Lys Asp Thr Leu Met Ile
                245             250             255
Ser Arg Thr Pro Glu Val Thr Cys Val Val Val Asp Val Ser His Glu
            260             265             270
Asp Pro Glu Val Lys Phe Asn Trp Tyr Val Asp Gly Val Glu Val His
        275             280             285
Asn Ala Lys Thr Lys Pro Arg Glu Glu Gln Tyr Asn Ser Thr Tyr Arg
290             295             300
Val Val Ser Val Leu Thr Val Leu His Gln Asp Trp Leu Asn Gly Lys
305             310             315             320
Glu Tyr Lys Cys Lys Val Ser Asn Lys Ala Leu Pro Ala Pro Ile Glu
                325             330             335
Lys Thr Ile Ser Lys Ala Lys Gly Gln Pro Arg Glu Pro Gln Val Tyr
            340             345             350
Thr Leu Pro Pro Ser Arg Glu Glu Met Thr Lys Asn Gln Val Ser Leu
        355             360             365
Thr Cys Leu Val Lys Gly Phe Tyr Pro Ser Asp Ile Ala Val Glu Trp
370             375             380
Glu Ser Asn Gly Gln Pro Glu Asn Asn Tyr Lys Thr Thr Pro Pro Val
385             390             395             400
Leu Asp Ser Asp Gly Ser Phe Phe Leu Tyr Ser Lys Leu Thr Val Asp
                405             410             415
Lys Ser Arg Trp Gln Gln Gly Asn Val Phe Ser Cys Ser Val Met His
            420             425             430
```

Glu Ala Leu His Asn His Tyr Thr Gln Lys Ser Leu Ser Leu Ser Pro
            435                 440                 445

Gly Lys
    450

<210> SEQ ID NO 253
<211> LENGTH: 120
<212> TYPE: PRT
<213> ORGANISM: Artificial Sequence
<220> FEATURE:
<223> OTHER INFORMATION: A17b5 VH domain

<400> SEQUENCE: 253

Gln Val Thr Leu Arg Glu Ser Gly Pro Ala Leu Val Lys Pro Thr Gln
 1               5                  10                  15

Thr Leu Thr Leu Thr Cys Thr Phe Ser Gly Phe Ser Leu Ser Thr Ala
             20                  25                  30

Gly Met Ser Val Gly Trp Ile Arg Gln Pro Pro Gly Lys Ala Leu Glu
         35                  40                  45

Trp Leu Ala Asp Ile Trp Trp Asp Asp Lys Lys His Tyr Asn Pro Ser
     50                  55                  60

Leu Lys Asp Arg Leu Thr Ile Ser Lys Asp Thr Ser Lys Asn Gln Val
 65                  70                  75                  80

Val Leu Lys Val Thr Asn Met Asp Pro Ala Asp Thr Ala Thr Tyr Tyr
                 85                  90                  95

Cys Ala Arg Asp Met Ile Phe Asn Trp Tyr Phe Asp Val Trp Gly Gln
            100                 105                 110

Gly Thr Thr Val Thr Val Ser Ser
        115                 120

<210> SEQ ID NO 254
<211> LENGTH: 213
<212> TYPE: PRT
<213> ORGANISM: Artificial Sequence
<220> FEATURE:
<223> OTHER INFORMATION: A17b5 VL chain

<400> SEQUENCE: 254

Asp Ile Gln Met Thr Gln Ser Pro Ser Thr Leu Ser Ala Ser Val Gly
 1               5                  10                  15

Asp Arg Val Thr Ile Thr Cys Ser Leu Ser Ser Arg Val Gly Tyr Met
             20                  25                  30

His Trp Tyr Gln Gln Lys Pro Gly Lys Ala Pro Lys Leu Leu Ile Tyr
         35                  40                  45

Asp Thr Tyr Tyr Leu Pro Ser Gly Val Pro Ser Arg Phe Ser Gly Ser
     50                  55                  60

Gly Ser Gly Thr Glu Phe Thr Leu Thr Ile Ser Ser Leu Gln Pro Asp
 65                  70                  75                  80

Asp Phe Ala Thr Tyr Tyr Cys Phe Gln Gly Ser Gly Tyr Pro Phe Thr
                 85                  90                  95

Phe Gly Gly Gly Thr Lys Val Glu Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu

```
                145                 150                 155                 160
Ser Val Thr Glu Gln Asp Ser Lys Asp Ser Thr Tyr Ser Leu Ser Ser
                    165                 170                 175

Thr Leu Thr Leu Ser Lys Ala Asp Tyr Glu Lys His Lys Val Tyr Ala
                    180                 185                 190

Cys Glu Val Thr His Gln Gly Leu Ser Ser Pro Val Thr Lys Ser Phe
                    195                 200                 205

Asn Arg Gly Glu Cys
    210

<210> SEQ ID NO 255
<211> LENGTH: 106
<212> TYPE: PRT
<213> ORGANISM: Artificial Sequence
<220> FEATURE:
<223> OTHER INFORMATION: A17b5 VL domain

<400> SEQUENCE: 255

Asp Ile Gln Met Thr Gln Ser Pro Ser Thr Leu Ser Ala Ser Val Gly
1               5                   10                  15

Asp Arg Val Thr Ile Thr Cys Ser Leu Ser Ser Arg Val Gly Tyr Met
                20                  25                  30

His Trp Tyr Gln Gln Lys Pro Gly Lys Ala Pro Lys Leu Leu Ile Tyr
            35                  40                  45

Asp Thr Tyr Tyr Leu Pro Ser Gly Val Pro Ser Arg Phe Ser Gly Ser
        50                  55                  60

Gly Ser Gly Thr Glu Phe Thr Leu Thr Ile Ser Ser Leu Gln Pro Asp
65                  70                  75                  80

Asp Phe Ala Thr Tyr Tyr Cys Phe Gln Gly Ser Gly Tyr Pro Phe Thr
                85                  90                  95

Phe Gly Gly Gly Thr Lys Val Glu Ile Lys
                100                 105

<210> SEQ ID NO 256
<211> LENGTH: 7
<212> TYPE: PRT
<213> ORGANISM: Artificial Sequence
<220> FEATURE:
<223> OTHER INFORMATION: A17b5 VLCDR2

<400> SEQUENCE: 256

Asp Thr Tyr Tyr Leu Pro Ser
1               5

<210> SEQ ID NO 257
<211> LENGTH: 450
<212> TYPE: PRT
<213> ORGANISM: Artificial Sequence
<220> FEATURE:
<223> OTHER INFORMATION: A17f5 VH chain

<400> SEQUENCE: 257

Gln Val Thr Leu Arg Glu Ser Gly Pro Ala Leu Val Lys Pro Thr Gln
1               5                   10                  15

Thr Leu Thr Leu Thr Cys Thr Phe Ser Gly Phe Ser Leu Ser Thr Ala
                20                  25                  30

Gly Met Ser Val Gly Trp Ile Arg Gln Pro Pro Gly Lys Ala Leu Glu
            35                  40                  45

Trp Leu Ala Asp Ile Trp Trp Asp Asp Lys Lys Asp Tyr Asn Pro Ser
        50                  55                  60
```

Leu Lys Asp Arg Leu Thr Ile Ser Lys Asp Thr Ser Lys Asn Gln Val
 65                  70                  75                  80

Val Leu Lys Val Thr Asn Met Asp Pro Ala Asp Thr Ala Thr Tyr Tyr
                 85                  90                  95

Cys Ala Arg Asp Met Ile Phe Asn Trp Tyr Phe Asp Val Trp Gly Gln
            100                 105                 110

Gly Thr Thr Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Arg Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450

<210> SEQ ID NO 258
<211> LENGTH: 120

```
<212> TYPE: PRT
<213> ORGANISM: Artificial Sequence
<220> FEATURE:
<223> OTHER INFORMATION: A17f5 VH domain

<400> SEQUENCE: 258
```

| Gln | Val | Thr | Leu | Arg | Glu | Ser | Gly | Pro | Ala | Leu | Val | Lys | Pro | Thr | Gln |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |

| Thr | Leu | Thr | Leu | Thr | Cys | Thr | Phe | Ser | Gly | Phe | Ser | Leu | Ser | Thr | Ala |
|     |     |     | 20  |     |     |     |     | 25  |     |     |     |     | 30  |     |     |

| Gly | Met | Ser | Val | Gly | Trp | Ile | Arg | Gln | Pro | Pro | Gly | Lys | Ala | Leu | Glu |
|     |     | 35  |     |     |     |     | 40  |     |     |     |     | 45  |     |     |     |

| Trp | Leu | Ala | Asp | Ile | Trp | Trp | Asp | Asp | Lys | Lys | Asp | Tyr | Asn | Pro | Ser |
|     | 50  |     |     |     |     | 55  |     |     |     |     | 60  |     |     |     |     |

| Leu | Lys | Asp | Arg | Leu | Thr | Ile | Ser | Lys | Asp | Thr | Ser | Lys | Asn | Gln | Val |
| 65  |     |     |     |     | 70  |     |     |     |     | 75  |     |     |     |     | 80  |

| Val | Leu | Lys | Val | Thr | Asn | Met | Asp | Pro | Ala | Asp | Thr | Ala | Thr | Tyr | Tyr |
|     |     |     |     | 85  |     |     |     |     | 90  |     |     |     |     | 95  |     |

| Cys | Ala | Arg | Asp | Met | Ile | Phe | Asn | Trp | Tyr | Phe | Asp | Val | Trp | Gly | Gln |
|     |     |     | 100 |     |     |     |     | 105 |     |     |     |     | 110 |     |     |

| Gly | Thr | Thr | Val | Thr | Val | Ser | Ser |
|     |     | 115 |     |     |     |     | 120 |

```
<210> SEQ ID NO 259
<211> LENGTH: 16
<212> TYPE: PRT
<213> ORGANISM: Artificial Sequence
<220> FEATURE:
<223> OTHER INFORMATION: A17f5 VH CDR2

<400> SEQUENCE: 259
```

| Asp | Ile | Trp | Trp | Asp | Asp | Lys | Lys | Asp | Tyr | Asn | Pro | Ser | Leu | Lys | Asp |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |

```
<210> SEQ ID NO 260
<211> LENGTH: 213
<212> TYPE: PRT
<213> ORGANISM: Artificial Sequence
<220> FEATURE:
<223> OTHER INFORMATION: A17f5 VL chain

<400> SEQUENCE: 260
```

| Asp | Ile | Gln | Met | Thr | Gln | Ser | Pro | Ser | Thr | Leu | Ser | Ala | Ser | Val | Gly |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |

| Asp | Arg | Val | Thr | Ile | Thr | Cys | Ser | Leu | Ser | Ser | Arg | Val | Gly | Tyr | Met |
|     |     |     | 20  |     |     |     |     | 25  |     |     |     |     | 30  |     |     |

| His | Trp | Tyr | Gln | Gln | Lys | Pro | Gly | Lys | Ala | Pro | Lys | Leu | Leu | Ile | Tyr |
|     |     |     | 35  |     |     |     |     | 40  |     |     |     |     | 45  |     |     |

| Asp | Thr | Phe | Arg | His | Thr | Ser | Gly | Val | Pro | Ser | Arg | Phe | Ser | Gly | Ser |
|     | 50  |     |     |     |     | 55  |     |     |     |     | 60  |     |     |     |     |

| Gly | Ser | Gly | Thr | Glu | Phe | Thr | Leu | Thr | Ile | Ser | Ser | Leu | Gln | Pro | Asp |
| 65  |     |     |     |     | 70  |     |     |     |     | 75  |     |     |     |     | 80  |

| Asp | Phe | Ala | Thr | Tyr | Tyr | Cys | Phe | Gln | Gly | Ser | Gly | Tyr | Pro | Phe | Thr |
|     |     |     |     | 85  |     |     |     |     | 90  |     |     |     |     | 95  |     |

| Phe | Gly | Gly | Gly | Thr | Lys | Val | Glu | Ile | Lys | Arg | Thr | Val | Ala | Ala | Pro |
|     |     |     | 100 |     |     |     |     | 105 |     |     |     |     | 110 |     |     |

| Ser | Val | Phe | Ile | Phe | Pro | Pro | Ser | Asp | Glu | Gln | Leu | Lys | Ser | Gly | Thr |
|     |     | 115 |     |     |     |     | 120 |     |     |     |     | 125 |     |     |     |

| Ala | Ser | Val | Val | Cys | Leu | Leu | Asn | Asn | Phe | Tyr | Pro | Arg | Glu | Ala | Lys |

```
                130                 135                 140
Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
                180                 185                 190

Cys Glu Val Thr His Gln Gly Leu Ser Ser Pro Val Thr Lys Ser Phe
                195                 200                 205

Asn Arg Gly Glu Cys
            210

<210> SEQ ID NO 261
<211> LENGTH: 106
<212> TYPE: PRT
<213> ORGANISM: Artificial Sequence
<220> FEATURE:
<223> OTHER INFORMATION: A17f5 VL domain

<400> SEQUENCE: 261

Asp Ile Gln Met Thr Gln Ser Pro Ser Thr Leu Ser Ala Ser Val Gly
1               5                   10                  15

Asp Arg Val Thr Ile Thr Cys Ser Leu Ser Ser Arg Val Gly Tyr Met
            20                  25                  30

His Trp Tyr Gln Gln Lys Pro Gly Lys Ala Pro Lys Leu Leu Ile Tyr
        35                  40                  45

Asp Thr Phe Arg His Thr Ser Gly Val Pro Ser Arg Phe Ser Gly Ser
50                  55                  60

Gly Ser Gly Thr Glu Phe Thr Leu Thr Ile Ser Ser Leu Gln Pro Asp
65                  70                  75                  80

Asp Phe Ala Thr Tyr Tyr Cys Phe Gln Gly Ser Gly Tyr Pro Phe Thr
                85                  90                  95

Phe Gly Gly Gly Thr Lys Val Glu Ile Lys
            100                 105

<210> SEQ ID NO 262
<211> LENGTH: 7
<212> TYPE: PRT
<213> ORGANISM: Artificial Sequence
<220> FEATURE:
<223> OTHER INFORMATION: A17f5 VL CDR2

<400> SEQUENCE: 262

Asp Thr Phe Arg His Thr Ser
1               5

<210> SEQ ID NO 263
<211> LENGTH: 213
<212> TYPE: PRT
<213> ORGANISM: Artificial Sequence
<220> FEATURE:
<223> OTHER INFORMATION: A17h4 VL chain

<400> SEQUENCE: 263

Asp Ile Gln Met Thr Gln Ser Pro Ser Thr Leu Ser Ala Ser Val Gly
1               5                   10                  15

Asp Arg Val Thr Ile Thr Cys Ser Pro Ser Ser Val Gly Tyr Met
            20                  25                  30

His Trp Tyr Gln Gln Lys Pro Gly Lys Ala Pro Lys Leu Leu Ile Tyr
        35                  40                  45
```

```
Asp Thr Tyr Tyr Leu Ala Ser Gly Val Pro Ser Arg Phe Ser Gly Ser
    50                  55                  60

Gly Ser Gly Thr Glu Phe Thr Leu Thr Ile Ser Ser Leu Gln Pro Asp
65                  70                  75                  80

Asp Phe Ala Thr Tyr Tyr Cys Phe Gln Gly Ser Gly Tyr Pro Phe Thr
                85                  90                  95

Phe Gly Gly Gly Thr Lys Val Glu Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210

<210> SEQ ID NO 264
<211> LENGTH: 106
<212> TYPE: PRT
<213> ORGANISM: Artificial Sequence
<220> FEATURE:
<223> OTHER INFORMATION: A17h4 VL domain

<400> SEQUENCE: 264

Asp Ile Gln Met Thr Gln Ser Pro Ser Thr Leu Ser Ala Ser Val Gly
1               5                   10                  15

Asp Arg Val Thr Ile Thr Cys Ser Pro Ser Ser Ser Val Gly Tyr Met
            20                  25                  30

His Trp Tyr Gln Gln Lys Pro Gly Lys Ala Pro Lys Leu Leu Ile Tyr
        35                  40                  45

Asp Thr Tyr Tyr Leu Ala Ser Gly Val Pro Ser Arg Phe Ser Gly Ser
    50                  55                  60

Gly Ser Gly Thr Glu Phe Thr Leu Thr Ile Ser Ser Leu Gln Pro Asp
65                  70                  75                  80

Asp Phe Ala Thr Tyr Tyr Cys Phe Gln Gly Ser Gly Tyr Pro Phe Thr
                85                  90                  95

Phe Gly Gly Gly Thr Lys Val Glu Ile Lys
            100                 105

<210> SEQ ID NO 265
<211> LENGTH: 10
<212> TYPE: PRT
<213> ORGANISM: Artificial Sequence
<220> FEATURE:
<223> OTHER INFORMATION: A17h4 VL CDR1

<400> SEQUENCE: 265

Ser Pro Ser Ser Ser Val Gly Tyr Met His
1               5                   10
```

```
<210> SEQ ID NO 266
<211> LENGTH: 7
<212> TYPE: PRT
<213> ORGANISM: Artificial Sequence
<220> FEATURE:
<223> OTHER INFORMATION: A17h4 VL CDR2

<400> SEQUENCE: 266

Asp Thr Tyr Tyr Leu Ala Ser
1               5

<210> SEQ ID NO 267
<211> LENGTH: 18
<212> TYPE: PRT
<213> ORGANISM: Artificial Sequence
<220> FEATURE:
<223> OTHER INFORMATION: Linker

<400> SEQUENCE: 267

Gly Gly Ser Ser Arg Ser Ser Ser Gly Gly Gly Ser Gly Gly
1               5                   10                  15

Gly Gly

<210> SEQ ID NO 268
<211> LENGTH: 15
<212> TYPE: PRT
<213> ORGANISM: Artificial Sequence
<220> FEATURE:
<223> OTHER INFORMATION: Linker

<400> SEQUENCE: 268

Gly Ser Gly Arg Ser Gly Gly Gly Ser Gly Gly Gly Gly Ser
1               5                   10                  15

<210> SEQ ID NO 269
<211> LENGTH: 14
<212> TYPE: PRT
<213> ORGANISM: Artificial Sequence
<220> FEATURE:
<223> OTHER INFORMATION: Linker

<400> SEQUENCE: 269

Glu Gly Lys Ser Ser Gly Ser Gly Ser Glu Ser Lys Ser Thr
1               5                   10

<210> SEQ ID NO 270
<211> LENGTH: 15
<212> TYPE: PRT
<213> ORGANISM: Artificial Sequence
<220> FEATURE:
<223> OTHER INFORMATION: Linker

<400> SEQUENCE: 270

Glu Gly Lys Ser Ser Gly Ser Gly Ser Glu Ser Lys Ser Thr Gln
1               5                   10                  15

<210> SEQ ID NO 271
<211> LENGTH: 14
<212> TYPE: PRT
<213> ORGANISM: Artificial Sequence
<220> FEATURE:
<223> OTHER INFORMATION: Linker

<400> SEQUENCE: 271

Glu Gly Lys Ser Ser Gly Ser Gly Ser Glu Ser Lys Val Asp
1               5                   10
```

<210> SEQ ID NO 272
<211> LENGTH: 14
<212> TYPE: PRT
<213> ORGANISM: Artificial Sequence
<220> FEATURE:
<223> OTHER INFORMATION: Linker

<400> SEQUENCE: 272

Gly Ser Thr Ser Gly Ser Gly Lys Ser Ser Glu Gly Lys Gly
 1               5                  10

<210> SEQ ID NO 273
<211> LENGTH: 18
<212> TYPE: PRT
<213> ORGANISM: Artificial Sequence
<220> FEATURE:
<223> OTHER INFORMATION: Linker

<400> SEQUENCE: 273

Lys Glu Ser Gly Ser Val Ser Ser Glu Gln Leu Ala Gln Phe Arg Ser
 1               5                  10                  15

Leu Asp

<210> SEQ ID NO 274
<211> LENGTH: 16
<212> TYPE: PRT
<213> ORGANISM: Artificial Sequence
<220> FEATURE:
<223> OTHER INFORMATION: Linker

<400> SEQUENCE: 274

Glu Ser Gly Ser Val Ser Ser Glu Glu Leu Ala Phe Arg Ser Leu Asp
 1               5                  10                  15

<210> SEQ ID NO 275
<211> LENGTH: 298
<212> TYPE: PRT
<213> ORGANISM: Human respiratory syncytial virus

<400> SEQUENCE: 275

Met Ser Lys Thr Lys Asp Gln Arg Thr Ala Lys Thr Leu Glu Arg Thr
 1               5                  10                  15

Trp Asp Thr Leu Asn His Leu Leu Phe Ile Ser Ser Cys Leu Tyr Lys
                20                  25                  30

Leu Asn Leu Lys Ser Ile Ala Gln Ile Thr Leu Ser Ile Leu Ala Met
            35                  40                  45

Ile Ile Ser Thr Ser Leu Ile Ile Ala Ala Ile Ile Phe Ile Ala Ser
        50                  55                  60

Ala Asn His Lys Val Thr Leu Thr Thr Ala Ile Ile Gln Asp Ala Thr
 65                 70                  75                  80

Asn Gln Ile Lys Asn Thr Thr Pro Thr Tyr Leu Thr Gln Asn Pro Gln
                85                  90                  95

Leu Gly Ile Ser Phe Ser Asn Leu Ser Glu Thr Thr Ser Gln Pro Ile
            100                 105                 110

Thr Ile Leu Ala Ser Thr Thr Pro Ser Ala Glu Ser Thr Pro Gln Ser
        115                 120                 125

Thr Thr Val Lys Thr Lys Asn Thr Thr Thr Thr Gln Ile Gln Pro Ser
    130                 135                 140

Lys Ser Thr Thr Lys Gln Arg Gln Asn Lys Pro Gln Asn Lys Pro Asn
145                 150                 155                 160

```
Asn Asp Phe His Phe Glu Val Phe Asn Val Pro Cys Ser Ile Cys
            165                 170                 175

Ser Asn Asn Pro Thr Cys Trp Ala Ile Cys Lys Arg Ile Pro Asn Lys
        180                 185                 190

Lys Pro Gly Lys Lys Thr Thr Thr Lys Pro Thr Lys Lys Pro Thr Ile
            195                 200                 205

Lys Thr Thr Lys Lys Asp Leu Lys Pro Gln Thr Thr Lys Ser Lys Glu
        210                 215                 220

Val Leu Thr Thr Lys Pro Thr Glu Lys Pro Thr Ile Asn Thr Thr Lys
225                 230                 235                 240

Thr Asn Ile Arg Thr Thr Leu Leu Ile Ser Asn Thr Thr Gly Asn Pro
                245                 250                 255

Glu His Thr Ser Gln Lys Glu Thr Leu His Ser Thr Thr Ser Glu Gly
            260                 265                 270

Asn Pro Ser Pro Ser Gln Val Tyr Thr Thr Ser Glu Tyr Leu Ser Gln
        275                 280                 285

Ser Leu Ser Pro Ser Asn Thr Thr Tyr Tyr
    290                 295
```

<210> SEQ ID NO 276
<211> LENGTH: 2165
<212> TYPE: PRT
<213> ORGANISM: Human respiratory syncytial virus

<400> SEQUENCE: 276

```
Met Asp Pro Ile Ile Asn Gly Asn Ser Ala Asn Val Tyr Leu Thr Asp
  1               5                  10                  15

Ser Tyr Leu Lys Gly Val Ile Ser Phe Ser Glu Cys Asn Ala Leu Gly
            20                  25                  30

Ser Tyr Ile Phe Asn Gly Pro Tyr Leu Lys Asn Asp Tyr Thr Asn Leu
        35                  40                  45

Ile Ser Arg Gln Asn Pro Leu Ile Glu His Met Asn Leu Lys Lys Leu
    50                  55                  60

Asn Ile Thr Gln Ser Leu Ile Ser Lys Tyr His Lys Gly Glu Ile Lys
65                  70                  75                  80

Leu Glu Glu Pro Thr Tyr Phe Gln Ser Leu Leu Met Thr Tyr Lys Ser
                85                  90                  95

Met Thr Ser Ser Glu Gln Ile Ala Thr Thr Asn Leu Leu Lys Lys Ile
            100                 105                 110

Ile Arg Arg Ala Ile Glu Ile Ser Asp Val Lys Val Tyr Ala Ile Leu
        115                 120                 125

Asn Lys Leu Gly Leu Lys Glu Lys Asp Lys Ile Lys Ser Asn Asn Gly
    130                 135                 140

Gln Asp Glu Asp Asn Ser Val Ile Thr Thr Ile Ile Lys Asp Asp Ile
145                 150                 155                 160

Leu Ser Ala Val Lys Asp Asn Gln Ser His Leu Lys Ala Asp Lys Asn
                165                 170                 175

His Ser Thr Lys Gln Lys Asp Thr Ile Lys Thr Thr Leu Leu Lys Lys
            180                 185                 190

Leu Met Cys Ser Met Gln His Pro Pro Ser Trp Leu Ile His Trp Phe
        195                 200                 205

Asn Leu Tyr Thr Lys Leu Asn Asn Ile Leu Thr Gln Tyr Arg Ser Asn
    210                 215                 220

Glu Val Lys Asn His Gly Phe Thr Leu Ile Asp Asn Gln Thr Leu Ser
225                 230                 235                 240
```

```
Gly Phe Gln Phe Ile Leu Asn Gln Tyr Gly Cys Ile Val Tyr His Lys
                245                 250                 255

Glu Leu Lys Arg Ile Thr Val Thr Thr Tyr Asn Gln Phe Leu Thr Trp
            260                 265                 270

Lys Asp Ile Ser Leu Ser Arg Leu Asn Val Cys Leu Ile Thr Trp Ile
        275                 280                 285

Ser Asn Cys Leu Asn Thr Leu Asn Lys Ser Leu Gly Leu Arg Cys Gly
290                 295                 300

Phe Asn Asn Val Ile Leu Thr Gln Leu Phe Leu Tyr Gly Asp Cys Ile
305                 310                 315                 320

Leu Lys Leu Phe His Asn Glu Gly Phe Tyr Ile Ile Lys Glu Val Glu
                325                 330                 335

Gly Phe Ile Met Ser Leu Ile Leu Asn Ile Thr Glu Glu Asp Gln Phe
                340                 345                 350

Arg Lys Arg Phe Tyr Asn Ser Met Leu Asn Asn Ile Thr Asp Ala Ala
            355                 360                 365

Asn Lys Ala Gln Lys Asn Leu Leu Ser Arg Val Cys His Thr Leu Leu
        370                 375                 380

Asp Lys Thr Val Ser Asp Asn Ile Ile Asn Gly Arg Trp Ile Ile Leu
385                 390                 395                 400

Leu Ser Lys Phe Leu Lys Leu Ile Lys Leu Ala Gly Asp Asn Asn Leu
                405                 410                 415

Asn Asn Leu Ser Glu Leu Tyr Phe Leu Phe Arg Ile Phe Gly His Pro
                420                 425                 430

Met Val Asp Glu Arg Gln Ala Met Asp Ala Val Lys Ile Asn Cys Asn
            435                 440                 445

Glu Thr Lys Phe Tyr Leu Leu Ser Ser Leu Ser Met Leu Arg Gly Ala
        450                 455                 460

Phe Ile Tyr Arg Ile Ile Lys Gly Phe Val Asn Asn Tyr Asn Arg Trp
465                 470                 475                 480

Pro Thr Leu Arg Asn Ala Ile Val Leu Pro Leu Arg Trp Leu Thr Tyr
                485                 490                 495

Tyr Lys Leu Asn Thr Tyr Pro Ser Leu Leu Glu Leu Thr Glu Arg Asp
            500                 505                 510

Leu Ile Val Leu Ser Gly Leu Arg Phe Tyr Arg Glu Phe Arg Leu Pro
        515                 520                 525

Lys Lys Val Asp Leu Glu Met Ile Ile Asn Asp Lys Ala Ile Ser Pro
530                 535                 540

Pro Lys Asn Leu Ile Trp Thr Ser Phe Pro Arg Asn Tyr Met Pro Ser
545                 550                 555                 560

His Ile Gln Asn Tyr Ile Glu His Glu Lys Leu Lys Phe Ser Glu Ser
                565                 570                 575

Asp Lys Ser Arg Arg Val Leu Glu Tyr Tyr Leu Arg Asp Asn Lys Phe
            580                 585                 590

Asn Glu Cys Asp Leu Tyr Asn Cys Val Val Asn Gln Ser Tyr Leu Asn
        595                 600                 605

Asn Pro Asn His Val Val Ser Leu Thr Gly Lys Glu Arg Glu Leu Ser
610                 615                 620

Val Gly Arg Met Phe Ala Met Gln Pro Gly Met Phe Arg Gln Val Gln
625                 630                 635                 640

Ile Leu Ala Glu Lys Met Ile Ala Glu Asn Ile Leu Gln Phe Phe Pro
                645                 650                 655
```

-continued

Glu Ser Leu Thr Arg Tyr Gly Asp Leu Glu Leu Gln Lys Ile Leu Glu
            660                 665                 670

Leu Lys Ala Gly Ile Ser Asn Lys Ser Asn Arg Tyr Asn Asp Asn Tyr
        675                 680                 685

Asn Asn Tyr Ile Ser Lys Cys Ser Ile Ile Thr Asp Leu Ser Lys Phe
    690                 695                 700

Asn Gln Ala Phe Arg Tyr Glu Thr Ser Cys Ile Cys Ser Asp Val Leu
705                 710                 715                 720

Asp Glu Leu His Gly Val Gln Ser Leu Phe Ser Trp Leu His Leu Thr
                725                 730                 735

Ile Pro His Val Thr Ile Ile Cys Thr Tyr Arg His Ala Pro Pro Tyr
            740                 745                 750

Ile Gly Asp His Ile Val Asp Leu Asn Asn Val Asp Glu Gln Ser Gly
        755                 760                 765

Leu Tyr Arg Tyr His Met Gly Gly Ile Glu Gly Trp Cys Gln Lys Leu
    770                 775                 780

Trp Thr Ile Glu Ala Ile Ser Leu Leu Asp Leu Ile Ser Leu Lys Gly
785                 790                 795                 800

Lys Phe Ser Ile Thr Ala Leu Ile Asn Gly Asp Asn Gln Ser Ile Asp
                805                 810                 815

Ile Ser Lys Pro Ile Arg Leu Met Glu Gly Gln Thr His Ala Gln Ala
            820                 825                 830

Asp Tyr Leu Leu Ala Leu Asn Ser Leu Lys Leu Leu Tyr Lys Glu Tyr
        835                 840                 845

Ala Gly Ile Gly His Lys Leu Lys Gly Thr Glu Thr Tyr Ile Ser Arg
    850                 855                 860

Asp Met Gln Phe Met Ser Lys Thr Ile Gln His Asn Gly Val Tyr Tyr
865                 870                 875                 880

Pro Ala Ser Ile Lys Lys Val Leu Arg Val Gly Pro Trp Ile Asn Thr
                885                 890                 895

Ile Leu Asp Asp Phe Lys Val Ser Leu Glu Ser Ile Gly Ser Leu Thr
            900                 905                 910

Gln Glu Leu Glu Tyr Arg Gly Glu Ser Leu Leu Cys Ser Leu Ile Phe
        915                 920                 925

Arg Asn Val Trp Leu Tyr Asn Gln Ile Ala Leu Gln Leu Lys Asn His
    930                 935                 940

Ala Leu Cys Asn Asn Lys Leu Tyr Leu Asp Ile Leu Lys Val Leu Lys
945                 950                 955                 960

His Leu Lys Thr Phe Phe Asn Leu Asp Asn Ile Asp Thr Ala Leu Thr
                965                 970                 975

Leu Tyr Met Asn Leu Pro Met Leu Phe Gly Gly Gly Asp Pro Asn Leu
            980                 985                 990

Leu Tyr Arg Ser Phe Tyr Arg Arg Thr Pro Asp Phe Leu Thr Glu Ala
        995                 1000                1005

Ile Val His Ser Val Phe Ile Leu Ser Tyr Tyr Thr Asn His Asp Leu
    1010                1015                1020

Lys Asp Lys Leu Gln Asp Leu Ser Asp Arg Leu Asn Lys Phe Leu
1025                1030                1035                1040

Thr Cys Ile Ile Thr Phe Asp Lys Asn Pro Asn Ala Glu Phe Val Thr
                1045                1050                1055

Leu Met Arg Asp Pro Gln Ala Leu Gly Ser Glu Arg Gln Ala Lys Ile
            1060                1065                1070

Thr Ser Glu Ile Asn Arg Leu Ala Val Thr Glu Val Leu Ser Thr Ala

```
             1075                1080                1085
Pro Asn Lys Ile Phe Ser Lys Ser Ala Gln His Tyr Thr Thr Thr Glu
             1090                1095                1100
Ile Asp Leu Asn Asp Ile Met Gln Asn Ile Glu Pro Thr Tyr Pro His
1105                1110                1115                1120
Gly Leu Arg Val Val Tyr Glu Ser Leu Pro Phe Tyr Lys Ala Glu Lys
                 1125                1130                1135
Ile Val Asn Leu Ile Ser Gly Thr Lys Ser Ile Thr Asn Ile Leu Glu
                 1140                1145                1150
Lys Thr Ser Ala Ile Asp Leu Thr Asp Ile Asp Arg Ala Thr Glu Met
                 1155                1160                1165
Met Arg Lys Asn Ile Thr Leu Leu Ile Arg Ile Leu Pro Leu Asp Cys
        1170                1175                1180
Asn Arg Asp Lys Arg Glu Ile Leu Ser Met Glu Asn Leu Ser Ile Thr
1185                1190                1195                1200
Glu Leu Ser Lys Tyr Val Arg Glu Arg Ser Trp Ser Leu Ser Asn Ile
                 1205                1210                1215
Val Gly Val Thr Ser Pro Ser Ile Met Tyr Thr Met Asp Ile Lys Tyr
            1220                1225                1230
Thr Thr Ser Thr Ile Ser Ser Gly Ile Ile Ile Glu Lys Tyr Asn Val
            1235                1240                1245
Asn Ser Leu Thr Arg Gly Glu Arg Gly Pro Thr Lys Pro Trp Val Gly
        1250                1255                1260
Ser Ser Thr Gln Glu Lys Lys Thr Met Pro Val Tyr Asn Arg Gln Val
1265                1270                1275                1280
Leu Thr Lys Lys Gln Arg Asp Gln Ile Asp Leu Leu Ala Lys Leu Asp
                 1285                1290                1295
Trp Val Tyr Ala Ser Ile Asp Asn Lys Asp Glu Phe Met Glu Glu Leu
        1300                1305                1310
Ser Ile Gly Thr Leu Gly Leu Thr Tyr Glu Lys Ala Lys Lys Leu Phe
            1315                1320                1325
Pro Gln Tyr Leu Ser Val Asn Tyr Leu His Arg Leu Thr Val Ser Ser
        1330                1335                1340
Arg Pro Cys Glu Phe Pro Ala Ser Ile Pro Ala Tyr Arg Thr Thr Asn
1345                1350                1355                1360
Tyr His Phe Asp Thr Ser Pro Ile Asn Arg Ile Leu Thr Glu Lys Tyr
                 1365                1370                1375
Gly Asp Glu Asp Ile Asp Ile Val Phe Gln Asn Cys Ile Ser Phe Gly
            1380                1385                1390
Leu Ser Leu Met Ser Val Val Glu Gln Phe Thr Asn Val Cys Pro Asn
            1395                1400                1405
Arg Ile Ile Leu Ile Pro Lys Leu Asn Glu Ile His Leu Met Lys Pro
        1410                1415                1420
Pro Ile Phe Thr Gly Asp Val Asp Ile His Lys Leu Lys Gln Val Ile
1425                1430                1435                1440
Gln Lys Gln His Met Phe Leu Pro Asp Lys Ile Ser Leu Thr Gln Tyr
                 1445                1450                1455
Val Glu Leu Phe Leu Ser Asn Lys Thr Leu Lys Ser Gly Ser His Val
            1460                1465                1470
Asn Ser Asn Leu Ile Leu Ala His Lys Ile Ser Asp Tyr Phe His Asn
        1475                1480                1485
Thr Tyr Ile Leu Ser Thr Asn Leu Ala Gly His Trp Ile Leu Ile Ile
        1490                1495                1500
```

```
Gln Leu Met Lys Asp Ser Lys Gly Ile Phe Glu Lys Asp Trp Gly Glu
1505                1510                1515                1520

Gly Tyr Ile Thr Asp His Met Phe Ile Asn Leu Lys Val Phe Phe Asn
            1525                1530                1535

Ala Tyr Lys Thr Tyr Leu Leu Cys Phe His Lys Gly Tyr Gly Lys Ala
            1540                1545                1550

Lys Leu Glu Cys Asp Met Asn Thr Ser Asp Leu Leu Cys Val Leu Glu
            1555                1560                1565

Leu Ile Asp Ser Ser Tyr Trp Lys Ser Met Ser Lys Val Phe Leu Glu
            1570                1575                1580

Gln Lys Val Ile Lys Tyr Ile Leu Ser Gln Asp Ala Ser Leu His Arg
1585                1590                1595                1600

Val Lys Gly Cys His Ser Phe Lys Leu Trp Phe Leu Lys Arg Leu Asn
                1605                1610                1615

Val Ala Glu Phe Thr Val Cys Pro Trp Val Val Asn Ile Asp Tyr His
                1620                1625                1630

Pro Thr His Met Lys Ala Ile Leu Thr Tyr Ile Asp Leu Val Arg Met
                1635                1640                1645

Gly Leu Ile Asn Ile Asp Arg Ile His Ile Lys Asn Lys His Lys Phe
                1650                1655                1660

Asn Asp Glu Phe Tyr Thr Ser Asn Leu Phe Tyr Ile Asn Tyr Asn Phe
1665                1670                1675                1680

Ser Asp Asn Thr His Leu Leu Thr Lys His Ile Arg Ile Ala Asn Ser
                1685                1690                1695

Glu Leu Glu Asn Asn Tyr Asn Lys Leu Tyr His Pro Thr Pro Glu Thr
                1700                1705                1710

Leu Glu Asn Ile Leu Ala Asn Pro Ile Lys Ser Asn Asp Lys Lys Thr
                1715                1720                1725

Leu Asn Asp Tyr Cys Ile Gly Lys Asn Val Asp Ser Ile Met Leu Pro
                1730                1735                1740

Leu Leu Ser Asn Lys Lys Leu Ile Lys Ser Ser Ala Met Ile Arg Thr
1745                1750                1755                1760

Asn Tyr Ser Lys Gln Asp Leu Tyr Asn Leu Phe Pro Met Val Val Ile
                1765                1770                1775

Asp Arg Ile Ile Asp His Ser Gly Asn Thr Ala Lys Ser Asn Gln Leu
                1780                1785                1790

Tyr Thr Thr Thr Ser His Gln Ile Ser Leu Val His Asn Ser Thr Ser
                1795                1800                1805

Leu Tyr Cys Met Leu Pro Trp His His Ile Asn Arg Phe Asn Phe Val
                1810                1815                1820

Phe Ser Ser Thr Gly Cys Lys Ile Ser Ile Glu Tyr Ile Leu Lys Asp
1825                1830                1835                1840

Leu Lys Ile Lys Asp Pro Asn Cys Ile Ala Phe Ile Gly Glu Gly Ala
                1845                1850                1855

Gly Asn Leu Leu Leu Arg Thr Val Val Glu Leu His Pro Asp Ile Arg
                1860                1865                1870

Tyr Ile Tyr Arg Ser Leu Lys Asp Cys Asn Asp His Ser Leu Pro Ile
                1875                1880                1885

Glu Phe Leu Arg Leu Tyr Asn Gly His Ile Asn Ile Asp Tyr Gly Glu
                1890                1895                1900

Asn Leu Thr Ile Pro Ala Thr Asp Ala Thr Asn Asn Ile His Trp Ser
1905                1910                1915                1920
```

```
Tyr Leu His Ile Lys Phe Ala Glu Pro Ile Ser Leu Phe Val Cys Asp
            1925                1930                1935

Ala Glu Leu Ser Val Thr Val Asn Trp Ser Lys Ile Ile Ile Glu Trp
        1940                1945                1950

Ser Lys His Val Arg Lys Cys Lys Tyr Cys Ser Ser Val Asn Lys Cys
        1955                1960                1965

Met Leu Ile Val Lys Tyr His Ala Gln Asp Asp Ile Asp Phe Lys Leu
        1970                1975                1980

Asp Asn Ile Thr Ile Leu Lys Thr Tyr Val Cys Leu Gly Ser Lys Leu
1985                1990                1995                2000

Lys Gly Ser Glu Val Tyr Leu Val Leu Thr Ile Gly Pro Ala Asn Ile
            2005                2010                2015

Phe Pro Val Phe Asn Val Val Gln Asn Ala Lys Leu Ile Leu Ser Arg
            2020                2025                2030

Thr Lys Asn Phe Ile Met Pro Lys Lys Ala Asp Lys Glu Ser Ile Asp
            2035                2040                2045

Ala Asn Ile Lys Ser Leu Ile Pro Phe Leu Cys Tyr Pro Ile Thr Lys
            2050                2055                2060

Lys Gly Ile Asn Thr Ala Leu Ser Lys Leu Lys Ser Val Val Ser Gly
2065                2070                2075                2080

Asp Ile Leu Ser Tyr Ser Ile Ala Gly Arg Asn Glu Val Phe Ser Asn
            2085                2090                2095

Lys Leu Ile Asn His Lys His Met Asn Ile Leu Lys Trp Phe Asn His
            2100                2105                2110

Val Leu Asn Phe Arg Ser Thr Glu Leu Asn Tyr Asn His Leu Tyr Met
            2115                2120                2125

Val Glu Ser Thr Tyr Pro Tyr Leu Ser Glu Leu Leu Asn Ser Leu Thr
            2130                2135                2140

Thr Asn Glu Leu Lys Lys Leu Ile Lys Ile Thr Gly Ser Leu Leu Tyr
2145                2150                2155                2160

Asn Phe His Asn Glu
            2165

<210> SEQ ID NO 277
<211> LENGTH: 391
<212> TYPE: PRT
<213> ORGANISM: Human respiratory syncytial virus

<400> SEQUENCE: 277

Met Ala Leu Ser Lys Val Lys Leu Asn Asp Thr Leu Asn Lys Asp Gln
1               5                   10                  15

Leu Leu Ser Ser Ser Lys Tyr Thr Ile Gln Arg Ser Thr Gly Asp Asn
            20                  25                  30

Ile Asp Thr Pro Asn Tyr Asp Val Gln Lys His Leu Asn Lys Leu Cys
        35                  40                  45

Gly Met Leu Leu Ile Thr Glu Asp Ala Asn His Lys Phe Thr Gly Leu
    50                  55                  60

Ile Gly Met Leu Tyr Ala Met Ser Arg Leu Gly Arg Glu Asp Thr Ile
65                  70                  75                  80

Lys Ile Leu Lys Asp Ala Gly Tyr His Val Lys Ala Asn Gly Val Asp
                85                  90                  95

Ile Thr Thr Tyr Arg Gln Asp Ile Asn Gly Lys Glu Met Lys Phe Glu
            100                 105                 110

Val Leu Thr Leu Ser Ser Leu Thr Ser Glu Ile Gln Val Asn Ile Glu
        115                 120                 125
```

-continued

```
Ile Glu Ser Arg Lys Ser Tyr Lys Lys Leu Leu Lys Glu Met Gly Glu
            130                 135                 140

Val Ala Pro Glu Tyr Arg His Asp Ser Pro Asp Cys Gly Met Ile Ile
145                 150                 155                 160

Leu Cys Ile Ala Ala Leu Val Ile Thr Lys Leu Ala Ala Gly Asp Arg
                165                 170                 175

Ser Gly Leu Thr Ala Val Ile Arg Arg Ala Asn Asn Val Leu Lys Asn
                180                 185                 190

Glu Ile Lys Arg Tyr Lys Gly Leu Ile Pro Lys Asp Ile Ala Asn Ser
            195                 200                 205

Phe Tyr Glu Val Phe Glu Lys His Pro His Leu Ile Asp Val Phe Val
210                 215                 220

His Phe Gly Ile Ala Gln Ser Ser Thr Arg Gly Gly Ser Arg Val Glu
225                 230                 235                 240

Gly Ile Phe Ala Gly Leu Phe Met Asn Ala Tyr Gly Ser Gly Gln Val
                245                 250                 255

Met Leu Arg Trp Gly Val Leu Ala Lys Ser Val Lys Asn Ile Met Leu
            260                 265                 270

Gly His Ala Ser Val Gln Ala Glu Met Glu Gln Val Val Glu Val Tyr
            275                 280                 285

Glu Tyr Ala Gln Lys Leu Gly Gly Glu Ala Gly Phe Tyr His Ile Leu
290                 295                 300

Asn Asn Pro Lys Ala Ser Leu Leu Ser Leu Thr Gln Phe Pro Asn Phe
305                 310                 315                 320

Ser Ser Val Val Leu Gly Asn Ala Ala Gly Leu Gly Ile Met Gly Glu
                325                 330                 335

Tyr Arg Gly Thr Pro Arg Asn Gln Asp Leu Tyr Asp Ala Ala Lys Ala
            340                 345                 350

Tyr Ala Glu Gln Leu Lys Glu Asn Gly Val Ile Asn Tyr Ser Val Leu
            355                 360                 365

Asp Leu Thr Ala Glu Glu Leu Glu Ala Ile Lys His Gln Leu Asn Pro
370                 375                 380

Lys Glu Asp Asp Val Glu Leu
385                 390

<210> SEQ ID NO 278
<211> LENGTH: 391
<212> TYPE: PRT
<213> ORGANISM: Human respiratory syncytial virus

<400> SEQUENCE: 278

Met Ala Leu Ser Lys Val Lys Leu Asn Asp Thr Leu Asn Lys Asp Gln
1               5                   10                  15

Leu Leu Ser Ser Ser Lys Tyr Thr Ile Gln Arg Ser Thr Gly Asp Ser
                20                  25                  30

Ile Asp Thr Pro Asn Tyr Asp Val Gln Lys His Ile Asn Lys Leu Cys
            35                  40                  45

Gly Met Leu Leu Ile Thr Glu Asp Ala Asn His Lys Phe Thr Gly Leu
        50                  55                  60

Ile Gly Met Leu Tyr Ala Met Ser Arg Leu Gly Arg Glu Asp Thr Ile
65                  70                  75                  80

Lys Ile Leu Arg Asp Ala Gly Tyr His Val Lys Ala Asn Gly Val Asp
                85                  90                  95

Val Thr Thr His Arg Gln Asp Ile Asn Gly Lys Glu Met Lys Phe Glu
```

```
            100                 105                 110
Val Leu Thr Leu Ser Ser Leu Thr Thr Glu Ile Gln Ile Asn Ile Glu
            115                 120                 125

Ile Glu Ser Arg Lys Ser Tyr Lys Lys Met Leu Lys Glu Met Gly Glu
            130                 135                 140

Val Ala Pro Glu Tyr Arg His Asp Ser Pro Asp Cys Gly Met Ile Ile
145                 150                 155                 160

Leu Cys Ile Ala Ala Leu Val Ile Thr Lys Leu Ala Ala Gly Asp Arg
                165                 170                 175

Ser Gly Leu Thr Ala Val Ile Arg Arg Ala Asn Asn Val Leu Lys Asn
                180                 185                 190

Glu Met Lys Arg Tyr Lys Gly Leu Leu Pro Lys Asp Ile Ala Asn Ser
                195                 200                 205

Phe Tyr Glu Val Phe Glu Lys Tyr Pro His Phe Ile Asp Val Phe Val
210                 215                 220

His Phe Gly Ile Ala Gln Ser Ser Thr Arg Gly Gly Ser Arg Val Glu
225                 230                 235                 240

Gly Ile Phe Ala Gly Leu Phe Met Asn Ala Tyr Gly Ala Gly Gln Val
                245                 250                 255

Met Leu Arg Trp Gly Val Leu Ala Lys Ser Val Lys Asn Ile Met Leu
                260                 265                 270

Gly His Ala Ser Val Gln Ala Glu Met Glu Gln Val Val Glu Val Tyr
                275                 280                 285

Glu Tyr Ala Gln Lys Leu Gly Gly Glu Ala Gly Phe Tyr His Ile Leu
            290                 295                 300

Asn Asn Pro Lys Ala Ser Leu Leu Ser Leu Thr Gln Phe Pro His Phe
305                 310                 315                 320

Ser Ser Val Val Leu Gly Asn Ala Ala Gly Leu Gly Ile Met Gly Glu
                325                 330                 335

Tyr Arg Gly Thr Pro Arg Asn Gln Asp Leu Tyr Asp Ala Ala Lys Ala
                340                 345                 350

Tyr Ala Glu Gln Leu Lys Glu Asn Gly Val Ile Asn Tyr Ser Val Leu
            355                 360                 365

Asp Leu Thr Ala Glu Glu Leu Glu Ala Ile Lys His Gln Leu Asn Pro
        370                 375                 380

Lys Asp Asn Asp Val Glu Leu
385                 390

<210> SEQ ID NO 279
<211> LENGTH: 241
<212> TYPE: PRT
<213> ORGANISM: Human respiratory syncytial virus

<400> SEQUENCE: 279

Met Glu Lys Phe Ala Pro Glu Phe His Gly Glu Asp Ala Asn Asn Arg
1               5                   10                  15

Ala Thr Lys Phe Leu Glu Ser Ile Lys Gly Lys Phe Thr Ser Pro Lys
                20                  25                  30

Asp Pro Lys Lys Lys Asp Ser Ile Ile Ser Val Asn Ser Ile Asp Ile
            35                  40                  45

Glu Val Thr Lys Glu Ser Pro Ile Thr Ser Asn Ser Thr Ile Met Asn
        50                  55                  60

Pro Thr Asn Glu Thr Asp Asp Thr Val Gly Asn Lys Pro Asn Tyr Gln
65                  70                  75                  80
```

```
Arg Lys Pro Leu Val Ser Phe Lys Glu Asp Pro Met Leu Ser Asp Asn
                 85                  90                  95
Pro Phe Ser Lys Leu Tyr Lys Glu Thr Ile Glu Thr Phe Asp Asn Asn
            100                 105                 110
Glu Glu Glu Ser Ser Tyr Ser Tyr Glu Glu Ile Asn Asp Gln Thr Asn
            115                 120                 125
Asp Asn Ile Thr Ala Arg Leu Asp Arg Ile Asp Glu Lys Leu Ser Glu
            130                 135                 140
Ile Leu Gly Met Leu His Thr Leu Val Val Ala Ser Ala Gly Pro Thr
145                 150                 155                 160
Ser Ala Arg Asp Gly Ile Arg Asp Ala Met Val Gly Leu Arg Glu Glu
                165                 170                 175
Met Ile Glu Lys Ile Arg Thr Glu Ala Leu Met Thr Asn Asn Arg Leu
            180                 185                 190
Glu Ala Met Ala Arg Leu Arg Asn Glu Glu Ser Glu Lys Met Ala Lys
            195                 200                 205
Asp Thr Ser Asp Glu Val Ser Leu Asn Pro Thr Ser Glu Lys Leu Asn
            210                 215                 220
Asn Leu Leu Glu Gly Asn Asp Ser Asp Asp Leu Ser Leu Glu Asp
225                 230                 235                 240
Phe
```

<210> SEQ ID NO 280
<211> LENGTH: 256
<212> TYPE: PRT
<213> ORGANISM: Human respiratory synctial virus

<400> SEQUENCE: 280

```
Met Glu Thr Tyr Val Asn Lys Leu His Glu Gly Ser Thr Tyr Thr Ala
1               5                   10                  15
Ala Val Gln Tyr Asn Val Leu Glu Lys Asp Asp Pro Ala Ser Leu
            20                  25                  30
Thr Ile Trp Val Pro Met Phe Gln Ser Ser Met Pro Ala Asp Leu Leu
            35                  40                  45
Ile Lys Glu Leu Ala Asn Val Asn Ile Leu Val Lys Gln Ile Ser Thr
50                  55                  60
Pro Lys Gly Pro Ser Leu Arg Val Met Ile Asn Ser Arg Ser Ala Val
65                  70                  75                  80
Leu Ala Gln Met Pro Ser Lys Phe Thr Ile Cys Ala Asn Val Ser Leu
                85                  90                  95
Asp Glu Arg Ser Lys Leu Ala Tyr Asp Val Thr Thr Pro Cys Glu Ile
            100                 105                 110
Lys Ala Cys Ser Leu Thr Cys Leu Lys Ser Lys Asn Met Leu Thr Thr
            115                 120                 125
Val Lys Asp Leu Thr Met Lys Thr Leu Asn Pro Thr His Asp Ile Ile
130                 135                 140
Ala Leu Cys Glu Phe Glu Asn Ile Val Thr Ser Lys Lys Val Ile Ile
145                 150                 155                 160
Pro Thr Tyr Leu Arg Ser Ile Ser Val Arg Asn Lys Asp Leu Asn Thr
                165                 170                 175
Leu Glu Asn Ile Thr Thr Thr Glu Phe Lys Asn Ala Ile Thr Asn Ala
            180                 185                 190
Lys Ile Ile Pro Tyr Ser Gly Leu Leu Leu Val Ile Thr Val Thr Asp
            195                 200                 205
```

Asn Lys Gly Ala Phe Lys Tyr Ile Lys Pro Gln Ser Gln Phe Ile Val
210                 215                 220

Asp Leu Gly Ala Tyr Leu Glu Lys Glu Ser Ile Tyr Tyr Val Thr Thr
225                 230                 235                 240

Asn Trp Lys His Thr Ala Thr Arg Phe Ala Ile Lys Pro Met Glu Asp
                245                 250                 255

<210> SEQ ID NO 281
<211> LENGTH: 64
<212> TYPE: PRT
<213> ORGANISM: Human respiratory syncytial virus

<400> SEQUENCE: 281

Met Glu Asn Thr Ser Ile Thr Ile Glu Phe Ser Ser Lys Phe Trp Pro
1               5                   10                  15

Tyr Phe Thr Leu Ile His Met Ile Thr Thr Ile Ile Ser Leu Leu Ile
                20                  25                  30

Ile Ile Ser Ile Met Ile Ala Ile Leu Asn Lys Leu Cys Glu Tyr Asn
                35                  40                  45

Ala Phe His Asn Lys Thr Phe Glu Leu Pro Arg Ala Arg Ile Asn Thr
50                  55                  60

<210> SEQ ID NO 282
<211> LENGTH: 574
<212> TYPE: PRT
<213> ORGANISM: Human respiratory syncytial virus
<220> FEATURE:

<400> SEQUENCE: 282

Met Glu Leu Pro Ile Leu Lys Ala Asn Ala Ile Thr Thr Ile Leu Ala
1               5                   10                  15

Ala Val Thr Leu Cys Phe Val Ser Ser Gln Asn Ile Thr Glu Glu Phe
                20                  25                  30

Tyr Gln Ser Thr Cys Ser Ala Val Ser Lys Gly Tyr Leu Ser Ala Leu
                35                  40                  45

Arg Thr Gly Trp Tyr Thr Ser Val Ile Thr Ile Glu Leu Ser Asn Ile
50                  55                  60

Lys Glu Asn Lys Cys Asn Gly Thr Asp Ala Lys Val Lys Leu Ile Lys
65                  70                  75                  80

Gln Glu Leu Asp Lys Tyr Lys Asn Ala Val Thr Glu Leu Gln Leu Leu
                85                  90                  95

Met Gln Ser Thr Pro Ala Ala Asn Asn Arg Ala Arg Arg Glu Leu Pro
                100                 105                 110

Arg Phe Met Asn Tyr Thr Leu Asn Asn Thr Lys Asn Thr Asn Val Thr
                115                 120                 125

Leu Ser Lys Lys Arg Lys Arg Arg Phe Leu Gly Phe Leu Leu Gly Val
130                 135                 140

Gly Ser Ala Ile Ala Ser Gly Ile Ala Val Ser Lys Val Leu His Leu
145                 150                 155                 160

Glu Gly Glu Val Asn Lys Ile Lys Ser Ala Leu Leu Ser Thr Asn Lys
                165                 170                 175

Ala Val Val Ser Leu Ser Asn Gly Val Ser Val Leu Thr Ser Lys Val
                180                 185                 190

Leu Asp Leu Lys Asn Tyr Ile Asp Lys Gln Leu Leu Pro Ile Val Asn
                195                 200                 205

Lys Gln Ser Cys Ser Ile Ser Asn Ile Glu Thr Val Ile Glu Phe Gln
210                 215                 220

```
Gln Lys Asn Asn Arg Leu Leu Glu Ile Thr Arg Glu Phe Ser Val Asn
225                 230                 235                 240

Ala Gly Val Thr Thr Pro Val Ser Thr Tyr Met Leu Thr Asn Ser Glu
            245                 250                 255

Leu Leu Ser Leu Ile Asn Asp Met Pro Ile Thr Asn Asp Gln Lys Lys
        260                 265                 270

Leu Met Ser Asn Asn Val Gln Ile Val Arg Gln Gln Ser Tyr Ser Ile
    275                 280                 285

Met Ser Ile Ile Lys Glu Glu Val Leu Ala Tyr Val Val Gln Leu Pro
290                 295                 300

Leu Tyr Gly Val Ile Asp Thr Pro Cys Trp Lys Leu His Thr Ser Pro
305                 310                 315                 320

Leu Cys Thr Thr Asn Thr Lys Glu Gly Ser Asn Ile Cys Leu Thr Arg
            325                 330                 335

Thr Asp Arg Gly Trp Tyr Cys Asp Asn Ala Gly Ser Val Ser Phe Phe
        340                 345                 350

Pro Gln Ala Glu Thr Cys Lys Val Gln Ser Asn Arg Val Phe Cys Asp
    355                 360                 365

Thr Met Asn Ser Leu Thr Leu Pro Ser Glu Val Asn Leu Cys Asn Val
370                 375                 380

Asp Ile Phe Asn Pro Lys Tyr Asp Cys Lys Ile Met Thr Ser Lys Thr
385                 390                 395                 400

Asp Val Ser Ser Ser Val Ile Thr Ser Leu Gly Ala Ile Val Ser Cys
            405                 410                 415

Tyr Gly Lys Thr Lys Cys Thr Ala Ser Asn Lys Asn Arg Gly Ile Ile
        420                 425                 430

Lys Thr Phe Ser Asn Gly Cys Asp Tyr Val Ser Asn Lys Gly Val Asp
    435                 440                 445

Thr Val Ser Val Gly Asn Thr Leu Tyr Tyr Val Asn Lys Gln Glu Gly
450                 455                 460

Lys Asn Leu Tyr Val Lys Gly Glu Pro Ile Ile Asn Phe Tyr Asp Pro
465                 470                 475                 480

Leu Val Phe Pro Ser Asp Glu Phe Asp Ala Ser Ile Ser Gln Val Asn
            485                 490                 495

Glu Lys Ile Asn Gln Ser Leu Ala Phe Ile Arg Lys Ser Asp Glu Leu
        500                 505                 510

Leu His Asn Val Asn Ala Gly Lys Ser Thr Thr Asn Ile Met Ile Thr
    515                 520                 525

Thr Ile Ile Ile Val Ile Ile Val Ile Leu Leu Ser Leu Ile Ala Val
530                 535                 540

Gly Leu Leu Leu Tyr Cys Lys Ala Arg Ser Thr Pro Val Thr Leu Ser
545                 550                 555                 560

Lys Asp Gln Leu Ser Gly Ile Asn Asn Ile Ala Phe Ser Ser
            565                 570

<210> SEQ ID NO 283
<211> LENGTH: 83
<212> TYPE: PRT
<213> ORGANISM: Human respiratory syncytial virus

<400> SEQUENCE: 283

Lys Arg Asp Pro Lys Thr Pro Ala Lys Met Leu Asn Lys Glu Thr Thr
1               5                   10                  15

Thr Asn Pro Thr Lys Asn Leu Thr Leu Lys Thr Thr Glu Arg Asp Thr
```

```
                     20                  25                  30

Ser Thr Ser Gln Ser Thr Val Leu Asp Thr Ser Thr Ser Lys His Ile
             35                  40                  45

Ile Leu Gln Gln Ser Leu His Ser Thr Thr Pro Glu Asn Thr Pro Asn
         50                  55                  60

Phe Thr Gln Thr Pro Thr Ala Ser Glu Pro Ser Thr Ser Asn Ser Thr
 65                  70                  75                  80

Gln Lys Thr

<210> SEQ ID NO 284
<211> LENGTH: 21
<212> TYPE: PRT
<213> ORGANISM: Bufo gargarizans
<220> FEATURE:
<223> OTHER INFORMATION: Asian toad Buforin II

<400> SEQUENCE: 284

Thr Arg Ser Ser Arg Ala Gly Leu Gln Phe Pro Val Gly Arg Val His
 1               5                  10                  15

Arg Leu Leu Arg Lys
             20

<210> SEQ ID NO 285
<211> LENGTH: 16
<212> TYPE: PRT
<213> ORGANISM: Homo sapiens
<220> FEATURE:
<223> OTHER INFORMATION: DPV3

<400> SEQUENCE: 285

Arg Lys Lys Arg Arg Arg Glu Ser Arg Lys Lys Arg Arg Arg Glu Ser
 1               5                  10                  15

<210> SEQ ID NO 286
<211> LENGTH: 17
<212> TYPE: PRT
<213> ORGANISM: Homo sapiens
<220> FEATURE:
<223> OTHER INFORMATION: DPV6

<400> SEQUENCE: 286

Gly Arg Pro Arg Glu Ser Gly Lys Lys Arg Lys Arg Lys Arg Leu Lys
 1               5                  10                  15

Pro

<210> SEQ ID NO 287
<211> LENGTH: 15
<212> TYPE: PRT
<213> ORGANISM: Homo sapiens
<220> FEATURE:
<223> OTHER INFORMATION: DPV7

<400> SEQUENCE: 287

Gly Lys Arg Lys Lys Lys Gly Lys Leu Gly Lys Lys Arg Asp Pro
 1               5                  10                  15

<210> SEQ ID NO 288
<211> LENGTH: 17
<212> TYPE: PRT
<213> ORGANISM: Homo sapiens
<220> FEATURE:
<223> OTHER INFORMATION: DPV7b

<400> SEQUENCE: 288
```

```
Gly Lys Arg Lys Lys Lys Gly Lys Leu Gly Lys Lys Arg Pro Arg Ser
 1               5                  10                  15

Arg

<210> SEQ ID NO 289
<211> LENGTH: 18
<212> TYPE: PRT
<213> ORGANISM: Artificial Sequence
<220> FEATURE:
<223> OTHER INFORMATION: DPV3/10

<400> SEQUENCE: 289

Arg Lys Lys Arg Arg Arg Glu Ser Arg Ala Arg Ser Pro Arg
 1               5                  10                  15

His Leu

<210> SEQ ID NO 290
<211> LENGTH: 19
<212> TYPE: PRT
<213> ORGANISM: Homo sapiens
<220> FEATURE:
<223> OTHER INFORMATION: DPV10/6

<400> SEQUENCE: 290

Ser Arg Arg Ala Arg Arg Ser Pro Arg Glu Ser Gly Lys Lys Arg Lys
 1               5                  10                  15

Arg Lys Arg

<210> SEQ ID NO 291
<211> LENGTH: 19
<212> TYPE: PRT
<213> ORGANISM: Homo sapiens
<220> FEATURE:
<223> OTHER INFORMATION: DPV1047

<400> SEQUENCE: 291

Val Lys Arg Gly Leu Lys Leu Arg His Val Arg Pro Arg Val Thr Arg
 1               5                  10                  15

Met Asp Val

<210> SEQ ID NO 292
<211> LENGTH: 18
<212> TYPE: PRT
<213> ORGANISM: Homo sapiens
<220> FEATURE:
<223> OTHER INFORMATION: DPV1048

<400> SEQUENCE: 292

Val Lys Arg Gly Leu Lys Leu Arg His Val Arg Pro Arg Val Thr Arg
 1               5                  10                  15

Asp Val

<210> SEQ ID NO 293
<211> LENGTH: 14
<212> TYPE: PRT
<213> ORGANISM: Homo sapiens
<220> FEATURE:
<223> OTHER INFORMATION: DPV10

<400> SEQUENCE: 293

Ser Arg Arg Ala Arg Arg Ser Pro Arg His Leu Gly Ser Gly
 1               5                  10
```

-continued

<210> SEQ ID NO 294
<211> LENGTH: 16
<212> TYPE: PRT
<213> ORGANISM: Homo sapiens
<220> FEATURE:
<223> OTHER INFORMATION: DPV15

<400> SEQUENCE: 294

Leu Arg Arg Glu Arg Gln Ser Arg Leu Arg Arg Glu Arg Gln Ser Arg
 1               5                  10                  15

<210> SEQ ID NO 295
<211> LENGTH: 22
<212> TYPE: PRT
<213> ORGANISM: Homo sapiens
<220> FEATURE:
<223> OTHER INFORMATION: DPV15b

<400> SEQUENCE: 295

Gly Ala Tyr Asp Leu Arg Arg Arg Glu Arg Gln Ser Arg Leu Arg Arg
 1               5                  10                  15

Arg Glu Arg Gln Ser Arg
             20

<210> SEQ ID NO 296
<211> LENGTH: 30
<212> TYPE: PRT
<213> ORGANISM: Artificial Sequence
<220> FEATURE:
<223> OTHER INFORMATION: GALA

<400> SEQUENCE: 296

Trp Glu Ala Ala Leu Ala Glu Ala Leu Ala Glu Ala Leu Ala Glu His
 1               5                  10                  15

Leu Ala Glu Ala Leu Ala Glu Ala Leu Glu Ala Leu Ala Ala
             20                  25                  30

<210> SEQ ID NO 297
<211> LENGTH: 21
<212> TYPE: PRT
<213> ORGANISM: Homo sapiens
<220> FEATURE:
<223> OTHER INFORMATION: Human fibrinogen beta chain

<400> SEQUENCE: 297

Lys Gly Ser Trp Tyr Ser Met Arg Lys Met Ser Met Lys Ile Arg Pro
 1               5                  10                  15

Phe Phe Pro Gln Gln
             20

<210> SEQ ID NO 298
<211> LENGTH: 20
<212> TYPE: PRT
<213> ORGANISM: Homo sapiens
<220> FEATURE:
<223> OTHER INFORMATION: Human fibrinogen gamma chain precursor

<400> SEQUENCE: 298

Lys Thr Arg Tyr Tyr Ser Met Lys Lys Thr Thr Met Lys Ile Ile Pro
 1               5                  10                  15

Phe Asn Arg Leu
             20

<210> SEQ ID NO 299

```
<211> LENGTH: 20
<212> TYPE: PRT
<213> ORGANISM: Artificial Sequence
<220> FEATURE:
<223> OTHER INFORMATION: Human fibrinogen alpha chain

<400> SEQUENCE: 299

Arg Gly Ala Asp Tyr Ser Leu Arg Ala Val Arg Met Lys Ile Arg Pro
1               5                   10                  15

Leu Val Thr Gln
            20

<210> SEQ ID NO 300
<211> LENGTH: 24
<212> TYPE: PRT
<213> ORGANISM: Homo sapiens
<220> FEATURE:
<223> OTHER INFORMATION: Human hCT (9-32)

<400> SEQUENCE: 300

Leu Gly Thr Tyr Thr Gln Asp Phe Asn Lys Phe His Thr Phe Pro Gln
1               5                   10                  15

Thr Ala Ile Gly Val Gly Ala Pro
            20

<210> SEQ ID NO 301
<211> LENGTH: 12
<212> TYPE: PRT
<213> ORGANISM: Artificial Sequence
<220> FEATURE:
<223> OTHER INFORMATION: HN-1

<400> SEQUENCE: 301

Thr Ser Pro Leu Asn Ile His Asn Gly Gln Lys Leu
1               5                   10

<210> SEQ ID NO 302
<211> LENGTH: 12
<212> TYPE: PRT
<213> ORGANISM: Influenza virus
<220> FEATURE:
<223> OTHER INFORMATION: Influenza virus nucleoprotein (NLS)

<400> SEQUENCE: 302

Asn Ser Ala Ala Phe Glu Asp Leu Arg Val Leu Ser
1               5                   10

<210> SEQ ID NO 303
<211> LENGTH: 30
<212> TYPE: PRT
<213> ORGANISM: Artificial Sequence
<220> FEATURE:
<223> OTHER INFORMATION: KALA

<400> SEQUENCE: 303

Trp Glu Ala Lys Leu Ala Lys Ala Leu Ala Lys Ala Leu Ala Lys His
1               5                   10                  15

Leu Ala Lys Ala Leu Ala Lys Ala Leu Lys Ala Cys Glu Ala
            20                  25                  30

<210> SEQ ID NO 304
<211> LENGTH: 10
<212> TYPE: PRT
<213> ORGANISM: Artificial Sequence
<220> FEATURE:
<223> OTHER INFORMATION: Ku70
```

```
<400> SEQUENCE: 304

Val Pro Met Leu Lys Pro Met Leu Lys Glu
1               5                   10

<210> SEQ ID NO 305
<211> LENGTH: 18
<212> TYPE: PRT
<213> ORGANISM: Artificial Sequence
<220> FEATURE:
<223> OTHER INFORMATION: MAP

<400> SEQUENCE: 305

Lys Leu Ala Leu Lys Leu Ala Leu Lys Ala Leu Lys Ala Ala Leu Lys
1               5                   10                  15

Leu Ala

<210> SEQ ID NO 306
<211> LENGTH: 27
<212> TYPE: PRT
<213> ORGANISM: Artificial Sequence
<220> FEATURE:
<223> OTHER INFORMATION: MPG

<400> SEQUENCE: 306

Gly Ala Leu Phe Leu Gly Phe Leu Gly Ala Ala Gly Ser Thr Met Gly
1               5                   10                  15

Ala Trp Ser Gln Pro Lys Lys Lys Arg Lys Val
            20                  25

<210> SEQ ID NO 307
<211> LENGTH: 16
<212> TYPE: PRT
<213> ORGANISM: Homo sapiens
<220> FEATURE:
<223> OTHER INFORMATION: Human Fibroblast growth factor 4

<400> SEQUENCE: 307

Ala Ala Val Ala Leu Leu Pro Ala Val Leu Leu Ala Leu Leu Ala Pro
1               5                   10                  15

<210> SEQ ID NO 308
<211> LENGTH: 9
<212> TYPE: PRT
<213> ORGANISM: Homo sapiens
<220> FEATURE:
<223> OTHER INFORMATION: Human N50 (NLS of NF-kB P50)

<400> SEQUENCE: 308

Val Gln Arg Lys Arg Gln Lys Leu Met
1               5

<210> SEQ ID NO 309
<211> LENGTH: 21
<212> TYPE: PRT
<213> ORGANISM: Artificial Sequence
<220> FEATURE:
<223> OTHER INFORMATION: Pep-1

<400> SEQUENCE: 309

Lys Glu Thr Trp Trp Glu Thr Trp Trp Thr Glu Trp Ser Gln Pro Lys
1               5                   10                  15

Lys Lys Arg Lys Val
            20
```

```
<210> SEQ ID NO 310
<211> LENGTH: 15
<212> TYPE: PRT
<213> ORGANISM: Artificial Sequence
<220> FEATURE:
<223> OTHER INFORMATION: Pep-7

<400> SEQUENCE: 310

Ser Asp Leu Trp Glu Met Met Met Val Ser Leu Ala Cys Gln Tyr
1               5                   10                  15

<210> SEQ ID NO 311
<211> LENGTH: 16
<212> TYPE: PRT
<213> ORGANISM: Drosophila antennapedia
<220> FEATURE:
<223> OTHER INFORMATION: Fruit Fly Penetratin

<400> SEQUENCE: 311

Arg Gln Ile Lys Ile Trp Phe Gln Asn Arg Arg Met Lys Trp Lys Lys
1               5                   10                  15

<210> SEQ ID NO 312
<211> LENGTH: 17
<212> TYPE: PRT
<213> ORGANISM: Drosophila antennapedia
<220> FEATURE:
<223> OTHER INFORMATION: Fruit Fly Penetratin variant

<400> SEQUENCE: 312

Gly Arg Gln Ile Lys Ile Trp Phe Gln Asn Arg Arg Met Lys Trp Lys
1               5                   10                  15

Lys

<210> SEQ ID NO 313
<211> LENGTH: 7
<212> TYPE: PRT
<213> ORGANISM: Drosophila antennapedia
<220> FEATURE:
<223> OTHER INFORMATION: Fruit Fly Short Penetratin

<400> SEQUENCE: 313

Arg Arg Met Lys Trp Lys Lys
1               5

<210> SEQ ID NO 314
<211> LENGTH: 17
<212> TYPE: PRT
<213> ORGANISM: Drosophila antennapedia
<220> FEATURE:
<223> OTHER INFORMATION: Fruit Fly Penetratin 42-58

<400> SEQUENCE: 314

Glu Arg Gln Ile Lys Ile Trp Phe Gln Asn Arg Arg Met Lys Trp Lys
1               5                   10                  15

Lys

<210> SEQ ID NO 315
<211> LENGTH: 7
<212> TYPE: PRT
<213> ORGANISM: Artificial Sequence
<220> FEATURE:
<223> OTHER INFORMATION: Poly Arginine R7

<400> SEQUENCE: 315
```

Arg Arg Arg Arg Arg Arg Arg
1               5

<210> SEQ ID NO 316
<211> LENGTH: 9
<212> TYPE: PRT
<213> ORGANISM: Artificial Sequence
<220> FEATURE:
<223> OTHER INFORMATION: Poly Arginine R9

<400> SEQUENCE: 316

Arg Arg Arg Arg Arg Arg Arg Arg
1               5

<210> SEQ ID NO 317
<211> LENGTH: 16
<212> TYPE: PRT
<213> ORGANISM: Rattus norvegicus
<220> FEATURE:
<223> OTHER INFORMATION: Rat pISL

<400> SEQUENCE: 317

Arg Val Ile Arg Val Trp Phe Gln Asn Lys Arg Cys Lys Asp Lys Lys
1               5                   10                  15

<210> SEQ ID NO 318
<211> LENGTH: 28
<212> TYPE: PRT
<213> ORGANISM: Mus musculus
<220> FEATURE:
<223> OTHER INFORMATION: Prion mouse PrPc1-28

<400> SEQUENCE: 318

Met Ala Asn Leu Gly Tyr Trp Leu Leu Ala Leu Phe Val Thr Met Trp
1               5                   10                  15

Thr Asp Val Gly Leu Cys Lys Lys Arg Pro Lys Pro
            20                  25

<210> SEQ ID NO 319
<211> LENGTH: 18
<212> TYPE: PRT
<213> ORGANISM: Mus musculus
<220> FEATURE:
<223> OTHER INFORMATION: Mouse pVEC

<400> SEQUENCE: 319

Leu Leu Ile Ile Leu Arg Arg Arg Ile Arg Lys Gln Ala His Ala His
1               5                   10                  15

Ser Lys

<210> SEQ ID NO 320
<211> LENGTH: 16
<212> TYPE: PRT
<213> ORGANISM: Mus musculus
<220> FEATURE:
<223> OTHER INFORMATION: Mouse pVEC variant

<400> SEQUENCE: 320

Leu Leu Ile Ile Leu Arg Arg Arg Ile Arg Lys Gln Ala His Ala His
1               5                   10                  15

<210> SEQ ID NO 321
<211> LENGTH: 18
<212> TYPE: PRT
<213> ORGANISM: Artificial Sequence
<220> FEATURE:

-continued

<223> OTHER INFORMATION: SAP

<400> SEQUENCE: 321

Val Arg Leu Pro Pro Pro Val Arg Leu Pro Pro Pro Val Arg Leu Pro
1               5                   10                  15
Pro Pro

<210> SEQ ID NO 322
<211> LENGTH: 7
<212> TYPE: PRT
<213> ORGANISM: Simian virus
<220> FEATURE:
<223> OTHER INFORMATION: SV-40 (NLS)

<400> SEQUENCE: 322

Pro Lys Lys Lys Arg Lys Val
1               5

<210> SEQ ID NO 323
<211> LENGTH: 18
<212> TYPE: PRT
<213> ORGANISM: Sus scrofa
<220> FEATURE:
<223> OTHER INFORMATION: Porcine SynB1

<400> SEQUENCE: 323

Arg Gly Gly Arg Leu Ser Tyr Ser Arg Arg Arg Phe Ser Thr Ser Thr
1               5                   10                  15
Gly Arg

<210> SEQ ID NO 324
<211> LENGTH: 10
<212> TYPE: PRT
<213> ORGANISM: Sus scrofa
<220> FEATURE:
<223> OTHER INFORMATION: Porcine SynB3

<400> SEQUENCE: 324

Arg Arg Leu Ser Tyr Ser Arg Arg Arg Phe
1               5                   10

<210> SEQ ID NO 325
<211> LENGTH: 17
<212> TYPE: PRT
<213> ORGANISM: Sus scrofa
<220> FEATURE:
<223> OTHER INFORMATION: Porcine SynB4

<400> SEQUENCE: 325

Ala Trp Ser Phe Arg Val Ser Tyr Arg Gly Ile Ser Tyr Arg Arg Ser
1               5                   10                  15
Arg

<210> SEQ ID NO 326
<211> LENGTH: 14
<212> TYPE: PRT
<213> ORGANISM: Human immunodeficiency virus
<220> FEATURE:
<223> OTHER INFORMATION: HIV type I Tat 47-60

<400> SEQUENCE: 326

Tyr Gly Arg Lys Lys Arg Arg Gln Arg Arg Pro Pro Gln
1               5                   10

-continued

```
<210> SEQ ID NO 327
<211> LENGTH: 11
<212> TYPE: PRT
<213> ORGANISM: Human immunodeficiency virus
<220> FEATURE:
<223> OTHER INFORMATION: HIV type I Tat 47-57

<400> SEQUENCE: 327

Tyr Gly Arg Lys Lys Arg Arg Gln Arg Arg Arg
 1               5                  10

<210> SEQ ID NO 328
<211> LENGTH: 10
<212> TYPE: PRT
<213> ORGANISM: Human immunodeficiency virus
<220> FEATURE:
<223> OTHER INFORMATION: HIV type I Tat 47-56

<400> SEQUENCE: 328

Tyr Gly Arg Lys Lys Arg Arg Gln Arg Arg
 1               5                  10

<210> SEQ ID NO 329
<211> LENGTH: 9
<212> TYPE: PRT
<213> ORGANISM: Human immunodeficiency virus
<220> FEATURE:
<223> OTHER INFORMATION: HIV type I Tat 48-56

<400> SEQUENCE: 329

Gly Arg Lys Lys Arg Arg Gln Arg Arg
 1               5

<210> SEQ ID NO 330
<211> LENGTH: 10
<212> TYPE: PRT
<213> ORGANISM: Human immundeficiency virus
<220> FEATURE:
<223> OTHER INFORMATION: HIV type I Tat 48-57

<400> SEQUENCE: 330

Gly Arg Lys Lys Arg Arg Gln Arg Arg Arg
 1               5                  10

<210> SEQ ID NO 331
<211> LENGTH: 9
<212> TYPE: PRT
<213> ORGANISM: Human immundeficiency virus
<220> FEATURE:
<223> OTHER INFORMATION: HIV type I Tat 49-57

<400> SEQUENCE: 331

Arg Lys Lys Arg Arg Gln Arg Arg Arg
 1               5

<210> SEQ ID NO 332
<211> LENGTH: 8
<212> TYPE: PRT
<213> ORGANISM: Human immundeficiency virus
<220> FEATURE:
<223> OTHER INFORMATION: HIV type I Tat 49-56

<400> SEQUENCE: 332

Arg Lys Lys Arg Arg Gln Arg Arg
 1               5

<210> SEQ ID NO 333
```

```
<211> LENGTH: 13
<212> TYPE: PRT
<213> ORGANISM: Human immundeficiency virus
<220> FEATURE:
<223> OTHER INFORMATION: HIV type I Tat 48-60

<400> SEQUENCE: 333

Gly Arg Lys Lys Arg Arg Gln Arg Arg Arg Pro Pro Gln
 1               5                  10

<210> SEQ ID NO 334
<211> LENGTH: 5
<212> TYPE: PRT
<213> ORGANISM: Human immundeficiency virus
<220> FEATURE:
<223> OTHER INFORMATION: HIV type I Tat 48-52

<400> SEQUENCE: 334

Gly Arg Lys Lys Arg
 1               5

<210> SEQ ID NO 335
<211> LENGTH: 36
<212> TYPE: PRT
<213> ORGANISM: Human immundeficiency virus
<220> FEATURE:
<223> OTHER INFORMATION: HIV type I Tat 37-72

<400> SEQUENCE: 335

Cys Phe Ile Thr Lys Ala Leu Gly Ile Ser Tyr Gly Arg Lys Lys Arg
 1               5                  10                  15

Arg Gln Arg Arg Arg Pro Pro Gln Phe Ser Gln Thr His Gln Val Ser
                20                  25                  30

Leu Ser Lys Gln
        35

<210> SEQ ID NO 336
<211> LENGTH: 35
<212> TYPE: PRT
<213> ORGANISM: Human immundeficiency virus
<220> FEATURE:
<223> OTHER INFORMATION: HIV type I Tat 38-72

<400> SEQUENCE: 336

Phe Ile Thr Lys Ala Leu Gly Ile Ser Tyr Gly Arg Lys Lys Arg Arg
 1               5                  10                  15

Gln Arg Arg Arg Pro Pro Gln Phe Ser Gln Thr His Gln Val Ser Leu
                20                  25                  30

Ser Lys Gln
        35

<210> SEQ ID NO 337
<211> LENGTH: 13
<212> TYPE: PRT
<213> ORGANISM: Human immundeficiency virus
<220> FEATURE:
<223> OTHER INFORMATION: HIV type I Tat 47-59

<400> SEQUENCE: 337

Tyr Gly Arg Lys Lys Arg Arg Gln Arg Arg Arg Pro Pro
 1               5                  10

<210> SEQ ID NO 338
<211> LENGTH: 27
<212> TYPE: PRT
```

```
<213> ORGANISM: Artificial Sequence
<220> FEATURE:
<223> OTHER INFORMATION: Transportan

<400> SEQUENCE: 338

Gly Trp Thr Leu Asn Ser Ala Gly Tyr Leu Leu Gly Lys Ile Asn Leu
1               5                   10                  15

Lys Ala Leu Ala Ala Leu Ala Lys Lys Ile Leu
            20                  25

<210> SEQ ID NO 339
<211> LENGTH: 21
<212> TYPE: PRT
<213> ORGANISM: Artificial Sequence
<220> FEATURE:
<223> OTHER INFORMATION: Transportan 10

<400> SEQUENCE: 339

Ala Gly Tyr Leu Leu Gly Lys Ile Asn Leu Lys Ala Leu Ala Ala Leu
1               5                   10                  15

Ala Lys Lys Ile Leu
            20

<210> SEQ ID NO 340
<211> LENGTH: 12
<212> TYPE: PRT
<213> ORGANISM: Artificial Sequence
<220> FEATURE:
<223> OTHER INFORMATION: Transportan derivative

<400> SEQUENCE: 340

Gly Trp Thr Leu Asn Ser Ala Gly Tyr Leu Leu Gly
1               5                   10

<210> SEQ ID NO 341
<211> LENGTH: 14
<212> TYPE: PRT
<213> ORGANISM: Artificial Sequence
<220> FEATURE:
<223> OTHER INFORMATION: Transportan derivative

<400> SEQUENCE: 341

Ile Asn Leu Lys Ala Leu Ala Ala Leu Ala Lys Lys Ile Leu
1               5                   10

<210> SEQ ID NO 342
<211> LENGTH: 34
<212> TYPE: PRT
<213> ORGANISM: Herpes simplex virus
<220> FEATURE:
<223> OTHER INFORMATION: Herpes simplex virus 1 VP22

<400> SEQUENCE: 342

Asp Ala Ala Thr Ala Thr Arg Gly Arg Ser Ala Ala Ser Arg Pro Thr
1               5                   10                  15

Glu Arg Pro Arg Ala Pro Ala Arg Ser Ala Ser Arg Pro Arg Arg Pro
            20                  25                  30

Val Asp

<210> SEQ ID NO 343
<211> LENGTH: 26
<212> TYPE: PRT
<213> ORGANISM: Artificial Sequence
<220> FEATURE:
<223> OTHER INFORMATION: VT5
```

-continued

<400> SEQUENCE: 343

Asp Pro Lys Gly Asp Pro Lys Gly Val Thr Val Thr Val Thr
1               5                   10                  15

Val Thr Gly Lys Gly Asp Pro Lys Pro Asp
            20                  25

<210> SEQ ID NO 344
<211> LENGTH: 27
<212> TYPE: PRT
<213> ORGANISM: Artificial Sequence
<220> FEATURE:
<223> OTHER INFORMATION: Signal sequence-based peptide

<400> SEQUENCE: 344

Gly Ala Leu Phe Leu Gly Trp Leu Gly Ala Ala Gly Ser Thr Met Gly
1               5                   10                  15

Ala Trp Ser Gln Pro Lys Lys Lys Arg Lys Val
            20                  25

<210> SEQ ID NO 345
<211> LENGTH: 18
<212> TYPE: PRT
<213> ORGANISM: Artificial Sequence
<220> FEATURE:
<223> OTHER INFORMATION: Amphiphilic model peptide

<400> SEQUENCE: 345

Lys Leu Ala Leu Lys Leu Ala Leu Lys Ala Leu Lys Ala Ala Leu Lys
1               5                   10                  15

Leu Ala

<210> SEQ ID NO 346
<211> LENGTH: 10
<212> TYPE: PRT
<213> ORGANISM: Artificial Sequence
<220> FEATURE:
<223> OTHER INFORMATION: Bacterial cell wall permeating

<400> SEQUENCE: 346

Lys Phe Phe Lys Phe Phe Lys Phe Phe Lys
1               5                   10

<210> SEQ ID NO 347
<211> LENGTH: 37
<212> TYPE: PRT
<213> ORGANISM: Homo sapiens
<220> FEATURE:
<223> OTHER INFORMATION: Human LL-37

<400> SEQUENCE: 347

Leu Leu Gly Asp Phe Phe Arg Lys Ser Lys Glu Lys Ile Gly Lys Glu
1               5                   10                  15

Phe Lys Arg Ile Val Gln Arg Ile Lys Asp Phe Leu Arg Asn Leu Val
            20                  25                  30

Pro Arg Thr Glu Ser
        35

<210> SEQ ID NO 348
<211> LENGTH: 31
<212> TYPE: PRT
<213> ORGANISM: Sus scrofa
<220> FEATURE:
<223> OTHER INFORMATION: Porcine cecropin P1

<400> SEQUENCE: 348

Ser Trp Leu Ser Lys Thr Ala Lys Lys Leu Glu Asn Ser Ala Lys Lys
1               5                   10                  15

Arg Ile Ser Glu Gly Ile Ala Ile Ala Ile Gln Gly Gly Pro Arg
            20                  25                  30

<210> SEQ ID NO 349
<211> LENGTH: 30
<212> TYPE: PRT
<213> ORGANISM: Homo sapiens
<220> FEATURE:
<223> OTHER INFORMATION: Human alpha defensin

<400> SEQUENCE: 349

Ala Cys Tyr Cys Arg Ile Pro Ala Cys Ile Ala Gly Glu Arg Arg Tyr
1               5                   10                  15

Gly Thr Cys Ile Tyr Gln Gly Arg Leu Trp Ala Phe Cys Cys
            20                  25                  30

<210> SEQ ID NO 350
<211> LENGTH: 36
<212> TYPE: PRT
<213> ORGANISM: Homo sapiens
<220> FEATURE:
<223> OTHER INFORMATION: Human beta defensin

<400> SEQUENCE: 350

Asp His Tyr Asn Cys Val Ser Ser Gly Gly Gln Cys Leu Tyr Ser Ala
1               5                   10                  15

Cys Pro Ile Phe Thr Lys Ile Gln Gly Thr Cys Tyr Arg Gly Lys Ala
            20                  25                  30

Lys Cys Cys Lys
        35

<210> SEQ ID NO 351
<211> LENGTH: 11
<212> TYPE: PRT
<213> ORGANISM: Artificial Sequence
<220> FEATURE:
<223> OTHER INFORMATION: Bactenecin

<400> SEQUENCE: 351

Arg Lys Cys Arg Ile Trp Ile Arg Val Cys Arg
1               5                   10

<210> SEQ ID NO 352
<211> LENGTH: 42
<212> TYPE: PRT
<213> ORGANISM: Sus scrofa
<220> FEATURE:
<223> OTHER INFORMATION: Porcine PR-39

<400> SEQUENCE: 352

Arg Arg Arg Pro Arg Pro Pro Tyr Leu Pro Arg Pro Arg Pro Pro Pro
1               5                   10                  15

Phe Phe Pro Pro Arg Leu Pro Pro Arg Ile Pro Pro Gly Phe Pro Pro
            20                  25                  30

Arg Phe Pro Pro Arg Phe Pro Gly Lys Arg
        35                  40

<210> SEQ ID NO 353
<211> LENGTH: 13

```
<212> TYPE: PRT
<213> ORGANISM: Bos taurus
<220> FEATURE:
<223> OTHER INFORMATION: Bovine Indolicidin

<400> SEQUENCE: 353

Ile Leu Pro Trp Lys Trp Pro Trp Trp Pro Trp Arg Arg
1               5                   10

<210> SEQ ID NO 354
<211> LENGTH: 27
<212> TYPE: PRT
<213> ORGANISM: Simian immunodeficiency virus
<220> FEATURE:
<223> OTHER INFORMATION: SIV MPS

<400> SEQUENCE: 354

Gly Ala Leu Phe Leu Gly Trp Leu Gly Ala Ala Gly Ser Thr Met Gly
1               5                   10                  15

Ala Trp Ser Gln Pro Lys Lys Lys Arg Lys Val
            20                  25

<210> SEQ ID NO 355
<211> LENGTH: 17
<212> TYPE: PRT
<213> ORGANISM: Artificial Sequence
<220> FEATURE:
<223> OTHER INFORMATION: pIs1

<400> SEQUENCE: 355

Pro Val Ile Arg Arg Val Trp Phe Gln Asn Lys Arg Cys Lys Asp Lys
1               5                   10                  15

Lys

<210> SEQ ID NO 356
<211> LENGTH: 330
<212> TYPE: PRT
<213> ORGANISM: Homo sapiens
<220> FEATURE:
<223> OTHER INFORMATION: hIgG1 heavy chain constant

<400> SEQUENCE: 356

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
```

145             150             155             160

Tyr Val Asp Gly Val Glu Val His Asn Ala Lys Thr Lys Pro Arg Glu
                165             170             175

Glu Gln Tyr Asn Ser Thr Tyr Arg Val Val Ser Val Leu Thr Val Leu
            180             185             190

His Gln Asp Trp Leu Asn Gly Lys Glu Tyr Lys Cys Lys Val Ser Asn
        195             200             205

Lys Ala Leu Pro Ala Pro Ile Glu Lys Thr Ile Ser Lys Ala Lys Gly
    210             215             220

Gln Pro Arg Glu Pro Gln Val Tyr Thr Leu Pro Pro Ser Arg Asp Glu
225             230             235             240

Leu Thr Lys Asn Gln Val Ser Leu Thr Cys Leu Val Lys Gly Phe Tyr
                245             250             255

Pro Ser Asp Ile Ala Val Glu Trp Glu Ser Asn Gly Gln Pro Glu Asn
            260             265             270

Asn Tyr Lys Thr Thr Pro Pro Val Leu Asp Ser Asp Gly Ser Phe Phe
        275             280             285

Leu Tyr Ser Lys Leu Thr Val Asp Lys Ser Arg Trp Gln Gln Gly Asn
    290             295             300

Val Phe Ser Cys Ser Val Met His Glu Ala Leu His Asn His Tyr Thr
305             310             315             320

Gln Lys Ser Leu Ser Leu Ser Pro Gly Lys
                325             330

<210> SEQ ID NO 357
<211> LENGTH: 326
<212> TYPE: PRT
<213> ORGANISM: Homo sapiens
<220> FEATURE:
<223> OTHER INFORMATION: hIgG2 heavy chain constant

<400> SEQUENCE: 357

Ala Ser Thr Lys Gly Pro Ser Val Phe Pro Leu Ala Pro Cys Ser Arg
1               5               10              15

Ser Thr Ser Glu Ser Thr Ala Ala Leu Gly Cys Leu Val Lys Asp Tyr
            20              25              30

Phe Pro Glu Pro Val Thr Val Ser Trp Asn Ser Gly Ala Leu Thr Ser
        35              40              45

Gly Val His Thr Phe Pro Ala Val Leu Gln Ser Ser Gly Leu Tyr Ser
    50              55              60

Leu Ser Ser Val Val Thr Val Pro Ser Ser Asn Phe Gly Thr Gln Thr
65              70              75              80

Tyr Thr Cys Asn Val Asp His Lys Pro Ser Asn Thr Lys Val Asp Lys
                85              90              95

Thr Val Glu Arg Lys Cys Cys Val Glu Cys Pro Pro Cys Pro Ala Pro
            100             105             110

Pro Val Ala Gly Pro Ser Val Phe Leu Phe Pro Pro Lys Pro Lys Asp
        115             120             125

Thr Leu Met Ile Ser Arg Thr Pro Glu Val Thr Cys Val Val Val Asp
    130             135             140

Val Ser His Glu Asp Pro Glu Val Gln Phe Asn Trp Tyr Val Asp Gly
145             150             155             160

Val Glu Val His Asn Ala Lys Thr Lys Pro Arg Glu Glu Gln Phe Asn
                165             170             175

Ser Thr Phe Arg Val Val Ser Val Leu Thr Val Val His Gln Asp Trp

```
                180                 185                 190
Leu Asn Gly Lys Glu Tyr Lys Cys Lys Val Ser Asn Lys Gly Leu Pro
            195                 200                 205

Ala Pro Ile Glu Lys Thr Ile Ser Lys Thr Lys Gly Gln Pro Arg Glu
            210                 215                 220

Pro Gln Val Tyr Thr Leu Pro Pro Ser Arg Glu Met Thr Lys Asn
225                 230                 235                 240

Gln Val Ser Leu Thr Cys Leu Val Lys Gly Phe Tyr Pro Ser Asp Ile
                245                 250                 255

Ala Val Glu Trp Glu Ser Asn Gly Gln Pro Glu Asn Asn Tyr Lys Thr
            260                 265                 270

Thr Pro Pro Met Leu Asp Ser Asp Gly Ser Phe Phe Leu Tyr Ser Lys
            275                 280                 285

Leu Thr Val Asp Lys Ser Arg Trp Gln Gln Gly Asn Val Phe Ser Cys
            290                 295                 300

Ser Val Met His Glu Ala Leu His Asn His Tyr Thr Gln Lys Ser Leu
305                 310                 315                 320

Ser Leu Ser Pro Gly Lys
            325

<210> SEQ ID NO 358
<211> LENGTH: 377
<212> TYPE: PRT
<213> ORGANISM: Homo sapiens
<220> FEATURE:
<223> OTHER INFORMATION: hIgG3 heavy chain constant

<400> SEQUENCE: 358

Ala Ser Thr Lys Gly Pro Ser Val Phe Pro Leu Ala Pro Cys Ser Arg
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Leu Gly Thr Gln Thr
65                  70                  75                  80

Tyr Thr Cys Asn Val Asn His Lys Pro Ser Asn Thr Lys Val Asp Lys
                85                  90                  95

Arg Val Glu Leu Lys Thr Pro Leu Gly Asp Thr Thr His Thr Cys Pro
            100                 105                 110

Arg Cys Pro Glu Pro Lys Ser Cys Asp Thr Pro Pro Pro Cys Pro Arg
        115                 120                 125

Cys Pro Glu Pro Lys Ser Cys Asp Thr Pro Pro Pro Cys Pro Arg Cys
130                 135                 140

Pro Glu Pro Lys Ser Cys Asp Thr Pro Pro Pro Cys Pro Arg Cys Pro
145                 150                 155                 160

Ala Pro Glu Leu Leu Gly Gly Pro Ser Val Phe Leu Phe Pro Pro Lys
                165                 170                 175

Pro Lys Asp Thr Leu Met Ile Ser Arg Thr Pro Glu Val Thr Cys Val
            180                 185                 190

Val Val Asp Val Ser His Glu Asp Pro Glu Val Gln Phe Lys Trp Tyr
        195                 200                 205

Val Asp Gly Val Glu Val His Asn Ala Lys Thr Lys Pro Arg Glu Glu
```

-continued

```
            210                 215                 220
Gln Tyr Asn Ser Thr Phe Arg Val Val Ser Val Leu Thr Val Leu His
225                 230                 235                 240

Gln Asp Trp Leu Asn Gly Lys Glu Tyr Lys Cys Lys Val Ser Asn Lys
                245                 250                 255

Ala Leu Pro Ala Pro Ile Glu Lys Thr Ile Ser Lys Thr Lys Gly Gln
                260                 265                 270

Pro Arg Glu Pro Gln Val Tyr Thr Leu Pro Pro Ser Arg Glu Glu Met
            275                 280                 285

Thr Lys Asn Gln Val Ser Leu Thr Cys Leu Val Lys Gly Phe Tyr Pro
        290                 295                 300

Ser Asp Ile Ala Val Glu Trp Glu Ser Ser Gly Gln Pro Glu Asn Asn
305                 310                 315                 320

Tyr Asn Thr Thr Pro Pro Met Leu Asp Ser Asp Gly Ser Phe Phe Leu
                325                 330                 335

Tyr Ser Lys Leu Thr Val Asp Lys Ser Arg Trp Gln Gln Gly Asn Ile
                340                 345                 350

Phe Ser Cys Ser Val Met His Glu Ala Leu His Asn Arg Phe Thr Gln
            355                 360                 365

Lys Ser Leu Ser Leu Ser Pro Gly Lys
        370                 375

<210> SEQ ID NO 359
<211> LENGTH: 327
<212> TYPE: PRT
<213> ORGANISM: Artificial Sequence
<220> FEATURE:
<223> OTHER INFORMATION: hIgG4 heavy chain constant

<400> SEQUENCE: 359

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Ser Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
    130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
```

```
                195                 200                 205
Pro Ser Ser Ile Glu Lys Thr Ile Ser Lys Ala Lys Gly Gln Pro Arg
210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
290                 295                 300

Cys Ser Val Met His Glu Ala Leu His Asn His Tyr Thr Gln Lys Ser
305                 310                 315                 320

Leu Ser Leu Ser Leu Gly Lys
                325

<210> SEQ ID NO 360
<211> LENGTH: 231
<212> TYPE: PRT
<213> ORGANISM: Artificial Sequence
<220> FEATURE:
<223> OTHER INFORMATION: hIgG1 Fc

<400> SEQUENCE: 360

Pro Lys Ser Cys Asp Lys Thr His Thr Cys Pro Pro Cys Pro Ala Pro
1               5                   10                  15

Glu Leu Leu Gly Gly Pro Ser Val Phe Leu Phe Pro Pro Lys Pro Lys
            20                  25                  30

Asp Thr Leu Met Ile Ser Arg Thr Pro Glu Val Thr Cys Val Val Val
        35                  40                  45

Asp Val Ser His Glu Asp Pro Glu Val Lys Phe Asn Trp Tyr Val Asp
    50                  55                  60

Gly Val Glu Val His Asn Ala Lys Thr Lys Pro Arg Glu Glu Gln Tyr
65                  70                  75                  80

Asn Ser Thr Tyr Arg Val Val Ser Val Leu Thr Val Leu His Gln Asp
                85                  90                  95

Trp Leu Asn Gly Lys Glu Tyr Lys Cys Lys Val Ser Asn Lys Ala Leu
            100                 105                 110

Pro Ala Pro Ile Glu Lys Thr Ile Ser Lys Ala Lys Gly Gln Pro Arg
        115                 120                 125

Glu Pro Gln Val Tyr Thr Leu Pro Pro Ser Arg Asp Glu Leu Thr Lys
    130                 135                 140

Asn Gln Val Ser Leu Thr Cys Leu Val Lys Gly Phe Tyr Pro Ser Asp
145                 150                 155                 160

Ile Ala Val Glu Trp Glu Ser Asn Gly Gln Pro Glu Asn Asn Tyr Lys
                165                 170                 175

Thr Thr Pro Pro Val Leu Asp Ser Asp Gly Ser Phe Phe Leu Tyr Ser
            180                 185                 190

Lys Leu Thr Val Asp Lys Ser Arg Trp Gln Gln Gly Asn Val Phe Ser
        195                 200                 205

Cys Ser Val Met His Glu Ala Leu His Asn His Tyr Thr Gln Lys Ser
    210                 215                 220

Leu Ser Leu Ser Pro Gly Lys
225                 230
```

<210> SEQ ID NO 361
<211> LENGTH: 232
<212> TYPE: PRT
<213> ORGANISM: Artificial Sequence
<220> FEATURE:
<223> OTHER INFORMATION: hIgG1 Fc

<400> SEQUENCE: 361

```
Glu Pro Arg Ser Cys Asp Lys Thr His Thr Cys Pro Pro Cys Pro Ala
 1               5                  10                  15

Pro Glu Leu Leu Gly Gly Pro Ser Val Phe Leu Phe Pro Pro Lys Pro
            20                  25                  30

Lys Asp Thr Leu Met Ile Ser Arg Thr Pro Glu Val Thr Cys Val Val
        35                  40                  45

Val Asp Val Ser His Glu Asp Pro Glu Val Lys Phe Asn Trp Tyr Val
    50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Pro Ala Pro Met Gln Lys Thr Ile Ser Lys Ala Lys Gly Gln Pro
        115                 120                 125

Arg Glu Pro Gln Val Tyr Thr Leu Pro Pro Ser Arg Asp Glu Leu Thr
    130                 135                 140

Lys Asn Gln Val Ser Leu Thr Cys Leu Val Lys Gly Phe Tyr Pro Arg
145                 150                 155                 160

His Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe
        195                 200                 205

Ser Cys Ser Val Met His Glu Ala Leu His Asn His Tyr Thr Gln Lys
    210                 215                 220

Ser Leu Ser Leu Ser Pro Gly Lys
225                 230
```

<210> SEQ ID NO 362
<211> LENGTH: 129
<212> TYPE: PRT
<213> ORGANISM: Artificial Sequence
<220> FEATURE:
<223> OTHER INFORMATION: Rsv6/11/21/22/23 Heavy chain

<400> SEQUENCE: 362

```
Gln Val Lys Leu Leu Glu Gln Ser Gly Gly Leu Val Gln Pro Gly
 1               5                  10                  15

Gly Ser Leu Arg Leu Ser Cys Ala Val Ser Gly Val Thr Phe Ser Ala
            20                  25                  30

Tyr Ala Met Ser Trp Val Arg Gln Ala Pro Gly Lys Gly Leu Glu Trp
        35                  40                  45

Val Ser Gly Ile Ser Gly Ser Gly Asp Ser Thr Asp Tyr Ala Asp Ser
    50                  55                  60
```

-continued

```
Val Lys Gly Arg Leu Thr Ile Ser Arg Asp Asn Ser Lys Asn Thr Leu
 65                  70                  75                  80

Tyr Leu Gln Met Asn Ser Leu Arg Ala Glu Asp Thr Ala Ile Tyr Tyr
                 85                  90                  95

Cys Ala Ser His Leu Pro Asp Tyr Trp Asn Leu Asp Tyr Thr Arg Phe
            100                 105                 110

Phe Tyr Tyr Met Asp Val Trp Gly Lys Gly Thr Thr Val Thr Val Ser
        115                 120                 125

Ser
```

<210> SEQ ID NO 363
<211> LENGTH: 5
<212> TYPE: PRT
<213> ORGANISM: Artificial Sequence
<220> FEATURE:
<223> OTHER INFORMATION: Rsv6/11/21/22/23 Heavy CDR1

<400> SEQUENCE: 363

```
Ala Tyr Ala Met Ser
 1               5
```

<210> SEQ ID NO 364
<211> LENGTH: 17
<212> TYPE: PRT
<213> ORGANISM: Artificial Sequence
<220> FEATURE:
<223> OTHER INFORMATION: Rsv6/11/21/22/23 Heavy CDR2

<400> SEQUENCE: 364

```
Gly Ile Ser Gly Ser Gly Asp Ser Thr Asp Tyr Ala Asp Ser Val Lys
 1               5                  10                  15

Gly
```

<210> SEQ ID NO 365
<211> LENGTH: 19
<212> TYPE: PRT
<213> ORGANISM: Artificial Sequence
<220> FEATURE:
<223> OTHER INFORMATION: Rsv6/11/21/22/23 Heavy CDR3

<400> SEQUENCE: 365

```
His Leu Pro Asp Tyr Trp Asn Leu Asp Tyr Thr Arg Phe Phe Tyr Tyr
 1               5                  10                  15

Met Asp Val
```

<210> SEQ ID NO 366
<211> LENGTH: 120
<212> TYPE: PRT
<213> ORGANISM: Artificial Sequence
<220> FEATURE:
<223> OTHER INFORMATION: Rsv13/19H Heavy chain

<400> SEQUENCE: 366

```
Gln Val Lys Leu Leu Glu Glu Ser Gly Gly Gly Leu Val Arg Leu Ala
 1               5                  10                  15

Gly Ser Leu Arg Leu Ser Cys Ala Ala Ser Gly Thr Thr Leu Ser Gly
             20                  25                  30

Tyr Thr Met His Trp Val Arg Gln Ala Pro Gly Lys Gly Leu Glu Trp
         35                  40                  45

Val Ser Ser Ile Thr Gly Gly Ser Asn Phe Ile Asn Tyr Ser Asp Ser
     50                  55                  60
```

```
Val Lys Gly Arg Phe Thr Ile Ser Arg Asp Asn Ala Lys Asn Ser Leu
 65                  70                  75                  80

Tyr Leu Gln Met Asn Ser Leu Thr Ala Glu Asp Thr Ala Val Tyr Tyr
                 85                  90                  95

Cys Ala Thr Ala Pro Ile Ala Pro Pro Tyr Phe Asp His Trp Gly Gln
            100                 105                 110

Gly Thr Leu Val Thr Val Ser Ser
        115                 120

<210> SEQ ID NO 367
<211> LENGTH: 5
<212> TYPE: PRT
<213> ORGANISM: Artificial Sequence
<220> FEATURE:
<223> OTHER INFORMATION: Rsv13/19H Heavy CDR1

<400> SEQUENCE: 367

Gly Tyr Thr Met His
 1               5

<210> SEQ ID NO 368
<211> LENGTH: 17
<212> TYPE: PRT
<213> ORGANISM: Artificial Sequence
<220> FEATURE:
<223> OTHER INFORMATION: Rsv13/19H Heavy CDR2

<400> SEQUENCE: 368

Ser Ile Thr Gly Gly Ser Asn Phe Ile Asn Tyr Ser Asp Ser Val Lys
 1               5                  10                  15

Gly

<210> SEQ ID NO 369
<211> LENGTH: 10
<212> TYPE: PRT
<213> ORGANISM: Artificial Sequence
<220> FEATURE:
<223> OTHER INFORMATION: Rsv13/19H Heavy CDR3

<400> SEQUENCE: 369

Ala Pro Ile Ala Pro Pro Tyr Phe Asp His
 1               5                  10

<210> SEQ ID NO 370
<211> LENGTH: 109
<212> TYPE: PRT
<213> ORGANISM: Artificial Sequence
<220> FEATURE:
<223> OTHER INFORMATION: Rsv 6/11/21/22 Light chain

<400> SEQUENCE: 370

Met Ala Glu Leu Thr Gln Ser Pro Gly Thr Leu Ser Leu Ser Pro Gly
 1               5                  10                  15

Glu Arg Ala Thr Leu Ser Cys Arg Ala Thr Gln Ser Ile Ser Ser Asn
                 20                  25                  30

Tyr Leu Ala Trp Tyr Gln Gln Arg Pro Gly Gln Ala Pro Arg Leu Leu
             35                  40                  45

Ile Tyr Gly Ala Ser Asn Arg Ala Thr Asp Ile Pro Asp Arg Phe Ser
         50                  55                  60

Gly Ser Gly Ser Gly Thr Asp Phe Thr Leu Thr Ile Ser Arg Leu Glu
 65                  70                  75                  80

Pro Glu Asp Phe Ala Met Tyr Tyr Cys Gln Gln Tyr Asp Ile Ser Pro
```

```
                85                  90                  95

Tyr Thr Phe Gly Gln Gly Thr Lys Leu Glu Ile Lys Arg
            100                 105

<210> SEQ ID NO 371
<211> LENGTH: 12
<212> TYPE: PRT
<213> ORGANISM: Artificial Sequence
<220> FEATURE:
<223> OTHER INFORMATION: Rsv 6/11/21/22 Light CDR1

<400> SEQUENCE: 371

Arg Ala Thr Gln Ser Ile Ser Ser Asn Tyr Leu Ala
1               5                   10

<210> SEQ ID NO 372
<211> LENGTH: 7
<212> TYPE: PRT
<213> ORGANISM: Artificial Sequence
<220> FEATURE:
<223> OTHER INFORMATION: Rsv 6/11/21/22 Light CDR2

<400> SEQUENCE: 372

Gly Ala Ser Asn Arg Ala Thr
1               5

<210> SEQ ID NO 373
<211> LENGTH: 9
<212> TYPE: PRT
<213> ORGANISM: Artificial Sequence
<220> FEATURE:
<223> OTHER INFORMATION: Rsv 6/11/21/22 Light CDR3

<400> SEQUENCE: 373

Gln Gln Tyr Asp Ile Ser Pro Tyr Thr
1               5

<210> SEQ ID NO 374
<211> LENGTH: 109
<212> TYPE: PRT
<213> ORGANISM: Artificial Sequence
<220> FEATURE:
<223> OTHER INFORMATION: Rsv23 Light Chain

<400> SEQUENCE: 374

Met Ala Glu Leu Thr Gln Ser Pro Val Thr Leu Ser Val Ser Pro Gly
1               5                   10                  15

Glu Arg Val Ala Leu Ser Cys Lys Ala Ser Gln Asn Ile Asn Asp Asn
            20                  25                  30

Leu Ala Trp Tyr Gln Gln Lys Pro Gly Gln Ala Pro Arg Leu Leu Ile
        35                  40                  45

Tyr Gly Ala Ser Ser Arg Ala Thr Gly Ile Pro Asp Arg Phe Ser Gly
    50                  55                  60

Ser Gly Ser Gly Thr Asp Phe Thr Leu Thr Ile Thr Arg Leu Glu Pro
65                  70                  75                  80

Glu Asp Phe Ala Val Tyr Tyr Cys Gln Gln Tyr Gly Gly Ser Pro Tyr
                85                  90                  95

Thr Phe Gly Gln Gly Thr Lys Leu Glu Ile Lys Arg Thr
            100                 105

<210> SEQ ID NO 375
<211> LENGTH: 11
<212> TYPE: PRT
```

```
<213> ORGANISM: Artificial Sequence
<220> FEATURE:
<223> OTHER INFORMATION: Rsv23 Light CDR1

<400> SEQUENCE: 375

Lys Ala Ser Gln Asn Ile Asn Asp Asn Leu Ala
1               5                   10

<210> SEQ ID NO 376
<211> LENGTH: 7
<212> TYPE: PRT
<213> ORGANISM: Artificial Sequence
<220> FEATURE:
<223> OTHER INFORMATION: Rsv23 Light CDR2

<400> SEQUENCE: 376

Gly Ala Ser Ser Arg Ala Thr
1               5

<210> SEQ ID NO 377
<211> LENGTH: 9
<212> TYPE: PRT
<213> ORGANISM: Artificial Sequence
<220> FEATURE:
<223> OTHER INFORMATION: Rsv23 Light CDR3

<400> SEQUENCE: 377

Gln Gln Tyr Gly Gly Ser Pro Tyr Thr
1               5

<210> SEQ ID NO 378
<211> LENGTH: 108
<212> TYPE: PRT
<213> ORGANISM: Artificial Sequence
<220> FEATURE:
<223> OTHER INFORMATION: Rsv13/19 Light Chain

<400> SEQUENCE: 378

Met Ala Glu Leu Thr Gln Ser Pro Ser Ser Leu Ser Ala Ser Val Gly
1               5                   10                  15

Asp Arg Val Thr Ile Thr Cys Arg Ala Thr Gln Ser Val Ser Asn Phe
            20                  25                  30

Leu Asn Trp Tyr Gln Gln Lys Pro Gly Glu Ala Pro Thr Leu Leu Ile
        35                  40                  45

Tyr Asp Ala Ser Thr Ser Gln Ser Gly Val Pro Ser Arg Phe Ser Gly
    50                  55                  60

Ser Gly Ser Gly Met Asp Phe Ser Leu Thr Ile Ser Ser Leu Gln Pro
65                  70                  75                  80

Glu Asp Leu Ala Met Tyr Tyr Cys Gln Ala Ser Ile Asn Thr Pro Leu
                85                  90                  95

Phe Gly Gly Gly Thr Arg Ile Asp Met Arg Arg Thr
            100                 105

<210> SEQ ID NO 379
<211> LENGTH: 11
<212> TYPE: PRT
<213> ORGANISM: Artificial Sequence
<220> FEATURE:
<223> OTHER INFORMATION: Rsv13/19 Light CDR1

<400> SEQUENCE: 379

Arg Ala Thr Gln Ser Val Ser Asn Phe Leu Asn
1               5                   10
```

<210> SEQ ID NO 380
<211> LENGTH: 7
<212> TYPE: PRT
<213> ORGANISM: Artificial Sequence
<220> FEATURE:
<223> OTHER INFORMATION: Rsv13/19 Light CDR2

<400> SEQUENCE: 380

Asp Ala Ser Thr Ser Gln Ser
1               5

<210> SEQ ID NO 381
<211> LENGTH: 8
<212> TYPE: PRT
<213> ORGANISM: Artificial Sequence
<220> FEATURE:
<223> OTHER INFORMATION: Rsv13/19 Light CDR3

<400> SEQUENCE: 381

Gln Ala Ser Ile Asn Thr Pro Leu
1               5

<210> SEQ ID NO 382
<211> LENGTH: 574
<212> TYPE: PRT
<213> ORGANISM: Artificial Sequence
<220> FEATURE:
<223> OTHER INFORMATION: Respiratory Syncytial Virus Strain A2 F protein

<400> SEQUENCE: 382

Met Glu Leu Leu Ile Leu Lys Ala Asn Ala Ile Thr Thr Ile Leu Thr
1               5                   10                  15

Ala Val Thr Phe Cys Phe Ala Ser Gly Gln Asn Ile Thr Glu Glu Phe
            20                  25                  30

Tyr Gln Ser Thr Cys Ser Ala Val Ser Lys Gly Tyr Leu Ser Ala Leu
        35                  40                  45

Arg Thr Gly Trp Tyr Thr Ser Val Ile Thr Ile Glu Leu Ser Asn Ile
    50                  55                  60

Lys Glu Asn Lys Cys Asn Gly Thr Asp Ala Lys Val Lys Leu Ile Lys
65                  70                  75                  80

Gln Glu Leu Asp Lys Tyr Lys Asn Ala Val Thr Glu Leu Gln Leu Leu
                85                  90                  95

Met Gln Ser Thr Pro Pro Thr Asn Asn Arg Ala Arg Arg Glu Leu Pro
            100                 105                 110

Arg Phe Met Asn Tyr Thr Leu Asn Asn Ala Lys Lys Thr Asn Val Thr
        115                 120                 125

Leu Ser Lys Lys Arg Lys Arg Arg Phe Leu Gly Phe Leu Leu Gly Val
    130                 135                 140

Gly Ser Ala Ile Ala Ser Gly Val Ala Val Ser Lys Val Leu His Leu
145                 150                 155                 160

Glu Gly Glu Val Asn Lys Ile Lys Ser Ala Leu Leu Ser Thr Asn Lys
                165                 170                 175

Ala Val Val Ser Leu Ser Asn Gly Val Ser Val Leu Thr Ser Lys Val
            180                 185                 190

Leu Asp Leu Lys Asn Tyr Ile Asp Lys Gln Leu Leu Pro Ile Val Asn
        195                 200                 205

Lys Gln Ser Cys Ser Ile Ser Asn Ile Glu Thr Val Ile Glu Phe Gln
    210                 215                 220

Gln Lys Asn Asn Arg Leu Leu Glu Ile Thr Arg Glu Phe Ser Val Asn

```
        225                 230                 235                 240
Ala Gly Val Thr Thr Pro Val Ser Thr Tyr Met Leu Thr Asn Ser Glu
                245                 250                 255

Leu Leu Ser Leu Ile Asn Asp Met Pro Ile Thr Asn Asp Gln Lys Lys
                260                 265                 270

Leu Met Ser Asn Asn Val Gln Ile Val Arg Gln Ser Tyr Ser Ile
                275                 280                 285

Met Ser Ile Ile Lys Glu Glu Val Leu Ala Tyr Val Val Gln Leu Pro
                290                 295                 300

Leu Tyr Gly Val Ile Asp Thr Pro Cys Trp Lys Leu His Thr Ser Pro
305                 310                 315                 320

Leu Cys Thr Thr Asn Thr Lys Glu Gly Ser Asn Ile Cys Leu Thr Arg
                325                 330                 335

Thr Asp Arg Gly Trp Tyr Cys Asp Asn Ala Gly Ser Val Ser Phe Phe
                340                 345                 350

Pro Gln Ala Glu Thr Cys Lys Val Gln Ser Asn Arg Val Phe Cys Asp
                355                 360                 365

Thr Met Asn Ser Leu Thr Leu Pro Ser Glu Ile Asn Leu Cys Asn Val
370                 375                 380

Asp Ile Phe Asn Pro Lys Tyr Asp Cys Lys Ile Met Thr Ser Lys Thr
385                 390                 395                 400

Asp Val Ser Ser Ser Val Ile Thr Ser Leu Gly Ala Ile Val Ser Cys
                405                 410                 415

Tyr Gly Lys Thr Lys Cys Thr Ala Ser Asn Lys Asn Arg Gly Ile Ile
                420                 425                 430

Lys Thr Phe Ser Asn Gly Cys Asp Tyr Val Ser Asn Lys Gly Met Asp
                435                 440                 445

Thr Val Ser Val Gly Asn Thr Leu Tyr Tyr Val Asn Lys Gln Glu Gly
                450                 455                 460

Lys Ser Leu Tyr Val Lys Gly Glu Pro Ile Ile Asn Phe Tyr Asp Pro
465                 470                 475                 480

Leu Val Phe Pro Ser Asp Glu Phe Asp Ala Ser Ile Ser Gln Val Asn
                485                 490                 495

Glu Lys Ile Asn Gln Ser Leu Ala Phe Ile Arg Lys Ser Asp Glu Leu
                500                 505                 510

Leu His Asn Val Asn Ala Gly Lys Ser Thr Thr Asn Ile Met Ile Thr
                515                 520                 525

Thr Ile Ile Ile Val Ile Ile Val Ile Leu Leu Ser Leu Ile Ala Val
                530                 535                 540

Gly Leu Leu Leu Tyr Cys Lys Ala Arg Ser Thr Pro Val Thr Leu Ser
545                 550                 555                 560

Lys Asp Gln Leu Ser Gly Ile Asn Asn Ile Ala Phe Ser Asn
                565                 570

<210> SEQ ID NO 383
<211> LENGTH: 28
<212> TYPE: DNA
<213> ORGANISM: Artificial Sequence
<220> FEATURE:
<223> OTHER INFORMATION: VH-g1(a/b)-REV primer

<400> SEQUENCE: 383
acaagatttg ggctcaacty tcttgtcc                                      28

<210> SEQ ID NO 384
```

```
<211> LENGTH: 23
<212> TYPE: DNA
<213> ORGANISM: Artificial Sequence
<220> FEATURE:
<223> OTHER INFORMATION: 5'L VLambda 1 primer

<400> SEQUENCE: 384
ggtcctgggc ccagtctgtg ctg                                              23

<210> SEQ ID NO 385
<211> LENGTH: 23
<212> TYPE: DNA
<213> ORGANISM: Artificial Sequence
<220> FEATURE:
<223> OTHER INFORMATION: 5'L VLambda 2 primer

<400> SEQUENCE: 385
ggtcctgggc ccagtctgcc ctg                                              23

<210> SEQ ID NO 386
<211> LENGTH: 23
<212> TYPE: DNA
<213> ORGANISM: Artificial Sequence
<220> FEATURE:
<223> OTHER INFORMATION: 5'L VLambda 3 primer

<400> SEQUENCE: 386
gctctgtgac ctcctatgag ctg                                              23

<210> SEQ ID NO 387
<211> LENGTH: 23
<212> TYPE: DNA
<213> ORGANISM: Artificial Sequence
<220> FEATURE:
<223> OTHER INFORMATION: 5'L VLambda 4/5 primer

<400> SEQUENCE: 387
ggtctctctc scagcytgtg ctg                                              23

<210> SEQ ID NO 388
<211> LENGTH: 23
<212> TYPE: DNA
<213> ORGANISM: Artificial Sequence
<220> FEATURE:
<223> OTHER INFORMATION: 5'L VLambda 6 primer

<400> SEQUENCE: 388
gttcttgggc caattttatg ctg                                              23

<210> SEQ ID NO 389
<211> LENGTH: 23
<212> TYPE: DNA
<213> ORGANISM: Artificial Sequence
<220> FEATURE:
<223> OTHER INFORMATION: 5'L VLambda 7 primer

<400> SEQUENCE: 389
ggtccaattc ycaggctgtg gtg                                              23

<210> SEQ ID NO 390
<211> LENGTH: 23
<212> TYPE: DNA
<213> ORGANISM: Artificial Sequence
<220> FEATURE:
<223> OTHER INFORMATION: 5'L VLambda 8 primer

<400> SEQUENCE: 390
```

```
gagtggattc tcagactgtg gtg                                              23
```

<210> SEQ ID NO 391
<211> LENGTH: 6822
<212> TYPE: DNA
<213> ORGANISM: Artificial Sequence
<220> FEATURE:
<223> OTHER INFORMATION: 28d11/pCAL vector

<400> SEQUENCE: 391

```
atgcattagt tattaatagt aatcaattac ggggtcatta gttcatagcc catatatgga       60
gttccgcgtt acataactta cggtaaatgg cccgcctggc tgaccgccca acgacccccg      120
cccattgacg tcaataatga cgtatgttcc catagtaacg ccaatagggg ctttccattg      180
acgtcaatgg gtggagtatt tacggtaaac tgcccacttg gcagtacatc aagtgtatca      240
tatgccaagt acgccccta ttgacgtcaa tgacggtaaa tggcccgcct ggcattatgc       300
ccagtacatg accttatggg actttcctac ttggcagtac atctacgtat tagtcatcgc      360
tattaccatg gtgatgcggt tttggcagta catcaatggg cgtggatagc ggtttgactc      420
acggggattt ccaagtctcc accccattga cgtcaatggg agtttgtttt ggcaccaaaa      480
tcaacgggac tttccaaaat gtcgtaacaa ctccgcccca ttgacgcaaa tgggcggtag      540
gcgtgtacgg tgggaggtct atataagcag agctggttta gtgaaccgtc agatccgcta      600
gcgattacgc caagctcgaa attaaccctc actaaaggga caaaagctg gagctccacc       660
gcggtggcgg ccgcccacca tggactggac ctggcggatc ctgttcctgg tggccgcggc      720
caccggggcc cacagccagc tgcagctgca ggagtcgggc ccaggactgg tgaaggtttc      780
ggacaccctg tccctcagct gcactgtctc tggtgactcc atcaatagtt attcctggag      840
ttggatccgg cagcccccag ggaagggact tgagtggatt ggatatctct attacagtgg      900
gagctccaat tatagtccct ccctcaaggg ccgagtcacc atgtcgctag acacgtccaa      960
gaaccagttt tccctgaagc ttcactctct gaccgctgcg acacggccg tctattactg      1020
tgcgagagga tcttgtggta gaaccacctg ctactggga aaccactact acatggacgt      1080
ctggggcaaa gggaccgcgg tcaccgtctc ctcacagctg cagctgcagg agtcgggccc      1140
aggactggtg aaggtttcgg acaccctgtc cctcagctgc actgtctctg gtgactccat      1200
caatagttat tcctggagtt ggatccggca gccccaggg aagggacttg agtggattgg      1260
atatctctat tacagtggga gctccaatta tagtccctcc ctcaagggcc gagtcaccat      1320
gtcgctagac acgtccaaga accagttttc cctgaagctt cactctctga ccgctgcgga      1380
cacggccgtc tattactgtg cgagaggatc ttgtggtaga accacctgct actgggaaaa      1440
ccactactac atggacgtct ggggcaaagg gaccgcggtc accgtctcct cagctagcac      1500
caagggcccc agcgtgttcc cctggccccc agcagcaag agcaccagcg gcggcaccgc      1560
cgccctgggc tgcctggtga aggactactt ccccgagccc gtgaccgtga gctggaacag      1620
cggcgccctg accagcggcg tgcacacctt ccccgccgtg ctgcagagca gcggcctgta      1680
cagcctgagc agcgtggtga ccgtgcccag cagcagcctg ggcacccaga cctacatctg      1740
caacgtgaac cacaagccca gcaacaccaa ggtggacaag aaggtggagc ccaagagctg      1800
cgacaaaact cacacatgcc caccgtgccc agcacctgaa ctcctggggg gaccgtcagt      1860
cttcctcttc cccccaaaac ccaaggacac cctcatgatc tcccgggacc ctgaggtcac      1920
atgcgtggtg gtggacgtga gccacgaaga ccctgaggtc aagttcaact ggtacgtgga      1980
```

```
cggcgtggag gtgcataatg ccaagacaaa gccgcgggag gagcagtaca acagcacgta    2040
ccgggtggtc agcgtcctca ccgtcctgca ccaggactgg ctgaatggca aggagtacaa    2100
gtgcaaggtc tccaacaaag ccctcccagc ccccatcgag aaaaccatct ccaaagccaa    2160
agggcagccc cgagaaccac aggtgtacac cctgccccca tcccgggatg agctgaccaa    2220
gaaccaggtc agcctgacct gcctggtcaa aggcttctat cccagcgaca tcgccgtgga    2280
gtgggagagc aatgggcagc cggagaacaa ctacaagacc acgcctcccg tgctggactc    2340
cgacggctcc ttcttcctct acagcaagct caccgtggac aagagcaggt ggcagcaggg    2400
gaacgtcttc tcatgctccg tgatgcatga ggctctgcac aaccactaca cgcagaagag    2460
cctctccctg tctccgggta acgggccaa gcgggcaccc gtgaagcaga ccctgaactt    2520
cgacctgctg aagctggccg cgacgtgga gagcaacccc ggccccatga ggctccctgc    2580
tcagctcctg gggctgctaa tgctctgggt ccctggctcg agtgaggttc tgcctgtgct    2640
gactcagcca ccctcagcgt ctgcgacccc cgggcagagg gtcaccatct cttgttctgg    2700
aagcagctcc aacatcgggc gtaatactgt aaactggtac cagcgtctcc caggaacggc    2760
ccccaaactc ctcatctata atactaatca gcggccctca ggggtccctg accgattctc    2820
tggctccaag tctggcacct cagccgccct ggccatcagt ggactccagt ctgaggatga    2880
ggctgagtat tactgtgcag cctgggatga cagcctgaat ggcctttctt gggtgttcgg    2940
cggagggacc aagctgaccg tcctaagtca gcccaaggct gccccctcgg tcactctgtt    3000
cccgccctcc tctgaggagc ttcaagccaa caaggccaca ctggtgtgtc tcataagtga    3060
cttctacccg ggagccgtga cagcctggaa ggcagatagc agccacgtca aggcgggagt    3120
ggagaccacc acaccctcca aacaaagcaa caacaagtac gcggccagca gctacctgag    3180
cctgacgcct gagcagtgga agtcccacaa aagctacagc tgccaggtca cgcatgaagg    3240
gagcaccgtg gagaagacaa ttgcccctac agaatgctca taaggccggg acggccggta    3300
ccaggtaagt gtacccaatt cgccctatag tgagtcgtat tacaattcac tcgatcgccc    3360
ttcccaacag ttgcgcagcc tgaatggcga atggagatcc aattttttaag tgtataatgt    3420 gttaaactac tgattctaat tgtttgtgta ttttagattc acagtcccaa ggctcatttc    3480
aggcccctca gtcctcacag tctgttcatg atcataatca gccataccac atttgtagag    3540
gttttacttg cttaaaaaaa cctcccacac ctccccctga acctgaaaca taaaatgaat    3600
gcaattgttg ttgttaactt gtttattgca gcttataatg gttacaaata aagcaatagc    3660
atcacaaatt tcacaaataa agcatttttt tcactgcatt ctagttgtgg tttgtccaaa    3720
ctcatcaatg tatcttaacg cgtaaattgt aagcgttaat attttgttaa aattcgcgtt    3780
aaatttttgt taaatcagct cattttttaa ccaataggcc gaaatcggca aaatccctta    3840
taaatcaaaa gaatagaccg agatagggtt gagtgttgtt ccagtttgga acaagagtcc    3900
actattaaag aacgtggact ccaacgtcaa agggcgaaaa accgtctatc agggcgatgg    3960
cccactacgt gaaccatcac cctaatcaag ttttttgggg tcgaggtgcc gtaaagcact    4020
aaatcggaac cctaaaggga gcccccgatt tagagcttga cggggaaagc cggcgaacgt    4080
ggcgagaaag gaagggaaga agcgaaagg agcgggcgct agggcgctgg caagtgtagc    4140
ggtcacgctg cgcgtaacca ccacacccgc cgcgcttaat gcgccgctac agggcgcgtc    4200
aggtggcact tttcggggaa atgtgcgcgg aacccctatt tgtttatttt tctaaataca    4260
ttcaaatatg tatccgctca tgagacaata accctgataa atgcttcaat aatattgaaa    4320
aaggaagaat cctgaggcgg aaagaaccag ctgtggaatg tgtgtcagtt agggtgtgga    4380
```

```
aagtccccag gctccccagc aggcagaagt atgcaaagca tgcatctcaa ttagtcagca    4440
accaggtgtg gaaagtcccc aggctcccca gcaggcagaa gtatgcaaag catgcatctc    4500
aattagtcag caaccatagt cccgcccta actccgccca tcccgcccct aactccgccc     4560
agttccgccc attctccgcc ccatggctga ctaattttt ttatttatgc agaggccgag     4620
gccgcctccg cctctgagct attccagaag tagtgaggag gcttttttgg aggcctaggc    4680
ttttgcaaag atcgatcaag agacaggatg aggatcgttt cgcatgattg aacaagatgg    4740
attgcacgca ggttctccgg ccgcttgggt ggagaggcta ttcggctatg actgggcaca    4800
acagacaatc ggctgctctg atgccgccgt gttccggctg tcagcgcagg ggcgcccggt    4860 tcttttgtc aagaccgacc tgtccggtgc cctgaatgaa ctgcaagacg aggcagcgcg     4920
gctatcgtgg ctggccacga cgggcgttcc ttgcgcagct gtgctcgacg ttgtcactga    4980
agcgggaagg gactggctgc tattgggcga agtgccgggg caggatctcc tgtcatctca    5040
ccttgctcct gccgagaaag tatccatcat ggctgatgca atgcggcggc tgcatacgct    5100
tgatccggct acctgcccat tcgaccacca agcgaaacat cgcatcgagc gagcacgtac    5160
tcggatggaa gccggtcttg tcgatcagga tgatctggac gaagaacatc aggggctcgc    5220
gccagccgaa ctgttcgcca ggctcaaggc gagcatgccc gacggcgagg atctcgtcgt    5280
gacccatggc gatgcctgct tgccgaatat catggtggaa aatggccgct tttctggatt    5340
catcgactgt ggccggctgg gtgtggcgga ccgctatcag gacatagcgt tggctacccg    5400
tgatattgct gaagaacttg gcggcgaatg ggctgaccgc ttcctcgtgc tttacggtat    5460
cgccgctccc gattcgcagc gcatcgcctt ctatcgcctt cttgacgagt tcttctgagc    5520
gggactctgg ggttcgaaat gaccgaccaa gcgacgccca acctgccatc acgagatttc    5580
gattccaccg ccgccttcta tgaaaggttg ggcttcggaa tcgttttccg ggacgccggc    5640
tggatgatcc tccagcgcgg ggatctcatg ctggagttct cgccacccc tagggggagg    5700 ctaactgaaa cacggaagga gacaataccg gaaggaaccc gcgctatgac ggcaataaaa    5760
agacagaata aaacgcacgg tgttgggtcg tttgttcata acgcggggt tcggtcccag     5820 ggctggcact ctgtcgatac cccaccgaga ccccattggg gccaatacgc ccgcgtttct    5880
tccttttccc cacccacc cccaagttcg ggtgaaggcc cagggctcgc agccaacgtc       5940
ggggcggcag gccctgccat agcctcaggt tactcatata ctttagat tgatttaaaa      6000 cttcattttt aatttaaaag gatctaggtg aagatccttt ttgataatct catgaccaaa    6060
atcccttaac gtgagttttc gttccactga gcgtcagacc ccgtagaaaa gatcaaagga    6120
tcttcttgag atcctttttt tctgcgcgta atctgctgct tgcaaacaaa aaaaccaccg    6180
ctaccagcgg tggtttgttt gccggatcaa gagctaccaa ctctttttcc gaaggtaact    6240
ggcttcagca gagcgcagat accaaatact gtccttctag tgtagccgta gttaggccac    6300
cacttcaaga actctgtagc accgcctaca tacctcgctc tgctaatcct gttaccagtg    6360
gctgctgcca gtggcgataa gtcgtgtctt accgggttgg actcaagacg atagttaccg    6420
gataaggcgc agcggtcggg ctgaacgggg ggttcgtgca cacagcccag cttggagcga    6480
acgacctaca ccgaactgag atacctacag cgtgagctat gagaaagcgc cacgcttccc    6540
gaagggagaa aggcggacag gtatccggta agcggcaggg tcggaacagg agagcgcacg    6600
agggagcttc caggggggaaa cgcctggtat ctttatagtc ctgtcgggtt cgccacctc    6660 tgacttgagc gtcgattttt gtgatgctcg tcagggggc ggagcctatg gaaaaacgcc     6720
```

```
agcaacgcgg cctttttacg gttcctggcc ttttgctggc cttttgctca catgttcttt    6780
cctgcgttat cccctgattc tgtggataac cgtattaccg cc                       6822
```

<210> SEQ ID NO 392
<211> LENGTH: 61
<212> TYPE: DNA
<213> ORGANISM: Artificial Sequence
<220> FEATURE:
<223> OTHER INFORMATION: FabLinkerCLambda-Fwd

<400> SEQUENCE: 392

```
gacartkgcc cmtrcagaat gctcataatt aattaataag gaggatataa ttatgaaaaa    60
g                                                                     61
```

<210> SEQ ID NO 393
<211> LENGTH: 42
<212> TYPE: DNA
<213> ORGANISM: Artificial Sequence
<220> FEATURE:
<223> OTHER INFORMATION: FabLinker-Rev-IT*

<400> SEQUENCE: 393

```
tgcggccgcc tacgctacgg tagcaaagcc agccagtgcc ac                       42
```

<210> SEQ ID NO 394
<211> LENGTH: 5882
<212> TYPE: DNA
<213> ORGANISM: Artificial Sequence
<220> FEATURE:
<223> OTHER INFORMATION: 2G12 pCAL IT* vector

<400> SEQUENCE: 394

```
gtggcacttt tcggggaaat gtgcgcggaa cccctatttg tttatttttc taaatacatt    60
caaatatgta tccgctcatg agacaataac cctgataaat gcttcaataa tattgaaaaa   120
ggaagagtat gagtattcaa catttccgtg tcgcccttat tccctttttt gcggcatttt   180
gccttcctgt ttttgctcac ccagaaacgc tggtgaaagt aaaagatgct gaagatcagt   240
tgggtgcacg agtgggttac atcgaactgg atctcaacag cggtaagatc cttgagagtt   300
ttcgccccga agaacgtttt ccaatgatga gcacttttaa agttctgcta tgtggcgcgg   360
tattatcccg tattgacgcc gggcaagagc aactcggtcg ccgcatacac tattctcaga   420
atgacttggt tgagtactca ccagtcacag aaaagcatct tacggatggc atgacagtaa   480
gagaattatg cagtgctgcc ataaccatga gtgataacac tgcggccaac ttacttctga   540
caacgatcgg aggaccgaag gagctaaccg cttttttgca acatggggga tcatgtaa    600 ctcgccttga tcgttgggaa ccggagctga atgaagccat accaaacgac gagcgtgaca   660
ccacgatgcc tgtagcaatg gcaacaacgt tgcgcaaact attaactggc gaactactta   720
ctctagcttc ccggcaacaa ttaatagact ggatggaggc ggataaagtt gcaggaccac   780
ttctgcgctc ggcccttccg gctggctggt ttattgctga taaatctgga gccggtgagc   840
gtgggtctcg cggtatcatt gcagcactgg ggccagatgg taagccctcc cgtatcgtag   900
ttatctacac gacggggagt caggcaacta tggatgaacg aaatagacag atcgctgaga   960
taggtgcctc actgattaag cattggtaac tgtcagacca agtttactca tatatacttt  1020
agattgattt aaaacttcat ttttaattta aaaggatcta ggtgaagatc ctttttgata  1080
atctcatgac caaaatccct taacgtgagt tttcgttcca ctgagcgtca gaccccgtag  1140
aaaagatcaa aggatcttct tgagatcctt ttttctgcg cgtaatctgc tgcttgcaaa  1200
```

```
caaaaaaacc accgctacca gcggtggttt gtttgccgga tcaagagcta ccaactcttt    1260
ttccgaaggt aactggcttc agcagagcgc agataccaaa tactgtcctt ctagtgtagc    1320
cgtagttagg ccaccacttc aagaactctg tagcaccgcc tacatacctc gctctgctaa    1380
tcctgttacc agtggctgct gccagtgcg ataagtcgtg tcttaccggg ttggactcaa    1440
gacgatagtt accggataag gcgcagcggt cgggctgaac ggggggttcg tgcacacagc    1500
ccagcttgga gcgaacgacc tacaccgaac tgagatacct acagcgtgag ctatgagaaa    1560
gcgccacgct tcccgaaggg agaaaggcgg acaggtatcc ggtaagcggc agggtcggaa    1620
caggagagcg cacgagggag cttccagggg gaaacgcctg gtatctttat agtcctgtcg    1680
ggtttcgcca cctctgactt gagcgtcgat ttttgtgatg ctcgtcaggg gggcggagcc    1740
tatgaaaaaa cgccagcaac gcggcctttt tacggttcct ggccttttgc tggcttttg    1800 ctcacatgtt ctttcctgcg ttatccctg attctgtgga taaccgtatt accgcctttg    1860
agtgagctga taccgctcgc cgcagccgaa cgaccgagcg cagcgagtca gtgagcgagg    1920
aagcgacacc atcgaatggc gcaaaacctt tcgcggtatg gcatgatagc gcccggaaga    1980
gagtcaattc agggtggtga atgtgaaacc agtaacgtta tacgatgtcg cagagtatgc    2040
cggtgtctct tatcagaccg tttcccgcgt ggtgaaccag gccagccacg tttctgcgaa    2100
aacgcgggaa aaagtggaag cggcgatggc ggagctgaat tacattccca accgcgtggc    2160
acaacaactg gcgggcaaac agtcgttgct gattggcgtt gccacctcca gtctggccct    2220
gcacgcgccg tcgcaaattg tcgcggcgat taaatctcgc gccgatcaac tgggtgccag    2280
cgtggtggtg tcgatggtag aacgaagcgg cgtcgaagcc tgtaaagcgg cggtgcacaa    2340
tcttctcgcg caacgcgtca gtgggctgat cattaactat ccgctggatg accaggatgc    2400
cattgctgtg gaagctgcct gcactaatgt tccggcgtta tttcttgatg tctctgacca    2460
gacacccatc aacagtatta ttttctccca tgaagacggt acgcgactgg gcgtggagca    2520
tctggtcgca ttgggtcacc agcaaatcgc gctgttagcg ggcccattaa gttctgtctc    2580
ggcgcgtctg cgtctggctg ctggcataa atatctcact cgcaatcaaa ttcagccgat    2640
agcggaacgg gaaggcgact ggagtgccat gtccggtttt caacaaacca tgcaaatgct    2700
gaatgagggc atcgttccca ctgcgatgct ggttgccaac gatcagatgg cgctgggcgc    2760
aatgcgcgcc attaccgagt ccgggctgcg cgttggtgcg gatatctcgg tagtgggata    2820
cgacgatacc gaagacagct catgttatat cccgccgtta accaccatca aacaggattt    2880
tcgcctgctg gggcaaacca gcgtggaccg cttgctgcaa ctctctcagg ccaggcggt    2940 gaagggcaat cagctgttgc ccgtctcact ggtgaaaaga aaaaccaccc tggcgcccaa    3000
tacgcaaacc gcctctcccc gcgcgttggc cgattcatta atgcagctgg cacgacaggt    3060
ttcccgactg gaaagcgggc agtgagcggt acccgataaa agcggcttcc tgacaggagg    3120
ccgttttgtt ttgcagccca cctcaacgca attaatgtga gttagctcac tcattaggca    3180
ccccaggctt tacactttat gcttccggct cgtatgttgt gtggaattgt gagcggataa    3240
caattgaatt aaggaggata taattatgaa ataccctgctg ccgaccgcag ccgctggtct    3300
gctgctgctc gcggcctagc cggccatggc cgccggtgtt ttatgaccc agtctccgtc    3360 taccctgtct gcttctgttg gtgacaccat caccatcacc tgccgtgctt ctcagtctat    3420
cgaaacctgg ctggcttggt accagcagaa accgggtaaa gctccgaaac tgctgatcta    3480
caaggcttct accctgaaaa ccggtgttcc gtctcgtttc tctggttctg gttctggtac    3540
```

-continued

| | |
|---|---|
| cgagttcacc ctgaccatct ctggtctgca gttcgacgac ttcgctacct accactgcca | 3600 |
| gcactacgct ggttactctg ctaccttcgg tcagggtacc cgtgttgaaa tcaaacgtac | 3660 |
| cgttgctgct ccgtctgttt tcatcttccc gccgtctgac gaacagctga atctggtac | 3720 |
| cgcttctgtt gtttgcctgc tgaacaactt ctacccgcgt gaagctaaag ttcagtggaa | 3780 |
| agttgacaac gctctgcagt ctggtaactc tcaggaatct gttaccgaac aggactctaa | 3840 |
| agactctacc tactctctgt cttctaccct gaccctgtct aaagctgact acgaaaagca | 3900 |
| caaagtttac gcttgcgaag ttacccacca gggtctgtct tctccggtta ccaaatcttt | 3960 |
| caaccgtggt gaatgctaat taattaataa ggaggatata attatgaaaa agacagctat | 4020 |
| cgcgattgca gtggcactgg ctggtttcgc taccgtagcc taggcggccg cagaagttca | 4080 |
| gctggttgaa tctggtggtg gtctggttaa agctggtggt tctctgatcc tgtcttgcgg | 4140 |
| tgtttctaac ttccgtatct ctgctcacac catgaactgg gttcgtcgtg ttccgggtgg | 4200 |
| tggtctggaa tgggttgctt ctatctctac ctcttctacc taccgtgact acgctgacgc | 4260 |
| tgttaaaggt cgtttcaccg tttctcgtga cgacctggaa gacttcgttt acctgcagat | 4320 |
| gcataaaatg cgtgttgaag acaccgctat ctactactgc gctcgtaaag ttctgaccg | 4380 |
| tctgtctgac aacgacccgt tcgacgcttg gggtccgggt accgttgtta ccgtttctcc | 4440 |
| ggcgtcgacc aaaggtccgt ctgttttccc gctggctccg tcttctaaat ctacctctgg | 4500 |
| tggtaccgct gctctgggtt gcctggtaa agactacttc ccggaaccgg ttaccgtttc | 4560 |
| ttggaactct ggtgctctga cctctggtgt tcacaccttc ccggctgttc tgcagtcttc | 4620 |
| tggtctgtac tctctgtctt ctgttgttac cgttccgtct tcttctctgg gtacccagac | 4680 |
| ctacatctgc aacgttaacc acaaaccgtc taacaccaaa gttgacaaga agttgaacc | 4740 |
| gaaatcttgc ctgcgatcgc ggccaggccg gccgcaccat caccatcacc atggcgcata | 4800 |
| cccgtacgac gttccggact acgcttctac tagttaggag ggtggtggct ctgagggtgg | 4860 |
| cggttctgag ggtggcggct ctgagggagg cggttccggt ggtggctctg ttccggtga | 4920 |
| ttttgattat gaaaagatgg caaacgctaa taaggggggct atgaccgaaa atgccgatga | 4980 |
| aaacgcgcta cagtctgacg ctaaaggcaa acttgattct gtcgctactg attacggtgc | 5040 |
| tgctatcgat ggtttcattg gtgacgtttc cggccttgct aatggtaatg gtgctactgg | 5100 |
| tgattttgct ggctctaatt cccaaatggc tcaagtcggt gacggtgata attcacctt | 5160 |
| aatgaataat ttccgtcaat atttaccttc cctccctcaa tcggttgaat gtcgccttt | 5220 |
| tgtctttggc gctggtaaac catatgaatt ttctattgat tgtgacaaaa taaacttatt | 5280 |
| ccgtggtgtc tttgcgtttc ttttatatgt tgccaccttt atgtatgtat tttctacgtt | 5340 |
| tgctaacata ctgcgtaata aggagtctta agctagctaa cgatcgccct tcccaacagt | 5400 |
| tgcgcagcct gaatggcgaa tgggacgcgc cctgtagcgg cgcattaagc gcggcgggtg | 5460 |
| tggtggttac gcgcagcgtg accgctacac ttgccagcgc cctagcgccc gctcctttcg | 5520 |
| ctttcttccc ttcctttctc gccacgttcg ccggctttcc ccgtcaagct ctaaatcggg | 5580 |
| ggctcccttt agggttccga tttagtgctt tacggcacct cgaccccaaa aaacttgatt | 5640 |
| agggtgatgg ttcacgtagt gggccatcgc cctgatagac ggtttttcgc cctttgacgt | 5700 |
| tggagtccac gttctttaat agtggactct tgttccaaac tggaacaaca ctcaacccta | 5760 |
| tctcggtcta ttcttttgat ttataaggga ttttgccgat ttcggcctat tggttaaaaa | 5820 |
| atgagctgat ttaacaaaaa tttaacgcga attttaacaa aatattaacg cttacaattt | 5880 |
| ag | 5882 |

```
<210> SEQ ID NO 395
<211> LENGTH: 214
<212> TYPE: PRT
<213> ORGANISM: Artificial Sequence
<220> FEATURE:
<223> OTHER INFORMATION: 30D8 Light Chain

<400> SEQUENCE: 395

Gln Ser Val Leu Thr Gln Ala Ser Ser Val Ser Val Ala Pro Gly Gln
 1               5                  10                  15

Thr Ala Arg Ile Thr Cys Gly Ala Asn Asn Ile Gly Ser Gln Asn Val
            20                  25                  30

His Trp Tyr Gln Gln Lys Pro Gly Gln Ala Pro Val Leu Val Val Tyr
        35                  40                  45

Asp Asp Arg Asp Arg Pro Ser Gly Ile Pro Asp Arg Phe Ser Gly Ser
    50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp Ser Ser Arg Asp Gln
                85                  90                  95

Ala Val Ile Phe Gly Gly Gly Thr Lys Leu Thr Val Leu Gly Gln Pro
            100                 105                 110

Lys Ala Ala Pro Ser Val Thr Leu Phe Pro Pro Ser Ser Glu Glu Leu
        115                 120                 125

Gln Ala Asn Lys Ala Thr Leu Val Cys Leu Ile Ser Asp Phe Tyr Pro
    130                 135                 140

Gly Ala Val Thr Val Ala Trp Lys Ala Asp Ser Ser Pro Val Lys Ala
145                 150                 155                 160

Gly Val Glu Thr Thr Thr Pro Ser Lys Gln Ser Asn Asn Lys Tyr Ala
                165                 170                 175

Ala Ser Ser Tyr Leu Ser Leu Thr Pro Glu Gln Trp Lys Ser His Arg
            180                 185                 190

Ser Tyr Ser Cys Gln Val Thr His Glu Gly Ser Thr Val Glu Lys Thr
        195                 200                 205

Ile Ala Pro Thr Glu Cys
    210

<210> SEQ ID NO 396
<211> LENGTH: 224
<212> TYPE: PRT
<213> ORGANISM: Artificial Sequence
<220> FEATURE:
<223> OTHER INFORMATION: 30D8 Fab Heavy Chain

<400> SEQUENCE: 396

Glu Val Gln Leu Leu Gln Ser Gly Ala Glu Leu Lys Lys Pro Gly Ala
 1               5                  10                  15

Ser Val Lys Ile Ser Cys Lys Thr Ser Gly Phe Thr Phe Ser Gly His
            20                  25                  30

Thr Ile Ala Trp Val Arg Gln Ala Pro Gly Gln Gly Leu Glu Trp Met
        35                  40                  45

Gly Trp Val Ser Thr Asn Asn Gly Asn Thr Glu Tyr Ala Gln Lys Ile
    50                  55                  60

Gln Gly Arg Val Thr Met Thr Met Asp Thr Ser Thr Ser Thr Val Tyr
65                  70                  75                  80

Met Glu Leu Arg Ser Leu Thr Ser Asp Asp Thr Ala Val Tyr Phe Cys
```

```
            85                  90                  95
Ala Arg Glu Trp Leu Val Met Gly Gly Phe Ala Phe Asp His Trp Gly
            100                 105                 110

Gln Gly Thr Leu Leu Thr Val Ser Ser Ala Ser Thr Lys Gly Pro Ser
            115                 120                 125

Val Phe Pro Leu Ala Pro Ser Ser Lys Ser Thr Ser Gly Gly Thr Ala
130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
            165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
            195                 200                 205

Lys Pro Ser Asn Thr Lys Val Asp Lys Arg Val Glu Pro Lys Ser Cys
            210                 215                 220

<210> SEQ ID NO 397
<211> LENGTH: 214
<212> TYPE: PRT
<213> ORGANISM: Artificial Sequence
<220> FEATURE:
<223> OTHER INFORMATION: 104E5 Light Chain

<400> SEQUENCE: 397

Asp Ile Gln Met Thr Gln Ser Pro Ser Ser Leu Pro Ala Ser Val Gly
1               5                   10                  15

Asp Arg Val Thr Ile Thr Cys Arg Ala Ser Gln Asn Ile Lys Thr Tyr
            20                  25                  30

Leu Asn Trp Tyr Gln Gln Lys Pro Gly Arg Ala Pro Lys Leu Leu Ile
        35                  40                  45

Ser Ala Val Ser Asn Leu Gln Ser Gly Val Pro Ser Arg Phe Ser Gly
    50                  55                  60

Thr Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Phe Ser Ile Pro Leu
                85                  90                  95

Thr Phe Gly Gly Gly Ala Lys Val Glu Ile Lys Arg Thr Val Ala Ala
            100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
            165                 170                 175

Ser Thr Leu Thr Leu Ser Lys Ala Asp Tyr Glu Lys His Lys Leu Tyr
            180                 185                 190

Ala Cys Glu Val Thr His Gln Gly Leu Ser Ser Pro Val Thr Lys Ser
            195                 200                 205

Phe Asn Arg Gly Glu Cys
            210
```

```
<210> SEQ ID NO 398
<211> LENGTH: 228
<212> TYPE: PRT
<213> ORGANISM: Artificial Sequence
<220> FEATURE:
<223> OTHER INFORMATION: 104E5 Fab Heavy Chain

<400> SEQUENCE: 398
```

| Gln | Val | Gln | Leu | Glu | Gln | Ser | Gly | Ala | Glu | Val | Lys | Pro | Gly | Ser |
|---|---|---|---|---|---|---|---|---|---|---|---|---|---|---|
| 1 | | | | 5 | | | | | 10 | | | | | 15 |

| Ser | Val | Lys | Val | Ser | Cys | Lys | Pro | Ser | Gly | Gly | Thr | Phe | Asp | Thr | Tyr |
| | | | 20 | | | | | 25 | | | | | 30 | | |

| Thr | Ile | Ser | Trp | Val | Arg | Gln | Ala | Pro | Gly | Gln | Arg | Leu | Glu | Trp | Leu |
| | | 35 | | | | | 40 | | | | | 45 | | | |

| Gly | Arg | Ile | Ile | Pro | Ser | Leu | Gly | Glu | Thr | Asn | Tyr | Ala | His | Lys | Leu |
| 50 | | | | | 55 | | | | | 60 | | | | | |

| Gln | Gly | Arg | Val | Thr | Ile | Thr | Ala | Asp | Lys | Ala | Thr | Ser | Val | Val | Tyr |
| 65 | | | | 70 | | | | | 75 | | | | | 80 | |

| Met | Asp | Leu | Ser | Asp | Leu | Thr | Ser | Glu | Asp | Ala | Ala | Val | Tyr | Tyr | Cys |
| | | | | 85 | | | | | 90 | | | | | 95 | |

| Ala | Phe | Arg | Ile | Thr | Gly | Pro | Val | Asp | Trp | Val | Trp | Asp | Tyr | Gly | Met |
| | | | 100 | | | | | 105 | | | | | 110 | | |

| Asp | Val | Trp | Gly | Gln | Gly | Thr | Thr | Val | Ser | Val | Ser | Ser | Ala | Ser | Ser |
| | | 115 | | | | | 120 | | | | | 125 | | | |

| Lys | Gly | Pro | Ser | Val | Phe | Pro | Leu | Ala | Pro | Ser | Ser | Lys | Ser | Thr | Ser |
| 130 | | | | | 135 | | | | | 140 | | | | | |

| Gly | Gly | Thr | Ala | Ala | Leu | Gly | Cys | Leu | Val | Lys | Asp | Tyr | Phe | Pro | Glu |
| 145 | | | | | 150 | | | | | 155 | | | | | 160 |

| Pro | Val | Thr | Val | Ser | Trp | Asn | Ser | Gly | Ala | Leu | Thr | Ser | Gly | Val | His |
| | | | 165 | | | | | 170 | | | | | 175 | | |

| Thr | Phe | Pro | Ala | Val | Leu | Gln | Ser | Ser | Gly | Leu | Tyr | Ser | Leu | Ser | Ser |
| | | | 180 | | | | | 185 | | | | | 190 | | |

| Val | Val | Thr | Val | Pro | Ser | Ser | Leu | Gly | Thr | Gln | Thr | Tyr | Ile | Cys |
| | | | 195 | | | | | 200 | | | | | 205 | |

| Asn | Val | Asn | His | Lys | Pro | Ser | Asn | Thr | Lys | Val | Asp | Lys | Arg | Val | Glu |
| | | 210 | | | | | 215 | | | | | 220 | | | |

| Pro | Lys | Ser | Cys |
| 225 | | | |

```
<210> SEQ ID NO 399
<211> LENGTH: 215
<212> TYPE: PRT
<213> ORGANISM: Artificial Sequence
<220> FEATURE:
<223> OTHER INFORMATION: 38F10 Light Chain

<400> SEQUENCE: 399
```

| Asp | Ile | Gln | Leu | Thr | Gln | Ser | Pro | Pro | Thr | Leu | Ser | Ala | Ser | Val | Gly |
|---|---|---|---|---|---|---|---|---|---|---|---|---|---|---|---|
| 1 | | | | 5 | | | | | 10 | | | | | 15 | |

| Asp | Arg | Val | Ser | Met | Thr | Cys | Arg | Ala | Ser | Gln | Ser | Ile | Ser | Asn | Trp |
| | | | 20 | | | | | 25 | | | | | 30 | | |

| Leu | Ala | Trp | Tyr | Gln | Gln | Lys | Pro | Gly | Lys | Ala | Pro | Lys | Leu | Leu | Ile |
| | | 35 | | | | | 40 | | | | | 45 | | | |

| Gln | Lys | Ala | Ser | Asn | Leu | Glu | Asp | Gly | Val | Pro | Ser | Arg | Phe | Thr | Ala |
| | 50 | | | | | 55 | | | | | 60 | | | | |

| Ser | Gly | Phe | Gly | Thr | Glu | Phe | Thr | Leu | Thr | Ile | Ser | Ser | Leu | Gln | Pro |
| 65 | | | | | 70 | | | | | 75 | | | | | 80 |

Asp Asp Phe Ala Thr Tyr Tyr Cys Gln Gln Tyr Asn Ser Tyr Ser Gly
                85                  90                  95

Leu Ser Phe Gly Gly Gly Thr Lys Val Asp Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215

<210> SEQ ID NO 400
<211> LENGTH: 227
<212> TYPE: PRT
<213> ORGANISM: Artificial Sequence
<220> FEATURE:
<223> OTHER INFORMATION: 38F10 Fab Heavy Chain

<400> SEQUENCE: 400

Glu Val Gln Leu Leu Glu Ser Gly Gly Asp Val Val Gln Pro Gly Lys
1               5                   10                  15

Ser Leu Arg Leu Ser Cys Thr Ala Ser Gly Phe Ser Ile Thr Asp Phe
            20                  25                  30

Gly Ile His Trp Val Arg Gln Ala Pro Gly Lys Gly Leu Glu Trp Val
        35                  40                  45

Ala Leu Ile Ser Tyr Asn Glu Val Asn Ile His Tyr Gly Glu Ser Val
    50                  55                  60

Arg Gly Arg Phe Thr Ile Ser Arg Asp Ile Ala Lys Asn Thr Val Tyr
65                  70                  75                  80

Leu Gln Met Asn Gly Leu Arg Pro Glu Asp Thr Gly Val Tyr Phe Cys
                85                  90                  95

Ala Arg Asp Val Trp Glu Asp Ser Trp Leu Ser Leu Ala Cys Phe Gln
            100                 105                 110

Glu Trp Gly Gln Gly Ser Leu Val Val Ser Ser Ala Ser Thr Lys
        115                 120                 125

Gly Pro Ser Val Phe Pro Leu Ala Pro Ser Ser Lys Ser Thr Ser Gly
    130                 135                 140

Gly Thr Ala Ala Leu Gly Cys Leu Val Lys Asp Tyr Phe Pro Glu Pro
145                 150                 155                 160

Val Thr Val Ser Trp Asn Ser Gly Ala Leu Thr Ser Gly Val His Thr
                165                 170                 175

Phe Pro Ala Val Leu Gln Ser Ser Gly Leu Tyr Ser Leu Ser Ser Val
            180                 185                 190

Val Thr Val Pro Ser Ser Ser Leu Gly Thr Gln Thr Tyr Ile Cys Asn
        195                 200                 205

Val Asn His Lys Pro Ser Asn Thr Lys Val Asp Lys Lys Val Glu Pro
    210                 215                 220

```
Lys Ser Cys
225

<210> SEQ ID NO 401
<211> LENGTH: 220
<212> TYPE: PRT
<213> ORGANISM: Artificial Sequence
<220> FEATURE:
<223> OTHER INFORMATION: 14G3 Light Chain

<400> SEQUENCE: 401

Asp Val Val Met Thr Gln Thr Pro Leu Ser Leu Ser Val Thr Pro Gly
1               5                   10                  15

Glu Pro Ala Ser Ile Ser Cys Arg Ser Ser Gln Ser Leu Leu Asp Ser
            20                  25                  30

Asp Asp Gly Asn Thr Tyr Leu Asp Trp Tyr Leu Gln Lys Pro Gly Gln
        35                  40                  45

Ser Pro Gln Leu Leu Ile Tyr Thr Leu Ser Tyr Arg Ala Ser Gly Val
    50                  55                  60

Pro Asp Arg Phe Ser Gly Ser Gly Ser Gly Thr Asp Phe Thr Leu Lys
65                  70                  75                  80

Ile Ser Arg Val Glu Ala Asp Asp Val Gly Ile Tyr Tyr Cys Met Gln
                85                  90                  95

Arg Met Glu Phe Pro Phe Thr Phe Gly Gln Gly Thr Arg Leu Asp Ile
            100                 105                 110

Lys Arg Thr Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
    130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
        195                 200                 205

Ser Pro Val Thr Lys Ser Phe Asn Arg Gly Glu Cys
    210                 215                 220

<210> SEQ ID NO 402
<211> LENGTH: 228
<212> TYPE: PRT
<213> ORGANISM: Artificial Sequence
<220> FEATURE:
<223> OTHER INFORMATION: 14G3 Fab Heavy Chain

<400> SEQUENCE: 402

Gln Val Gln Leu Gln Glu Ser Gly Pro Gly Leu Val Lys Pro Ser Gln
1               5                   10                  15

Thr Leu Ser Leu Thr Cys Thr Val Ser Gly Ala Ser Ile Ser Ser Asp
            20                  25                  30

Asn His Tyr Trp Ser Trp Ile Arg Gln Pro Pro Gly Lys Gly Leu Glu
        35                  40                  45

Trp Ile Ala Ser Ile Tyr Tyr Thr Gly Gly Thr Asn Tyr Asn Pro Ser
    50                  55                  60

Leu Lys Ser Arg Leu Ala Leu Ser Ile Asp Thr Ser Gly Asp Gln Phe
65                  70                  75                  80
```

```
Ser Leu Lys Leu Ser Ser Val Thr Ala Ala Asp Thr Ala Val Tyr Tyr
                85                  90                  95

Cys Val Arg Gly Leu Phe Phe Ile Thr Ala Arg Pro Tyr Trp Tyr Phe
            100                 105                 110

Asp Leu Trp Gly Arg Gly Thr Leu Val Ala Val Ser Ser Ala Ser Thr
        115                 120                 125

Lys Gly Pro Ser Val Phe Pro Leu Ala Pro Ser Ser Lys Ser Thr Ser
130                 135                 140

Gly Gly Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Leu Tyr Ser Leu Ser Ser
            180                 185                 190

Val Val Thr Val Pro Ser Ser Ser Leu Gly Thr Gln Thr Tyr Ile Cys
        195                 200                 205

Asn Val Asn His Lys Pro Ser Asn Thr Lys Val Asp Lys Arg Val Glu
    210                 215                 220

Pro Lys Ser Cys
225

<210> SEQ ID NO 403
<211> LENGTH: 214
<212> TYPE: PRT
<213> ORGANISM: Artificial Sequence
<220> FEATURE:
<223> OTHER INFORMATION: 90D3 Light Chain

<400> SEQUENCE: 403

Ala Ile Arg Leu Thr Gln Ser Pro Ser Ser Leu Ser Ala Ser Val Gly
  1               5                  10                  15

Asp Arg Val Ser Ile Thr Cys Arg Ala Ser Gln Ser Ile Ser Asn Phe
             20                  25                  30

Leu Asn Trp Tyr Gln Gln Lys Pro Gly Arg Ala Pro Lys Leu Leu Ile
         35                  40                  45

Ser Ala Ala Ser Ser Leu Gln Gly Gly Val Pro Ser Arg Phe Ser Gly
 50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Thr Tyr Ile Ser Leu Tyr
                85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205
```

Phe Asn Arg Gly Glu Cys
    210

<210> SEQ ID NO 404
<211> LENGTH: 226
<212> TYPE: PRT
<213> ORGANISM: Artificial Sequence
<220> FEATURE:
<223> OTHER INFORMATION: 90D3 Fab Heavy Chain

<400> SEQUENCE: 404

Gln Val Gln Leu Val Glu Ser Gly Gly Gly Leu Val Lys Pro Gly Gly
1               5                   10                  15

Ser Leu Arg Leu Ser Cys Val Gly Ser Gly Phe Thr Leu Lys Asn Tyr
            20                  25                  30

Glu Met Asn Trp Val Arg Gln Ala Pro Gly Gln Gly Leu Gln Tyr Ile
        35                  40                  45

Ser Tyr Ile Ser Ser Ser Gly Asn Val Val Lys Tyr Val Asp Ser Val
    50                  55                  60

Gln Gly Arg Phe Thr Ile Ser Arg Asp Asn Ala Gly Asn Ser Leu Tyr
65                  70                  75                  80

Leu Gln Met Asn Asn Leu Arg Ala Glu Asp Thr Ala Thr Tyr Tyr Cys
                85                  90                  95

Val Arg Gly Phe Ser Ile Asp Lys Tyr Asp Ser Ser Val Asp Glu Tyr
            100                 105                 110

Trp Gly Gln Gly Ile Ala Val Thr Val Ser Ser Ala Ser Thr Lys Gly
        115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Lys Val Glu Pro Lys
    210                 215                 220

Ser Cys
225

<210> SEQ ID NO 405
<211> LENGTH: 10
<212> TYPE: PRT
<213> ORGANISM: Artificial Sequence
<220> FEATURE:
<223> OTHER INFORMATION: 30D8 VH CDR1

<400> SEQUENCE: 405

Gly Phe Thr Phe Ser Gly His Thr Ile Ala
1               5                   10

<210> SEQ ID NO 406
<211> LENGTH: 17
<212> TYPE: PRT
<213> ORGANISM: Artificial Sequence
<220> FEATURE:
<223> OTHER INFORMATION: 30D8 VH CDR2

```
<400> SEQUENCE: 406

Trp Val Ser Thr Asn Asn Gly Asn Thr Glu Tyr Ala Gln Lys Ile Gln
1               5                   10                  15
Gly

<210> SEQ ID NO 407
<211> LENGTH: 12
<212> TYPE: PRT
<213> ORGANISM: Artificial Sequence
<220> FEATURE:
<223> OTHER INFORMATION: 30D8 VH CDR3

<400> SEQUENCE: 407

Glu Trp Leu Val Met Gly Gly Phe Ala Phe Asp His
1               5                   10

<210> SEQ ID NO 408
<211> LENGTH: 11
<212> TYPE: PRT
<213> ORGANISM: Artificial Sequence
<220> FEATURE:
<223> OTHER INFORMATION: 30D8 VL CDR1

<400> SEQUENCE: 408

Gly Ala Asn Asn Ile Gly Ser Gln Asn Val His
1               5                   10

<210> SEQ ID NO 409
<211> LENGTH: 7
<212> TYPE: PRT
<213> ORGANISM: Artificial Sequence
<220> FEATURE:
<223> OTHER INFORMATION: 30D8 VL CDR2

<400> SEQUENCE: 409

Asp Asp Arg Asp Arg Pro Ser
1               5

<210> SEQ ID NO 410
<211> LENGTH: 12
<212> TYPE: PRT
<213> ORGANISM: Artificial Sequence
<220> FEATURE:
<223> OTHER INFORMATION: 30D8 VL CDR3

<400> SEQUENCE: 410

Gln Val Trp Asp Ser Ser Arg Asp Gln Ala Val Ile
1               5                   10

<210> SEQ ID NO 411
<211> LENGTH: 10
<212> TYPE: PRT
<213> ORGANISM: Artificial Sequence
<220> FEATURE:
<223> OTHER INFORMATION: 104E5 VH CDR1

<400> SEQUENCE: 411

Gly Gly Thr Phe Asp Thr Tyr Thr Ile Ser
1               5                   10

<210> SEQ ID NO 412
<211> LENGTH: 17
<212> TYPE: PRT
<213> ORGANISM: Artificial Sequence
<220> FEATURE:
```

```
<223> OTHER INFORMATION: 104E5 VH CDR2

<400> SEQUENCE: 412

Arg Ile Ile Pro Ser Leu Gly Glu Thr Asn Tyr Ala His Lys Leu Gln
 1               5                  10                  15

Gly

<210> SEQ ID NO 413
<211> LENGTH: 16
<212> TYPE: PRT
<213> ORGANISM: Artificial Sequence
<220> FEATURE:
<223> OTHER INFORMATION: 104E5 VH CDR3

<400> SEQUENCE: 413

Arg Ile Thr Gly Pro Val Asp Trp Val Trp Asp Tyr Gly Met Asp Val
 1               5                  10                  15

<210> SEQ ID NO 414
<211> LENGTH: 11
<212> TYPE: PRT
<213> ORGANISM: Artificial Sequence
<220> FEATURE:
<223> OTHER INFORMATION: 104E5 VL CDR1

<400> SEQUENCE: 414

Arg Ala Ser Gln Asn Ile Lys Thr Tyr Leu Asn
 1               5                  10

<210> SEQ ID NO 415
<211> LENGTH: 7
<212> TYPE: PRT
<213> ORGANISM: Artificial Sequence
<220> FEATURE:
<223> OTHER INFORMATION: 104E5 VL CDR2

<400> SEQUENCE: 415

Ala Val Ser Asn Leu Gln Ser
 1               5

<210> SEQ ID NO 416
<211> LENGTH: 9
<212> TYPE: PRT
<213> ORGANISM: Artificial Sequence
<220> FEATURE:
<223> OTHER INFORMATION: 104E5 VL CDR3

<400> SEQUENCE: 416

Gln Gln Ser Phe Ser Ile Pro Leu Thr
 1               5

<210> SEQ ID NO 417
<211> LENGTH: 10
<212> TYPE: PRT
<213> ORGANISM: Artificial Sequence
<220> FEATURE:
<223> OTHER INFORMATION: 38F10 VH CDR1

<400> SEQUENCE: 417

Gly Phe Ser Ile Thr Asp Phe Gly Ile His
 1               5                  10

<210> SEQ ID NO 418
<211> LENGTH: 17
<212> TYPE: PRT
<213> ORGANISM: Artificial Sequence
```

```
<220> FEATURE:
<223> OTHER INFORMATION: 38F10 VH CDR2

<400> SEQUENCE: 418

Leu Ile Ser Tyr Asn Glu Val Asn Ile His Tyr Gly Glu Ser Val Arg
1               5                   10                  15

Gly

<210> SEQ ID NO 419
<211> LENGTH: 15
<212> TYPE: PRT
<213> ORGANISM: Artificial Sequence
<220> FEATURE:
<223> OTHER INFORMATION: 38F10 VH CDR3

<400> SEQUENCE: 419

Asp Val Trp Glu Asp Ser Trp Leu Ser Leu Ala Cys Phe Gln Glu
1               5                   10                  15

<210> SEQ ID NO 420
<211> LENGTH: 11
<212> TYPE: PRT
<213> ORGANISM: Artificial Sequence
<220> FEATURE:
<223> OTHER INFORMATION: 38F10 VL CDR1

<400> SEQUENCE: 420

Arg Ala Ser Gln Ser Ile Ser Asn Trp Leu Ala
1               5                   10

<210> SEQ ID NO 421
<211> LENGTH: 7
<212> TYPE: PRT
<213> ORGANISM: Artificial Sequence
<220> FEATURE:
<223> OTHER INFORMATION: 38F10 VL CDR2

<400> SEQUENCE: 421

Lys Ala Ser Asn Leu Glu Asp
1               5

<210> SEQ ID NO 422
<211> LENGTH: 10
<212> TYPE: PRT
<213> ORGANISM: Artificial Sequence
<220> FEATURE:
<223> OTHER INFORMATION: 38F10 VL CDR3

<400> SEQUENCE: 422

Gln Gln Tyr Asn Ser Tyr Ser Gly Leu Ser
1               5                   10

<210> SEQ ID NO 423
<211> LENGTH: 12
<212> TYPE: PRT
<213> ORGANISM: Artificial Sequence
<220> FEATURE:
<223> OTHER INFORMATION: 14G3 VH CDR1

<400> SEQUENCE: 423

Gly Ala Ser Ile Ser Ser Asp Asn His Tyr Trp Ser
1               5                   10

<210> SEQ ID NO 424
<211> LENGTH: 16
<212> TYPE: PRT
```

```
<213> ORGANISM: Artificial Sequence
<220> FEATURE:
<223> OTHER INFORMATION: 14G3 VH CDR2

<400> SEQUENCE: 424

Ser Ile Tyr Tyr Thr Gly Gly Thr Asn Tyr Asn Pro Ser Leu Lys Ser
 1               5                  10                  15

<210> SEQ ID NO 425
<211> LENGTH: 15
<212> TYPE: PRT
<213> ORGANISM: Artificial Sequence
<220> FEATURE:
<223> OTHER INFORMATION: 14G3 VH CDR3

<400> SEQUENCE: 425

Gly Leu Phe Phe Ile Thr Ala Arg Pro Tyr Trp Tyr Phe Asp Leu
 1               5                  10                  15

<210> SEQ ID NO 426
<211> LENGTH: 17
<212> TYPE: PRT
<213> ORGANISM: Artificial Sequence
<220> FEATURE:
<223> OTHER INFORMATION: 14G3 VL CDR1

<400> SEQUENCE: 426

Arg Ser Ser Gln Ser Leu Leu Asp Ser Asp Asp Gly Asn Thr Tyr Leu
 1               5                  10                  15

Asp

<210> SEQ ID NO 427
<211> LENGTH: 7
<212> TYPE: PRT
<213> ORGANISM: Artificial Sequence
<220> FEATURE:
<223> OTHER INFORMATION: 14G3 VL CDR2

<400> SEQUENCE: 427

Thr Leu Ser Tyr Arg Ala Ser
 1               5

<210> SEQ ID NO 428
<211> LENGTH: 9
<212> TYPE: PRT
<213> ORGANISM: Artificial Sequence
<220> FEATURE:
<223> OTHER INFORMATION: 14G3 VL CDR3

<400> SEQUENCE: 428

Met Gln Arg Met Glu Phe Pro Phe Thr
 1               5

<210> SEQ ID NO 429
<211> LENGTH: 10
<212> TYPE: PRT
<213> ORGANISM: Artificial Sequence
<220> FEATURE:
<223> OTHER INFORMATION: 90D3 VH CDR1

<400> SEQUENCE: 429

Gly Phe Thr Leu Lys Asn Tyr Glu Met Asn
 1               5                  10

<210> SEQ ID NO 430
<211> LENGTH: 17
```

```
<212> TYPE: PRT
<213> ORGANISM: Artificial Sequence
<220> FEATURE:
<223> OTHER INFORMATION: 90D3 VH CDR2

<400> SEQUENCE: 430

Tyr Ile Ser Ser Ser Gly Asn Val Val Lys Tyr Val Asp Ser Val Gln
1               5                   10                  15
Gly

<210> SEQ ID NO 431
<211> LENGTH: 14
<212> TYPE: PRT
<213> ORGANISM: Artificial Sequence
<220> FEATURE:
<223> OTHER INFORMATION: 90D3 VH CDR3

<400> SEQUENCE: 431

Gly Phe Ser Ile Asp Lys Tyr Asp Ser Ser Val Asp Glu Tyr
1               5                   10

<210> SEQ ID NO 432
<211> LENGTH: 11
<212> TYPE: PRT
<213> ORGANISM: Artificial Sequence
<220> FEATURE:
<223> OTHER INFORMATION: 90D3 VL CDR1

<400> SEQUENCE: 432

Arg Ala Ser Gln Ser Ile Ser Asn Phe Leu Asn
1               5                   10

<210> SEQ ID NO 433
<211> LENGTH: 7
<212> TYPE: PRT
<213> ORGANISM: Artificial Sequence
<220> FEATURE:
<223> OTHER INFORMATION: 90D3 VL CDR2

<400> SEQUENCE: 433

Ala Ala Ser Ser Leu Gln Gly
1               5

<210> SEQ ID NO 434
<211> LENGTH: 9
<212> TYPE: PRT
<213> ORGANISM: Artificial Sequence
<220> FEATURE:
<223> OTHER INFORMATION: 90D3 VL CDR3

<400> SEQUENCE: 434

Gln Gln Thr Tyr Ile Ser Leu Tyr Thr
1               5

<210> SEQ ID NO 435
<211> LENGTH: 7
<212> TYPE: PRT
<213> ORGANISM: Artificial Sequence
<220> FEATURE:
<223> OTHER INFORMATION: 58c5 VH CDR1

<400> SEQUENCE: 435

Ser Asp Asn Tyr Tyr Trp Thr
1               5

<210> SEQ ID NO 436
```

```
<211> LENGTH: 6
<212> TYPE: PRT
<213> ORGANISM: Artificial Sequence
<220> FEATURE:
<223> OTHER INFORMATION: sc5 VH CDR1

<400> SEQUENCE: 436

Gly Ser Asn Trp Trp Asn
1               5

<210> SEQ ID NO 437
<211> LENGTH: 5
<212> TYPE: PRT
<213> ORGANISM: Artificial Sequence
<220> FEATURE:
<223> OTHER INFORMATION: 30D8 VH CDR1

<400> SEQUENCE: 437

Gly His Thr Ile Ala
1               5

<210> SEQ ID NO 438
<211> LENGTH: 5
<212> TYPE: PRT
<213> ORGANISM: Artificial Sequence
<220> FEATURE:
<223> OTHER INFORMATION: 104E5 VH CDR1

<400> SEQUENCE: 438

Thr Tyr Thr Ile Ser
1               5

<210> SEQ ID NO 439
<211> LENGTH: 5
<212> TYPE: PRT
<213> ORGANISM: Artificial Sequence
<220> FEATURE:
<223> OTHER INFORMATION: 38F10 VH CDR1

<400> SEQUENCE: 439

Asp Phe Gly Ile His
1               5

<210> SEQ ID NO 440
<211> LENGTH: 7
<212> TYPE: PRT
<213> ORGANISM: Artificial Sequence
<220> FEATURE:
<223> OTHER INFORMATION: 14G3 VH CDR1

<400> SEQUENCE: 440

Ser Asp Asn His Tyr Trp Ser
1               5

<210> SEQ ID NO 441
<211> LENGTH: 5
<212> TYPE: PRT
<213> ORGANISM: Artificial Sequence
<220> FEATURE:
<223> OTHER INFORMATION: 90D3 VH CDR1

<400> SEQUENCE: 441

Asn Tyr Glu Met Asn
1               5

<210> SEQ ID NO 442
<211> LENGTH: 645
```

<212> TYPE: DNA
<213> ORGANISM: Artificial Sequence
<220> FEATURE:
<223> OTHER INFORMATION: 30D8 Light Chain

<400> SEQUENCE: 442

```
cagtctgtgc tgacgcaggc atcctcggtg tcagtggccc caggacagac ggccagaatt      60
acctgtgggg caaacaacat tggaagtcaa aatgttcact ggtaccagca gaagccaggc     120
caggccctg ttttggtcgt ctatgatgat cgcgaccggc cctcaggat ccctgaccga      180
ttctctggct ccaactctgg gaatacggcc accctgacca tcagcagggt cgaggccggg     240
gatgaggccg actattactg tcaggtgtgg gatagtagtc gtgatcaggc cgtaattttt     300
ggcggaggga ccaagctgac cgtcctaggt cagcccaagg ctgccccctc ggtcactctg     360
ttcccgccct cctctgagga gcttcaagcc aacaaggcca cactggtgtg tctcataagt     420
gacttctacc cgggagccgt gacagtggcc tggaaggcag atagcagccc cgtcaaggcg     480
ggagtggaga ccaccacacc ctccaaacaa agcaacaaca gtacgcggc cagcagctac     540
ctgagcctga cgcctgagca gtggaagtcc cacagaagct acagctgcca ggtcacgcat     600
gaagggagca ccgtggagaa gacaattgcc cctacagaat gctca                    645
```

<210> SEQ ID NO 443
<211> LENGTH: 672
<212> TYPE: DNA
<213> ORGANISM: Artificial Sequence
<220> FEATURE:
<223> OTHER INFORMATION: 30D8 Fab Heavy Chain

<400> SEQUENCE: 443

```
gaggtgcagc tgttgcagtc tggagcagag ttgaagaagc ctggggcctc agtgaagatc      60
tcctgcaaga cttctggttt cacctttagc ggtcatacta tcgcctgggt gcgacaggcc     120
cctggacaag gcttgagtg gatgggctgg gtcagcacta taatggaaa cacagagtat      180
gcacagaaga tccagggcag agtcaccatg actatggaca tcaacgag cacagtctac       240
atggagttga ggagcctgac atctgacgac acggccgtgt atttctgtgc gagagagtgg     300
ctggtcatgg ggggcttcgc ctttgaccac tggggccagg gaaccctgct caccgtctcc     360
tcagcctcca ccaagggccc atcggtcttc cccctggcac cctcctccaa gagcacctct     420
gggggcacag cggccctggg ctgcctggtc aaggactact ccccgaacc ggtgacggtg      480
tcgtggaact caggcgccct gaccagcggc gtgcacacct tcccggctgt cctacagtcc    540
tcaggactct actccctcag cagcgtggtg accgtgccct ccagcagctt gggcacccag     600
acctacatct gcaacgtgaa tcacaagccc agcaacacca aggtggacaa gagagttgag     660
cccaaatctt gt                                                         672
```

<210> SEQ ID NO 444
<211> LENGTH: 645
<212> TYPE: DNA
<213> ORGANISM: Artificial Sequence
<220> FEATURE:
<223> OTHER INFORMATION: 104E5 Light Chain

<400> SEQUENCE: 444

```
gacatccaga tgacccagtc tccatcctcc ctgcctgcat ctgtgggaga cagagtcacc      60
atcacttgcc gggcaagtca gaacattaag acctatttaa attggtatca gcagaaacca    120
gggagagccc ctaaactcct gatctctgct gtgtccaatt tacaaagtgg ggtcccgtca    180
```

| | |
|---|---|
| aggttcagtg gcaccggatc tgggacagat tcactctca ccatcagcag tctgcaacct | 240 |
| gaagattttg caacttacta ctgtcagcag agtttcagta ttccgctcac tttcggcgga | 300 |
| ggggccaagg tggagatcaa acgaactgtg gctgcaccat ctgtcttcat cttcccgcca | 360 |
| tctgatgagc agttgaaatc tggaactgcc tctgttgtgt gcctgctgaa taacttctat | 420 |
| cccagagagg ccaaagtaca gtggaaggtg gataacgccc tccaatcggg taactcccag | 480 |
| gagagtgtca cagagcagga cagcaaggac agcacctaca gcctcagcag caccctgacg | 540 |
| ctgagcaaag cagactacga gaaacacaaa ctctacgcct gcgaagtcac ccatcagggc | 600 |
| ctgagctcgc ccgtcacaaa gagcttcaac aggggagagt gctaa | 645 |

<210> SEQ ID NO 445
<211> LENGTH: 684
<212> TYPE: DNA
<213> ORGANISM: Artificial Sequence
<220> FEATURE:
<223> OTHER INFORMATION: 104E5 Fab Heavy Chain

<400> SEQUENCE: 445

| | |
|---|---|
| caggtccaat tggaacagtc tggggctgag gtgaagaagc ctgggtcctc ggtgaaggtc | 60 |
| tcctgcaagc cttctggagg caccttcgac acatacacta tcagctgggt gcgacaggcc | 120 |
| cctggacaac gtcttgagtg gctgggaagg atcatccctt cacttggtga aacaaactat | 180 |
| gcacacaaac tccagggcag agtcacgatt accgcggaca agccacgag tgtcgtctat | 240 |
| atggacctga gcgacctgac atccgaggac gcggccgtct attactgtgc atttcgtata | 300 |
| actggacctg tcgactgggt ctgggactat gggatggacg tctggggcca agggaccacg | 360 |
| gtcagcgtct cgtcagcctc cagcaagggc ccatcggtct tcccctggc accctcctcc | 420 |
| aagagcacct ctgggggcac agcggccctg ggctgcctgg tcaaggacta cttccccgaa | 480 |
| ccggtgacgg tgtcgtggaa ctcaggcgcc ctgaccagcg gcgtgcacac cttcccggct | 540 |
| gtcctacagt cctcaggact ctactccctc agcagcgtgg tgaccgtgcc ctccagcagc | 600 |
| ttgggcaccc agacctacat ctgcaacgtg aatcacaagc ccagcaacac caaggtggac | 660 |
| aagagagttg agcccaaatc ttgt | 684 |

<210> SEQ ID NO 446
<211> LENGTH: 684
<212> TYPE: DNA
<213> ORGANISM: Artificial Sequence
<220> FEATURE:
<223> OTHER INFORMATION: 38F10 Light Chain

<400> SEQUENCE: 446

| | |
|---|---|
| ccggccatgg ccgccggtga catccagttg acccagtctc cccccaccct gtctgcgtct | 60 |
| gtgggagaca gagtctccat gacttgccgg gccagtcaga gtattagtaa ctggttggcc | 120 |
| tggtatcagc aaaaaccagg gaaagcccct aaactcctca tccagaaggc gtccaattta | 180 |
| gaagatggcg tccccctcac gttcaccgcc agtggatttg gacagaatt cactctcacc | 240 |
| atcagcagcc tacagcctga tgatttcgca acttattact gtcaacagta taatagttac | 300 |
| tcaggcctca gtttcggcgg agggaccaag gtggacatca aacgaactgt ggctgcacca | 360 |
| tctgtcttca tcttcccgcc atctgatgag cagttgaaat ctggaactgc ctctgttgtg | 420 |
| tgcctgctga ataacttcta tcccagagag gccaaagtac agtggaaggt ggataacgcc | 480 |
| ctccaatcgg gtaactccca ggagagtgtc acagagcagg acagcaagga cagcacctac | 540 |
| agcctcagca gcaccctgac gctgagcaaa gcagactacg agaaacacaa agtctacgcc | 600 |

```
tgcgaagtca cccatcaggg cctgagctcg cccgtcacaa agagcttcaa caggggagag    660
tgctaattaa ttaataagga ggat                                          684
```

<210> SEQ ID NO 447
<211> LENGTH: 726
<212> TYPE: DNA
<213> ORGANISM: Artificial Sequence
<220> FEATURE:
<223> OTHER INFORMATION: 38F10 Fab Heavy Chain

<400> SEQUENCE: 447

```
gcggccgcag aggtgcagct gttggagtct gggggagacg tggtccagcc tgggaagtcc     60
ctgagactct cctgcacagc ctctggattc agcatcactg actttggcat ccactgggtc    120
cgccaggctc caggcaaggg gctggagtgg gtggccctta tttcatataa cgaagtaaat    180
atacactatg cgagtccgt gaggggccgc ttcaccatct ccagagacat tgccaagaac    240
acagtatatc tgcagatgaa tggcctgaga cctgaagaca cgggtgtgta ttttttgtgcg   300 agggatgtct gggaggactc gtggctgtca cttgcgtgct tccaggaatg gggccagggc    360
tccctggtcg tcgtctcatc agcctccacc aagggcccat cggtcttccc cctggcaccc    420
tcctccaaga gcacctctgg gggcacagcg ccctgggct gcctggtcaa ggactacttc     480
cccgaaccgg tgacggtgtc gtggaactca ggcgccctga ccagcggcgt gcacaccttc    540
ccggctgtcc tacagtcctc aggactctac tccctcagca gcgtggtgac cgtgccctcc    600
agcagcttgg gcacccagac ctacatctgc aacgtgaatc acaagcccag caacaccaag    660
gtggacaaga agttgagcc caaatcttgt ggtcggccag gccggccgca ccatcaccat    720
caccat                                                              726
```

<210> SEQ ID NO 448
<211> LENGTH: 663
<212> TYPE: DNA
<213> ORGANISM: Artificial Sequence
<220> FEATURE:
<223> OTHER INFORMATION: 14G3 Light Chain

<400> SEQUENCE: 448

```
gatgttgtga tgacccagac tccactctcc ctgtccgtca cccctggaga gccggcctcc     60
atctcctgca ggtctagtca gagcctcttg gatagtgatg atggaaacac ctatttggac    120
tggtacctgc agaagccagg gcagtctcca cagctcctga tctatacact ttcctatcgg    180
gcctctggag tcccagacag gttcagtggc agtgggtcag gcactgattt cacactgaaa    240
atcagcaggg tggaggctga cgatgttgga atttattact gcatgcaacg tatggagttt    300 ccccttcacct tcggccaagg gacacgactg gacattaaac gaactgtggc tgcaccatct    360
gtcttcatct tcccgccatc tgatgagcag ttgaaatctg gaactgcctc tgttgtgtgc    420
ctgctgaata acttctatcc cagagaggcc aaagtacagt ggaaggtgga taacgccctc    480
caatcgggta actcccagga gagtgtcaca gagcaggaca gcaaggacag cacctacagc    540
ctcagcagca ccctgacgct gagcaaagca gactacgaga aacacaaagt ctacgcctgc    600
gaagtcaccc atcagggcct gagctcgccc gtcacaaaga gcttcaacag gggagagtgc    660
taa                                                                 663
```

<210> SEQ ID NO 449
<211> LENGTH: 684
<212> TYPE: DNA

<213> ORGANISM: Artificial Sequence
<220> FEATURE:
<223> OTHER INFORMATION: 14G3 Fab Heavy Chain

<400> SEQUENCE: 449

| | | |
|---|---|---|
| caggtgcagc tgcaggagtc gggcccagga ctggtgaagc cttcacagac cctgtccctc | 60 |
| acctgcactg tctctggtgc ctccatcagc agtgataatc actactggag ttggattcga | 120 |
| cagccccccg ggaagggcct ggagtggatt gcttccatct attacactgg tgcaccaac | 180 |
| tacaacccgt ccctcaagag tcgactcgcc ttatcaatag acacgtccgg ggaccagttc | 240 |
| tccttgaagc tgagctctgt gactgccgca gacacggccg tctattactg tgtcaggggc | 300 |
| ttgttttca taacagctcg tccctactgg tacttcgatc tctggggccg tggcaccctg | 360 |
| gtcgctgtct cctcagcctc caccaagggc ccatcggtct tccccctggc accctcctcc | 420 |
| aagagcacct ctgggggcac agcggccctg gcctgcctgg tcaaggacta cttccccgaa | 480 |
| ccggtgacgg tgtcgtggaa ctcaggcgcc ctgaccagcg gcgtgcacac cttcccggct | 540 |
| gtcctacagt cctcaggact ctactccctc agcagcgtgg tgaccgtgcc ctccagcagc | 600 |
| ttgggcaccc agacctacat ctgcaacgtg aatcacaagc ccagcaacac caaggtggac | 660 |
| aagagagttg agcccaaatc ttgt | 684 |

<210> SEQ ID NO 450
<211> LENGTH: 642
<212> TYPE: DNA
<213> ORGANISM: Artificial Sequence
<220> FEATURE:
<223> OTHER INFORMATION: 90D3 Light Chain

<400> SEQUENCE: 450

| | | |
|---|---|---|
| gccatccggt tgacccagtc tccatcctcc ctgtctgcat ctgtaggaga cagagtcagc | 60 |
| atcacttgcc gggcaagtca gagtattagc aacttttaa attggtatca gcagaaacca | 120 |
| gggagagccc cgaaactcct gatctctgct gcatccagtt tgcaaggtgg ggtcccatca | 180 |
| agattcagtg gcagtggatc tgggacagat ttcactctca ccatcagcag tctgcaacct | 240 |
| gaagattttg caacttacta ctgtcaacag acttacattt ccctgtacac ctttggccag | 300 |
| gggaccaaac tggagatcaa acgaactgtg gctgcaccat ctgtcttcat cttcccgcca | 360 |
| tctgatgagc agttgaaatc tggaactgcc tctgttgtgt gcctgctgaa taacttctat | 420 |
| cccagagagg ccaaagtaca gtggaaggtg gataacgccc tccaatcggg taactcccag | 480 |
| gagagtgtca cagagcagga cagcaaggac agcacctaca gcctcagcag cacccctgacg | 540 |
| ctgagcaaag cagactacga gaaacacaaa gtctacgcct gcgaagtcac ccatcagggc | 600 |
| ctgagctcgc ccgtcacaaa gagcttcaac aggggagagt gc | 642 |

<210> SEQ ID NO 451
<211> LENGTH: 723
<212> TYPE: DNA
<213> ORGANISM: Artificial Sequence
<220> FEATURE:
<223> OTHER INFORMATION: 90D3 Fab Light Chain

<400> SEQUENCE: 451

| | | |
|---|---|---|
| gcggccgcac aggtgcagct ggtggagtcg ggggaggcc tggtaaagcc tggagggtcc | 60 |
| ctgagactct cgtgtgtagg ctctggattc acccctcaaga attatgagat gaattgggtc | 120 |
| cgccaggctc cagggcaggg gctacaatat atttcataca tcagtagcag tggcaatgtc | 180 |
| gttaagtacg tagactctgt gcagggccga ttcaccatct ccagagacaa cgccgggaat | 240 |

```
tcgctgtatc tccaaatgaa caacctgagg gccgaggaca cggccactta ttactgtgtg    300
agaggttttt cgatcgataa gtatgatagc agtgttgatg aatactgggg ccagggaatc    360
gcggtcaccg tctcctcagc ctccaccaag ggcccatcgg tcttccccct ggcaccctcc    420
tccaagagca cctctggggg cacagcggcc ctgggctgcc tggtcaagga ctacttcccc    480
gaaccggtga cggtgtcgtg gaactcaggc gccctgacca gcggcgtgca caccttcccg    540
gctgtcctac agtcctcagg actctactcc ctcagcagcg tggtgaccgt gccctccagc    600
agcttgggca cccagaccta catctgcaac gtgaatcaca agcccagcaa caccaaggtg    660
gacaagaaag ttgagcccaa atcttgtggt cggccaggcc ggccgcacca tcaccatcac    720
cat                                                                  723
```

<210> SEQ ID NO 452
<211> LENGTH: 227
<212> TYPE: PRT
<213> ORGANISM: Artificial Sequence
<220> FEATURE:
<223> OTHER INFORMATION: 56E11 Heavy Chain

<400> SEQUENCE: 452

Glu Val Gln Leu Gln Glu Ser Gly Pro Gly Leu Val Lys Pro Ser Glu
1               5                   10                  15

Thr Leu Ser Leu Thr Cys Ser Val Ser Gly Val Ser Ile Asn Ser Asn
            20                  25                  30

Asn Tyr Phe Trp Ala Trp Ile Arg Gln Pro Pro Gly Lys Gly Leu Glu
        35                  40                  45

Trp Ile Gly Asn Ile Tyr Tyr Gly Gly Ser Thr His Tyr Asn Ala Ser
    50                  55                  60

Leu Gln Ser Arg Val Thr Ile Ser Val Asp Thr Ser Lys Ser Gln Phe
65                  70                  75                  80

Ser Leu Lys Leu Asn Ser Val Thr Ser Ala Asp Thr Ala Val Tyr Tyr
                85                  90                  95

Cys Ala Ala Ser Glu Ser Ile Phe Trp Asp Tyr Tyr Gly Leu Asp
            100                 105                 110

Val Trp Gly Gln Gly Thr Thr Val Thr Val Ser Ser Ala Ser Thr Lys
        115                 120                 125

Gly Pro Ser Val Phe Pro Leu Ala Pro Ser Ser Lys Ser Thr Ser Gly
    130                 135                 140

Gly Thr Ala Ala Leu Gly Cys Leu Val Lys Asp Tyr Phe Pro Glu Pro
145                 150                 155                 160

Val Thr Val Ser Trp Asn Ser Gly Ala Leu Thr Ser Gly Val His Thr
                165                 170                 175

Phe Pro Ala Val Leu Gln Ser Ser Gly Leu Tyr Ser Leu Ser Ser Val
            180                 185                 190

Val Thr Val Pro Ser Ser Leu Gly Thr Gln Thr Tyr Ile Cys Asn
        195                 200                 205

Val Asn His Lys Pro Ser Asn Thr Lys Val Asp Lys Val Glu Pro
    210                 215                 220

Lys Ser Cys
225

<210> SEQ ID NO 453
<211> LENGTH: 216
<212> TYPE: PRT
<213> ORGANISM: Artificial Sequence
<220> FEATURE:
<223> OTHER INFORMATION: 56E11 Light Chain

<400> SEQUENCE: 453

Gln Ala Val Leu Thr Gln Pro Pro Ser Ala Ser Gly Ser Pro Gly Gln
1               5                   10                  15

Ser Val Thr Ile Ser Cys Thr Gly Thr Ser Ser Asp Val Gly Gly Tyr
            20                  25                  30

Asn Tyr Val Ser Trp Tyr Gln Gln His Pro Gly Lys Ala Pro Arg Leu
        35                  40                  45

Ile Ile Ser Glu Val Thr Lys Arg Pro Ser Gly Val Pro Gly Arg Phe
    50                  55                  60

Ser Gly Ser Lys Ser Gly Asn Thr Ala Ser Leu Thr Val Ser Gly Leu
65                  70                  75                  80

Gln Ala Glu Asp Glu Ala Asp Tyr Tyr Cys Ser Ser Tyr Ala Gly Ser
                85                  90                  95

Arg His Val Val Phe Gly Gly Gly Thr Lys Leu Thr Val Leu Gly Gln
            100                 105                 110

Pro Lys Ala Ala Pro Ser Val Thr Leu Phe Pro Pro Ser Ser Glu Glu
        115                 120                 125

Leu Gln Ala Asn Lys Ala Thr Leu Val Cys Leu Ile Ser Asp Phe Tyr
    130                 135                 140

Pro Gly Ala Val Thr Val Ala Trp Lys Ala Asp Ser Ser Pro Val Lys
145                 150                 155                 160

Ala Gly Val Glu Thr Thr Thr Pro Ser Lys Gln Ser Asn Asn Lys Tyr
                165                 170                 175

Ala Ala Ser Ser Tyr Leu Ser Leu Thr Pro Glu Gln Trp Lys Ser His
            180                 185                 190

Arg Ser Tyr Ser Cys Gln Val Thr His Glu Gly Ser Thr Val Glu Lys
        195                 200                 205

Thr Ile Ala Pro Ala Glu Cys Ser
    210                 215

<210> SEQ ID NO 454
<211> LENGTH: 236
<212> TYPE: PRT
<213> ORGANISM: Artificial Sequence
<220> FEATURE:
<223> OTHER INFORMATION: 17C9 Heavy Chain

<400> SEQUENCE: 454

Gln Val Gln Leu Gln Gln Trp Gly Ala Gly Leu Val Arg Pro Ser Glu
1               5                   10                  15

Thr Leu Ser Leu Thr Cys Ala Val Tyr Gly Asp Ser Phe Asn Asp Tyr
            20                  25                  30

Phe Trp Thr Trp Ile Arg Gln Thr Pro Gly Lys Gly Leu Glu Trp Ile
        35                  40                  45

Gly Glu Ile Ser His Ser Gly Ser Thr Asn Tyr Ser Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ala Val Thr Ala Ala Asp Thr Thr Val Tyr Phe Cys Ala
                85                  90                  95

Arg Gly Val Arg Ser Arg Pro Pro Ser Tyr Arg Gly Ser Gly Ser
            100                 105                 110

Pro Pro Tyr Tyr His Tyr Gly Met Asp Val Trp Gly Gln Gly Thr Thr

-continued

```
            115                 120                 125
Val Thr Val Ser Ser Ala Ser Thr Lys Gly Pro Ser Val Phe Pro Leu
    130                 135                 140

Ala Pro Ser Ser Lys Ser Thr Ser Gly Gly Thr Ala Ala Leu Gly Cys
145                 150                 155                 160

Leu Val Lys Asp Tyr Phe Pro Glu Pro Val Thr Val Ser Trp Asn Ser
                165                 170                 175

Gly Ala Leu Thr Ser Gly Val His Thr Phe Pro Ala Val Leu Gln Ser
            180                 185                 190

Ser Gly Leu Tyr Ser Leu Ser Ser Val Val Thr Val Pro Ser Ser Ser
        195                 200                 205

Leu Gly Thr Gln Thr Tyr Ile Cys Asn Val Asn His Lys Pro Ser Asn
    210                 215                 220

Thr Lys Val Asp Lys Arg Val Glu Pro Lys Ser Cys
225                 230                 235

<210> SEQ ID NO 455
<211> LENGTH: 214
<212> TYPE: PRT
<213> ORGANISM: Artificial Sequence
<220> FEATURE:
<223> OTHER INFORMATION: 17C9 Light Chain

<400> SEQUENCE: 455

Glu Ile Val Leu Thr Gln Ser Pro Ser Thr Leu Ser Ala Ser Val Gly
  1               5                  10                  15

Asp Arg Val Thr Ile Thr Cys Arg Ala Ser Gln Asn Ile Asn Thr Trp
             20                  25                  30

Leu Ala Trp Tyr Gln Gln Lys Pro Gly Lys Ala Pro Lys Leu Leu Ile
         35                  40                  45

Tyr Ala Ala Ser Phe Leu Gln Ser Gly Val Pro Ser Arg Phe Ser Gly
    50                  55                  60

Ser Gly Ser Gly Thr Asp Phe Thr Leu Thr Ile Ser Asn Leu Gln Pro
65                  70                  75                  80

Glu Asp Phe Ala Thr Tyr Phe Cys Gln Gln Ala Asn Ser Phe Pro Arg
                85                  90                  95

Thr Phe Gly Gln Gly Thr Lys Val Glu Val Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 456
<211> LENGTH: 221
<212> TYPE: PRT
```

<213> ORGANISM: Artificial Sequence
<220> FEATURE:
<223> OTHER INFORMATION: 69F6 Heavy Chain

<400> SEQUENCE: 456

Gln Met Gln Leu Val Gln Ser Gly Ala Glu Val Arg Lys Pro Gly Glu
 1               5                  10                  15

Ser Leu Lys Ile Ala Cys Lys Gly Ser Gly Tyr Ser Phe Thr Ser Tyr
            20                  25                  30

Trp Ile Ala Trp Val Arg Gln Met Pro Gly Lys Gly Leu Glu Trp Leu
        35                  40                  45

Gly Ile Ile Phe Pro Asn Asp Ser Asp Ala Thr Tyr Ser Pro Ser Phe
    50                  55                  60

Gln Gly Gln Val Thr Met Ser Val Asp Lys Ser Ile Ser Thr Ala Tyr
65                  70                  75                  80

Leu Gln Trp Asn Ser Leu Lys Ala Ser Asp Thr Ala Val Tyr Phe Cys
                85                  90                  95

Ala Arg Gln Tyr Tyr Leu Gly Ser Phe Glu Ser Trp Gly Gln Gly Thr
            100                 105                 110

Thr Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys
    210                 215                 220

<210> SEQ ID NO 457
<211> LENGTH: 216
<212> TYPE: PRT
<213> ORGANISM: Artificial Sequence
<220> FEATURE:
<223> OTHER INFORMATION: 69F6 Light Chain

<400> SEQUENCE: 457

Glu Ile Val Leu Thr Gln Ser Pro Ser Ser Leu Ser Ala Ser Val Gly
 1               5                  10                  15

Asp Arg Val Thr Ile Ser Cys Gln Ala Ser Gln Asp Ile Ser Asn Tyr
            20                  25                  30

Leu Asn Trp Tyr Gln Gln Lys Pro Gly Lys Ala Pro Arg Leu Leu Ile
        35                  40                  45

Tyr Asp Ala Ser Tyr Leu Asp Thr Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Phe Ala Thr Tyr Tyr Cys Gln Gln Tyr Asp Asp Leu Arg Gly
                85                  90                  95

Gly Phe Thr Phe Gly Pro Gly Thr Lys Val Asp Val Lys Arg Thr Val
            100                 105                 110

-continued

Ala Ala Pro Ser Val Phe Ile Phe Pro Pro Ser Asp Glu Gln Leu Lys
            115                 120                 125

Ser Gly Thr Ala Ser Val Val Cys Leu Leu Asn Asn Phe Tyr Pro Arg
130                 135                 140

Glu Ala Lys Val Gln Trp Lys Val Asp Asn Ala Leu Gln Ser Gly Asn
145                 150                 155                 160

Ser Gln Glu Ser Val Thr Glu Gln Asp Ser Lys Asp Ser Thr Tyr Ser
                165                 170                 175

Leu Ser Ser Thr Leu Thr Leu Ser Lys Ala Asp Tyr Glu Lys His Lys
            180                 185                 190

Val Tyr Ala Cys Glu Val Thr His Gln Gly Leu Ser Ser Pro Val Thr
        195                 200                 205

Lys Ser Phe Asn Arg Gly Glu Cys
    210                 215

<210> SEQ ID NO 458
<211> LENGTH: 12
<212> TYPE: PRT
<213> ORGANISM: Artificial Sequence
<220> FEATURE:
<223> OTHER INFORMATION: 56E11 VH CDR1

<400> SEQUENCE: 458

Gly Val Ser Ile Asn Ser Asn Asn Tyr Phe Trp Ala
1               5                   10

<210> SEQ ID NO 459
<211> LENGTH: 16
<212> TYPE: PRT
<213> ORGANISM: Artificial Sequence
<220> FEATURE:
<223> OTHER INFORMATION: 56E11 VH CDR2

<400> SEQUENCE: 459

Asn Ile Tyr Tyr Gly Gly Ser Thr His Tyr Asn Ala Ser Leu Gln Ser
1               5                   10                  15

<210> SEQ ID NO 460
<211> LENGTH: 14
<212> TYPE: PRT
<213> ORGANISM: Artificial Sequence
<220> FEATURE:
<223> OTHER INFORMATION: 56E11 VH CDR3

<400> SEQUENCE: 460

Ser Glu Ser Ile Phe Trp Asp Tyr Tyr Tyr Gly Leu Asp Val
1               5                   10

<210> SEQ ID NO 461
<211> LENGTH: 14
<212> TYPE: PRT
<213> ORGANISM: Artificial Sequence
<220> FEATURE:
<223> OTHER INFORMATION: 56E11 VL CDR1

<400> SEQUENCE: 461

Thr Gly Thr Ser Ser Asp Val Gly Gly Tyr Asn Tyr Val Ser
1               5                   10

<210> SEQ ID NO 462
<211> LENGTH: 7
<212> TYPE: PRT
<213> ORGANISM: Artificial Sequence
<220> FEATURE:

```
<223> OTHER INFORMATION: 56E11 VL CDR2

<400> SEQUENCE: 462

Glu Val Thr Lys Arg Pro Ser
 1               5

<210> SEQ ID NO 463
<211> LENGTH: 10
<212> TYPE: PRT
<213> ORGANISM: Artificial Sequence
<220> FEATURE:
<223> OTHER INFORMATION: 56E11 VL CDR3

<400> SEQUENCE: 463

Ser Ser Tyr Ala Gly Ser Arg His Val Val
 1               5                  10

<210> SEQ ID NO 464
<211> LENGTH: 10
<212> TYPE: PRT
<213> ORGANISM: Artificial Sequence
<220> FEATURE:
<223> OTHER INFORMATION: 17C9 VH CDR1

<400> SEQUENCE: 464

Gly Asp Ser Phe Asn Asp Tyr Phe Trp Thr
 1               5                  10

<210> SEQ ID NO 465
<211> LENGTH: 16
<212> TYPE: PRT
<213> ORGANISM: Artificial Sequence
<220> FEATURE:
<223> OTHER INFORMATION: 17C9 VH CDR2

<400> SEQUENCE: 465

Glu Ile Ser His Ser Gly Ser Thr Asn Tyr Ser Pro Ser Leu Lys Ser
 1               5                  10                  15

<210> SEQ ID NO 466
<211> LENGTH: 25
<212> TYPE: PRT
<213> ORGANISM: Artificial Sequence
<220> FEATURE:
<223> OTHER INFORMATION: 17C9 VH CDR3

<400> SEQUENCE: 466

Gly Val Arg Ser Arg Pro Pro Ser Tyr Arg Gly Ser Gly Ser Pro
 1               5                  10                  15

Pro Tyr Tyr His Tyr Gly Met Asp Val
                20                  25

<210> SEQ ID NO 467
<211> LENGTH: 11
<212> TYPE: PRT
<213> ORGANISM: Artificial Sequence
<220> FEATURE:
<223> OTHER INFORMATION: 17C9 VL CDR1

<400> SEQUENCE: 467

Arg Ala Ser Gln Asn Ile Asn Thr Trp Leu Ala
 1               5                  10

<210> SEQ ID NO 468
<211> LENGTH: 7
<212> TYPE: PRT
```

```
<213> ORGANISM: Artificial Sequence
<220> FEATURE:
<223> OTHER INFORMATION: 17C9 VL CDR2

<400> SEQUENCE: 468

Ala Ala Ser Phe Leu Gln Ser
 1               5

<210> SEQ ID NO 469
<211> LENGTH: 9
<212> TYPE: PRT
<213> ORGANISM: Artificial Sequence
<220> FEATURE:
<223> OTHER INFORMATION: 17C9 VL CDR3

<400> SEQUENCE: 469

Gln Gln Ala Asn Ser Phe Pro Arg Thr
 1               5

<210> SEQ ID NO 470
<211> LENGTH: 10
<212> TYPE: PRT
<213> ORGANISM: Artificial Sequence
<220> FEATURE:
<223> OTHER INFORMATION: 69F6 VH CDR1

<400> SEQUENCE: 470

Gly Tyr Ser Phe Thr Ser Tyr Trp Ile Ala
 1               5                  10

<210> SEQ ID NO 471
<211> LENGTH: 17
<212> TYPE: PRT
<213> ORGANISM: Artificial Sequence
<220> FEATURE:
<223> OTHER INFORMATION: 69F6 VH CDR2

<400> SEQUENCE: 471

Ile Ile Phe Pro Asn Asp Ser Asp Ala Thr Tyr Ser Pro Ser Phe Gln
 1               5                  10                  15
Gly

<210> SEQ ID NO 472
<211> LENGTH: 9
<212> TYPE: PRT
<213> ORGANISM: Artificial Sequence
<220> FEATURE:
<223> OTHER INFORMATION: 69F6 VH CDR3

<400> SEQUENCE: 472

Gln Tyr Tyr Leu Gly Ser Phe Glu Ser
 1               5

<210> SEQ ID NO 473
<211> LENGTH: 10
<212> TYPE: PRT
<213> ORGANISM: Artificial Sequence
<220> FEATURE:
<223> OTHER INFORMATION: 69F6 VL CDR1

<400> SEQUENCE: 473

Gln Ala Ser Asp Ile Ser Asn Tyr Leu Asn
 1               5                  10

<210> SEQ ID NO 474
<211> LENGTH: 7
```

```
<212> TYPE: PRT
<213> ORGANISM: Artificial Sequence
<220> FEATURE:
<223> OTHER INFORMATION: 69F6 VL CDR2

<400> SEQUENCE: 474

Asp Ala Ser Tyr Leu Asp Thr
 1               5

<210> SEQ ID NO 475
<211> LENGTH: 11
<212> TYPE: PRT
<213> ORGANISM: Artificial Sequence
<220> FEATURE:
<223> OTHER INFORMATION: 69F6 VL CDR3

<400> SEQUENCE: 475

Gln Gln Tyr Asp Asp Leu Arg Gly Gly Phe Thr
 1               5                  10

<210> SEQ ID NO 476
<211> LENGTH: 648
<212> TYPE: DNA
<213> ORGANISM: Artificial Sequence
<220> FEATURE:
<223> OTHER INFORMATION: 56E11 Light Chain

<400> SEQUENCE: 476
caggctgtgc tgactcagcc tccctccgcg tccgggtctc ctggacagtc agtcaccatc      60
tcctgcactg gaaccagcag tgacgttggt ggttataatt atgtctcctg gtaccaacaa     120
caccccggga agcccccag  actcataatt tctgaagtca ctaagcggcc ctcagggtc     180 cctggtcgct ctccggctc  caagtctggc aacacggcct ccctgaccgt ctctgggctc    240
caggctgagg atgaggctga ttattactgc agctcatatg caggcagcag catgtggtt     300 ttcggcggag ggaccaagtt gaccgtcctc ggtcagccca aggctgcccc ctcggtcact    360
ctgttcccgc cctcctctga ggagcttcaa gccaacaagg ccacactggt gtgtctcata    420
agtgacttct acccgggagc cgtgacagtg gcctggaagg cagatagcag ccccgtcaag    480
gcgggagtgg agaccaccac accctccaaa caaagcaaca caagtacgc  ggccagcagc    540 tacctgagcc tgacgcctga gcagtggaag tcccacagaa gctacagctg ccaggtcacg    600
catgaaggga gcaccgtgga agacaattg  cccctgcag  aatgctca                 648

<210> SEQ ID NO 477
<211> LENGTH: 681
<212> TYPE: DNA
<213> ORGANISM: Artificial Sequence
<220> FEATURE:
<223> OTHER INFORMATION: 56E11 Heavy Chain

<400> SEQUENCE: 477
gaggtgcagc tgcaggagtc gggcccagga ctggtgaagc cttcggagac cctgtccctc      60
acctgcagtg tctctggtgt ctccatcaac agcaacaatt atttctgggc ctggatccgc    120
cagcccccag gcaaggggct ggagtggatt gggaatatct attatggtgg agcaccccac    180
tacaatgcgt ccctgcagag tcgagtcacc atatccgtag acacgtccaa gagccagttc    240
tccctgaagc tgaactctgt gacctccgcc gacacggctg tgtattactg cgcggcttcc    300
gagtctatct ttgggactac tactacggc  ctggacgtct ggggccaagg gaccacggtc    360
accgtctcct ctgcctccac caagggccca tcggtcttcc cctggcacc  ctcctccaag    420
```

| | | |
|---|---|---|
| agcacctctg ggggcacagc ggccctgggc tgcctggtca aggactactt ccccgaaccg | 480 | |
| gtgacggtgt cgtggaactc aggcgccctg accagcggcg tgcacacctt cccggctgtc | 540 | |
| ctacagtcct caggactcta ctccctcagc agcgtggtga ccgtgccctc agcagcttg | 600 | |
| ggcacccaga cctacatctg caacgtgaat cacaagccca gcaacaccaa ggtggacaag | 660 | |
| aaagttgagc ccaaatcttg t | 681 | |

<210> SEQ ID NO 478
<211> LENGTH: 642
<212> TYPE: DNA
<213> ORGANISM: Artificial Sequence
<220> FEATURE:
<223> OTHER INFORMATION: 17C9 Light Chain

<400> SEQUENCE: 478

| | | |
|---|---|---|
| gaaattgtgt tgacccagtc tccttccacc ctgtctgcat ctgtaggaga cagagtcacc | 60 | |
| atcacttgcc gggccagtca gaatattaat acctggttgg cctggtatca gcagaaacca | 120 | |
| gggaaagccc ctaagctcct gatctatgct gcatcctttt gcaaagtgg ggtcccatca | 180 | |
| aggttcagcg gcagtggatc tgggacagat ttcactctca ccatcagcaa cttgcagcct | 240 | |
| gaagattttg caacttactt ttgtcaacag gctaacagtt tccctcggac cttcggccag | 300 | |
| gggaccaagg tggaagtcaa acgaactgtg gctgcaccat ctgtcttcat cttcccgcca | 360 | |
| tctgatgagc agttgaaatc tggaactgcc tctgttgtgt gcctgctgaa taacttctat | 420 | |
| cccagagagg ccaaagtaca gtggaaggtg gataacgccc tccaatcggg taactcccag | 480 | |
| gagagtgtca cagagcagga cagcaaggac agcacctaca gcctcagcag cacctgacg | 540 | |
| ctgagcaaag cagactacga gaaacacaaa gtctacgcct gcgaagtcac ccatcagggc | 600 | |
| ctgagctcgc ccgtcacaaa gagcttcaac aggggagagt gc | 642 | |

<210> SEQ ID NO 479
<211> LENGTH: 708
<212> TYPE: DNA
<213> ORGANISM: Artificial Sequence
<220> FEATURE:
<223> OTHER INFORMATION: 17C9 Heavy Chain

<400> SEQUENCE: 479

| | | |
|---|---|---|
| caggtacagc tgcagcagtg gggcgcagga ctggtgaggc cttcggagac cctgtccctc | 60 | |
| acctgcgctg tctatggtga ctccttcaat gattacttct ggacgtggat ccgccagacc | 120 | |
| ccaggaaagg ggctggagtg gattggggaa atcagtcata gtggaagcac caactacagc | 180 | |
| ccgtccctca agagtcgagt caccatatca gttgacacgt ccaagaacca gttctccctg | 240 | |
| aaactcagcg ctgtgaccgc cgcggacacg actgtgtatt tctgtgcgag aggtgtccgc | 300 | |
| tcccgacccc ctccgagtta ccgtggctcg ggctccccc cttactacca ttacggtatg | 360 | |
| gacgtctggg gccaagggac cacggtcacc gtctcctcag cctccaccaa gggcccatcg | 420 | |
| gtcttccccc tggcaccctc ctccaagagc acctctgggg gcacagcggc cctgggctgc | 480 | |
| ctggtcaagg actacttccc cgaaccggtg acggtgtcgt ggaactcagg cgccctgacc | 540 | |
| agcggcgtgc acaccttccc ggctgtccta cagtcctcag gactctactc cctcagcagc | 600 | |
| gtggtgaccg tgccctccag cagcttgggc acccagacct acatctgcaa cgtgaatcac | 660 | |
| aagcccagca acaccaaggt ggacaagaga gttgagccca atcttgt | 708 | |

<210> SEQ ID NO 480
<211> LENGTH: 648

```
<212> TYPE: DNA
<213> ORGANISM: Artificial Sequence
<220> FEATURE:
<223> OTHER INFORMATION: 69F6 Light Chain

<400> SEQUENCE: 480
gaaattgtgt tgacccagtc tccatcctcc ctgtctgcat ctgtcggaga cagagtcacc      60
atctcttgcc aggcgagtca ggacattagc aactatttaa attggtatca acagaaacca     120
gggaaagccc ctaggctcct gatctacgat gcatcctatt tggacacagg ggtcccatca     180
aggttcagtg aagtggatc tgggacagat tttactttca ccatcagcag cctacagcct     240
gaagattttg caacatatta ctgtcaacaa tatgatgatc tccggggggg gttcactttc     300
ggccctggga ccaaagtgga cgtcaaacga actgtggctg caccatctgt cttcatcttc     360
ccgccatctg atgagcagtt gaaatctgga actgcctctg ttgtgtgcct gctgaataac     420
ttctatccca gagaggccaa agtacagtgg aaggtggata acgcctccaa atcgggtaac     480
tcccaggaga gtgtcacaga gcaggacagc aaggacagca cctacagcct cagcagcacc     540
ctgacgctga gcaaagcaga ctacgagaaa cacaaagtct acgcctgcga agtcacccat     600
cagggcctga gctcgcccgt cacaaagagc ttcaacaggg gagagtgc                  648

<210> SEQ ID NO 481
<211> LENGTH: 663
<212> TYPE: DNA
<213> ORGANISM: Artificial Sequence
<220> FEATURE:
<223> OTHER INFORMATION: 69F6 Heavy Chain

<400> SEQUENCE: 481
cagatgcagc tggtgcagtc tggagcagag gtgagaaagc cggggagtc tctgaagatc       60
gcctgtaagg gttccggata cagttttacc agctactgga tcgcctgggt gcgccagatg     120
cccgggaaag gcctggaatg gctggggatc atctttccta atgactctga tgccacatac     180
agcccgtcct tccaaggcca ggtcaccatg tcagtcgaca gtccatcag caccgcctac     240
ctgcagtgga acagcctgaa ggcctcggac accgccgtgt attttgtgc gagacagtat     300
tatcttggct cgtttgaatc ctggggccaa ggaaccacgg tcaccgtctc ctcagcctcc     360
accaagggcc catcggtctt ccccctggca ccctcctcca agagcacctc tgggggcaca     420
gcggccctgg gctgcctggt caaggactac ttccccgaac cggtgacggt gtcgtggaac     480
tcaggcgccc tgaccagcgg cgtgcacacc ttcccggctg tcctacagtc ctcaggactc     540
tactccctca gcagcgtggt gaccgtgccc tccagcagct gggcaccca gacctacatc     600
tgcaacgtga atcacaagcc cagcaacacc aaggtggaca gaaagttga gcccaaatct     660
tgt                                                                  663

<210> SEQ ID NO 482
<211> LENGTH: 7
<212> TYPE: PRT
<213> ORGANISM: Artificial Sequence
<220> FEATURE:
<223> OTHER INFORMATION: 56E11 VH CDR1

<400> SEQUENCE: 482

Ser Asn Asn Tyr Phe Trp Ala
 1               5

<210> SEQ ID NO 483
<211> LENGTH: 5
```

```
<212> TYPE: PRT
<213> ORGANISM: Artificial Sequence
<220> FEATURE:
<223> OTHER INFORMATION: 17C9 VH CDR1

<400> SEQUENCE: 483

Asp Tyr Phe Trp Thr
1               5

<210> SEQ ID NO 484
<211> LENGTH: 5
<212> TYPE: PRT
<213> ORGANISM: Artificial Sequence
<220> FEATURE:
<223> OTHER INFORMATION: 69F6 VH CDR1

<400> SEQUENCE: 484

Ser Tyr Trp Ile Ala
1               5

<210> SEQ ID NO 485
<211> LENGTH: 574
<212> TYPE: PRT
<213> ORGANISM: Respiratory syncytial virus
<220> FEATURE:
<223> OTHER INFORMATION: F Protein

<400> SEQUENCE: 485

Met Glu Leu Leu Ile Leu Lys Ala Asn Ala Ile Thr Thr Ile Leu Thr
1               5                   10                  15

Ala Val Thr Phe Cys Phe Ala Ser Gly Gln Asn Ile Thr Glu Glu Phe
                20                  25                  30

Tyr Gln Ser Thr Cys Ser Ala Val Ser Lys Gly Tyr Leu Ser Ala Leu
            35                  40                  45

Arg Thr Gly Trp Tyr Thr Ser Val Ile Thr Ile Glu Leu Ser Asn Ile
        50                  55                  60

Lys Lys Asn Lys Cys Asn Gly Thr Asp Ala Lys Ala Lys Leu Ile Lys
65                  70                  75                  80

Gln Glu Leu Asp Lys Tyr Lys Asn Ala Val Thr Glu Leu Gln Leu Leu
                85                  90                  95

Met Gln Ser Thr Gln Ala Thr Asn Asn Arg Ala Arg Arg Glu Leu Pro
            100                 105                 110

Arg Phe Met Asn Tyr Thr Leu Asn Asn Ala Lys Lys Thr Asn Val Thr
        115                 120                 125

Leu Ser Lys Lys Arg Lys Arg Arg Phe Leu Gly Phe Leu Leu Gly Val
130                 135                 140

Gly Ser Ala Ile Ala Ser Gly Val Ala Val Ser Lys Val Leu His Leu
145                 150                 155                 160

Glu Gly Glu Val Asn Lys Ile Lys Ser Ala Leu Leu Ser Thr Asn Lys
                165                 170                 175

Ala Val Val Ser Leu Ser Asn Gly Val Ser Val Leu Thr Ser Lys Val
            180                 185                 190

Leu Asp Leu Lys Asn Tyr Ile Asp Lys Gln Leu Leu Pro Ile Val Asn
        195                 200                 205

Lys Gln Ser Cys Ser Ile Ser Asn Ile Glu Thr Val Ile Glu Phe Gln
    210                 215                 220

Gln Lys Asn Asn Arg Leu Leu Glu Ile Thr Arg Glu Phe Ser Val Asn
225                 230                 235                 240

Ala Gly Val Thr Thr Pro Val Ser Thr Tyr Met Leu Thr Asn Ser Glu
```

245                 250                 255
Leu Leu Ser Leu Ile Asn Asp Met Pro Ile Thr Asn Asp Gln Lys Lys
            260                 265                 270

Leu Met Ser Asn Asn Val Gln Ile Val Arg Gln Gln Ser Tyr Ser Ile
        275                 280                 285

Met Ser Ile Ile Lys Glu Glu Val Leu Ala Tyr Val Val Gln Leu Pro
    290                 295                 300

Leu Tyr Gly Val Ile Asp Thr Pro Cys Trp Lys Leu His Thr Ser Pro
305                 310                 315                 320

Leu Cys Thr Thr Asn Thr Lys Glu Gly Ser Asn Ile Cys Leu Thr Arg
            325                 330                 335

Thr Asp Arg Gly Trp Tyr Cys Asp Asn Ala Gly Ser Val Ser Phe Phe
        340                 345                 350

Pro Gln Ala Glu Thr Cys Lys Val Gln Ser Asn Arg Val Phe Cys Asp
    355                 360                 365

Thr Met Asn Ser Leu Thr Leu Pro Ser Glu Val Asn Leu Cys Asn Val
370                 375                 380

Asp Ile Phe Asn Pro Lys Tyr Asp Cys Lys Ile Met Thr Ser Lys Thr
385                 390                 395                 400

Asp Val Ser Ser Ser Val Ile Thr Ser Leu Gly Ala Ile Val Ser Cys
            405                 410                 415

Tyr Gly Lys Thr Lys Cys Thr Ala Ser Asn Lys Asn Arg Gly Ile Ile
        420                 425                 430

Lys Thr Phe Ser Asn Gly Cys Asp Tyr Val Ser Asn Lys Gly Val Asp
    435                 440                 445

Thr Val Ser Val Gly Asn Thr Leu Tyr Tyr Val Asn Lys Gln Glu Gly
450                 455                 460

Lys Ser Leu Tyr Val Lys Gly Glu Pro Ile Ile Asn Phe Tyr Asp Pro
465                 470                 475                 480

Leu Val Phe Pro Ser Asp Glu Phe Asp Ala Ser Ile Ser Gln Val Asn
            485                 490                 495

Glu Lys Ile Asn Gln Ser Leu Ala Phe Ile Arg Lys Ser Asp Glu Leu
        500                 505                 510

Leu His Asn Val Ile Ala Gly Lys Ser Thr Thr Asn Ile Met Ile Thr
    515                 520                 525

Thr Ile Ile Ile Val Ile Ile Val Ile Leu Leu Ser Leu Ile Ala Val
530                 535                 540

Gly Leu Leu Leu Tyr Cys Lys Ala Arg Ser Thr Pro Val Thr Leu Ser
545                 550                 555                 560

Lys Asp Gln Leu Ser Gly Ile Asn Asn Ile Ala Phe Ser Asn
            565                 570

<210> SEQ ID NO 486
<211> LENGTH: 574
<212> TYPE: PRT
<213> ORGANISM: Artificial Sequence
<220> FEATURE:
<223> OTHER INFORMATION: Motavizumab MARM F protein

<400> SEQUENCE: 486

Met Glu Leu Leu Ile Leu Lys Ala Asn Ala Ile Thr Thr Ile Leu Thr
 1               5                  10                  15

Ala Val Thr Phe Cys Phe Ala Ser Gly Gln Asn Ile Thr Glu Glu Phe
            20                  25                  30

Tyr Gln Ser Thr Cys Ser Ala Val Ser Lys Gly Tyr Leu Ser Ala Leu

```
            35                  40                  45
Arg Thr Gly Trp Tyr Thr Ser Val Ile Thr Ile Glu Leu Ser Asn Ile
 50                  55                  60
Lys Lys Asn Lys Cys Asn Gly Thr Asp Ala Lys Ala Lys Leu Ile Lys
 65                  70                  75                  80
Gln Glu Leu Asp Lys Tyr Lys Asn Ala Val Thr Glu Leu Gln Leu Leu
                 85                  90                  95
Met Gln Ser Thr Gln Ala Thr Asn Asn Arg Ala Arg Arg Glu Leu Pro
            100                 105                 110
Arg Phe Met Asn Tyr Thr Leu Asn Asn Ala Lys Lys Thr Asn Val Thr
        115                 120                 125
Leu Ser Lys Lys Arg Lys Arg Arg Phe Leu Gly Phe Leu Leu Gly Val
130                 135                 140
Gly Ser Ala Ile Ala Ser Gly Val Ala Val Ser Lys Val Leu His Leu
145                 150                 155                 160
Glu Gly Glu Val Asn Lys Ile Lys Ser Ala Leu Leu Ser Thr Asn Lys
                165                 170                 175
Ala Val Val Ser Leu Ser Asn Gly Val Ser Val Leu Thr Ser Lys Val
            180                 185                 190
Leu Asp Leu Lys Asn Tyr Ile Asp Lys Gln Leu Leu Pro Ile Val Asn
        195                 200                 205
Lys Gln Ser Cys Ser Ile Ser Asn Ile Glu Thr Val Ile Glu Phe Gln
210                 215                 220
Gln Lys Asn Asn Arg Leu Leu Glu Ile Thr Arg Glu Phe Ser Val Asn
225                 230                 235                 240
Ala Gly Val Thr Thr Pro Val Ser Thr Tyr Met Leu Thr Asn Ser Glu
                245                 250                 255
Leu Leu Ser Leu Ile Asn Asp Met Pro Ile Thr Asn Asp Gln Lys Glu
            260                 265                 270
Leu Met Ser Asn Asn Val Gln Ile Val Arg Gln Gln Ser Tyr Ser Ile
        275                 280                 285
Met Ser Ile Ile Lys Glu Glu Val Leu Ala Tyr Val Val Gln Leu Pro
290                 295                 300
Leu Tyr Gly Val Ile Asp Thr Pro Cys Trp Lys Leu His Thr Ser Pro
305                 310                 315                 320
Leu Cys Thr Thr Asn Thr Lys Glu Gly Ser Asn Ile Cys Leu Thr Arg
                325                 330                 335
Thr Asp Arg Gly Trp Tyr Cys Asp Asn Ala Gly Ser Val Ser Phe Phe
            340                 345                 350
Pro Gln Ala Glu Thr Cys Lys Val Gln Ser Asn Arg Val Phe Cys Asp
        355                 360                 365
Thr Met Asn Ser Leu Thr Leu Pro Ser Glu Val Asn Leu Cys Asn Val
        370                 375                 380
Asp Ile Phe Asn Pro Lys Tyr Asp Cys Lys Ile Met Thr Ser Lys Thr
385                 390                 395                 400
Asp Val Ser Ser Ser Val Ile Thr Ser Leu Gly Ala Ile Val Ser Cys
                405                 410                 415
Tyr Gly Lys Thr Lys Cys Thr Ala Ser Asn Lys Asn Arg Gly Ile Ile
            420                 425                 430
Lys Thr Phe Ser Asn Gly Cys Asp Tyr Val Ser Asn Lys Gly Val Asp
        435                 440                 445
Thr Val Ser Val Gly Asn Thr Leu Tyr Tyr Val Asn Lys Gln Glu Gly
        450                 455                 460
```

```
Lys Ser Leu Tyr Val Lys Gly Glu Pro Ile Ile Asn Phe Tyr Asp Pro
465                 470                 475                 480

Leu Val Phe Pro Ser Asp Glu Phe Asp Ala Ser Ile Ser Gln Val Asn
                485                 490                 495

Glu Lys Ile Asn Gln Ser Leu Ala Phe Ile Arg Lys Ser Asp Glu Leu
            500                 505                 510

Leu His Asn Val Ile Ala Gly Lys Ser Thr Thr Asn Ile Met Ile Thr
        515                 520                 525

Thr Ile Ile Ile Val Ile Ile Val Ile Leu Ser Leu Ile Ala Val
    530                 535                 540

Gly Leu Leu Leu Tyr Cys Lys Ala Arg Ser Thr Pro Val Thr Leu Ser
545                 550                 555                 560

Lys Asp Gln Leu Ser Gly Ile Asn Asn Ile Ala Phe Ser Asn
                565                 570
```

<210> SEQ ID NO 487
<211> LENGTH: 574
<212> TYPE: PRT
<213> ORGANISM: Artificial Sequence
<220> FEATURE:
<223> OTHER INFORMATION: 58C5 MARM F protein

<400> SEQUENCE: 487

```
Met Glu Leu Leu Ile Leu Lys Ala Asn Ala Ile Thr Thr Ile Leu Thr
1               5                   10                  15

Ala Val Thr Phe Cys Phe Ala Ser Gly Gln Asn Ile Thr Glu Glu Phe
            20                  25                  30

Tyr Gln Ser Thr Cys Ser Ala Val Ser Lys Gly Tyr Leu Ser Ala Leu
        35                  40                  45

Arg Thr Gly Trp Tyr Thr Ser Val Ile Thr Ile Glu Leu Ser Lys Ile
    50                  55                  60

Lys Lys Asn Lys Cys Asn Gly Thr Asp Ala Lys Ala Lys Leu Ile Lys
65                  70                  75                  80

Gln Glu Leu Asp Lys Tyr Lys Asn Ala Val Thr Glu Leu Gln Leu Leu
                85                  90                  95

Met Gln Ser Thr Gln Ala Thr Asn Asn Arg Ala Arg Arg Glu Leu Pro
            100                 105                 110

Arg Phe Lys Asn Tyr Thr Leu Asn Asn Ala Lys Lys Thr Asn Val Thr
        115                 120                 125

Leu Ser Lys Lys Arg Lys Arg Arg Phe Leu Gly Phe Leu Leu Gly Val
    130                 135                 140

Gly Ser Ala Ile Ala Ser Gly Val Ala Val Ser Lys Val Leu His Leu
145                 150                 155                 160

Glu Gly Glu Val Asn Lys Ile Lys Ser Ala Leu Leu Ser Thr Asn Lys
                165                 170                 175

Ala Val Val Ser Leu Ser Asn Gly Val Ser Val Leu Thr Ser Lys Val
            180                 185                 190

Leu Asp Leu Lys Asn Tyr Ile Asp Lys Gln Leu Leu Pro Ile Val Asn
        195                 200                 205

Lys Gln Ser Cys Ser Ile Ser Asn Ile Glu Thr Val Ile Glu Phe Gln
    210                 215                 220

Gln Lys Asn Asn Arg Leu Leu Glu Ile Thr Arg Glu Phe Ser Val Asn
225                 230                 235                 240

Ala Gly Val Thr Thr Pro Val Ser Thr Tyr Met Leu Thr Asn Ser Glu
                245                 250                 255
```

-continued

```
Leu Leu Ser Leu Ile Asn Asp Met Pro Ile Thr Asn Asp Gln Lys Lys
            260                 265                 270

Leu Met Ser Asn Asn Val Gln Ile Val Arg Gln Gln Ser Tyr Ser Ile
            275                 280                 285

Met Ser Ile Ile Lys Glu Gly Val Leu Ala Tyr Val Val Gln Leu Pro
290                 295                 300

Leu Tyr Gly Val Ile Asp Thr Pro Cys Trp Lys Leu His Thr Ser Pro
305                 310                 315                 320

Leu Cys Thr Thr Asn Thr Lys Glu Gly Ser Asn Ile Cys Leu Thr Arg
                325                 330                 335

Thr Asp Arg Gly Trp Tyr Cys Asp Asn Ala Gly Ser Val Ser Phe Phe
            340                 345                 350

Pro Gln Ala Glu Thr Cys Lys Val Gln Ser Asn Arg Val Phe Cys Asp
            355                 360                 365

Thr Met Asn Ser Leu Thr Leu Pro Ser Glu Val Asn Leu Cys Asn Val
    370                 375                 380

Asp Ile Phe Asn Pro Lys Tyr Asp Cys Lys Ile Met Thr Ser Lys Thr
385                 390                 395                 400

Asp Val Ser Ser Ser Val Ile Thr Ser Leu Gly Ala Ile Val Ser Cys
                405                 410                 415

Tyr Gly Lys Thr Lys Cys Thr Ala Ser Asn Lys Asn Arg Gly Ile Ile
            420                 425                 430

Lys Thr Phe Ser Asn Gly Cys Asp Tyr Val Ser Asn Lys Gly Val Asp
            435                 440                 445

Thr Val Ser Val Gly Asn Thr Leu Tyr Tyr Val Asn Lys Gln Glu Gly
    450                 455                 460

Lys Ser Leu Tyr Val Lys Gly Glu Pro Ile Ile Asn Phe Tyr Asp Pro
465                 470                 475                 480

Leu Val Phe Pro Ser Asp Glu Phe Asp Ala Ser Ile Ser Gln Val Asn
            485                 490                 495

Glu Lys Ile Asn Gln Ser Leu Ala Phe Ile Arg Lys Ser Asp Glu Leu
            500                 505                 510

Leu His Asn Val Ile Ala Gly Lys Ser Thr Thr Asn Ile Met Ile Thr
    515                 520                 525

Thr Ile Ile Ile Val Ile Ile Val Ile Leu Leu Ser Leu Ile Ala Val
    530                 535                 540

Gly Leu Leu Leu Tyr Cys Lys Ala Arg Ser Thr Pro Val Thr Leu Ser
545                 550                 555                 560

Lys Asp Gln Leu Ser Gly Ile Asn Asn Ile Ala Phe Ser Asn
                565                 570
```